United States Patent
Ishihara et al.

(10) Patent No.: US 6,534,496 B1
(45) Date of Patent: Mar. 18, 2003

(54) THERMOGENIC COMPOSITION AND BENZAZEPINE THERMOGENICS

(75) Inventors: Yuji Ishihara, Itami (JP); Yukio Fujisawa, Tsukuba (JP); Naoki Furuyama, Kobe (JP)

(73) Assignee: Takeda Chemical Industries, Inc., Osaka (JP)

( * ) Notice: Subject to any disclaimer, the term of this patent is extended or adjusted under 35 U.S.C. 154(b) by 0 days.

(21) Appl. No.: 09/402,806

(22) PCT Filed: Apr. 16, 1998

(86) PCT No.: PCT/JP98/01753

§ 371 (c)(1),
(2), (4) Date: Oct. 7, 1999

(87) PCT Pub. No.: WO98/46590

PCT Pub. Date: Oct. 22, 1998

(30) Foreign Application Priority Data

Apr. 17, 1997 (JP) ............................................. 9-100675
Feb. 24, 1998 (JP) ........................................... 10-041495

(51) Int. Cl.⁷ .......................... A61K 31/55; A61P 3/04; C07D 223/16
(52) U.S. Cl. ........................... 514/212.07; 514/213.01; 514/217.01; 514/217.02; 540/523; 540/593; 540/594; 540/595
(58) Field of Search ................................ 540/523, 593, 540/594, 595; 514/212.07, 213.01, 217.01, 217.02

(56) References Cited

U.S. PATENT DOCUMENTS 5,273,974 A * 12/1993 Goto et al. ................. 514/221
5,462,934 A   10/1995 Goto et al. ................. 514/183
5,698,553 A * 12/1997 Prucher et al. .......... 514/222.8

FOREIGN PATENT DOCUMENTS

| DE | 2016136 | 10/1971 |
|----|---------|---------|
| EP | 0163537 A | 12/1985 |
| EP | 0378207 A | 7/1990 |
| EP | 0487071 A | 5/1992 |
| EP | 0560235 A | 9/1993 |
| EP | 0562832 A | 9/1993 |
| EP | 0567090 A | 10/1993 |
| EP | 0607864 A | 7/1994 |
| EP | 0655451 A | 5/1995 |
| JP | 10-53529 | * 2/1998 |
| WO | WO 91/03243 | 3/1991 |
| WO | WO 94/29290 | 12/1994 |

OTHER PUBLICATIONS

Ishihara et al., Regioselective Friedel–Crafts Acylation of 2,3,4,5–Tetrahydro–1H–2–benzazepine and Related Nitrogen Heterocycles, J. Chem. Soc. Perkin Trans. I, vol. 20, pp. 2993–2999, Oct. 1994.*
Yamamoto et al., Docking Analysis of a Series of Benzylamino Acetylcholinesterase Inhibitors with a Phthalimide, Benzoyl, or Indanone Moiety, Journal of Medicinal Chemistry, vol. 37, No. 19, pp. 3141–3153, Sep. 1994.*
Y. Ishihara et al, "Central Cholinergic Agents. 6. Synthesis and Evaluation of . . . "J. Med. Chem., 1994, 37, pp. 2292–2299.

* cited by examiner

*Primary Examiner*—Brenda Coleman
(74) *Attorney, Agent, or Firm*—Mark Chao; Elaine M. Ramesh

(57) ABSTRACT

The object of the present invention is to provide a prophylactic and/or therapeutic drug for obesity and obesity-associated diseasestor diabetes with a reduced risk for central side effects and high universality in usage. Another object of the present invention is to provide a pharmaceutical composition comprising a compound of the following formula:

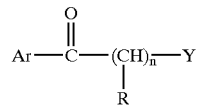

wherein Ar represents phenyl which may be substituted and/or condensed; n represents an integer of 1 to 10; R represents hydrogen or a hydrocarbon group which may be substituted, which may not be the same in its n occurrences; R may be bound to either Ar or a substituent for Ar; Y represents an amino group which may be subsituted or a nitrogen-containing saturated heterocyclic group which may be substituted, or a salt thereof, which can be used for a thermogenic agent, an antiobesity agent, a lipolytic agent, or a prophylactic and/or treating drug for obesity-associated diseases.

13 Claims, 1 Drawing Sheet

THERMOGENIC COMPOSITION AND BENZAZEPINE THERMOGENICS

This Application is National Stage of International Application Ser. No. PCT/JP98/01753, filed Apr. 16, 1998.

TECHNICAL FIELD

The present invention relates to a medicine and, more particularly, to a thermogenic agent (thermogenesis accelerator) for use as a prophylactic and/or treating drug for obesity and obesity-associated disease and its active compound, namely an aminoketone derivative or a salt thereof.

BACKGROUND ART

As treating drugs for obesity, centrally-acting anorexics such as mazindol have been used-clinically However, central anorexics have gastrointestinal side effects such as nausea and vomiting in addition to central side effects such as addiction and, therefore, are indicated only in limited cases, e.g. advanced obesity.

On the other hand, β3 adrenergic receptor agonists have been proposed as peripherally-acting antiobesity drugs [Nature, 309, 163–165, 1984; J. Med. Chem., 35, 3081–3084, 1992, etc.]. However, mutations of the β3 adrenergic receptor gene have been reported in a fairly large number of obese persons (New Engl. J. Med., 333, 343–347, 1995; Lancet, 346, 1433–1434, 1995; Biochem. Biophys. Res. Commun., 215, 555–560, 1995) and it is logical to assume that the antiobesity effect of any β3 adrenergic receptor agonist is self-limited.

As synthetic drugs, aminoketone derivatives having a variety of biological and pharmacological activities have been proposed (Japanese Patent Unexamined Publication No. 140149/1993, WO 9307140, EP 560235, EP 562832, Japanese Patent Unexamined Publication No. 169569/1990, U.S. Pat. No. 5,106,856, Japanese Patent Unexamined Publication No. 22333/1979, Japanese Patent Unexamined Publication No. 167546/1984, EP-A-0378207, Japanese Patent Unexamined Publication No. 206875/1994, Japanese Patent Unexamined Publication No. 206854/1995, Japanese Patent Unexamined Publication No. 309835/1995, WO 9103243, Khim.-Farm., Zh., 21, 569, (1987), Chem. Abstr., 89, 36594y (1978), Journal of the Pharmaceutical Society of Japan, 97, 540 (1977), EP 163537, Chem. Abstr., 91, 211631y (1979), Helvetica Chimica Acta, 51, 1616 (1968), Japanese Patent Unexamined Publication No. 97952/1977, Japanese Patent Unexamined Publication No. 7185/1984, FR-M3635, Chem. Abstr., 67, 54087k (1967), 68, 105121x (1968), 75, 88548s (1971), 76, 153682t (1972)). However, none of the literature discloses, or even suggests, that such derivatives ever have activity validating their use as prophylactic and/or treating drugs for obesity or obesity-associated disease, as lipolytic agents, or as thermogenic agents.

For example, Japanese Patent Unexamied Publication No. 140149/1993 describes a fused heterocyclic derivative of the following chemical formula or a salt thereof as a cholinesterase inhibitor:

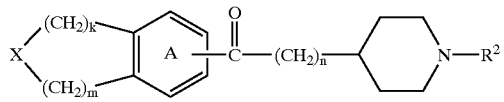

wherein X represents $R^1$—N< ($R^1$ represents hydrogen, a hydrocarbon group which may be substituted, or an acyl group which may be substituted), oxygen, or sulfur; $R^2$ reprehsents hydrogen or a hydrocarbon group which may be substituted; ring A represents a benzene ring which may be substituted; k represents an integer of 0–3; m represents an integer of 1–8; and n represents an integer of 1–6. Spedifically described is a compounds of the following formula:

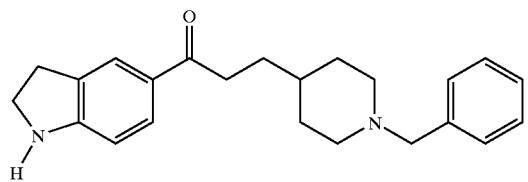

WO 9307140 discloses a compound of the following formula as a cholinesterase inhibitor:

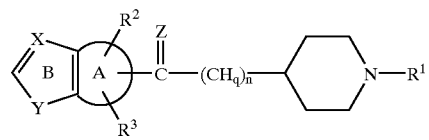

wherein ring A represents benzo, thieno, pyrido, pyrazino, pyrimido, furano, seleno, pyrrolo, thiazolo, or imidazolo; $R^1$ represents phenyl, phenyl($C_{1-6}$)alkyl, cinnamyl, or heteroarylmethyl (heteroaryl=imidazolo, thiazolo, thieno, pyrido, or isoxazolo); said phenyl and heteroaryl may each have 1 or2 substituent groups selected,from the class consisting of ($C_{1-6}$)alkyl, ($C_{1-6}$) alkoxy, and halogen; $R^2$ and $R^3$ independently represent hydrogen, ($C_{1-6}$)alkoxy, or ($C_{1-6}$) alkyl may have 1–3 substituent groups selected from fluorine, benzyloxy, hydroxy, phenyl, benzyl, halogen, nitro, cyano, $CO_2R^4$, $CONHR^4$, $NR^4R^5$, $NR^4COR^5$, and $SO_pCH_2Ph$ (where p represents 0, 1, or 2); or $R^2$ and $R^3$ may jointly and in combination with the adjacent carbon atom form a 5- or 6-membered ring (where the ring atoms are selected from the class consisting of carbon, nitrogen, and oxygen; e.g. methylenedioxy, ethylenedioxy, or a lactam, ring); $R^4$ and $R^5$ independently represent hydrogen or ($C_{1-6}$)alkyl, or $R^4$ and $R^5$ of $NR^4R^5$ may jointly and in, combination with the adjacent nitrogen form a 4- through 8-membered ring containing at least one nitrogen atom (the other ring atoms are carbon and oxygen and/or nitrogen); $R^4$ and $R^5$ of $NR^4COR^5$ may jointly and in combination with the adjacent nitrogen and carbon atoms form a 4- through 8-membered lactam ring; X represents nitrogen or CH; Y represents oxygen, sulfur, or $NR^6$; $R^6$ represents hydrogen, ($C_{1-6}$)alkyl, $CO(C_{1-6})$alkyl, or $SO_2$-phenyl (the phenyl may have 1 to 5 substituent groups independently selected from among ($C_{1-4}$)alkyl species); n represents an integer of 1 through 4; q in n occurrences independently represents 1 or 2; z represents oxygen or sulfur. The following compound is typically disclosed as a cholinesterase inhibitor:

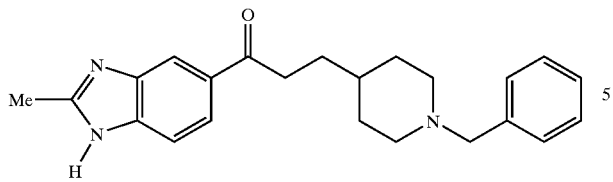
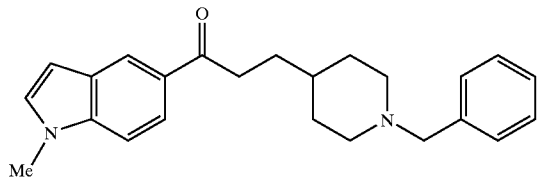

EP 560235 discloses a fused heterocyclic ketone derivative of the following formula or its salt as a cholinesterase inhibitor:

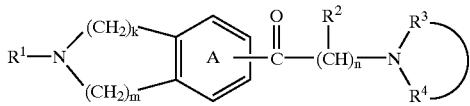

wherein $R^1$ represents hydrogen, a hydrocarbon group which may be substituted, or an acyl group which may be substituted; ring A represents a benzene ring which may be further substituted; n represents an integer of 1 through 10; $R^2$, $R^3$, and $R^4$ may be the same or different and each represents hydrogen or a hydrocarbon group which may be substituted; $R^3$ and $R^4$ may jointly and in combination with the adjacent nitrogen atom form a heterocyclic group which may be substituted; $R^2$ may not be the same in n occurrences; k represents an integer of 0 to 3; m represents an integer of 1 to 8; provided, however, that when k=0 and m=2, n>1. Specifically, the compound of the following formula is disclosed as a cholinesterase inhibitor:

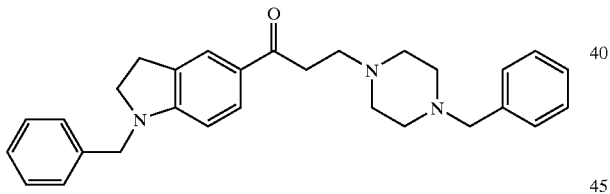

EP 562832 discloses a compound of the formula:

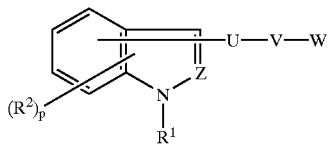

wherein $R^1$ and $R^2$ independently represent hydrogen or an organic group; p represents 0, 1, 2, or 3; U represents —CO— or —CH(OR$^3$)— (where $R^3$ represents hydrogen or a hydroxy-protecting group); V represents an aliphatic hydrocarbon group which may be unsaturated; W represents a nitrogen-containing group. Specifically, the compound of the following formula is mentioned as a cholinesterase inhibitor:

Japanese Patent Unexamined Publication No. 169569/1990 discloses acyclic amine derivative of the following formula or a pharmacologically acceptable salt thereof:

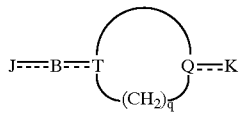

where J represents,
(a) (1) phenyl, (2) pyridyl, (3) pyrazyl, (4) quinolyl, (5) cyclohexyl, (6) quinoxalyl, or (7) furyl, each substituted or unsubstituted,
(b) a univalent or bivalent group, the phenyl moiety of which may be substituted, which is selected from the class consisting of (1) indanyl, (2) indanonyl, (3), indenyl, (4) indenonyl, (5) indandionyl, (6) tetralonyl, (7) benzosuberonyl, (8) indanolyl, (9) a group of the formula:

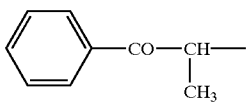

(c) a univalent group derived from a cyclic amide compound,
(d) a lower alkyl group, or
(e) a group of the formula $R^1$—CH=CH— (where $R^1$ represents hydrogen or lower alkoxycarbonyl);
B represents a group of the formula —(C(R$^2$)H)$_n$—, a group of the formula —CO—(C(R$^2$)H)$_n$—, a group of the formula —NR$^2$—(C(R$^2$)H)$_n$— (where R$^2$ represents hydrogen, lower alkyl, acyl, lower alkylsulfonyl, phenyl which may be substituted, or benzyl), a group of the formula —CO—NR$^4$—(C(R$^2$)H)$_n$— (where R$^4$ represents hydrogen, lower alkyl, or phenyl), a group of the formula —CH=CH—(C(R$^2$)H)$_n$—, a group of the formula —O—COO—(C(R$^2$)H)$_n$—, a group of the formula —O—CO—NH—(C(R$^2$)H)$_n$—, a group of the formula —NH—CO—(C(R$^2$)H)$_n$—, a group of the formula —CH$_2$—CO—NH—((R$^2$)H)$_n$—, a group of the formula —CO—NH—(C(R$^2$)H)$_n$—, a group of the formula —C(OH)H—(C(R$^2$)H)$_n$— (in each of the above formulas, n represents an integer of 0–10; R$^2$ represents hydrogen or methyl in the sense that the alkylene group of the formula —(C(R$^2$)H)$_n$— is either unsubstituted or substituted by one or more than one methyl group), a group of the formula =(CH—CH=CH)$_b$— (where b represents an integer of 1 to 3), a group of the formula =CH—(CH$_2$)$_c$— (where c represents an integer of 0 or 1 to 9), a group of the formula =(CH—CH)$_d$= (where d represents an integer of 0 or 1–5), a group of the formula =CO—CH=CH—CH$_2$—, a group of the formula —CO—CH$_2$—C(OH)H—CH$_2$—, a group of the formula —C(CH$_3$)H—CO—NH—CH$_2$—, a group of the formula —CH=CH—CO—NH—(CH$_2$)$_2$—, a group of the formula —NH—, a group of the formula —O—, a group of the formula —S—, a dialkylaminoalkylcarbonyl group, or a lower alkoxycarbonyl group;

T represents nitrogen or carbon;

Q represents nitrogen, carbon or a group of the formula: >N®O;

K represents hydrogen, substituted or unsubstituted phenyl, arylalkyl, the phenyl moiety of which may be substituted, cinnamyl, the phenyl moiety of which may be substituted, lower alkyl, pyridylmethyl, cycloalkylalkyl, adamantanemethyl, furylmethyl, cycloalkyl, lower alkoxycarbonyl, or acyl;

q represents an integer of 1 to 3;

⇌ in the formula represents a single bond or a double bond. Specifically, the following compound is typically disclosed as a cholinesterase inhibitor:

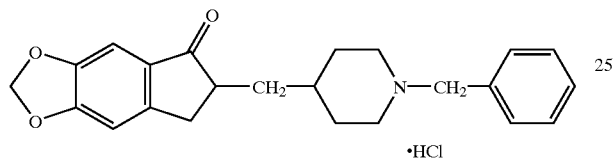

·HCl

U.S. Pat. No. 5,106,856 discloses a compound of the formula:

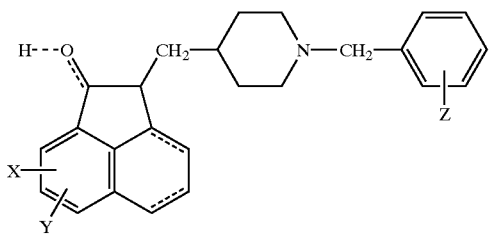

wherein X represents hydrogen, hydroxy, nitro, lower alkyl, or lower alkoxy; Y represents hydrogen or lower alkoxy, or X and Y jointly form OCH$_2$O. Specifically, the following compound is disclosed as a cholinesterase inhibitor:

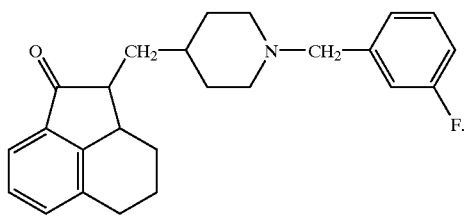

Japanese Patent Unexamined Publication No. 22333/1979 discloses a compound of the following formula as a synthetic intermediate of base thioether compounds having antifungal, antibacterial and antiinflammatory activities:

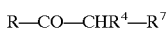

wherein R represents 2-dibenzothienyl, for instance; R$^4$ represents H, for instance; R$^7$ represents —(CH$_2$)$_n$—Z (where n represents 1, 2, or 3; Z represents —NR$^1$R$^2$ (R$^1$ and R$^2$ independently represent H or C$_{1-4}$ alkyl or jointly represent C$_{4-7}$ alkylene or 3-oxapentamethylene), for instance.

Japanese Patent Unexamined Publication No. 167546/1984 discloses a compound of the formula:

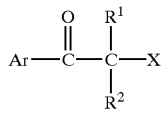

wherein Ar typically represents

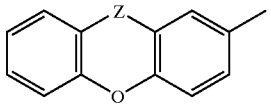

(Z represents a direct bond, —CH$_2$—, —CH$_2$CH$_2$—, or —O—);

X represents an amino group of the formula —N(R$^{11}$)(R$^{12}$) where

R$^{11}$ represents hydrogen, C$_{1-12}$ alkyl, C$_{2-4}$ alkyl substituted by one or more members selected from the following class: OH, C$_{1-4}$ alkoxy, CN, and —COO(C$_{1-4}$ alkly), or C$_{3-5}$ alkenyl, cyclohexyl, C$_{7-9}$ phenylalkyl, phenyl, or phenyl substituted by C1, C$_{1-4}$ alkyl, OH, C$_{1-4}$ alkoxy, or —COO(C$_{1-4}$ alkyl); or R$^{11}$ and R$^1$ taken together represent —CH$_2$OCH$_2$—;

R$^{12}$ has one of the meanings given to R$^{11}$ or, taken together with R$^{11}$, represents a C$_{5-7}$ alkylene group or a C$_{3-7}$ alkylene group interrupted by —O—, —S—, or —N(R$^{14}$)— or, taken together with R$^2$, represents C$_{1-8}$ alkylene, C$_{7-10}$ phenylalkylene, C$_{2-4}$ oxyalkylene, or azaalkylene;

R$^1$ and R$^2$ independently represent C$_{1-8}$ alkyl.

Specifically, the compound of the following formula is disclosed as a photocurable color composition:

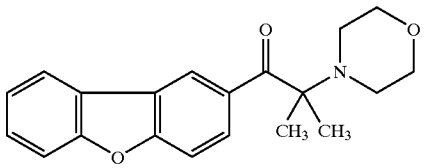

EP-A-0378207 discloses a cyclic amine compound of the following formula or a salt thereof:

wherein B represents a saturated or unsaturated 5- through 7-membered aza-heterocyclic group which may be substituted; A represents a bond or an alkylene or alkenylene group which may be substituted by a hydrocarbon residue, oxo, or hydroxy;

⇌ represents a single bond or a double bond (however, when A represents a bond,

⇌ represents a single bond);

R$_2$ and R$_3$ independently represent hydrogen or a hydrocarbon residue which may be substituted (provided, however, that both $R_2$ and $R_3$ do not concurrently represent hydrogen) or may jointly and in combination with the adjacent nitrogen atom form a cycloamino group; n represents 0, 1, or 2; and p represents 1 or 2. Specifically the following compound, among others, is mentioned as a cholinesterase inhibitor:

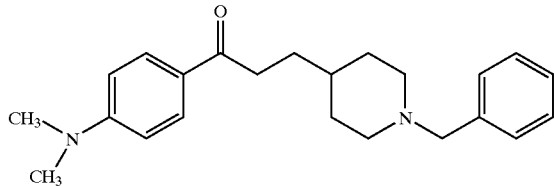

Japanese Patent Unexamined Publication No. 206875/1994 discloses a cholinesterase inhibitor characterized by comprising a heterocyclic compound of the following formula or a salt thereof:

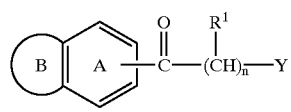

wherein ring A represents a benzene ring which may be further substituted; ring B represents a nonaromatic hetero ring containing 2 or more hetero atoms, which may be the same or different, as ring members, which may be substituted; $R^1$ represents hydrogen or a hydrocarbon group which may be substituted and may not be the same in n occurrences; Y represents an amino group which may be substituted or a nitrogen-containing saturated heterocyclic group which may be substituted; n represents an integer of 1 through 10. Specifically, the following compound, for instance, is described:

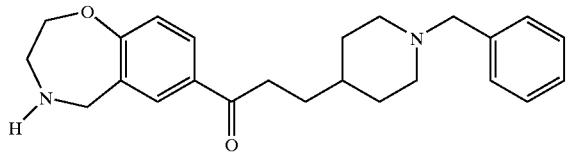

Japanese Patent Unexamined Publication No. 206854/1995 discloses a tricyclic fused heterocyclic derivative of the following formula or a salt thereof:

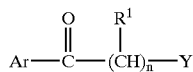

where Ar represents a tricyclic benzenoid system including at least one hetero ring, which system may optionally be substituted; n represents an integer of 2 through 10; $R^1$ represents hydrogen or a hydrocarbon group which may be substituted; $R^1$ may not be the same in n occurrences; Y represents, as each unsubstituted or substituted, 4-piperidinyl, 1-piperazinyl, or 4-benzyl-1-piperidinyl. Specifically, the compound of the following formula is mentioned as a cholinesterase inhibitor:

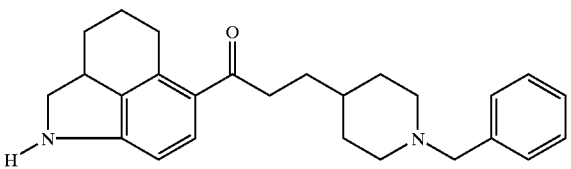

Japanese Patent Unexamined Publication No. 309835/1995 discloses a tetracyclic fused hetero system of the following formula or a salt thereof.

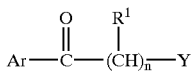

wherein Ar represents a tetracyclic fused hetero system which may be substituted; n represents an integer of 1 through 10; $R^1$ represents hydrogen or A hydrocarbon group which may be substituted; $R^1$ may not be the same in n occurrences; Y means an amino group which may be substituted or a nitrogen-containing saturated heterocyclic group which may be substituted. Typically, the compound of the following formula is mentioned as a cholinesterase inhibitor:

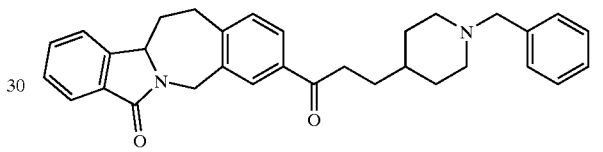

WO 910 3243 discloses a compound of the following formula or a pharmaceutically acceptable salt thereof, which finds application as an antipsychotic drug:

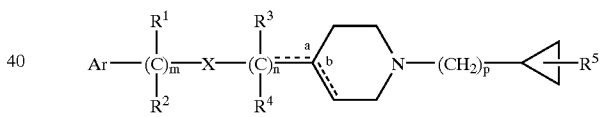

wherein m represents 0 through 3; n represents 0 through 3; both of m and n do not concurrently represent 0; p represents 0 through 3; X represents O, S, SO, $SO_2$, $NR^6$, $CR^7R^8$, CO, or CHOH; $R^1$, $R^3$, and $R^7$ independently represent hydrogen, $C_{1-5}$ alkyl, halogen, $NR^{10}R^{11}$, OH, COOH, $C_{2-6}$ carboalkoxy, CN, Ar, $C_{1-5}$ alkoxy, or $C_{1-5}$alkylthio; $R^2$, $R^4$, and $R^8$ independently represent hydrogen, $C_{1-5}$ alkyl, $C_{2-6}$ carboalkoxy, CN, $C_{1-5}$ alkoxy, or $Ar^1$; when X represents O, S, SO, $SO_2$, or $NR^6$, $R^1$, $R^2$, $R^3$, and $r^4$ are not $C_{1-5}$ alkoxy, $C_{1-5}$ alkylthio, $NR^{10}R^{11}$, or OH; $R^5$ represents hydrogen, alkyl, halogen, OH, or alkenyl; $R^6$ represents hydrogen, $C_{1-5}$ alkyl, or $Ar^1$; Ar and $Ar^1$ respectively represent naphthyl, pyridyl, pirimidyl, indolyl, quinolinyl, isoquinolinyl, or phenyl, each substituted or unsubstituted, $C_{1-3}$ alkyl, $C_{1-3}$ alkoxy, $C_{1-3}$ haloalkyl as substituted by 1–7 halogen atoms, SH, $S(O)_t$—$C_{1-3}$ alkyl (t=1, 2, or 3), $C_{2-6}$ dialkylamino, halogen, $C_{1-3}$ alkylamino, $NH_2$, CN, $NO_2$, $SO_3H$, tetraz-ole, COOH, $C_{2-6}$ carbalkoxy, $CONH_2$, $SO_2NO_2$, $COR^9$, $CONR^{12}R^{13}$, $SO_2NR^{12}R^{13}$, $Ar^2$, $OAr^2$, or $SAr^2$; $Ar^2$ represents naphthyl or phenyl, which may be substituted by $C_{1-3}$ alkyl, $C_{1-3}$ haloalkyl as substituted by 1 to 7 halogen atoms, $C_{1-3}$ alkoxy, halogen, or $C_{1-3}$ alkylthio; $R^9$, $R^{10}$, $R^{11}$, $R^{12}$, and $R^{13}$ respectively represent hydrogen, $C_{1-5}$ alkyl, or phenyl; $R^{10}$ and $R^{11}$ may jointly form a $C_{3-6}$alkylene chain;

$R^{12}$ and $R^{13}$ may jointly form a $C_{3-6}$ alkylene chain; a or b represents a double bond or a single bond and both a and b do not concurrently represent a double bond.

It is disclosed in Khim.-Farm. Zh. 21, 569, 1987 that a compound of the following general formula has antiinflammatory activity:

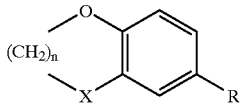

wherein R=Ac, COEt, COPr, COCHMe$_2$, CO(CH$_2$)$_2$Cl, CO(CH$_2$)$_3$Cl, COCH$_2$NMe$_2$, CO(CH$_2$)$_2$NMe$_2$, CO(CH$_2$)$_3$NMe$_2$, all inclusive of salts thereof, or R=COCH=CHPh; X=CH$_2$ or O; n=1, 2, or 3.

It is mentioned in Chemical Abstracts, 89, 36594y, 1978 that a compound of the following general formula has anticonvulsant, arterial blood pressure-lowering, and local anesthetic actions:

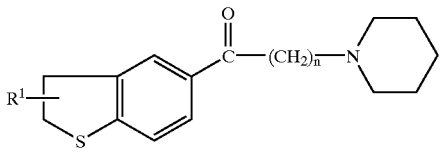

wherein $R^1$=H, Me; n=2, 3.

It is reported in Journal of the Pharmaceutical Society of Japan, 97, 540, 1977 that a compound of the following general formula has antidepressant activity:

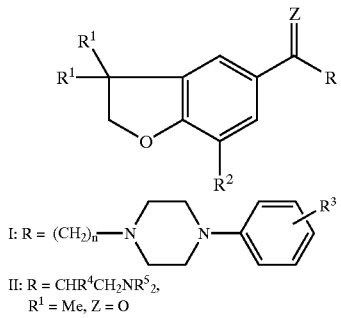

wherein $R^1$=H, Me; $R^2$=H, Cl, Me; $R^3$=H, F, Me, OMe, Cl; n=1, 2, 3; Z=O, OH, H (Compound (I)) or $R^2$=H, Cl; $R^4$=H, Me; $NR^5{}_2$=NMe$_2$, morpholino, or piperidino (Compound (II)).

EP 163537 mentions that a compound of the following general formula has muscle relaxant activity:

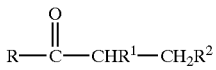

wherein R=4-cycloalkylphenyl, 3,4-methylenedioxyphenyl, 2,3-dihydro-5-benzofuranyl; $R^1$=alkyl, cycloalkyl, cyclopentylmethyl; $R^2$=substituted or unsubstituted pyrrolidino, piperidino, hexahydro-1H-azepin-1-yl, octahydro-1-azocinyl.

It is reported in Chemical Abstracts 91, 211631y, 1979 that a compound of the following formula was synthesized as a derivative of the alkaloid cytisine and that this derivative was found to have anticholinergic activity:

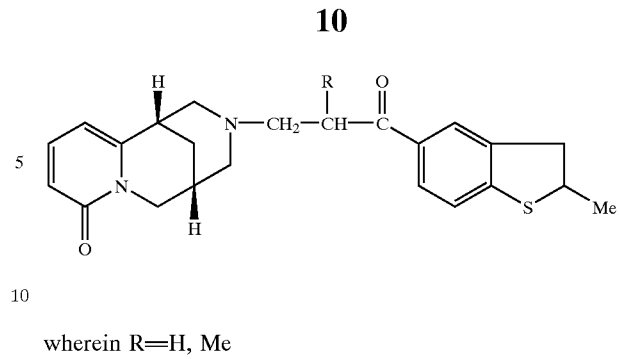

wherein R=H, Me

Helvetica Chimica Acta, 51, 1616, 1968 describes compounds of the following formula (A) and formula (B) as synthetic intermediates of the sympathomimetic alkanolamine of the following formula (C):

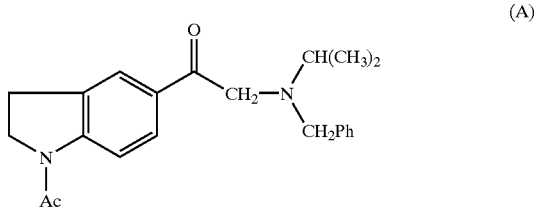

(A)

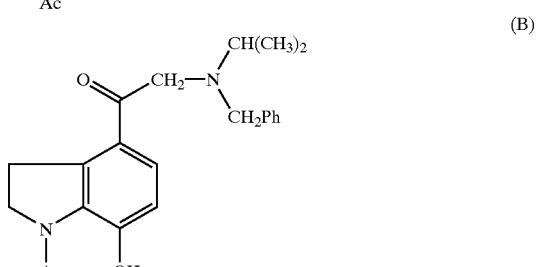

(B)

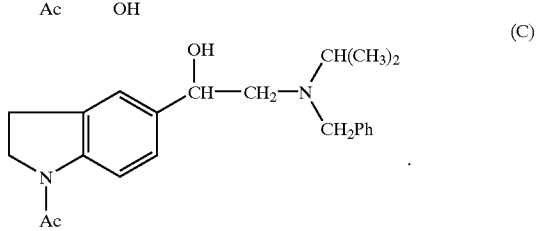

(C)

Japanese Patent Unexamined Publication No. 97952/1977 describes a synthetic intermediate for the production of an aminoalcohol derivative having antihypertensive, anticonvulsant, vasodilative, and sedative activities; said aminoalcohol derivative having the formula:

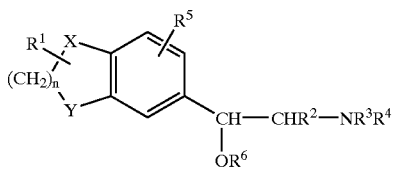

wherein $R^1$=H, alkyl, phenyl; $R^2$=$C_{1-3}$ alkyl; $R^3$=alkenyl, alkinyl, cycloalkyl, alkyl; $R^4$=H, alkyl; $NR^3R^4$=morpholino, pyrrolidino, piperidino; $R^5$=H, $C_{1-3}$ alkyl; $R^6$=H, acyl; n=1 through 3; X=S, O, NH; Y=CH$_2$, S, and said synthetic intermediate being represented by the following formula:

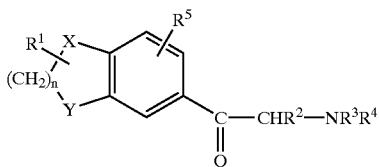

wherein the respective symbols have the same meanings as defined above.

It is disclosed in Japanese Patent Unexamined. Publication No. 7158/1984 that a 1,5-benzodioxepine derivative of the following formula and its acid addition salt have vasodepress or antihypertensive activity:

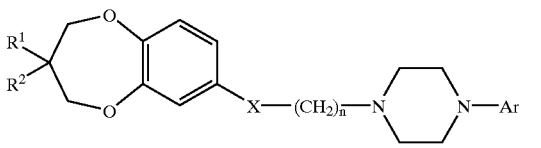

wherein $R^1$ represents hydrogen or $C_{1-3}$ alkyl; $R^2$ represents $C_{1-3}$ alkyl; X represents —CH(OH)— or

Ar represents

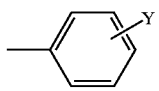

wherein Y represents hydrogen, —OCH$_3$, halogen, or

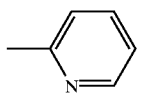

n represents an integer of 1 through 5.

FR-M3635 discloses a compound of the following formula:

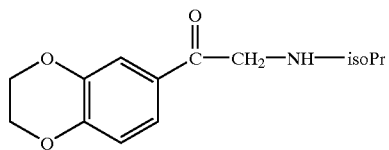

as a synthetic intermediate of the sympathomimetic 1,4-benzodioxane of the formula:

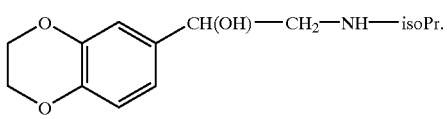

Furthermore, Chemical Abstracts, 67, 54087k (1967), 68, 105121x (1968), 75, 88548s (1971), and 76, 153682t (1972) describe processes for synthesis of 1,4-benzodioxane derivatives of the formula:

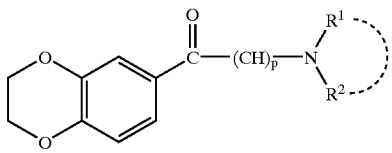

wherein

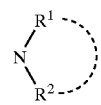

represents an amino group which may be substituted or a cycloamino group which may be substituted; p represents 1 or 2. However, none of those literature contains teachings about the biological activity or pharmacological activity of the compounds.

DISCLOSURE OF INVENTION

The demand exists for development of a prophylactic and/or treating drug for obesity and obesity-associated disease which should have a reduced risk for adverse effects on the central nervous system and could be more universally administered than the known antiobesity compounds.

In view of the above state of the art, the inventors of the present invention explored for new thermogenic and antiobesity substances having no central side effects with due diligence and discovered that, regardless of the kinds of substituent groups that may be present, a structurally unique aminoketone, derivative of the following formula (I):

(I)

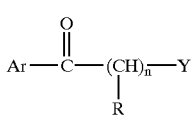

wherein Ar represents a phenyl group which may be substituted and/or condensed; n represents an integer of 1 to 10; R represents hydrogen atom or a hydrocarbon group which may be substituted, which may not be the same in n occurrences; R may be bound to either Ar or a substituent or Ar; Y represents an amino group which may be subsituted or a nitrogen-containing saturated heterocyclic group which may be substituted or its salt, has surprisingly high thermogenesisa accelerating activity, lipolysis accelerating activity, intraadipocellular cAMP concentration-increasing activity, and a prophylactic and treating effect on obesity and obesity-associated diseases. The present invention has been developed on the basis of the above findings.

The present invention, therefore, relates to:

(1) A thermogenic composition comprising a compound of the formula:

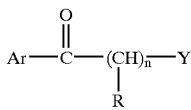

wherein Ar represents an optionally condensed phenyl group which may be substituted; n represents an integer of 1 to 10; R represents a hydrogen atom or a hydrocarbon group which may be substituted, which may not be the same in n occurrences; R may be bound to either Ar or a substituent on Ar; Y represents an amino group which may be substituted or a nitrogen-containing saturated heterocyclic group which may be substituted, or a salt thereof, (2) A thermogenic composition according to (1), wherein Ar represents a group of the formula:

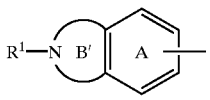

wherein $R^1$ represents a hydrogen atom, a hydrocarbon group which may, be substituted, an acyl group, or a heterocyclic group which may be substituted; ring A represents a benzene ring which may be substituted; ring B' represents a 5- to 9-membered nitrogen-containing heterocyclic ring which may be substituted by oxo, (3) A thermogenic composition according to (1), wherein Ar represents a group of the formula:

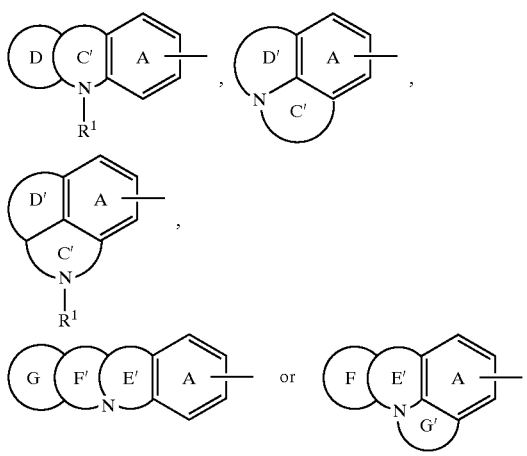

wherein king A represents a benzene ring which may be substituted; ring C', ring D', ring E', king F' and ring G' independently represent a 5- to 9-membered nitrogen-containing heterocyclic king which may be substituted by oxo; ring D, ring F and ring G independently represent a ring which may be substituted; $R^1$ represents a hydrogen atom, a hydrocarbon group which may be substituted, an acyl group, or, a heterocyclic group which may be substituted, (4) The thermogenic composition according to (1), wherein Ar represents a group of the formula:

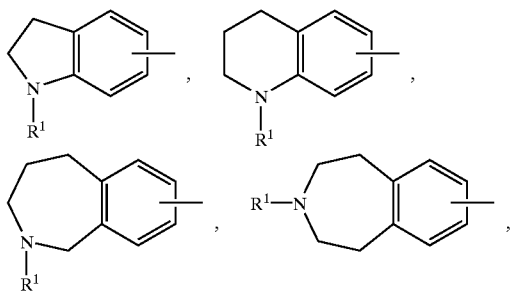

-continued

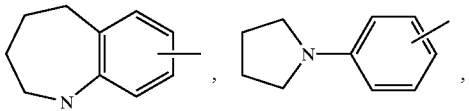

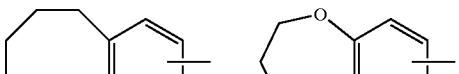

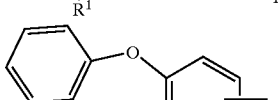

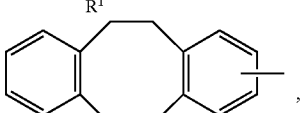

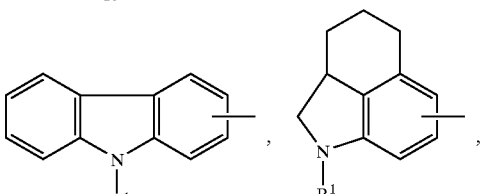

wherein $R^1$ represents a hydrogen atom, a hydrocarbon group which may be substituted, an acyl group, or a heterocyclic group which may be substituted, (5) A thermogenic composition according to (1), wherein R represents a hydrogen atom, (6) A thermogenic composition according to (1), wherein Y represents a group of the formula:

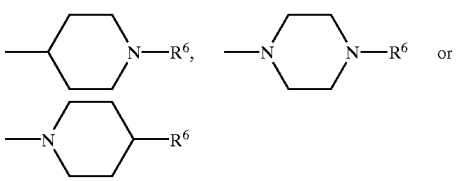

wherein $R^6$ represents (i)a phenyl-$C_{1-6}$ alkyl group which may be substituted by $C_{1-6}$ alkyl which may be substituted, $C_{1-6}$ alkoxy which may be substituted, halogen, nitro, mono- or di-$C_{1-6}$ alkyl-carbamoyloxy, hydroxy, cyano, carboxyl, $C_{1-6}$ alkoxy-carbonyl, carbamoyl, mono-lower alkyl-carbamoyl, di-lower alkyl-carbamoyl, cyclic aminocarbonyl which may be substituted, amino, mono-lower alkylamino, di-lower alkylamino, 5- to 7-membered cyclic amino which may contain 1 to 3 hetero atoms selected from the group consisting of nitrogen, oxygen, and sulfur, in addition to carbon and one nitrogen atom, $C_{1-6}$ alkyl-carbonylamino, phenylsulfonylamino which may be substituted, $C_{1-6}$ alkylsulfonylamino, amidino which may be substituted, ureido which may be substituted, sulfo, or heterocyclic group which may be substituted, (ii) a hydrogen atom, (iii) a $C_{1-6}$ alkyl group which may be substituted by halogen, hydroxy, $C_{16}$ alkoxy, amino, mono- or di-$C_{1-6}$ alkylamino, carboxyl, cyano, heterocyclic group which may be substituted, or $C_{1-6}$ alkoxy-carbonyl, (iv) a $C_{1-6}$ alkyl-carbonyl group which may be substituted by mono- or di-$C_{1-6}$ alkylamino, or $C_{1-6}$ alkoxy-carbonyl, (v) a benzoyl group which may be substituted, (vi) a $C_{1-6}$ alkylsulfonyl group, (vii) an aminocarbonyl group which may be substituted, (viii) a $C_{1-6}$ alkoxy-carbonyl group, (ix) a fluorenyl group which may be substituted, or (x) a naphthyl-$C_{1-6}$alkyl group which may be substituted, (7) A thermogenic composition according to (1), wherein Y represents a 1-benzyl-4-piperidinyl group, a 4-benzyl-1-piperazinyl group or a 4-benzyl-1-piperidinyl group, each benzyl of which may be substituted respectively, (8) A thermogenic composition according to (1), wherein n represents an integer of 1 to 6, (9) A thermogenic composition according to (1), wherein R represents a hydrogen atom, n represents 2, and Y represents a 1-benzyl-4-piperidinyl group,

(10) A thermogenic composition according to (1), comprising a compound of the formula:

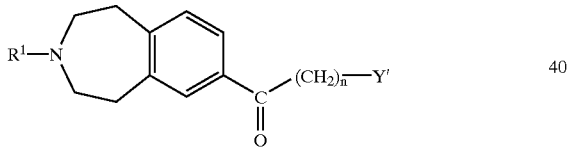

wherein $R^1$ represents a hydrogen atom, a hydrocarbon group which may be substituted, an acyl group, or a heterocyclic group which may be substituted; Y' represents a 4-piperidinyl group in which nitrogen may be substituted; n represents an integer of 3 to 6, or a salt thereof,

(11) A thermogenic composition according to (1), comprising a compound of the formula:


wherein the symbols are as defined in (10), or a salt thereof,

(12) A thermogenic composition according to (1), comprising a compound of the formula:

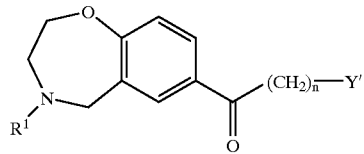

wherein the symbols are As defined in (10), or a salt thereof,

(13) A thermogenic composition according to (1), which, is for an antiobese agent,

(14) A thermogenic composition according to (1), which is for a lipolytic agent,

(15) A thermogenic composition according to (1), which is for a prophylactic and/or treating agent for obesity-associated disease or diabetes,

(16) A compound of the formula:

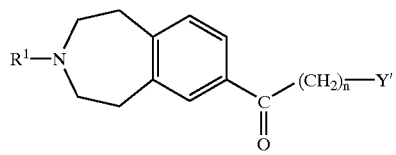

wherein the symbols are as defined in (10), or a salt thereof,

(17) A compound according to (16), wherein the substituent on a hydrocarbon group and a heterocyclic group, defined as $R^1$, is selected from the group consisting of halogen, alkyl which may be substituted, alkoxy which may be substituted, hydroxy, nitro, cyano, carboxyl, $C_{1-6}$ alkoxy-carbonyl, carbamoyl, aminothiocarbonyl, mono-lower alkyl-carbamoyl, di-lower alkyl-carbamoyl, cyclicamino-carbonyl which may be substituted, amino, mono-lower alkyl-amino, di-lower alkyl-amino, 5- to 7-membered cyclic amino-which may contain 1 to 3 hetero atoms selected from the group consisting of nitrogen, oxygen, and sulfur, in addition to carbon and one nitrogen atom, $C_{1-6}$ alkyl-carbonylamino, phenylsulfonylamino which may be substituted, $C_{1-6}$ alkyl-sulfonylamino, amidino which may be substituted, ureido which may be substituted, and heterocyclic group which may be substituted,

(18) A compound of the formula:

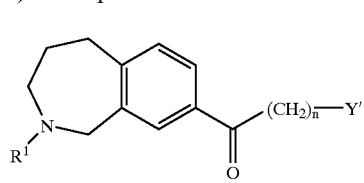

wherein the symbols are as defined in (10), or a salt thereof,

(19) A compound according to (18), wherein the substituent on a hydrocarbon group and a heterocyclic group, defined as $R^1$, is selected from the group consisting of halogen, alkyl which may be substituted, alkoxy which may be substituted, hydroxy, nitro, cyano, carboxyl, $C_{1-6}$ alkoxy-carbonyl, carbamoyl, aminothiocarbonyl, mono-lower alkyl-carbamoyl, di-lower alkyl-carbamoyl, cyclicamino-carbonyl which may be substituted, amino, mono-lower alkyl-amino, di-lower alkyl-amino, 5- to 7-membered cyclic amino which may contain 1 to 3 hetero atoms selected from the group consisting of nitrogen, oxygen, and sulfur, in addition to carbon and one nitrogen atom, $C_{1-6}$ alkyl-carbonylamino, phenylsulfonylamino which may be substituted, $C_{1-6}$ alkyl-sulfonylamino, amidino which may be substituted, ureido which may be substituted, and heterocyclic group which may be substituted,

(20) A compound of the formula:

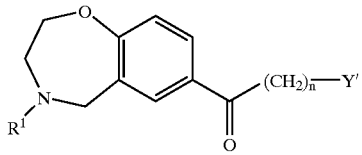

wherein the symbols are as defined in (10),

(21) A compound according to (20), wherein the substituent on a hydrocarbon group and a heterocyclic group, defined as $R^1$, is selected from the group consisting of halogen, alkyl which may be substituted, alkoxy which may be substituted, hydroxy, nitro, cyano, carboxyl, $C_{1-6}$ alkoxy-carbonyl, carbamoyl, aminothiocarbonyl, mono-lower alkyl-carbamoyl, di-lower alkyl-carbamoyl, cyclicamino-carbonyl which may be substituted, amino, mono-lower alkyl-amino, di-lower alkyl-amino, 5- to 7-membered cyclic amino which may contain 1 to 3 hetero atoms selected from the group consisting of nitrogen, oxygen, and sulfur, in addition to carbon and one nitrogen atom, $C_{1-6}$ alkyl-carbonylamino, phenylsulfonylamino which may be substituted, $C_{1-6}$ alkyl-sulfonylamino, amidino which may be substituted, ureido which may be substituted, and heterocyclic group which may be substituted,

(22) A compound according to (16), wherein $R^1$ represents a $C_{1-6}$ alkyl group or a $C_{7-16}$ aralkyl group, each of which may be substituted respectively,

(23) A compound according to (22), wherein the substituent on a $C_{1-6}$ alkyl group or a $C_{7-16}$ aralkyl, group, defined as $R^1$, is selected from the group consisting of halogen, alkyl which may be substituted, alkoxy which may be substituted, hydroxy, nitro, cyano, carboxyl, $C_{1-6}$ alkoxy-carbonyl, carbamoyl, aminothiocarbonyl, mono-lower alkyl-carbamoyl, di-lower alkyl-carbamoyl,cyclicamino-carbonyl which may be substituted, amino, mono-lower alkyl-amino, di-lower alkyl-amino, 5- to 7-membered cyclic amino which may contain 1 to-3 hetero atoms selected from the group consisting of nitrogen, oxygen, and sulfur, in addition to carbon and one nitrogen atom, $C_{1-6}$ alkyl-carbonylamino, phenylsulfonylamino which may be substituted, $C_{1-6}$ alkyl-sulfonylamino, amidino which may be substituted, ureido which may be substituted, and heterocyclic group which may be substituted,

(24) A compound according to (16); wherein $R^1$ represents a phenyl-$C_{1-4}$ alkyl group which may be substituted,

(25) A compound according to (24), wherein the substituent on a phenyl-$C_{1-4}$ alkyl group, defined as $R^1$, is selected from the group consisting of halogen, alkyl which may be substituted, alkoxy which may be substituted, hydroxy, nitro, cyano, carboxyl, $C_{1-6}$ alkoxy-carbonyl, carbamoyl, aminothiocarbonyl, mono-lower alkyl-carbamoyl, di-lower alkyl-carbamoyl, cyclicamino-carbonyl which may be substituted, amino, mono-lower alkylamino, di-lower alkylamino, 5- to 7-membered cyclic amino which may contain 1 to 3 hetero atoms selected from the group consisting of nitrogen, oxygen, and sulfur, in addition to carbon and one nitrogen atom, $C_{1-6}$ alkyl-carbonylamino, phenylsulfonylamino which may be substituted, $C_{1-6}$ alkyl-sulfonylamino, amidino which may be substituted, ureido which may be substituted, and heterocyclic group which may be substituted,

(26) A compound according to (16), wherein $R^1$ represents a benzyl group which may be substituted, the substitutent being selected from the group consisting of $C_{1-4}$ alkyl, trihalogeno-$C_{1-4}$ alkyl, halogen, nitro, cyano, $C_{1-4}$ alkoxy, trihalogeno-$C_{1-4}$ alkoxy, carbamoyl, (4-$C_{1-4}$ alkyl (e.g. methyl, etc.)-1-piperazinyl)carbonyl, aminothiocarbonyl, carboxyl, $C_{1-4}$ alkoxy-carbonyl, $C_{1-4}$ alkoxy-carbonyl-$C_{1-4}$ alkoxy, carboxyl-$C_{1-4}$ alkoxy, $C_{1-4}$ alkoxy-carbonyl-$C_{1-6}$ alkyl, carboxyl-$C_{1-6}$ alkyl, amino, acetylamino, $C_{1-4}$ alkylsulfonylamino, (4-$C_{1-4}$ alkylphenyl)sulfonylamino, ureido, 3-$C_{1-4}$ alkyl-ureido, amidino, dihydrothiazolyl, and dihydroimidazolyl,

(27) A compound according to (16), wherein $R^1$ represents a benzyl group which may be substituted, the substitutent being selected from the group consisting of $C_{1-4}$ alkyl, trihalogeno-$C_{1-4}$ alkyl, halogen, nitro, cyano, carbamoyl, $C_{1-4}$ alkoxycarbonyl, $C_{1-4}$ alkoxycarbonyl-$C_{1-4}$ alkoxy, amino, acetylamino, $C_{1-4}$ alkylsulfonylamino, 3-$C_{1-4}$ alkyl-ureido, amidino and dihydroimidazolyl,

(28) A compound according to (16), wherein Y' represents the formula:

wherein $R^6$ represents (i) a phenyl-$C_{1-6}$ alkyl group which may be substituted, the substitutent being selected from the group consisting of $C_{1-6}$ alkyl which may be substituted, $C_{1-6}$ alkoxy which may be substituted, halogen, nitro, mono- or di-$C_{1-6}$ alkyl-carbamoyloxy, hydroxy, cyano, carboxyl, C-$_{1-6}$ alkoxycarbonyl, carbamoyl, mono-lower alkyl-carbamoyl, di-lower alkyl-carbamoyl, cyclicamino-carbonyl which may be substituted, amino, mono-lower alkylamino, di-lower alkylamino, 5- to 7-membered cyclic amino which may contain 1 to 3 hetero atoms selected from the group consisting of nitrogen, oxygen, and sulfur, in addition to carbon and one nitrogen atom, $C_{1-6}$ alkyl-carbonylamino, phenylsulfonylamino which may be substituted, $C_{1-6}$ alkyl-sulfonylamino, amidino which may be substituted, ureido which may be substituted, or heterocyclic group which may be substituted, (ii) a hydrogen atom, (iii) a $C_{1-6}$ alkyl group which may be substituted, the substitutent being selected from the group consisting of halogen, hydroxy, $C_{1-6}$ alkoxy, amino, mono- or di-$C_{1-6}$ alkylamino, carboxyl, cyano and $C_{1-6}$ alkoxy-carbonyl, or (iv) a $C_{1-6}$ alkyl-carbonyl group which may be substituted by mono- or di-$C_{1-6}$ alkyl-amino, or $C_{1-6}$ alkoxy-carbonyl,

(29) A compound according to (28), wherein $R^6$ represents a benzyl group which may be substituted, the substitutent being selected from the group consisting of $C_{1-4}$ alkyl, trihalogeno-$C_{1-4}$ alkyl, halogen, nitro, cyano, $C_{1-4}$ alkoxy, hydroxy, carbamoyl, (4-$C_{1-4}$ alkylpiperazinyl)carbonyl, morpholinocarbonyl, carboxyl, $C_{1-4}$ alkoxy-carbonyl, $C_{1-4}$ alkoxy-carbonyl-$C_{1-4}$ alkyl, carboxyl-$C_{1-4}$ alkoxy, $C_{1-4}$ alkoxy-carbonyl-$C_{1-6}$ alkyl, carboxyl-$C_{1-6}$ alkyl, amino, acetylamino, $C_{1-4}$ alkylsulfonylamino, (4-$C_{1-4}$ alkyl-phenyl)sulfonylamino, ureido, 3-$C_{1-4}$ alkylureido, amidino, dihydrothiazolyl, and dihydroimidazolyl,

(30) A compound according to (28), wherein $R^6$ represents a benzyl group which may be substituted, the substitutent being selected from the group consisting of $C_{1-4}$ alkyl, trihalogeno-$C_{1-4}$ alkyl, halogen, nitro, hydroxy, carbamoyl, amino, amidino and dihydroimidazolyl,

(31) A compound according to (16), wherein n represents an integer of 3,4 or 5,

(32) 3-(1-acetyl-4-piperidinyl)-1-[3-(phenylmethyl)-2,3,4,5-tetrahydro-1H-3-benzazepin-7-yl]-1-propanone or salts thereof,

(33) A compound according to (16), which is 4-[1-[(2-methylphenyl)methyl]-4-piperidinyl]-1-[3-[(2-methylphenyl)methyl]-2,3,4,5-tetrahydro-1H-3-benzazepin-7-yl]-1-butanone or salts thereof,

(34) A compound according to (16), which is 4-[1-[(3-chlorophenyl)methyl]-4-piperidinyl]-1-[3-[(2-methylphenyl)methyl]-2,3,4,5-tetrahydro-1H-3-benzazepin-7-yl]-1-butanone or salts thereof,

(35) 3-[1-[(2-fluorophenyl)methyl]-4-piperidinyl]-1-[4-(phenylmethyl)-2,3,4,5-tetrahydro-1,4-benzoxazepin-7-yl]-1-propanone or salts thereof,

(36) 1-[4-(phenylmethyl)-2,3,4,5-tetrahydro-1,4-benzoxazepin-7-yl]-3-[1-[(3,4,5-trimethoxyphenyl)methyl]-4-piperidinyl]-1-propanone or salts thereof,

(37) 3-[1-(phenylmethyl)-4-piperidinyl]-1-[2-(phenylmethyl)-2,3,4,5-tetrahydro-1H-2-benzazepin-8-yl]-1-propanone or salt thereof,

(38) A compound according to (18), which is ethyl 2-methyl-2-[3-[[4-[4-[2-[(2-methylphenyl)methyl]-2,3,4,5-tetrahydro-1H-2-benzazepin-8-yl]-4-oxobutyl]-1-piperidinyl]methyl]phenyl]propionate or salt thereof,

(39) A compound according to (16), which is 4-[1-[(2-chlorophenyl)methyl]-4-piperidinyl]-1-[3-[(2-methylphenyl)methyl]-2,3,4,5-tetrahydro-1H-3-benzazepin-7-yl]-1-butanone or salt thereof,

(40) 1-(1-methyl-1,2,3,4-tetrahydroquinolin-7-yl)-3-[1-(phenylmethyl)-4-piperidinyl]-1-propanone or salt thereof,

(41) A method of producing a compound of the formula:

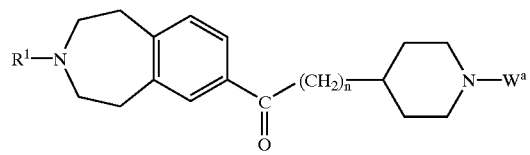

wherein $R^1$ is as defined in (10); n represents an integer of 3 to 6; $W^a$ represents a protective group for the N atom or a hydrogen atom, or a salt thereof, which comprises reacting a compound of the formula:

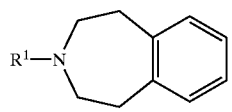

wherein $R^1$ is as defined above, or salt thereof, with a compound of the formula:

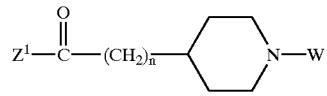

wherein $Z^1$ represents a leaving group; W represents a protective group; n is as defined above, or salt thereof, if necessary, followed by deprotectioning reaction,

(42) A method of producing a compound according to (28), which comprises reacting a compound of the formula:

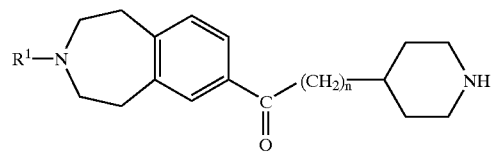

wherein the symbols are as defined in (41), or a salt thereof, with a compound of the formula:

$R^{6a}$—$Z^{1a}$ wherein $R^{6a}$ represents (i)a phenyl-$C_{1-6}$ alkyl group which may be substituted, the substitutent being selected from the group consisting of $C_{1-6}$ alkyl which may be substituted, $C_{1-6}$ alkoxy which may be substituted, halogen, nitro, mono- or di-$C_{1-6}$, alkyl-carbamoyloxy, hydroxy, cyano, carboxyl, $C_{1-6}$ alkoxy-carbonyl, carbamoyl, mono-lower alkyl-carbamoyl, di-lower alkyl-carbamoyl, cyclicamino-carbonyl which may be substituted, amino, mono-lower alkylamino, di-lower alkylamino, 5- to 7-membered cyclic amino which may contain 1 to 3 hetero atoms selected from the group consisting of nitrogen, oxygen, and sulfur, in addition to carbon and one nitrogen atom, $C_{1-6}$ alkyl-carbonylamino, phenylsulfonylamino which may be substituted, $C_{1-6}$ alkyl-sulfonylamino, amidino which may be substituted, ureido which may be substituted, or heterocyclic group which may be substituted, (ii)a $C_{1-6}$ alkyl group which may be substituted, the substitutent being selected from the group consisting of halogen, hydroxy, $C_{1-6}$ alkoxy, amino, mono- or di-$C_{1-6}$ alkylamino carboxyl, cyano and $C_{1-6}$ alkoxy-carbonyl, or (iv)a $C_{1-6}$ alkyl-carbonyl group which may be substituted by mono- or di-$C_{1-6}$ alkyl-amino, or $C_{1-6}$ alkoxy-carbonyl; $Z^{1a}$ represents a leaving group, or salt thereof,

(43) A method of producing a compound of the formula:

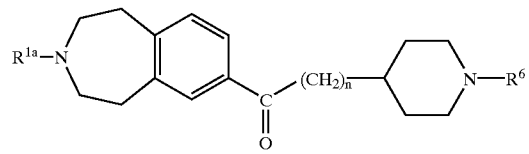

wherein $R^{1a}$ represents a hydrocarbon group which may be substituted, or an acyl group; n is as defined in (41); $R^6$ is as defined in (28), or thereof, which comprises reacting a compound of the formula:

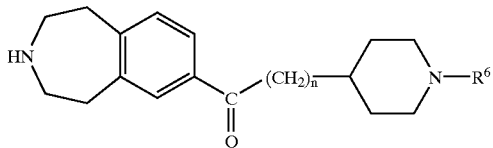

wherein the symbols ate as defined above or salt thereof, with a compound of the formula:

$$R^{1a}-Z^{1a}$$

wherein $R^{1a}$ is as defined above; and $Z^{1a}$ represents a leaving group, or salt thereof,

(44) A pharmaceutical composition which comprises the compound according to (16), and

(45) Use of a compound of the formula:

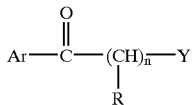

wherein Ar represents an optionally condensed phenyl group which may be substituted; n represents an integer of 1 to 10; R represents a hydrogen atom or a hydrocarbon group which may be substituted, which may not be the same in n occurrences; R may be bound to either Ar or a substituent on Ar; Y represents an amino group which may be substituted or a nitrogen-containing saturated heterocyclic group which may be substituted, or a salt thereof, for preparering a composition for thermogenic, antiobese or lipolytic agent, or prophylactic and/or treating agent for obesity-associated disease or diabetes.

In the above formula, Ar represents "a phenyl group which may be substituted and/or condensed (forming a fused ring system)".

The "substituent" for the "phenyl group which may be substituted and/or condensed" includes but is not limited to (i) a lower alkyl group which may a halogenated, (ii) a halogen atom(e.g. fluorine, chlorine, bromine, iodine etc.), (iii) a lower akylenedioxy group (e.g. a $C_{1-3}$ alkylenedioxy group such as methylenedioxy, ethylenedioxy, etc.), (iv) nitror group, (V) cyano group, (vi) hydroxy group, (vii) a lower alkoxy group which may be halogenated, (viii) a lower cycloalky group (e.g. a $C_{3-6}$ cycloalkyl group such as cyclopropyl, cyclobutyl, cyclopentyl, cyclohexyl, etc.), (ix) a lower alkylthio group which may be halogenated, (x) an amino group, (xi) a mono- lower alkylamino group(e.g. a mono-$C_{1-6}$ alkylamino group such as methylamiano, ethylamino, propylamino, etc.), (xii) a di-lower alkylamino group (e.g. a di-$C_{1-6}$ alkylamino group such as dimethylamino, diethylamino, etc.), (xiii) a 5- to 7-membered cycloamino group which may have 1 to 3 hetero atoms selected from the group consisting of nitrogen atom, oxygen atom, and sulfur atom in addition to one nitrogen atom (e.g. pyrroligdino, piperidino, piperazino, morpholino, thiomorpholino, etc.), (xiv) a lower alkyl-carbonylamino (e.g. a $C_{1-6}$ alkyl-carbonylamino group such as acetylamino, propionylamino, butyrylamino, etc.), (xv) an aminocarbonyloxy group, (xvi) a mono- lower alkylamino-carbonyloxy group (e.g. mono-$C_{1-6}$alkylamino-carbonyloxy such as methylaminocarbonyloxy, ethylaminocarbonyloxy, etc.), (xvii) a di-lower alkylaminocarbonyloxy group (e.g. a di-$C_{1-6}$ alkylamino-carbonyloxy group such as dimethylaminocarbonyloxy, diethylaminocarbonyloxy, etc.), (xviii) a lower alkylsulfonylamino group (e.g. a $C_{1-6}$ alkylsulfonylamino group such as methylsulfonylamino, ethylsulfonylamino, propylsulfonylamino, etc.), (xix) a lower alkoxy-carbonyl group (e.g. a $C_{1-6}$ alkoxy-carbonyl group such as methoxycarbonyl, ethoxycarbonyl, propoxycarbonyl, isobutoxycarbonyl, etc.), (xx) carboxyl group, (xxi) a lower alkyl-carbonyl group (e.g. a $C_{1-6}$ alkyl-carbonyl group such as methylcarbonyl, ethylcarbonyl, butylcarbonyl, etc.), (xxii) a lower cycloalkyl-carbonyl group (a $C_{3-6}$ cycloalkyl-carbonyl group such as cyclopropylcarbonyl, cyclobutylcarbonyl, cyclopentylcarbonyl, cyclohexylcarbonyl, etc.), (xxiii) a carbamoyl group, (xxiv) a mono-lower alkyl-carbamoyl group (e.g. a mono-$C_{1-6}$ alkyl-carbamoyl group such as methylcarbamoyl, ethylcarbamoyl, propylcarbamoyl, butylcarbamoyl, etc.), (xxv) a di-lower alkyl-carbamoyl group (e.g. a di-$C_{1-6}$ alkyl-carbamoyl group such as diethylcarbamoyl, dibutylcarbamoyl, etc.), (xxvi) a lower alkylsulfonyl group (e.g. a $C_{1-6}$ alkylsulfonyl group such as methylsulfonyl, ethylsulfonyl, propylsulfonyl, etc.), (xxvii) a lower cycloalkylsulfonyl group (e.g. $C_{3-6}$ cycloalkylsulfonyl such as cyclopentylsulfonyl, cyclohexylsulfonyl, etc.), (xxviii) a phenyl group, (xxix) a naphthyl group, (xxx) a monophenyl-lower alkyl group (e.g. a mono-phenyl-$C_{1-6}$ alkyl group such as benzyl, phenylethyl, etc.), (xxxi) a diphenyl-lower alkyl group (e.g. a diphenyl-$C_{1-6}$ alkyl group such as diphenylmethyl, diphenylethyl, etc.), (xxxii) a monophenyl-lower alkyl-carbonyloxy group (e.g. a monophenyl-$C_{1-6}$ alkyl-carbonyloxy group such as phenylmethylcarbonyloxy, phenylethylcarbonyloxy, etc.), (xxxiii) a diphenyl-lower alkyl-carbonyloxy group (e.g. a diphenyl-$C_{1-6}$ alkyl-carbonyloxy group such as diphenylmethylcarbonyloxy, diphenylethylcarbonyloxy, etc.), (xxxiv) a phenoxy group, (xxxv) a monophenyl-lower alkyl-carbonyl group (e.g. a monophenyl-$C_6$ alkyl-carbonyl group such as phenylmethylcarbonyl, phenylethylcarbonyl, etc.), (xxxvi) a diphenyl-lower alkyl-carbonyl group (e.g. a diphenyl-$C_{1-6}$ alkyl-carbonyl group such as diphenylmethylcarbonyl, diphenylethylcarbonyl, etc.), (xxxvii) a benzoyl group, (xxxviii) a phenoxycarbonyl group, (xxxix) a phenyl-lower alkyl-carbamoyl group (e.g. a phenyl-$C_{1-6}$ alkyl-carbamoyl group such as phenylmethylcarbamoyl, phenylethylcarbamoyl, etc.), (xxxx) a phenylcarbamoyl group, (xxxxi) a phenyl-lower alkyl-carbonylamino group (e.g. a phenyl-$C_{1-6}$ alkyl-carbonylamino group such as phenyl-methylcarbonylamino, phenylethylcarbonylamino, etc.), (xxxxii) a phenyl-lower alkylamino group (e.g. a phenyl-$C_{1-6}$ alkylamino group such as phenyl-methylamino, phenyl-ethylamino, etc.), (xxxxiii) a phenyl-lower alkylsulfonyl group (e.g. a phenyl-$C_{1-6}$ alkyl-sulfonyl group such as phenylmethylsulfonyl, phenylethylsulfonyl, etc.), (xxxxiv) a phenylsulfonyl group (xxxxv) a phenyl-lower alkyl-sulfinyl group (e.g. a phenyl-$C_{1-6}$ alkylsulfinyl group such as phenylmethylsulfinyl, phenylethyisulfinyl, etc.), (xxxxvi) a phenyl-lower alkylsulfonylamino group (e.g. a phenyl-$C_{1-6}$ alkylsulfonylamino group such as phenylmethylsulfonylamino, phenylethylsulfonylamino, etc.), and (xxxxvii) a phenylsulfonylamino group (the (xxviii) a phenyl group, (xxix) a naphthyl group, (xxx) a monophenyl-lower alkyl group, (xxxi) a diphenyl-lower alkyl group, (xxxii) a monophenyl-lower alkyl-carbonyloxy group, (xxxiii) a diphenyl-lower alkyl-carbonyloxy group, (xxxiv) a phenoxy group, (xxxv) a monophenyl-lower alkyl-carbonyl group, (xxxvi) a diphenyl-lower alkyl-carbonyl group, (xxxvii) a benzoyl group, (xxxviii) a phenoxycarbonyl group, (xxxix) a phenyl-lower alkyl-carbamoyl group, (xxxx) a phenylcarbamoyl group, (xxxxi) a phenyl-lower alkyl-carbonylamino group, (xxxxii) a phenyl-lower alkyl-amino group, (xxxxiii) a phenyl-lower alkyl-sulfonyl group, (xxxxiv) a phenylsulfonyl group, (xxxxv) a phenyl-lower alkyl-sulfinyl group, (xxxxvi) a phenyl-lower alkyl-sulfonylamino group and (xxxxvii) a phenylsulfonylamino group may in turn have 1 to 4 substituent groups selected from the group consisting of, for example, lower alkyl (e.g. $C_{1-6}$ alkyl such as, methyl, ethyl, propyl, isopropyl, butyl, sec-butyl, tert-butyl, pentyl, hexyl, etc.), lower alkoxy (e.g. $C_{1-6}$ alkoxy such as methoxy, ethoxy, propoxy, isopopoxy, n-butoxy, isobutoxy, sec-butoxy, tert-butoxy, etc.), halogen (e.g. chlorine, bromine, iodine, etc.), hydroxy, benzyloxy, amino, mono-lower alkyl-amino (e.g. mono-$C_{1-6}$ alkylamino such as methylamino, ethylamino, propylamino, etc.), di-lower alkyl-amino (e.g. di-$C_{1-6}$ alkylamino such as dimethylamino, diethylamino, etc.), nitro, lower alkyl-carbonyl (e.g. $C_{1-6}$ alkyl-carbonyl such as methylcarbonyl, ethylcarbonyl, butylcarbonyl, etc.), and benzoyl), among others.

The above-mentioned "lower alkyl group which may be halogenated" includes a lower alkyl group (e.g. a $C_{1-6}$ alkyl group such as methyl, ethyl, propyl, isopropyl, butyl, sec-butyl, tert-butyl, pentyl, hexyl, etc.) optionally having 1 to 3 halogen atoms (e.g. chlorine, bromine, iodine). Specifically, methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, butyl, 4,4,4-trifluorobutyl, isobutyl, sec-butyl, tert-butyl, pentyl, isopentyl, neopefntyl, 5,5,5-trifluoropentyl, hekyl, 6,6,6-trifluorohexyl, etc. can be mentioned.

The above-mentioned "lower alkoxy group which may be halogenated" includes but is not limited to a lower, alkoxy group (e.g. a $C_{1-6}$ alkoxy group such as methoxy, ethoxy, propoxy, isopropoxy, n-butoxy, isobutoxy, sec-butoxy, tert-butoxy, etc.) optionally having 1 to 3 halogen atoms (e.g. chlorine, bromine, iodine). Specifically, methoxy, difluoromethoxy, trifluoromethoxy, ethoxy, 2,2,2-trifluoroethoxy, n-propoxy, isopropoxy, n-butoxy, 4,4,4-trifluorobutoxy, isobutoxy, sec-butoxy, pentyloxy, hexyloxy, etc. can be mentioned.

The above-mentioned "lower alkylthio group which may be halogenated" includes but is not limited to a lower alkkylthio group (e.g. a $C_{1-6}$ alkylthio group such as methylthio, ethylthio, n-propylthio, isopropylthio, n-butylthio, isobutylthio, sec-butylthio, tert-butylthio, etc.) optionally having 1 to 3 halogen atoms (chlorine, bromine, iodine). Specifically, methylthio, difluoromethylthio, trifluoromethylthio, ethylthio, n-propylthio, isopropylthio, n-butylthio, 4,4,4-trifluorobutylthio, isobutylthio, sec-butylthio, tert-butylthio, penthylthio, hexylthio, etc. can be mentioned.

The preferred "substituent" for the "phenyl group which may be substituted and/or condensed" includes (i) an amino group, (ii) a mono-lower alkylamino group (e.g. a mono-$C_{1-6}$ alkylamino group such as methylamino, ethylamino, propylamino, etc.), (iii) a di-lower alkylamino group (e.g. a di-$C_{1-6}$ alkylamino group such as dimethylamino, diethylamino, etc.)i (iv) a 5- to 7-membered cycloamino group which may have 1 to 3 hetero-atoms selected from the group consisting of nitrogen, oxygen, and sulfur in addition to one nitrogen atom (e.g. pyrrolidino, piperidino, piperazino, morpholino, thiomorpholino, etc.), (v) a lower alkyl-carbonylamino group (e.g. a $C_{1-6}$ alkyl-carbonylamino group such as acetylamino, propionylamino, butyrylamino, etc.), (vi) an aminocarbonyloxy group, (vii) a mono-lower alkylamino-carbonyloxy group (e.g. a mono-$C_{1-6}$ alkylamino-carbonyloxy group such as methylaminocarbonyloxy, ethylaminocarbonyloxy, etc.), (viii) a di-lower alkylamino-carbonyloxy group (e.g. a di-$C_{1-6}$ alkylamino-carbonyloxy group such as dimethylaminocarbonyloxy, diethylaminocarbonyloxy, etc.), (ix) a lower alkylsulfonylamino group (e.g. a $C_{1-6}$ alkylsulfonylamino group such as methylsulfonylamino, ethylsulfonylamino, propylsulfonylamino, etc.), (x) a phenyl-lower alkylamino group (e.g. a phenyl-$C_{1-6}$ alkylamino group such as phenylmetlhylamino, phenylethylamino, etc.), (xi) a phenyl-lower alkylsulfonylamino group (e.g. a phenyl-$C_{1-6}$ alkylsulfonylamino group such as phenylmethylsulfonylamino, phenylethylsulfonylamino, etc.), (xii) a phenylsulfonylamino group, (xiii) a halogen atom (e.g. fluorine, chlorine), (xiv) a lower alkyl group which may be halogenated (e.g. methyl, ethyl, isopropyl, tert-butyl, trifluoromethyl, etc.), and (xv) a lower akloxy group which may be halogenated (e.g. methoxy, ethoxy, isopropoxy, tert-butoxy, trifluoromethoxy, etc.). Particularly preferred is a 5- to 7-membered cycloamino group optionally having 1 to 3 hetero atoms selected from the group consisting of nitrogen, oxygen, and sulfur in addition to one nitrogen atom (e.g. pyrrolidino, piperidino, piperazino, morpholino, or thiomorpholino etc.).

The manner of condensation of the "phenyl group" of "phenyl group which may be substituted and/or condensed" includes but is not limited to:

(1) fusion to a monocyclic hetero ring which may be substituted,
(2) fusion to a bicyclic hetero system which may be substituted or to two similar or dissimilar monocyclic rings (at least one of the two rings is a monocyclic hetero ring), and
(3) fusion to a tricyclic hetero ring which may be substituted.

The group formed as the "phenyl group" of the "phenyl group which may be substituted and/or condensed" is fused to a monocyclic hetero ring includes but is not limited to the group of the formula:

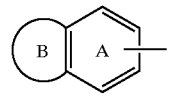

wherein ring B represents a hetero ring which may be substituted; ring A represents a benzene ring which may be substituted.

The substituent for ring A may be the same as the "substituent" for the "phenyl group which may be substituted and/or condensed".

The "hetero ring" of the "hetero ring which may be substituted", for ring B includes but is not limited to 4- to 14-membered rings, preferably 5- to 9-membered rings, which may be aromatic or nonaromatic. The hetero atom, which may be a nitrogen atom, an oxygen atom, and/or a sulfur atom, may range from 1 to 3 or 4. Thus, for example, pyridine, pyrazine, pyrimidine, imidazole, furan, thiophene, dihydropyridine, diazepine, oxazepine, pyrrolidine, piperidine, hexamethyleneimine, heptamethyleneimine, tetrahydrofuran, piperazine, homopiperazine, tetrahydrooxazepine, morpholine, thiomorpholinre, pyyrole, pyrazole, 1,2,3-triazole, oxazole, oxazoline, thiazole, thiazoline, isoxazole, imidazoline, etc. can be mentioned. Particularly preferred are 5- to 9-membered nonaromatic hetero rings containing one hetero atom or two similar or dissimilar hetero atoms (e.g. pyrrolidine, piperidine, hexamethyleneimine, heptamethyleneimine, tetrahydrofuran, piperazine, homopiperazine, tetrahydrooxazepine, morpholine, thiomorpholine, etc.). In particular, nonaromatic hetero rings containing one hetero atom selected from the group consisting a nitrogen atom, an oxygen atom, and a sulfur atom and nonaromatic nitrogen-containing hetero rings containing one hetero atom selected from the group consisting of a nitrogen atom, an oxygen atom, and a sulfur atom in addition to one nitrogen atom can be used with advantage.

The "substituent" for the "hetero ring which may be substituted" for ring B may be situated on any ring carbon atom of ring B. The substituent which may thus be present on a ring carbon atom of ring B may range from 1 to 5 in number and can be selected from the group consisting of (i) halogen (e.g. fluorine, chlorine, bromine, iodine), (ii) nitro, (iii) cyano, (iv) oxo, (v) hydroxy, (vi) lower alkyl (e.g. $C_{1-6}$ alkyl such as methyl, ethyl, propyl, isopropyl, butyl, isobutyl, tert-butyl, sec-butyl, etc.), (vii) lower alkoxy (e.g. $C_{1-6}$ alkoxy such as methoxy, ethoxy, n-propyloxy, i-propyloxy, n-butyloxy, etc.), (viii) lower alkylthio (e.g. $C_{1-6}$ alkylthio such as methylthio, ethylthio, propylthio, etc.), (ix) amino, (x) mono-lower alkylamino (e.g. mono-$C_{1-6}$ alkylamino such as methylamino, ethylamino, propylamino, etc.), (xi) di-lower alkylamino (e.g. di-$C_{1-6}$ alkylamino such as dimethylamino, diethylamino, etc.), (xii) 5- to 7-membered cycloamino which may have 1 to 3 hetero-atoms selected from the group consisting of nitrogen, oxygen, and sulfur in addition to carbon and one nitrogen atom (e.g. pyrrolidino, piperidino, piperazino, morpholino, thiomorpholino, etc.), (xiii) lower alkyl-carbonylamino (e.g. $C_{1-6}$ alkyl-carbonylamino such as acetylamino, propionylamino, butyrylamino, etc.), (xiv) lower alkylsulfonylamino (e.g. $C_{1-6}$ alkylsulfonylamino such as methylsulfonylamino, ethylsulfonylamino, etc.), (xv) lower alkoxy-carbonyl (e.g. $C_{1-6}$ alkoxy-carbonyl such as methoxycarbonyl, ethoxycarbonyl, propoxycarbonyl, etc.), (xvi) carboxyl, (xvii) lower alkyl-carbonyl (e.g $C_{1-6}$ alkyl-carbonyl such as methylcarbonyl, ethylcarbonyl, propylcarbonyl, etc.), (xviii) carbamoyl, (xix) mono-lower alkylcarbamoyl (e.g. mono-$C_{1-6}$ alkylcarbamoyl such as methylcarbamoyl, ethylcarbamoyl, etc.), (xx) di-lower alkylcarbamoyl (e.g. di-$C_{1-6}$ alkyl-carbamoyl such as dimethylcarbamoyl, diethylcarbamoyl, etc.), (xxi) lower alkylsulfonyl (e.g. $C_{1-6}$ alkylsulfonyl such as methylsulfonyl, ethylsulfonyl, propylsulfonyl, etc.).

Particularly preferred are oxo and lower alkyl (e.g. $C_{1-6}$ alkyl such as methyl, ethyl, propyl, isopropyl, butyl, isobutyl, tert-butyl, sec-butyl, etc.), oxo being chosen in many instances.

When ring B has a nitrogen atom as a ring member, a substituent may be present on a nitrogen atom. Thus, ring B may have >N—$R^1$, wherein $R^1$ represents hydrogen atom, a hydrocarbon group which may be substituted, an acyl group, or a heterocyclic group which may be substituted.

The "hydrocarbon group" of the "hydrocarbon group which may be substituted for $R^1$ is the group available upon elimination of one hydrogen atom from a hydrocarbon compound, including acyclic (linear) or cyclic hydrocarbon groups such as alkyl, alkenyl, alkinyl, cycloalkyl, aryl, and aralkyl groups. Preferred among such hydrocarbon groups are $C_{1-16}$ hydrocarbon groups, which may be acyclic, cyclic, or acyclic-cyclic.

The acyclic and cyclic hydrocarbon groups mentioned above include (1) straight-chain or branched lower alkyl groups (e.g. $C_{1-6}$ alkyl such as methyl, ethyl, propyl, isopropyl, butyl, isobutyl, tert-butyl, sec-butyl, pentyl, hexyl, etc.), (2) straight-chain or branched lower alkenyl groups (e.g. $C_{2-6}$ alkenyl such as vinyl, allyl, isopropenyl, butenyl, isobutenyl, sec-butenyl, etc.), (3) straight-chain or branched lower alkynyl groups (e.g. $C_{2-6}$ alkynyl such as propargyl, ethynyl, butynyl, 1-hexynyl, etc.), (4) monocyclic lower cycloalkyl groups (e.g. monocyclic $C_{3-6}$ cycloalkyl such as cyclopropyl, cyclobutyl, cyclopentyl, cyclohexyl, etc.), (5) bridged cyclic saturated lower hydrocarbon groups (e.g. bridged cyclic saturated $C_{8-14}$ hydrocarbon groups such as bicyclo[3.2.1]oct-2-yl, bicyclo[3.3.1]non-2-yl, adamantan-1-yl, etc.), and (6) aryl groups (e.g. $C_{6-14}$ aryl such as phenyl, 1-naphthyl, 2-naphthyl, biphenyl, 2-indenyl, 2-anthryl, etc.; preferably, phenyl).

The preferred acyclic-cyclic hydrocarbon group mentioned above includes (1) lower aralkyl groups (e.g. $C_{7-16}$ aralkyl groups such as phenyl-$C_{1-10}$ alkyl (e.g. benzyl, phenylethyl, phenylpropyl, phenylbutyl, phenylpentyl, phenylhexyl, etc.), naphthyl-$C_{1-6}$ alkyl (e.g. a-naphthylmethyl etc.), diphenyl-$C_{1-3}$ alkyl (e.g. diphenylmethyl, diphenylethyl, etc.), among others), (2) arylalkenyl groups (e.g. $C_{6-14}$ aryl-$C_{2-12}$ alkenyl groups such as phenyl-$C_{2-12}$ alkenyl (e.g. styryl, cinnamyl, 4-phenyl-2-butenyl, 4-phenyl-3-butenyl, etc.) among others), (3) aryl-$C_{2-12}$ alkynyl groups (e.g. $C_{6-14}$ aryl-$C_{2-12}$ alkynyl groups such as phenyl-$C_{2-12}$ alkynyl (e.g. phenylethynyl, 3-phenyl-2-propynyl, 3-phenyl-1-propynyl, etc.) among others), (4) lower cycloalkyl-lower alkyl groups (e.g. $C_{3-7}$ cycloalkyl-$C_{1-6}$ alkyl groups such as cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropylbutyl, cyclopropylbutyl, cyclobutylbutyl, cyclopentylbutyl, cyclohexylbutyl, cycloheptylbutyl, cyclopropylpentyl, cyclobutylpentyl, cyclopentylpentyl, cyclohexylpentyl, cycloheptylpentyl, cyclopropylhexyl, cyclobutylhexyl, cyclopentylhexyl, cyclohexylhexyl, etc.), (5) aryl-aryl groups (e.g. biphenyl etc.), or (6) aryl-aryl-$C_{1-10}$ alkyl groups (e.g. biphenylmethyl, biphenylethyl, etc.).

The preferred "hydrocarbon group" for the "hydrocarbon group which may be substituted" for $R^1$ includes but is not limited to:

(1) straight-chain, branched or cyclic alkyl group, preferably, straight-chain or branched $C_{1-6}$ alkyl groups (e.g. $C_{1-6}$ methyl, ethyl, propyl, isopropyl, butyl, isobutyl, tert-butyl, sec-butyl, pentyl, hexyl, etc.), cyclic $C_{3-8}$ alkyl group (e.g. cyclopropyl, cyclobutyl, cyclopentyl, cyclohexyl, etc.), straight-chain-branched-cyclic $C_{4-12}$ alkyl group (e.g. cyclopropylmethyl, cyclopentylmethyl, cyclohexylmethyl, cyclohexylethyl (4-methylhexyl)methyl etc.), and (2) $C_{7-16}$ aralkyl groups (e.g. phenyl-$C_{1-10}$ alkyl (e.g. benzyl, phenylethyl, phenylpropyl, phenylbutyl, phenylpentyl, phenylhexyl, etc.), naphthyl-$C_{1-6}$ alkyl (e.g. a-naphthylmethly etc.), diphenyl-$C_{1-3}$ alkyl (e.g. diphenylmethyl, diphenylethyl, etc.), among others); the still more preferred are $C_{7-10}$ aralkyl groups (e.g. phenyl-$C_{1-4}$ alkyl such as benzyl, phenylethyl, phenylpropyl, etc.).

The "hydrocarbon group" for $R^1$ may be substituted and the substituent that may be present includes groups which are generally used as substituent groups for hydrocarbon groups. The substituent includes but is not limited to: (i) halogen (e.g. fluorine, chlorine, bromine, iodine), (ii) nitro, (iii) cyano, (iv) oxo, (v) hydroxy, (vi) lower alkyl (e.g. $C_{1-6}$ alkyl such as methyl, ethyl, propyl, isopropyl, butyl, isobutyl, tert-butyl, sec-butyl, etc.) which may be substituted by phenyl, (vii) lower alkoxy (e.g. $C_{1-6}$ alkoxy such as methoxy, ethoxy, n-propyloxy, i-propyloxy, n-butyloxy, etc.) which may be substituted by phenyl, (viii) lower alkylthio (e.g. $C_{1-6}$ alkylthio such as methylthio, ethylthio, propylthio, etc.) which may be substituted by phenyl, (ix) amino, (x) mono-lower alkylamino (e.g. mono-$C_{1-6}$ alkylamino such as methylamino, ethylamino, propylamino, etc.), (xi) di-lower alkylamino (e.g. di-$C_{1-6}$ alkylamino such as dimethylamino, diethylamino, etc.), (xii) 5- to 7-membered cycloamino which may have 1 to 3 hetero atoms selected from the group consisting of nitrogen, oxygen, and sulfur in addition to carbon and one nitrogen atom (e.g. pyrrolidino, piperidino, piperazino, morpholino, thiomorpholino, etc.), (xiii) lower alkyl-carbonylamino (e.g. $C_{1-6}$-alkyl-carbonylamino such as acetylamino, propionylamino, butyrylamino, etc.), (xiv) lower alkylsulfonylamino (e.g. $C_{1-6}$ alkylsulfonylamino such as methylsulfonylamino, ethylsulfonylamino, etc.), (xv) lower alkoxy-carbonyl (e.g. $C_{1-6}$ alkoxy-carbonyl such as methoxycarbonyl, ethoxycarbonyl, propoxycarbonyl, etc.), (xvi) carboxyl, (xvii) lower alkyl-carbonyl (e.g. $C_{1-6}$ alkyl-carbonyl such as methylcarbonyl, ethylcarbonyl, propylcarbonyl, xetc.), (xviii) carbamoyl, (xix) mono-lower alkyl-carbamoyl (e.g. mono-$C_{1-6}$ alkyl-carbamoyl such as methylcarbamoyl, ethylcarbamoyl, etc.), (xx) di-lower alkyl-carbamoyl (e.g. di-$C_{1-6}$ alkyl-carbamoyl such as dimethylcarbamoyl, diethylcarbamoyl, etc.), (xxi) lower alkylsulfonyl (e.g. $C_{1-6}$ alkylsulfonyl such as methylsulfonyl, ethylsulfonyl, propylsulfonyl, etc.), (xxii) lower alkoxy-carbonyl-loweralkyl (e.g. $C_{1-6}$ alkyl-carbonyl-$C_{1-6}$ alkyl such as methoxycarbonylmethyl, ethoxycarbonylmethyl, tert-butoxycarbonylmethyt, methoxycarbonylethyl, methoxycarbonylmethyl, methoxycarbbnyl(dimethyl)methyl, ethoxycarbonyl (dimethyl)methyl, tert-butoxycarbonyl(dimethyl)methyl, etc.), (xxiii) carboxy-lower alkyl (e.g. carboxy-$C_{1-6}$ alkyl such as carboxymethyl, carboxyethyl, carboxy(dimethyl) methyl, etc.), (xxiv) heterocyclic group which may be substituted, (xxv) alkyl which may be substituted, (xxvi) alkoxy which may be substituted, (xxvii) ureido which may be substituted (e.g. ureido, 3-methylureido, 3-ethylureido, 3-phenylureido, 3-(4-fluorophenyl)ureido, 3-(2-methylphenyl)ureido, 3-(4-methoxyphenyl)ureido, 3-(2,4-difluorophenyl)ureido, 3-(3,5-bis(trifluoromethyl)phenyl) ureido, 3-benzylureido, 3-(1-naphtyl)ureido, 3-(2-biphenyl) ureido, etc.), (xxviii) thioureido which may be substituted (e.g. thioureido, 3-methylthioureido, 3-ethylthioureido, 3-phenylthioureido, 3-(4-fluorophenyl)thioureido, 3-(4-methyiphenyl)thioureido, 3-(4-methoxyphenyl) thioureido, 3-(2,4-dichlorophenyl)thioureido, 3-benzylthioureido, 3-(1-naphtyl)thioureido, etc.), (xxix) amidino which may be substituted (e.g. amidino, $N^1$-methylamidino, $N^1$-ethylamidino, $N^1$-phenylamidino, $N^1,N^1$-dimethylamidino, $N^1,N^2$-dimethylamidino, $N^1$-methyl-,$N^1$-ethylamidino, $N^1,N^1$-diethylamidino, $N^1$-methyl-,$N^1$-phenylamidino, $N^1,N^1$-di(4-nitrophenyl) amidino, etc.), (xxx) guanidino which may be substituted (e.g. guanidino, 3-mrthylguanidino, 3,3-dimethylguanidino, 3,3-diethylguanidino, etc.), (xxxi) cyclic aminocarbonyl which may be-substituted (e.g. pyrrolidinocarbonyl, piperidinocarpbonyl (4-methylpiperidino)carbonyl, (4-phenylpiperidino)carbonyl, (4-benzylpiperidino) carbonyl, (4-benzoylpiperidino)carbonyl, (4-(4-fluorobenzoyl)piperidino)carbonyl, (4-methylpiperazino) carbonyl, (4-phenylpiperazino)carbonyl, (4-(4-nitrophenyl )piperazino)carbonyl, (4-benzylpiperazino)carbonyl, morpholinocarbonyl, thiomorpholinocarbonyl, etc.), (xxxii) aminothiocarbonyl which may be substituted (e.g. aminothiocarbonyl, methylaminothiocarbonyl, dimethylaminothiocarbonyl, etc.), (xxxiii) aminosulfonyl which may be substituted (e.g. aminosulfonyl, methylaminosulfonyl, dimethylaminosulfonyl, etc.), (xxxiv) phenylsulfonylamino which may be substituted (e.g. phenylsulfonylamino, (4-methylphenyl)sulfonylamino, (4-chlorophenyl)sulfonylamino, (2,5-dichlrophenylsulfonylamino, (4-methoxyphenyl) sulfonylamino, (4-acetylaminophenyl)sulfonylamino, (4-nitrophenyl)phenylsulfonylamino, etc.), (xxxv) sulfo, (xxxvi) sulfino, (xxxvii) sulfeno, (xxxviii) $C_{1-6}$ alkyl-sulfo (e.g. methylsulfo, ethylsulfo, propylsulfo, etc.), (xxxix) $C_{1-6}$ alkyl-sulfino (e.g. methylsulfino, ethylsulfino, propylsulfino, etc.), (xxxx) $C_{1-6}$ alkyl-sulfeno (e.g. methylsulfeno, ethylsulfeno, propylsulfeno, etc.), (xxxxi) phosphono, (xxxxii) di-$C_{1-6}$ alkoxy-phosphoryl (e.g. dimethoxyphosphoryl, diethoxyphosphoryl, dipropoxyphosphoryl, etc). 1 to 5 (preferably 1 to 3) groups selected from among the above-mentioned groups may be present as substituents.

Preferably, the "substituent" for the "hydrocarbon group which may be substituted" includes but is not limited to: halogen, alkyl which may be substituted, alkoxy which may be substituted, hydroxy, nitro, cyano, carboxyl, $C_{1-6}$ alkoxy-carbonyl, carbamoyl, aminothiocarbonyl, mono-lower alkyl-carbamoyl, di-lower alkyl-carbamoyl, cyclic aminocarbonyl which may be substituted, amino, mono-lower alkylamino, di-lower alkylamino,5- to 7-membered cycloamino which may have 1 to 3 hetero atoms selected from the group consisting of nitrogen, oxygen, and sulfur in addition to carbon and one nitrogen atom, $C_{1-6}$ alkyl-carbonylamino, phenylsulfonylamino which may be substituted, $C_{1-6}$ alkylsulfonylamino, amidino which may be substituted, ureido which may be substituted, heterocyclic group which may be substituted.

The "heterocyclic group" of the "heterocyclic group which may be substituted" includes those available upon elimination of one hydrogen atom from a monocyclic heteroring, bicyclic heteroring, polycyclic hetero ring such as tricyclic heteroring, tetracyclic heteroring; and so on. The heteroring may be aromatic or nonaromatic. 1 to 6 hetero atoms such as nitrogen, oxygen, sulfur, etc. can be used.

Specifically, the group, available upon elimination of one hydrogen atom from the "hetero ring" of the "hetero ring which may be substituted" as mentioned for ring B. In addition, the group available upon elimination of one hydrogen atom from the monocyclic heteroring such as triazole, thiadiazolel, oxadiazole, oxathiadiazole, triazine, tetrazole, and so on, the bicyclic hetero ring such as indole, dihydroindole, isoindole, dihydroisoindole, benztofuran, dihydrobenzofuran, benzimidazole, benzoxazole, benzisoxazole, benzothiazole, indazole, quinoline, tetrahydroquinoline, isoquinoline, tetrahydroisoquinoline, tetrahydro-1H-1-benzazepine, tetrahydro-1H-2-benzazepine, tetrahydro-1H-3-benzazepine, tetrahydrobenzoxazepine, quinazoline, tetrafiydroquinazoline, quinoxaline, tetrahydroquinoxaline, benzodioxan, benzodioxole, benzothiazine imidazopyridine, and so on, polycyclic heteroring (e.g. tricyclic heteroring, tetracyclic heteroring such as acridine, tetrahydroacridine, pyrroloquinoline, pyrroloindole, cyclopentoindole, isoindolobenzazapine, etc.).

The "heterocyclic group" of the "heterocyclic group which may be substituted" is preferably the group available upon elimination of one hydrogen atom from the monocyclic or bicyclic heteroring as mentioned above.

The "substituent" for the above "heterocyclic group which may be substituted" includes the groups mentioned for the "substituent" on the "hetero ring which may be substituted" for ring B (excluding the above "heterocyclic group which may be substituted").

As the "substituent" for the "alkyl which may be substituted" and the "alkoxy which may be substituted", for example, (i) to (xxiv) and (xxvii) to (xxxxii) of the "substituent" for the "hydrocarbon group which may be substituted " as represented by $R^1$, can be used.

As the "substituent" for the "ureido which may be substituted", "thioureido which may be substituted", "amidino which may be substituted", "guanidino which may be substituted", "aminothiocarbonyl which may be substituted", "aminosulfonyl which may be substituted" and the "phenylsulfonylamino which may be substituted", for example, (i) to (xxvi) and (xxxv) to (xxxxii) of the "substituent" for the "hydrocarbon group which may be substituted" as represented by $R^1$, can be used.

The "hydrocarbon group which may be substituted" as represented by $R^1$ preferably includes (i) a $C_{1-6}$ alkyl group, and (ii) a phenyl-$C_{1-6}$ alkyl group which may be substituted by halogen, nitro, $C_{1-6}$ alkyl, or $C_{1-6}$ alkoxy, and more preferably includes benzyl group which may be substituted by $C_{1-4}$ alkyl (e.g. methyl etc.), trihalogeno-$C_{1-4}$alkyl (e.g. trihalogeno-methyl etc.), halogen (fluorine, chlorine, etc.), nitro, cyano, $C_{1-4}$ alkoxy (methoxy etc.), trihalogeno (e.g. fluorine, chlorine, etc.)-$C_{1-4}$ alkoxy(methoxy etc.), hydroxy, carbamoyl, (4-$C_{1-4}$ alkyl (e.g. methyl, etc.)-1-piperazinyl) carbonyl, aminothioc-arbonyl, morpholinocarbonyl, carboxyl, $C_{1-4}$ alkoxy( e.g. methoxy, etc.)-carbonyl, $C_{1-4}$ alkoxy (e.g. ethoxy, etc.)-carbonyl-$C_{1-4}$ alkoxy (e.g. methoxy, etc.), carboxyl-$C_{1-4}$ alkoxy (e.g. methoxy, etc.), $C_{1-4}$ alkoxy (e.g. ethoxy, etc.)-carbonyl-$C_{1-6}$alkyl (isopropyl, etc.), carboxyl-$C_{1-6}$ alyl(isopropyl, etc.), amino, acetylamino, $C_{1-4}$ alkyl (imethyl, etc.)sulfonylamino, (4-$C_{1-4}$ alkyl(methyl, etc.)phenyl)sulfonylamino, ureido, 3-$C_{1-4}$ alkyl(methyl, etc.)-ureido, amidino, dihydrothiazolyl, or dihydroimidazolyl.

More preferably, $R^1$ is a benzyl group which may be substituted by the group consisting of $C_{1-4}$ alkyl (e.g. methyl etc.), trihalogeno-$C_{1-4}$ alkyl (e.g. methyl etc.), halogen (fluorine, chlorine, etc.), nitro, cyano, carbamoyl, $C_{1-4}$ alkoxy( e.g. methoxy, etc.)-carbonyl, $C_{1-4}$ alkoxy (e.g. ethoxy, etc.)-carbonyl-$C_{1-4}$ alkoxy (e.g. methoxy, etc.), amino, acetylamino, $C_{1-4}$ alkyl (methyl, etc.)sulfonylamino, 3-$C_{1-4}$ alkyl(methyl, etc.)-ureido, amidino, and dihydroimidazolyl.

Still more preferably, $R^1$ is a benzyl group which may be substituted by $C_{1-4}$ alkyl (e.g. methyl etc.), and furthermore preferably, $R^1$ is a benzyl group which may be substituted by methyl.

The "acyl group", represented by $R^1_1$, includes but is not limited to —(C=O)—$R^2$, —$SO_2$—$R^2$, —SO—$R^2$, —(C=O)$NR^3R^2$, —(C=O)O—$R^2$, —(C=S)O—R, and —(C=S)$NR^3R^2$ ($R^2$ and $R^3$ may be the same or different and each represents (i) hydrogen atom, (ii) a hydrocarbon group which may be substituted, or (iii) a heterocyclic group which may be substituted, or $R^2$ and $R^3$ may jointly and in combination with the adjacent nitrogen atom form a nitrogen-containing saturated heterocyclic group which may be substituted).

Preferred, among them, are —(C=O)—$R^2$, —$SO_2$—$R^2$, —SO—$R^2$, —(C=O)$NR^3R^2$, and —(C=O)O—$R^2$ ($R^2$ and $R^3$ are as defined above). In particular, —(C=O)—$R^2$ or —(C=O)$NR^3R^2$ ($R^2$ and $R^3$ are as defined above) is most frequently selected.

The "hydrocarbon group" of the "hydrocarbon group which may be substituted" for $R^2$ and $R^3$ is the group available upon elimination of one hydrogen atom from a hydrocarbon compound. As examples, acyclic or cyclic hydrocarbon groups such as alkyl, alkenyl, alkinyl, cycloalkyl, aryl, and aralkyl groups can be mentioned. Specifically, the same species as those mentioned for the "hydrocarbon group" of the "hydrocarbon group which may be substituted" for $R^1$ can be mentioned. Among them, acyclic or cyclic $C_{1-16}$ hydrocarbon groups are preferred. Particularly preferred are a lower ($C_{1-6}$)alkyl group, a lower ($C_{2-6}$)alkenyl group, a $C_{7-16}$ aralkyl group, and a $C_{6-14}$ aryl group. Among them, a lower($C_{1-6}$)alkyl group, a $C_{7-16}$ aralkyl group, and $C_{6-14}$ aryl are most generally selected.

The "heterocyclic group" of the "heterocyclic group which may be substituted" includes the available upon elimination of one hydrogen atom from a monocyclic heteroring, bicyclic heteroring, polycyclic hetero ring such as tricyclic heteroring, tetracyclic heteroring and so on. The heteroring may be aromatic or nonaromatic. 1 to 6 hetero atoms such as nitrogen, oxygen, sulfur, etc. can be used.

Specifically, the group available upon elimination of one hydrogen atom from the "hetero ring" of the "hetero ring which may be substituted" as mentioned for ring B. In addition to, the group available upon elimination of one hydrogen atom from the monocyclic heteroring such as triazole, thiadiazole, oxadiazole, oxathiadiazole, triazine, tetrazole, and so on, the bicyclic hetero ring such as indole, dihydroindole, isoindole, dihydroisoindole, benzofuran, dihydrobenzofuran, benzimidazole, benzoxazole, benzisoxazole, benzothiazole, indazole, quinolfine, tetrahydroquinoline, isoquinoline, tetrahydroisoquinoline, tetrahydro-1H-1-benzazepine, tetrahydro-1H-2-benzazepine, tetrahydro-1H-3-benzazepine, tetrahydrobenzoxazepine, quinazoline, tetrahydroquinazoline, quinoxaline, tetrahydroquinoxaline, benzodioxan, benzodioxole, benzothiazine, imidazopyridine, and so on, polycyclic heteroring (e.g. tricyclic heteroring, tetracyclic heteroring such as acridine, tetrahydroacridine, pyrroloquinoline, pyrroloindole, cyclopentoindole, isoindolobenzazapine, etc.).

The "heterocyclic group" of the "heterocyclic group which may be substituted" is preferably the group available upon elimination of one hydrogen atom from the monocyclic or bicyclic heteroring as mentioned above.

The "nitrogen-containing saturated heterocyclic group which may be substituted", which is optionally formed by $R^2$ and $R^3$ in combination with the adjacent nitrogen atom, includes 5- to 9-membered nitrogen-containing heterocyclic groups which may contain 1 to 3 hetero atoms such as nitrogen, oxygen and sulfur in addition to carbon and one nitrogen atom. Preferred among such nitrogen-containing saturated heterocyclic groups is the group having a valence bond on a ring nitrogen atom. The group having a valence bond on a ring nitrogen atom includes groups of the formula

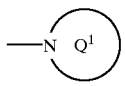

wherein ring $Q^1$ represents a 5- to 9-membered nitrogen-containing saturated heterocyclic group which may contain 1 or 2 hetero atoms such as nitrogen, oxygen, sulfur, etc., in addition to carbon and one nitrogen atom. For example, the following groups can be generally selected.

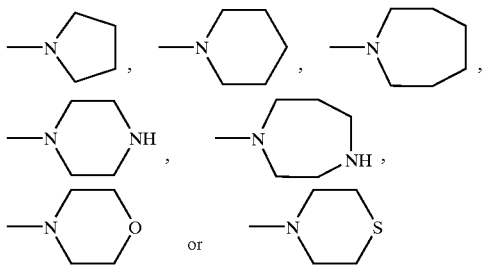

The preferred substituent groups for the "hydrocarbon group" and "heterocyclic group" for $R^2$ and $R^3$ and for the "nitrogen-containing saturated heterocyclic group" for $NR^2R^3$ include but are not limited to (i) halogen (e.g. fluorine, chlorine, bromine, iodine), (ii) nitro, (iii) cyano, (iv) oxo, (v) hydroxy, (vi) hydrocarbon which may be substituted, (vii) lower alkoxy (e.g. $C_{1-6}$ alkoxy such as methoxy, ethoxy, n-propyloxy, i-propyloxy, n-butyloxy, etc.) which may be substituted by phenyl, (viii) lower alkylthio ($C_{1-6}$ alkylthio such as methylthio, ethylthio, propylthio, etc.) which may be substituted by phenyl, (ix) amino, (x) mono-lower alkylamino (mono-$C_{1-6}$ alkylamino such as methylamino, ethylamino, propylamino, etc.), (xi) di-lower alkylamino (e.g. di-$C_{1-6}$ alkylamino such as dimethylamino, diethylamino, etc.), (xii) 5- to 7-membered cycloamino which may have 1 to 3 hetero atoms selected from the group consisting of nitrogen, oxygen, and sulfur in addition to carbon and one nitrogen atom (e.g. pyrrolidino, piperidino, piperazino, morpholino, thiomorpholino, etc.), (xiii) lower alkyl-carbonylamino (e.g. $C_{1-6}$ alkyl-carbonylamino such as acetylamino, propionylamino, butyrylamino, etc.), (xiv) lower alkyl-sulfonylamino (e.g. $C_{1-6}$ alkyl-sulfonylamino such as methylsulfonylamino, thyisulfonylamino etc.), (xv) lower alkoxy-carbonyl (e.g. $C_{1-6}$ alkoxy-carbonyl such as methoxycarbonyl, ethoxycarbonyl, propoxycarbonyl, etc.), (xvi) carboxyl, (xvii) lower alkyl-carbonyl (e.g $C_{1-6}$ alkyl-carbonyl such as methylcarbonyl, ethylcarbonyl, propylcarbonyl, etc.), (xviii) carbamoyl, (xix) mono-lower alkyl-carbamoyl (e.g. mono-$C_{1-6}$ alkyl-carbamoyl such as methylcarbamoyl, ethylcarbamoyl, etc.), (xx) di-lower alkyl-carbamoyl (e.g. di-$C_{1-6}$ alkyl-carbamoyl such as dimethylcarbamoyl, diethylcarbamoyl, etc.), (xxi) lower alkylsulfonyl (e.g. $C_{1-6}$ alkylsulfonyl such as methylsulfonyl, ethylsulfonyl, propylsulfonyl, etc.), (xxii) lower alkoxy-carbonyl-lower alkyl (e.g. $C_{1-6}$ alkyl-carbonyl-$C_{1-6}$ alkyl such as methoxycarbonylmethyl, ethoxycarbonylmethyl, tert-butoxycarbonylmethyl, methoxycarbonylethyl, methoxycarbonylmethyl, methoxycarbonyl(dimethyl)methyl, ethoxycarbonyl (dimethyl)methyl, tert-butoxycarbonyl(dimethyl)methyl, etc.), (xxiii) carboxy-lower alkyl (e.g. carboxy-$C_{1-6}$ alkyl such as carboxymethyl, carboxyethyl, carboxy(dimethyl) methyl, etc.), (xxiv) heterocyclic ring which may be substituted. 1 to 5 (preferably 1 to 3) groups selected from among the above-mentioned groups may be present as substituents.

The above-mentioned "lower alkoxy" and "lower alkylthio" may respectively have phenyl as a substituent.

The "hydrocarbon" and "substituent" for the "hydrocarbon which may be substituted" includes the respective groups mentioned for the "hydrocarbon group" and "substituent" of the "hydrocarbon group which may be substituted" which has been mentioned for $R^1$.

The "heterocyclic ring" of the "heterocyclic ring which may be substituted" may for example be the group available upon elimination of one hydrogen atom from the "hetero ring" of the "hetero ring which may be substituted" represented by ring B.

The "substituent" for the "heterocyclic ring which (may be substituted" includes the same species as mentioned for the substituent for the "hetero ring which may be substituted" for ring B (exclusive of the above-mentioned "heterocyclic group which may be substituted").

The preferred $R^2$ and $R^3$ includes but are not limited to: a phenyl group which may be substituted by $C_{1-4}$ alkyl (methyl, ethyl, etc.) or $C_{1-4}$ alkoxy (methoxy, ethoxy, etc.), a $C_{1-4}$ alkyl group (methyl, ethyl, etc.), a halogeno (e.g. fluoro, chloro, etc.)$C_{1-4}$ alkyl (methyl, ethyl, etc.) group, a benzyl group, a naphthyl group, a pyridyl group, a thienyl group, a furyl group and hydrogen atom.

The preferred "acyl group" for $R^1$ includes a formyl group, a acetyl group, a trihalogeno (e.g. fluoro, etc.)acetyl group, a pyridylcarbonyl group, a thienylcarbonyl group, a furylcarbonyl group, a phenacyl group, a benzoyl group, a $C_{1-4}$ alkyl(e.g. methyl, etc.)benzoyl group, $C_{1-4}$ alkoxy(e.g. methoxy, etc.)benzoyl group, a benzenesulfonyl group, a naphthylsulfonyl group, and a thienylsulfonyl group. And more preferably, —(C=O)—$R^{2'}$ (where $R^{2'}$ represents a phenyl or phenyl-C1-6 alkyl group, which may be substituted by $C_{1-6}$ alkyl or $C_{1-6}$ alkoxy).

The "heterocyclic group" of the "heterocyclic group which may be substituted" for $R^1$ may be the group available upon elimination of one hydrogen atom from a monocyclic heteroring, bicyclic heteroring, polycyclic hetero ring such as tricyclic heteroring, tetracyclic heteroring and so on. The heteroring may be aromatic or nonaromatic. 1 to 6 hetero atoms such as nitrogen, oxygen, sulfur, etc. can be used.

Specifically, the group available upon elimination of one hydrogen atom from the "hetero ring" of the "hetero ring which may be substituted" as mentioned for ring B. In addition to, the group available upon elimination of one hydrogen atom from the monocyclic heteroring such as triazole, thiadiazole, oxadiazole, oxathiadiazole, triazine, tetrazole, and so on, the bicyclic hetero ring such as indole, dihydroindole, isoindole, dihydroisoindole, benzofuran, dihydrobenzofuran, benzimidazole, benzoxazole, benzisoxazole, benzothiazole, indazole, quinoline, tetrahydroquinoline, isoquinoline, tetrahydroisoquinoline, tetrahydro-1H-1-benzazepine, tetrahydro-1H-2-benzazepine, tetrahydro-1H-3-benzazepine, tetrahydrobenzoxazepine, quinazoline, tetrahydroquinazoline, quinoxaline, tetrahydroquinoxaline, benzodioxan, benzodioxole, benzothiazine, imidazopyridine, and so on, polycyclic heteroring (e.g. tricyclic heteroring, tetracyclic heteroring such as acridine, tetrahydroacridine, pyrroloquinoline, pyrroloindole, cyclopentoindole, isoindolobenzazapine, etc.).

The "heterocyclic group" of the "heterocyclic group which may be substituted" is preferably the group available upon elimination of one hydrogen atom from the monocyclic or bicyclic heteroring as mentioned above, and is morepreferably, a pyridyl group can be uded.

The "substituent" for the above "heterocyclic group which may be substituted" includes the groups mentioned for the "substituent" on the "hetero ring which may be substituted" for ring B (excluding the above "heterocyclic group which may be substituted"), and the "substitution" for the "hydrocarbon group which may be substituted" which has been mentioned for $R^1$.

Preferably, $R^1$ represents (i) a hydrogen atom, (ii) a $C_{1-6}$ alkyl group, (iii) a phenyl-$C_{1-6}$ alkyl group which may be substituted by halogen, nitro, $C_{1-6}$ alkyl or $C_{1-6}$ alkoxy, or (iv) —(C=O)—$R^2$ (where $R^2$ represents a phenyl or phenyl-$C_{1-6}$ alkyl group, which may be substituted by $C_{1-6}$ alkyl or $C_{1-6}$ alkoxy).

The group which is formed as the "phenyl" of the "phenyl group which may be substituted and/or condensed" is fused to a monocyclic hetero ring which may be substituted specifically includes groups of the following formula

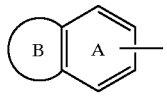

which are available upon elimination of one hydrogen atom each from bicyclic benzenoid systems such as 2,3-dihydrobenzofuran; 3,4-dihydro-2H-1-benzothiopyran; 2,3-dihydro-1H-indole; 1,2,3,4-tetrahydroquinoline; 2,3-dihydro-1H-isoindole; 1,2,3,4-tetrahydroisoquinoline; benzazepines such as 2,3,4,5-tetrahydro-1H-1-benzazepine, 2,3,4,5-tetrahydro-1H-2-benzazepine, 2,3,4,5-tetrahydro-1H-3-benzazepine, etc.; benzazocines such as 1,2,3,4,5,6-hexahydro-1-benzazocine, 1,2,3,4,5,6-hexahydro-2-benzazocine, 1,2,3,4,5,6-hexahydro-3-benzazocine, etc.; benzazonines such as 2,3,4,5,6,7-hexahydro-1H-1-benzazonine, 2,3,4,5,6,7-hexahydro-1H-2-benzazonine, 2,3,4,5,6,7-hexahydro-1H-3-benzazonine, 2,3,4,5,6,7-hexahydro-1H-4-benzazonine, etc.; benzoxazoles such as 2,3-dihydrobenzoxazole etc.; benzothiozoles such as 2,3-dihydrobenzothiazole etc.; benzimidazoles such as 2,3-dihydro-1H-benzimidazole, etc.; benzoxazines such as 3,4-dihydro-1H-2,1-benzoxazine, 3,4-dihydro-1H-2,3-benzoxazine, 3,4-dihydro-2H-1,2-benzoxazine, 3,4-dihydro-2H-1,4-benzoxazine, 3,4-dihydro-2H-1,3-benzoxazine, 3,4-dihydro-2H-3,1-benzoxazine, etc.; benzothiazines such as 3,4-dihydro-1H-2,1-benzothiazine, 3,4-dihydro-1H-2,3-benzothiazine, 3,4-dihydro-2H-1,2-benzothiazine, 3,4-dihydro-2H-1,4-benzothiazine, 3,4-dihydro-2H-1,3-benzothiazine, 3,4-dihydro-2H-3,1-benzothiazine; etc.; benzodiazines such as 1,2,3,4-tetrahydrocinnoline, 1,2,3,4-tetriahydrophthalazine, 1,2,3,4-tetrahydroquinazoline, 1,2,3,4-tetrahydroquinoxaline, etc.; benzoxathiins such as 3,4-dihydro-1,2-benzoxathiin, 3,4-dihydro-2,1-benzoxathiin, 2,3-dihydro-1,4-benzoxathiin, 1,4-dihydro-2,3-benzoxathiin, 4H-1,3-benzoxathiin, 4H-3,1-benzoxathiin, etc.; benzodioxins such as 3,4-dihydro-1,2-benzodioxin, 2,3-dihydro-1,4-benzodioxin, 1,4-dihydro-2,3-benzodioxin, 4H-1,3-benzodioxin, etc.; benzodithiins such as 3,4-dihydro-1,2-benzodithiin, 2,3-dihydro-1,4-benzodithiin, 1,4-dihydro-2,3-benzodithiin, 4H-1,3-benzodithiin, etc.; benzoxazepines such as 2,3,4,5-tetrahydro-1,2-benzoxazepine, 2,3,4,5-tetrahydro-1,3-benzoxazepine, 2,3,4,5-tetrahydro-1,4-benzoxazepine, 2,3,4,5-tetrahydro-1,5-benzoxazepine, 1,3,4,5-tetrahydro-2,1-benzoxazepine, 1,3,4,5-tetrahydro-2,3-benzoxazepine, 1,3,4,5-tetrahydro-2,4-benzoxazepine, 1,2,4,5-tetrahydro-3,1-benzoxazepine, 1,2,4,5-tetrahydro-3,2-benzoxazepine, 1,2,3,5-tetrahydro-4,1-benzoxazepine, etc.; benzothiazepines such as 2,3,4,5-tetrahydro-1,2-benzothiazepine, 2,3,4,5-tetrahydro-1,4-benzothiazepine, 2,3,4,5-tetrahydro-1,5-benzothiazepine, 1,3,4,5-tetrahydro-2,1-benzothiazepine, 1,3,4,5-tetrahydro-2,4-benzothiazepine, 1,2,4,5-tetrahydro-3,1-benzothiazepine, 1,2,4,5-tetrahydro-3,2-benzothiazepine, 1,2,3,5-tetrahydro-4,1-benzothiazepine, etc.; benzodiazepines such as 2,3,4,5-tetrahydro-1H-1,2-benzodiazepine, 2,3,4,5-tetrahydro-1H-1,3-benzodiazepine, 2,3,4,5-tetrahydro-1H-1,4-benzodiazepine, 2,3,4,5-tetrahydro-1H-1,5-benzodiazepine, 2,3,4,5-tetrahydro-1H-2,3-benzodiazepine, 2,3,4,5-tetrahydro-1H-2,4-benzodiazepine, etc.; benzodioxepins such as 4,5-dihydro-1,3-benzodioxepin, 4,5-dihydro-3H-1,2-benzodioxepin, 2,3-dihydro-5H-1,4-benzodioxepin, 3,4-dihydro-2H-1,5-benzodioxepin, 4,5-dihydro-1H-2,3-benzodioxepin, 1,5-dihydro-2,4-benzodioxepin, etc.; benzodithiepins such as 4,5-dihydro-1H-2,3-benzodithiepin, 1,5-dihydro-2,4-benzodithiepin, 3,4-dihydro-2H-1,5-benzodithiepin, 2,3-dihydro-5H-1,4-benzodithiepin, etc.; benzoxazocinesgsuch as, 3,4,5,6-tetrahydro-2H-1,5-benzoxazocine, 3,4,5,6-tetrahydro-2H-1,6-benzoxazocine, etc.; benzothiazocines such as 3,4,5,6-tetrahydro-2H-1,5-benzothiazocine, 3,4,5,6-tetrahydro-2H-1,6-benzothiazocine, etc.; benzodiazocines such as 1,2,3,4,5,6-hexahydro-1,6-benzodiazocine etc.; benzoxathiocines such as 2,3,4,5-tetrahydro-1,6-benzoxathiocine etc.; benzodioxocines such as 2,3,4,5-tetrahydro-1,6-benzodioxocine etc.; benzotrioxepins such as 1,3,5-benzotrioxepin, 5H-1,3,4-benzotrioxepin, etc.; benzoxathiazepines such as 3,4-dihydro-1H-5,2,1-benzoxathiazepine, 3,4-dihydro-2H-5,1,2-benzoxathiazepine, 4,5-dihydro-3,1,4-benzoxathiazepine, 4,5-dihydro-3H-1,2,5-benzoxathiazepine, etc.; benzoxadiazepines such as 2,3,4,5-tetrahydro-1,3,4-benzoxadiazepine etc.; benzothiadiazepines such as 2,3,4,5-tetrahydro-1,3,5-benzothiadiazepine etc.; benzotriazepines such as 2,3,4,5-tetrahydro-1H-1,2,5-benzotriazepine etc.; benztxathiepins such as 4,5-dihydro-1,3,2-benzoxathiepin, 4,5-dihydro-1H-2,3-benzoxathiepin, 3,4-dihydro-2H-1,5-benzoxathiepin, 4,5-dihydro-3H-1,2-benzoxathiepin, 4,5-dihydro-3H-2,1-benzoxathiepin, 2,3-dihydro-5H-1,4-benzoxathiepin, 2,3-dihydro-5H-4,1-benzoxathiepin, etc. Particularly preferred are groups available upon elimination of one hydrogen atom each from such bicyclic benzenoid systems as 2,3,4,5-tetrahydro-1H-3-benzazepine, 2,3,4,5-tetrahydro-1H-2-benzazepine, 2,3-dihydro-1H-indolet 2,3,4,5-tetrahydro-1,4-benzoxazepine, and so forth.

As preferred examples of the group formed as the "phenyl group" of the "phenyl group which may be substituted and/or condensed" is fused to a monocyclic hetero ring which may be substituted, groups of the following formula can be mentioned.

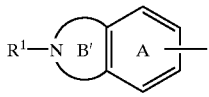

wherein ring B represents a 5- to 9-membered nitrogen-containing hetero ring which may be substituted by oxo in addition to $R^1$; ring A and $R^1$ are as defined herein before.

The "5- to 9-membered nitrogen-containing hetero ring" of the "5- to 9-membered nitrogen-containing hetero ring which may be substituted by oxo" includes 5- to 9-membered nitrogen-containing hetero rings which may contain 1 to 3 hetero atoms, e.g. nitrogen, oxygen, and sulfur, in addition to carbon and one nitrogen atom. Preferably, 5- to 9-membered nonaromatic nitrogen-containing hetero rings (such as pyrrolidine, piperidine, hexamethyleneimine, heptamethyleneimine, piperazine, homopiperazine, tetrahydrooxazepine, morpholine, thiomorpholine, etc.) are selected. The following are particularly preferred examples of the group formed as the "phenyl group" of the "phenylgroup which may be substituted and/or condensed" is fused to a monocyclic hetero ring:

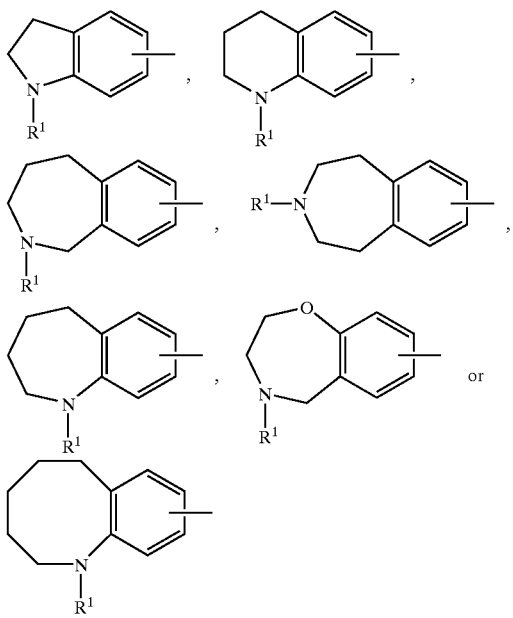

wherein $R^1$ is as defined herein before, for the best result, the groups represented as following formula:

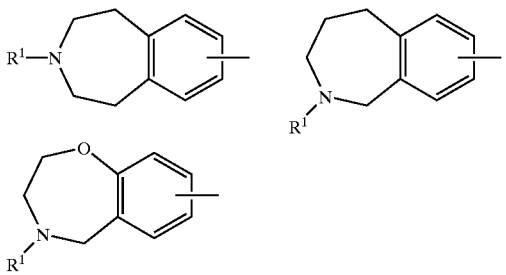

wherein $R^1$ is as defined herein before, can be used.

The group which is formed as the "phenyl group" of the "phenyl group which may be substituted and/or condensed" is fused to a bicyclic hetero system which may be substituted or two similar or dissimilar rings at least one of which is& monocyclic hetero ring, which may be substituted, includes but is not limited to groups of the following formula.

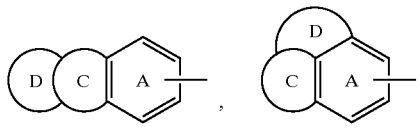

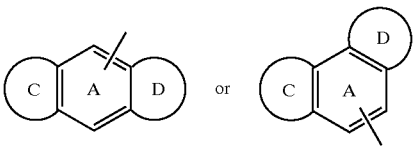

wherein ring A is as defined hereinbefore; ring C and ring D are such that one represents a hetero ring which may be substituted with the other being a 5- to 9-membered ring which may be substituted and optionally containing one or more hetero atoms.

The "hetero ring" of the "hetero ring which may be substituted" as mentioned above for either ring C or ring D includes but is not limited to 4- to 14-membered hetero rings, preferably 5- to 9-membered hetero rings, each containing 1 to 3 hetero atoms such as nitrogen, oxygen and/or sulfur as ring members. This hetero ring may be whichever of an aromatic hetero ring and a nonaromatic hetero ring. Thus, for example, pyridine, pyrazine, pyrimidine, imidazole, furan, thiophene, dihydropyridine, diazepine, oxazepine, pyrrolidine, piperidine, hexamethyleneimine, heptamethyleneimine, tetrahydrofuran, piperazine, homopiperaziner, tetrahydrooxazepine, morpholine, thiomorpholine, etc. can be mentioned.

The "substituent" for the "hetero ring which may be substituted" has the same meaning as the "substituent" for the "hetero ring which may be substituted" which has been mentioned for ring B.

The "5- to 9-membered ring optionally containing one or more hetero atoms" of the "5- to 9-membered ring which may be substituted and optionally containing one or more hetero atoms" which has been mentioned for either ring C or ring D includes 5- to 9-membered hetero rings (e.g. pyridine, pyrazine, pyrimidine, imidazole, furan, thiophene, dihydropyridine, diazepine, oxazepine, pyrrolidine, piperidine, hexamethyleneimine, heptamethyleneimine, tetrahydrofuran, piperazine, homopiperazine, tetrahydrooxazepine, morpholine, thiomorpholine, etc.) and 5- to 9-membered carbocyclic rings.

The "5- to 9-membered carbocyclic ring" mentioned above may be a saturated ring or an unsaturated ring and is preferably selected from among benzene, cyclopentane, cyclopentene, cyclohexane, cyclohexene, cyclohexadiene, cycloheptane, cycloheptene, cycloheptadiene, and so forth. Particularly, benzene or cyclohexane is preferred.

The "substituent" for the "5- to 9-membered ring which may be substituted and optionally containing one or more hetero atoms" has the same meaning as the "substituent for any carbon atom" of the "hetero ring which may be substituted" as mentioned for ring B.

The group which is formed as the "phenyl group" of the "phenyl group which may be substituted and/or condensed" is fused to a bicyclic hetero system which may be substituted includes:

(1) the phenyl group fused to a bicyclic hetero system corresponding to the group available upon elimination of one hydrogen atom from the benzene ring of a tricyclic benzenoid system of the formula

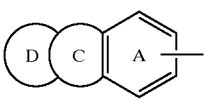

e.g. carbazole, 1,2,3,4,4a,9a-hexahydrocarbazole, 9,10-dihydroacridine, 1,2,3,4-tetrahydroacridine, 10,11- dihydro-5H-dibenz[b,f]azepine, 5,6,7,12-tetrahydrodibenz[b,g]azocine, 6,11-dihydro-5H-dibenz[b,e]azepine, 6,7-dihydro-5H-dibenz[c,e]azepine, 5,6,11,12-tetrahydrodibenz[b,f]azocine, dibenzofuran, 9H-xanthene, 10,11-dihydrodibenz[b,f]oxepin, 6,11-dihydrodibenz[b,e]oxepin, 6,7-dihydro-5H-dibenz[b,g]oxocine, dibenzothiophene, 9H-thioxanthene, 10,11-dihydrodibenzo[b,f]thiepin, 6,11-dihydrodibenzo[b,e]thiepin, 6,7-dihydro-5H-dibenzo[b,g]thiocine, 10H-phenothiazine, 10H-phenoxazine, 5,10-dihydrophenazine, 10,11-dibenzo[b,f][1,4]thiazepine, 10,11-dihydrodibenz[b,f][1,4]oxazepine, 2,3,5,6,11,11a-hexahydro-1H-pyrrolo[2,1-b][3]benzazepine, 10,11-dihydro-5H-dibenzo[b,e][1,4]diazepine, 5,11-dihydrodibenz[b,e][1,4]oxazepine, 5,11-dihydrodibenzo[b,f][1,4]thiazepine, 10,11-dihydro-5H-dibenzo[b,e][1,4]diazepine, 1,2,3,3a,8,8a-hexahydropyrrolo[2,3-b]indole, etc.;

(2) the bicyclic hetero system-fused phenyl group of the formula

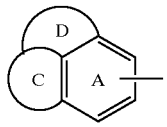

which corresponds to the group available upon elimination of one hydrogen atom from the benzene ring of a tricyclic benzenoid system and, as such, includes but is not limited to 1H,3H-naphth[1,8-cd][1.2]oxazine, naphth[1,8-de]-1,3-oxazine, naphth[1,8-de]-1,2-oxazine, 1,2,2a,3,4,5-hexahydrobenz[cd]indole, 2,3,3a,4,5,6-hexahydro-1H-benzo[de]quinoline, 4H-pyrrolo[3,2,1-ij]quinoline, 1,2,5,6-tetrahydro-4H-pyrrolo[3,2,1-ij]quinoline, 5,6-dihydro-4H-pyrrolo[3,2,1-ij]quinoline, 1H,5H-benzo[ij]quinoliizine, azepino[3,2,1-hi]indole, 1,2,4,5,6,7-hexahydroazepino[3,2,1-hi]indole, 1H-pyrido[3,2,1-jk][1]benzazepine, 5,6,7,8-tetrahydro-1H-pyrido[3,2,1-jk][1]benzazepine, 1,2,5,6,7,8-hexahydro-1H-pyrido[3,2,1-jk][1]benzazepine, 2,3-dihydro-1H-benz[de]isoquinolinet 1,2,3,4,4a,5,6,7-octahydronaphth[1,8-bc]azepine, 2,3,5,6,7,8-hexahydro-1H-pyrido[3,2,1-jk][1]benzazepine, etc.;

(3) the phenyl group fused to two similar or dissimilar rings (at least one of the two rings is a monocyclic hetero ring), which corresponds to the group tricyclic benzenoid system of the formula

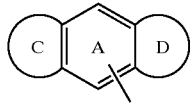

and, as such, includes but is no limited to 1,2,3,5,6,7-hexahydrobenzo[1,2-b:4,5-b,]dipyrrole, 1,2,3,5,6,7-hexahydrocyclopent[f]indole, etc.; and (4) the phenyl group fused to two similar or dissimilar rings (at least one of the two rings is a monocyclic hetero ring), which corresponds to the group available upon elimination of one hydrogen atom from a tricyclic benzenoid system of the formula

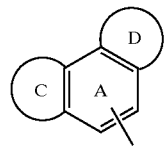

and, as such, includes but is not limited to 1,2,3,6,7,8-hexahydrocyclopent[e]indole, 2,3,4,7,8,9-hexahydro-1H-cyclopenta[f]quinoline, and so forth.

The preferred group which is formed as the "phenyl group" of the "phenyl group which may be substituted and/or condensed" is fused to a bicyclic hetero system includes groups of the formula

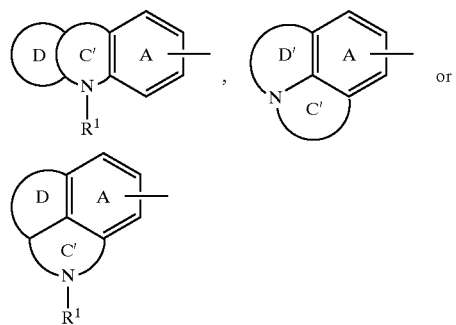

wherein ring C' and ring D' independently represent a 5- to 9-membered nitrogen-containing hetero ring which may be substituted by oxo in addition to $R^1$; ring A, ring D, and $R_1$ are as defined hereinbefore.

The "5- to 9-membered nitrogen-containing hetero ring", of the "5- to 9-membered nitrogen-containing hetero ring which may be substituted by oxo" includes 5- to 9-membered nitrogen-containing hetero rings which may contain 1 to 3 hetero atoms, such as nitrogen, oxygen, and/or sulfur, in addition to carbon and one nitrogen atom. Preferred are 5- to 9-membered nonaromatic nitrogen-containing hetero rings (e.g. pyrrolidine, piperidine, hexamethylenedimine, heptamethyleneimine, piperazine, homopiperazine, tetrahydrooxazepine, morpholine, thiomorpholine, etc.).

The still more preferred group which is formed as the "phenyl group" of the "phenyl grop which may be substituted and/or condensed" is fused to a bicyclic hetero system includes groups of the following formula:

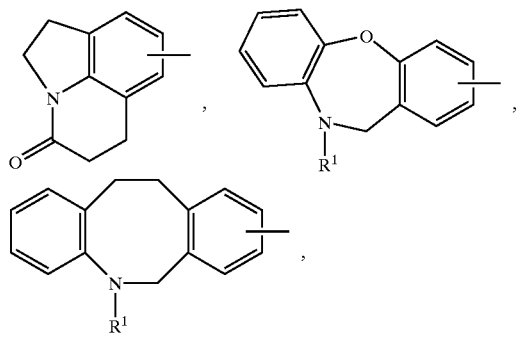

-continued

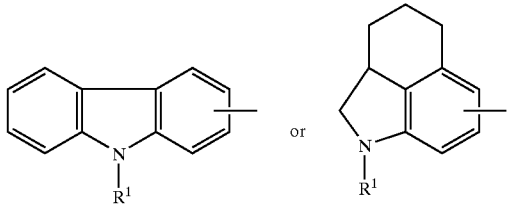

wherein R¹ is as defined hereinbefore.

The group which is formed as the "phenyl group" of the "phenyl group which may be substituted and/or condensed" is fused to a tricyclic hetero system which may be substituted includes but is not limited to groups of the following formula:

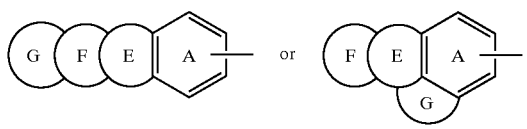

wherein ring A is as defined hereinbefore; ring E, ring F, and ring G are such that at least one of the three rings is a hetero ring which may be substituted, with the other ring or rings each representing a 5- to 9-membered ring which may be substituted and optionally containing one or more hetero atoms.

The "hetero ring" of, and "substituent" on, the "hetero ring which may be substituted" as mentioned for at least one of ring E, ring F, and ring G includes the rings and substituent groups specifically mentioned for the "hetero ring" of, and "substituent" on, the "hetero ring which may be substituted" for rings C and D.

The "5- to 9-membered ring optionally containing one or more hetero atoms" of, and "substituent" on, the "5- to 9-membered hetero ring which may be substituted and optionally containing one or more hetero atoms" which has been mentioned for ring E, ring F, and/or ring G includes the rings and groups specifically mentioned for the "5- to 9-membered ring optionally containing one or more hetero atoms" of, and "substituents" on, the "5- to 9-membered hetero ring which may be substituted and optionally containing one or more hetero atoms" which has been mentioned for ring C or ring D.

The group which is formed as the "phenyl group" of the "phenyl group which may be substituted and/or condensed" is fused to a tricyclic hetero system which may be substituted more specifically includes (1) the phenyl group fused to a tricyclic hetero system:

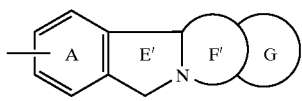

where ring E' and ring F' are defined hereinafter, which corresponds to the group available upon elimination of one hydrogen atom from the benzene ring of a tetracyclic hetero system and, as such, includes but is not limited to 2H-isoindolo[2,1-e]purine, 1H-pyrayzolo[4',3':3,4]pyrido[2,1-a]isoindole, 1H-pyrido[2',3':4,5]imidazo[2,1-a]isoindole, 2H,6H-pyrido[1',2':3,4]imidazo[5,1-a]isoindole, 1H-isoindolo[2,1-a]benzimidazole, 1H-pyrido[3',4':4,5]pyrrolo[2,1-a]isoindole, 2H-pyrido[4',3':4,5]pyrrolo[2,1-a]isoindole, 1H-isoindolo[2,1-a]indole, 2H-isoindolo[1,2-a]isoindole, 1H-cyclopenta[4,5]pyrimido[2,1-a]isoindole, 2H,4H-pyrano[4',3':4,5][1,3]oxazino[2,3-a]isoindole, 2H-isoindolo[2;1-a][3,1]benzoxazine, 7H-isoindolo[1,2-b][1,3]benzoxazine, 2H-pyrido[2',1':3,4]pyrazino[2,1-a]isoindole, pyrido[2',3':4,5]pyrimido[2,1-a]isoindole, pyrido[3',2':5,6]pyrimido[2,1-a]isoindole, 1H-pyrido[1,2':3,4]pyrimido[2,1-a]isoindole, isoindolo[2,1-a]quinazoline, isoindolo[2,1-a]quinoxaline, isoindolo[1,2-a]isoquinoline, isoindolo[2,1-b]isoquinoline, isoindolo[2,1-a]quinoline, 6H-oxazino[3',4':3,4][1,4]diazepino[2,1a]isoindole, azepino[2',1':3,4]pyrazino[2,1-a]isoindole, 2H,6H-pyrido[2',1':3,4][1,4]diazepino[2,1-a]isoindole, 1H-isoindolo[1,2-b][1,3,4]benzotriazepine, 2H-isoindolo[2,1-a][1;3,4]benzotriazepine, isoindolo[2,1-d][1,4]benzoxazepine, 1H-isoindolo[2,1-b][2,4]benzodiazepine, 1H-isoindolo[2,1-c][2,3]benzodiazepine, 2H-isoindolo[1,2-a][2,4]benzodiazepine, 2H-isoindolo[2,1-d][1,4]benzodiazepine, 5H-indolo[2,1-b][3]benzazepine, 2H-isoindolo[1,2-a][2]benzazepine, 2H-isoindolo[1,2-b][3]benzazepine, 2H-isoindolo[2,1-b][2]benzazepine, 2H-isoindolo[1,2-b][1,3,4]benzoxadiazocine, isoindolo[2,1-b][1,2,6]benzotriazocine, 5H-4,8-methano-1H-[1,5]diazacycloundecino[1,11-a]indole, etc.;

(2) the phenyl group fused to a tricyclic hetero system:

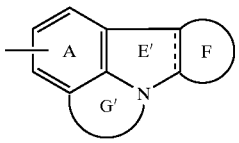

wherein ----- represents a single bond or a double bond; ring E' and ring G' are as defined hereinafter, which corresponds to the group available upon elimination of one hydrogen atom from a tetracyclic benzenoid system and, as such, includes 1H,4H-pyrrolo[3',2':4,5]pyrrolo[3,2,1-ij]quinoline, pyrrolo[3,2,1-jk]carbazole, 1H-furo[2',3':4,5]pyrrolo[3,2,1-ij]quinoline, 1H,4H-cyclopenta[4,5]pyrrolo[1,2,3-de]quinoxaline, 1H,4H-cyclopenta[4,5]pyrrolo[312,1-ij]quinoline, pyrido[3',4':4,5:]pyrrolo[1,2,3-de]benzoxazine, [1,4]oxazino[2,3,4-jk]carbazole; 1H,3H-[1,3]oxazino[5,4,3-jk]carbazole, pyrido[3',4':4,5]pyrrolo[1,2,3-de][1,4]benzothiazine, 4H-pyrrolo[3,2,1-de]phenanthridine, 4H,5H-pyrido[3,2,1-de]phenanthridine, 1H,4H-3a,6a-diazafluoranthene, 1-oxa-4,6a-diazafluoranthene, 4-oxa-2,10b-diazafluoranthene, 1-thia-4,6a-diazafluoranthene, 1H-pyrazino[3,2,1-jk]carbazole, 1H-indolo[3,2,1-de][1,5]naphthyridine, benzo[b]pyrano[2,3,4-hi]indolizine, 1H,3H-benzo[b]pyrano[3,4,5-hi]indolizine, 1H,4H-pyrano[2',3':4,5]pyrrolo[3,2,1-ij]quinoline, 1H,3H-benzo[b]thiopyrano[3,4,5-hi]indolizine, 1H-pyrido[3,2,1-jk]carbazole, 4H-3-oxa-11b-azacyclohepta[jk]fluorene, 2H-azepino[1',2':1,2]pyrimidino[4,5-b]indole, 1H,4H-cyclohepta[4,5]pyrrolo6[1,2,3-de]quinoxaline, 5H-pyrido[3',4':4 5]pyrrolo[1,2,3-ef][1,5]benzoxazepine, 4H-pyrido[3',4':4,5]pyrrolo[3,2,1-jk][4,1]benzothiazepine, 5H-pyrido[3',4':4,5]pyrrolo[1,2,3-ef][1,5]benzothiazepine, 5H-pyrido[4'1,3':4,5]pyrrolo[1,2,3-ef][1,5]benzothiazepine, [1,2,4]triazepino[6,5,4-jk]carbazole, [1,2,4]triazepino[6,7,1-jk]carbazole, [1,2,5]triazepino[3,4,5-jk]carbazole, 5H-[1,4]oxazepino[2,3,4-jk]carbazole, 5H-[1,4]thiazepino[2,3,4-jk]carbazole, [1,4]diazepino[3,2,1-jk]carbazole, [1,4]diazepino[6,7,1-jk]carbazole, azepino[3,2,1-jk]carbazole 1H-cycloocta[4,5]pyrrolo[1,2,3-de]quinoxaline, and 1H-cycloocta[4,5]pyrrolo[3,2,1-ij]quinoline;

(3) the phenyl group fused to a tricyclic hetero ring:

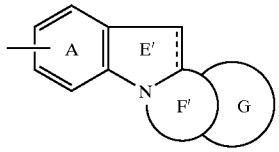

where ----- represents a single bond or a double bond; ring E' and ring F' are as defined hereinafter, which; corresponds to the group available upon elimination of one hydrogen atom from a tetracyclic benzenoid system and, as such, includes but is not limited to 1H-indolo[1,2-a]benzimidazole, 1H-indolo[1,2-b]indazole, pyrrolo[2',1':3,4]pyrazino[1,2-a]indole, 1H,5H-pyrrolo[1',2':4,5]pyrazino[1,2-a]indole 2H-pyrido[2',3':3,4]pyrrolo[1,2-a]indole, 1H-pyrrolo[2',3':3,4]pyrido[1,2-a]indole, 1H-indolo[1,2-a]indole, 6H-isoindolo[2,1-a]indole, 6H-indolo[1,2-c][1,3]benzoxazine, 1H-indolo[1,2-b][1,2]benzothiazine, pyrimido[4',5':4,5]pyrimido[1,6-a]indole, pyrazino[2',3':3,4]pyrido[1,2-a]indole, 6H-pyrido[1',2':3,4]pyrimido[1,6-a]indole, indolo[1,2-b]cinnoline, indolo[1,2-a]quinazoline, indolo[1,2-c]quinazoline, indolo[2,1-b]quinazoline, indolo[1,2-a]quinoxaline, indolo[1,2-a][1,8]naphthyridine, indolo[1,2-b]-2,6-naphthyridine, indolo[1,2-b][2:,7]naphthyridine, indolo[1,2-h]-1,7-naphthyridine, indolo[1,2-b]isoquinoline, indolo[2,1-a]isoquinoline, indolo[1,2-a]quinoline, 2H,6H-pyrido[2',1':3,4][1,4]diazepino[1,2-a]indole, 1H-indolo[2,1-c][1,4]benzodiazepine, 2H-indolo[1,2-d][1,4]benzodiazepine, 2H-indolo[1,2-a][2,3]benzodiazepine, 2H-indolo[2,1-b][1,3]benzodiazepine, 1H-indolo[1,2-b][2]benzazepine, 2H-indolo[1,2-a][1]benzazepine, 2H-indolo[2,1-a][2]benzazepine, indolo[1,2-e][1,5]benzodiazocine, and indolo[2,1-b][3]benzazocine;

(4) the phenyl group fused to a tricyclic heterocyclic ring:

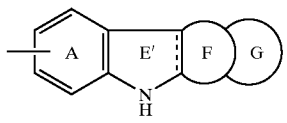

wherein ----- represents a single bond or a double bond; ring E' is as defined hereinafter, which corresponds to the group available upon elimination of one hydrogen atom from a tetracyclic benzenoid system and, as such, includes but is not limited to 1H-imidazo[1',2':1,2]pyrido[3,4-b]indole, 1H-imidazo[1',2':1,6]pyrido[4,3-b]indole, 1H-imidazo[1',5':1,2]pyrido[3,4-b]indole, 1H-imidazo[1',5':1,6]pyrido[4,3-b]indole, 1H-pyrido[2',1':2,3]imidazo[4,5-b]indole, imidazo[4,5-a]carbazole, imidazo[4,5-c]carbazole, pyrazolo[3,4-c]carbazole, 2H-pyrazino[1',2':1,5]pyrrolo[2,3-b]indole, 1H-pyrrolo[1,',2':1,2]pyrimido[4,5-b]indole, 1H-indolizino[6,7-b]indole, 1H-indolizino[8,7-b]indole, indolo[2,3-b]indole; indolo[3,2-b]indole, pyrrolo[2,3-a]carbazole, pyrrolo[2,3-b]carbazole, pyrrolo[2,3-c]carbazole, pyrrolo[3,2-a]carbazole, pyrrolo[3,2-b]carbazole, pyrrolo[3,2-c]carbazole, pyrrolo[3,4-a]carbazole, pyrrolo[3,4-b]carbazole, pyrrolo[3,4-c]carbazole, 1H-pyrido[3',4':4,5]furo[3,2-b]indole, 1H-furo[3,4-a]carbazole, 1H-furo[3,4-b]carbazole, 1H-furo[3,4-c]carbazole, 2H-furo[2,3-a]carbazole, 2H-furo[2,3-c]carbazole, 2H-furo[3,2-a]carbazole, 2H-furo[3,2-c]carbazole, 1H-pyrido[3',4':4,5]thieno[2,3-b]indole, thieno[3',2':5,6]thiopyrano[4,3-b]indole, thieno[3',4':5,6]thiopyrano[4,3-b]indole, 1H-[1]benzothieno[2,3-b]indole, 1H-[1]benzothieno[3,2-b]indole, 1H-thieno[3,4-a]carbazole, 2H-thieno[2,3-b]carbazole, 2H-thieno[3,2-a]carbazole, 2H-thieno[3,2-b]carbazole, cyclopenta[4,5]pyrrolo[2,3-f]quinoxaline, cyclopenta[5,6]pyrido[2,3-b]indole, pyrido[2',3':3,4]cyclopenta[1,2-b]indole, pyrido[2',3':4,5]cyclopenta[1,2-b]indole, pyrido[3',4':3,4]cyclopenta[1,2-b]indole, pyrido[3',4':4,5]cyclopenta[1,2-b]indole, pyrido[4',3':4,5]cyclopenta[1,2-b]indole, 1H-cyclopenta[5,6]pyrano[2,3-b]indole, 1H-cyclopenta[5,6]thiopyrano[4,3-b]indole, cyclopenta[a]carbazole, cyclopenta[c]carbazole, indeno[1,2-b]indole, indeno[2,1-b]indole, [1,2,4]triazino[4',3':1,2]pyrido[3,4-b]indole, 1,3,5-triazino[1',2':1,1]pyrido[3,4-b]indole, 1H-[1,4]oxazino[4',3':1,2]pyrido[3,4-b]indole, 1H-[1,4]oxazino[4',3':1,6]pyrido[3,4-b]indole, 4H-[1,3]oxazino[3',4':1,2]pyrido[3,4-b]indole, indolo[3,2-b][1,4]benzoxazine, 1,3-oxazino[6,5-b]carbazole, 2H-pyrimido[2',1':2,3][1,3]thiazino[5,6-b]indole, 2H-[1,3]thiazino[3',2':1,2]pyrido[3,4-b]indole, 4H-1,3]thiazino[3',4':1,2]pyrido[3,4-b]indole, indolo[2,3-b][1,4]benzothiazine, indolo[3,2-b][1,4]benzothiazine, indolo[3,2-c][2,1]benzothiazine, 1,4-thiazino[2,3-a]carbazole, [11,4]thiazino[2,3-b]carbazole, [1,4]thiazino[2,3-c]carbazole, 1,4-thiazino[3,2-b]carbazole, 1,4-thiazino[3,2-c]carbazole, 1H-indolo[2,3-g]pteridine, 1H-indolo[3,2-g]pteridine, pyrazino[1',2':1,2]pyrido[3,4-b]indole, pyrazino[1',2':1,2]pyrido[4,3-b]indole, 1H-pyrido[2',3':5,6]pyrazino[2,3-b]indole, 1H-pyrido[3',2':5,6]pyrazino[2,3-b]indole, 1H-pyrido[3',4':5,6]pyrazino[2,3-b]indole, pyrido[1',2':1,2]pyrimido[4,5-b]indole, pyrido[1',2':1,2]pyrimido[5,4-b]indole, pyrido[2',1':2,3]pyrimido[4,5-b]indole, pyrimido[1',2':1,2]pyrido[3,4-b]indole, pyrimido[1',2':1,6]pyrido[3,4-b]indole, pyrimido[5',4':5,6]pyrano[2,3-b]indole, pyridazino[4',5':5,6]thiopyrano4,5-b]indole, 1H-indolo[3,2-c]cinnoline, 1H-indolo[2,3-b]quinoxaline, 1H-pyrazino[2,3-a]carbazole, 1H-pyrazino[2,3-b]carbazole, 1H-pyrazino[2,3-c]carbazole, 1H-pyridazino[3,4-c]carbazole, 1H-pyridazino[4,5-b]carbazole, 1H-pyrimido[4,5-a]carbazole, 1H-pyrimido[4,5-c]carbazole, 1H-pyrimido[5,4-a]carbazole, 1H-pyrimido[5,4-b]carbazole, 1H-pyrimido[5,4-c]carbazole, 7H-1,4-dioxino[2',3':5,6][1,2]dioxino[3,4-b]indole, 6H-[1,4]benzodioxino[2,3-b]indole, 6H-[1,4]benzodioxino[2,3-b]indole, 1H-indolo[2,3-b]-1,5-naphthyridine, 1H-indolo[2,3-b][1,6]naphthyridine, 1H-indolo[2,3-b][1,8]naphthyridine, 1H-indolo[2,3-c]-1,5-naphthyridine, 1H-indolo[2,3-c][1,6]naphthyridine 1H-indolo[2,3-c][1,7]naphthyridine, 1H-indolo[2,3-c][1,8]naphthyridine, 1H-indolo[3,2-b]-1,5-naphthyridine, 1H-indolo[3,2-b][1,7]naphthyridine, 1H-indolo[3,2-b][1,8]naphthyridine, 1H-indolo[3,2-c][1,8]naphthyridine, indolo[2,3-a]quinolizine, indolo[2,3-b]quinolizine, indolo[3,2-a]quinolizine, indolo[3,2-b]quinolizine, pyrano[4',3':5,6]pyrido[3,4-b]indole, pyrido[4',3':4,5]pyrano[3,2-b]indole, pyrido[4',3':5,6]pyrano[2,3-b]indole, pyrido[4',3':5,6]pyrano[3,4-b]indole, 1H-indolo[2,3-c]isoquinoline, 1H-indolo[3,2-c]isoquinoline, 1H-indolo[2,3-c]quinoline, 1H-indolo[3,2-c]quinoline, 1H-pyrido[$2_1$,3-a]carbazole 1H-pyrido[2,3-b]carbazole, 1H-pyrido[2,3-c]carbazole, 1H-pyrido[3,2-a]carbazole, 1H-pyrido[3,2-b]carbazole, 1H-pyrido[3,2-c]carbazole, 1H-pyrido[3,4-a]carbazole, 1H-pyrido[3,4-b]carbazole, 1H-pyrido[3,4-c]carbazole, 1H-pyrido[4,3-a]carbazole, 1H-pyrido[4,3-b]carbazole, 1H-pyrido[4,3-c]carbazole, 1H-quindoline, 1H-quinindoline, 1H-pyrano[3',4':5,6]pyrano[4,3-b]indole, [1]benzopyrano[2,3-b]indole, [1]benzopyrano[3,2-b]indole, [1]benzopyrano[3,4-b]indole, [1]benzopyrano[4,3-b]indole, [2]benzopyrano[4,3-b]indole, pyrano[2,3-a]carbazole, pyrano[2,3-b]carbazole₁ pyrano[2,3-c]carbazole, pyrano[3,2-a]carbazole, pyrano[3,2-c]carbazole, pyrano[3,4-a]carbazole, 1H-phosphinolino[4,3-b]indole, [1]benzothiopyrano[2,3-b]indole, [1]benzothiopyrano[3,2-b]indole, [1]benzothiopyrano[3,4-b]indole, [1]benzothiopyrano[4,3-b]indole, [2]benzothiopyrano[4,3-b]indole, 1H-benzo[a]carbazole, 1H-benzo[b]carbazole, 1H-benzo[c]carbazole, [1,6,2]oxathiazepino[2',3':1,2]pyrido[3,4-b]indole, 1H-azepino[1',2':1,2]pyrido[3,4-b]indole, 1H-pyrido[1',2':1,2]azepino[4,5-b]indole, 2H-pyrido[1',2':1,2]azepino[3,4-b]indole, 1H-pyrido[3',2':5,6]oxepino[3,2-b]indole, 1H-pyrido[4',3':5,6]oxepino[3,2-b]indole, 2H-pyrido[2',3':5,6]oxepino[2,3-b]indole, 2H-pyrido[2',3':5,6]oxepino[3,2-b]indole, 2H-pyrido[3',4':5,6]oxepino[3,2-b]indole, pyrido[2',3':4,5]cyclohepta[1,2-b]indole, pyrido[3',2':3,4]cyclohepta[1,2-b]indole, pyrido[3',4':4,5]cyclohepta[1,2-b]indole, pyrido[3',4':5,6]cyclohepta[1,2-b]indole, 2H-pyrano[3',2':2,3]azepino[4,5-b]indole, 1H-indolo[3,2-b][1,5]benzoxazepine, 1H-indolo[3,2-d][1,2]benzoxazepine, 1H-indolo[2,3-c][1,5]benzothiazepine, [1,4]diazepino[2,3-a]carbazole, indolo[2,3-b][1,5]benzodiazepine, indolo[2,3-d][1,3]benzodiazepine, indolo[3,2-b][1,4]benzodiazepine, indolo[3,2-b][1,5]benzodiazepine, indolo[3,2-d][1,3]benzodiazepine, indolo[3,2-d][2,3]benzodiazepine, indolo[2,3-a][3]benzazepine, indolo[2,3-c][1]benzazepine, indolo[2,3-d][1]benzazepine, indolo[2,3-d][2]benzazepine, indolo[3,2-b][1]benzazepine, indolo[3,2-c][1]benzazepine, indolo[3,2-d][1]benzazepine, 1H-indolo[2,1-b][3]benzazepine, 1H-[1]benzoxepino[5,4-b]indole, 1H-[2]benzoxepino[4,3-b]indole, 1H-[1]benzothiepino[4,5-b]indole, 1H-[1]benzothiepino[5,4-b]indole, benzo[3,4]cyclohepta[1,2-b]indole, benzo[4,5]cyclohepta[1,2-b]indole, benzo[5,6]cyclohepta[1,2-b]indole, benzo[6,7]cyclohepta[1,2-b]indole, cyclohepta[b]carbazole, 4H-[1,5]oxazocino[5',4':1,6]pyrido[3,4-b]indole, azocino[1',2':1,2]pyrido[3,4-b]indole, 2,6-methano-2H-azecino[4,3-b]indole, 3,7-methano-3H-azecino[5,4-b]indole, pyrido[1',2':1,8]azocino[5,4-b]indole, pyrido[4',3':6,7]oxocino[2,3-b]indole, pyrido[4',3':6,7]oxocino[4,3-b]indole, 1,5-methano-1H-azecino[3,4-b]indole, 2,6-methano-1H-azecino[5,4-b,]indole, 1H-pyrido[3',4':5,6]cycloocta[1,2-b]indole, 1,4-ethanooxocino[3,4-b]indole, pyrano[3',4':5,6]cycloocta[1,2-b]indole, 1H-indolo[2,3-c][1,2,5,6]benzotetrazocine, 1H-indolo[2,3-c][1,6]benzodiazocine, 6,13b-methano-13bH-azecino[5,4-b]indole, oxocino[3,2-a]carbazole, 1H-benzo[g]cycloocta[b]indole, 6,3-(iminomethano)-2H-1,4-thiazonino[9,8-b]indole, 1H,3H-[1,4]oxazonino[4',3':1,2]pyrido[3,4-b]indole, 2H-3,6-ethanoazonino[5,4-b]indole, 2H-3,7-methanoazacycloundecino[5,4-b]indole, 1H-6,12b-ethanoazonino[5,4-b]indole, indolo[3,2-e][2]benzazonine, 5,9-methanoazacycloundecino[5,4-b]-indole, 3,6-ethano-3H-azecino[5,4-b]indole, 3,7-imethano-3H-azacycloundecino[5,4-b]indole, pyrano[4',3':8,9]azecino[5,4-b]indole, 1H-indolo[2,3-c][1,7]benzodiazecine, 1H-indolo[3,2-e][2]benzazecine, benzo[b]pyrrolo[3,2-b]indole, benzo[e]pyrrolo[3,2-g]indole, benzo[e]pyrrolo[3,2,1-hi]indole, benzo[e]pyrrolo[3,4-b]indole, benzo[g]pyrrolo[3,4-b]indole, 1H-benzo[f]pyrrolo[1,2-a]indole, 1H-benzo[g]pyrrolo[1,2-a]indole, 2H-benzo[e]pyrrolo[1,2-a]indole, 1H-benzo[f]pyrrolo[2,1-a]isoindole, 1H-benzo[g]pyrrolo[2,1-a]isoindole, 2H-benzo[e]pyrrolo[2,1-a]isoindole, isoindolo[6,7,1-cde]indole, spiro[cyclohexane-1,5'-[5H]pyrrolo[2,1-a]isoindole], isoindolo[7,1,2-hij]quinoline, 7,11-methanoazocino[1,2-a]indole, 7,11-methanoazocino[2,1-a]isoindole, dibenz[cd,f]indole, dibenz[cd,g]indole, dibenz[d,f]indole, 1H-dibenz[e,g]indole, 1H-dibenz[e,g]isoindole, naphth[1,2,3-cd]indole, naphth[1,8-ef]indole, naphth[1,8-fg]indole, naphth[3,2,1-cd]indole, 1H-naphth[1,2-e]indole, 1H-naphth[1,2-f]indole, 1H-naphth[1,2-g]indole, 1H-naphth[2,1-e]indole, 1H-naphth[2,3-e]indole, 1H-naphth[1,2-f]isoindole, 1H-naphth[2,3-e]isoindole, spiro[1H-carbazole-1,1'-cyclohexane], spiro[2H-carbazole-2,1'-cyclohexane], spiro[3H-carbazole-3,1'-cyclohexane], cyclohepta[4,5]pyrrolo[3,2-f]quinoline, cyclohepta[4,5]pyrrolo[3,2-h]quinoline, azepino[4,5-b]benz[e]indole, 1H-azepino[1,2-a]benz[f]indole, 1H-azepino[2,1-a]benz[f]isoindole, benzo[e]cyclohepta[b]indole, and benzo[g]cyclohepta[b]indole;

(5) the phenyl group fused to a tricyclic hetero system:

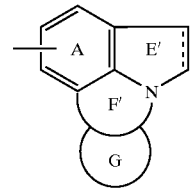

wherein ----- represents a single bond or a double bond; ring E' and ring F' are as defined hereinafter, which corresponds to the group available upon elimination of one hydrogen atom from a tetracyclic hetero ring system and, as such, includes but is not limited to 1H-dipyrrolo[2,3-b:3',2',1'-hi]indole, spiro[cyclopentane-1,2'(1'H)-pyrrolo[3,2,1-hi]indole], spiro[imidazolidine-4,1'(2'H)-[4H]pyrrolo[3,2,1-ij]quinoline], pyrido[2,3-b]pyrrolo[3,2,1-hi]indole, pyrido[4,3-b]pyrrolo[3,2,1-hi]indole, benzo[de]pyrrolo[3,2,1-ij]quinoline, 3H-pyrrolo[3,2,1-de]acridine, 1H-pyrrolo[3,2,1-de]phenanthridine, spiro[cyclohexane-1,6'-[6H]pyrrolo[3,2,1-ij]quinoline], 4,9-methanopyrrolo[3,2,1-1m][1]benzazocine, spiro[cycloheptane-1,6'-[6H]pyrrolo[3,2,1-ij]quinoline], 1H-pyrano[3,4-d]pyrrolo[3,2,1-jk][1]benzazepine, 3H-benzo[b]pyrrolo[3,2,1-jk][4,1]benzoxazepine, 7H-indolo[1,7-ab][4,1]benzoxazepine, benzo[b]pyrrolo[3,2,1-jk][1,4]benzodiazepine, indolo[1,7-ab][1,4]benzodiazepine, indolo[1,7-ab][1]benzazepine, indolo[7,1-ab][3]benzazepine, 1H-cyclohepta[d][3,2,1-jk][1]benzazepine, spiro[azepino[3,2,1-hi]indole-7(4H),1'-cyclohexane], 4H-5,11-methanopyrrolo[3,2,1-no][1]benzazacycloundecine, spiro[azepino[3,2,1-hi]indole-7(4H),1'-cyclooctane], and so forth.

The "phenyl group fused to a tricyclic hetero system" includes not only the phenyl group fused to tricyclic hetero systems containing an optionally hydrogenated indole or isoindole ring but also the phenyl group fused to the following and other tricyclic hetero systems, inclusive of the corresponding dihydro, tetrahydro, hexahydro, octahydro, and decahydro compounds. For example, fluoranthene, acephenanthrylene, aceanthrylene, triphenylene, pyrene, chrysene, naphthacene, pleiadene, benz[a]anthracene, indeno[1,2-a]indene, cyclopenta[a]phenanthrene, pyrido[1',2':1,2]imidazo[4,5-b]quinoxaline, 1H-2-oxapyrene, spiro[piperidine-4,9'-xanthene], etc. can be mentioned.

The preferred group which is formed as the "phenyl group" of the "phenyl group which may be substituted and/or condensed" is fused to a tricyclic hetero system which may be substituted includes groups of the following formulas.

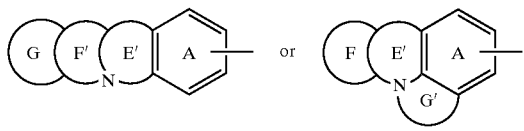

wherein ring E', ring F', and ring G' independently represent a 5- to 9-membered nitrogen-containing hetero ring which may be substituted by oxo in addition to $R^1$, ring A, ring F, ring G are as defined hereinbefore.

Particularly preferred is the group of the formula:

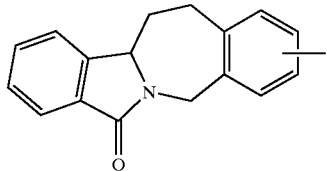

The "5- to 9-membered nitrogen-containing hetero ring" of the "5- to 9-membered nitrogen-containing hetero ring which may be substituted by oxo" includes the rings specifically mentioned for the "5- to 9-membered nitrogen-containing hetero ring" for ring C' and ring D'.

The preferred group which is formed as (2) the "phenyl group" of the "phenyl group which may be, substituted and/or condensed" for Ar is fused to a bicyclic hetero system which may be substituted or two similar or dissimilar monocyclic rings (at least one of the two rings is a monocyclic hetero ring) which may be substituted and (3) the "phenyl group" is fused to a tricyclic hetero system include the following groups:

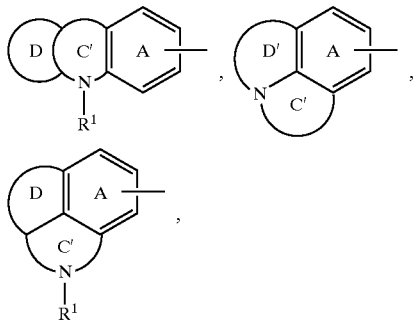

-continued

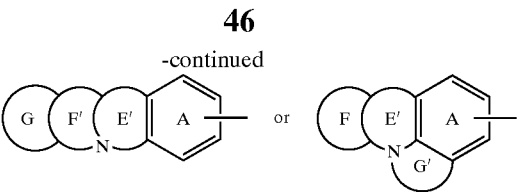

wherein the respective symbols are as defined hereinbefore.

Particularly preferred examples of the "phenyl group which may be substituted and/or condensed" for Ar are groups of the following formula:

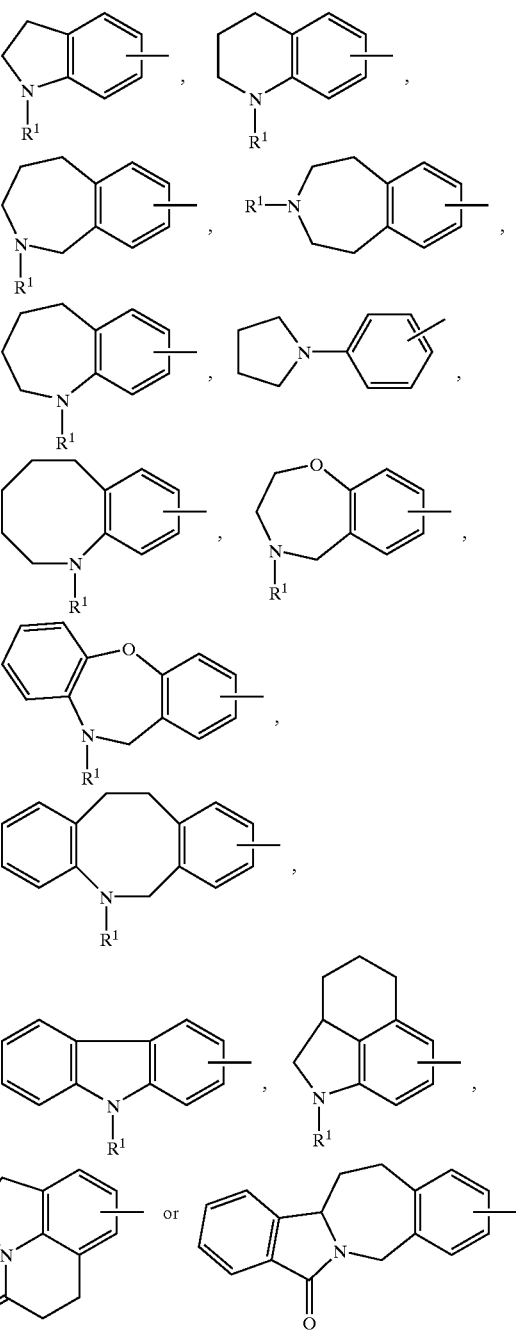

wherein $R^1$ is as defined hereinbefore.

For the best result, "phenyl group which may be substituted and/or condensed" for Ar are groups of the following formula:

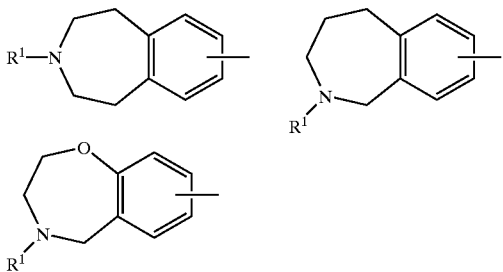

wherein R¹ is as defined hereinbefore.

In the formula, n represents an integer of 1 to 10, preferably 1 to 6, and more preferably 2 to 6, furtheremore preferably 3 to 6, for the best result 3, 4 or 5.

In the formula, R represents hydrogen atom or a hydrocarbon group which may be substituted, which may not be the same in its n occurrences.

The "hydrocarbon group" of, and "substituent" on, the hydrocarbon group which may be substituted" for R have the same meanings as the "hydrocarbon group" of, and "substituent" on, the "hydrocarbon group which may be substituted", which has been mentioned for R¹.

R may be bound to Ar or a substituent on Ar.

The compound of formula (I) wherein R is bound to Ar or a substituent or Ar includes compounds of the formula:

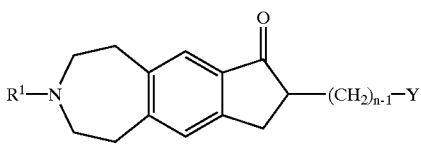

wherein R¹, n, and Y are as defined hereinbefore, compounds of the formula:

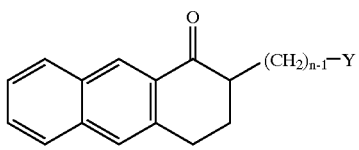

wherein n and Y are as defined hereinbefore, and compounds of the formula:

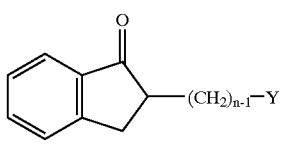

wherein n and Y are as defined hereinbefore.

Preferably, R is hydrogen atom.

In the formula, Y represents an amino group which may be substituted or a nitrogen-containing saturated heterocyclic group which may be substituted.

The "amino group which may be substituted" for Y includes but is not limited to groups of the formula:

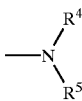

wherein $R^4$ and $R^5$ may be the same or different and each represents hydrogen atom, a hydrocarbon group which may be substituted, or an acyl group.

The "hydrocarbon group" of, and "substituent" on, the hydrocarbon group which may be substituted" for $R^4$ and $R^5$ includes but is not limited to the respective species mentioned for the "hydrocarbon group" and "substituent" for $R^1$.

The preferred hydrocarbon group which may be substituted as represented by $R^4$ and $R^5$ includes (1) a straight-chain or branched lower alkyl groups (e.g. $C_{1-6}$ alkyl such as methyl, ethyl, propyl, isopropyl, butyl, isobutyl, tert-butyl, sec-butyl, pentyl, hexyl, etc.) which may have 1 to 3 substituent groups selected from the group cinsisting of, (i) halogen (e.g. fluorine, chlorine, bromine, iodine), (ii) lower alkoxy (e.g. $C_{1-6}$ alkoxy such as methoxy, ethoxy, n-propyloxy, i-propyloxy, n-butyloxy, etc.), and (iii) hydroxy, and so on, and (2) lower aralkyl (e.g. $C_{7-16}$ aralkyl such as phenyl-$C_{1-10}$ alkyl (such as benzyl, phenethyl, phenylpropyl, phenylbutyl, phenylpentyl, phenylhexyl, etc.), naphthyl-$C_{1-6}$ alkyl (such as a-naphthylmethyl etc.), or diphenyl-$C_{1-3}$ alkyl (such as diphenylmethyl, diphenylethyl, etc.), and so on), which may have 1 to 3 substituents selected from the group consisting of (i) halogen (e.g. fluorine, chlorine, bromine, iodine), (ii) lower alkoxy (e.g. $C_{1-6}$ alkoxy such as methoxy, ethoxy, n-propyloxy, i-propyloxy, n-butyloxy, etc.), and (iii) hydroxy and so on.

The more preferred examples are (1) unsubstituted straight-chain or branched lower alkyl groups (e.g. $C_{1-6}$ alkyl such as methyl, ethyl, propyl, isopropyl, butyl, isobutyl, tert-butyl, sec-butyl, pentyl, hexyl, etc.) and (2) unsubstituted lower aralkyl groups such as $C_{7-16}$ aralkyl (e.g. phenyl-$C_{1-10}$ alkyl (such as benzyl, phenethyl, phenylpropyl, phenylbutyl, phenylpentyl, phenylhexyl, etc.), naphthyl-$C_{1-6}$ alkyl (e.g. a-naphthylmethyl etc.) and diphenyl-$C_{1-3}$ alkyl (e.g. diphenylmethyl, diphenylethyl, etc.), and so on.

The "acyl group" for $R^4$ and $R^5$ includes but is not limited to the species mentioned for the "acyl group" for $R^1$.

The "nitrogen-containing saturated heterocyclic group" of the "nitrogen-containing saturated heterocyclic group which may be substituted" for Y includes 5- to 9-membered nitrogen-containing saturated heterocyclic groups optionally containing 1 to 3 hetero atoms, such as nitrogen, oxygen and/or sulfur, in addition to carbon and one nitrogen atom. Each of those nitrogen-containing saturated heterocyclic groups may have a valence bond on a ring nitrogen atom or on a ring carbon atom. The group having a valence bond on a ring nitrogen atom includes groups of the formula:

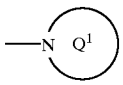

wherein ring $Q^1$ represents a 5- to 9-membered nitrogen-containing saturated heterocyclic group which may contain 1 or 2 hetero atoms selected from among nitrogen, oxygen, sulfur, etc. in addition to carbon and one nitrogen atom. More specifically, the following groups can be generally selected:

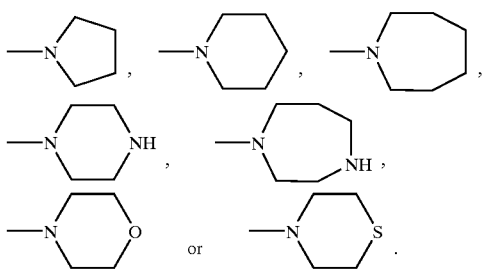

The group having a valence bond on a ring carbon atom includes but is not limited to groups of the formula:

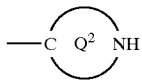

wherein ring $Q^2$ represents a 5- to 9-membered nitrogen-containing saturated heterocyclic group which may contain 1 or 2 hetero atoms selected from among nitrogen, oxygen, sulfur, etc. in addition to carbon and one nitrogen atom. Preferred examples are groups of the following formulas:

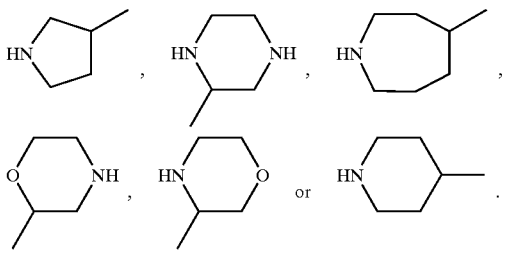

The "substituent" that may-be present on the "nitrogen-containing saturated heterocyclic group which may be substituted", as mentioned for Y, includes (1) those groups specifically mentioned for the "substituent" on the "nitrogen-containing hetero ring which may be substituted" which may be formed by $R^2$ and $R^3$ in combination with the adjacent nitrogen atom, and (2) the groups mentioned for the "hydrocarbon group which may be substituted", the "acyl group", and the "heterocyclic group which may be substituted" for $R^1$.

The preferred "nitrogen-containing saturated heterocyclic group" of the "nitrogen-containing saturated heterocyclic group which may be substituted" for Y includes 4-piperidinyl, 1-piperidinyl, or 1-piperazinyl.

Preferably, Y represents a group of the formula:

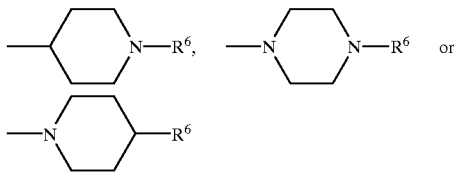

wherein $R^6$ represents the group same as defined for $R^1$.

More preferably, Y represents a group of the formula:

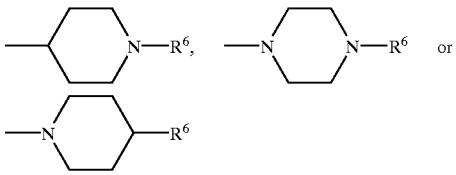

wherein $R^6$ represents (i) a phenyl-$C_{1-6}$ alkyl group which may be substituted by $C_{1-6}$ alkyl, $C_{1-6}$ alkoxy, halogen, nitro, mono- or di-$C_{1-6}$ alkyl-carbamoyloxy, hydroxy, cyano, carboxyl, $C_{1-6}$ alkoxy-carbonyl, carbamoyl, mono-lower alkyl-carbamoyl, di-lower alkyl-carbamoyl, cyclicamino-carbonyl which may be substituted, amino, mono-lower alkylamino, di-lower alkylamino, 5- to 7-membered cyclic amino which may contain 1 to 3 hetero atoms selected from the group consisting of nitrogen, oxygen, and sulfur, in addition to carbon and one nitrogen atom, $C_{1-6}$ alkyl-carbonylamino, phenylsulfonylamino, $C_{1-6}$ alkyl-sulfonylamino, amidino, ureido, or heterocyclic ring (the above mentioned $C_{1-6}$ alkyl, $C_{1-6}$ alkoxy, carbamoyl, cyclicamino-carbonyl, amino, phenylsulfonylamino, amidino, ureido, an d heterocyclic ring may be still substituted by the "substituentt" for the "hydrocarbon group which may be substituted" which has been mentioned for $R^1$), (ii)a hydrogen atom, (iii) a $C_{1-6}$ alkyl group which may be substituted by halogen, hydroxy, $C_{1-6}$ alkoxy, amino, mono- or di-$C_{1-6}$ alkylamino, carboxyl, cyano or $C_{1-6}$ alkoxy-carbonyl, or (iv)a $C_{1-6}$ alkyl-carbonyl group which may be substituted by mono-or di-$C_{1-6}$ alkyl-amino or $C_{1-6}$ alkoxy-carbonyl, preferably $R^6$ represents a benzyl group which may be substituted, the substitutent being selected from the group consisting of $C_{1-4}$ alkyl (e.g. methyl etc.), trihalogeno (e.g. fluoro etc.)-$C_{1-4}$ alkyl (e.g. methyl etc.), halogen (e.g. fluoro, chloro etc.), nitro, cyano, $C_{1-4}$ alkoxy,(e.g. methoxy etc.), hydroxy, carbamoyl, (4-$C_{1-4}$ alkyl (e.g. methyl etc.) piperazinyl)carbonyl, morpholinocarbonyl, carboxyl, $C_{1-4}$ alkoxy (e.g. methoxy etc.)carbonyl, $C_{1-4}$ alkoxy (e.g. ethoxy etc.)carbonyl-$C_{1-4}$ alkoxy (e.g. methoxy etc.), carboxyl-$C_{1-4}$ alkoxy (e.g. methoxy etc.), $C_{1-4}$ alkoxy (e.g. ethoxy etc.) carbonyl-$C_{1-6}$ alkyl (e.g. isopropyl etc.), carboxyl-$C_{16}$alkyl (e.g. isopropyl etc.), amino, acetylamino, $C_{1-4}$ alkyl (e.g. methyl etc.)sulfonylamino, (4-$C_{1-4}$ alkyl (e.g. methyl etc.) phenyl)sulfonylamino, ureido, 3-$C_{1-4}$ alkyl (e.g. methyl etc.) ureido, amidino, dihydrothiazolyl, or dihydroimidazolyl, more preferably $R^6$ represents a benzyl group which may be substituted by $C_{1-4}$ alkyl (e.g. methyl etc.), trihalogeno (e.g. fluoro etc.)-$C_{1-4}$ alkyl (e.g. methyl etc.), halogen (e.g. fluoro, chloro etc.), nitro, hydroxy, carbamoyl, amino, amidino, dihydroimidazolyl.

Particularly, Y is a group most usually selected from the group consisting of 1-benzyl-4-piperidihyl, 4-benzyl-1-piperidinyl, 4-benzyl-1-piperazinyl, 1-acetyl-4-piperidinyl, 1-[(2-methylphenyl)methyl]-4-piperidinyl, 1-[(3-chlorophenyl)methyl]-4-piperidinyl, 1-[(2-chlorophenyl) methyl]-4-piperidinyl, 1-[(3-nitrophenyl)methyl]-4-piperidinyl, 1-[(3-(trifluoromethyl)phenyl)methyl]-4-piperidinyl are preferred, with 1-benzyl-4-piperidinyl, 1-acetyl-4-piperidinyl, 1-[(2-methylphenyl)methyl]-4-piperidinyl, 1-[(3-chlorophenyl)methyl]-4-piperidinyl, 1-[(2-chlorophenyl)methyl]-4-piperidinyl, 1-[(3-nitrophenyl)methyl]-4-piperidinyl, 1-[[3-(trifluoromethyl) phenyl]methyl]-4-piperidinyl.

For the best result, Y represents a group of the formula:

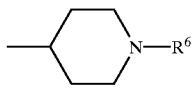

wherein $R^6$ is as defined hereinbefore, for the still best result, 1-acetyl-4-piperidinyl, 1-[(2-methylphenyl)methyl]-4-piperidinyl, 1-[(3-chlorophenyl)methy]-4-piperidinyl, 1-[(2-chlorophenyl)methy]-4-piperidinyl can be used.

Among compounds of formula (I), the preferred compounds are such that

Ar represents a group of the formula:

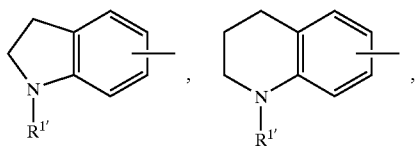

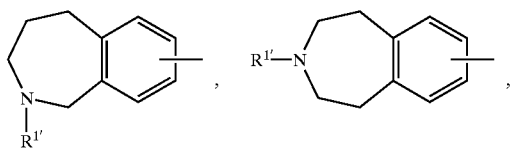

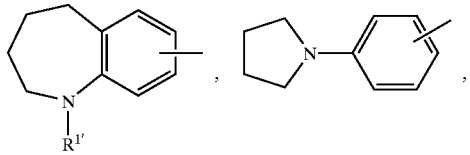

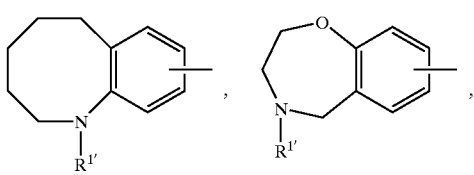

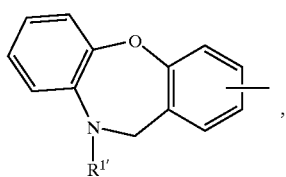

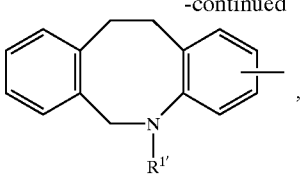

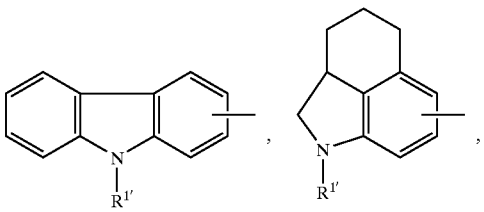

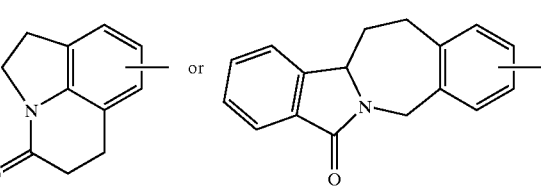

wherein $R^1$ represents (i) hydrogen atom, (ii) a $C_{1-6}$ alkyl group, (iii) a phenyl-$C_{1-6}$ alkyl group which may be substituted by $C_{1-6}$ alkyl, $C_{1-6}$ alkoxy, halogen, or nitro, or (iv) —(C=O)-$R^{2'}$ ($R^{2'}$ represents a phenyl or phenyl-$C_{1-6}$ alkyl group, which may be substituted by $C_{1-6}$ alkyl or $C_{1-6}$ alkoxy);

n is 2,3 or 4;

R represents hydrogen atom; and

Y represents a group of the formula:

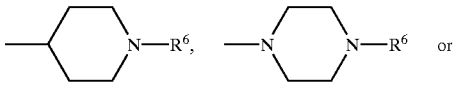 

wherein $R^6$ represents a phenyl-$C_{1-6}$ alkyl group which may be substituted by $C_{1-6}$ alkyl, $C_{1-6}$ alkoxy, halogen, nitro, mono- or di-$C_{1-6}$ alkyl-carbamoyloxy, (ii) hydrogen atom, (iii) a $C_{1-6}$ alkyl group which may be substituted by halogen, hydroxy, $C_{1-6}$ alkoxy, amino, mono- or di-$C_{1-6}$ alkylamino, carboxyl, or $C_{1-6}$ alkoxy-carbonyl, or (iv) a $C_{1-6}$ alkyl-carbonyl group.

More specifically, the following compounds of the compound categories (I), inclusive of their salts, are preferred.

TABLE 1

$$\text{Ar} - \overset{\overset{\displaystyle O}{\|}}{\underset{\underset{\displaystyle R}{|}}{C}} - (CH)_n - Y \qquad (I)$$

| Compound No. | Ar | R | Y | n |
|---|---|---|---|---|
| 1 | 4-MeO-benzyl-N-(7-membered ring fused to methyl-benzene) | H | 4-(N-benzyl)piperidinyl | 2 |
| 2 | Et-N-(7-membered ring fused to methyl-benzene) | H | 4-(N-benzyl)piperidinyl | 2 |
| 3 | H-N-(7-membered ring fused to methyl-benzene) | H | 4-(N-benzyl)piperidinyl | 2 |
| 4 | 4-MeO-benzyl-N-(7-membered ring fused to methyl-benzene) | H | 4-(N-benzyl)-N'-methyl-piperazinyl | 2 |
| 5 | 4-MeO-benzoyl-N-(7-membered ring fused to methyl-benzene) | H | 4-(N-benzyl)piperidinyl | 2 |
| 6 | benzyl-N-(7-membered ring fused to methyl-benzene) | H | 4-(N-benzyl)piperidinyl | 2 |
| 7 | benzyl-N-(7-membered O-containing ring fused to methyl-benzene) | H | 4-(N-benzyl)piperidinyl | 2 |
| 8 | 4-MeO-benzyl-N-(7-membered O-containing ring fused to methyl-benzene) | H | 4-(N-benzyl)piperidinyl | 2 |

TABLE 1-continued $$Ar-\underset{R}{\underset{|}{C}}-(CH)_n-Y \quad (I)$$
(with C=O)

| Compound No. | Ar | R | Y | n |
|---|---|---|---|---|
| 9 | (1-methyl-substituted tricyclic indoline) | H | (4-methylpiperidinyl-N-benzyl) | 2 |

TABLE 2

$$Ar-\underset{R}{\underset{|}{C}}-(CH)_n-Y \quad (I)$$

| Compound No. | Ar | R | Y | n |
|---|---|---|---|---|
| 10 | (N-benzyl-methyl-benzazepine, 7-membered) | H | (N-benzylpiperazinyl) | 2 |
| 11 | (methyl-benzazepine, 7-membered, NH) | H | (4-methylpiperidinyl-N-benzyl) | 2 |
| 12 | (N-methyl-methyl-tetrahydroquinoline) | H | (4-methylpiperidinyl-N-benzyl) | 2 |
| 13 | (N-ethyl-methyl-tricyclic indoline) | H | (4-methylpiperidinyl-N-benzyl) | 2 |
| 14 | (N-propyl-methyl-tricyclic indoline) | H | (4-methylpiperidinyl-N-benzyl) | 2 |

TABLE 2-continued
$$\underset{R}{Ar-\overset{O}{\underset{\|}{C}}-(CH)_n-Y} \quad (I)$$
| Compound No. | Ar | R | Y | n |
|---|---|---|---|---|
| 15 | 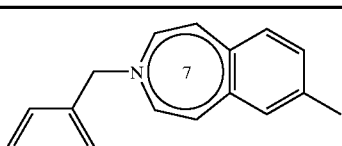 | H | 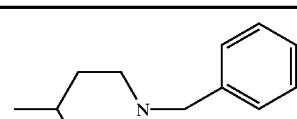 | 2 |
| 16 | 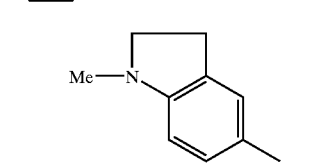 | H | 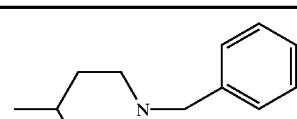 | 2 |
| 17 | 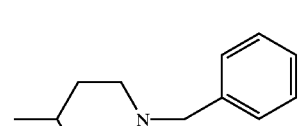 | H | 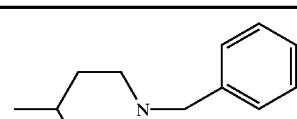 | 2 |
| 18 | 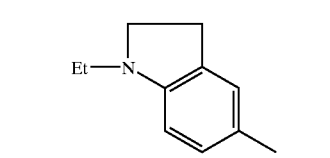 | H | 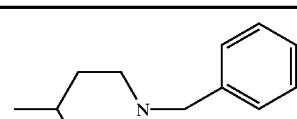 | 2 |
TABLE 3
$$\underset{R}{Ar-\overset{O}{\underset{\|}{C}}-(CH)_n-Y} \quad (I)$$
| Compound No. | Ar | R | Y | n |
|---|---|---|---|---|
| 19 | 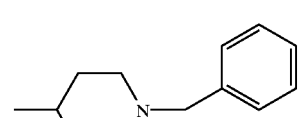 | H | 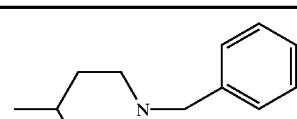 | 2 |
| 20 | 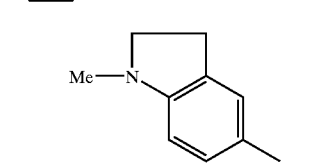 | H | 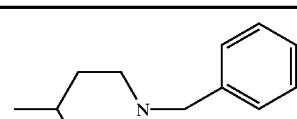 | 2 |
| 21 | 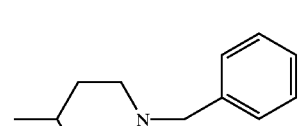 | H | 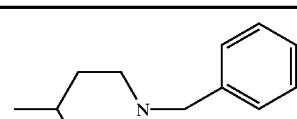 | 2 |

TABLE 3-continued
(I)
$$Ar-\overset{O}{\underset{R}{C}}-(CH)_n-Y$$
| Compound No. | Ar | R | Y | n |
|---|---|---|---|---|
| 22 | 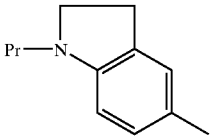 | H | 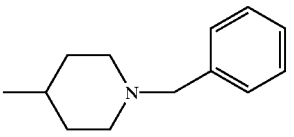 | 2 |
| 23 | 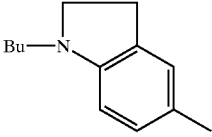 | H | 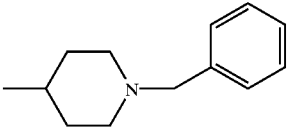 | 2 |
| 24 | 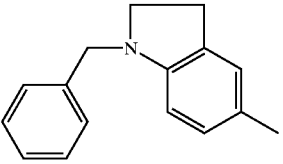 | H | 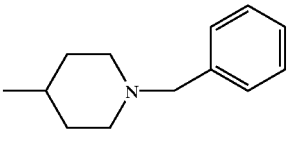 | 2 |
| 25 | 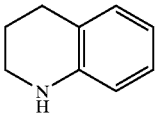 | H | 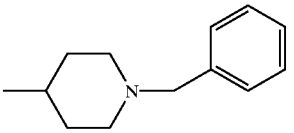 | 2 |
| 26 | 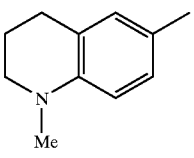 | H | 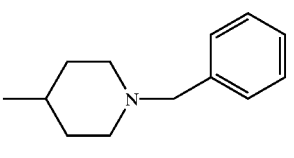 | 2 |
| 27 | 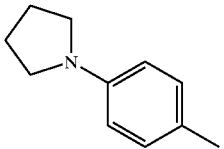 | H | 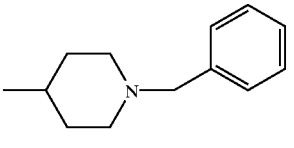 | 2 |
TABLE 4
(I)
$$Ar-\overset{O}{\underset{R}{C}}-(CH)_n-Y$$
| Compound No. | Ar | R | Y | n |
|---|---|---|---|---|
| 28 | 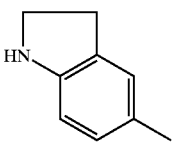 | H | 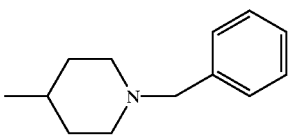 | 2 |

TABLE 4-continued $$Ar-\overset{O}{\underset{\|}{C}}-\underset{R}{(CH)_n}-Y \qquad (I)$$

| Compound No. | Ar | R | Y | n |
|---|---|---|---|---|
| 29 | 2-methyl-N-methyl-indole (7-membered ring labeled) | H | 4-benzylpiperidinyl | 2 |
| 30 | 6-methyl-thiochroman | H | 4-benzylpiperidinyl | 2 |
| 31 | N-benzoyl-6-methyl-benzoxazepine (7) | H | 4-benzylpiperidinyl | 2 |
| 32 | N-phenylacetyl-6-methyl-benzoxazepine (7) | H | 4-benzylpiperidinyl | 2 |
| 33 | N-(2-methoxybenzoyl)-6-methyl-benzoxazepine (7) | H | 4-benzylpiperidinyl | 2 |
| 34 | N-(4-methoxybenzoyl)-6-methyl-benzoxazepine (7) | H | 4-benzylpiperidinyl | 2 |
| 35 | N-(2-methylbenzoyl)-6-methyl-benzoxazepine (7) | H | 4-benzylpiperidinyl | 2 |

TABLE 4-continued
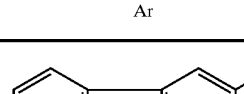
(I)
| Compound No. | Ar | R | Y | n |
|---|---|---|---|---|
| 36 | 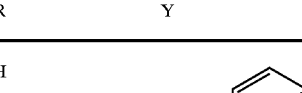 | H | 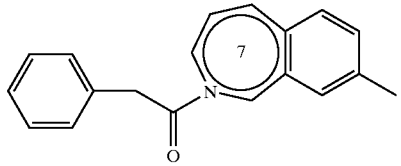 | 2 |
TABLE 5
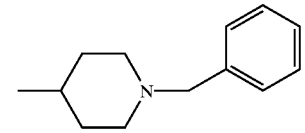
(I)
| Compound No. | Ar | R | Y | n |
|---|---|---|---|---|
| 37 | 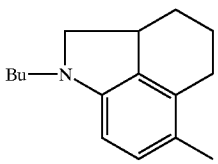 | H | 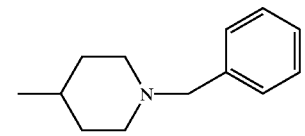 | 2 |
| 38 | 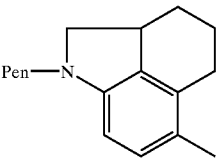 | H | 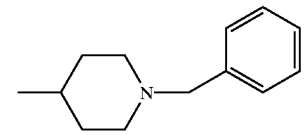 | 2 |
| 39 | 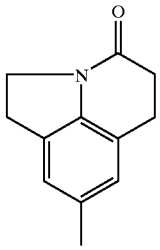 | H | 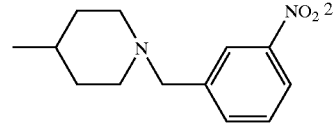 | 2 |
| 40 | (structure with ketone and methyl) | H | (4-piperidinyl-CH2-3-nitrophenyl) | 2 |

TABLE 5-continued $$Ar-\overset{O}{\underset{R}{C}}-(CH)_n-Y \quad (I)$$

| Compound No. | Ar | R | Y | n |
|---|---|---|---|---|
| 41 | 8-methyl-pyrrolo[3,2,1-ij]quinolin-4(5H)-one-ring | H | 4-methylpiperidinyl-CH2-(2-methylphenyl) | 2 |
| 42 | 8-methyl-pyrrolo[3,2,1-ij]quinolin-4(5H)-one-ring | H | 4-methylpiperidinyl-CH2-(3-methylphenyl) | 2 |
| 43 | 8-methyl-pyrrolo[3,2,1-ij]quinolin-4(5H)-one-ring | H | 4-methylpiperidinyl-CH2-(3-chlorophenyl) | 2 |
| 44 | N-acetyl-methyl-dibenzoxazepine (7-membered) | H | 4-benzylpiperidinyl | 2 |
| 45 | NH-methyl-dibenzoxazepine (7-membered) | H | 4-benzylpiperidinyl | 2 |

TABLE 6

$$\text{Ar} - \overset{\overset{O}{\|}}{\underset{R}{C}} - (CH)_n - Y \quad (I)$$

| Compound No. | Ar | R | Y | n |
|---|---|---|---|---|
| 46 | 5-methyl-indoline (HN) | H | 4-(3-chlorobenzyl)piperidine | 2 |
| 47 | 1-ethyl-8-methyl-benzazepine (7-membered) | H | 4-benzylpiperidine | 2 |
| 48 | 1-propyl-8-methyl-benzazepine (7-membered) | H | 4-benzylpiperidine | 2 |
| 49 | 4-(4-chlorobenzyl)-benzoxazepine (7-membered) | H | 4-benzylpiperidine | 2 |
| 50 | 4-(4-fluorobenzyl)-7-methyl-benzoxazepine (7-membered) | H | 4-benzylpiperidine | 2 |
| 51 | 4-(4-nitrobenzyl)-7-methyl-benzoxazepine (7-membered) | H | 4-benzylpiperidine | 2 |
| 52 | 1-benzyl-methyl-tricyclic indoline | H | 4-benzylpiperidine | 2 |
| 53 | 1-acetyl-methyl-tricyclic indoline | H | 4-benzylpiperidine | 2 |

TABLE 6-continued $$Ar-\underset{R}{\overset{O}{\overset{\|}{C}}}-(CH)_n-Y \quad (I)$$

| Compound No. | Ar | R | Y | n |
|---|---|---|---|---|
| 54 | (indole fused with 7-membered lactam ring bearing methyl-substituted benzene) | H | 4-benzylpiperidin-1-yl | 2 |

TABLE 7

$$Ar-\underset{R}{\overset{O}{\overset{\|}{C}}}-(CH)_n-Y \quad (I)$$

| Compound No. | Ar | R | Y | n |
|---|---|---|---|---|
| 55 | N-benzoyl-methyl-substituted tricyclic indoline | H | 4-benzylpiperidin-1-yl | 2 |
| 56 | dibenzazocine (NH), methyl-substituted | H | 4-benzylpiperidin-1-yl | 2 |
| 57 | dibenzazocine (N-benzyl), methyl-substituted | H | 4-benzylpiperidin-1-yl | 2 |
| 58 | 5-methylindoline | H | 4-(3-methylbenzyl)piperidin-1-yl | 2 |
| 59 | 5-methylindoline | H | 4-(3-fluorobenzyl)piperidin-1-yl | 2 |

TABLE 7-continued

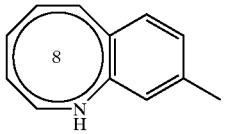

| Compound No. | Ar | R | Y | n |
|---|---|---|---|---|
| 60 | 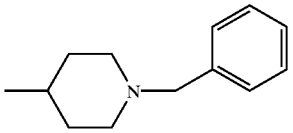 | H | 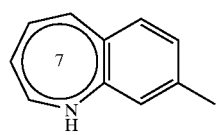 | 2 |
| 61 | 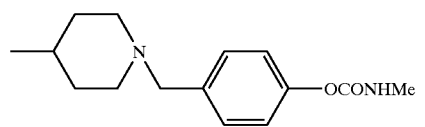 | H | 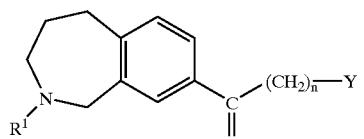—OCONHMe | 2 |

In the above chemical formulas of Compound 1 to Compound 61, Me stands for methyl, Et for ethyl, Bu for butyl, Pr for propyl, iPr for isopropyl, Pen for pentyl, MeO for methoxy, Ph for phenyl, and Ac for acetyl.

The compounds of the following formulas:

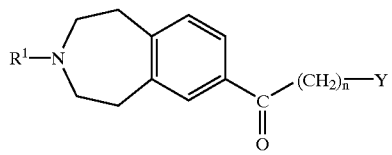

wherein $R^1$ represents a hydrogen atom, a hydrocarbon group which maybe substituted, an acyl group, or a heterocyclic group which may be substituted; n represents an integer of 1 to 10; Y represents an amino group which may be substituted or a nitrogen-containing saturated heterocyclic group which may be substituted, or a salt thereof, are more preferred.

The salt of said compound (I), (Ia), (Ib), or (Ic) is preferably a biologically acceptable acid addition salt. The salt, thus, includes salts with inorganic acids (such as hydrochloric acid, phosphoric acid, hydrobromic acid, sulfuric acid, etc.) and salts with organic acids (such as acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.).

In addition, in cases compound (I) of the present invention has an acidic group such as —COOH, the compound (I) may form salts with inorganic bases (such as sodium, potassium, calcium, magnesium,etc.) ammonia, etc. or organic bases (such as triethylamine etc.). Such salts are also subsumed in the concept of the objective compound of the present invention.

Furthermore, said compound (I) may be a hydrate or an anhydrous compound.

Compound (I) and its salts, mentioned above, can be produced in accordance with the per se known processes. Referring to the formula, (1) where the "phenyl which may be substituted and/or condensed" for Ar does not form a fused ring system, the process described in Japanese Patent Unexamined Publication No. 173867/1991 (EP-A-0378207) or Japanese Patent Unexamined Publication No. 79151/1989 (EP-A-0296560) can be used.

(2) where the "phenyl which may be substituted and/or condensed" for Ar is fused to a monocyclic hetero ring which may be substituted, the process described in Japanese Patent Unexamined Publication No. 140149/1993 (EP-A-0487071), Japanese Patent Unexamined Publication No. 166676/1994 (EP-A-0560235), Japanese Patent Unexamined Publication No. 206875/1994 (EP-A-0567090) or Japanese Patent Unexamined Publication No. 169569/1990 (U.S. Pat. No. 4,895,841) can be used.

(3) where the "phenyl which may be substituted and/or condensed" for Ar is fused to a bicyclic hetero system which may be substituted or two similar or dissimilar monocyclic rings (at least one of the two rings is a monocyclic hetero ring) which may be substituted, the process described in Japanese Patent Unexamined Publication No. 206854/1995 (EP-A-0607864) can be used.

(4) where the "phenyl which may be substituted and/or condensed for Ar is fused to a tricyclic hetero system which may be substituted, the process described in Japanese Patent Unexamined Publication No. 309835/1995 (EP-A-0655451) can be used.

A method of producing the compound (Ia), (Ib), (Ic) or a salt thereof is hereinafter described in detail.

Although the following description of the production process is applicable not only to the compound (Ia), (Ib), (Ic) themselves but also to the above-described salt thereof, the salt is also referred to as the compound (Ia–c) in the description below.

The compound (Ia–c) can be produced by reacting (1), a compound represented, by the formula:

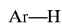 (II)

wherein Ar represents the group represented by following formulas:

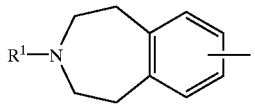

for the production of (Ia),

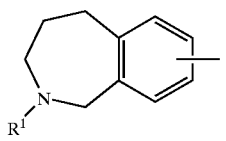

for the production of (Ib),

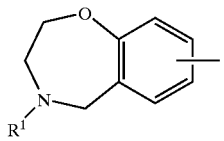

for the production of (Ic), or salt thereof, and (2) a compound represented by the formula:

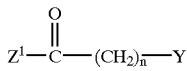 (III)

wherein $Z^1$ represents a leaving group; the other symbols have the same definitions as above or a salt thereof.

The leaving group for $Z^1$ is exemplified by a halogen atom (e.g., chlorine, bromine, iodine etc.), a $C_{1-6}$ alkylsulfonyloxy group (e.g., methanesulfonyloxy, ethanesulfonyloxy etc.) or a $C_{6-10}$ arylsulfonyloxy group (e.g., benzenesulfonyloxy, p-toluenesulfonyloxy etc.), with preference given to a halogen atom (e.g., chlorine etc.) and others.

The compound (II) or a salt thereof can be produced by known methods or modifications thereof such as the methods described in Indian Journal of Chemistry, 2, 211(1964), Indian Journal of Chemistry, 12, 247(1974), Bulletin of The Chemical Society of Japan, 43,1824(1970), Chemical Pharmaceutical Bulletin, 20, 1328(1972), Chemical Pharmaceutical Bulletin, 27, 1982(1979), Helvetica Chimica Acta, 46, 1696(1963), Synthesis,541(1979), U.S. Pat. No. 3,682,962, U.S. Pat. No. 3,911,126, Ger.Offen. 2,314,392, Ger. 1,545, 805, Journal of Chemical Society, 1381(1949), Canadian Journal of Chemistry, 42, 2904(1964), Journal of Organic Chemistry, 28, 3058(1963), Journal of American Chemical Society, 76, 3194(1954), 87, 1397(1965), 88, 4061(1966) and Japanese Patent Unexamined Publication No. 41539/1974.

The compound (III) or a salt thereof can be produced by known methods or modifications thereof such as the methods described in Chemical Pharmaceutical Bulletin, 41, 529–538(1993), Chemical Pharmaceutical Bulletin, 34, 3747–3761(1986) and EP-A-0,378,207.

Salts of the compounds (II) and (III) include salts with inorganic acids (e.g., hydrochloric acid, phosphoric acid, hydrobromic acid, sulfuric acid etc.) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.). When having an acidic group such as —COOH, the compounds (II) and (III) may form a salt with an inorganic base (e.g., alkaline metal or alkaline earth metal (e.g., sodium, potassium, calcium, magnesium etc.), ammonia etc.) or an organic base (e.g., tri–$C_{1-3}$ alkylamine such as triethylamine etc.).

The reaction between the compound (III) or a salt thereof and the compound (II) or a salt thereof can be carried out by, for example, reacting them in the absence of a solvent or in a solvent as necessary. Any solvent for ordinary chemical represents can be used for this reaction, as long as the reaction is not interfered with the reaction. Such solvents include organic solvents such as hydrocarbon solvents (e.g., pentane, hexane, benzene, toluene, nitrobenzene etc.), halogenated hydrocarbon solvents (e.g., dichloromethane, chloroform, 1,2-dichloroethane, carbon tetrachloride etc.), ether solvents (e.g., ethyl ether, tetrahydrofuran, dioxane, diemthoxyethane etc.), nitroalkanes (e.g., nitromethane, nitroethane etc.), and carbon disulfide, with preference given to dichloromethane, 1,2-dichloroethane, nitrobenzene, carbon disulfide and others. The amount of solvent used is normally about 0.5 to about 100 ml, preferably about 5 to about 20 ml per mmol of the compound (III) or a salt thereof. Reaction temperature is normally about –30 to about 150° C., preferably about 20 to about 100° C. Reaction time is normally about 0.5 to about 72 hours, preferably about 1 to about 16 hours.

Lewis acids can be used in this rection if necessary. Such lewis acids include aluminum chloride, aluminum bromide, zinc chloride, titanium chloride, tin (IV) chloride, boron trifluoride, iron (II) chloride, iron (III) chloride, antimony (V) pentachloride, bismuth (III) chloride, mercury (II) chloride, hydrogen fluoride, sulfuric acid and polyphosphoric acid, with preference given to aluminum chloride and others. The amount of Lewis acid used is normally about 1 to about 10 mol, preferably about 2 to about 10 mol per mol of the compound (III) or a salt thereof. The amount of the compound (II) or a salt thereof used is normally about 1 to about 20 mol, preferably about 1 to about 5 mol per mol of the compound (III) or a salt thereof.

In the above reaction, the position at which the following group:

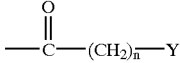

in the compound (III) or a salt thereof is introduced to the compound (II) or a salt thereof may be any one of the possible positions of substitution in ring A. However, when the compound (II) or a salt thereof has a 2,3,4,5-tetrahydro-1H-2-benzazepine skeleton(provided that ring A has no substituent), it is introduced mainly at the 8-position. However, compounds having an introduction at other positions (6-,7- or 9-positions) may be produced and separated.

With respect to the above reactions, provided that the starting material compound has an amino group, a carboxyl group, a hydroxy group or another group as a substituent therefor, such substituent may have a protecting group in common use in peptide chemistry etc. as introduced therein. The desired compound can be obtained by removing the protecting group as necessary completion of the reaction.

Protecting groups for the amino group include a form group a $C_{1-6}$ alkyl-carbonyl group which may be substituted (e.g., acetyl, ethylcarbonyl etc.), a benzyl group, a $C_{1-6}$ alkyl-oxycarbonyl group (e.g., methoxycarbonyl, ethoxycarbonyl etc.), a phenyloxycarbonyl, group (e.g., phenoxycarbonyl etc.), an acyl group such as a $C_{7-15}$alkyloxy-carbonyl group (e.g., b genyloxycarbonyl, fluorenyloxycarbonyl etc.), a hydrocarbon group ( e.g. trityl, phthaloyl, etc.). Substituents for these protecting groups include halogen atom (e.g., fluorine, chlorine, bromine, iodine etc.), $C_{1-6}$ alkyl-carbonyl (e.g., methylcarbonyl, ethylcarbonyl, butylcarbonyl etc.) and nitro, the number of substituents being about 1 to about 3. Protecting groups for the carboxyl group include a $C_{1-6}$ alkyl group which may be substituted (e.g., methyl, ethyl, n-propyl, isopropyl, n-butyl, tert-butyl etc.), a phenyl group, a trityl group and a silyl group. Substituents for these protecting groups include halogen (e.g., fluorine, chlorine, bromine or iodine etc.), formyl, $C_{1-6}$ alkyl-carbonyl (e.g., methylcarbonyl, ethylcarbonyl, butylcarbonyl etc.) and nitro, the number of substituents being about 1 to about 3.

Protecting groups for the hydroxyl group include a $C_{1-6}$ alkyl group which may be substituted (e.g., methyl, ethyl, n-propyl, isopropyl, n-butyl, tert-butyl eta.), a phenyl group, a $C_{7-10}$ aralkyl group (e.g, benzyl etc.), a formyl group, a $C_{1-6}$ alkylcarbonyl group (e.g., acetyl, ethylcarbonyl etc.), a phenyloxycarbonyl group (e.g., phenoxycarbonyl etc.), a $C_{7-10}$ aralkyl-carbonyl group (e.g., benzyloxycarbonyl etc.), a pyranyl group, a furanyl group and a silyl group. Substituents for these protecting groups include halogen (e.g., fluorine, chlorine, bromine, iodine etc.), $C_{1-6}$ alkyl, phenyl, $C_{7-10}$ aralkyl and nitro, the number of substituents being about 1 to 4.

These protecting groups can be removed by known methods or modifications thereof, including treatments With acid, base, reducing agents, ultraviolet rays, hydrazine, phenylhydrazine, sodium N-methyldithiocarbamate, tetrabutylammonium fluoride and palladium acetate.

When the compound (Ia–c) or a salt thereof thus obtained has an acylamino group which may be substituted, it can be converted to a compound or a salt thereof having a primary or secondary amino group by deacylation. The starting material compound (Ia–c) or a salt thereof having an acylamino group which may be substituted may be as isolated and purified by known means such as concentration, liquid property conversion, redissolution, solvent extraction, fractional distillation, distillation, crystallization, recrystallization and chromatography, or may be used in the form of a reaction mixture as such, without isolation, as a starting material. Accordingly, the compound (Ia–c) or a salt thereof having an acylamino group which may be substituted is kept at a temperature of normally about 10 to about 150° C., preferably about 50 to about 100° C., in an aqueous solution of antacid such as a mineral acid (e.g., nitric acid, hydrochloric acid, hydrobromic acid, iodic acid, sulfuric acid etc.) or a base such as an alkaline metal hydroxide ((e.g., sodium hydroxide, potassium hydroxide, barium hydroxide, lithium hydroxide etc.). The amount of such acid or base used is normally about 1 to about 100 mol, preferably about 1 to about 40 mol per mol of the compound (XII) or a salt thereof. The strength of acid or base is normally about about 0.1 to about 10 N, preferably about 2 to about 10 N. Although varying depending on reaction temperature, reaction time is normally about 1 to about 24 hours, preferably about 2 to about 10 hours.

By means of introducing a hydrocarbon group which may be substituted to a primary or secondary amino group of the thus-obtained compound (Ia–c) or a salt thereof, the compound (Ia–c) or a salt thereof having an amino group which may be substituted for by hydrocarbon which may be substituted was produced. The starting material compound (Ia–c) or a salt thereof having an primary or secondary amino group may be used after isolation and purification by known means such as concentration, liquid property conversion, redissolution, solvent extraction, fractional distillation, distillation, crystallization, recrystallization and chromatography, or may be used in the form of a reaction mixture as such, without isolation, as a starting material. Accordingly, the compound (Ia–c) or a salt thereof having an amino group substituted for by hydrocarbon which may be substituted can also be produced by reaction between the compound (Ia–c) or a salt thereof having a primary or secondary amino group and a compound represented by the formula:

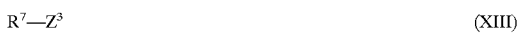

$$R^7-Z^3 \qquad (XIII)$$

wherein $R^7$ represents a hydrocarbon group which may be substituted; $Z^3$ represents a leaving group.

The optionally substituted hydrocarbon group for $R^7$ is exemplified by the same optionally substituted hydrocarbon groups as specified for $R^1$ or $R^6$ above.

The leaving group for $Z^3$ is exemplified by a halogen atom (e.g., chlorine, bromine and iodine etc.), a $C_{1-6}$ alkylsulfonyloxy group (e.g., methanesulfonyloxy, ethanesulfonyloxy etc.) or a $C_{6-10}$ arylsufonyloxy group (e.g., benzenesulfonyloxy, p-toluenesulfonyloxy etc.), with preference given to methanesulfonyloxy, or a halogen atom (e.g., chlorine, bromine etc.).

This reaction can be carried out in the presence or absence of a solvent, with a base added as necessary. Bases for this purpose include inorganic bases such as sodium carbonate, potassium carbonate, lithium carbonate, sodium hydroxide, potassium hydroxide, sodium methoxide, sodium ethoxide and sodium hydride, and organic bases such as pyridine, 4-dimethylaminopyridine and triethylamine. Any solvent can be used, as long as it does not interfere with the reaction, such solvents include lower alcohols such as methanol, ethanol, propanol, isopropanol, n-butanol and t-butanol, ethers such as dioxane, ether and tetrahydrofuran, aromatic hydrocarbons such as toluene, benzene and xylene, halogenated hydrocarbons such dichloromethane, 1,2-dichloroethane, amides such as dimethylformamide, dimethylacetamide and hexamethylphosphonotriamide, esters such as ethyl acetate and butyl acetate and nitriles such as acetonitrile and propionitrile. This reaction can be carried out under cooling conditions (about 0 to about 10° C.), at room temperature (about 10 to about 40° C.) or under heating conditions (about 40 to about 120° C.). Reaction time is normally about 10 minutes to about 48 hours, preferably about 2 to about 16 hours. The amount of compound (XIII) used is preferably about 0.3 to about 5.0 mol per mol of the compound (Ia–c) or a salt thereof having a primary or secondary amino group. The amount of base used is normally about 1 or more mol, preferably about 1.1 to about 5 mol per mol of the compound (Ia–c) or a salt thereof having a primary or secondary amino group.

Also this reaction may be accelerated as appropriate in the presence of an iodide such as sodium iodide, potassium iodide or lithium iodide. In this case, the amount of iodide used is normally about 1 to about 5 mol, preferably about 1.1 to about 1.5 mol per mol of the compound (XIII).

The compound (XIII) can be produced by known method or modifications thereof.

The compound (Ia–c) thus obtained can be converted to a salt by a conventional method when it is in a free form, and can be converted to a free form or another salt by a conventional method when it is in a salt form. The compound (Ia–c) or a salt thereof can be isolated and purified by known methods as described above. Also, the compound (Ia–c) or a salt thereof involves steric isomers based on the presence-of asymmetric carbon atoms. These isomers can also be isolated and purified by known methods as described above or other methods such as fractional recrystallization, and chromatography using optically active columns.

The following compounds of the compound categories (I), inclusive of their salts, are preferred novel compound.

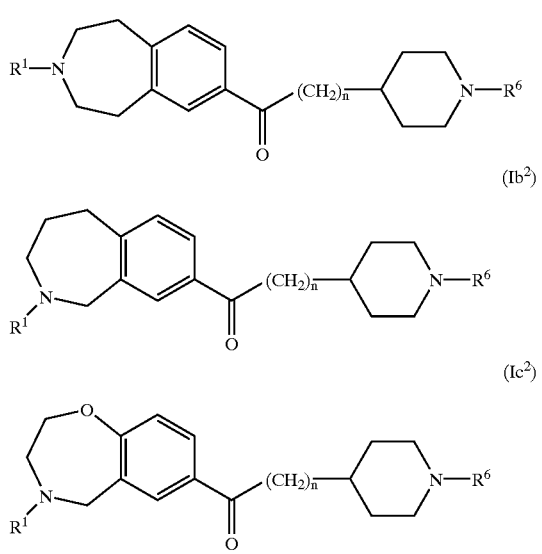

wherein $R^1$ is as defined hereinbefore; $R^6$ represents the group same as defined for $R^1$; n represents an integer of 3 to 6.

The prefered novel compounds (Ia$^2$), (Ib$_2$) and (Ic$^2$) or salts thereof can be can be produced in accordance with the per se known processes (e.g. EP-A-0487071, EP-A-0567090, etc.) or modifications thereof.

A method of producing the compound (Ia$^2$) or a salt thereof is hereinafter described in detail.

Although the following description of the production process is applicable not only to the compound (Ia$^2$) itself but also to the above-described salt thereof, the salt is also6referred to as the compound (Ia$^2$) in the description below.

The compound (Ia$^2$: $R^6$=W or H) can be produced by reacting a compound represented by the formula:

wherein $R^1$ is defined as hereinbefore, or sart thereof, with a compound represented by the formula:

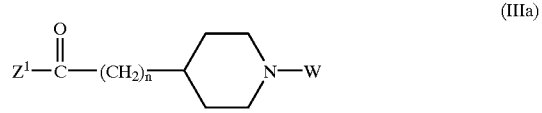

wherein $Z^1$ represents a leaving group; W represents a protective group; n represents an integer of 3 to 6, if necessary, followed by deprotectioning reaction.

The leaving group for $Z^1$ is exemplified by a halogen atom (e.g., chlorine, bromine, iodine etc.), a $C_{1-6}$ alkylsulfonyloxy group (e.g., methanesulfonyloxy, ethanesulfonyloxy etc.) or a $C_{6-10}$ arylsulfonyloxy group (e.g., benzenesulfonyloxy, p-toluenesulfonyloxy etc.), with preference given to a halogen atom (e.g., chlorine etc.) and others.

The compound (IIa) or a salt thereof can be produced by known methods or modifications thereof such as the methods described in Journal of Organic Chemistry, 34, 2235 (1969), Journal of Organic Chemistry, 54, 5574(1989), Tetrahedron Letters, 35, 3023(1977) and EP-A-0,487,071.

The compound (IIIa) or a salt thereof can be produced by known methods or modifications thereof such as the methods described in Chemical Pharmaceutical Bulletin, 41, 529–538(1993), Chemical Pharmaceutical Bulletin 34, Bulletin, 34, 3747–3761(1986), EP-A-0,378,207 and EP-A-0,487,071.

Salts of the compounds (IIa) and (IIIa) include salts with inorganic acids (e.g., hydrochloric acid, phosphoric acid, hydrobromic acid, sulfuric acid etc.) and salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid etc.). When having an acidic group such as —COOH, the compounds (IIa) and (IIIa) may form a salt with an inorganic base (e.g., alkaline metal or alkaline earth metal(e.g., sodium, potassium, calcium, magnesium etc.), ammonia etc.) or an organic base (e.g., tri–$C_{1-3}$ alkylamine such as triethylamine etc.).

The reaction between the compound (IIIa) or a salt thereof and the compound (IIa) or a salt thereof can be carried out by, for example, reacting them in the absence of a solvent or in a solvent as necessary. Any solvent for ordinary chemical represents can be used for this reaction, as long as the reaction is not interfered with the reaction. Such solvents include organic solvents such as hydrocarbon solvents (e.g., pentane, hexane, benzene, toluene, nitrobenzene etc.), halogenated hydrocarbon solvents (e.g., dichloromethane, chloroform, 1,2-dichloroethane, carbon tetrachloride etc.), ether solvents (e.g., ethyl ether, tetrahydrofuran, dioxane, diemthoxyethane etc.), nitroalkanes (e.g., nitromethane, propionitrile etc.), and carbon disulfide, with preference given to, dichloromethane, 1,2-dichloroethane, nitrobenzene, carbon disulfide and others. The amount of solvent used is normally about 0.5 to about 100 ml, preferably about 5to about 20 ml per mmol of the compound (IIIa) or a salt thereof. Reaction temperature is normally about −30 to about 150° C., preferably about 20 to about 100° C. Reaction time is normally about 0.5 to about 72 hours, preferably about 1 to about 16 hours.

Lewis acids can be used in this rection if necessary. Such lewis acids include aluminum chloride, aluminum bromide, zinc chloride, titanium chloride, tin (IV) chloride, boron trifluoride, iron (II) chloride, iron (III) chloride, antimony (V) pentachloride, bismuth (III) chloride, mercury (II) chloride, hydrogen fluoride, sulfuric acid and polyphosphoric acid, with preference given to aluminum chloride and others. The amount of Lewis acid used is normally about 1 to about 10 mol, preferably about 2 to about 10 mol per mol of the compound (IIIa) or a salt thereof. The amount of the compound (IIa) or a salt thereof used is normally about 1 to about 20 mol. preferably about 1 to about 5mol per mol of the compound (IIIa) or a salt thereof.

In the above reaction, the position at which the following group:

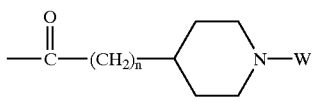

in the compound (IIIa) or a salt thereof is introduced to the compound (IIa) or a salt thereof may be any one of the possible positions of substitution in benzene ring in the compound (IIa). However, it is introduced mainly at the 7-position. However, compounds having an introduction at other positions (6, or 9-positions) may be produced and separated.

Protecting groups for the amino group represented as W, for example, include the hydrocarbon group which may be substituted and the acyl groups, specifically, an acyl group such as a formyl group, a $C_{1-6}$ alkyl-carbonyl group which may be substituted (e.g. acetyl, ethylcarbonyl etc.), a benzoyl group, a $C_{1-6}$ alkyl-oxycarbonyl group (e.g. methoxycarbonyl, ethoxycarbonyl etc.), a phenyloxycarbonyl group (e.g. phenoxycarbonyl etc.), a $C_{7-15}$ aralkylbxycarbonyl group (e.g. benzyloxycarbonyl, fluorenyloxycarbonyl etc.), a hydrocarbon group such as a trityl group and a phthaloyl group. Substituents for these protecting groups include halogen (e.g., fluorine, chlorines bromine, iodine etc.), $C_{1-6}$ alkyl-carbonyl (e.g., methylcarbonyl, ethylcarbonyl, butylcarbonyl etc.) and nitro, the number of substituents being about 1 to about 3.

With respect to the above reactions, provided that the starting material compound has an amino group, a carboxyl group, a hydroxy group or another group as a substituent therefor, such substituent may have a protecting group in common use in peptide chemistry etc. as introduced therein. The desired compound can be obtained by removing the protecting group as necessary upon completion of the reaction.

Protecting groups for the amino group is the group represented as W hereinbefore and so on.

Protecting groups for the carboxyl group include a $C_{1-6}$ alkyl group which may be substituted (e.g. methyl, ethyl, n-propyl, isopropyl, n-butyl, tert-butyl etc.), a phenyl group, a trityl group, and a silyl group. Substituents for these protecting groups include halogen (e.g. fluorine, chlorine, bromine or iodine etc.), formyl, $C_{1-6}$ alkyl-carbonyl (e.g., methylcarbonyl, ethylcarbonyl, butylcarbonyl etc.) and nitro, the number of substituents being about 1 to about 3.

Protecting groups for the hydroxyl group include a $c_{1-6}$ alkyl group which may be substituted (e.g. methyl, ethyl, n-propyl, isopropyl, n-butyl, tert-butyl etc.), a phenyl group, a $C_{7-10}$ aralkyl group (e.g. benzyl etc.), a formyl group,a $C_{1-6}$ alkylcatbdnyl group (e.g., acetyl, ethylcarbonyl etc.), a phenyloxycarbonyl group (e.g. phenoxycarbonyl etc.), a $C_{7-10}$ aralkyl-carbonyl group (e.g. benzyloxycarbonyl etc.), a pyranyl group, a furanyl group and a silyl group. Substituents for these protecting groups include halogen (e.g. fluorine, chlorine, bromine, iodine etc.), $C_{1-6}$ alkyl, phenyl, $C_{7-10}$ aralkyl and nitro, the number of substituents being about 1 to 4.

These protecting groups can be removed by known methods or modifications thereof, including treatments with acid, base, reducing agents, ultraviolet rays, hydrazine, phenylhydrazine, sodium N-methyldithiocarbamate, tetrabutylammonium fluoride and palladium acetate.

When the compound (Ia$^2$) or a salt thereof thus obtained, can be converted to a compound (Ia$^2$: R$^6$=H) or a salt thereof, by removing the protecting group with the known method or its modifications such as thereof, including treatments with acid, base, reducing agents, ultraviolet rays, hydrazine, phenylhydrazine, sodium N-methyldithiocarbamate, tetrabutylammonium fluoride and palladium acetate.

More specificaly, when the protecting group for the compound (Ia$^2$) represented by W, is an acyl group, the protectiong group can be removed by deacylation described below. That is, the compound (Ia$^2$) or a salt thereof, is kept at a temperature of normally about 10 to about 150° C., preferably about 50 to about 100° C., in an aqueous solution of an acid such as a mineral acid (e.g., nitric acid, hydrochloric acid, hydrobromic acid, iodic acid, sulfuric acid etc.) or a base such as an alkaline metal hydroxide (e.g., sodium hydroxide, potassium hydroxide, barium hydroxide, lithium hydroxide etc.). The amount of such acid or base used is normally about 1 to about 100 mol, preferably about 1 to about 40 mol per mol of the compound (IIa) or a salt thereof. The strength of acid or base is normally about about 0.1 to about 10 N, preferably about 2 to about 10 N. Although varying depending on reaction temperature, reaction time is normally about 1 to about 24 hours, preferably about 2 to about 10 hours.

The compound (Ia$^2$) in which R$^1$ is an acyl group, or a salt thereof, can be converted to the compound (Ia$^2$: R$^1$=H) or a salt thereof by deacylation. The condition of deacylation is similar to the case that the protecting group of the amino group represented by W, is an acyl group.

The compound (Ia$^2$) having an acylamino group which may be substituted, or a salt thereof, can be converted to the compound (Ia$^2$) having a primary or secondary amino group, or a salt thereof, by deacylation. The condition of deacylation is similar to the case that the protecting group of the amino group represented by W, is an acyl group.

When the compound (Ia$^2$) wherein R$^6$ is a hydrogen atom (Ia$^2$: R$^6$=H) or a salt thereof is obtained, it can be converted to a compound (Ia$^2$) wherein R$^6$ is not a hydrogen atom by the reaction with the compound of the formula:

$$R^{6a}-Z^{1a}$$

wherein $Z^{1a}$ represents a leaving group; $R^{6a}$ represents a hydrocarbon group which may be substituted or an acyl group.

When the compound (Ia$^2$) wherein R$^1$ is a hydrogen atom (Ia$^2$: R$^1$=H) or a salt thereof is obtained, it can be converted to a compound (Ia$^2$) wherein R$^1$ is not a hydrogen atom by the reaction with the compound of the formula:

$$R^{1a}-Z^{1a}$$

wherein $Z^{1a}$ represents a leaving group; $R^{1a}$ represents a hydrocarbon group which may be substituted or an acyl group.

When the compound (Ia$^2$) having a primary or secondary amino group or a salt thereof is obtained, it can be converted to a compound (Ia$^2$) in which the amino group is substituted by R$^7$, by the reaction with the compound of the formula:

$$R^7-Z^3$$

wherein $Z^3$ represents a leaving group; $R^7$ represents a hydrocarbon group which may be substituted.

The "hydrocarbon group which may be substituted" and the "acyl group" mentioned as $R^{1a}$ include but are not limited the "hydrocarbon group which may be substituted" and the "acyl group" mentioned as $R^1$.

The "hydrocarbon group which may be substituted" and the "acyl group" mentioned as $R^{6a}$ include but are not limited the "hydrocarbon group which may be substituted" and the "acyl group" mentioned as $R^6$.

The "hydrocarbon group which may be substituted" mentioned as $R^7$ include but are not limited the hydrocarbon group which may be substituted" mentioned as $R^1$ or $R^6$.

The leaving groups for $Z^{1a}$ and $Z^3$ are exemplified by a halogen atoms (e.g. chlorine, bromine and iodine etc.), a $C_{1-6}$ alkylsulfonyloxy group (e.g. methanesulfonyloxy, ethanesulfonyloxy etc.) or a $C_{6-10}$ arylsufonyloxy group (e.g. benzenesulfonyloxy, p-toluenesulfonyloxy etc.), with preference given to methanesulfonyloxy, or a halogen atom (e.g. chlorine, bromine etc.) and others.

This reaction can be carried out in the presence or absence of a solvent, if necessary, with a base. Bases for this purpose include inorganic bases such as sodium carbonate, potassium carbonate, lithium carbonate, sodium hydroxide, potassium hydroxide, sodium methoxide, sodium ethoxide and sodium hydride, and organic bases such as pyridine, 4-dimethylaminopyridine and triethylamine. Any solvent can be used, as long as it does not interfere with the reaction. Such solvents include lower alcohols such as methanol, ethanol, propanol, isopropanol, n-butanol and t-butanol, ethers such as dioxane, ether and tetrahydrofuran, aromatic hydrocarbons such as toluene, benzene and xylene, halogenated hydrocarbons such dichloromethane, 1,2-dichloroethane, amides such as dimethylformamide, dimethylacetamide and hexamethylphosphonotriamide, esters such as ethyl acetate and butyl acetate, nitrites such as acetonitrile and propionitrile.

This reaction can be carried out under cooling conditions' (about 0 to about 10° C.), at room temperature (about 10 to about 40° C.) or under heating conditions (about 40 to about 120° C.). Reaction time is normally about 10 minutes to about 48 hours, preferably about 2 to about 16 hours. The amount of compounds of formula: $R^{6a}$—$Z^{1a}$, $R^{1a}$—$Z^{1a}$ or $R^7$—$Z^3$ used is preferably about 0.3 to about 5.0 mol per mol of the compound ($Ia^2$) or a salt thereof. The amount of base used is normally about 1 or more mol, preferably about 1.1 to about 5 mol per mol of the compound ($Ia^2$) or a salt thereof.

Also this reaction may be accelerated as appropriate in the presence of an iodide such as sodium iodide, potassium iodide or lithium iodide. In this case, the amount of iodide used is normally about 1 to about 5 mol, preferably about 1.1 to about 1.5 mol per mol of the compounds of formula: $R^{6a}$—$Z_{1a}$, $R^{1a}$—$Z^{1a}$ or $R^7$—$Z^3$ The compounds of formula: $R^{6a}$—, $Z^{1a}$, $R^{1a}$—$Z^{1a}$ or $R^7$—$Z^3$ can be produced by known method or modifications thereof.

The starting material compound ($Ia^2$) or a salt thereof may be used after isolation and purification by known means such as concentration, liquid property conversion, redissolution, solvent extraction, fractional distillation, distillation, crystallization, recrystallization and chromatography, or may be used in the form of a reaction mixture as such, without isolation, as a starting material.

The compound ($Ia^2$) thus obtained can be converted to a salt by a conventional method when it is in a free form, and can be converted to a free form or another salt by a conventional method when it is in a salt form. The compound ($Ia^2$) or a salt thereof can be isolated and purified by known methods as described above. Also, the compound ($Ia^2$) or a salt thereof involves stereoisomers based on the presence of asymmetric carbon atoms. These isomers can also be isolated and purified by known methods as described above or other methods such as fractional recrystallization, and chromatography using optically active columns.

The above compound (I), inclusive of its salt, acts on the peripheral adipocytes of mammals (e.g. man, macacus, mouse, rat, canine, feline, bovine, etc.) to express intraadipocyte cAMP-increasing, lipolysis accelerating, and thermogenesis accelerating effects and, as such, show remarkable body weight reducing (strictly, adipose mass-reducing) and body weight gain-suppressive effects.

The pharmacologic activity of compound (I), inclusive of its salt, is well isolated from its CNS activity as compared with the known centrally-acting anorectics such as mazindol. Thus, compound (I), inclusive of its salt, is characterized by low toxicity, with no central action at all or only a very slight central action. Moreover, the compound expresses marked efficacy in an oral regimen. The acute toxicity ($LD_{50}$) of the compound (I) or salt according to the present invention is not less than about 100 mg/kg.

Therefore,the compound (I) inclusive of its salt can be used with advantage as a safe prophylactic and/or treating drug for obesity (adiposis), obesity-associated diseases, and complications of obesity in man and other mammals.

The disease in which the compound (I) or salt of the invention can be indicated includes but is not limited to: (1) obesity, (2) obesity-associated diseases such as (i) diabetes (particularly non-insulin-dependent diabetes), (ii) hyperlipemia, (iii) atherosclerosis, (iv) hypertension, and (3) complications of obesity such as (i) glucose tolerance abnormality, (ii) hyperinsulinemia, (iii) hypoHDL emia, (iv) hyperuricemia, (v) gout, (vi) angina pectoris, (vii) myocardial infarction, (viii) cardiac. dysfunction, (ix) hypercardia, (x) heart failure, (xi) chronic nephritis, (xii) Pickwick's syndrome, (xiii) sleep apnea syndrome, (xiv) fatty liver, (xv) cholelithiasis, (xvi) pancreatitis, (xvii) arthritis deformans, (xviii) spondylolisthes is, (xix) hypoovarianism, (xx) emmeniopathy, (xxi) sterility, (xxii) tonsilar hypertrophy, (xxiii) parotid intumescence, and so forth. Particularly, the above compound (I) inclusive of its salt can be used with advantage in the prevention or treatment of obesity and non-insulin-dependent diabetes.

The above compound (I) inclusive of its salt can be safely administered, either as it is or as a pharmaceutical dosage form prepared using a pharmacologically acceptable carrier, for example, tablets (inclusive of dragees, film-coated tablets, etc.), powders, granules, capsules (inclusive of soft capsules), solutions, injections, suppositories, timed-release preparations, etc., either orally or parenterally (e.g. locally, rectally or intravenously) to man and other mammals. The content of compound (I) or a salt thereof in the dosage form of the invention is about 0.1 to about 100 weight % of the whole composition. Compound (I) inclusive of its salt according to the invention is usually formulated with a medicinally acceptable carrier, vehicle, or excipient and administered orally or parenterally to man and other mammals.

The dosage depends on the recipient's background, route of administration, type of disease to be treated, clinical status and symptoms, and other factors. For use as an antiobese drug, for instance, in a human adult (body weight ca 70 kg), the recommended daily dosage is about 0.01–10, 000 mg, preferably about 0.1 to about 2,000 mg, more preferably about 0.5 to about 1,000 mg, and still more preferably about 25 to about 500 mg, in terms of the active compound (Compound (I) or its salt). The above dosage can be administered once or in 2 to 4 divided doses daily.

As the pharmaceutically acceptable carrier mentioned above, various organic and inorganic carriers which are conventional as pharmaceutical preparation material can be employed. Such the carrier includes but is not limited to the excipient, lubricant, binder, and disintegrator for solid dosage forms and the solvent, solubilizer, suspending agent, isotonizing agent, buffer and local anesthetic for liquid dosage forms. Where necessary, various pharmaceutical additives such as the preservative, antioxidant, coloring agent, sweetener, adsorbent, wetting agent, etc. can also be included in formulations.

The preferred excipient includes but is not limited to lactose, sucrose, D-mannitol, starch, corn starch, crystalline cellulose, and light silicic anhydride. The preferred lubricant includes but is not limited to magnesium stearate, calcium stearate, talc, and colloidal silica.

The preferred binder includes but is not limited to crystalline cellulose, sucrose, D-mannitol, dextrin, hydroxypropylcellulose, hydroxypropylmethylcellulose, polyvinylpyrrolidone, starch, sucrose, gelatin, methylcellulose, and carboxymethylcellulose sodium.

The preferred disintegrator includes but is not limited to starch, carboxymethylcellulose, carboxymethylcellulose calcium, croscarmellose sodium, carboxymethylstarch sodium, and L-hydroxypropylcellulose.

The preferred solvent includes but is not limited to water for injection, alcohol, propylene glycol, macrogol, sesame oil, corn oil, etc.

The preferred solubilizer includes but is not limited to polyethylene glycol, propylene glycol, D-mannitol, benzyl benzoate, ethanol, trisaminomethane, cholesterol, triethanolamine, sodium carbonate, and sodium citrate.

The preferred suspending agent includes but is not limited to surfactants such as stearoyltriethanolamide, sodium lauryl sulfate, laurylaminopropionic acid, lecithin, benzalkonium chloride, benzethonium chloride, glyceryl monostearate, etc. and hydrophilic macromolecular substances such as polyvinyl alcohol, polyvinylpyrrolidone, carboxymethylcellulose sodium, methylcellulose, hydroxymethylcellulose, hydroxyethylcellulose, and hydroxypropylcellulose.

The preferred isotonizing agent includes but is not limited to glucose, D-sorbitol, sodium chloride, glycerin, and D-mannitol.

The preferred buffer includes but is not limited to phosphate, acetate, carbonate, citrate, and other buffers.

A preferred example of said local anesthetic is benzyl alcohol.

The preferred antiseptic includes but is not limited to p-hydroxybenzoic esters, chlorobutanol, benzyl alcohol, phenethyl alcohol, dehydroacetic acid, and sorbic acid.

The preferred antioxidant includes but is not limited to salts of sulfurous acid, ascorbic acid, etc.

MODE OF WORKING THE INVENTION

Figure 2:
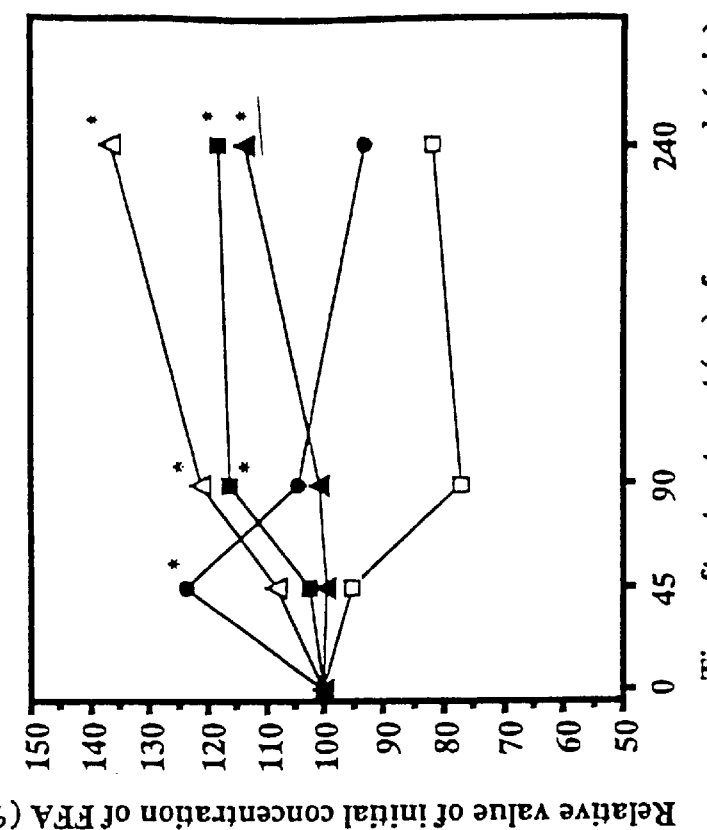
FIG. 2 shows the change in the relative value of free fatty acid concentration after oral administration of compound (1) with respect to the baseline concentration immediately before administration. In the diagram showing the change in said relative value, Δ—Δ represents Compound 6 in Table 1, ■—■ represents Compound 12 in Table 2, ▲—▲ represents Compound 7 in Table 1, ●—● represents Compound 1 in Table 1, and □—□ represents control.
* stands for significant difference from the free fatty acid concentration (baseline) immediately before administration as tested by ANOVA (*p<0.05 vs. baseline).

The following examples illustrate the present invention in further detail. It should be understood that these examples are by no means defining the metes and bounds of the invention and that many changes and modifications may be made by those skilled in the art without departing from the spirit and scope of the invention as claimed.

EXPERIMENTAL EXAMPLE 1

Assay of Intraadipocellular cAMP Concentration-increasing Activity in Murine Preadipocyte Line 3T3-L1

The intraadipocyte cAMP concentration-increasing activity of the above compound (I) was determined in an assay system using murine preadipocyte line 3T3-L1. Thus, 3T3-L1 preadipocytes were seeded onto a 96-well microtiter plate (10,000 cells/well) and cultured for 5–6 days until a confluent growth was formed. Thereafter, the adipocytes were further cultured for 72 hours. The test compound (I) ($10^{-5}$M, $10^{-6}$M, $10^{-7}$M, $10^{-8}$M, and $10^{-9}$M) was then added and the plate was allowed to sit at 37° C. for 40 minutes. The cells were washed with 3 portions of phosphate buffer at 4° C. (100 μl/well). Then, 0.1 N hydrochloric acid was added and the cells were denatured at 95° C. for 10 minutes. From each well, 25 μl was aspirated and dissolved in 75 μl of the assay a buffer included in Cyclic AMP Enzyme Immunoassay Kit (Kayman Chemical Company, USA). Using a 50 μl portion as the sample, cAMP was assayed using the above-mentioned Kit. Thus, using a 96-well microtiter plate pre-coated with anti-rabbit IgG mouse antibody, the above sample (50 μl) as well as the Cyclic AMP Tracer (50 μl) and Cyclic AMP Rabbit Antibody (50 μl) from the Kit were added and the plate was incubated at room temperature for 18 hours. After asperation, the plate was washed with 4 portions of the wash buffer (400 μl/well). Then, 200 μl of the color reagent included in the Kit was added to each well and the plate was incubated at room temperature with'shaking for 60 minutes. After completion of the reaction, the absorbance was measured at 405 nm to quantitate the cAMP.

The assayed values of cAMP at the $10^{-5}$M, $10^{-6}$M, $10^{-7}$M $10^{-8}$M, and $10^{-9}$M levels of the test compound are shown in Tables 8 to 13. Each value is the mean result of 4 experiments. The test for statistical significance against the CAMP concentration of the control experiment (the test compound not added) was carried out by the known ANOVA. (* p<05 vs. control)

TABLE 8

| Compound No. | cAMP (pmol/ml) Concentration of test compound | | | | | |
|---|---|---|---|---|---|---|
| | $10^{-5}$M | $10^{-6}$M | $10^{-7}$M | $10^{-8}$M | $10^{-9}$M | Control |
| 1 | 2321.7* | 927.8* | 149.6* | 15.6* | NT | 3.0 |
| 2 | 61.8* | 7.5* | 4.0 | 3.3 | NT | 3.0 |
| 3 | 91.4* | 11.8* | 4.4 | 4.0 | NT | 3.0 |
| 4 | 14.7* | 5.7* | 3.7* | 1.6 | NT | 1.1 |
| 5 | 81.1* | 15.8* | 3.9* | 3.0 | NT | 1.1 |
| 6 | 7003.0* | 2318.6* | 347.1* | 50.4* | 24.2* | 8.8 |
| 7 | 1515.9* | 400.8* | 70.8* | 26.9* | NT | 2.1 |
| 8 | 889.1* | 204.6* | 33.6* | 5.8 | NT | 2.1 |
| 9 | 203.3* | 36.9* | 6.8* | 3.5 | NT | 2.1 |
| 10 | 120.8* | 17.6* | 5.5 | 4.0 | NT | 3.6 |

NT = not tested

TABLE 9

| Compound No. | cAMP (pmol/ml) Concentration of test compound | | | | | |
|---|---|---|---|---|---|---|
| | $10^{-5}$M | $10^{-6}$M | $10^{-7}$M | $10^{-8}$M | $10^{-9}$M | Control |
| 11 | 31.4* | 10.4* | 5.3 | 5.0 | NT | 3.6 |
| 12 | 1073.9* | 88.6* | 10.3* | 4.6* | NT | 3.0 |
| 13 | 349.4* | 63.9* | 11.2* | 7.0* | NT | 3.0 |
| 14 | 192.1* | 31.7* | 7.4* | 6.0* | NT | 3.3 |
| 15 | 104.9* | 17.6* | 6.0* | 4.6* | NT | 3.3 |
| 16 | 620.6* | 53.0* | 5.5* | 4.5* | NT | 3.3 |
| 17 | 192.1* | 23.9* | 6.0* | 4.7* | NT | 3.3 |
| 18 | 64.7* | 19.2* | 5.0 | 4.8 | 5.5 | 2.0 |
| 19 | 3428.3* | 957.8* | 141.8* | 29.4* | 3.4 | 2.0 |
| 20 | 54.6* | 11.9* | 4.1 | 3.0 | 3.1 | 1.8 |

NT = not tested

TABLE 10

| Compound No. | cAMP (pmol/ml) Concentration of test compound | | | | | |
|---|---|---|---|---|---|---|
| | $10^{-5}$M | $10^{-6}$M | $10^{-7}$M | $10^{-8}$M | $10^{-9}$M | Control |
| 21 | 52.1* | 10.2* | 5.3* | 3.8 | 3.9 | 1.8 |
| 22 | 116.2* | 19.8* | 5.4* | 3.1 | 3.5 | 1.8 |
| 23 | 177.2* | 42.6* | 15.3* | 10.5* | 8.4 | 5.2 |
| 24 | 320.5* | 31.0* | 10.0* | 9.1* | 5.6 | 5.2 |
| 25 | 141.3* | 18.1* | 9.1* | 7.7 | 8.1 | 5.2 |
| 26 | 324.7* | 28.7* | 9.4* | 7.5 | 5.9 | 5.2 |
| 27 | 221.6* | 16.3* | 6.6* | 4.9 | 5.3 | 2.5 |
| 28 | 37.4* | 17.9* | 6.6 | 4.5 | 3.4 | 3.4 |
| 29 | 54.8* | 12.6* | 5.0 | 3.0 | 3.0 | 3.4 |
| 30 | 51.0* | 13.6* | 7.7 | 7.5 | 7.7 | 4.3 |

NT = not tested

TABLE 11

| Compound No. | cAMP (pmol/ml) Concentration of test compound | | | | | |
|---|---|---|---|---|---|---|
| | $10^{-5}$M | $10^{-6}$M | $10^{-7}$M | $10^{-8}$M | $10^{-9}$M | Control |
| 31 | 52.5* | 15.9* | 9.9 | 7.8 | 6.1 | 8.7 |
| 32 | 57.8* | 14.2* | 7.0 | 6.5 | 4.8 | 8.7 |
| 33 | 27.4* | 11.3* | 6.7 | 6.1 | 6.6 | 5.6 |
| 34 | 55.3* | 14.7* | 8.5 | 7.5 | 7.1 | 5.6 |
| 35 | 32.3* | 12.2* | 7.1 | 5.8 | 4.2 | 5.6 |
| 36 | 143.5* | 26.4* | 9.4 | 9.0 | 6.3 | 7.5 |
| 37 | 84.0* | 16.7* | 9.0 | 7.7 | 4.1 | 7.5 |
| 38 | 214.3* | 23.6* | 7.9* | 4.5 | 4.2 | 2.0 |

TABLE 11-continued

| Compound No. | cAMP (pmol/ml) Concentration of test compound | | | | | |
|---|---|---|---|---|---|---|
| | $10^{-5}$M | $10^{-6}$M | $10^{-7}$M | $10^{-8}$M | $10^{-9}$M | Control |
| 39 | 112.0* | 15.1* | 7.9* | 5.7 | 7.7 | 2.0 |
| 40 | 116.3* | 18.1* | 6.7 | 4.9 | 3.9 | 5.6 |

NT = not tested

TABLE 12

| Compound No. | cAMP (pmol/ml) Concentration of test compound | | | | | |
|---|---|---|---|---|---|---|
| | $10^{-5}$M | $10^{-6}$M | $10^{-7}$M | $10^{-8}$M | $10^{-9}$M | Control |
| 41 | 76.1* | 18.6* | 5.5 | 4.3 | 2.1 | 2.8 |
| 42 | 193.3* | 44.2* | 11.6* | 7.1 | 4.0 | 2.8 |
| 43 | 1139.2* | 238.5* | 24.8* | 7.6 | 5.8 | 3.2 |
| 44 | 137.2* | 24.9* | 8.7* | 5.0 | 4.3 | 3.2 |
| 45 | 162.8* | 23.0* | 6.1 | 6.5 | 6.2 | 3.1 |
| 46 | 46.1* | 13.3* | 6.2 | 4.8 | 3.7 | 3.1 |
| 47 | 135.5* | 23.7* | 10.2* | 6.5 | 3.9 | 3.3 |
| 48 | 93.0* | 15.4* | 7.9* | 6.5 | 4.7 | 3.3 |
| 49 | 558.3* | 59.3* | 10.2* | 7.7* | 6.6 | 2.1 |
| 50 | 913.2* | 150.7* | 24.0* | 8.5* | 3.1 | 2.1 |

NT = not tested

TABLE 13

| Compound No. | cAMP (pmol/ml) Concentration of test compound | | | | | |
|---|---|---|---|---|---|---|
| | $10^{-5}$M | $10^{-6}$M | $10^{-7}$M | $10^{-8}$M | $10^{-9}$M | Control |
| 51 | 1433.6* | 285.9* | 63.6* | 17.0* | 7.3 | 2.9 |
| 52 | 218.6* | 36.8* | 7.1 | 3.4 | 3.1 | 2.9 |
| 53 | 933.4* | 104.3* | 32.9* | 7.3 | 4.5 | 2.9 |
| 54 | 216.9* | 35.1* | 7.9 | 6.2 | 6.8 | 3.6 |
| 55 | 1229.2* | 123.1* | 18.1* | 12.9* | 8.6 | 3.6 |
| 56 | 623.0* | 147.3* | 25.0* | 8.8 | 6.8 | 3.6 |
| 57 | 1291.4* | 36.0* | 9.6* | 6.5 | 4.0 | 3.6 |
| 58 | 32.4* | 13.2* | 5.9 | 7.0 | 7.1 | 4.5 |
| 59 | 28.2* | 11.6* | 7.7 | 6.9 | 6.1 | 4.5 |
| 60 | 61.0* | 19.9* | 10.1* | 8.5 | 7.8 | 4.5 |
| 61 | 61.7* | 10.5* | 9.2 | 4.3 | 4.5 | 3.6 |

NT = not tested

TEST EXAMPLE 2

Assay of Murine Serum Free Fatty Acid-increasing Activity

Male C57BL6/N mice (6 per group) were dosed orally with 1 mg/kg of compound (I). After dosing, 50 μl of blood was successively drawn from the suborbital vein (immediately before dosing and 45, 90, and 240 minutes after dosing). Each blood sample was centrifuged at 3000 rpm for 5 minutes and the serum was separated. The serum free fatty acid concentration was determined using NEFA C-Test Wako (Wako Pure Chemical Industries).

Thus, the serum was distributed onto a 96-well: microtiter plate, 3 μl/well, and mixed with 60 μl of Color Reagent A from the Kit and the plate was allowed to sit at 37° C. for 10 minutes. Then, 120 μl of Color Reagent B from the Kit was added and, after mixing, the plate was further allowed to sit at 37° C. for 10 minutes. After completion of the reaction, the absorbance was measured at 540 nm to quantitate the free fatty acid (oleic acid equivalent concentration).

Figure 1:
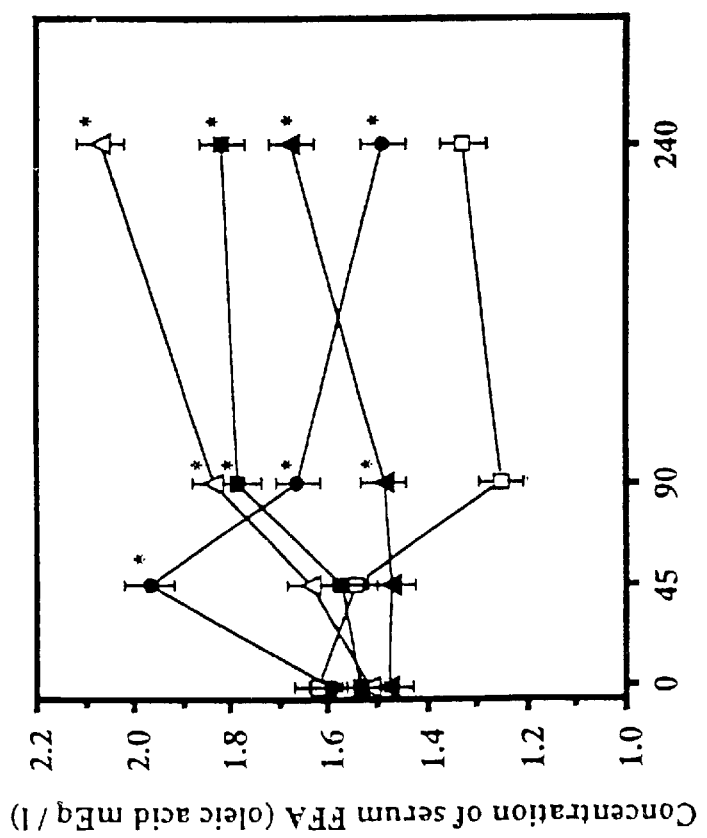
FIG. 1 shows the time course of serum free fatty acid concentration after oral administration of compound (1) in mice. In the diagram showing the change in serum free acid concentration, Δ—Δ represents Compound 6 in Table 1, ■—■ represents Compound 12 in Table 2, ▲—▲ represents Compound 7 in Table 1, ●—● represents Compound 1 in Table 1, and □—□ represents control.
* stands for significant difference from control (the test compound not added) as tested by ANOVA (*p<0.05 vs. control).

The results are shown in FIGS. 1 and 2.

It is apparent from Tables 8–13 and FIGS. 1 and 2 that the above compound (I), inclusive of its salt, has potent intraadipocyte cAMP-increasing activity, lipolytic activity, and thermogenic activity. Compound No. in Tables 8–13 corresponds to Compound No. in Tables 1–7.

PREPARATION EXAMPLE 1

| | |
|---|---|
| (1) 3-[1-(Phenylmethyl)-4-piperidinyl]-1-[2-(phenylmethyl)-2,3,4,5-tetrahydro-1H-2-benzazepin-8-yl]-1-propanone (Compound No. 6) dihydrochloride | 1 g |
| (2) Lactose | 197 g |
| (3) Corn starch | 50 g |
| (4) Magnesium stearate | 2 g |

A mixture of 1 g of (1), 197 g of (2), and 20 g of corn starch was kneaded with a paste prepared from 15 g of corn starch and 25 ml of water and the whole mixture was granulated. Then, 15 g of corn starch and 2 g of (4) were added and the resulting composition was compressed with a tablet machine to provide 2000 tablets (Compound No. 6·2HCl content: 0.5 mg/tablet) each 3 mm in diameter.

PREPARATION EXAMPLE 2

| | |
|---|---|
| (1) 3-[1-(Phenylmethyl)-4-piperidinyl]-1-[2-(phenylmethyl)-2,3,4,5-tetrahydro-1H-2-benzazepin-8-yl]-1-propanone (Compound No. 6) dihydrochloride | 2 g |
| (2) Lactose | 197 g |
| (3) Corn starch | 50 g |
| (4) Magnesium stearate | 2 g |

A mixture of 2 g of (1), 197 g of (2), and 20 g of corn starch was kneaded with a paste prepared from 15 g of corn starch and 25 ml of water and the whole mixture was granulated. Then, 15 g of corn starch and 2 g of (4) were added and the resulting composition was compressed with a tablet machine to prepare 2000 tablets (Compound No. 6·2HCl content: 1.0 mg/tablet) each 3 mm in diameter.

PREPARATION EXAMPLE 3

| | |
|---|---|
| (1) 3-[1-(Phenylmethyl)-4-piperidinyl]-1-[2-(phenylmethyl)-2,3,4,5-tetrahydro-1H-2-benzazepin-8-yl]-1-propanone (Compound No. 6) dihydrochloride | 25 g |
| (2) Lactose | 80 g |
| (3) Corn starch | 42 g |
| (4) Talc powder | 3 g |
| (5) Magnesium stearate | 0.5 g |

A mixture of 25 g of (1), 80 g of (2), and 21 g of corn starch was kneaded with a paste prepared from 10 g of corn starch and 9 ml of water, and the whole mixture was granulated. Then, 11 g of corn starch, 3 g of (4), and 0.5 g of (5) were added and the resulting composition was compressed with a tablet machine to prepare 1000 tablets (Compound No. 6·2HCl content: 25 mg/tablet) each 3 mm in diameter.

PREPARATION EXAMPLE 4

| | |
|---|---|
| (1) 3-[1-(Phenylmethyl)-4-piperidinyl]-1-[2-(phenylmethyl)-2,3,4,5-tetrahydro-1H-2-benzazepin-8-yl]-1-propanone (Compound No. 6) dihydrochloride | 10.0 mg |
| (2) Lactose | 60.0 mg |
| (3) Corn starch | 35.0 mg |
| (4) Gelatin | 3.0 mg |
| (5) Magnesium stearate | 2.0 mg |

A mixture of 10.0 mg of (1), 60 mg of (2), and 35 mg of (3) was kneaded with 0.03 ml of 10% aqueous gelatin solution (3.0 mg as gelatin) and the whole mixture was granulated using a 1 mm-mesh sieve, dried at 40° C., and resieved. After addition of 2.0 mg of (5), the granulation was compressed. The core tablets thus obtained were sugar-coated with an aqueous suspension of sucrose, titanium dioxide, talc, and gum arabic. The coated tablets were glazed with beeswax to provide coated tablets.

REFERENCE EXAMPLE 1

4-Formyl-2,3,4,5-tetrahydro-1,4-benzoxazepine

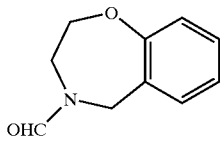

Acetic anhydride (30 ml), was added dropwise to formic acid (90 ml) at room temperature and after the mixture was stirred for 30 minutes, a solution of 2,3,4,5-tetrahydro-1,4-benzoxazepine (13.0 g) in ethyl acetate (50 ml) was added dropwise at:room temperature. The mixture was then stirred for 30 minutes, after which it was diluted with ice-water and extracted with ethyl acetate. The extract was washed successively with water, aqueous solution of sodium hydroxide ($NaOH/H_2O$), and saturated aqueous solution of sodium chloride ($NaCl/H_2O$) and dried over anhydrous magnesium sulfate ($MgSO_4$). The solvent was then distilled off under reduced pressure and the residue was purified by silica gel column chromatography (eluent: ethyl acetate) to provide the title compound (14.4 g) as a viscous oil.

$^1$H-NMR (CDCl$_3$) δ: 3.70–4.16 (4H, m), 4.48 and 4.061 (2H, each s), 7.00–7.40 (4H, m), 8.06 and 8.20 (1H, each s).

REFERENCE EXAMPLE 2

3-Formyl-2,3,4,5-tetrahydro-1H-3-benzazepine

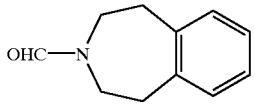

Acetic anhydride (40 ml) was added dropwise to formic acid (80 ml) at room temperature and after the mixture was stirred for 30 minutes, a solution of 2,3,4,5-tetrahydro-1H-3-benzazepine (30 g),in ethyl acetate (80 ml) was added dropwise at room temperature. The mixture was then stirred for 30 minutes, after which it was diluted with ice-water and extracted with ethyl acetate. The extract was washed successively with water, aqueous solution of sodium hydroxide ($NaOH/H_2O$), and saturated $NaCl/H_2O$ and dried over $MgSO_4$. The solvent was then distilled off under reduced pressure and the residue was purified by silica gel column chromatography (eluent: ethyl acetate) and recrystallized from-n-hexane to provide the title compound (29 g) as colorless crystals melting at 65–66° C.

$^1$H-NMR (CDCl$_3$) δ: 2.86–2.98 (4H, m), 3.45–3.52 (2H, m), 3.64–3.71 (2H, m), 7.09–7.23 (4H, m), 8.17 (1H, br).

REFERENCE EXAMPLE 3

3-Trifluoroacetyl-2,3,4,5-tetrahydro-1H-3-benzazepine

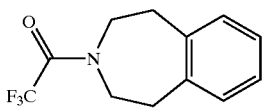

To a solution of 2,3,4,5-tetrahydro-1H-3-benzazepine (3.0 g, 0.02 mol) and triethylamine (10 ml) in tetrahydrofuran was added trifluoroacetic anhydride (6 ml) dropwise at 0° C. This mixture was stirred at from temperature for 24 hours, at the end of which time it was diluted with diluted hydrochloric acid and extracted with ethyl acetate. The extract was washed with water and dried over MgSO$_4$ and the solvent was distilled off under reduced pressure. The residue was purified by silica gel column chromatography (eluent: hexane-ethyl acetate) to provide the title compound (3.4 g) as colorless crystals melting at 73–74° C.

$^1$H-NMR (CDCl$_3$) δ: 2.92–3.05 (4H, m), 3.64–3.83 (4H, m), 7.10–7.25 (4H, m).

REFERENCE EXAMPLE 4

2-Formyl-2,3,4,5-tetrahydro-1H-2-benzazepine

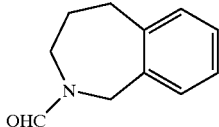

Acetic anhydride (20 ml) was added dropwise to formic acid (60 ml) at room temperature and after the mixture was stirred for 30 minutes, a solution of 2,3,4,5-tetrahydro 1H-2-benzazepine (10.71 g, 72.75 mmol) in ethyl acetate (5 ml) was added dropwise at room temperature. This mixture was stirred for 3 hours, after which it was diluted with ice-water and extracted with ethyl acetate. The extract was washed successively with water, aqueous solution of potassium carbonate (K$_2$CO$_3$), and saturated NaCl/H$_2$O and dried over MgSO$_4$. The solvent was then distilled off under reduced pressure and the residue was purified by silica gel column chromatography (eluent: ethyl acetate) to provide the title compound (11.35 g) as colorless oil.

REFERENCE EXAMPLE 5

5-Formyl-5,6,11,12-tetrahydrodibenz[bf]azocine

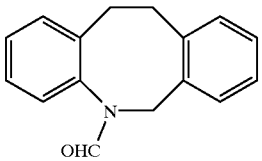

Acetic anhydride (3.7 ml) was added dropwise to formic acid (7.4 ml) at room temperature and after the mixture was stirred for 30 minutes, a solution of 5,6,11,12-tetrahydrodibenz[bf]azocine (free base, 4.25 g, 20.3 mmol) in ethyl acetate (30 ml) was added dropwise at room temperature. The mixture was then stirred for 3 hours, after which it was diluted with ice-water and extracted with ethyl acetate. The extract was washed successively with water, aqueous solution of sodium hydroxide (NaOH/H$_2$O), and saturated NaCl/H$_2$O and dried over MgSO$_4$. The solvent was-then distilled off under reduced pressure and the residue was purified by silica gel column chromatography (eluent: hexane-ethyl acetate), followed by recrystallization from hexane to provide the title compound (4.1 g) as colorless crystals melting at 98–99° C.

$^1$H-NMR (CDCl$_3$) δ: 3.09 (4H, br), 4.88 (2H, br)) 7.00–7.20 (8H, m), 8.25 (1H, s).

EXAMPLE 1

3-(1-Acetyl-4-piperidinyl)-1-[4-(phenylmethyl)-2,3,4,5-tetrahydro-1,4-benzoxazepin-7-yl]-1-propanone Hydrochloride

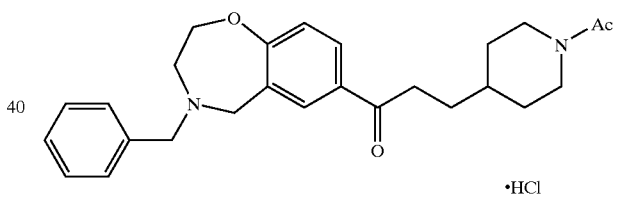

1) 3-(1-Acetyl-4-piperidinyl)propionic acid (8.10 g, 40.7 mmol) was added portionwise to thionyl chloride (40 ml, 550 mmol) with ice-bath cooling. After 5 minutes of stirring, the excess thionyl chloride was distilled off and the residue was washed with hexane to provide 3-(1-acetyl-4-piperidinyl)propionyl chloride as light-yellow solid. Aluminum chloride (15.8 g, 119 mmol) powders were then added portionwise to a mixed solution of the above acid chloride and 4-formyl-2,3,4,5-tetrahydro-1,4-benzoxazepine (6.00 g, 33.8 mmol) in 1,2-dichloroethane (30 ml) with ice-bath cooling. This mixture was then stirred at room temperature for 18 hours, at the end of which time it was poured in ice-water and extracted with ethyl acetate. The extract was washed with saturated NaCl/H$_2$O and dried over MgSO$_4$, and the solvent was distilled off under reduced pressure. The residue was purified by silica gel column chromatography (eluent: ethyl acetate-methanol=9:1) to provide 3-(1-acetyl-4-piperidinyl)-1-(4-formyl-2,3,4,5-tetrahydro-1,4-benzoxazepin-7-yl)-1-propanone (6.77 g) as light-yellow oil.

$^1$H-NMR (CDCl$_3$) δ: 1.00–1.38 (2H, m), 1.45–1.90(4H, m), 2.09 (3H, s), 2.54 (1H, m), 2.90–3.15 (3H, m), 3.75–3.90

(2H, m), 3.93–4.00 (1H, m), 4.10–4.23 (2H, m), 4.56 and 4.67 (2H, each bs), 7.10 (1H, dd, J=8.6, 2.8 Hz), 7.80–8.00 (2H, m), 8.09 and 8.22 (1H, each s).

2) A solution of the 3-(1-acetyl-4-piperidinyl)-1-(4-formyl 2,3,4,5-tetrahydro-1,4-benzoxazepin-7-yl)-1-propanone (6.77 g) in methanol (100 ml) and concentrated hydrochloric acid (100 ml) were heated together at 80–85° C. for 2 hours. The methanol was then distilled off and the residual aqueous solution was made basic with saturated aqueous solution of potassium carbonate and extracted with ethyl acetate-tetrahydrofuran (2:1). The extract was washed with saturated NaCl/H$_2$O and dried over MgSO$_4$, and the solvent was distilled off under reduced pressure to provide 3-(1-acetyl-4-piperidinyl)-1-(2,3,4,5-tetrahydro-1,4-benzoxazepin-7-yl)-1-propanone (6.04 g) as light-yellow oil.

$^1$H-NMR (CDCl$_3$) δ: 1.00–1.38 (2H, m), 1.40–1.90 (4H, m), 2.08 (3H, s), 2.53 (1H, m), 2.90–3.10 (3H, m), 3.25 (2H, t-like, J=4.4 Hz), 3.70–3.90 (1H, m), 4.00–4.20 (3H, m), 4.55–4.70 (1H, m), 7.07 (1H, d, J=8.6 Hz), 7.60–7.85 (2H, m).

3) Benzyl bromide (6.04 g, 18.3 mmol) was added dropwise to a mixed solution of 3-(1-acetyl-4-piperidinyl)-1-(2,3,4,5-tetrahydro-1,4-benzoxazepin-7-yl)-1-propanone (3.13 g, 18.3 mmol), obtained in 2), and potassium carbonate (K$_2$CO$_3$) (3.2 g) in ethanol (100 ml) with ice-bath cooling and the mixture was stirred at room temperature for 20 hours. The solvent was then distilled off and the residue was dissolved in water-ethyl acetate and extracted with ethyl acetate. The extract was washed with saturated NaCl/H$_2$O and dried over MgSO$_4$ and the solvent was distilled off under reduced pressure. The residue was purified by silica gel column chromatography (eluent: ethyl acetate-methanol=9:1) to provide the free base (6.01 g) of the title compound as colorless oil.

$^1$H-NMR (CDCl$_3$) δ: 1.00–1.65 (2H, m), 1.45–1.85 (4H, m), 2.09 (3H, s), 2.53 (1H, dt, J=12.8, 2.6 Hz), 2.85–3.15 (4H, m), 3.68 (2H, s), 3.75–3.90 (1H, m), 3.86 (2H, s), 4.10–4.25 (2H, m), 4.55–4.70 (1H, m), 7.07 (1H, d, J=8.2 Hz), 7.20–7.45 (5H, m), 7.66 (1H, d, J=2.2 Hz), 7.82 (1H, dd, J=8.2, 2.2 Hz).

The above free base (0.2 g) was dissolved in methanol, treated with 1 molar equivalent of hydrogen chloride (HCl, dissolved in ethyl acetate), and precipitated from ethyl acetate-ether to provide the title compound (0.15 g) as colorless amorphous powders.

Elemental analysis, for C$_{26}$H$_{32}$N$_2$O$_3$HCl.1.5H$_2$O. Calcd.: C, 64.65; H, 7.30; N, 5.80. Found: C, 64.44; H, 7.16; N, 5.53.

EXAMPLE 2

1-[4-(Phenylmethyl)-2,3,4,5-tetrahydro-1,4-benzoxazepin-7-yl]-3-(4-piperidinyl)-1-propanone Dihydrochloride

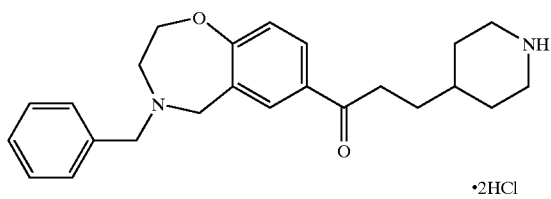

•2HCl

A mixture of 3-(1-acetyl-4-piperidinyl)-1-[4-(phenylmethyl)-2,3,4,5-tetrahydro-1,4-benzoxazepin-7-yl]-1-propanone (6.00 g, 14.3 mmol), obtained in Example 1, and concentrated hydrochloric acid (60 ml) was refluxed for 6 hours. After cooling, the mixture was made basic with saturated potassium carbonate/H$_2$O and extracted with ethyl acetate-tetrahydrofuran (3:1). The extract was washed with saturated NaCl/H$_2$O and dried over MgSO$_4$ and the solvent was distilled off under reduced pressure to provide the free base (5.12 g) of the title compound as oil.

$^1$H-NMR (CDCl$_3$) δ: 1.00–1.80 (10H, m), 2.58 (2H, dt, J=12.0, 2.2 Hz), 2.92 (2H, t, J=7.6 Hz), 3.00–3.20 (3H, m), 3.68 (2H, s), 3.86 (2H, s), 4.14 (2H, t, J=4.6 Hz), 7.07 (1H, d, J=8.2 Hz), 7.20–7.40 (5H, m), 7.66 (1H, d, J=2.2 Hz), 7.83 (1H, dd, J=8.2, 2.2 Hz).

The above free base (0.2 g) was dissolved in methanol, treated with 2 molar equivalents of HCl (dissolved in ethyl acetate), and precipitated from ethyl acetate-ether to provide the title compound (0.15 g) as colorless amorphous powders.

Elemental analysis, for C$_{24}$H$_{30}$N$_2$O$_2$.2HCl.2.5H$_2$O. Calcd.: C, 62.53; H, 8.09; N, 6.08. Found: C, 62.61; H, 7.81; N, 5.95.

EXAMPLE 3

3-[1-[(2-Methylphenyl)methyl]-4-piperidinyl]-1-[4-(phenylmethyl)-2,3,4,5-tetrahydro-1,4-benzoxazepin-7-yl]-1-propanone Dihydrochloride

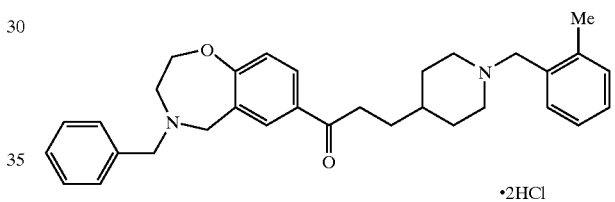

•2HCl

A solution of 2-methylbenzyl bromide (0.29 g, 1.57 mmol) in ethanol (2 ml) was added dropwise to a solution of 1-[4-(phenylmethyl)-2,3,4,5-tetrahydro-1,4-benzoxazepin-7-yl]-3-(4-piperidinyl)-1-propanone (free base, 0.60 g, 1.59 mmol), obtained in Example 2, and potassium carbonate (0.3 g) in ethanol (25 ml) with ice-bath cooling and the mixture was stirred at room temperature for 4 hours. The solvent was then distilled off and the residue was dissolved in water-ethyl acetate and extracted with ethyl acetate. The extract was washed with saturated NaCl/H$_2$O and dried over MgSO$_4$ and the solvent was distilled off under reduced pressure. The residue was purified by silica gel column chromatography (eluent: ethyl acetate-methanol=9:1) to provide the free base (543 mg) of the title compound as colorless crystals melting at 82–83° C.

$^1$H-NMR (CDCl$_3$) δ: 1.18–1.40 (3H, m), 1.55–1.75 (4H, m), 1.92 (2H, t-like, J=10.6 Hz), 2.33 (3H, s), 2.80–2.95 (4H, m), 3.08 (2H, t-like, J=4.4 Hz), 3.45 (2H, s), 3.67 (2H, s), 3.85 (2H, s), 4.13 (2H, t-like, J=4.4 Hz), 7.00–7.40 (10H, m), 7.64 (1H, d, J=2.2 Hz), 7.80 (1H, dd, J=8.4, 2.2 Hz).

The above free base (543 mg) was dissolved in methanol, treated with 2 molar equivalents of HCl (dissolved in ethyl acetate), and precipitated from ethanol-ether to provide the title compound (594 mg) as colorless powders melting at 232–234° C.

Elemental analysis, for C$_{32}$H$_{38}$N$_2$O$_2$.2HCl. Calcd.: C, 69.18; H, 7.26; N, 5.04. Found: C, 68.64; H, 7.24; N, 4.91.

EXAMPLE 4

3-[1-[(3-Methylphenyl)methyl]-4-piperidinyl]-1-[4-(phenylmethyl)-2,3,4,5-tetrahydro-1,4-benzoxazepin-7-yl]-1-propanone Dihydrochloride

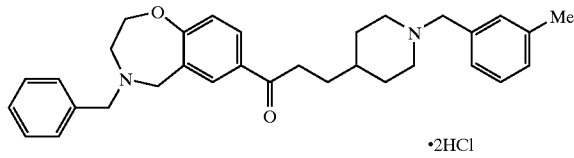

•2HCl

Using 1-[4-(phenylmethyl)-2,3,4,5-tetrahydro-1,4-benzoxazepin-7-yl]-3-(4-piperidinyl)-1-propanone (free base), obtained in Example 2, and 3-methylbenzyl bromide, the procedure of Example 3 was similarly repeated to provide the title compound as colorless, powders melting at 212–214° C.

$^1$H-NMR (CDCl$_3$, free base) δ: 1.20–1.40 (3H, m), 1.55–1.75 (4H, m), 1.98 (2H, t-like, J=10.6 Hz), 2.34 (3H, s), 2.80–2.95 (4H, m), 3.07 (2H, t-like, J=4.4 Hz), 3.45 (2H, s), 3.66 (2H, s), 3.85 (2H, s), 4.13 (2H, t-like, J=4.4 Hz), 7.00–7.40 (10H, m), 7.64 (1H, d, J=2.2 Hz), 7.81 (1H, dd, J=8.4, 2.2 Hz). Elemental analysis, for C$_{32}$H$_{38}$N$_2$O$_2$.2HCl.0.5H$_2$O. Calcd.: C, 68.08; H, 7.32; N, 4.96. Found: C, 67.84; H, 7.51; N, 4.93.

EXAMPLE 5

3-[1-[(4-Methylphenyl)methyl]-4-piperidinyl]-1-[4-(phenylmethyl)-2,3,4,5-tetrahydro-1,4-benzoxazepin-7-yl]-1-propanone Dihydrochloride

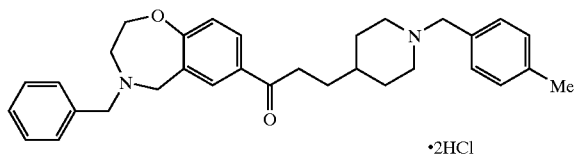

•2HCl

Using 1-[4-(phenylmethyl)-2,3,4,5-tetrahydro-1,4-benzoxazepin-7-yl]-3-(4-piperidinyl)-1-propanone (free base), obtained in Example 2, and 4-methylbenzyl bromide, the procedure of Example 3 was similarly repeated to provide the title compound as colorless powders melting at 236–238° C.

$^1$H-NMR (CDCl$_3$, free base) δ: 1.20–1.40 (3H, m); 1.50–1.80 (4H, m), 1.96 (2H, t-like, J=11.0 Hz), 2.35 (3H, s), 2.80–2.95 (4H, m), 3.08 (2H, t-like, J=4.4 Hz), 3.42 (2H, s), 3.67 (2H, s), 3.85 (2H, s), 4.13 (2H, t-like, J=4.4 Hz), 7.05 (1H, d, J=8.4 Hz), 7.10–7.40 (9H, m), 7.64 (1H, d, J=2.2 Hz), 7.81 (1H, dd, J=8.4, 2.2 Hz). Elemental analysis, for C$_{32}$H$_{38}$N$_2$O$_2$.2HCl.0.5H$_2$O. Calcd.: C, 68.08; H, 7.32; N, 4.96. Found: C, 68.54; H, 7.18; N, 4.97.

EXAMPLE 6

3-[1-[(2-Fluorophenyl)methyl]-4-piperidinyl]-1-[4-(phenylmethyl)-2,3,4,5-tetrahydro-1,4-benzoxazepin-7-yl]-1-propanone Dihydrochloride

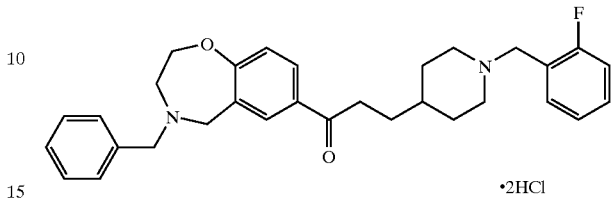

•2HCl

Using 1-[4-(phenylmethyl)-2,3,4,5-tetrahydro-1,4-benzoxazepin-7-yl]-3-(4-piperidinyl)-1-propanone (free base), obtained in Example 2, and 2-fluorobenzyl bromide, the procedure of Example 3 was similarly repeated to provide the title compound as colorless powders melting at 242–244° C.

$^1$H-NMR (CDCl$_3$, free base) δ: 1.20–1.45 (3H, m), 1.60–1.75 (4H, m), 2.00 (2H, t-like, J=12.2 Hz), 2.85–2.95 (4H, m), 3.07 (2H, t-like, J=4.4 Hz), 3.56 (2H, s), 3.67 (2H, s), 3.85 (2H, s), 4.12 (2H, t-like, J=4.4 Hz), 6.95–7.45 (10H, m), 7,64 (1H, d, J=2.2 Hz), 7.81 (1H, dd, J=8.6, 2.2 Hz). Elemental analysis, for C$_{31}$H$_{35}$FN$_2$O$_2$.2HCl. Calcd.: C, 66.54; H, 6.66; N, 5.01. Found: C, 66.42; H, 6.63; N, 4.94.

EXAMPLE 7

3-[1-[(3-Fluorophenyl)methyl]-4-piperidinyl]-1-[4-(phenylmethyl)-2,3,4,5-tetrahydro-1,4-benzoxazepin-7-yl]-1-propanone Dihydrochloride

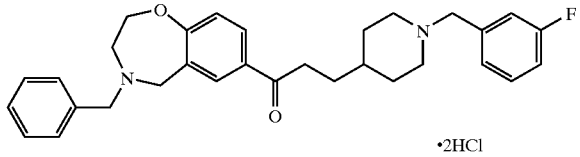

•2HCl

Using 1-[4-(phenylmethyl)-2,3,4,5-tetrahydro-1,4-benzoxazepin-7-yl]-3-(4-piperidinyl)-1-propanone (free base), obtained in Example 2, and 3-fluorobenzyl bromide, the procedure of Example 3 was similarly repeated to provide the title compound as colorless powders melting at 241–243° C.

$^1$H-NMR (CDCl$_3$, free base) δ: 1.20–1.40 (3H, m), 1.60–1.75 (4H, m), 1.95 (2H, t-like, J=11.0 Hz), 2.80–3.00 (4H, m), 3.07 (2H, t-like, J=4.4 Hz), 3.46 (2H, s), 3.66 (2H, s), 3.85 (2H, s), 4.13 (2H, t-like, J=4.4 Hz), 6.85–7.40 (10H, m), 7.65 (1H, d, J=2.2 Hz), 7.81 (1H, dd, J=8.4, 2.2 Hz). Elemental analysis, for C$_{31}$H$_{35}$FN$_2$O$_2$.2HCl.0.5H$_2$O. Calcd.: C, 65.49; H, 6.74; N, 4.93. Found: C, 65.49; H, 6.79; N, 4.82.

EXAMPLE 8

3-[1-[(4-Fluorophenyl)methyl]-4-piperidinyl]-1-[4-(phenylmethyl)-2,3,4 5-tetrahydro-1,4-benzoxazepin-7-yl]-1-propanone Dihydrochloride

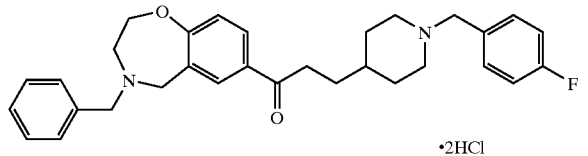

•2HCl

Using 1-[4-(phenylmethyl)-2,3,4,5-tetrahydro-1,4-benzoxazepin-7-yl]-3-(4-piperidinyl)-1-propanone (free base), obtained in Example 2, and 4-fluorobenzyl bromide, the procedure of Example 3 was similarly repeated to provide the title compound as colorless powders melting at 212–214° C.

$^1$H-NMR (CDCl$_3$, free base) δ: 1.20–1.40 (3H, m), 1.60–1.75 (4H, m), 1.93 (2H, t-like, J=11.0 Hz), 2.80–2.95 (4H, m), 3.07 (2H, t-like, J=4.4 Hz), 3.45 (2H, s), 3.66 (2H, s), 3.84 (2H, s), 4.13 (2H, t-like, J=4.4 Hz), 6.90–7.10 (4H, m), 7.20–7.40 (6H, m), 7.65 (1H, d, J=2.2 Hz), 7.81 (1H, dd, J=8.0, 2.2 Hz). Elemental analysis, for C$_{31}$H$_{35}$FN$_2$O$_2$.2HCl.0.5H$_2$O. Calcd.: C, 65.49; H, 6.74; N, 4.93. Found: C, 66.00; H, 6.60; N, 4.77.

EXAMPLE 9

1-[4-(Phenylmethyl)-2,3,4,5-tetrahydro-1,4-benzoxazepin-7-yl]-3-[1-[(2-pyridyl)methyl]-4-piperidinyl]-1-propanone Trihydrochloride

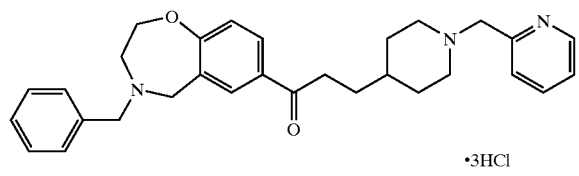

•3HCl

Using 1-[4-(phenylmethyl)-2,3,4,5-tetrahydro-1,4-benzoxazepin-7-yl]-3-(4-piperidinyl)-1-propanone (free base), obtained in Example 2, and 2-picolyl chloride, the procedure of Example 3 was similarly repeated to provide the title compound as colorless powders melting at 238–240° C.

$^1$H-NMR (CDCl$_3$, free base) δ: 1.25–1.50 (3H, m), 1.60–1.80 (4H, m), 2.06 (2H, t-like, J=10.8 Hz), 2.80–3.00 (4H, m), 3.08 (2H, t-like, J=4.4 Hz), 3.64 (2H, s), 3.67 (2H, s), 3.85 (2H, s), 4.13 (2H, t-like, J=4.4 Hz), 7.06 (1H, d, J=8.2 Hz), 7.10–7.20 (1H, m), 7.25–7.55 (5H, m), 7.42 (1H, d, J=7.8 Hz), 7.60–7.70 (2H, m), 7.82 (1H, dd, J=8.2, 2.2 Hz), 8.55 (1H, d, J=4.4 Hz). Elemental analysis, for C$_{30}$H$_{35}$N$_3$O$_2$.3HCl. Calcd.: C, 62.23; H, 6.62; N, 7.26. Found: C, 61.80; H, 6.64; N, 7.25.

EXAMPLE 10

1-[4-(Phenylmethyl)-2,3,4,5-tetrahydro-1,4-benzoxazepin-7-yl]-3-[1-[(3-pyridyl)methyl]-4-piperidinyl]-1-propanone Trihydrochloride

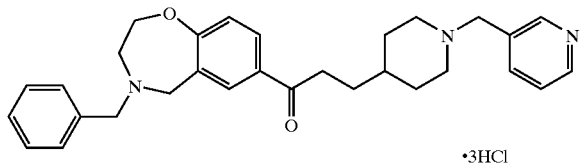

•3HCl

Using 1-[4-(phenylmethyl)-2,3,4,5-tetrahydro-1,4-benzoxazepin-7-yl]-3-(4-piperidinyl)-1-propanone (free base), obtained in Example 2, and 3-picolyl chloride, the procedure of Example 3 was similarly repeated to provide the title compound as colorless powders melting at 228–230° C.

$^1$H-NMR (CDCl$_3$, free base) δ: 1.20–1.40 (3H, m), 1.60–1.80 (4H, m), 1.98 (2H, t-like, J=10.6 Hz), 2.80–3.00 (4H, m), 3.07 (2H, t-like, J=4.0 Hz), 3.50 (2H, s), 3.67 (2H, s), 3.85 (2H, s), 4.13 (2H, t-like, J=4.0 Hz), 7.06 (1H, d, J=8.4 Hz), 7.20–7.40 (6H, m), 7.60–7.75, (2H, m), 7.81 (1H, dd, J=8.4, 1.4 Hz), 8.45–8.55 (1H, m). Elemental analysis, for C$_{30}$H$_{35}$N$_3$O$_2$.3HCl.2H$_2$O. Calcd.: C, 58.59; H, 6.88; N, 6.83. Found: C, 58.85; H, 6.73; N, 6.78.

EXAMPLE 11

1-[4-(Phenylmethyl)-2,3,4,5-tetrahydro-1,4-benzoxazepin-7-yl]-3-[1-[(4-pyridyl)methyl]-4-piperidinyl]-1-propanone Trihydrochloride

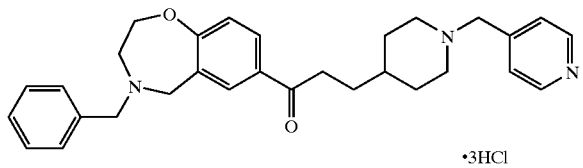

•3HCl

Using 1-[4-(phenylmethyl)-2,3,4,5-tetrahydro-1,4-benzoxazepin-7-yl]-3-(4-piperidinyl)-1-propanone (free base), obtained in Example 2, and 4-picolyl chloride, the procedure of Example 3 was similarly repeated to provide the title compound as colorless powders melting at 243–245° C.

$^1$H-NMR (CDCl$_3$, free base) δ: 1.20–1.50 (3H, m), 1.60–1.80 (4H, m), 1.98 (2H, t-like, J=10.2 Hz), 2.70–3.00 (4H, m), 3.07 (2H, t-like, J=4.2 Hz), 3.47 (2H, s), 3.66 (2H, s), 3.84 (2H, s), 4.13 (2H, t-like, J=4.2 Hz), 7.06 (1H, d, J=8.4 Hz), 7.20–7.40 (7H, m), 7.65 (1H, d, J=1.8 Hz), 7.82 (1H, dd, J=8.2, 1.8 Hz), 8.52 (1H, d, J=4.4 Hz). Elemental analysis, for C$_{30}$H$_{35}$N$_3$O$_2$.3HCl.0.5H$_2$O. Calcd.: C, 61.28; H, 6.69; N, 7.15. Found: C, 61.59; H, 6.67; N, 7.14.

EXAMPLE 12

1-[4-(Phenylmethyl)-2,3,4,5-tetrahydro-1,4-benzoxazepin-7-yl]-3-[1-[(2-trifluoromethylphenyl)methyl]-4-piperidinyl]-1-propanone Dihydrochloride

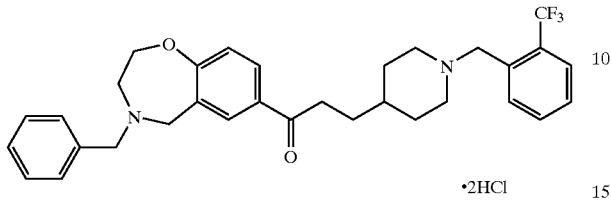

•2HCl

Using 1-[4-(phenylmethyl)-2,3,4,5-tetrahydro-1,4-benzoxazepin-7-yl]-3-(4-piperidinyl)-1-propanone (free base), obtained in Example 2, and 2-(trifluoromethyl)benzyl bromide, the procedure of Example 3 was similarly repeated to provide the title compound as colorless powders melting at 223–225° C.

$^1$H-NMR (CDCl$_3$, free base) δ: 1.20–1.45 (3H, m), 1.60–1.90 (4H, m), 1.95–2.03 (2H, m), 2.80–3.00 (4H, m), 3.08 (2H, t-like, J=4.2 Hz), 3.63 (2H, s), 3.67 (2H, s), 3.86 (2H, s), 4.10–4.20 (2H, m), 7.07 (1H, d, J=8.4 Hz), 7.20–7.40 (6H, m), 7.45–7.70 (3H, m), 7.80–7.90 (2H, m). Elemental analysis, for C$_{32}$H$_{35}$F$_3$N$_2$O$_2$.2HCl.0.5H$_2$O. Calcd.: C, 62.14; H, 6.19; N, 4.53. Found: C, 62.53; H, 5.84; N, 4.61.

EXAMPLE 13

1-[4-(Phenylmethyl)-2,3,4,5-tetrahydro-1,4-benzoxazepin-7-yl]-3-[1-[(3-trifluoromethylphenyl)methyl]-4-piperidinyl]-1-propanone Dihydrochloride

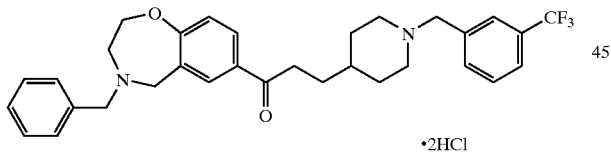

•2HCl

Using 1-[4-(phenylmethyl)-2,3,4,5-tetrahydro-1,4-benzoxazepin-7-yl]-3-(4-piperidinyl)-1-propanone (free base), obtained in Example 2, and 3-(trifluoromethyl)benzyl bromide, the procedure of Example 3 was similarly repeated to provide the title compound as colorless powders melting at 235–237° C.

$^1$H-NMR (CDCl$_3$, free base) δ: 1.20–1.45 (3H, m), 1.60–1.80 (3H, m), 1.85–2.10 (3H, m), 2.75–2.95 (4H, m), 3.08 (2H, t-like, J=4.2 Hz), 3.53 (2H, s), 3.67 (2H, s), 3.86 (2H, s), 4.10–4.20 (2H, m), 7.06 (1H, d, J=8.4 Hz), 7.20–7.60 (9H, m), 7.65 (1H, d, J=2.2 Hz), 7.82 (1H, dd, J=8.4, 2.2 Hz). Elemental analysis, for C$_{32}$H$_{35}$F$_3$N$_2$O$_2$.2HCl.0.5H$_2$O. Calcd.: C, 62.14; H, 6.19; N, 4.53. Found: C, 62.43; H, 6.04; N, 4.61.

EXAMPLE 14

1-[4-(Phenylmethyl)-2,3,4,5-tetrahydro-1,4-benzoxazepin-7-yl]-3-[1-[(4-trifluoromethylphenyl)methyl]-4-piperidinyl]-1-propanone Dihydrochloride

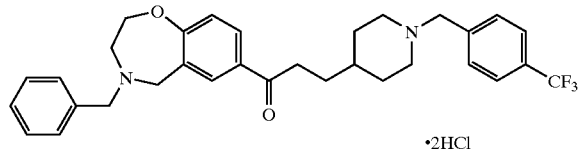

•2HCl

Using 1-[4-(phenylmethyl)-2,3,4,5-tetrahydro-1,4-benzoxazepin-7-yl]-3-(4-piperidinyl)-1-propanone (free base), obtained in Example 2, and 4-(trifluoromethyl)benzyl bromide, the procedure of Example 3 was similarly repeated to provide the title compound as colorless powders melting at 239–241° C.

$^1$H-NMR (CDCl$_3$, free base) δ: 1.20–1.45 (3H, m), 1.60–1.80 (4H, m), 1.85–2.10 (2H, m), 2.75–2.95 (4H, m), 3.08 (2H, t-like, J=4.2 Hz), 3.53 (2H, s), 3.67 (2H, s), 3.85 (2H, s), 4.10–4.20 (2H, m), 7.06 (1H, d, J=8.4 Hz), 7.20–7.65 (9H, m), 7.65 (1H, d, J=2.2 Hz), 7.82 (1H, dd, J=8.4, 2.2 Hz). Elemental analysis, for C$_{32}$H$_{35}$F$_3$N$_2$O$_2$.2HCl. Calcd.: C, 63.05; H, 6.12; N, 4.60. Found: C, 62.81; H, 6.11; N, 4.79.

EXAMPLE 15

3-[1-[(1,3-Benzodioxol-5-yl)methyl]-4-piperidinyl]-1-[4-(phenylmethyl)-2,3,4,5-tetrahydro-1,4-benzoxazepin-7-yl]-1-propanone Dihydrochloride

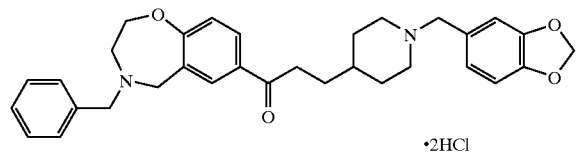

•2HCl

Using 1-[4-(phenylmethyl-2,3,4,5-tetrahydro-1,4-benzoxazepin-7-yl]-3-(4-piperidinyl)-1-propanone (free base), obtained in Example 2, and 5-bromomethyl-1,3-benzdioxole, the procedure of Example 3 was similarly repeated to provide the title compound as colorless powders melting at 233–235° C.

$^1$H-NMR (CDCl$_3$, free base) δ: 1.15–1.40 (3H m), 1.55–1.75 (4H, m), 1.80–2.00 (2H, m), 2.80–2.95 (4H, m), 3.07 (2H, t-like, J=4.2 Hz), 3.38 (2H, s), 3.66 (2H, s), 3.85 (2H, s), 4.13 (2H, t-like J=4. 2 Hz), 5.92 (2H, s), 6.73 (2H, s), 6.85 (1H, s), 7.05 (1H, d, J=8.2 Hz), 7.20–7.40 (5H, m), 7.64 (1H, d, J=1.8 Hz), 7.81 (1H, dd, J=8.6, 2.2 Hz). Elemental analysis, for C$_{32}$H$_{36}$N$_2$O$_4$.2HCl.0.5H$_2$O. Calcd.: C, 64.64; H, 6.61; N, 4.71. Found: C, 64.65; H, 6.50; N, 4.66.

EXAMPLE 16

3-[1-[(3,5-Dinitrophenyl)methyl]-4-piperidinyl]-1-[4-(phenylmethyl)-2,3,4,5-tetrahydro-1,4-benzoxazepin-7-yl]-1-propanone Dihydrochloride

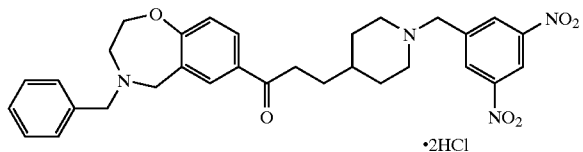

·2HCl

Using 1-[4-(phenylmethyl)-2,3,4,5-tetrahydro-1,4-benzoxazepin-7-yl]-3-(4-piperidinyl)-1-propanone (free base), obtained in Example 2, and 3,5-dinitrobenzyl bromide, the procedure of Example 3 was similarly repeated to provide the title compound as colorless powders melting at 232° C. (dec.).

$^1$H-NMR (CDCl$_3$, free base) δ: 1.20–1.50 (3H, m), 1.60–1.90 (4H, m), 2.00–2.20 (2H, m), 2.80–3.00 (4H, m), 3.08 (2H, t-like, J=4.4 Hz), 3.68 (4H, s), 3.85 (2H, s), 4.14 (2H, t-like, J=4.4 Hz), 7.06 (1H, d, J=8.4 Hz), 7.20–7.40 (5H, m), 7.66 (1H, d, J=2.2 Hz), 7.82 (1H, dd, J=8.4, 2.2 Hz), 8.55 (2H, d, J=2.2 Hz), 8.92 (1H, s). Elemental analysis, for C$_{31}$H$_{34}$N$_4$O$_6$.2HCl.0.5H$_2$O. Calcd.: C, 58.13; H, 5.82; N, 8.75. Found: C, 58.39; H, 5.76; N, 8.65.

EXAMPLE 17

3-[1-[(3,5-Difluorophenyl)methyl]-4-piperidinyl]-1-[4-(phenylmethyl)-2,3,4,5-tetrahydro-1,4-benzoxazepin-7-yl]-1-propanone Dihydrochloride

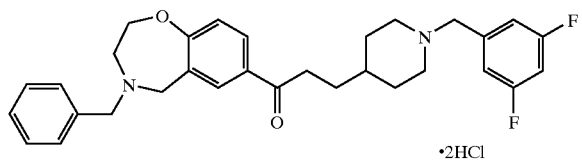

·2HCl

Using 1-[4-(phenylmethyl)-2,3,4,5-tetrahydro-1,4-benzoxazepin-7-yl]-3-(4-piperidinyl)-1-propanone (free base), obtained in Example 2, and 3,5-difluorobenzyl bromide, the procedure of Example 3 was similarly repeated to provide the title compound as colorless powders melting at 241–243° C.

$^1$H-NMR (CDCl$_3$, free base) δ: 1.20–1.45 (3H, m), 1.55–1.65 (4H, m), 1.85–2.10 (2H, m), 2.80–3.00 (4H, m), 3.07 (2H, t-like, J=4.4 Hz), 3.43 (2H, s), 3.67 (2H, s), 3.85 (2H, m), 4.13 (2H, t-like, J=4.4 Hz), 6.66 (1H, tt, J=8.8, 2.2 Hz), 6.80–6.95 (2H, m), 7.06 (1H, d, J=8.4 Hz), 7.20–7.40 (5H, m), 7.65 (1H, d, J=1.8 Hz), 7.81 (1H, dd, J=8.4, 2.2 Hz). Elemental analysis, for C$_{31}$H$_{34}$F$_2$N$_2$O$_2$.2HCl. Calcd.: C, 64.47; H, 6.28; N, 4.85. Found: C, 64.66; H, 6.25; N, 4.79.

EXAMPLE 18

1-[4-(Phenylmethyl)-2,3,4,5-tetrahydro-1,4-benzoxazepin-7-yl]-3-[1-[[3,5-bis(trifluoromethyl)phenyl]methyl]-4-piperidinyl]-1-propanone Dihydrochloride

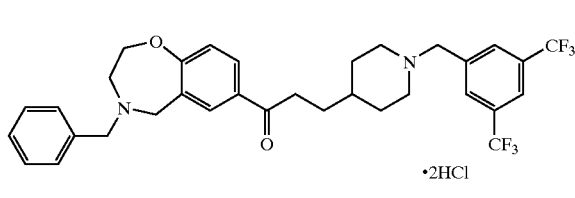

·2HCl

Using 1-[4-(phenylmethyl)-2,3,4,5-tetrahydro-1,4-benzoxazepin-7-yl]-3-(4-piperidinyl)-1-propanone (free base), obtained in Example 2, and 3,5-bis(trifluoromethyl)benzyl bromide, the procedure of Example 3 was similarly repeated to provide the title compound as colorless powders melting at 234–236° C.

$^1$H-NMR (CDCl$_3$, free base) δ: 1.20–1.45 (3H, m), 1.60–1.80 (4H, m), 1.90–2.10 (2H, m), 2.80–3.00 (4H, m), 3.08 (2H, t-like, J=4.2 Hz), 3.57 (2H, s), 3.67 (2H, s), 3.85 (2H, s), 4.14 (2H, t-like, J=4.2 Hz), 7.06 (1H, d, J=8.4 Hz), 7.20–7.40 (5H, m), 7.66 (1H, d, J=2.2 Hz), 7.75–7.85 (4H, m). Elemental analysis, for C$_{33}$H$_{34}$F$_6$N$_2$O$_2$.2HCl. Calcd.: C, 58.50; H, 5.36; N, 4.13. Found: C, 58.22; H, 5.40; N, 3.96.

EXAMPLE 19

1-[4-(Phenylmethyl)-2,3,4,5-tetrahydro-1,4-benzoxazepin-7-yl]-3-[1-[(3,4,5-trimethoxyphenyl)methyl]-4-piperidinyl]-propanone Dihydrochloride

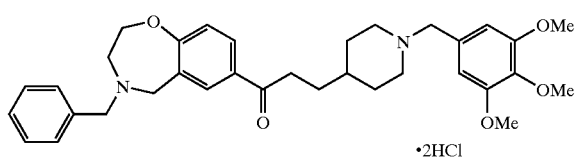

·2HCl

Using 1-[4-(phenylmethyl)-2,3,4,5-tetrahydro-1,4-benzoxazepin-7-yl]-3-(4-piperidinyl)-1-propanone (free base), obtained in Example 2, and 3,4,5-trimethoxybenzyl bromide, the procedure of Example 3 was similarly repeated to provide the title compound as colorless amorphous powders.

$^1$H-NMR (CDCl$_3$, free base) δ: 1.20–1.45 (3H, m), 1.60–1.80 (4H, m), 1.90–2.05 (2H, m), 2.80–3.00 (4H, m), 3.07 (2H, t-like, J=4.0 Hz), 3.42 (2H, s), 3.67 (2H, s), 3.80–3.90 (11H, m), 4.13 (2H, t-like, J=4.0 Hz), 6.57 (2H, s), 7.06 (1H, d, J=8.4 Hz), 7.20–7.40 (5H, m), 7.65 (1H, d, J=1.8 Hz), 7.82 (1H, dd, J=8.4, 1.8 Hz). Elemental analysis, for C$_{34}$H$_{42}$N$_2$O$_5$.2HCl.H$_2$O. Calcd.: C, 62.86; H, 7.14; N, 4.31. Found: C, 62.78; H, 7.31; N, 4.02.

EXAMPLE 20

3-[1-[(2-Chlorophenyl)methyl]-4-piperidinyl]-1-[4-(phenylmethyl)-2,3,4,5-tetrahydro-1,4-benzoxazepin-7-yl]-1-propanone Dihydrochloride

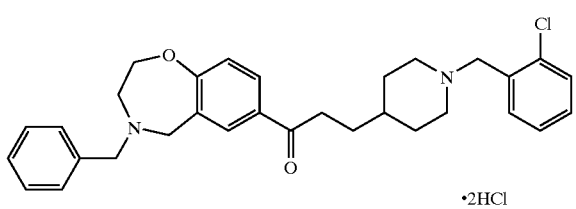

•2HCl

Using 1-[4-(phenylmethyl)-2,3,4,5-tetrahydro-1,4-benzoxazepin-7-yl]-3-(4-piperidinyl)-1-propanone (free base), obtained in Example 2, and 2-chlorobenzyl chloride, the procedure of Example 3 was similarly repeated to provide the title compound as colorless morphous powders.

$^1$H-NMR (CDCl$_3$, free base) δ: 1.10–1.36 (3H, m), 1.47–1.68 (4H, m), 1.90–2.06 (2H, m), 2.75–2.88 (4H, m), 2.99 (2H, t-like, J=4.2 Hz), 3.50 (2H, s), 3.58 (2H, s), 3.76 (2H, s), 4.04 (2H, t-like, J=4.2 Hz), 6.96 (1H, d, J=8.4 Hz), 7.02–7.44 (9H, m) 7.55 (1H, d, J=2.2 Hz), 7.72 (1H, dd, J=2.2, 8.4 Hz). Elemental analysis, for C$_{31}$H$_{35}$ClN$_2$O$_2$.2HCl.2H$_2$O. Calcd.: C, 60.84; H, 6.75; N, 4.58. Found: C, 60.67; H, 6.46; N, 4.31.

EXAMPLE 21

3-[1-[(3-Chlorophenyl)methyl]-4-piperidinyl]-1-[4-(phenylmethyl)-2,3,4,5-tetrahydro-1,4-benzoxazepin-7-yl]-1-propanone Dihydrochloride

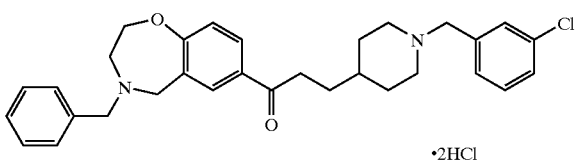

•2HCl

Using 1-[4-(phenylmethyl)-2,3,4,5-tetrahydro-1,4-benzoxazepin-7-yl]-3-(4-piperidinyl)-1-propanone (free base), obtained in Example 2, and 3-chlorobenzyl bromide, the procedure of Example 3 was similarly repeated to provide the title compound as colorless amorphous powders.

$^1$H-NMR (CDCl$_3$, free base) δ: 1.18–1.43 (3H, m), 1.55–1.78 (4H, m), 1.86–2.02 (2H, m), 2.80–2.96 (4H, m), 3.08 (2H, t-like, J=4.4 Hz), 3.45 (2H, s), 3.67 (2H, s), 3.85 (2H, s), 4.14 (2H, t-like, J=4.4 Hz), 7.06 (1H, d, J=8.4 Hz), 7.15–7.38 (9H, m), 7.64 (1H, d, J=2.2 Hz), 7.81 (1H, dd, J=2.2, 8.4 Hz). Elemental analysis, for C$_{31}$H$_{35}$ClN$_2$O$_2$.2HCl.1.5H$_2$O. Calcd.: C, 61.75; H, 6.69; N, 4.65. Found: C, 61.63; H, 6.70; N, 4.39.

EXAMPLE 22

3-[1-[(4-Chlorophenyl)methyl]-4-piperidinyl]-1-[4-(phenylmethyl)-2,3,4,5-tetrahydro-1,4-benzoxazepin-7-yl]-1-propanone Dihydrochloride

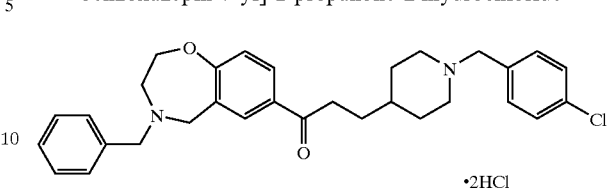

•2HCl

Using 1-[4-(phenylmethyl)-2,3,4,5-tetrahydro-1,4-benzoxazepin-7-yl]-3-(4-piperidinyl)-1-propanone (free base), obtained in Example 2, and 4-chlorobenzyl bromide, the procedure of Example 3 was similarly repeated to provide the title compound as colorless amorphous powders.

$^1$H-NMR (CDCl$_3$, free base) δ: 1.16–1.40 (3H, m), 1.52–1.77 (4H, m), 1.85–2.01 (2H, m), 2.78–2.96 (4H, m), 3.08 (2H, t-like, J=4.2 Hz), 3.44 (2H, s), 3.67 (2H, s), 3.85 (2H, s), 4.14 (2H, t-like, J=4.3 Hz), 7.05 (1H, d, J=8.4 Hz), 7.15–7.37 (9H, m), 7.64 (1H, d, J=2.2 Hz), 7.81 (1H, dd, J=2.2, 8.4 Hz). Elemental analysis, for C$_{31}$H$_{35}$ClN$_2$O$_2$.2HCl.2H$_2$O. Calcd.: C, 60.84; H, 6.75; N, 4.58. Found: C, 61.26; H, 6.43; N, 4.48.

EXAMPLE 23

3-(1-Acetyl-4-piperidinyl)-1-[3-(phenylmethyl)-2,3,4,5-tetrahydro-1H-3-benzazepin-7-yl]-1-propanone Hydrochloride

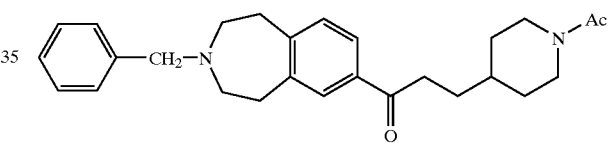

•HCl 1) 3-(1-Acetyl-4-piperidinyl)propionic acid (32.0 g, 0.16 mol) was added in small portions to thionyl chloride (150 ml) under ice cooling. After the mixture was stirred for 5 minutes, the excess thionyl chloride was distilled off and the residue was rinsed with hexane to give 3-(1-acetyl-4-piperidinyl)propionyl chloride as light-yellow solid. Aluminum chloride (66.0 g, 0.49 mmol) powders were added portionwise to a mixed solution of the above acid chloride and 3-formyl-2,3,4,5-tetrahydro-1H-3-benzazepine (23.0 g, 0.131 mol), obtained in Reference Example 2, in 1,2-dichloroethane (100 ml) with ice-bath cooling. This mixture was stirred at room temperature for 20 hours. It was then poured in ice-water and extracted with ethyl acetate. The extract was washed with saturated NaCl/H$_2$O and dried over MgSO$_4$. The solvent was then distilled off under reduced pressure and the residue was purified by silica gel column chromatography (eluent: ethyl acetate-methanol=9:1) to provide 3-(1-acetyl-4-piperidinyl)-1-(3-formyl-2,3,4,5-tetrahydro-1H-3-benzazepin-7-yl)-1-propanone (44 g) as light-yellow oil.

$^1$H-NMR (CDCl$_3$) δ: 1.02–1.31 (2H, m), 1.49–1.88 (5H, m), 2.09 (3H, s), 2.44–2.62 (1H, m), 2.92–3.12 (7H, m), 3.47–3.56 (2H, m), 3.64–3.88 (3H, m), 4.54–4.68 (1H, m), 7.22–7.30 (1H, m), 7.70–7.80 (2H, m), 8.17 (1H, br).

2) A solution of 3-(1-acetyl-4-piperidinyl)-1-(3-formyl-2,3,4,5-tetrahydro-1H-3-benzazepin-7-yl)-1-propanone (44 g), obtained in 1), in methanol (300 ml) and concentrated hydrochloric acid (300 ml) were heated together at 80–85° C. for 2 hours. The methanol was distilled off and the residual aqueous solution was made basic with sodium hydroxide/H$_2$O and extracted with ethyl acetate. The extract was washed with saturated NaCl/H$_2$O and dried over MgSO$_4$ and the solvent was distilled off under reduced pressure to provide 3-(1-acetyl-4-piperidinyl)-1-(2,3,4,5-tetrahydro-1H-3-benzazepin-7-yl)-1-propanone (40 g) as light-yellow oil.

$^1$H-NMR (CDCl$_3$) δ: 1.02–1.30 (2H, m), 1.45–1.88, (5H, m), 2.08 (3H, s), 2.43–2.62 (1H, m), 2.88–3.12 (12H, m), 3.73–3.88 (1H, m), 4.54–4.68 (1H, m), 7.13–7.21 (1H, m), 7.63–7.73 (2H, m).

3) Benzyl bromide (5.73 g, 33.5 mmol) was added dropwise to a solution of 3-(1-acetyl-4-piperidinyl)-1-(2,3,4,5-tetrahydro-1H-3-benzazepin-7-yl)-1-propanone (11.0 g, 33.5 mmol), obtained in 2), and potassium carbonate (6.0 g) in ethanol (200 ml) with ice-bath cooling and the mixture was stirred at room temperature for 14 hours. The solvent was then distilled off and the residue was dissolved in water-ethyl acetate and extracted with ethyl acetate. The extract was washed with saturated NaCl/H$_2$O and dried over MgSO$_4$ and the solvent was distilled off. The residue was purified by silica gel column chromatography (eluent: ethyl acetate-methanol=10:1) to provide the free base (10.8 g) of the title compound as colorless oil.

$^1$H-NMR (CDCl$_3$) δ: 1.02–1.37 (2H, m), 1.47–1.86 (5H, m), 2.08 (3H, s), 2.43–2.68 (5H, m), 2.81–3.10 (7H, m), 3.64 (2H, s), 3.72–3.88 (1H, m), 4.53–4.68 (1H, m), 7.16 (1H, d, J=7.7 Hz), 7.21–7.41(5H, m), 7.64–7.75 (2H, m).

The above free base (6 g) was dissolved in methanol, treated with 1 molar equivalent of HCl (dissolved in ethyl acetate), and precipitated from ethyl acetate-ether to provide the title compound (5.85 g) as colorless amorphous powders.

Elemental analysis, for C$_{27}$H$_{34}$N$_2$O$_2$.HCl.0.5H$_2$O. Calcd.: C, 69.88; H, 7.82; N, 6.04. Found: C, 69.58; H, 7.98; N, 5.74.

EXAMPLE 24

1-[3-(Phenylmethyl)-2,3,4,5-tetrahydro-1H-3-benzazepin-7-yl]-3-(4-piperidinyl)-1-propanone Dihydrochloride

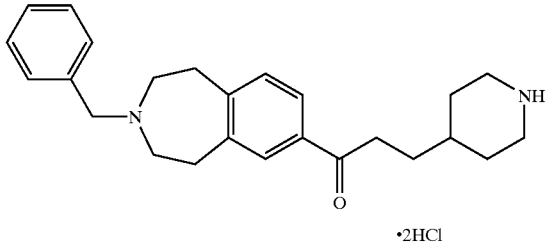

•2HCl

A mixture of 3-(1-acetyl-4-piperidinyl)-1-[3-(phenylmethyl)-2,3,4,5-tetrahydro-1H-3-benzazepin-7-yl]-1-propanone (free base, 8.0 g, 19.1 mmol), obtained in Example 23, and concentrated hydrochloride acid (80 ml) was refluxed for 4 hours. After cooling, the mixture was made basic with sodium hydroxide/H$_2$O and extracted with ethyl acetate. The extract was washed with saturated NaCl/H$_2$O and dried over MgSO$_4$ and the solvent was distilled off under reduced pressure to provide the free base (7.1 g) of the title compound as oil.

$^1$H-NMR (CDCl$_3$) δ: 1.04–1.52 (3H, m), 1.59–2.10 (5H, m), 2.48–2.70 (6H, m), 2.80–3.16 (8H, m), 3.63 (2H, s), 7.15 (1H, d, J=7.7 Hz), 7.20–7.40 (5H, m), 7.63–7.74 (2H, m).

The above free base (0.2 g) was dissolved in methanol, treated with 2 molar equivalents of HCl (dissolved in ethyl acetate), and precipitated from ethyl acetate-ether to provide the title compound (0.15 g) as colorless amorphous powders.

Elemental analysis, for C$_{25}$H$_{32}$N$_2$O.2HCl.H$_2$O. Calcd.: C, 64.23; H, 7.76; N, 5.99. Found: C, 64.58; H, 7.57; N, 5.69.

EXAMPLE 25

4-(1-Acetyl-4-piperidinyl)-1-[3-(phenylmethyl)-2,3,4,5-tetrahydro-1H-3-benzazepin-7-yl]-1-butanone Hydrochloride

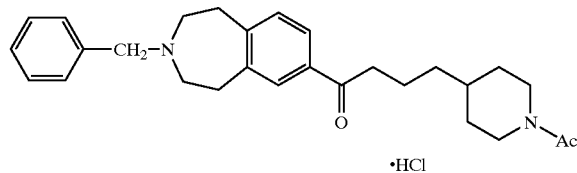

•HCl 1) 4-(1-Acetyl-4-piperidinyl)butyric acid (2.6 g, 12 mmol) was added in small portions to thionyl chloride (12 ml) with ice-bath cooling. After the mixture was stirred for 5 minutes, the excess thionyl chloride was distilled off and the residue was washed with hexane to provide 4-(1-acetyl-4-piperidinyl)butyryl chloride as light-yellow solid. Aluminum chloride (66,0 g, 0.49 mol) powders were added in small portions to a mixed solution of the above acid chloride and 3-trifluoroacetyl-2,3,4,5-tetrahydro-1H-3-benzazepine (2.5 g, 10 mmol), obtained in Reference Example 3, in 1,2-dichloroethane (10 ml) with ice-bath cooling. This mixture was stirred at room temperature for 2 days, then poured in ice-water, and extracted with ethyl acetate. The extract was washed with saturated NaCl/H$_2$O and dried over MgSO$_4$ The solvent was then distilled off under reduced pressure and the residue was purified by silica gel column chromatography (eluent: ethyl acetate-methanol=9:1) to provide 4-(1-acetyl-4-piperidinyl)-1-(3-trifluoroacetyl-2,3,4,5-tetrahydro-1H-3-benzazepin-7-yl)-1-butanone (3.7 g) as colorless crystals melting at 101–102° C.

$^1$H-NMR (CDCl$_3$) δ: 0.98–1.64 (5H, m), 1.66–1.86 (4H, m), 2.08 (3H, s), 2.44–2.61 (1H, m), 2.90–3.11 (7H, m), 3.67–3.87 (5H, m), 4.52–4.66 (1H, m), 7.20–7.30 (1H, m), 7.72–7.80 (2H, m).

2). To a solution of 4-(1-acetyl-4-piperidinyl)-1-(3-trifluoroacetyl-2,3,4,5-tetrahydro-1H-3-benzazepin-7-yl)-1-butanone (3.4 g, 7.8 mmol), obtained in 1), in methanol (50 ml) was added 1 mol/l potassium carbonate/H$_2$O (15 ml) dropwise at room temperature and the mixture was stirred for 24 hours. The methanol was then distilled off and the residual aqueous solution was extracted with ethyl acetate-tetrahydrofuran. The extract was washed with saturated NaCl/H$_2$O and dried over MgSO$_4$. The solvent was then distilled off under reduced pressure to provide 4-(1-acetyl-4-piperidinyl)-1-(2,3,4,5-tetrahydro-1H-3-benzazepin-7-yl)-1-butanone (2.6 g) as colorless crystals melting at 90–91° C.

$^1$H-NMR (CDCl$_3$) δ: 0.98–1.64 (5H, m), 1.66–1.99 (5H, m), 2.08 (3H, s) 2.43–2.61 (1H, m), 2.88–3.10 (11H, m), 3.72–3.86 (1H, m), 4.52–4.66 (1H, m), 7.14–7.22 (1H, m), 7.66–7.74 (2H, m).

3) Benzyl bromide (2.6 g, 15 mmol) was added dropwise to a mixed solution of 4-(1-acetyl-4-piperidinyl)-1-(2,3,4,5- tetrahydro-1H-3-benzazepin-7-yl)-1-butanone (5.2 g, 15 mmol), obtained in 2), and potassium carbonate, (6.3 g) in acetonitrile (10:0 ml) at room temperature and the mixture was stirred at 50° C. for 12 hours. The solvent was then distilled off and the residue was dissolved in water-ethyl acetate and extracted with ethyl acetate. The extract was washed with saturated NaCl/H$_2$O and dried over MgSO$_4$. The solvent was distilled off under reduced pressure and the residue was purified by silica gel column chromatography (eluent: ethyl acetate-methanol=10:1) to provide the free base (4.9 g) of the title compound as colorless crystals melting at 85–86° C.

$^1$H-NMR (CDCl$_3$) δ: 0.95–1.84 (9H, m), 2.08 (3H, s), 2.43–2.70 (5H, m), 2.87–3.10 (7H, m), 3.64 (2H, s), 3.70–3.85 (1H, m), 4.52–4.66 (1H, m), 7.16 (1H, d, J=8.1 Hz), 7.21–7.39 (5H, m), 7.64–7.74 (2H, m).

The above free base (0.5 g) was dissolved in methanol, treated with 1 molar equivalent of HCl (dissolved in ethyl acetate), and precipitated from n-hexane to provide the title compound (0.48 g) as colorless amorphous powders.

Elemental analysis, for C$_{28}$H$_{36}$N$_2$O$_2$HCl.2.5H$_2$O. Calcd.: C, 65.42; H, 8.23; N, 5.45. Found: C, 65.39; H, 8.07; N, 5.24.

EXAMPLE 26

1-[3-(Phenylmethyl)-2,3,4,5-tetrahydro-1H-3-benzazepin-7-yl]-4-(4-piperidinyl)-1-butanone Dihydrochloride

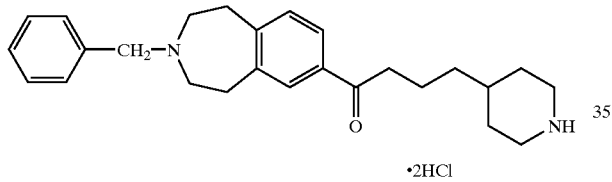

•2HCl

Using 4-(1-acetyl-4-piperidinyl)-1-[3-(phenylmethyl)-2,3,4,5-tetrahydro-1H-3-benzazepin-7-yl]-1-butanone (free base), obtained in Example 25, the procedure of Example 24 was similarly repeated to provide the title compound as colorless powders melting at 201–203° C.

$^1$H-NMR (CDCl$_3$, free base) δ: 0.98–1.50 (5H, m), 1.62–1.83 (5H, m), 2.47–2.70 (6H, m), 2.84–3.15 (8H, m), 2.64 (2H, s), 7.16 (1H, d, J=7.7 Hz), 7.21–7.40 (5H, m), 7.65–7.75 (2H, m). Elemental analysis, for C$_{26}$H$_{34}$N$_2$O.2HCl. Calcd.: C, 67.38; H, 7.83; N, 6.04. Found: C, 66.91; H, 7.85; N, 6.23.

EXAMPLE 27

1-[3-[(4-Fluorophenyl)methyl]-2,3,4,5-tetrahydro-1H-3-benzazepin-7-yl]-3-(1-acetyl-4-piperidinyl)-1-propanone Hydrochloride

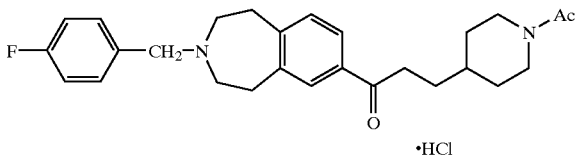

•HCl

Using 3-(1-acetyl-4-piperidinyl)-1-(2,3,4,5-tetrahydro-1H-3-benzazepin-7-yl)-1-propanone (free base), obtained in Example 23-2), and 4-fluorobenzyl bromide, the procedure of Example 23-3) was similarly repeated to provide the title compound as amorphous powders.

$^1$H-NMR (CDCl$_3$, free base) δ: 1.00–1.32 (2H, m), 1.46–1.93 (5H, m), 2.08 (3H, s), 2.43–2.68 (5H, m), 2.83–3.12 (7H, m), 3.59 (2H, s), 3.73–3.88 (1H, m), 4.54–4.68 (1H, m), 7.01 (2H, t-like, J=8.6 Hz), 7.16 (1H, d, J=7.3 Hz), 7.25–7.37 (2H, m), 7.66–7.75 (2H, m). Elemental analysis, for C$_{27}$H$_{33}$FN$_2$O$_2$HCl.3H$_2$O. Calcd.: C, 61.53; H, 7.65; N, 5.31. Found: C, 61.14; H, 7.59; N, 4.89.

EXAMPLE 28

3-[1-[(2-Methylphenyl)methyl]-4-piperidinyl]-1-[3-(phenylmethyl)-2,3,4,5-tetrahydro-1H-3-benzazepin-7-yl]-1-propanone Dihydrochloride

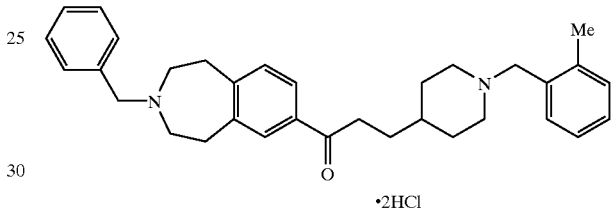

•2HCl

A solution of 2-methylbenzyl bromide (185 mg, 1.0 mmol) in acetonitrile (2 ml) was added dropwise to a suspension of 1-[3-(phenylmethyl)-2,3,4,5-tetrahydro-1H-3-benzazepin-7-yl]-3-(4-piperidinyl)-1-propanone (free base, 377 mg, 1.00 mmol), obtained in Example 24, and potassium carbonate (166 mg) in acetonitrile, (25 ml) with ice-bath cooling and the mixture was stirred at 60° C. for 2 hours. The solvent was then distilled off and the residue was dissolved in water-ethyl acetate and extracted with ethyl acetate. The extract was washed with saturated NaCl/H$_2$O and dried over MgSO$_4$ and the solvent was distilled off under reduced pressure. The residue was purified by silica gel column chromatography (eluent: ethyl acetate-methanol=9:1) to provide the free base (430 mg) of the title compound as colorless oil.

$^1$H-NMR (CDCl$_3$) δ: 1.13–1.39 (3H, m), 1.57–1.74 (4H, m), 1.82–2.07 (2H, m), 2.35 (3H, s), 2.55–2.70 (4H, m), 2.80–3.03 (8H, m), 3.41 (2H, s), 3.63 (2H, s), 7.09–7.40 (10H, m), 7.64–7.74 (2H, m).

The above free base (420 mg) was dissolved in methanol, treated with 2 molar equivalents of HCl (dissolved in ethyl acetate), and precipitated from ethanol-ether to provide the title compound (400 mg) as amorphous powders.

Elemental analysis, for C$_{33}$H$_{40}$N$_2$O.2HCl.H$_2$O. Calcd.: C, 69.34; H, 7.76; N, 4.90. Found: C, 69.06; H, 7.39; N, 4.72.

EXAMPLE 29

3-[1-[(3-Chlorophenyl)methyl]-4-piperidinyl]-1-[3-(phenylmethyl)-2,3,4,5-tetrahydro-1H-3-benzazepin-7-yl]-1-propanone Dihydrochloride

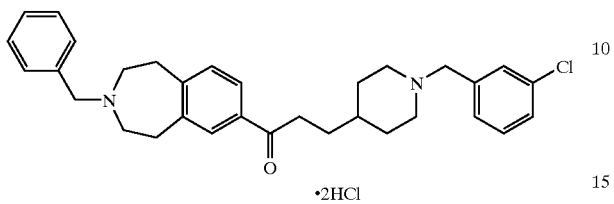

•2HCl

Using 1-[3-(phenylmethyl)-2,3,4,5-tetrahydro-1H-3-benzazepin-7-yl]-3-(4-piperidinyl)-1-propanone (free base), obtained in Example 24, and 3-chlorobenzyl bromide, the procedure of Example 28 was similarly repeated to provide the title compound as amorphous powders.

$^1$H-NMR (CDCl$_3$, free base) δ: 1.18–1.43 (3H, m), 1.58–1.76 (4H, m), 1.86–2.02 (2H, m), 2.57–2.69 (4H, m), 2.79–3.03 (8H, m), 3.44 (2H, s), 3.64 (2H, s), 7.10–7.40 (10H, m), 7.64–7.75 (2H, m). Elemental analysis, for C$_{32}$H$_{37}$ClN$_2$O.2HCl.H$_2$O. Calcd.: C, 64.92; H, 6.98; N, 4.73. Found: C, 64.37; H, 6.80; N, 4.48.

EXAMPLE 30

3-[1-(2-Phenylethyl)-4-piperidinyl]-1-[3-(phenylmethyl)-2,3,4,5-tetrahydro-1H-3-benzazepin-7-yl]-1-propanone Dihydrochloride

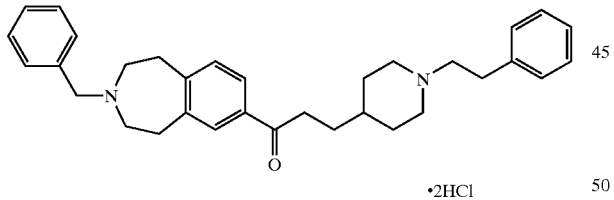

•2HCl

Using 1-[3-(phenylmethyl)-2,3,4,5-tetrahydro-1H-3-benzazepin-7-yl]-3-(4-piperidinyl)-1-propanone (free base), obtained in Example 24, and phenethyl bromide, the procedure of Example 28 was similarly repeated to provide the title compound as amorphous powders.

$^1$H-NMR (CDCl$_3$, free base) δ: 1.22–1.47 (3H, m), 1.62–2.10 (6H, m), 2.50–2.72 (6H, m), 2.76–3.10 (10H, m), 3.64 (2H, s), 7.10–7.40 (11H, m), 7.65–7.74 (2H, m). Elemental analysis, for C$_{33}$H$_{40}$N$_2$O.2HCl.1.5H$_2$O. Calcd.: C, 68.26; H, 7.81; N, 4.82. Found: C, 68.25; H, 7.99; N, 4.66.

EXAMPLE 31

3-([1-((2-Chlorophenyl)methyl)-4-piperidinyl]-1[-3-(phenylmethyl)-2,3,4,5-tetrahydro-1H-3-benzazepin-7-yl]-1-propanone Dihydrochloride

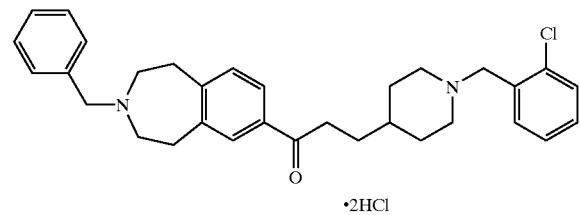

•2HCl

Using 1-[3-(phenylmethyl)-2,3,4,5-tetrahydro-1H-3-benzazepin-7-yl]-3-(4-piperidinyl)-1-propanone (free base), obtained in Example 24, and 2-chlorobenzyl bromide, the procedure of Example 28 was similarly repeated to provide the title compound as amorphous powders.

$^1$H-NMR (CDCl$_3$, free base) δ: 1.20–1.44 (3H, m), 1.59–1.82 (4H, m), 1.97–2.15 (2H, m), 2.57–2.70 (4H, m), 2.82–3.04 (8H, m), 3.59 (2H, s), 3.63 (2H, s), 7.10–7.40 (9H, m), 7.48 (1H, dd, J=1.8, 7.0 Hz), 7.65–7.75 (2H, m). Elemental analysis, for C$_{32}$H$_{37}$ClN$_2$O.2HCl.1.5H$_2$O. Calcd.: C, 63.95; H, 7.04; N, 4.66. Found: C, 63.91; H, 7.31; N, 4.16.

EXAMPLE 32

3-[1-[(4-Chlorophenyl)methyl]-4-piperidinyl]-1-[3-(phenylmethyl)-2,3,4,5-tetrahydro-1H-3-benzazepin-7-yl)]-1-propanone Dihydrochloride

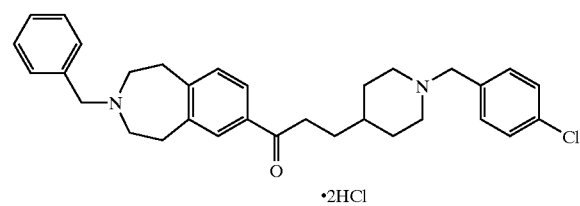

•2HCl

Using 1-[3-(phenylmethyl)-2,3,4,5-tetrahydro-1H-3-benzazepin-7-yl]-3-(4-piperidinyl)-1-propanone (free base), obtained in Example 24, and 4-chlorobenzyl bromide, the procedure of Example 28 was similarly repeated to provide the title compound as amorphous powders.

$^1$H-NMR (CDCl$_3$, free base) δ: 1.16–1.40 (3H, m), 1.58–1.80 (4H, m), 1.85–2.01 (2H, m), 2.55–2.70 (4H, m), 2.77–3.03 (8H, m), 3.43 (2H, s), 3.63 (2H, s), 7.15 (1H, d, J=7.6 Hz), 7.20–7.40 (9H, m), 7.64–7.75 (2H, m). Elemental analysis, for C$_{32}$H$_{37}$ClN$_2$O.2HCl.1.5H$_2$O. Calcd.: C, 63.95; H, 7.04; N, 4.66. Found C, 64.11; H, 6.86; N, 4.48.

EXAMPLE 33

3-(1-Benzoyl-4-piperidinyl)-1-[3-(phenylmethyl)-2,3,4,5-tetrahydro-1H-3-benzazepin-7-yl]-1-propanone Hydrochloride

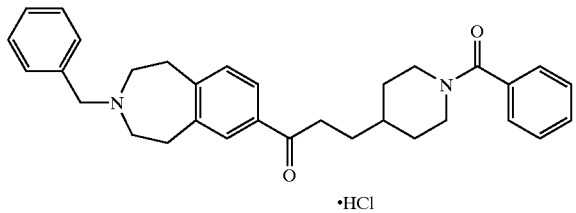

·HCl

Using 1-[3-(phenylmethyl)-2,3,4,5-tetrahydro-1H-3-benzazepin-7-yl]-3-(4-piperidinyl)-1-propanone (free base), obtained in Example 24, and benzoyl chloride, the procedure of Example 28 was similarly repeated to provide the title compound as colorless powders melting at 118–121° C.

$^1$H-NMR (CDCl$_1$, free base) δ: 1.08–1.40 (2H, m), 1.50–1.98 (5H, mm), 2.57–3.07 (12H, m), 3.64 (22H, s), ca. 3.75 (1H, br), ca. 4.70 (1H, br), 7.70 (1H, d, J=7.7 Hz), 7.23–7.43 (10H, m), 7.65–7.74 (2H, m). Elemental analysis, for C$_{32}$H$_{36}$N$_2$O$_2$.HCl.1.5H$_2$O. Calcd.: C, 70.64; H, 7.41; N, 5.15. Found: C, 70.75; H, 7.30; N, 4.91.

EXAMPLE 34

3-(1-Methyl-4-piperidinyl)-1-[3-(phenylmethyl)-2,3,4,5-tetrahydro-1H-3-benzazepin-7-yl]-1-propanone Dihydrochloride

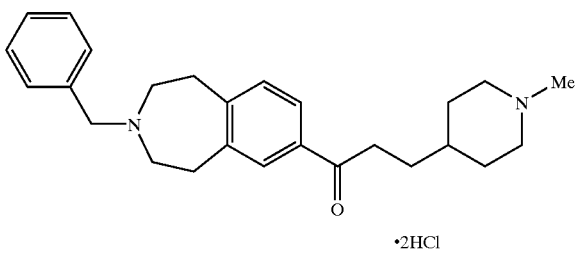

·2HCl

Using 1-[3-(phenylmethyl)-2,3,4,5-tetrahydro-1H-3-benzazepin-7-yl]-3-(4-piperidinyl)-1-propanone (free base), obtained in Example 24, and methyl iodide, the procedure of Example 28 was similarly repeated to provide the title compound as amorphous powders.

$^1$H-NMR (CDCl$_3$, free base) δ: 1.18–1.40 (3H, m), 1.55–2.00 (6H, m), 2.26 (3H, s), 2.57–2.69 (4H, m), 2.79–3.04 (8H, m), 3.64 (2H, s), 7.16 (1H, d, J=7.7 Hz), 7.25–7.40 (5H, m), 7.65–7.75 (2H, m). Elemental analysis, for C$_{26}$H$_{34}$N$_2$O$_2$.HCl.H$_2$O. Calcd.: C, 64.86; H, 7.95; N, 5.82. Found: C, 64.98; H, 7.96; N, 5.66.

EXAMPLE 35

Ethyl 2-[4-[3-oxo-3-[3-(phenylmethyl)-2,3,4,5-tetrahydro-1H-3-benzazepin-7-yl]propyl]-1-piperidinyl]ethanoate Dihydrochloride

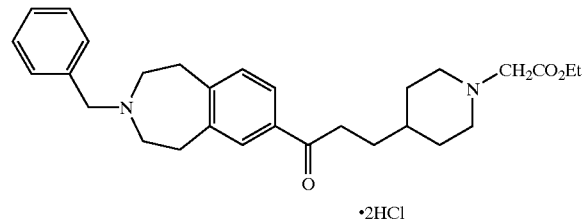

·2HCl

Using 1-[3-(phenylmethyl)-2,3,4,5-tetrahydro-1H-3-benzazepin-7-yl]-3-(4-piperidinyl)-1-propanone (free base), obtained in Example 24, and ethyl bromoacetate, the procedure of Example 28 was similarly repeated to provide the title compound as amorphous powders.

$^1$H-NMR (CDCl$_3$, free base) δ: 1.20–1.50 (6H, m), 1.55–1.78 (4H, m), 2.05–2.20 (2H, m), 2.57–2.68 (4H, m), 2.83–3.03 (8H, m), 3.19 (2H, s), 3.64 (2H, s), 4.18 (2H, q, J=7.1 Hz), 7.16 (1H, d, J=7.6 Hz), 7.20–7.40 (5H, m), 7.64–7.74 (2H, m). Elemental analysis, for C$_{29}$H$_{38}$N$_2$O$_3$.2HCl.2H$_2$O. Calcd.: C, 60.94; H, 7.76; N, 4.90. Found: C, 60.54; H, 7.90; N, 4.78.

EXAMPLE 36

Ethyl 2-[4-[3-oxo-3-[3-(phenylmethyl)-2,3,4,5-tetrahydro-1H-3-benzazepin-7-yl]propyl]-1-piperidinyl]carboxylate Hydrochloride

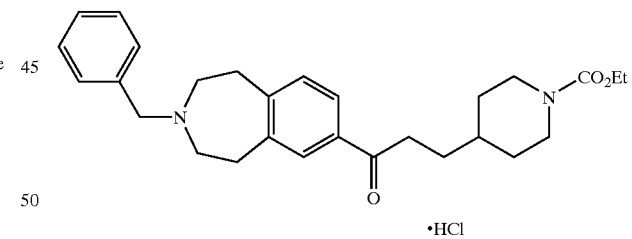

·HCl

Using 1-[3-(phenylmethyl)-2,3,4,5-tetrahydro-1H-3-benzazepin-7-yl]-3-(4-piperidinyl)-1-propanone (free base), obtained in Example 24, and ethyl chlorocarbonate, the procedure of Example 28 was similarly repeated to provide the title compound as amorphous powders.

$^1$H-NMR (CDCl$_3$, free base) δ: 1.03–1.32 (5H, m), 1.38–1.80 (5H, m), 2.50–2.83 (6H, m), 2.88–3.06 (6H, m), 3.64 (2H, s), 4.03–4.24 (4H, m), 7.16 (1H, d, J=7.3 Hz), 7.20–7.40 (5H, m), 7.65–7.75 (2H, m). Elemental analysis, for C$_8$H$_{36}$N$_2$O$_3$.HCl.0.5H$_2$O. Calcd.: C, 68.07; H, 7.75; N, 5.67. Found: C, 67.99; H, 7.98; N, 5.55.

EXAMPLE 37

3-(1-Methylsulfonyl-4-piperidinyl)-1-[3-(phenylmethyl)-2,3,4,5-tetrahydro-1H-3-benzazepin-7-yl]-1-propanone

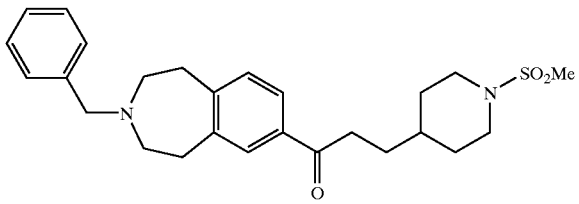

Using 1-[3-(phenylmethyl)-2,3,4,5-tetrahydro-1H-3-benzazepin-7-yl]-3-(4-piperidinyl)-1-propanone (free base), obtained in Example 24, and methanesulfonyl chloride the procedure of Example 28 was similarly repeated to provide the title compound as colorless powders melting at 134–137° C.

$^1$H-NMR (CDCl$_3$) δ: 1.23–1.54 (3H, m), 1.60–1.90 (4H, m), 2.53–2.73 (6H, m), 2.76 (3H, s), 2.92–3.05 (6H, m), 3.66 (2H, s), 3.73–3.87 (2H, m), 7.17 (1H, d, J=7.7 Hz), 7.22–7.40 (5H, m), 7.65–7.74 (2H, m). Elemental analysis, for C$_{26}$H$_{34}$N$_2$O$_3$S.0.5H$_2$O. Calcd.: C, 67.36; H, 7.61; N, 6.04. Found: C, 67.52; H, 7.43; N, 6.15.

EXAMPLE 38

N1-methyl 2-[4-[3-oxo-3-(3-(phenylmethyl)-2,3,4,5-tetrahydro-1H-3-benzazepin-7-yl]propyl]-1-piperidinyl]carboxylate Hydrochloride

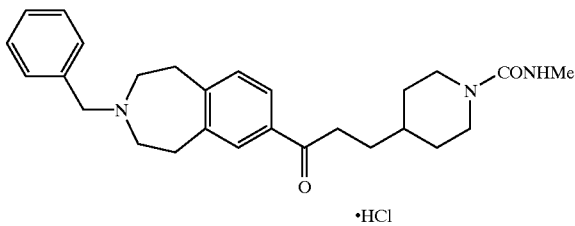

Using 1-[3-(phenylmethyl)-2,3,4,5-tetrahydro-1H-3-benzazepin-7-yl]-3-(4-piperidinyl)-1-propanone (free base), obtained in Example 24, and methyl isocyanate, the procedure of Example 28 was similarly repeated to provide the title compound as amorphous powders.

$^1$H-NMR (CDCl$_1$, free base) δ: 1.05–1.33 (2H, m), 1.37–1.80 (5H, m), 2.57–2.85 (9H, m), 2.90–3.04 (6H, m), 3.64 (2H, s), 3.85–4.00 (2H, m), ca. 4.4 (1H, br), 7.16 (1H, d, J=7.7 Hz), 7.22–7.40 (5H, m), 7.65–7.75 (2H, m). Elemental analysis, for C$_{27}$H$_{35}$N$_3$O$_2$.HCl.3H$_2$O. Calcd.: C, 61.88; H, 8.08; N, 8.02. Found: C, 61.58; H, 7.83; N, 7.62.

EXAMPLE 39

1-[3-[(4-Fluorophenyl)methyl]-2,3,4,5-tetrahydro-1H-3-benzazepin-7-yl]-3-(4-piperidinyl)-1-propanone Dihydrochloride

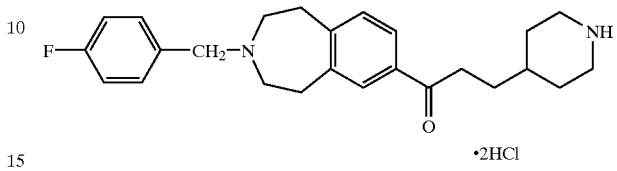

Using 1-[3-[(4-fluorophenyl)methyl]-2,3,4,5-tetrahydro-1H-3-benzazepin-7-yl]-3-(1-acetyl-4-piperidinyl)-1-propanone (free base) as obtained in Example 27, the procedure of Example 24 was similarly repeated to provide the title compound as colorless powders melting at 225–227° C. (dec.).

$^1$H-NMR (CDCl$_3$, free base) δ: 1.02–1.55 (3H, m), 1.58–1.82 (5H, m), 2.48–2.68 (6H, m), 2.80–3.12 (8H, m), 3.59 (2H, s), 7.02 (2H, t-like, J=8.8 Hz), 7.16 (1H, d, J=7.7 Hz), 7.25–7.37 (2H, m), 7.65–7.74 (2H, m). Elemental analysis, for C$_{25}$H$_{31}$FN$_2$O.2HCl.0.5H$_2$O. Calcd.: C, 63.02; H, 7.19; N, 5.88. Found: C, 63.18; H, 7.25; N, 5.80.

EXAMPLE 40

1-[3-[(4-Fluorophenyl)methyl]-2,3,4,5-tetrahydro-1H-3-benzazepin-7-yl]-3-[1-[(4-methoxyphenyl)methyl]-4-piperidinyl]-1-propanone Dihydrochloride

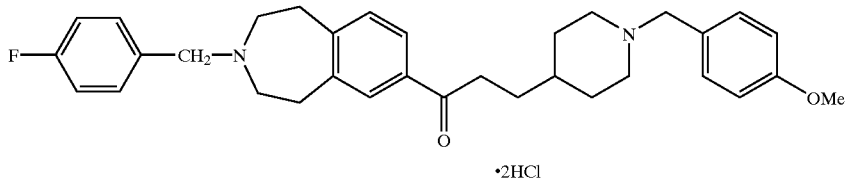

Using 1-[3-[(4-fluorophenyl)methyl]-2,3,4,5-tetrahydro-1H-3-benzazepin-7-yl]-3-(4-piperidinyl)-1-propanone (free base), obtained in Example 39, and 4-methoxybenzyl chloride, the procedure of Example 28 was similarly repeated to provide the title compound as colorless powders melting at 235–238° C. (dec.).

$^1$H-NMR (CDCl$_3$, free base) δ: 1.16–1.40 (3H, m), 1.57–2.00 (6H, m), 2.54–2.67(4H, m), 2.78–3.02 (8H, m), 3.43 (2H, s), 3.59 (2H, s), 3.80 (3H, s), 6.84 (2H, d, J=8.8 Hz), 7.01 (2H, t-like, J=8.8 Hz), 7.10–7.37 (5H, m), 7.64–7.73 (2H, m). Elemental analysis, for $C_{33}H_{39}FN_2O_2 \cdot 2HCl \cdot 0.5H_2O$. Calcd.: C, 66.44; H, 7.10; N, 4.70. Found: C, 66.54; H, 7.05; N, 4.70.

EXAMPLE 41

3-[1-[(4-Chlorophenyl)methyl]-4-piperidinyl]-1-[3-[(4-fluorophenyl)methyl]-2,3,4,5-tetrahydro-1H-3-benzazepin-7-yl]-1-propanone Dihydrochloride

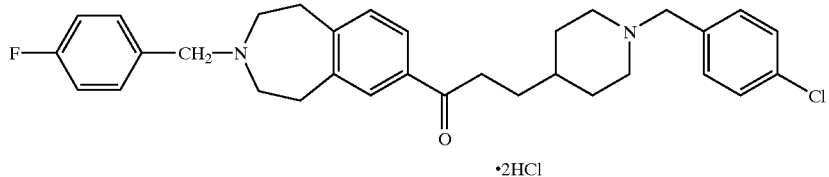

Using 1-(3-[(4-fluorophenyl)methyl]-2,3,4,5-tetrahydro-1H-3-benzazepin-7-yl]-3-(4-piperidinyl)-1-propanone (free base), obtained in Example 39, and 4-chlorobenzyl bromide, the procedure of Example 28 was similarly repeated to provide the title compound as colorless powders melting at 219–222° C. (dec.).

$^1$H-NMR (CDCl$_3$, free base) δ: 1.17–1.40 (3H, m), 1.53–2.00 (6H, m), 2.54–2.65 (4H, m), 2.78–3.00 (8H, m), 3.43 (2H, s), 3.59 (2H, s), 7.01 (2H, t-like, J=8.8 Hz), 7.15 (1H, d, J=7.3 Hz), 7.20–7.37 (6H, m), 7.65–7.75 (2H, m). Elemental analysis, for $C_{32}H_{36}ClFN_2O \cdot 2HCl$. Calcd.: C, 64.92; H, 6.47; N, 4.73. Found: C, 64.61; H, 6.43; N, 4.64.

EXAMPLE 42

1-[3-[(4-Fluorophenyl)methyl]-2,3,4,5-tetrahydro-1H-3-benzazepin-7-yl]-3-(1-methyl-4-piperidinyl)-1-propanone Dihydrochloride

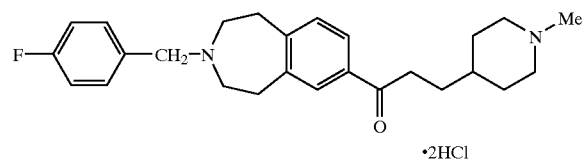

Using 1-[3-[(4-fluorophenyl)methyl]-2,3,4,5-tetrahydro-1H-3-benzazepin-7-yl]-3-(4-piperidinyl)-1-propanone (free base), obtained in Example 39, and methyl iodide, the procedure of Example 28 was similarly repeated to provide the title compound as colorless powders melting at 213–216° C. (dec.).

$^1$H-NMR (CDCl$_3$, free base) δ: 1.18–1.43 (3H, m)t 1.58–1.98 (6H, m), 2.26 (3H, s), 2.55–2.67 (4H, m), 2.73–3.04 (8H, m), 3.59 (2H, s), 7.02 (2H, t-like, J=8.7 Hz), 7.16 (1H, d, J=7.6 Hz), 7.25–7.37 (2H, m), 7.65–7.75 (2H, m). Elemental analysis, for $C_{26}H_{33}FN_2O \cdot 2HCl \cdot 0.25H_2O$. Calcd.: C, 64.25; H, 7.36; N, 5.76. Found: C, 64.23; H, 7.55; N, 5.63.

EXAMPLE 43

Ethyl 2-methyl-2-[4-[[4-[3-[3-[(4-fluorophenyl) methyl]-2,3,4,5-tetrahydro-1H-3-benzazepin-7-yl]-3-oxopropyl]-1-piperidinyl]methyl]phenyl]propionate Dihydrochloride Using 1-[3-[(4-fluorophenyl)methyl]-2,3,4,5-tetrahydro-1H-3-benzazepin-7-yl]-3-(4-piperidinyl)-1-propanone (free base), obtained in Example 39, and ethyl 2-methyl-2-[4-(bromomethyl)phenyl]propionate, the procedure of Example 28 was similarly repeated to provide the title compound as colorless powders melting at 228–231° C. (dec.).

$^1$H-NMR (CDCl$_3$, free base) δ: 1.14–1.42 (6H, m), 1.52–1.81 (10H, m), 1.85–2.02 (2H, m), 2.55–2.67 (4H, m), 2.82–3.03 (8H, m), 3.46 (2H, s), 3.59 (2H, s), 4.12 (2H, q, J=7.2 Hz), 7.01 (2H, t-like, J=8.6 Hz), 7.15 (1H, d, J=7.7 Hz), 7.20–7.38 (6H, m), 7.64–7.73 (2H, m). Elemental analysis, for $C_{38}H_{47}FN_2O_3 \cdot 2HCl$. Calcd.: C, 67.95; H, 7.35; N, 4.17. Found: C, 67.81; H, 7.34; N, 4.24.

EXAMPLE 44

1-[3-[(4-Fluorophenyl)methyl]-2,3,4,5-tetrahydro-1H-3-benzazepin-7-yl]-3-[1-[(3,4-dimethoxyphenyl) methyl]-4-piperidinyl]-1-propanone Dihydrochloride

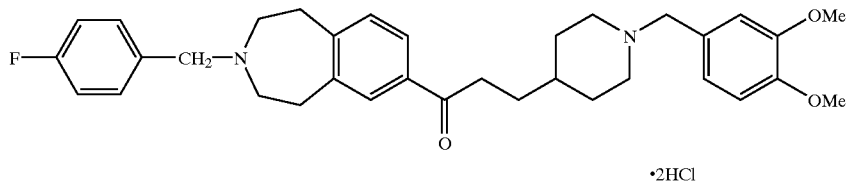

•2HCl

Using 1-[3-[(4-fluorophenyl)methyl]-2,3,4,5-tetrahydro-1H-3-benzazepin-7-yl]-3-(4-piperidinyl)-1-propanone (free base), obtained in Example 39, and mesylate of 3,4-dimethoxybenzyl alchol, the procedure of Example 28 was similarly repeated to provide the title compound as colorless powders melting at 199–203° C.

$^1$H-NMR (CDCl$_3$, free base) δ: 1.22–1.45 (3H, m), 1.60–2.07 (6H, m), 2.55–2.67 (4H, m), 2.83–3.04 (8H, m), 33.45 (2H, s), 3.59 (2H, s) 3.87 (3H S), 3.89 (3H, s), 6.81 (2H, s), 6.92 (1H s), 7.001 (2H, t-like, J=8.8 Hz), 7.15 (1H, d, J=7.3 Hz), 7.24–7.37 (2H, m), 7.63–7.74 (2H, m). Elemental analysis, for C$_{34}$H$_{41}$FN$_2$O$_3$.2HCl.H$_2$O. Calcd.: C, 64.25; H, 7.14; N, 4.41. Found: C, 64.59; H, 6.93; N, 4.33.

EXAMPLE 45

Ethyl 2-[4-[[4-[3-[3-[(4-fluorophenyl)methyl]-2,3,4,5-tetrahydro-1H-3-benzazepin-7-yl]-3-oxopropyl]-1-piperidinyl]methyl]phenoxy]ethanoate Dihydrochloride

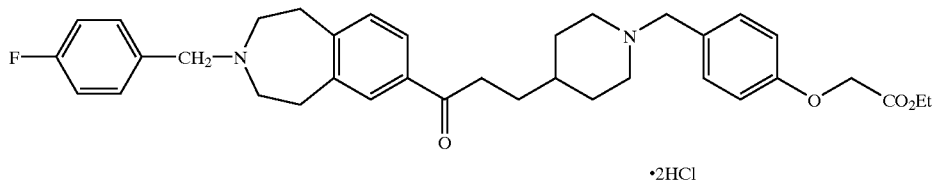

•2HCl

Using 1-[3-[(4-fluorophenyl)methyl]-2,3,4,5-tetrahydro-1H-3-benzazepin-7-yl]-3-(4-piperidinyl)-1-propanone (free base), obtained in Example 39, and ethyl 2-[4-(bromomethyl)phenoxy]ethanoate, the procedure of Example 28 was similarly repeated to provide the title compound as colorless powders melting at 206–208° C.

$^1$H-NMR (CDCl$_3$, free base) δ: 1.15–1.44 (6H, m), 1.57–2.00 (6H, m), 2.53–2.67 (4H, m), 2.78–3.02 (8H, m), 3.42 (2H, s), 3.58 (2H, s), 4.27 (2H, q, J=7.1 Hz), 4.61 (2H, s), 6.85 (2H, d, J=8.8 Hz), 7.01 (2H, t-like, J=8.6 Hz), 7.10–7.37 (5H, m), 7.63–7.72, (2H, m). Elemental analysis, for C$_{36}$H$_{43}$FN$_2$O$_4$.2HCl.0.5H$_2$O. Calcd.: C, 64.66; H, 6.93; N, 4.19. Found: C, 64.52; H, 6.84; N, 4.19.

EXAMPLE 46

1-[3-[(4-Fluorophenyl)methyl]-2,3,4,5-tetrahydro-1H-3-benzazepin-7-yl]-3-[1-(phenylmethyl)-4-piperidinyl)-1-propanone Dihydrochloride

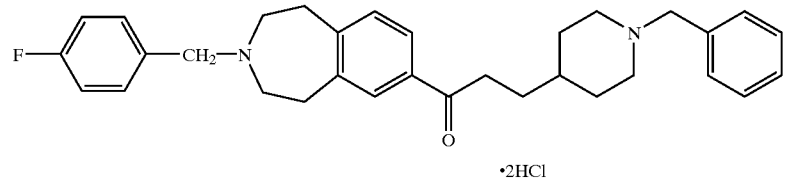

•2HCl

Using 1-[3-[(4-fluorophenyl)methyl]-2,3,4,5-tetrahydro-1H-3-benzazepin-7-yl]-3-(4-piperidinyl)-1-propanone (free base), obtained in Example 39, and benzyl bromide, the procedure of Example 28 was similarly repeated to provide the title compound as colorless powders melting at 217–220° C.

$^1$H-NMR (CDCl$_3$, free base) δ: 1.16–1.42 (3H, m), 1.57–1.80 (4H, m), 1.84–2.00 (2H, m), 2.52–2.67 (4H, m), 2.80–3.02 (8H, m), 3.48 (2H, s), 3.59 (2H, s), 7.01 (2H, t-like, J=8.8 Hz), 7.10–7.38 (8H, m), 7.64–7.74 (2H, m). Elemental analysis, for C$_{32}$H$_{37}$FN$_2$O.2HCl. Calcd.: C, 68.93; H, 7.05; N, 5.02. Found: C, 68.51; H, 7.12; N, 4.95.

EXAMPLE 47

1-[3-[(4-Fluorophenyl)methyl]-2,3,4,5-tetrahydro-1H-3-benzazepin-7-yl]-3-[1-[[4-(2-methyl-2-propyl)phenyl]methyl]-4-piperidinyl]-1-propanone Dihydrochloride Using 1-[3-[(4-fluorophenyl)methyl]-2,3,4,5-tetrahydro-1H-3-benzazepin-7-yl]-3-(4-piperidinyl)-1-propanone (free base), obtained in Example 39, and ethyl 4-(bromomethyl)benzoate, the procedure of Example 28 was similarly repeated to provide the title compound as colorless powders melting at 212–218° C. (dec.).

$^1$H-NMR (CDCl$_3$, free base) δ: 1.17–1.45 (6H, m), 1.53–1.80 (4H, m), 1.86–2.04 (2H, m), 2.55–2.67 (4H, m), 2.78–3.03 (8H, m), 3.52 (2H, s), 3.59 (2H, s), 4.37 (2H, q, J=7.1 Hz), 7.01 (2H, t-like, J=8.8 Hz), 7.15 (1H, d, J=7.7 Hz), 7.24–7.43 (4H, m), 7.65–7.74 (2H, m), 7.98 (2H, d, J=8.1 Hz). Elemental analysis, for C$_{35}$H$_{41}$FN$_2$O$_3$.2HCl.0.5H$_2$O. Calcd.: C, 65.82; H, 6.94; N, 4.39. Found: C, 65.70; H, 6.74; N, 4.14.

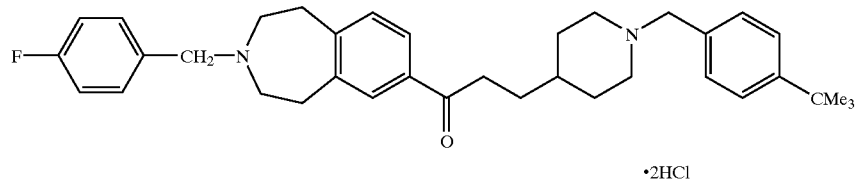

·2HCl

Using 1-[3-[(4-fluorophenyl)methyl]-2,3,4,5-tetrahydro-1H-3-benzazepin-7-yl]-3-(4-piperidinyl)-1-propanone (free base), obtained in Example 39, and 4-(t-butyl)benzyl bromide, the procedure of Example 28 was similarly repeated to provide the title compound as colorless powders melting at 230–236° C. (dec.).

$^1$H-NMR (CDCl$_3$, free base) δ: 1.20–1.44 (12H, m), 1.58–1.80 (4H, m), 1.85–2.00 (2H, m), 2.55–2.65 (4H, m), 2.82–3.01 (8H, m), 3.45 (2H, s), 3.59 (2H, s), 7.01 (2H, t-like, J=8.8 Hz), 7.10–7.37 (7H, m), 7.65–7.73 (2H, m). Elemental analysis, for C$_{36}$H$_{45}$FN$_2$O.2HCl.0.5H$_2$O. Calcd.: C, 69.44; H, 7.77; N, 4.50. Found: C, 69.43; H, 7.82; N, 4.49.

EXAMPLE 48

Ethyl 4-[[4-[3-[3-[(4-fluorophenyl)methyl]-2,3,4,5-tetrahydro-1H-3-benzazepin-7-yl]-3-oxopropyl]-1-piperidinyl]methyl]benzoate Dihydrochloride

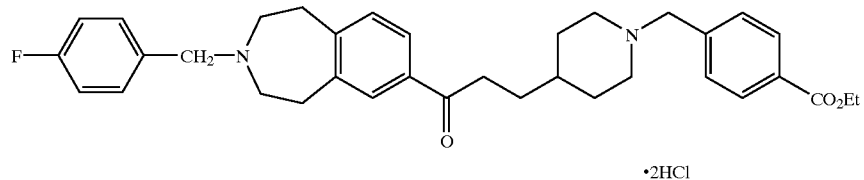

·2HCl

EXAMPLE 49

1-[3-[(4-Fluorophenyl)methyl]-2,3,4,5-tetrahydro-1H-3-benzazepin-7-yl]-3-[1-[(4-phenylphenyl)methyl]-4-piperidinyl]-1-propanone Dihydrochloride

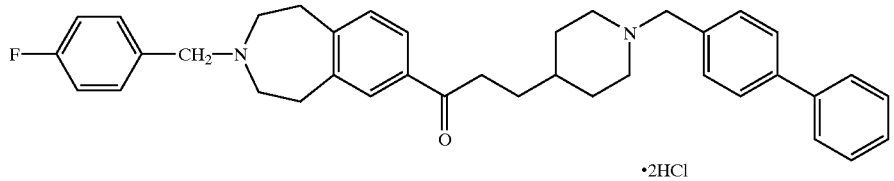

•2HCl

Using 1-[3-[(4-fluorophenyl)methyl]-2,3,4,5-tetrahydro-1H-3-benzazepin-7-yl]-3-(4-piperidinyl)-1-propanone (free base), obtained in Example 39, and 4-(bromomethyl)biphenyl, the procedure of Example 28 was similarly repeated to provide the title compound as colorless powders melting at 225–228° C. (dec.).

$^1$H-NMR (CDCl$_3$, free base) δ: 1.22–1.48 (3H, m), 1.50–1.75 (4H, m), 1.90–2.10 (2H, m), 2.45–2.60 (4H, m), 2.75–3.00 (8H, m), 3.50 (2H, s), 3.57 (2H, s), 6.92 (2H, t-like, J=8.8 Hz), 7.06 (1H, d, J=7.7 Hz), 7.14–7.40 (7H, m), 7.43–7.64 (6H, m). Elemental analysis, for C$_{38}$H$_{41}$FN$_2$O.2HCl.0.5H$_2$O. Calcd.: C, 71.02; H, 6.90; N, 4.36. Found: C, 70.84; H, 6.63; N, 4.23.

EXAMPLE 50

1-[3-[(4-Fluorophenyl)methyl]-2,3,4,5-tetrahydro-1H-3-benzazepin-7-yl]-3-[1-[(4-hydroxyphenyl)methyl]-4-piperidinyl]-1-propanone Dihydrochloride

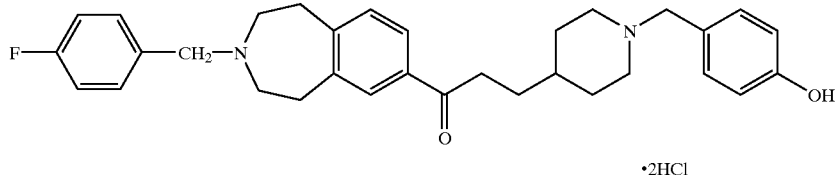

•2HCl

A mixture of 1-[3-[(4-fluorophenyl)methyl]-2,3,4,5-tetrahydro-1H-3-benzazepin-7-yl]-3-[1-[(4-methoxyphenyl)methyl]-4-piperidinyl]-1-propanone (65 mg, 0.11 mmol, free base), obtained in Example 40, and 48% hydrobromic acid (4 ml) was heated for 2 hours with stirring. After cooling, the reaction mixture was made basic with 10% sodium hydroxide/H$_2$O and extracted with ethyl acetate. The extract was washed with saturated NaCl/H$_2$O and dried over MgSO$_4$ and the solvent was distilled off under reduced pressure. The residue was purified by silica gel column chromatography (eluent: ethyl acetate-methanol=10:1) to provide the free base (50 mg) of the title compound as colorless oil.

$^1$H-NM-R (CDCl$_3$, free base) δ: 1.37–1.60 (3H, m), 1.63–1.88(4H, m), 2.14–2.34 (2H, m), 2.55–2.68 (4H, m), 2.88–3.05 (6H, m), 3.12–3.27 (2H, m), 3.59 (2H, s), 3.68 (2H, s), ca. 5.8 (1H, br), 6.70 (2H, d, J=8.4 Hz), 7.01 (2H, t-like, J=8.6 Hz), 7.08–7.20 (3H, m), 7.24–7.37 (2H, m), 7.63–7.73 (2H, m).

The above free base (45 mg) was dissolved in methanol, treated with 2 molar equivalents of HCl (dissolved in ethyl acetate), and precipitated from isopropyl alcohol-ether to provide the title compound (35 mg) as colorless powders melting at 166–169° C.

Elemental analysis, for C$_{32}$H$_{37}$FN$_2$O$_2$.2HCl.H$_2$O. Calcd.: C, 64.97; H, 6.99; N, 4.74. Found: C, 64.72; H, 7.05; N, 4.66.

EXAMPLE 51

3-(1-Acetyl-4-piperidinyl)-1-[2-(phenylmethyl)-2,3,4,5-tetrahydro-1H-2-benzazepin-8-yl]-1-propanone Hydrochloride

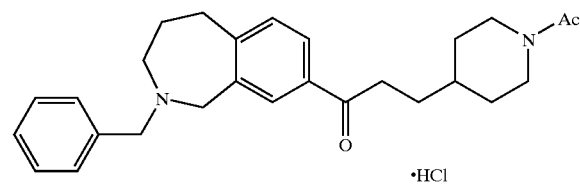

•HCl 1) 3-(1-Acetyl-4-piperidinyl)propionic acid (6.82 g, 34.2 mmol) was added portionwise to thionyl chloride (35 ml) with ice-bath cooling. After the mixture was stirred for 5 minutes, the excess thionyl chloride was distilled off and the residue was washed with hexane to provide 3-(1-acetyl-4-piperidinyl)propionyl chloride as light-yellow solid. Aluminum chloride (13.3 g, 99.7 mmol) powders were added in small portions to admixed solution of the above acid chloride and 2-formyl-2,3,4,5-tetrahydro-1H-2-benzazepine (5.00 g, 28.5 mmol), obtained in Reference Example 5, in 1,2-dichloroethane (25 ml) with ice-bath cooling. This mixture was stirred at room temperature for 18 hours. It was then poured in ice-water and extracted with ethyl acetate. The extract was washed with saturated NaCl/H$_2$O and dried over MgSO$_4$ and the solvent was distilled off under reduced pressure. The residue was purified by silica gel column chromatography (eluent: ethyl acetate-methanol=9:1) to provide 3-(1-acetyl-4-piperidinyl)-1-(2-formyl-2,3,4,5-tetrahydro-1H-2-benzazepin-8-yl)-1-propanone (7.06 g) as light-yellow oil.

$^1$H-NMR (CDCl$_3$) δ: 1.00–1.29 (2H, m), 1.42–1.93 (7H, m), 2.09 (3H, s), 2.42–2.62 (1H, m), 2.90–3.12 (5H, m), 3.61–3.87 (3H, m), 4.46–4.68 (2Hi m), 7.19–7.30 (1H, m), 7.71–8.17 (3H, m).

2) A solution of 3-(1-acetyl-4-piperidinyl)-1-(2-formyl-2,3,4,5-tetrahydro-1H-2-benzazepin-8-yl)-1-propanone (7.03 g, 20.5 mmol), prepared in 1), in methanol (100 ml) was mixed with concentrated hydrochloric acid (100 ml) and the mixture was heated at 80–85° C. for 1 hour. The methanol was then distilled off and the residual aqueous solution was made basic with NaOH/H$_2$O and extracted with ethyl acetate-tetrahydrofuran (2:1). The extract was washed with saturated NaCl/H$_2$O and dried over MgSO$_4$. The solvent was then distilled off under reduced pressure to provide 3-(1-acetyl-4-piperidinyl)-1-(2,3,4,5-tetrahydro-1H-2-benzazepin-8-yl)-1-propanone (4.92 g) as light-yellow oil.

3) Benzyl bromide (2.57 g, 15.0 mmol) was added dropwise to a mixed solution of 3-(1-acetyl-4-piperidinyl)-1-(2,3,4,15-tetrahydro-1H-2-benzazepin-8-yl)-1-propanone (4.92 g, 15.0 mmol), obtained in 2), and potassium carbonate (3.0 g) in ethanol (100 ml) with n ice-bath cooling and the mixture was stirred at room temperature for 18 hours. The solvent was then distilled off and the residue was dissolved in water-ethyl acetate and extracted with ethyl acetate. The extract was washed with saturated NaCl/H$_2$O and dried over MgSO$_4$ and the solvent was distilled off under reduced pressure. The residue was purified by silica gel column chromatography (eluent: ethyl acetate-methanol=9:1) to provide the free base (3.01 g) of the title compound as colorless oil.

$^1$H-NMR (CDCl$_3$, free base) δ: 1.00–1.31 (2H, m), 1.45–1.90 (7H, m), 2.09 (3H, s), 2.44–2.61 (1H, m), 2.87–3.18 (7H, m), 3.54 (2H, s), 3.72–3.87 (1H, m), 3.92 (2H, s), 4.54–4.69 (1H, m), 7.17–7.40 (6H, m), 7.50 (1H, d, J=1.8 Hz), 7.76 (1H, dd, J=1.8, 7.7 Hz).

The above free base (0.1 g) was dissolved in methanol, treated with 1 molar equivalent of HCl (dissolved in ethyl acetate), and precipitated from ethyl acetate-ether to provide the title compound (80 mg) as colorless amorphous powders.

Elemental analysis, for C$_{27}$H$_{34}$N$_2$O$_2$.HCl.3H$_2$O. Calcd.: C, 63.70; H, 8.12; N, 5.50. Found: C, 63.76; H, 7.64; N, 4.95.

EXAMPLE 52

3-(1-Acetyl-4-piperidinyl)-1-[2-[(4-methoxyphenyl)methyl]-2,3,4,5-tetrahydro-1H-2-benzazepin-8-yl]-1-propanone Hydrochloride

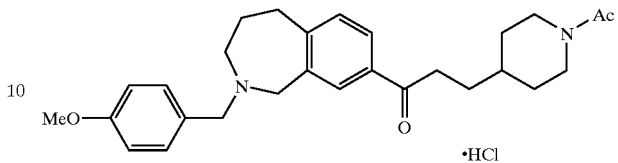

Using 3-(1-acetyl-4-piperidinyl)-1-(2,3,4,5-tetrahydro-1H-2-benzazepin-8-yl)-1-propanone (free base), obtained in Example 51-2), and 4-methoxybenzyl chloride, the procedure of Example 51-3) was similarly repeated to provide the title compound as amorphous powders.

$^1$H-NMR (CDCl$_3$, free base) δ: 1.01–1.30 (2H, m), 1.45–1.86 (7H, m), 2.09 (3H, s), 2.43–2.62 (1H, m), 2.87–3.17 (7H, m), 3.48 (2H, s), 3.74–3.95 (6H, m), 4.54–4.68 (1H, m), 6.86 (2H, d, J=8.4 Hz), 7.13–7.29 (3H, m), 7.52 (1H, d, J=1.6 Hz), 7.76 (1H, dd, J=1.6, 7.8 Hz). Elemental analysis, for C$_{28}$H$_{36}$N$_2$O$_3$.HCl.2.5H$_2$O. Calcd.: C, 63.44; H, 7.99; N, 5.28. Found: C, 63.35; H, 7.63; N, 4.96.

EXAMPLE 53

1-[2-(Phenylmethyl)-2,3,4,5-tetrahydro-1H-2-benzazepin-8-yl]-3-(4-piperidinyl)-1-propanone Dihydrochloride

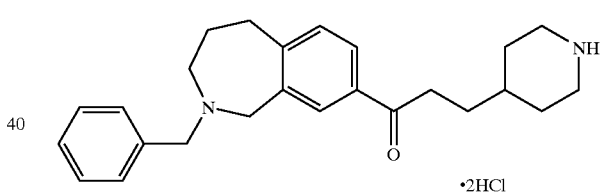

A mixture of 3-(1-acetyl-4-piperidinyl)-1-[2-(phenylmethyl)-2,3,4,5-tetrahydro-1H-2-benzazepin-8-yl]-1-propanone (free base, 3.00 g, 7.17 mmol), obtained in Example 51, and concentrated hydrochloric acid (30 ml) was refluxed for 15 hours. After cooling, the reaction mixture was made basic with NaOH/H$_2$O and extracted with ethyl acetate. The extract was washed with saturated NaCl/H$_2$O and dried over MgSO$_4$. The solvent was then distilled off under reduced pressure to provide the free base (2.38 g) of the title, compound as oil.

$^1$H-NMR (CDCl$_3$, free base) δ: 1.04–1.28 (2H, m), 1.32–1.88 (8H, m), 2.50–2.67 (2H, m), 2.84–3.18 (8H, m), 3.54 (2H, s), 3.92 (2H, s), 7.15–7.37 (6H, m), 7.50 (1H, d, J=1.8 Hz), 7.76 (1H, dd, J=1.8, 7.7 Hz).

The above free base (0.1 g) was dissolved in methanol, treated with 2 molar equivalents of HCl (dissolved in ethyl acetate), and precipitated from ether to provide the title compound (70 mg) as colorless amorphous powders.

Elemental analysis, for C$_{25}$H$_{32}$N$_2$O.2HCl.1.5H$_2$O. Calcd.: C, 63.02; H, 7.83; N, 5.88. Found: C, 63.19; H, 7.95; N, 6.09.

EXAMPLE 54

3-[1-[(2-Chlorophenyl)methyl]-4-piperidinyl]-1-[2-(phenylmethyl)-2,3,4,5-tetrahydro-1H-2-benzazepin-8-yl]-1-propanone Dihydrochloride

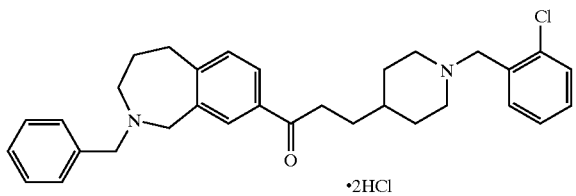

•2HCl

Using 1-[2-(phenylmethyl)-2,3,4,5-tetrahydro-1H-2-benzazepin-8-yl]-3-(4-piperidinyl)-1-propanone (free base), obtained in Example 53, and 2-chlorobenzyl bromide, the procedure of Example 51-3) was similarly repeated to provide the title compound as amorphous powders.

$^1$H-NMR (CDCl$_3$, free base) δ: 1.20–1.45 (3H, m), 1.50–1.85 (4H, m), 1.90–2.20 (2H, m), 2.80–3.05 (6H, m), 3.13 (2H, t-like, J=5.4 Hz), 3.53 (2H, s), 3.60 (2H, s), 3.91 (2H, s), 7.10–7.40 (9H, m), 7.45–7.55 (2H, m), 7.76 (1H, dd, J=7.8, 1.4 Hz). Elemental analysis, for C$_{32}$H$_{37}$ClN$_2$O.2HCl.0.5H$_2$O. Calcd.: C, 65.92; H, 6.92; N, 4.80. Found: C, 65.61; H, 7.36; N, 4.55.

EXAMPLE 55

3-[1-[(3-Chlorophenyl)methyl]-4-piperidinyl]-1-[2-(phenylmethyl)-2,3,4,5-tetrahydro-1H-2-benzazepin-8-yl]-1-propanone Dihydrochloride

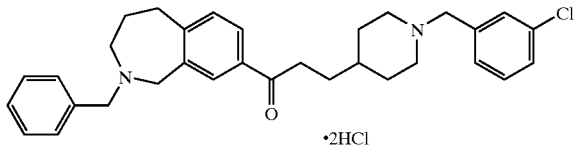

•2HCl

Using 1-[2-(phenylmethyl)-2,3,4,5-tetrahydro-1H-2-benzazepin-8-yl]-3-(4-piperidinyl)-1-propanone (free base), obtained in Example 53, and 3-chlorobenzyl bromide, the procedure of Example 51-3) was similarly repeated to provide the title compound as amorphous powders.

$^1$H-NMR (CDCl$_3$, free base) δ: 1.20–1.45 (3H, m), 1.50–1.85 (4H, m), 1.85–2.10 (2H, m), 2.80–3.00 (6H, m), 3.12 (2H, t-like, J=5.2 Hz), 3.14 (2H, s), 3.52 (2H, s), 3.90 (2H, s), 7.10–7.40 (10H, m), 7.49 (1H, d, J=1.8 Hz), 7.76 (1H, dd, J=7.6, 1.8 Hz). Elemental analysis, for C$_{32}$H$_{37}$ClN$_2$O.2HCl.0.5H$_2$O. Calcd.: C, 65.92; H, 6.92; N, 4.80. Found: C, 65.59; H, 7.29; N, 4.73.

EXAMPLE 56

3-[1-[(4-Chlorophenyl)methyl]-4-piperidinyl]-1-[2-(phenylmethyl)-2,3,4,5-tetrahydro-1H-2-benzazepin-8-yl]-1-propanone Dihydrochloride

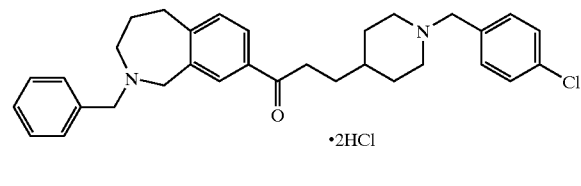

•2HCl

Using 1-[2-(phenylmethyl)-2,3,4,5-tetrahydro-1H-2-benzazepin-8-yl]-3-(4-piperidinyl)-1-propanone (free base), obtained in Example 53, and 4-chlorobenzyl bromide, the procedure of Example 51-3) was similarly repeated to provide the title compound as amorphous powders.

$^1$H-NMR (CDCl$_3$, free base) δ: 1.20–1.40 (3H, m), 1.60–1.80 (4N, m), 1.85–2.00 (2H, m), 2.80–3.00 (6H, m), 3.12 (2H, t-like, J=5.2 Hz), 3.43 (2H, s), 3.53 (2H, s), 3.91 (2H, s), 7.10–7.40 (10H, m), 7.49 (1H, d, J=1.4 Hz), 7.76 (1H, dd, J=7.7, 1.4 Hz). Elemental analysis, for C$_{32}$H$_{37}$ClN$_2$O.2HCl.H$_2$O. Calcd.: C, 64.92; H, 6.98; N, 4.73. Found: C, 65.03; H, 7.17; N, 4.53.

EXAMPLE 57

3-[1-[(2,6-Dichlorophenyl)methyl]-4-piperidinyl]-1-(2-(phenylmethyl)-2,3,4,5-tetrahydro-1H-2-benzazepin-8-yl]-1-propanone Dihydrochloride

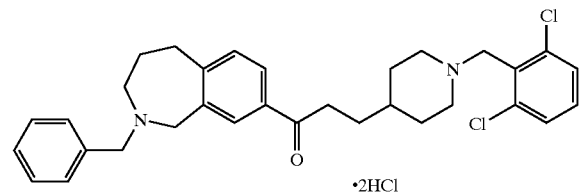

•2HCl

Using 1-[2-(phenylmethyl)-2,3,4,5-tetrahydro-1H-2-benzazepin-8-yl]-3-(4-piperidinyl)-1-propanone (free base), obtained in Example 53, and 2,6-dichlorobenzyl bromide, the procedure of Example 51-3) was similarly repeated to provide the title compound as amorphous powders.

$^1$H-NMR (CDCl$_3$, free base) δ: 1.15–1.40 (3H, m), 1.50–1.90 (4H, m), 2.10–2.30 (2H, m), 2.80–3.00 (6H, m), 3.13 (2H, t-like, J=5.2 Hz), 3.53 (2H, s), 3.70 (2H, s), 3.91 (2H, s), 7.00–7.40 (9H, m), 7.8 (1H, bs), 7.75 (1H, dd, J=7.7, 1.4 Hz). Elemental analysis, for C$_{32}$H$_{36}$Cl$_2$N$_2$O.2HCl.H$_2$O. Calcd.: C, 61.35; H, 6.44; N, 4.47. Found: C, 61.33; H, 6.49; N, 4.33.

EXAMPLE 58

3-[1-[(3,4-Dichlorophenyl)methyl]-4-piperidinyl]-1-[2-(phenylmethyl)-2,3,4,5-tetrahydro-1H-2-benzazepin-8-yl]-1-propanone Dihydrochloride

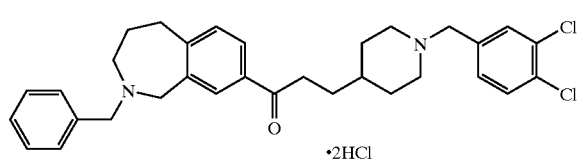

•2HCl

Using 1-[2-(phenylmethyl)-2,3,4,5-tetrahydro-1H-2-benzazepin-8-yl]-3-(4-piperidinyl)-1-propanone (free base), obtained in Example 53, and 3,4-dichlorobenzyl bromide, the procedure of Example 51-3) was similarly repeated to provide the title compound as amorphous powders.

$^1$H-NMR (CDCl$_3$, free base) δ: 1.15–1.40 (3H, m), 1.50–1.85 (4H, m), 1.90–2.00 (2H, m), 2.80–3.00 (6H, m), 3.13 (2H, t-like, J=5.2 Hz), 3.41 (2H, s), 3.53 (2H, s), 3.91 (2H, s), 7.10–7.45 (9H, m), 7.49 (1H, d, J=1.6 Hz), 7.76 (1H, dd, J=7.9, 1.6 Hz). Elemental analysis, for $C_{32}H_{36}Cl_2N_2O$.2HCl.H$_2$O. Calcd.: C, 61.35; H, 6.44; N, 4.47. Found: C, 61.46; H, 6.63; N, 4.24.

EXAMPLE 59

3-[1-(9H-9-Fluorenyl)-4-piperidinyl]-1-[2-(phenylmethyl)-2,3,4,5-tetrahydro-1H-2-benzazepin-8-yl]-1-propanone Dihydrochloride

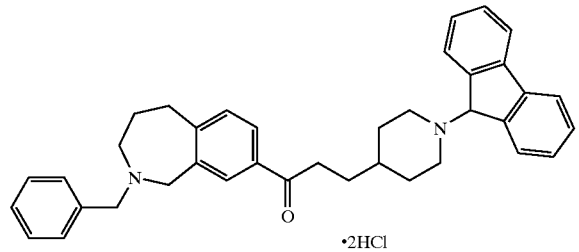

•2HCl

Using 1-[2-(phenylmethyl)-2,3,4,5-tetrahydro-1H-2-benzazepin-8-yl]-3-(4-piperidinyl)-1-propanone (free base), obtained in Example 53, and 9-bromofluorene, the procedure of Example 51-3) was similarly repeated to provide the title compound as amorphous powders.

$^1$H-NM (CDCl$_3$, free base) δ: 1.20–1.40 (3H, m), 1.50–1.80 (4H, m), 2.48 (2H, t-like, J=10.4 Hz), 2.65–2.80 (2H, m), 2.86 (2H, t-like, J=7.6 Hz), 2.95 (2H, t-like, J=5.6 Hz), 3.12 (2H, t-like, J=5.2 Hz), 3.52 (2H, s), 3.90 (2H, s), 4.83 (1H, s), 7.10–7.80 (16H, m). Elemental analysis, for $C_{38}N_4ON_2O$.2HCl.2H$_2$O. Calcd.: C, 70.25; H, 7.14; N, 4.31. Found: C, 70.28; H, 6.93; N, 4.31.

EXAMPLE 60

1-[2-(2-Phenylethyl)-2,3,4,5-tetrahydro-1H-2-benzazepin-8-yl]3-[1-(phenylmethyl)-4-piperidinyl]-1-propanone Dihydrochloride

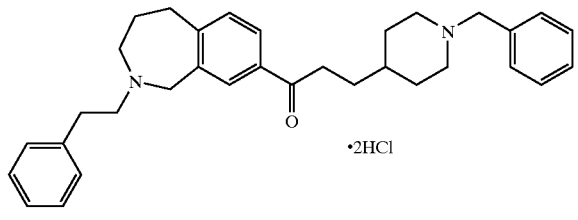

•2HCl

Using 3-[1-(phenylmethyl)-4-piperidinyl]-1-(2,3,4,5-tetrahydro-1H-2-benzazepin-8-yl)-1-propanone (free base) and phenethyl bromide, the procedure of Example 51-3) was similarly repeated to provide the title compound as amorphous powders.

$^1$H-NMR (CDCl$_3$, free base) δ: 1.20–1.43 (3H, m), 1.60–2.03 (8H, m), 2.54–2.67 (2H, m), 2.76–3.01 (8H, m), 3.19 (2H, t-like, J=5.3 Hz), 3.50 (2H, s), 4.01 (2H, s), 7.10–7.36 (11H, m), 7.69–7.77 (2H, m). Elemental analysis, for $C_{33}H_4ON_2O$.2HCl.1.5H$_2$O. Calcd.: C, 68.26; H, 7.81; N, 4.82. Found: C, 68.14; H, 8.02; N, 4.81.

EXAMPLE 61

3-(1-Acetyl-4-piperidinyl)-1-[1-(4-pyridyl)-2,3-dihydroindol-5-yl]-1-propanone

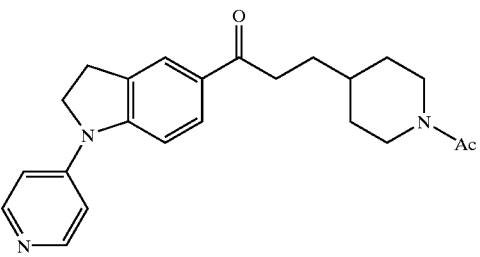

A mixed solution of 3-(1-acetyl-4-piperidinyl)-1-(2,3-dihydroindol-5-yl)-1-propanone (0.4 g, 1.33 mmol) and 4-chloropyridine hydrochloride (0.2 g, 1.33 mmol) in 1-butanol (4 ml) was heated and stirred for 3 hours. The solvent was then distilled off and the residue was dissolved in 5% sodium hydroxide/H$_2$O-ethyl acetate and extracted with ethyl acetate. The extract was washed with saturated NaCl/H$_2$O and dried over MgSO$_4$. The solvent was then distilled off under reduced pressure and the residue was purified by silica gel column chromatography (eluent: ethyl acetate-methanol=10:1) to provide the title compound (0.35 g) as colorless powders melting at 157–158° C.

$^1$H-NMR (CDCl$_3$) δ: 1.02–1.31 (2H, m), 1.48–1.88 (5H, m), 2.09 (3H, s), 2.44–2.62 (1H, m), 2.89–3.12 (3H, m), 3.24 (2H, t, J=8.6 Hz), 3.74–3.88 (1H, m), 4.10 (2H, t, J=8.6 Hz), 4.55–4.68 (1H, m), 7.10 (2H, d, J=6.6 Hz), 7.31 (1H, d, J=8.1 Hz), 7.77–7.89 (2H, m), 8.49 (2H, d, J=6.6 Hz). Elemental analysis, for $C_{23}H_{27}N_3O_2$.0.25H$_2$O. Calcd.: C, 72.32; H, 7.25; N, 11.00. Found: C, 72.31; H, 7.17; N, 10.99.

EXAMPLE 62

3-(4-Piperidinyl)-1-[1-(4-pyridyl)-2,3-dihydroindol-5-yl]-1-propanone Dihydrochloride

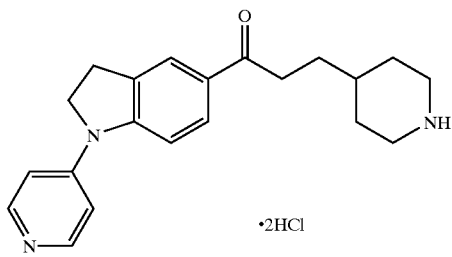

A mixture of 3-(1-acetyl-4-piperidinyl)-1-[1-(4-pyridyl)-2,3-dihydroindol-5-yl]-1-propanone (0.17 g, 7.17 mmol), obtained in Example 61, and concentrated hydrochloric acid (4 ml) was refluxed for 13 hours. The excess hydrochloric acid was distilled off under reduced pressure and the residue was washed with 2-propanol and ether in that order. The solid thus obtained was dried over diphosphorus pentoxide under reduced pressure to provide the title compound (0.14 g) as amorphous powders.

$^1$H-NMR (CDCl$_3$, free base) δ: 1.07–1.87 (8H, m), 2.52–2.68 (2H, m), 2.94 (2H, t, J=7.5 Hz), 3.04–3.18 (2H, m), 3.24 (2H, t, J=8.6 Hz), 4.10 (2H, t, J=8.6 Hz), 7.11 (2H, d, J=6.6 Hz), 7.31 (1H, d, J=8.4 Hz), 7.78–7.88 (2H, m), 8.49 (2H, d, J=6.6 Hz). Elemental analysis, for C$_{21}$H$_{25}$N$_3$O$_2$.2HCl.H$_2$O. Calcd.: C, 59.16; H, 6.86; N, 9.85. Found: C, 59.74; H, 7.09; N, 10.12.

EXAMPLE 63

3-[1-(Phenylmethyl)-4-piperidinyl]-1-[1-(4-pyridyl)-2,3-dihydroindol-5-yl]-1-propanone Dihydrochloride

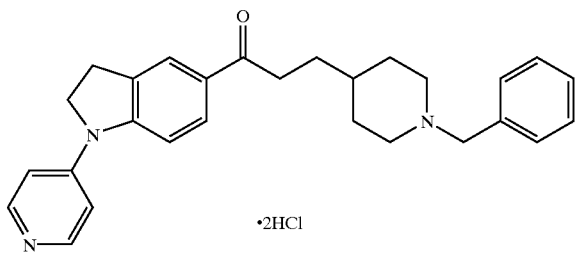

Using 3-[1-(phenylmethyl)-4-piperidinyl]-1-(2,3-dihydroindol-5-yl]-1-propanone, the procedure of Example 61 was similarly repeated to provide the title compound as amorphous powders.

$^1$H-NMR (CDCl$_3$, free base) δ: 1.16–1.45 (3H, m), 1.53–2.04 (6H, m), 2.80–2.97 (4H, m), 3.22 (2H, t, J=8.5 Hz), 3.49 (2H, s), 4.09 (2H, t, J=8.5 Hz), 7.09 (2H, d, J=6.3 Hz), 7.20–7.40 (6H, m), 7.77–7.88 (2H, m), 8.48 (2H, d, J=6.3 Hz). Elemental analysis, for C$_{28}$H$_{31}$N$_3$O.2HCl.H$_2$O Calcd.: C, 65.11; H, 6.83; N, 8.14. Found: C, 65.12; H, 6.69; N, 7.84.

EXAMPLE 64

2-[1-(Phenylmethyl)-4-piperidinyl]-1-[1-(4-pyridyl)-2,3-dihydroindol-5-yl]-1-ethanone Dihydrochloride

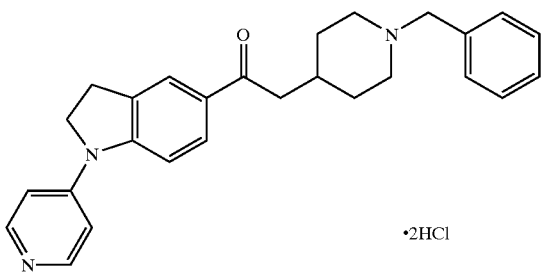

Using 2-[1-(phenylmethyl)-4-piperidinyl]-1-(2,3-dihydroindol-5-yl]-1-ethanone, the procedure of Example was similarly repeated to provide the title compound as amorphous powders.

$^1$H-NMR (CDCl$_3$, free base) δ: 1.25–1.48 (2H, m), 1.66–1.81 (2H, m), 1.84–2.10 (3H, m), 2.77–2.95 (4H, m), 3.22 (2H, t, J=8.6 Hz), 3.50 (2H, s), 4.08 (2H, t, J=8.6 Hz), 7.09 (2H, d, J=6.2 Hz), 7.19–7.37 (6H, m), 7.76–7.85 (2H, m), 8.48 (2H, d, J=6.2 Hz). Elemental analysis, for C$_{27}$H$_{29}$N$_3$O.2HCl.2.5H$_2$O. Calcd.: C, 61.25; H, 6.85; N, 7.94. Found: C, 61.06; H, 6.70; N, 7.85.

EXAMPLE 65

3-[1-(Phenylmethyl)-4-piperidinyl]-1-[1-[(4-methylphenyl)methyl]-2,3-dihydroindol-5-yl]-1-propanone Fumarate

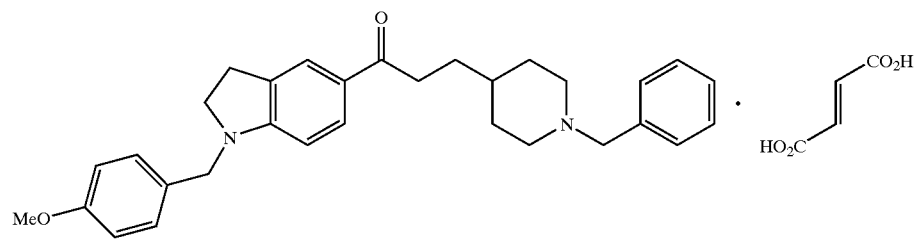

A mixed solution of 3-[1-(phenylmethyl)-4-piperidinyl]-1-(2,3-dihydroindol-5-yl)-1-propanone (free base, 0.35 g, 1.0 mmol), 4-methoxybenzyl chloride (0.16 g, 1.0 mmol), potassium iodide (0.17 g), and potassium carbonate (0.14 g) in acetonitrile (15 ml) was heated with stirring for 14 hours. The solvent was then distilled off and the residue was dissolved in water-ethyl acetate and extracted with ethyl acetate. The extract was washed with sodium thiosulfate/$H_2O$ and saturated $NaCl/H_2O$ in that order and dried over $MgSO_4$. The solvent was distilled off under reduced pressure and the residue was purified by silica gel column chromatography (eluent: ethyl acetate-methanol=30:1) to provide the free base (0.34 g) of the title compound as colorless oil.

$^1$H-NMR (CDCl$_3$, free base) δ: 1.16–1.42 (3H, m), 1.58–1.79 (4H, m), 1.56–2.02 (2H, m), 2.79–2.94 (4H, m), 3.01 (2H, t, J=8.4 Hz), 3.40–355 (4H, m), 3.80 (3H, s), 4.31 (2H, s), 6.42 (1H, d, J=8.0 Hz), 6.87 (2H, d, J=8.8 Hz), 7.15–7.36 (7H, m), 7.66–7.78 (2H, m).

The above free base (0.34 g) was dissolved in methanol, treated with 1 molar equivalent of fumaric acid (dissolved in methanol), and precipitated from ethyl acetate to provide the title compound (0.32 g) as colorless powders melting at 95–98° C.

Elemental analysis, for $C_{31}H_{36}N_2O_2 \cdot C_4H_4O_4 \cdot 0.5H_2O$ Calcd.: C, 70.80; H, 6.96; N, 4.71. Found: C, 70.40; H, 6.93; N, 4.61.

EXAMPLE 66

8-[3-(1-Acetyl-4-piperidinyl)-1-oxopropyl]-1,2,5,6-tetrahydro-4H-pyrrolo[3,2,1-ij]quinolin-4-one

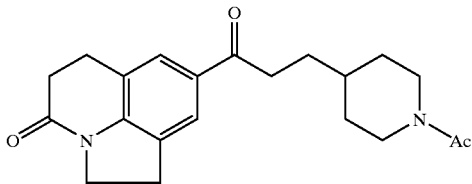

A mixed solution of 8-[3-(4-piperidinyl)-1-oxopropyl]-1,2,5,6-tetrahydro-4H-pyrrolo[3,2,1-ij]quinolin-4-one (free base, 0.30 g, 0.96 mmol) and acetic anhydride (0.11 ml, 1.16 mmol) in ethyl acetate (25 ml) was heated at 55–60° C. with stirring for 1 hour. The solvent was then distilled off and the residue was purified by silica gel column chromatography (eluent: ethyl acetate-methanol=10:1) to provide the title compound (0.185 g) as colorless powders melting at 160–161° C.

$^1$H-NMR (CDCl$_3$) δ: 1.02–1.30 (2H, m), 1.48–1.87 (5H, m), 2.09 (3H, s), 2.53 (1H, dt, J=2.6, 13.0 Hz), 2.72 (2H, t, J=7.7 Hz), 2.89–3.12 (5H, m), 3.23 (2H, t, J=8.4 Hz), 3.73–3.87 (1H, m), 4.14 (2H, t, J=8.4 Hz), 4.54–4.68 (1H, m), 7.67 (1H, s), 7.72 (1H, s). Elemental analysis, for $C_{21}H_{26}N_2O_3$. Calcd.: C, 71.16; H, 7.39; N, 7.90. Found C, 70.92; H, 7.36; N, 7.83.

EXAMPLE 67

3-(1-Acetyl-4-piperidinyl)-1-(1-acetyl-1,2,2a,3,4,5-hexahydrobenz[cd]indol-6-yl)-1-propanone

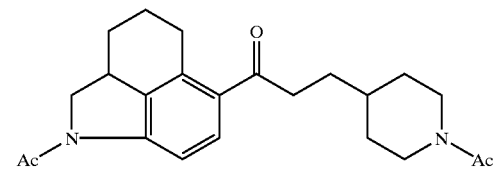

A mixed solution of 3-(1-acetyl-4-piperidinyl)-1-(1,2,2a,3,4,5-hexahydrobenz[cd]indol-6-yl)-1-propanone (free base, 0.15 g, 0.44 mmol) and acetic anhydride (0.066 ml, 0.69 mmol) in ethyl acetate (20 ml) was heated at 70–75° C. with stirring for 1 hour. The solvent was then distilled off and the residue was purified by silica gel column chromatography (eluent: ethyl acetate-methanol=20:1) to provide the title compound (0.155 g) as colorless crystals melting at 130–132° C.

$^1$H-NMR (CDCl$_3$) δ: 1.02–1.86 (11H, m), 2.05–2.31 (8H, m), 2.43–2.61 (1H, m), 2.83–3.12 (3H, m), 3.17–3.36 (1H, m), 3.60 (1H, t, J=10.4 Hz), 3.73–3.87 (1H, m), 4.26 (1H, t, J=9.0 Hz), 4.53–4.67 (1H, m), 7.71 (1H, d, J=8.4 Hz), 7.92 (1H, d, J=8.4 Hz). Elemental analysis, for $C_{23}H_3ON_2O_3$. Calcd.: C, 722.22; H, 7.91; N, 7.32. Found: C, 72.05; H, 7.98; N, 70.37.

EXAMPLE 68

3-(1-Acetyl-4-piperidinyl)-1-[1-(phenylmethyl)-1,2,2a,3,4,5-hexahydrobenz[cd]indol-6-yl]-1-propanone Hydrochloride

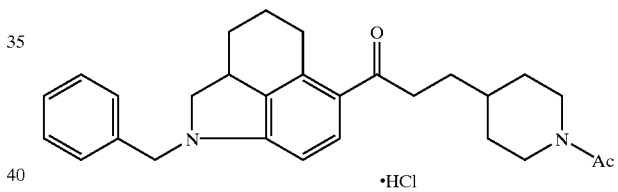

•HCl

Benzyl bromide (75 mg, 0.44 mmol) was added dropwise to a mixed solution of 3-(1-acetyl-4-piperidinyl)-1-(1,2,2a,3,4,5-hexahydrobenz[cd]indol-6-yl)-1-propanone (free base, 0.15 g, 0.44 mmol) and potassium carbonate (80 mg) in methanol (20 ml) with ice-bath cooling and the mixture was then stirred at room temperature for 14 hours. The solvent was then distilled off and the residue was dissolved in water-ethyl acetate and extracted with ethyl acetate. The extract was washed with saturated $NaCl/H_2O$ and dried over $MgSO_4$ and the solvent was distilled off under. reduced pressure. The residue was purified by silica gel column chromatography (eluent: ethyl acetate-methanol=40:1) to provide the free base (0.14 g) of the title compound as colorless oil.

$^1$H-NMR (CDCl$_3$, free base) δ: 1.00–1.89 (9H, m), 1.96–2.20 (5H, m), 2.52 (1H, dt, J=2.9, 12.8 Hz), 2.77–3.40 (7H, m), 3.61 (1H, t, J=7.9 Hz), 3.72–3.87 (1H, m), 4.10 (1H, d, J=15.0 Hz), 4.44–4.66 (2H, m), 6.30 (1H, d, J=8.4 Hz), 7.22–7.45 (5H, m), 7.67 (1H, d, J=8.4 Hz).

The above free base (0.13 g) was dissolved in methanol, treated with 1 molar equivalent of HCl (dissolved in ethyl acetate), and precipitated from ether to provide the title compound (0.12 g) as colorless amorphous powders.

Elemental analysis, for $C_{28}H_{34}N_2O_2 \cdot HCl \cdot 2.5H_2O$. Calcd.: C, 65.67; H, 7.87; N, 5.47. Found.: C, 65.65; H, 7.61; N, 5.36.

EXAMPLE 69

3-(1-Acetyl-4-piperidinyl)-1-(5,6,11,12-tetrahydrodibenz[bf]azocin-8-yl)-1-propanone

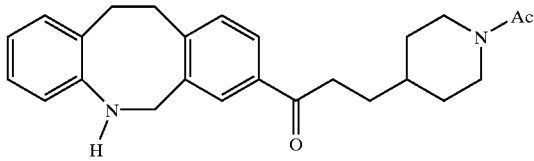

1) 3-(1-Acetyl-4-piperidinyl)propionic acid (4.0 g, 20.0 mmol) was added portionwise to thionyl chloride (2.0 ml) with ice-bath cooling. After the mixture was stirred for 5 minutes, the excess thionyl chloride was distilled off and the residue was washed with hexane to give 3-(1-acetyl-4-piperidinyl)propionyl chloride as light-yellow solid. Aluminum chloride (8.3 g, 62.2 mmol) powders were added in small portions to a mixed solution of the above acid chloride and 5-formyl-5,6,11,12-tetrahydrobenz[bf]azocine (4.0 g, 16.85 mmol), obtained in Example 5, in 1,2-dichloroethane (15 ml) with ice-bath cooling. This mixture was stirred at room temperature for 16 hours, then poured in ice-water, and extracted with ethyl acetate. The extract was washed with saturated NaCl/$H_2O$ and dried over $MgSO_4$ and the solvent was distilled off under reduced pressure. The residue was purified by silica gel column chromatography (eluent: ethyl acetate-methanol=20:1) to provide 3-(1-acetyl-4-piperidinyl)-1-(5-formyl-5,6,11,12-tetrahydrodibenz[bf]azocin-8-yl)-1-propanone (6.5 g) as light yellow oil.

$^1$H-NMR (CDCl$_3$) δ: 1.00–1.28 (2H, m), 1.42–1.85 (5H, m), 2.08 (3H, s), 2.51 (dt, J=2.9, 12.7 Hz), 2.87–3.23 (7H, m), 3.72–3.87 (1H, m), 4.54–4.68 (1H, m), 4.94 (2H, br), 7.03–7.25 (5H, m), 7.64–7.82 (2H, m), 8.26 (1H, s).

2) A solution of 3-(1-acetyl-4-piperidinyl)-1-(5-formyl-5,6,11,12-tetrahydrodibenz[bf]azocin-8-yl)-1-propanone (6.5 g, 15.5 mmol), obtained in 1), in methanol (70 ml) was mixed with concentrated hydrochloric acid (70 ml) and the mixture was heated at 80–85° C. for 2 hours. The methanol was then distilled off and the residual aqueous solution was made basic with sodium hydroxide/$H_2O$ and extracted with ethyl acetate. The extract was washed with saturated NaCl/$H_2O$ and dried over $MgSO_4$. The solvent was then distilled off under reduced pressure and the residue was precipitated from ethyl acetate-ether to provide the title compound (4.4 g) as colorless powders melting at 153–155° C.

$^1$H-NMR (CDCl$_3$) δ: 1.00–1.33 (2H, m), 1.41–2.05 (6H, m), 2.08 (3H, s), 2.42–2.60 (1H, m), 2.86–3.09 (3H, m), 3.13–3.26 (2H, m), 3.29–3.42 (2H, m), 3.72–3.86 (1H, m), 4.50 (2H, s), 4.52–4.68 (1H, m), 6.50 (1H, dd, J=0.7, 7.7 Hz), 6.69 (1H, t, J=7.3 Hz), 6.85–7.02 (2H, m), 77.11 (1H, d, J=8.1 Hz), 7.64 (1H, dd, J=1.8, 7.7 Hz), 7.70 (1H, d, J=1.8 Hz). Elemental analysis, for C$_{25}$H$_{30}$N$_2$O$_2$.0.5H$_2$O. Calcd.: C, 75.16; H, 7.82; N, 7.01. Found: C, 75.11; H, 7.61; N, 7.00.

EXAMPLE 70

3-(1-Acetyl-4-piperidinyl)-1-[5-(phenylmethyl)-5,6,11,12-tetrahydrodibenz[bf]azocin-8-yl]-1-propanone Hydrochloride

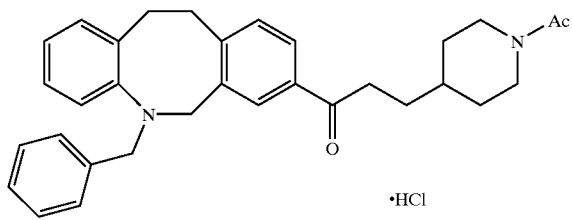

·HCl

Benzyl bromide (0.7 g, 4.09 mmol) was added to a mixed solution of 3-(1-acetyl-4-piperidinyl)-1-(5,6,11,12-tetrahydrodibenz[bf]azocin-8-yl)-1-propanone (0.8 g, 2.04 mmol), obtained in Example 69, and potassium carbonate (0.37 g) in methanol (30 ml) and the mixture was refluxed for 1 hour. The solvent was then distilled off and the residue was dissolved in water-ethyl acetate and extracted with ethyl acetate. The extract was washed with saturated NaCl/$H_2O$ and dried over $MgSO_4$ and the solvent was distilled off under reduced pressure. The residue was purified by silica gel column chromatography (eluent: ethyl acetate) to provide the free base (0.94 g) of the title compound as colorless oil.

$^1$H-NMR (CDCl$_3$, free base) δ: 0.98–1.32 (2H, m), 1.42–1.83 (5H, m), 2.08 (3H, s), 2.51 (1H, dt, J=2.6, 12.8 Hz), 2.85 (2H, t, J=7.1 Hz), 3.01 (1H, dt, J=2.6, 12.8 Hz), 3.14–3.23 (2H, m, 3.27–3.38 (2H, m), 3.72–3.87 (1H, m), 4.27 (2H, s), 4.38 (2H, s), 4.54–4.67 (1H, m), 6.80–6.92 (1H, m), 6.97–7.40 (10H, m), 7.67 (1H, dd, J=1.8, 7.7 Hz).

The above free base (0.45 g) was dissolved in methanol, treated with 1 molar equivalent of HCl (dissolved in ethyl acetate), and precipitated from ethyl acetate to provide the title compound (0.4 g) as colorless powders melting at 155–158° C.

Elemental analysis, for C$_{32}$H$_{36}$N$_2$O$_2$.HCl.H$_2$O. Calcd.: C, 71.82; H, 7.35; N, 5.23. Found: C, 71.60; H, 7.27; N, 5.21.

EXAMPLE 71

3-(4-Piperidinyl)-1-[5-(phenylmethyl)-5,6,11,12-tetrahydrodibenz[bf]azocin-8-yl]-1-propanone Dihydrochloride

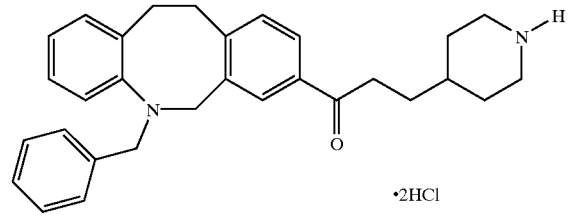

·2HCl

A mixture of 3-(1-acetyl-4-piperidinyl)-1-[5-(phenylmethyl)-5,6,11,12-tetrahydrodibenz[bf]azocin-8-yl]-1-propanone (free base, 0.45 g, 0.94 mmol), obtained in Example 70, and concentrated hydrochloric acid (4 ml) was refluxed for 4 hours. After cooling, the reaction mixture was made basic with NaOH/$H_2O$ and extracted with ethyl acetate. The extract was washed with saturated NaCl/$H_2O$ and dried over $MgSO_4$. The solvent was then distilled off under reduced pressure to provide the free base (0.395 g) of the title compound as oil.

¹H-NMR (CDCl₃, free base) δ: 1.05–1.85 (7H, m), 2.43–2.91 (5H, m), 2.99–3.40 (6H, m), 4.26 (2H, s), 4.37 (2H, s), 6.78–6.90 (1H, m), 6.97–7.40 (10H, m), 7.67 (1H, dd, J=1.8, 8.0 Hz).

The above free base (0.38 g) was dissolved in methanol, treated with 2 molar equivalents of HCl (dissolved in ethyl acetate), and precipitated from ethyl acetate to provide the title compound (0.36 g) as colorless amorphous powders.

Elemental analysis, for C₃₀H₃₄N₂O.2HCl.1.5H₂O. Calcd.: C, 66.91; H, 7.30; N, 5.20. Found: C, 66.67; H, 7.43; N, 4.72.

EXAMPLE 72

3-(4-Piperidinyl)-1-(5,6,11,12-tetrahydrodibenz[bf]azocin-8-yl)-1-propanone Dihydrochloride

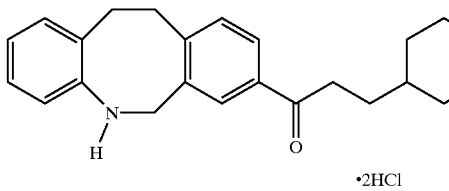

•2HCl

Using 3-(1-acetyl-4-piperidinyl)-1-(5,6,11,12-tetrahydrodibenz[bf]azocin-8-yl)-1-propanone (free base) obtained in Example 69, the procedure of Example 71 was similarly repeated to provide the title compound as amorphous powders.

¹H-NMR (CDCl₃, free base) δ: 1.02–1.28 (2H, m), 1.30–2.00 (6H, m), 2.47–2.68 (2H, m), 2.91 (2H, t, J=7.7 Hz), 2.98–3.40 (6H, m), ca. 4.0 (1H, br), 4.49 (2H, s), 6.50 (1H, dd, J=1.1, 7.7 Hz), 6.69 (1H, dt, J=1.1, 7.3 Hz), 6.84–7.01 (2H, m), 7.11 (1H, d, J=7.7 Hz), 7.65 (1H, dd, J=1.8, 7.7 Hz), 7.70 (1H, d, J=1.8 Hz). Elemental analysis, for C₂₃H₂₈N₂O.2HCl.0.5H₂O. Calcd.: C, 64.18; H, 7.26; N, 6.51. Found: C, 63.64; H, 7.00; N, 6.03.

EXAMPLE 73

3-(1-Acetyl-4-piperidinyl)-1-[5-[(4-fluorophenyl)methyl]-5,6,11,12-tetrahydrodibenz[bf]azocin-8-yl]-1-propanone Hydrochloride

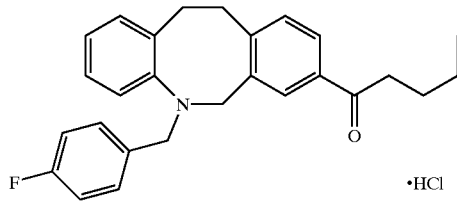

•HCl

Using 3-(1-acetyl-4-piperidinyl)-1-(5,6,11,12-tetrahydrodibenz[bf]azocin-8-yl)-1-propanone, obtained in Example 69, and 4-fluorobenzyl bromide, the procedure of Example 70 was similarly repeated to provide the title compound as amorphous powders.

¹H-NMR (CDCl₃, free base) δ: 1.00–1.27 (2H, m), 1.40–1.83 (5H, m), 2.08 (3H, s), 2.43–2.60 (1H, m), 2.86 (2H, t, J=7.1 Hz), 2.93–3.20 (3H, m), 3.26–3.37 (2H, m), 3.72–3.87 (1H, m), 4.2,3 (2H, s), 4.34 (2H, s), 4.53–4.68 (1H, m), 6.80–7.36 (10H, m), 7.66 (1H, dd, J=1.8, 7.7 Hz). Elemental analysis, for C₃₂H₃₅FN₂O₂. HCl. 2H₂O. Calcd.: C, 67.30; H, 7.06; N, 4.90. Found: C, 66.81; H, 6.92; N, 4.73.

EXAMPLE 74

1-[5-[(4-Fluorophenyl)methyl]-5,6,11,12-tetrahydrodibenz[bf]azocin-8-yl]-3-(4-piperidinyl)-1-propanone Dihydrochloride

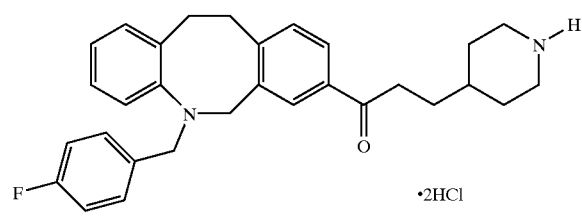

•2HCl

Using 3-(1-acetyl-4-piperidinyl)-1-[5-[(4-fluorophenyl)methyl]-5,6,11,12-tetrahydrodibenz[bf]azocin-8-yl])-1-propanone (free base) obtained in Example 73, the procedure of Example 71 was similarly repeated to provide the title compound as amorphous powders.

¹H-NMR (CDCl₃, free base) δ: 1.08–1.52 (3H, m), 1.56–1.82 (4H, m), ca. 2.1 (1H, br), 2.61 (2H, dt, J=2.2, 12.0 Hz), 2.85 (2H t, J=7.5 Hz), 3.05–3.22 (4H, m), 3.25–3.38 (2H, m), 4.23 (2H, s), 4.34 (2H, s), 6.80–7.38 (10H, m), 7.67 (1H, dd, J=1.8, 7.8 Hz). Elemental analysis, for C₃₀H₃₃FN₂O. 2HCl. H₂O. Calcd.: C, 65.81; H, 6.81; N, 5.12. Found: C, 65.65; H. 6.99; N, 4.80.

EXAMPLE 75

1-[5-[(4-Fluorophenyl)methyl]-5,6,11,12-tetrahydrodibenz[bf]azocin-8-yl]-3-[1-[(3-methylphenyl)methyl]-4-piperidinyl]-1-propanone Dihydrochloride

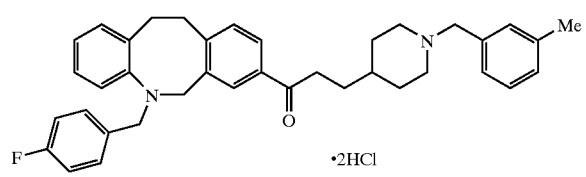

•2HCl

Using 1-[5-[(4-fluorophenyl)methyl]-5,6,11,12-tetrahydrodibenz[bf]azocin-8-yl]-3-(4-piperidinyl)-1-propanone (free base), obtained in Example 74, and 3-methylbenzyl bromide, the procedure of Example 70 was similarly repeated to provide the title compound as amorphous powders.

¹H-NMR (CDCl₃, free base) δ: 1.16–1.42 (3H, m), 1.52–1.80 (4H, m), 1.83–2.00 (2H, m), 2.34 (3H, s), 2.77–2.96 (4H, m), 3.09–3.20 (2H, m), 3.24–3.37 (2H, m), 3.45 (2H, s), 4.22 (2H, s), 4.34 (2H, s), 6.78–7.37 (14H, m), 7.66 (1H, dd, J=1.5, 7.9 Hz). Elemental analysis, for C₃₈H₄₁FN₂O. 2HCl. 0.5H₂O. Calcd.: C, 71.02; H, 6.90; N, 4.36. Found: C, 70.63; H, 7.05; N, 4.22.

EXAMPLE 76

3-[1-[(3-Chlorophenyl)methyl]-4-piperidinyl]-1-[5-[(4-fluorophenyl)methyl]-5,6,11,12-tetrahydrodibenz[bf]azocin-8-yl]-1-propanone

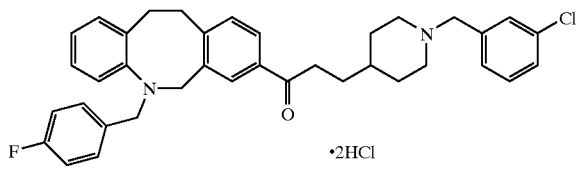

•2HCl

Using 1-[5-[(4-fluorophenyl)methyl]-5,6,11,12-tetrahydrodibenz[bf]azocin-8-yl]-3-(4-piperidinyl)-1-propanone (free base), obtained in Example 74, and 3-hlorobenzyl bromide, the procedure of Example 70 was similarly repeated to provide the title compound as amorphous powders.

$^1$H-NMR (CDCl$_3$, free base) δ: 1.14–1.42 (3H, m), 1.50–1.80 (4H, m), 1.84–2.01 (2H, m), 2.77–2.92 (4H, m), 3.08–3.20 (2H, m), 3.24–3.36 (2H, m), 3.44 (2H, s), 4.23 (2H, s), 4.34 (2H, s), 6.80–7.37 (14H, m), 7.66 (1H, dd, J=1.8, 7.7 Hz). Elemental analysis, for C$_{37}$H$_{38}$ClFN$_2$O. 2HCl. 0.5H$_2$O. Calcd.: C, 67.02; H, 6.23; N, 4.22. Found: C, 67.02; H, 6.48; N, 3.96.

EXAMPLE 77

3-(1-Acetyl-4-piperidinyl)-1-[4-[(4-fluorophenyl)methyl]-2,3,4,5-tetrahydro-1,4-benzoxazepin-7-yl]-1-propanone Hydrochloride

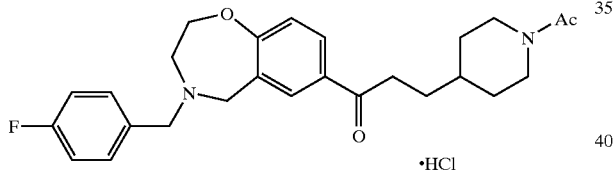

•HCl

Using 3-(1-acetyl-4-piperidinyl)-1-(2,3,4,5-tetrahydro-1,4-benzoxazepin-7-yl )-1-propanone (free base), obtained in Example 1–2), and 4-fluorobenzyl bromide, the procedure of Example 1–3) was similarly repeated to provide the-title compound as colorless powders melting at 186–188° C.

$^1$H-NMR (CDCl$_3$, free base) δ: 1.00–1.35 (3H, m), 1.40–1.90 (4H, m), 2.09 (3H, s), 2.20–2.65 (1H , m), 2.85–3.15 (4H, m), 3.64 (2H, s), 3.70–3.90 (1H, m), 3.84 (2H, s), 4.10–4.20 (2H, m), 4.55–4.70 (1H, m), 6.95–7.10 (3H, m), 7.25–7.40 (2H, m), 7.64 (1H, d, J=2.2 Hz), 7.82 (1H, dd, J=8.4, 2.2 Hz,) Elemental analysis, for C$_{26}$H$_{31}$FN$_2$O$_3$. HCl. Calcd.: C, 65.74; H, 6.79; N, 5.90. Found: C, 65.42; H, 6.81; N, 5.92.

EXAMPLE 78

1-[4-[(4-Fluorophenyl)methyl]-2,3,4,5-tetrahydro-1,4-benzoxazepin-7-yl]-3-(4-piperidinyl)-1-propanone Dihydrochloride

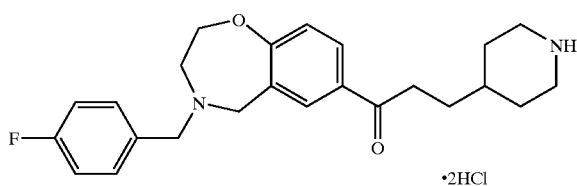

•2HCl

Using 3-(1-acetyl-4-piperidinyl)-1-[4-[(4-fuorophenyl)methyl]-2,3,4,5-tetrahydro-1,4-benzoxazeepin-7-yl]-1-propanone ((free base) obtained in Example 77, the procedure of Example 2 was:similarly repeated to provide the title compound as colorless powders melting at 173–174° C.

$^1$H-NMR (CDCl$_3$, free base) δ: 1.00–1.60 (4H, m), 1.60–1.80 (5H, m), 2.58 (2H, dt, J=12.8, 2.2 Hz), 2.92 (2H, t, J=7.6 Hz), 3.00–3.15 (3H, m), 3.63 (2H, s), 3.83 (2H, s), 4.10–4.20 (2H, m), 6.95–7.10 (3H, m), 7.20–7.35 (2H, m), 7.64 (1H, d, J=1.8 Hz), 7.82 (1H, dd, J=8.5, 1.8 Hz). Elemental analysis, for C$_{24}$H$_{29}$FN$_2$O$_2$. 2HCl. 0.5H$_2$O. Calcd.: C, 60.25; H, 6.74; N, 5.86. Found: C, 60.38; H, 6.78; N, 5.76.

EXAMPLE 79

1-[4-[(4-Fluorophenyl)methyl]-2,3,4,5-tetrahydro-1,4-benzoxazepin-7-yl]-3-[1-[(3-methylphenyl)methyl]-4-piperidinyl]-1-propanone Dihydrochloride

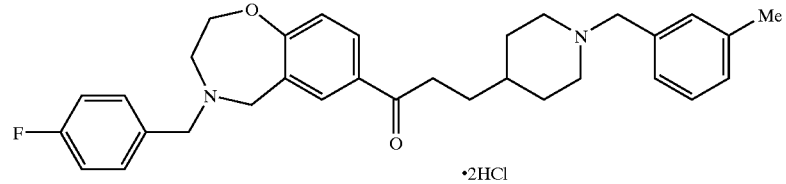

•2HCl

Using 1-[4-[(4-fluorophenyl)methyl]-2,3,4,5-tetrahydro-1,4-benzoxazepin-7-yl]-3-(4-piperidinyl)-1-propanone (free base), obtained in Example 78, and 3-methylbenzyl bromide, the procedure of Example 3 was similarly repeated to provide the title compound as colorless powders melting at 223–225° C.

$^1$H-NMR (CDCl$_3$, free base) δ: 1.20–1.40 (3H, m), 1.50–1.80 (4H, m), 1.80–2.00(2H, m), 2.33 (3H, s), 2.80–2.95 (4H, m), 3.05 (2H, t-like, J=4.0 Hz), 3.44 (2H, s), 3.62 (2H, s), 3.82 (2H, s), 4.12 (2H, t-like, J=4.0 Hz), 6.95–7.35 (9H, m), 7.63 (1H, d, J=2.2 Hz), 7.81 (1H, dd, J=8.4, 2.2 Hz). Elemental analysis, for C₃₂H₃₇FN₂O₂·2HCl. Calcd.: C, 67.01; H, 6.85; N, 4.88. Found: C, 66.73; H, 6.83; N, 4.86.

EXAMPLE 80

3-[1-[(3-Chlorophenyl)methyl]-4-piperidinyl]-1-[4-[(4-fluorophenyl)methyl]-2,3,4,5-tetrahydro-1,4-benzoxazepin-7-yl]-1-propanone Dihydrochloride

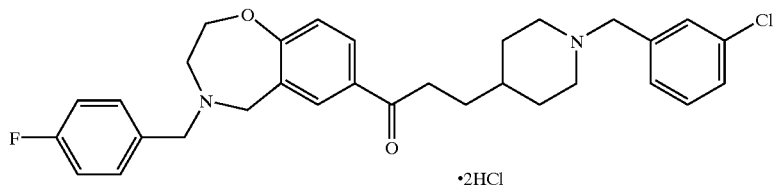

Using 1-[4-[(4-fluor6phenyl)methyl]-2,3,4,5-tetrahydro-1,4-benzoxazepin-7-yl]-3-(4-piperidinyl)-1-propanone (free base), obtained in Example 78, and 3-chlorobenzyl bromide, the procedure of Example 3 was similarly repeated to provide the title compound as colorless powders melting at 224–225° C.

¹H-NMR (CDCl₃, free base) δ: 1.20–1.45 (3H, m), 1.50–1.80 (4H, m), 1.80–2.00 (2H, m), 2.80–2.95 (4H, m), 3.06 (2H, t-like, J=4.0 Hz), 3.44 (2H, s), 3.63 (2H, s), 3.83 (2H, s),. 4.10–4.20 (22H, m), 6.95–7.10 (3H, m), 7.10–7.35 (6H, m), 7.64 (1H, d, J=2.2 Hz), 7.81 (1H, dd, J=8.2, 2.2 Hz). Elemental analysis, for C₃₁H₃₄ClFN₂O₂·2HCl. Calcd.: C, 62.68; H, 6.11; N, 4.72. Found: C, 62.58; H, 6.13; N, 4.66.

EXAMPLE 81

3-[1-[(3-Fluorophenyl)methyl]-4-piperidiny]-1-[4-[(4-fluorophenyl)methyl]-2,3,4,5-tetrahydro-1,4-benzoxazepin-7-yl]-1-propanone Dihydrochloride

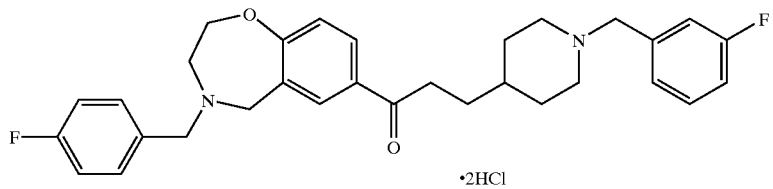

Using 1-[4-[(4-fluorophenyl)methyl]-2,3,4,5-tetrahydro-1,4-benzoxazepin-7-yl]-3-(4-piperidinyl) -1-propanone (free base), obtained in Example 78, and 3-fluorobenzyl bromide, the procedure of Example 3 was similarly repeated to provide the title compound as colorless powders melting at 228–231° C.

¹H-NMR (CDCl₃, free base) δ: 1.20–1.40 (3H, m), 1.50–1.80 (4H, m), 1.80–2.00 (2H, m), 2.80–2.95 (4H, m), 3.06 (2H, t-like, J=4.0 Hz), 3.46 (2H, s), 3.62 (2H, s), 3.83 (2H, s), 4.10–4.20 (2H, m), 6.85–7.15 (6H, m), 7.20–7.35 (3H, m), 7.63 (1H, d, J=2.2 Hz), 7.81 (1H, dd, J=8.4, 2.2 Hz). Elemental analysis, for C₃₁H₃₄F₂N₂O₂·2HCl. Calcd.: C, 64.67; H, 6.28; N, 4.85. Found: C, 64.32; H, 6.27; N, 4.87.

EXAMPLE 82

1-[4-[(4-Fluorophenyl)methyl]-2,3,4,5-tetrahydro-1,4-benzoxazepin-7-yl]-3-[1-[[3-(trifluoromethyl)phenyl]methyl]-4-piperidinyl]-1-propanone Dihydrochloride

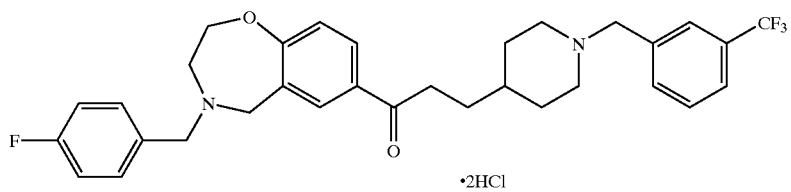

Using 1-[4-[(4-fluorophenyl)methyl]-1,2,3,4,5-tetrahydro-1,4-benzoxazepin-7-yl]-3-(4-piperidinyl)-1-propanone (free base), obtained in Example 78, and 3-(trifluoromethyl)benzyl bromide, the procedure of Example 3 was similarly repeated to provide the title compound as colorless powders melting at 225–227° C.

¹H-NMR (CDCl₃, free base) δ: 1.20–1.45 (3H, m), 1.60–1.80 (4H, m), 1.85–2.05 (2H, m), 2.80–2.95 (4H, m), 3.06 (2H, t-like, J=4.4 Hz), 3.52 (2H, s), 3.63 (2H, s), 3.83 (2H, s), 4.13 (2H, t-like, J=4.4 Hz), 6.95–7.10 (3H, m), 7.20–7.35 (2H, m), 7.35–7.60 (4H, m), 7.64 (1H, d, J=2.2 Hz), 7.82 (1H, dd, J=8.4, 2.2 Hz). Elemental analysis, for C₃₂H₃₄F₄N₂O₂·2HCl. Calcd.: C, 61.25; H, 5.78; N, 4.46. Found: C, 61.29; H, 5.77; N, 4.21.

EXAMPLE 83

1-[4-[(4-Fluorophenyl)methyl]-2,3,4,5-tetrahydro-1,4-benzoxazepin-7-yl]-3-[1-[(2-methylphenyl)methy]-4-piperidinyl]-1-propanone Dihydrochloride

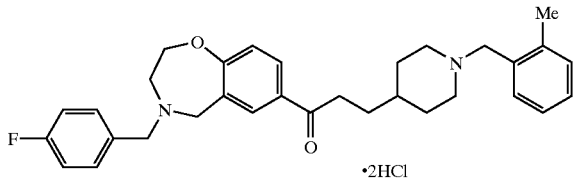

Using 1-[4-[(4-fluorophenyl)methyl]-2,3,4,5-tetrahydro-1,4-benzoxazepin-7-yl]-3-(4-piperidinyl)-1-propanone (free base), obtained in Example 78, and 2-methylbenzyl bromide, the procedure of Example 3 was similarly repeated to provide the title compound as colorless powders melting at 216–219° C.

$^1$H-NMR (CDCl$_3$, free base) δ: 1.15–1.40 (3H, m), 1.60–1.75 (4H, m), 1.90–2.05 (2H, m), 2.35 (3H, s), 2.80–2.95 (4H, m), 3.06 (2H, t-like, J=4.4 Hz), 3.42 (2H, s), 3.62 (2H, s), 3.83 (2H, s), 4.12 (2H, t-like, J=4.4 Hz), 6.95–7.00 (6H, m), 7.20–7.35 (3H, m), 7.63 (1H, d, J=2.2 Hz), 7.81 (1H, dd, J=8.4, 2.2 Hz). Elemental analysis, for C$_{32}$H$_{37}$FN$_2$O$_2$. 2HCl. 0.5H$_2$O. Calcd.: C, 65.97; H, 6.92; N, 4.81. Found: C, 66.38; H, 6.75; N, 4.75.

EXAMPLE 84

3-[1-[(2-Chlorophenyl)methyl]-4-piperidinyl]-1-[4-[(4-fluorophenyl)methyl]-2,3,4,5-tetrahydro-1,4-benzoxazepin-7-yl]-1-propanone Dihydrochloride

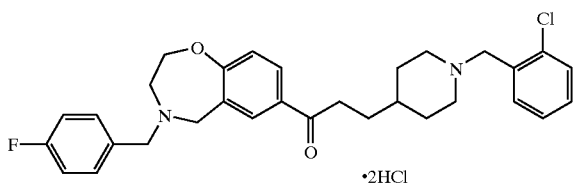

Using 1-[4-[(4-fluorophenyl)methyl]-2,3,4,5-tetrahydro-1,4-benzoxazepin-7-yl]-3-(4-piperidinyl)-1-propanone (free base), obtained in Example 78, and 2-chlorobenzyl bromide, the procedure of Example 3 was similarly repeated to provide the title compound as colorless powders melting at 227–229° C.

$^1$H-NMR (CDCl$_3$, free base) δ: 1.20–1.45 (3H, m), 1.60–1.80 (4H, m), 2.00–2.20 (2H, m), 2.85–3.00 (4H, m), 3.06 (2H, t-like, J=4.4 Hz), 3.60 (2H, s), 3.63 (2H, s), 3.83 (2H, s), 4.13 (2H, t-like, J=4.4 Hz), 6.95–7.40 (8H, m), 7.49 (1H, dd, J=7.2, 2.2 Hz), 7.64 (1H, d, J=2.2 Hz),7.82 (1H, dd, J=8.4, 2.2 Hz). Elemental analysis, for C$_{31}$H$_{34}$ClFN$_2$O$_2$. 2HCl. 0.5H$_2$O. Calcd.: C, 61.75; H, 6.18; N, 4.65. Found: C, 62.15; H, 6.09; N, 4.73.

EXAMPLE 85

3-[1-[(2-Fluorophenyl)methyl]-4-piperidinyl]-1-[4-[(4-fluorophenyl)methyl]-2,3,4,5-tetrahydro-1,4-benzoxazepin-7-yl]-1-propanone Dihydrochloride

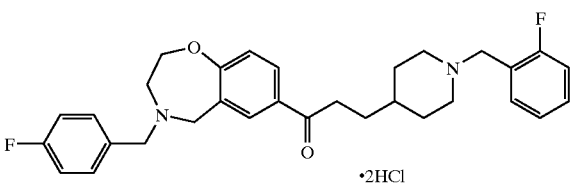

Using 1-[4-[(4-fluorophenyl)methyl]-2,3,4,5-tetrahydro-1,4-benzoxazepin-7-yl]-3- (4-piperidinyl)-1-propanone (free base), obtained in Example 78, and 2-fluorobenzyl bromide, the procedure of Example 3 was similarly repeated to provide the title compound as colorless powders melting at 235–2386° C.

$^1$H-NMR (CDCl$_3$, free base) δ: 1.20–1.40 (3H, m), 1.50–1.80 (4H, m), 1.80–2.10 (2H, m), 2.80–3.00 (4H, m), 3.06 (2H, t-like, J=4.4 Hz), 3.57 (2H, s), 3.63 (2H, s), 3.83 (2H, s), 4.13 (2H, t-like, J=4.4 Hz), 6.95–7.40 (9H, m), 7.63 (1H, d, J=2.2 Hz), 7.81 (1H, dd, J=8.4, 2.2 Hz). Elemental analysis, for C$_{31}$H$_{34}$F$_2$N$_2$O$_2$. 2HCl. Calcd.: C, 64.67; H, 6.28; N, 4.85. Found: C, 64.30; H, 6.36; N, 4.87.

EXAMPLE 86

1-[4-[(4-Fluorophenyl)methyl]-2,3,4,5-tetrahydro-1,4-benzoxazepin-7-yl]-3-[1-[[2-(trifluoromethyl)phenyl]methyl]-4-piperidinyl]-1-propanone Dihydrochloride

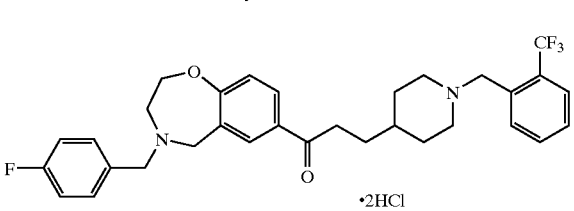

Using 1-[4-[(4-fluorophenyl)methyl]-2,3,4,5-tetrahydro-1,4-benzoxazepin-7-yl]-3-(4-piperidinyl)-1-propanone (free base), obtained in Example 78, and 2-(trifluoromethyl)benzyl bromide, the procedure of Example 3 was similarly repeated to provide the title compound as colorless powders melting at 203–204° C.

$^1$H-NMR (CDCl$_3$, free base) δ: 1.20–1.50 (3H, m), 1.50–1.90 (4H, m), 1.90–2.10 (2H, m), 2.80–3.00 (4H, m), 3.06 (2H, t-like, J=4.4 Hz), 3.63 (4H, s), 3.83 (2H, s), 4.13 (2H, t-like, J=4.4 Hz), 6.95–7.10 (3H, m), 7.20–7.35 (3H, m), 7.45–7.70 (3H, m), 7.75–7.85 (2H, m). Elemental analysis, for C$_{32}$H$_{34}$F$_4$N$_2$O$_2$. 2HCl. Calcd.: C, 61.25; H, 5.78; N, 4.46. Found: C, 60.96; H, 5.79; N, 4.32.

EXAMPLE 87

1-[4-[(4-Fluorophenyl)methyl]-2,3,4,5-tetrahydro-1,
4-benzoxazepin-7-yl]-3-[1-[(4-methylphenyl)
methyl]-4-piperidinyl]-1-propanone Dihydrochloride

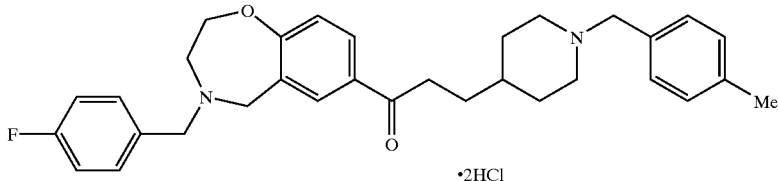

•2HCl

Using 1-[4-[(4-fluorophenyl)methyl]-2,3,4,5-tetrahydro-1,4-benzoxazepin-7-yl]-3-(4-piperidinyl)-1-propanone (free base), obtained in Example 78, and 4-methylbenzyl bromide, the procedure of Example 3 was similarly repeated to provide the title compound as colorless powders melting at 240–242° C.

$^1$H-NMR (CDCl$_3$, free base) δ: 1.20–1.40 (3H, m), 1.50–1.75 (4H, m), 1.85–2.00 (2H, m), 2.33 (3H, s), 2.80–3.00 (4H, m), 3.06 (2H, t-like, J=4.4 Hz), 3.45 (2H, s), 3.62 (2H, s), 3.83 (2H, s), 4.05–4.20 (2H, m), 6.95–7.35 (9H, m), 7.63 (1H, d, J=2.2 Hz), 7.80 (1H, dd, J=8.2, 2.2 Hz). Elemental analysis, for $C_{32}H_{37}FN_2O_2$. 2HCl. Calcd.: C, 67.01; H, 6.85; N, 4.88. Found: C, 66.80; H, 6.77; N, 4.69.

EXAMPLE 88

1-[4-[(4-Fluorophenyl)methyl]-2,3,4,5-tetrahydro-1,
4-benzoxazepin-7-yl]-3-[1-[[4-(trifluoromethyl)
phenyl]methyl]-4-piperidinyl]-1-propanone
Dihydrochloride

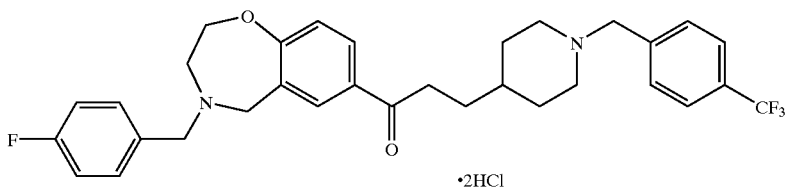

•2HCl

Using 1-[4-[(4-fluorophenyl)methyl]-2,3,4,5-tetrahydro-1,4-benzoxazepin-7-yl]-3-(4-piperidinyl)-1-propanone (free base), obtained in Example 78, and 4-(trifluoromethyl)benzyl bromide, the procedure of Example 3 was similarly repeated to provide the title compound as colorless powders melting at 234–237° C.

$^1$H-NMR (CDCl$_3$, free base) δ: 1.20–1.40 (3H, m), 1.60–1.80 (4H, m), 1.85–2.05 (2H, m), 2.80–3.00 (4H, m), 3.07 (2H, t-like, J=4.4 Hz), 3.52 (2H, s), 3.63 (2H, s), 3.83 (2H, s), 4.10–4.20 (2H, m), 6.95–7.10 (3H, m), 7.20–7.35 (2H, m), 7.44 (2H, d, J=8.0 Hz), 7.56 (2H, d, J=8.0 Hz), 7.63 (1H, d, J=2.2 Hz), 7.81 (1H, dd, J=8.4, 2.2 Hz). Elemental analysis, for $C_{32}H_{34}F_4N_2O_2$. 2HCl. Calcd.: C, 61.25; H, 5.78; N, 4.46. Found: C, 60.91; H, 5.85; N, 4.33.

EXAMPLE 89

3-(1-acetyl-4-piperidinyl)-1-(3-(4-methoxyphenyl)
methyl)-2,3,4,5-tetrahydro-1H-3-benzazepin-7-yl)-1-
propanone Dihydrochloride

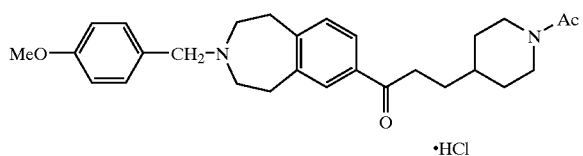

•HCl

Using 3-(1-acetyl-4-piperidinyl)-1-(2,3,4,5-tetrahydro-1H-3-benzazepin-7-yl)-1-propanone (free base) as obtained in Example 23–1), 4-methoxybenzyl chloride, and potassium iodide, the procedure of Example 23–3) was similarly repeated to provide the title compound as colorless amorphous powders.

$^1$H NMR (CDCl$_3$, free base) δ: 1.02–1.30 (2H, m), 1.47–1.85 (5H, m), 2.08 (3H, s), 2.44–2.68 (5H, m), 2.90–3.11 (7H, m), 3.58 (2H, s), 3.73–3.87 (4H, m), 4.54–4.69 (1H, m), 6.87 (2H, d, J=8.4 Hz), 7.16 (1H, d, J=7.7 Hz), 7.26 (2H, d, J=8.4 Hz), 7.65–7.74 (2H, m). Elemental analysis, for $C_{28}H_{36}N_2O_3$. HCl. 3H$_2$O. Calcd.: C, 62.38; H, 8.04; N, 5.20. Found: C, 62.60; H, 7.79; N, 5.47.

EXAMPLE 90

1-[3-[(4-Methoxyphenyl)methyl]-2,3,4,5-tetrahydro-
1H-3-benzazepin-7-yl]-3-(4-piperidinyl)-1-
propanone

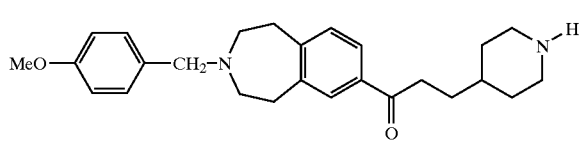

A mixture of 3-(1-acetyl-4-piperidinyl)-1-[3-[(4-methoxyphenyl)methyl]-2,3,4,5-tetrahydro-1H-3- benzazepin-7-yl]-1-propanone (free base, 2.2 g, 4.9 mmol) as obtained in Example 89, 2N-sodium hydroxide/$H_2O$ (50 ml), and ethylene glycol (50 ml) was heated at 155–160° C. with stirring for 4 hours. After spontaneous cooling, the reaction mixture was diluted: with water and extracted with ethyl acetate. The extract was washed with saturated NaCl/$H_2O$ and dried over $MgSO_4$. After the insoluble matter was filtered off with the aid of Hyflo-Super-Cel, the solvent was distilled off under reduced pressure. The residue was dried in vacuo to provide the title compound (2.0 g) as oil.

$^1$H NMR (CDCl$_3$) δ: 1.08–32 (2H, m), 1.35–1.55 (1H, m), 1.61–1.83 (4H, m), ca. 2.2 (1H, br), 2.50–2.70 (6H, m), 2.87–3.20 (8H, m), 3.58 (2H, s), 3.81 (3H, s), 6.87 (2H, d, J=8.4 Hz), 7.16 (1H, d, J=7.3 Hz), 7.26 (2H, d, J=8.4 Hz), 7.65–7.74 (2H, m).

EXAMPLE 91

3-[1-[(4-fluorophenyl)methyl]-4-piperidinyl]-1-[3-[(4-methoxyphenyl)methyl]-2,3,4,5-tetrahydro-1H-3-benzazepin-7-yl]-1-propanone Dihydrochloride

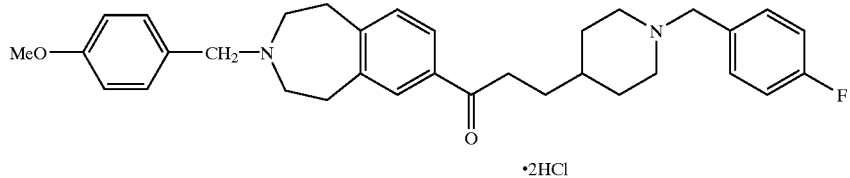

·2HCl

Using 1-[3-[(4-methoxyphenyl)methyl]-2,3,4,5-tetrahydro-1H-3-benzazepin-7-yl]-3-(4-piperidinyl)-1-propanone as obtained in Example 90 and 4-fluorobenzyl bromide, the procedure of Example 28 was similarly repeated to provide the title compound as colorless, powders melting at 218–226° C. (dec.).

$^1$H NMR (CDCl$_3$, free base) δ: 1.15–1.38 (3H, m), 1.52–1.80 (4H, m), 1.83–2.00 (2H, m), 2.55–2.67 (4H, m), 2.78–3.02 (8H, m), 3.44 (2H, s), 3.57 (2H, s), 3.81 (3H, s), 6.87 (2H, d, J=8.8 Hz), 6.99 (2H, t like, J=8.8 Hz), 7.15 (1H, d, J=7.7 Hz), 7.20–7.32 (4H, m), 7.64–7.73 (2H, m). Elemental analysis, for $C_{33}H_{39}FN_2O_2$. 2HCl. Calcd.: C, 67.45; H, 7.03; N, 4.77. Found: C, 67.16; H, 6.85; N, 4.66.

EXAMPLE 92

3-[1-[(4-fluorophenyl)methyl]-4-piperidinyl]-1-[3-[(4-hydroxyphenyl)methyl]-2,3,4,5-tetrahydro-1H-3-benzazepin-7-yl]-1-propanone Dihydrochloride

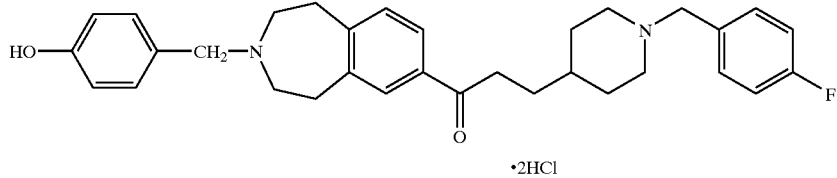

·2HCl

A mixture of 3-[1-[(4-fluorophenyl)methyl]-4-piperidinyl]-1-[3-[(4-methoxyphenyl)methyl]-2,3,4,5-tetrahydro-1H-3-benzazepin-7-yl]-1-propanone (free base, 0.8 g, 1.55 mmol) as obtained in Example 91 and 48% HBr (50 ml) was refluxed for 4 hours. After cooling, the reaction mixture was made basic with aqueous sodium hydroxide solution and extracted with ethyl acetate. The extract was washed with saturated NaCl/$H_2O$ and dried over $MgSO_4$ and the solvent was distilled off under reduced pressure. The residue was purified by silica gel column chromatography (eluent: ethyl acetate-methanol =5:1) to provide the free base (0.4 g),of the title compound as colorless oil.

$^1$H NMR (CDCl$_3$) δ: 1.17–1.40 (3H, m), 1.54–2.10(6H, m), 2.56–2.68 (4H, m), 2.80–3.03 (8H, m), 3.45 (2H, s), 3.56 (2H, s), 6.77 (2H, d, J=8.4 Hz), 6.98 (2H, t like, J=86 Hz), 7.12–7.33 (6H, m), 7.63–7.74 (2H, m).

A solution of the above free base (0.36 g) in methanol was treated with 2 equivalents of HCl (in ethyl acetate) and the product was precipitated from n-hexane to provide the title compound (0.3 g) as colorless amorphous powders.

Elemental analysis, for $C_{32}H_{37}FN_2O_2$. 2HCl. $H_2O$. Calcd.: C, 64.97; H, 6.99; N, 4.74. Found: C, 64.68; H, 7.27; N, 4.65.

EXAMPLE 93

1-[3-[(4-methbyphenyl)methyl]-2,3,4,5-tetrahydro-
1H-3-benzazepin-7-yl]3-[1-[[4-(tert-butyl)phenyl]
methyl]-4-piperidinyl]-1-propanone Dihydrochloride

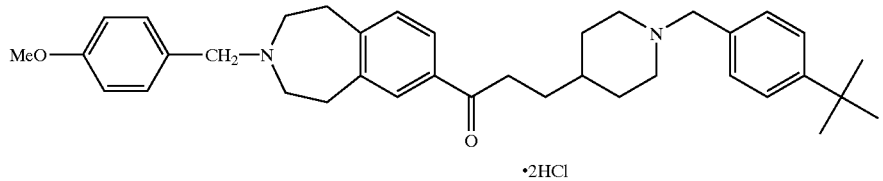

Using 1-[3-[(4-methoxyphenyl)methyl]-2,3,4,5-tetrahydro-1H-3-benzazepin-7-yl]-3-(4-piperidinyl)-1-propanone as obtained in Example 90 and 4-fluorobenzyl bromide, the procedure of Example 28 was similarly repeated to provide the title compound as colorless powders melting at 241–244° C. (dec.).

$^1$H NMR (CDCl$_3$, free base) δ: 1.20–1.40 (12H, m), 1.54–79 (.4H, m), 1.84–2.00 (2H, m), 2.55–2.67 (4H, m), 2.82–3.01 (8H, m), 3.45 (2H, s), 3.57 (2H, s), 3.81 (3H, s), 6.86 (2H, d, J=8.4 Hz), 7.14 (1H, d, J=7.7 Hz), 7.18–7.37 (6H, m), 7.63–7.72 (2H, m). Elemental analysis, for C$_{37}$H$_{48}$N$_2$O$_2$. 2HCl. Calcd.: C, 71.02; H, 8.05; N, 4.48. Found: C, 70.84; H, 8.08; N, 4.50.

EXAMPLE 94 ethyl 2-methyl-2-[4-[[4-[3-[3-[(4-methoxyphenyl)
methyl]-2,3,4,5-tetrahydro-1H-3-benzazepin-7-yl]-3-
oxopropyl]-1-piperidinyl]methyl]phenyl]propionate
Dihydrochloride

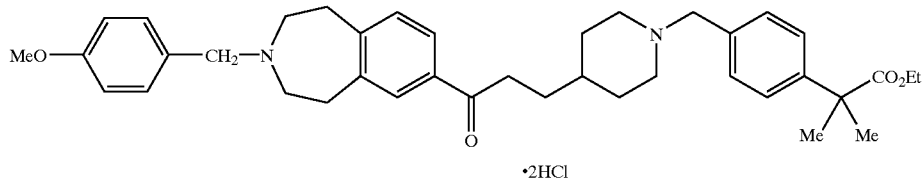

Using 1-[3-[(4-methoxyphenyl)methyl]-2,3,4,5-tetrahydro-1H-3-benzazepin-7-yl]-3-(4-piperidinyl)-1-propanone as obtained in Example 90 and ethyl 2-methyl-2-[4-(bromomethyl)phenyl]propionate, the procedure of Example 28 was similarly repeated to provide the title compound as colorless powders melting at 221–224° C. dec.).

$^1$NMR (CDCl$_3$, free base) δ: 1.13–1.43 (6H, m), 1.56 (6H, s), 1.60–1.80 (4H, m), 1.84–2.01 (2H, m), 2.56–2.68 (4H, m), 2.82–3.02 (8H, m), 3.45 (2H, s), 3.58 (2H, s), 3.81 (3H, s), 4.12 (2H, q. J=7.1Hz), 6.87 (2H, d, J=8.8 Hz), 7.14 (1H, d, J=7.7 Hz), 7.20–7.33 (6H, m), 7.65–7.73 (2H, m). Elemental analysis, for C$_{39}$H$_{50}$N$_2$O$_4$. 2HCl. Calcd.: C, 68.51; H, 7.67; N, 4.10. Found: C, 68.13; H, 7.67; N, 4.16.

EXAMPLE 95

3-[1-(4-chlorobenzoyl)-4-piperidinyl]-1-[3-
(phenlimethyl)-2,3,4,5-tetrahydro-1H-3-benzazepin-
7-yl]-1-propanone Hydrochloride

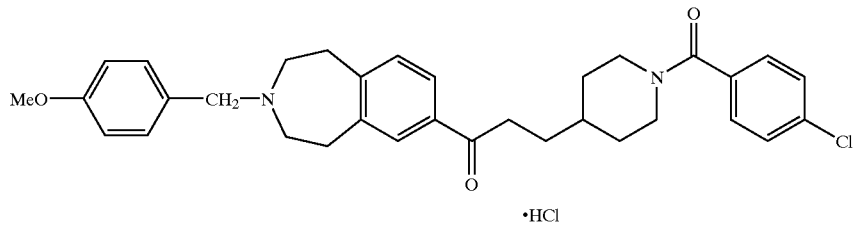

Using 1-[3-[(4-methoxyphenyl)methyl]-2,3,4,5-tetrahydro-1H-3-benzazepin-7-yl]-3-(4-piperidinyl)-1-propanone as obtained in Example 90 and 4-chlorobenzoyl chloride, the procedure of Example 28 was similarly repeated to provide the title compound as colorless amorphous powders.

¹H NMR (CDCl₃, free base) δ: 1.05–1.38 (2H, m), 1.50–1.95 (5H, m), 2.54–3.10 (12H, m), 3.52–3.93 (6H, m), ca. 4.65 (1H, br), 6.87 (2H, d, J=8.8 Hz), 7.16 (1H, d, J=7.7 Hz), 7.21–7.42 (6H, m), 7.64–7.73 (2H, m). Elemental analysis, for C₃₃H₃₇ClN₂O₃. HCl. 1.5H₂O. Calcd.: C, 65.13; H, 6.79; N, 4.60. Found: C, 65.30; H, 6.76; N, 4.44.

EXAMPLE 96

3-[1-[(3,4-Dichlorophenyl)methyl]-4-piperidinyl]-1-[3-[(4-methoxyphenyl)methyl]-2,3,34,5-tetrahydro-1H-3-benzazepin-7-yl]-1-propanone Dihydrochloride

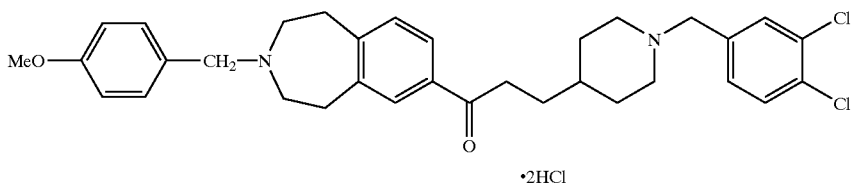

•2HCl

Using 1-[3-[(4-methoxyphenyl)methyl]-2,3,4,5-tetrahydro-1H-3-benzazepin-7-yl]-3-(4-piperidinyl)-1-propanone as obtained in Example 90 and 3,4-dichlorobenzyl chloride, the procedure of Example 28 was similarly repeated to provide the title compound as colorless powders melting at 220–223° C. (dec.).

¹H NMR (CDCl₃, free base) δ: 1.15–1.41 (3H, m), 1.55–1.80 (4H, m), 1.86–2.01 (2H, m), 2.55–2.67 (4H, m), 2.76–3.02 (8H, m), 3.41 (2H, s), 3.58 (2H, s), 3.81 (3H, s), 6.87 (2H, d, J=8.4 Hz), 7.10–7.30 (4H, m), 7.37 (1H, d, J=8.1 Hz), 7.42 (1H, d, J=1.8 Hz), 7.65–7.73 (2H, m). Elemental analysis, for C₃₃H₃₈Cl₂N₂O₂. 2HCl. 0.5H₂O. Calcd.: C, 61.21; H, 6.38; N, 4.33. Found: C, 61.43; H, 6.33; N, 4.58.

EXAMPLE 97

1-[3-[(4-Methoxyphenyl)methyl]-2,3,4,5-tetrahydro-1H-3-benzazepin-7-yl]-3-[1-[(4-phenylphenyl)methyl]-4-piperidinyl]-1-propanone Dihydrochloride Using 1-[3-[(4-methoxyphenyl)methyl]-2,3,4,5-tetrahydro-1H-3-benzazepin-7-yl]-3-(4-piperidilnyl)-1-propanone as obtained in Example 90 and 4-phenylbenzyl bromide, the procedure of Example 28 was similarly repeated to provide the title compound as colorless powders melting at 220–225° C. (dec.).

¹H NMR (CDCl₃, free base) δ: 1.21–1.41 (3H, m), 1.53–1.80 (4H, m), 1.88–2.06 (2H, m), 2.55–2.67 (4H, m), 2.86–3.00 (8H, m), 3.53 (21H, s), 3.58 (2H, s), 3.81 (3H, s), 6.87 (2H, d, J=8.4 Hz), 7.15 (1H, d, J=7.8 Hz), 7.20–7.30 (2H, m), 7.31–7.49 (5H, m), 7.51–7.63 (4H, m), 7.65–7.73 (2H, m). Elemental analysis, for C₃₉H₄₄N₂O₂. 2HCl. 0.5H₂O. Calcd.: C, 71.55; H, 7.24; N, 4.28. Found: C, 71.28; H, 7.13; N, 4.43.

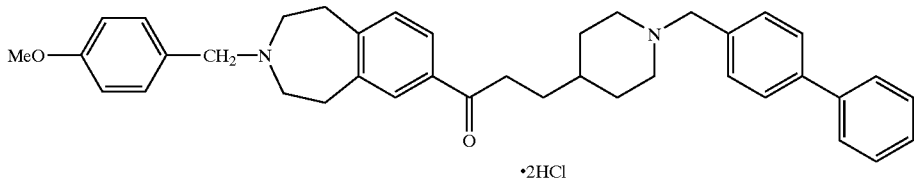

•2HCl

EXAMPLE 98

1-[3-[(4-Methoxyphenyl)methyl]-2,3,4,5-tetrahydro-1H-3-benzazepin-7-yl]-3-[1-(4-phenylbenzoyl)-4-piperidinyl]-1-propanone Hydrochloride

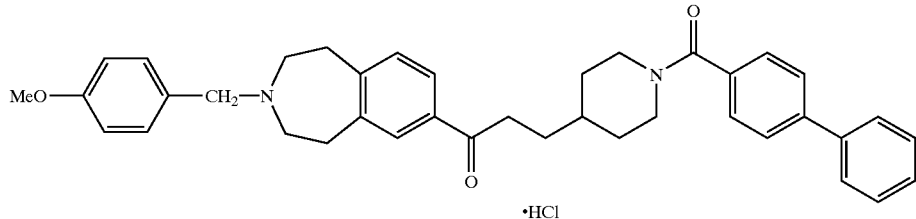

•HCl

To a mixed solution of 1-[3-[(4-methoxyphenyl)-methyl] 2,3,4,5-tetrahydro-1H-3-benzazepin-7-yl]-3-[4-piperidinyl)-1-propanone as obtained in Example 90 (0.5 g, 1.23 mmol), 4-phenylbenzoic acid (0.24 g, 1.21 mmol) and triethylamine (0.22 ml) in N,N-dimethylformamide (DMF) (6 ml) was added diethyl cyanophosphonate (0.2 g, 1.23 mmol) with ice cooling, and the mixture was stirred on ice for 20 minutes. After addition of water (1 ml), the reaction mixture was stirred at room temperature, diluted with water (about 200 ml) and extracted with ethyl acetate. The extract was washed with saturated NaCl/H$_2$O and dried over MgSO$_4$, and the solvent was distilled off under reduced pressure. The residue was purified by silica gel column chromatography (eluent: ethyl acetate-methanol=40:1) to provide the free base (0.57g) of the title compound as colorless oil.

$^1$H NMR (CDCl$_3$) δ: 1.07–1.40 (3H, m), 1.50–1.96 (4H, m), 2.47–3.06 (1.2H, m), 3.58 (2H, s), ca. 3.65–3.98 (4H, m), ca. 4.7 (1H, br), 6.87 (2H, d, J=8.8 Hz), 7.16 (1H, d, J=7.7 Hz), 7.20–7.30 (2H, m), 7.32–7.53 (5H, m), 7.55–7.75 (6H, m).

A solution of the above free base (0.54 g) in methanol was treated with 1 equivalent of HCl (in ethyl acetate) and precipitated from ethanol-ethyl acetate to provide the title-:compound as colorless powders melting at 212–215° C.

Elemental analysis, for C$_{39}$H$_{42}$N$_2$O$_3$. HCl. Calcd.: C, 75.16; H, 6.95; N, 4.49. Found: C, 75.04; H, 6.95; N, 4.47.

EXAMPLE 99

1- [4- [(4-Fluorophenyl)methyl]-2,3,4,5-tetrahydro-1,4-benzoxazepin-7-yl]-3-[1-[(3-phenylphenyl)methyl]-4-piperidinyl]-1-propanone Ddihydrochloride

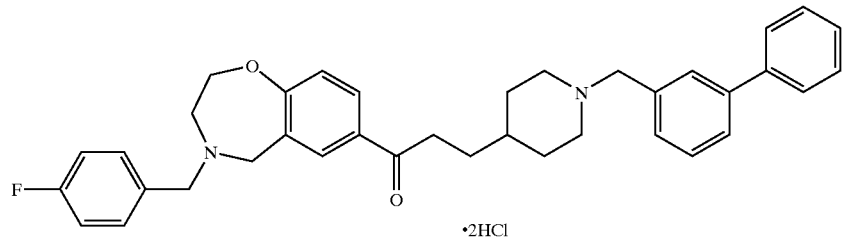

•2HCl

Using 1-[4-[(4-fluorophenyl)methyl]-2,3,4,5-tetrahydro-1,4-benzoxazepin-7-yl]-3-(4-piperidinyl)-1-propanone (free base) as obtained in Example 78 and 4-phenylbenzyl bromide, the procedure of Example 28 was similarly repeated to provide the title compound as colorless powders melting at 187–189° C.

$^1$H NMR (CDCl$_3$, free base) δ: 1.14–1.44 (3H, m), 1.53–1.80 (4H, m), 1.88–2.07 (2H, m), 2.83–3.00 (4H, m), 3.06 (2H, t like, J=4.2 Hz), 3.56 (2H, s), 3.63 (2H, s), 3.83 (2H, s), 4.12 (2H, t like, J=4.2 Hz), 6.94–7.08 (3H, m), 7.20–7.66 (12H, m), 7.81 (1H, dd, J=2.2, 8.4 Hz). Elemental analysis, for C$_{37}$H$_{39}$FN$_2$O$_2$. 2HCl. 0.5H$_2$O. Calcd.: C, 68.94; H, 6.57; N, 4.35. Found: C, 68.71; H, 6.47; N, 4.45.

EXAMPLE 100

Ethyl 2-Methyl-2-[4-[[4-[3-[4-[(4-fluorophenyl)methyl]-2,3,4,5-tetrahydro-1,4-benzoxazepin-7-yl]-3-oxopropyl]-1-piperidinyl]methyl]phenyl]propionate Dihydrochloride

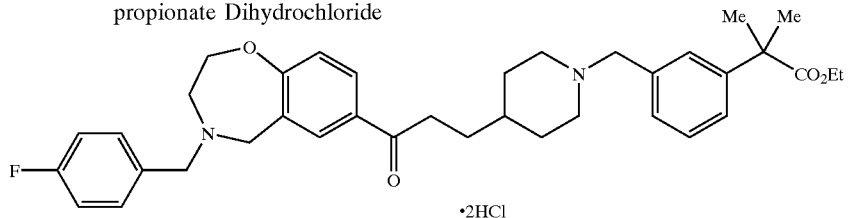

Using 1-[4-[(4-fluorophenyl)methyl]-2,3,4,5-tetrahydro-1,4-benzoxazepin-7-yl]-3-(4-piperidinyl)-1-propanone (free base) as obtained in Example 78 and ethyl 2-methyl-2-[4-(bromomethyl)phenyl]propionate, the procedure of Example 28 was similarly repeated to provide the title compound as colorless powders melting at 188–190° C.

$^1$H NMR (CDCl$_3$, free base) δ: 1.13–1.40 (6H, m), 1.50–1.80 (10H, m), 1.84–2.02 (2H, m), 2.80–2.97 (4H, m), 3.06 (2H, t like, J=4.4 Hz), 3.48 (2H, s), 3.63 (2H, s), 3.83 (2H, s), 4.05–4.19 (4H, m), 6.95–7.10 (3H, m), 7.16–7.34 (6H, m), 7.63 (1H, d, J=2.2 Hz), 7.81, (1H, dd, J=2.2, 8.3 Hz). Elemental analysis, for C$_{37}$H$_{45}$FN$_2$O$_4$. 2HCl. Calcd.: C, 65.97; H, 7.03; N, 4.16. Found: C, 65.74; H, 6.99; N, 4.19.

EXAMPLE 101

1-[4-[(4-Fluorophenyl)methyl]-2,3,4,5-tetrahydro-1,4-benzoxazepin-7-yl]-3-[1-(1-naphthylimethyl)-4-piperidinyl]-1-propanone Dihydrochloride

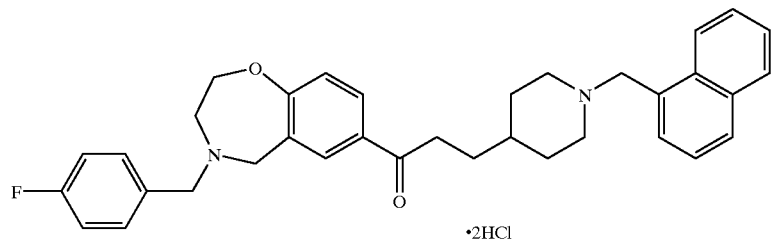

Using 1-[4-[(4-fluorophenyl)methyl]-2,3,4,5-tetrahydro-1,4-benzoxazepin-7-yl]-3-(4-piperidinyl)-1-propanone (free base) as obtained in Example 78, 1-(methylchloride) naphthalene, and potassium iodide, the procedure of Example 28 was similarly repeated to provide the title compound as colorless amorphous powders.

$^1$H NMR (CDCl$_3$, free base) δ: 1.15–1.42 (3H, m), 1.55–1.68 (4H, m), 1.94–2.11 (2H, m), 2.82–3.10 (6H, m), 3.63 (2H, s), 3.83 (2H, s), 3.88 (2H, s), 4.13 (2H, t like, J=4.4 Hz), 6.95–7.10 (3H, m), 7.22–1.33 (2H, m), 7.35–7.57 (4H, m), 7.63 (1H, d, J=2.2 Hz), 7.73–7.90 (3H, m), 8.26–8.36 (1H, m). Elemental analysis, for C$_{35}$H$_{37}$FN$_2$O$_2$. 2HCl. 1.5H$_2$O. Calcd.: C, 66.03; H, 6.65; N, 4.40. Found: C, 65.83; H, 6.91; N, 4.10.

EXAMPLE 102

Diethyl 5-[[4-[3-[4-[(4-fluorophenyl)methyl]-2,3,4,5-tetrahydro-1,4-benzoxazepin-7-yl]-3-oxopropyl]-1-piperidinyl]methyl]-1,3-benzodioxole-2,2-dicarboxylate Dihydrochloride

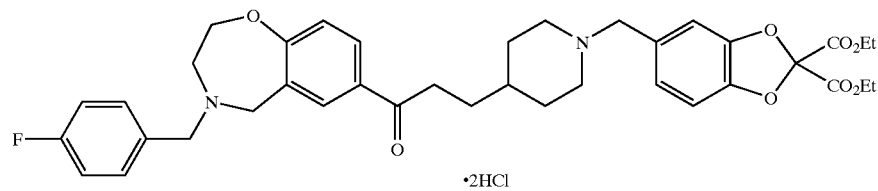

Using 1-[4-[(4-fluorophenyl)methyl]-2,3,4,5-tetrahydro-1,4-benzoxazepin-7-yl]-3-(4-piperidinyl)-1-propanone (free base) as obtained in Example 78 and mesylate of diethyl 5-hydroxymethyl-1,3-benzodioxole-2,2-dicarboxylate, the procedure of Example 28 was similarly repeated to provide the title compound as colorless powders melting at 199° C. (dec.).

$^1$H NMR (CDCl$_3$, free base) δ: 1.10–1.40 (3H, m), 1.34 (6H, t, J=7.0 Hz), 1.50–1.75 (4H, m), 1.80–2.00 (2H, m), 2.75–3.00 (4H, m), 3.06 (2H, t-like, J=4.0 Hz), 3.39 (2H, s), 3.63 (2H, s), 3.83 (2H, s), 4.10–4.20 (2H, m), 4.36 (4H, q, J=7.0 Hz), 6.84 (2H, s), 6.90–7.10 (4H, m), 7.20–7.35 (2H, m), 7.63 (1H, d, J=2.2 Hz), 7.81 (1H, dd, J=8.4, 2.2 Hz). Elemental analysis, for C$_{38}$H$_{43}$FN$_2$O$_8$. 2HCl. 0.5H$_2$O. Calcd.: C, 60.32; H, 6.13; N, 3.70. Found: C, 60.47; H, 6.03; N, 3.87.

EXAMPLE 103

Ethyl 2-[3-[[4-[3-[4-[(4-fluorophenyl)methyl]-2,3,4,5-tetrahydro-1,4-benzoxazepin-7-yl]-3-oxopropyl]-1-piperidinyl]methyl]phenoxy]ethanoate Dihydrochloride To a solution of ethyl 2-[3-[[4-[3-[4-[(4-fluorophenyl)methyl]-2,3,4,5-tetrahydro-1,4-benzoxazepin-7-yl]-3-oxopropyl]-1-piperidinyl]methyl]phenoxy]ethanoate dihydrochloride (0.35 g, 0.378 mmol) as obtained in Example 103 in ethanol (10 ml) was added 1N-sodium hydroxide/H$_2$O (10 ml), and the mixture was refluxed for 2 hours. The ethanol was then distilled off and the residual aqueous solution was extracted with ethyl acetate. The extract was washed with saturated NaCl/H$_2$O and dried over MgSO$_4$, and the solvent was distilled off under reduced pressure. The residue was dissolved in methanol, treated with 2 equivalents of HCl (in ethyl acetate), and precipitated from ether to provide the title compound as colorless powders melting at 201–204° C.

$^1$H NMR (CDCl$_3$, free base) δ: 1.10–1.35 (3H, m), 1.40–2.00 (8H, m), 2.60–3.30 (7H, m), 3.50 (2H, s), 3.70–3.90 (4H, m), 4.00–4.30 (2H, m), 6.55–7.10 (7H, m), 7.20–7.30 (2H, m), 7.61 (1H, s), 7.75 (1H, dd, J=8.2, 2.2 Hz). Elemental analysis, for C$_{33}$H$_{37}$FN$_2$O$_5$. 2HCl. 0.5H$_2$O. Calcd.: C, 61.68; H, 6.27; N, 4.36. Found: C, 61.79; H, 6.32; N, 4.21.

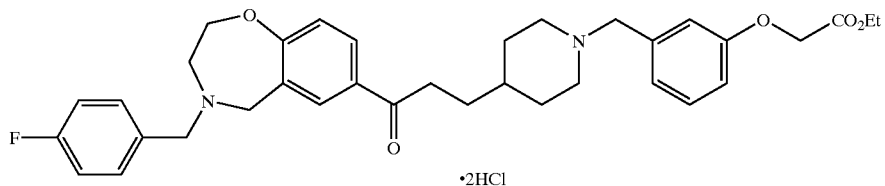

·2HCl

Using 1-(4-[(4-fluorophenyl)methyl]-2,3,4,5-tetrahydro-1,4-benzoxazepin-7-yl]-3-(4-piperidinyl)-1-propanone (free base) as obtained in Example 78 and ethyl 2-[4-(bromomethyl)phenoxy]ethanoate, the procedure of Example 28 was similarly repeated to provide the title compound as colorless powders melting at 200–203° C.

$^1$H NMR (CDCl$_3$, free base) δ: 1.10–1.45 (3H, m), 1.29 (3H, t, J=7.0 Hz), 1.50–1.75 (4H, m), 1.80–2.00 (2H, m), 2.80–3.00 (4H, m), 3.06 (2H, t-like, J=4.0 Hz), 3.45 (2H, s), 3.63 (2H, s), 3.83 (2H, s), 4.10–4.20 (2H, m), 4.27 (2H, q, J=7.0 Hz), 4.62 (2H, s), 6.75–6.85 (1H, m), 6.90–7.15 (5H, m), 7.20–7.35 (3H, m), 7.63 (1H, d, J=2.2 Hz), 7.81 (1H, dd, J=8.4, 2.2 Hz). Elemental analysis, for C$_{35}$H$_{41}$FN$_2$O$_5$. 2HCl. 0.5H$_2$O. Calcd.: C, 62.68; H, 6.61, N, 4.18. Found: C, 62.93; H, 6.48; N, 4.39.

EXAMPLE 104

3-[[4-[3-[4-[(4-Fluorophenyl)methyl]-2,3,4,5-tetrahydro-1,4-benzoxazepin-7-yl]-3-oxopropyl]-1-piperidinyl]methyl]phenoxyacetic acid Dihydrochloride

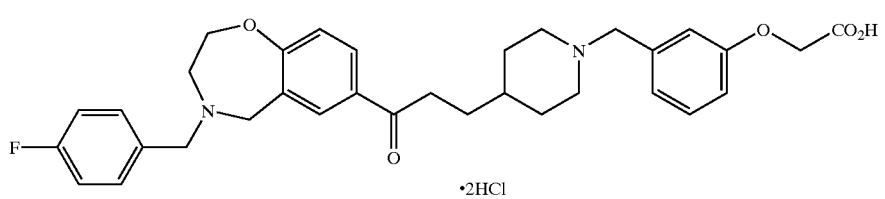

·2HCl

EXAMPLE 105

Ethyl 4-[[4-[3-[4-[(4-fluorophenyl)methyl]-2,3,4,5-tetrahydro-1,4-benzoxazepin-7-yl]-3-oxopropyl]-1-piperidinyl]methyl]-1-Benzenesulfonate

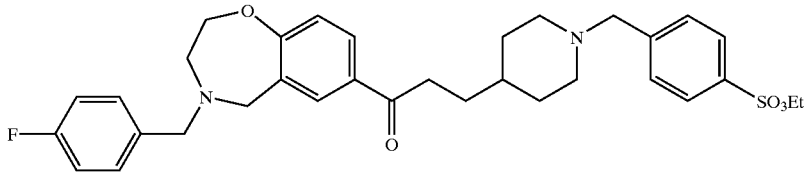

Using 1-[4-[(4-fluorophenyl)methyl]-2,3,4,5-tetrahydro-1,4-benzoxazepin-7-yl]-3-(4-piperidinyl)-1-propanone (free base) as obtained in Example 78 and ethyl 4-(bromomethyl)-1-benzenesulfonate, the procedure of Example 28 was similarly repeated to provide the title compound as colorless oil.

$^1$H NMR (CDCl$_3$) δ: 1.20–1.40 (6H, m), 1.50–1.80 (4H, m), 1.85–2.05 (2H, m), 2.75–2.95 (4H, m), 3.07 (2H, t-like, J=4.0 Hz), 3.55 (2H, s), 3.63 (2H, s), 3.83 (2H, s), 4.05–4.20 (4H, m), 6.95–7.10 (3H, m), 7.20–7.35 (2H, m), 7.45–7.65 (3H, m), 7.75–7.90 (3H, m).

EXAMPLE 106

4-[[4-[3-[4-[(4-Fluorophnyl)methyl]-2,3,4,5-tetrahydro-1,4-benzoxazepin-7-yl]-3-oxopropyl]-1-piperidinyl]methyl]-1-benzensulfonic acid Hydrochloride

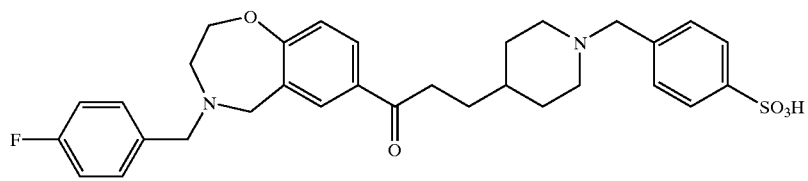

A solution of ethyl 4-[[4-[3-[4-[(4-fluorophenyl)methyl]-2,3,4,5-tetrahydro-1,4-benzoxazepin-7-yl]-3-oxopropyl)-1-piperidinyl]methyl]-1-benzenesulfonate as obtained in Example 105 in methanol was treated with 1 equivalent of HCl (in ethyl acetate) and precipitated from ether to provide the title compound as colorless amorphous powders.

$^1$H NMR (DMSO-d$_6$) δ: 1.40–2.00 (7H, m), 2.70–3.60 (:10H, m), 4.20–4.80 (8H, m), 7.15–7.40 (3H, m), 7.45–7.80 (6H, m), 7.95–8.10 (2H, m), 10.10–10.30 (1H, br), , 11.20–11.50 (1H, br). Elemental analysis, for C$_{31}$H$_{35}$FN$_2$O$_5$S. HCl. H$_2$O. Calcd.: C, 59.94; H, 6.61; N, 4.51. Found: C, 60.58; H, 6.46; N, 4.61.

EXAMPLE 107

1-[4-[(4-Fluorophenyl)methyl]-2,3,4,5-tetrahydro-1,4-benzoxazepin-7-yl]-3-[1-(1-phenylethyl)-4-piperidinyl]-1-propanone Dihydrochloride

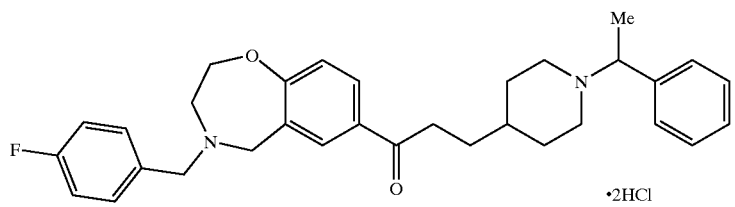

Using 1-[4-[(4-fluorophenyl)methyl]-2,3,4,5-tetrahydro-1,4-benzoxazepin-7-yl]-3-(4-piperidinyl)-1-propanone (free base) as obtained in Example 78 and 1-(bromoethyl)benzene, the procedure of Example 28 was similarly repeated to provide the title compound as colorless powders melting at 235–237° C.

$^1$H NMR (CDCl$_3$, free base) δ: 1.10–1.45 (3H, m), 1.38 (3H, d, J=6.6 Hz), 1.50–2.10 (6H, m), 2.75–2.95 (3H, m), 3.00–3.15 (3H, m), 3.30–3.50 (1H, m), 3.62 (2H, s), 3.82 (2H, s), 4.12 (2H, t-like, J=4.4 Hz), 6.95–7.10 (3H, m), 7.20–7.45 (7H, m), 7.62 (1H, d, J=2.2 Hz), 7.80 (1H, dd, J=8.4, 2.2 Hz). Elemental analysis, for C$_{32}$H$_{37}$FN$_2$O$_2$. 2HCl. 0.5H$_2$O. Calcd.: C, 65.97; H, 6.92; N, 4.81. Found: C, 65.85; H, 6.80; N, 4.81.

EXAMPLE 108

1-[4-[(4-Fluorophenyl)methyl]-2,3,4,5-tetrahydro-4-benzoxazepin-7-yl]-3-[1-[[4-(tert-butyl)phenyl]methyl]-4-piperidinyl]-1-propanone Dihydrochloride

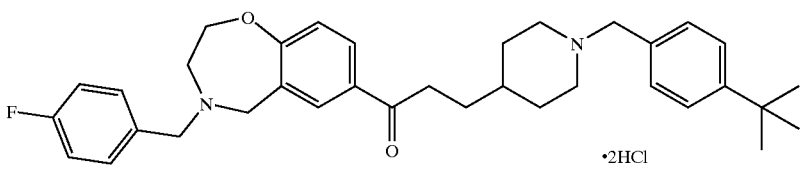

Using 1-[4-[(4-fluorophenyl)methyl]-2,3,4,5-teitrahydro-1,4-benzoxazepin-7-yl]-3-(4-piperidinyl)-1-propanone (free base) as obtained in Example 78 and 4-(tert-butyl)benzyl bromide, the procedure of Example 28 was similarly repeated to provide the title compound as colorless-powders melting at 240–243° C.

$^1$H NMR (CDCl$_3$, free base) δ: 1.20–1.50(3H, m), 1.31 (9H, s), 1.60–1.80(4H, m), 1.85–2.05(2H, m), 2.85–2.95 (4H, m), 3.05(2H, t-like, J=4.0 Hz), 3.46(2H, s), 3.61(2H, s), 3.82(2H, s), 4.10–4.20(2H, m), 6.90–7.10(4H, m), 7.20–7.40(5H, m), 7.63(1H, d, J=2.0 Hz), 7.80(1H, dd. J=8.1, 2.0 Hz). Elemental analysis, for C$_{35}$H$_{43}$FN$_2$O$_2$. 2HCl. H$_2$O. Calcd.: C, 66.34; H, 7.47; N, 4.42. Found: C, 66.50; H, 7.42; N, 4.38.

EXAMPLE 109

2-(1-Acetyl-4-piperidinyl)-1-[3-(phenylmethyl)-2,3,4,5-tetrahydro-1H-3-benzazepin7-yl]-1-ethanone Hydrochloride

1) Using (1-acetyl-4-piperidinyl)acetic acid and 3-formyl-2,3,4,5-tetrahydro-1H-3-benzazepine as obtained in Reference Example 2, the procedure of Example 23-1) was similarly repeated to provide 2-(1-acetyl-4-piperidinyl)-1-(3-formyl-2,3,4,5-tetrahydro-1H-3-benzazepin-7-yl)-1-ethanone as light-yellow oil.

$^1$H NMR (CDCl$_3$, free base) δ: 1.08–1.33 (2H, m), 1.68–1.94 (2H, m), 2.09 (3H, s), 2.14–2.39 (1H, m), 2.51–2.70 (1H, m), 2.77–3.20 (7H, m), 3.44–3.56 (2H, m), 3.63–3.88 (3H, m), 4.55–4.70 (1H, m), 7.20–7.30 (1H, m)7.70–7.80 (2H, m), 8.16 (1H, s). 2) Using 2-(1-acetyl-4-piperidinyl)-1-(3-formyl-2,3,4,5-tetrahydro-1H-3-benzazepin-7-yl)-1-ethanone as obtained in 1), the procedure of,Example 23–2) was similarly repeated to provide 2-(4-piperidinyl)-1-(2,3,4,5-tetrahydro-1H-3-benzazepin-7-yl)-1-ethanone as light-yellow oil.

$^1$H NMR (CDCl$_3$, free base) δ: 1.07–1.32 (2H, m), 1.67–1.94 (2H, m), 2.09 (3H, s), 2.12–2.35 (1H, m), 2.50–2.68 (1H, m), 2.81–3.19 (12H, m), 3.72–3.87 (1H, m), 4.55–4.68 (1H, m), 7.19 (1H, d, J=8.4 Hz), 7.65–7.75 (2H, m). 3) Using 2-(4-piperidinyl)-1-(2,3,4,5-tetrahydro-1H-3-benzazepin-7-yl)-1-ethanone as obtained in 2), the procedure of Example 23–3) was similarly repeated to provide the title compound as colorless amorphous powders.

$^1$H NMR (CDCl$_3$, free base) δ: 1.06–1.31 (2H, m), 1.68–1.92 (2H, m), 2.08 (3H, s), 2.12–2.36 (1H, m), 2.48–2.69 (5H, m), 2.80–3.17 (7H, m), 3.64 (2H, s), 3.72–3.86 (1H, m), 4.54–4.68 (1H, m), 7.17 (1H, d, J=8.1 Hz), 7.20–7.40 (5H, m), 7.64–7.73 (2H, m). Elemental analysis, for C$_{26}$H$_{32}$N$_2$O$_2$. HCl. 1.5H$_2$O. Calcd.: C, 66.72; H, 7.75; N, 5.99. Found: C, 66.46; H, 7.87; N, 5.64.

EXAMPLE 110

1-[3-(Phenylmethyl)-2,3,4,5-tetrahydro-1H-3-benzazepin-7-yl]-2-(4-piperidinyl)-1-ethanone Dihydrochloride

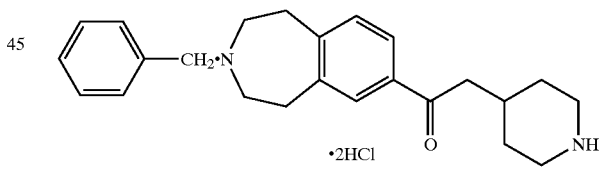

Using 2-(1-acetyl-4-piperidinyl)-1-[3-(phenyl-methyl)-2,3,4,5-tetrahydro-1H-3-benzazepin-7-yl]-1-ethanone hydrochloride as obtained in Example 109, the procedure of Example 24 was similarly repeated to provide the title compound as colorless amorphous powders.

$^1$H NMR (CDCl$_3$, free base) δ: 1.10–1.37 (2H, m), 1.66–1.84 (2H, m), 1.97–2.24 (2H, m), 2.48–2.75 (6H, m), 2.84(2H, d, J=7.0 Hz), 2.90–3.18 (6H, m), 3.64 (2H, s), 7.16 (1H, d, J=7.7 Hz), 7.20–7.40 (5H, m), 7.64–7.74 (2H, m). Elemental analysis, for C$_{24}$H$_{30}$N$_2$O. 2HCl. 0.5H$_2$O. Calcd.: C, 64.86; H, 7.48; N, 6.30. Found: C, 65.20; H, 7.97; N, 6.18.

EXAMPLE 111

2-[1-(Phenylmethyl)-4-piperidinyl]-1-[3-(phenylmethyl)-2,3,4,5-tetrahydro-1-3-benzazepin-7-yl]-1-ethanone Dihydrochloride

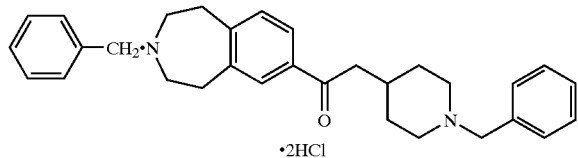

Using 1-[3-(phenylmethyl)-2,3,4,5-tetrahydro-1H-3-benzazepin-7-yl]-2-(4-piperidinyl)-1-ethanone (free base) as obtained in Example 110 and benzyl bromide, the procedure of Example 28 was similarly repeated to provide the title compound as colorless powders melting at 242–245° C. (dec.).

$^1$H NMR (CDCl$_3$, free base) δ: 1.23–1.47 (2H, m), 1.64–1.80 (2H, m), 1.84–2.10 (3H, m), 2.55–2.70 (4H, m), 2.77–3.03 (8H, m), 3.48 (2H, s), 3.63 (2H, s), 7.10–7.40 (11H, m), 7.63–7.72 (2H, m). Elemental analysis, for C$_{31}$H$_{36}$N$_2$O. 2HCl. Calcd.: C, 70.85; H, 7.29; N, 5.33. Found: C, 70.88; H, 7.36; N, 5.31.

EXAMPLE 112

2-[1-[(4-Fluorophenyl)methyl]-4-piperidinyl]-1-[3-(phenylmethyl)-2,3,4,5-tetrahydro-1H-3-benzazepin-7-yl]-1-ethanone Dihydrochloride

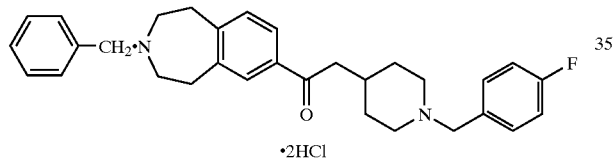

Using 1-[3-(phenylmethyl)-2,3,4,5-tetrahydro-1H-3-benzazepin-7-yl]-2-(4-piperidinyl)-1-ethanone (free base) as obtained in Example 110 and 4-fluorobenzyl bromide, the procedure of Example 28 was similarly repeated to provide the title, compound as colorless powders melting at 243–247° C. (dec.).

$^1$H NMR (CDCl$_3$, free base) δ: 1.21–1.45 (2H, m), 1.63–1.80 (2H, m), 1.90–2.08 (3H, m), 2.57–2.70 (4H, m), 2.76–2.90 (4H, m), 2.92–3.04 (4H, m), 3.44 (2H, s), 3.64 (2H, s), 6.99 (2H, t like, J=8.8 Hz), 7.15 (1H, d, J=8.0 Hz), 7.20–7.40 (7H, m), 7.63–7.73 (2H, m). Elemental analysis, for C$_{31}$H$_{35}$FN$_2$O. 2HCl. Calcd.: C, 68.50; H, 6.86; N, 5.15. Found: C, 68.61; H, 6.90; N, 5.24.

EXAMPLE 113

1-[3-(Phenylmethyl)-2,3,4,5-tetrahydro 1H-3-benzazepin-7-yl]-4-[1-(phenylmethyl)-4-piperidinyl]-1-butanone Dihydrochloride

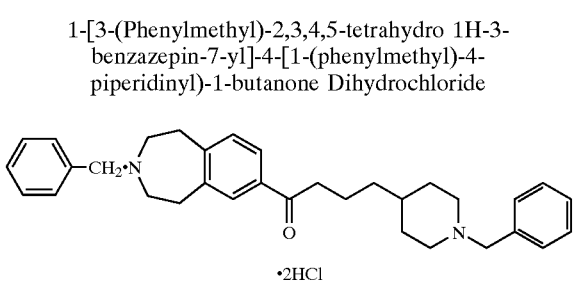

Using 1-[3-(phenylmethyl)-2,3,4,5-tetrahydro-1H-3-benzazepin-7-yl]-4-(4-piperidinyl)-1-butanone (free base) as obtained in Example 26 and benzyl bromide, the procedure of Example 28 was similarly repeated to provide the title compound as colorless powders melting at 220–222° C. (dec.).

$^1$H NMR (CDCl$_3$, free base) δ: 1.10–1.37 (5H, m), 1.55–1.80 (4H, m), 1.83–2.00 (2H, m), 2.57–2.68 (4H, m), 2.80–3.03 (8H, m), 3.48 (2H, s), 3.63(2H, s), 7.15 (1H, d, J=8.1 Hz), 7.18–7.40 (10H, m), 7.64–7.73 (2H, m). Elemental analysis, for C$_{33}$H$_{40}$N$_2$O. 2HCl. Calcd.: C, 71.60; H, 7.65; N, 5.06. Found: C, 71.53; H, 7.81; N, 5.26.

EXAMPLE 114

4- [1-[(4-Fluorophenyl)methyl]-4-piperidinyl]-1-[3-(phenylmethyl)-2,3,4,5-tetrahydro-1H-3-benzazepin-7-yl]-1-butanone Dihydrochloride

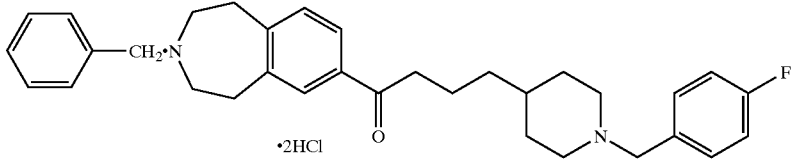

Using 1-[3-(phenylmethyl)-2,3,4,5-tetrahydro-1H-3-benzazepin-7-yl]-4-(4-piperidinyl)-1-butanone (free base) as obtained in Example 26 and 4-fluorobenzyl bromide, the procedure of Example 28 was similarly repeated to provide the title compound as colorless powders melting at 226–229° C. (dec.).

$^1$H NMR (CDCl$_3$, free base) δ: 1.10–1.37 (5H, m), 1.57–1.80 (4H, m), 1.83–2.00 (2H, m), 2.57–2.68 (4H, m), 2.77–3.03 (8H, m), 3.43 (2H, s), 3.63 (2H, s), 6.98 (2H, t like, J=88 Hz), 7.15 (1H, d, J=7.7 Hz),f, 7.20–7.40 (7H, m), 7.65–7.73 (2H, m). Elemental analysis, for C$_{33}$H$_{39}$FN$_2$O. 2HCl. Calcd.: C, 69.34; H, 7.23; N, 4.90. Found: C, 69.28; H, 7.07; N, 4.95.

EXAMPLE 115

2-(1-[(2-Methylphenyl)methyl]-4-piperidinyl]-1-(3 (phenylmethyl)-2,3,4,5-tetrahydro-1H-3-benzazepin-7-yl]-1-ethanone Dihydrochloride

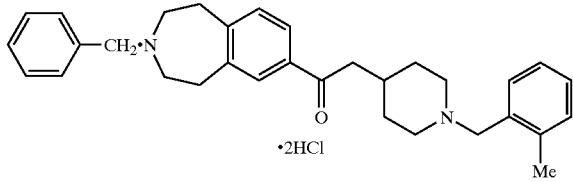

Using 1-[3-(phenylmethyl)-2,3,4,5-tetrahydro-1H-3-benzazepin-7-yl]-2-(4-piperidinyl)-1-ethanone (free base) as obtained in Example 110 and 2-methylbenzyl bromide, the procedure of Example 28 was similarly repeated to provide the title compound as colorless amorphous powders.

$^1$H NMR (CDCl$_3$, free base) δ: 1.20–1.43 (2H, m), 1.60–1.80 (2H, m), 1.90–2.12 (3H, m), 2.35 (3H, s), 2.58–2.70 (4H, m), 2.77–2.92 (4H, m), 2.93–3.03 (4H, m), 3.42 (2H, s), 3.64 (2H, s), 7.07–7.19 (4H, m), 7.21–7.40 (6H, m), 7.65–7.74 (2H, m). Elemental analysis, for C$_{32}$H$_{38}$N$_2$O. 2HCl. H$_2$O. Calcd.: C, 68.93; H, 7.59; N, 5.02. Found: C, 68.52; H, 7.75; N, 4.76.

EXAMPLE 116

2-[1-[(3-Methylphenyl)methyl]-4-piperidinyl]-1-(3-(phenylmethyl)-2,3,4,5-tetrahydro-1H-3-benzazepin-7-yl]-1-ethanone Dihydrochloride

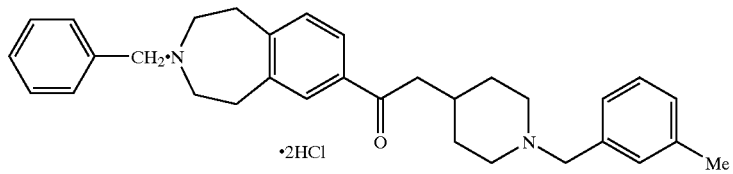

Using 1-[3-(phenylmethyl)-2,3,4,5-tetrahydro-1H-3-benzazepin-7-yl]-2-(4-piperidinyl)-1-ethanone (free base) as obtained in Example 110 and 3-methylbenzyl bromide, the procedure of Example 28 was similarly repeated to provide the title compound as colorless amorphous powders.

$^1$H NMR (CDCl$_3$, free base) δ: 1.22–1.47 (2H, m), 1.64–1.80 (2H, m), 1.88–2.08 (3H, m), 2.34 (3H, s), 2.57–2.68 (4H, m), 2.78–3.03 (8H, m), 3.45 (2H, s), 3.63 (2H, s), 7.00–7.38 (10H, m), 7.62–7.73 (2H, m). Elemental analysis, for C$_{32}$H$_{38}$N$_2$O. 2HCl. H$_2$O. Calcd.: C, 68.93; H, 7.59; N, 5.02. Found: C, 69.08; H, 7.66; N, 4.83.

EXAMPLE 117

2-[1-[(4-Methylphenyl)methyl]-4-piperidinyl]-1-[3-(phenylmethyl)-2,3,4,5-tetrahydro-1H-3-benzazepin-7-yl]-1-ethanone Dihydrochloride

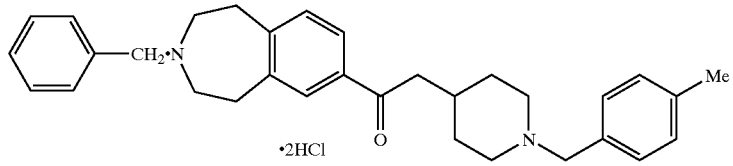

Using 1-[3-(phenylmethyl)-2,3,4,5-tetrahydro-1H-3-benzazepin-7-yl]-2-(4-piperidinyl)-1-ethanone (free base) as obtained in Example 110 and 4-methylbenzyl bromide, the procedure of Example 28 was similarly repeated to provide the title compound as colorless powders melting at 229–233° C.

$^1$H NMR (CDCl$_3$, free base) δ: 1.21–1.47 (2H, mi), 1.64–1.81 (2H, m), 1.88–2.09 (3H, m), 2.33 (3H, s), 2.57–2.70 (4H, m), 2.78–3.03 (8H, m), 3.45 (2H, s), 3.63

(2H, s), 7.05–7.40 (10H, m), 7.64–7.703 (2H, m). Elemental analysis, for $C_{32}H_{38}N_2O \cdot 2HCl \cdot 0.5H_2O$. Calcd.: C, 70.06; H, 7.53; N, 5.11. Found: C, 70.48; H, 7.31; N, 5.16.

EXAMPLE 118

4-[1-[(2-Methylphenyl)methyl]-4-piperidinyl]-1-[3-(phenylmethyl)-2,3,4,5-tetrahydro-1H-3-benzazepin-7-yl]-1-butanone Dihydrochloride

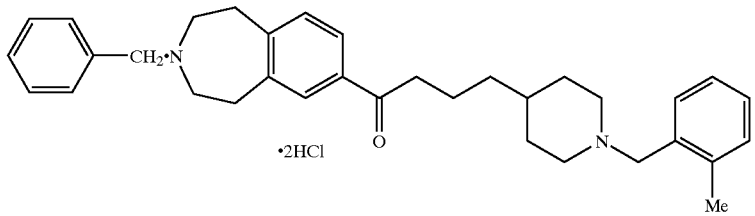

Using 1-[3-(phenylmethyl)-2,3,4,5-tetrahydro-1H-3-benzazepin-7-yl]-4-(4-piperidinyl)-1-butanone (free base) as obtained in Example 26 and 2-methylbenzyl bromide, the procedure of Example 28 was similarly repeated to provide the title compound as colorless powders melting at 226–229° C. (dec.).

$^1$H NMR (CDCl$_3$, free base) δ: 1.07–1.38 (5H, m), 1.56–1.82 (4H, m), 1.85–2.02 (2H, m), 2.34 (3H, s), 2.57–2.68 (4H, m), 2.77–3.04 (8H, m), 3.41 (2H, s), 3.63 (2H, s), 7.07–7.40 (10H, m), 7.64–7.73 (2H, m). Elemental analysis, for $C_{34}H_{42}N_2O \cdot 2HCl \cdot 0.5H_2O$. Calcd.: C, 70.82; N, 7.87; N, 4.86. Found: C, 71.00; H, 7.97; N, 4.65.

EXAMPLE 119

4-[1-[(3-Methylphenyl)methyl]-4-piperidinyl]-1-[3-(phenylmethyl)-2,3,4,5-tetrahydro-1H-3-benzazepin-7-yl]-1-butanone Dihydrochloride

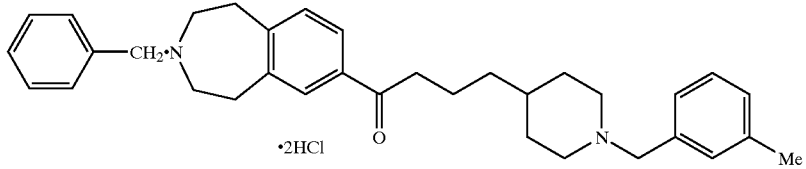

Using 1-[3-(phenylmethyl)-2,3,4,5-tetrahydro-1H-3-benzazepin-7-yl]-4-(4-piperidinyl)-1-butanone (free base) as obtained in Example 26 and 3-methylbenzyl bromide, the procedure of Example 28 was similarly repeated to provide the title compound as colorless powders melting at 222–225° C. (dec.).

$^1$H NMR (CDCl$_3$, free base) δ: 1.13–1.39 (5H, m), 1.57–2.00 (6H, m), 2.34 (3H, s), 2.55–2.70 (4H, m), 2.80–303 (8H, m), 3.44 (2H, s), 3.63 (2H, s), 7.00–7.40 (10H, m), 7.64–7.73 (2H, m). Elemental analysis, for $C_{34}H_{42}N_2O \cdot 2HCl$. Calcd.: C, 71.94; H, 7.81; N, 4.94. Found: C, 71.93; H, 7.49; N, 4.81.

EXAMPLE 120

4-[1-[(4-Methylphenyl)methyl]-4-piperidinyl]-1-[3-(phenylmethyl)-2,3,4,5-tetrahydro-1H-3-benzazepin-7-yl]-1-butanone Dihydrochloride

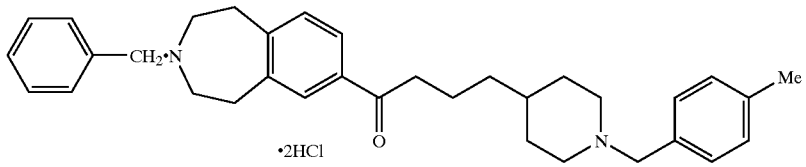

Using 1[3-(phenylmethyl)-2,3,4,5-tetrahydro-1H-3-benzazepin-7-yl]-4-(4-piperidinyl)-1-butanone (free base) as obtained in Example 260 and 4-methylbenzyl bromide, the procedure of Example 28 was similarly repeated to provide the title compound as colorless powders melting at 207–210° C. (dec.).

$^1$H NMR (CDCl$_3$, free base) δ: 1.13–1.38 (5H, m), 1.58–2.00 (6H, m), 2.33 (3H, s), 2.57–2.70 (4H, m), 2.80–3.04 (8H, m), 3.45 (2H, s), 3.64 (2H, s), 7.07–7.40

(10H, m), 7.64–7.74 (2H, m). Elemental analysis, for C$_{34}$H$_{42}$N$_2$O. 2HCl. Calcd.: C, 71.94; H, 7.81; N, 4.94. Found: C, 71.55; H, 7.60; N, 4.77.

EXAMPLE 121

Ethyl 2-methyl-2-[4-[[7-[3-(1-acetyl-4-piperidinyl) propanoyl]-,2,3,4,5-tetrahydro-1H-3-benzazepin-3-yl]methyl)phenyl)propionate Hydrochloride

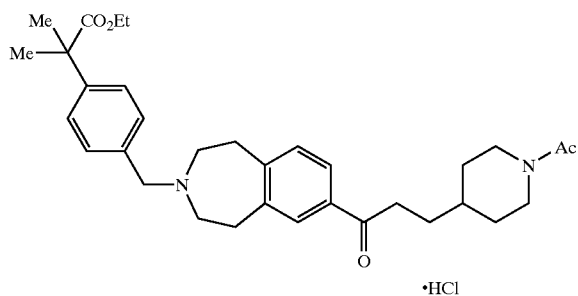

Using 3-(1-acetyl-4-piperidinyl)-1-(2,3,4,5-tetrahydro-1H-3-benzazepin-7-yl)-1-propanone as obtained in Example 23–2) and ethyl 2-methyl-2-[4-(bromomethyl)phenyl] propionate, the procedure of Example 23–3) was similarly repeated to provide the title compound as colorless, amorphous powders.

$^1$H NMR (CDCl$_3$, free base) δ: 1.02–1.28 (6H, m), 1.45–1.85 (10H, m), 2.08 (3H, s), 2.44–2.70 (5H, m), 2.90–3.10 (7H, m), 3.61 (2H, s), 3.72–3.88 (1H, m), 4.13 (2H, q, J=7.2 Hz), 4.53–4.68 (1H, m), 7.17 (1H, d, J=7.7 Hz), 7.30 (4H, s), 7.66–7.75 (2H, m). Elemental analysis, for C$_{33}$H$_{44}$N$_2$O$_4$. HCl. 2H$_2$O. Calcd.: C, 65.49; H, 8.16; N, 4.63. Found: C, 65.05; H, 7.71; N, 4.37.

EXAMPLE 122

Ethyl 2-methyl-2-[3-[[7-[3-(1-acetyl-4-piperidinyl) propanoyl]-2,3,4,5-tetrahydro-1H-3-benzazepin-3-yl]methyl]phenyl]propionate Hydrochloride

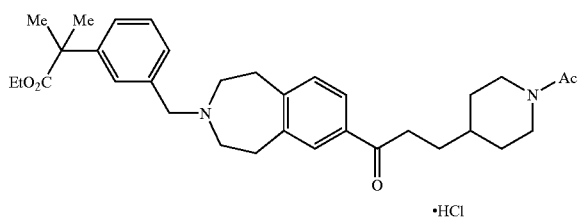

Using 3-(1-acetyl-4-piperidinyl)-1-(2,3,4,5-tetrahydro-1H-3-benzazepin-7-yl) -1-propanone as obtained in Example 23–2) and ethyl 2-methyl-2-[3-(bromomethyl) phenyl]propionate, the procedure of Example 23–3) was similarly repeated to provide the title compound as colorless amorphous powders.

$^1$H NMR (CDCl$_3$, free base) δ: 1.00–1.28 (6H, m), 1.4.6–1.86 (10H, m), 2.08 (3H, s), 2.43–2.68 (5H, m), 2.90–3.11 (7H, m), 3.63 (2H, s), 3.71–3.87 (1H, m), 4.13 (2H, q, J=7.1 Hz), 4.53–4.68 (1H, m), 7.12–7.34 (5H, m), 7.65–7.74 (2H, m). Elemental analysis, for C$_{33}$H$_{44}$N$_2$O$_4$. HCl. 2H$_2$O. Calcd.: C, 65.49; H, 8.16; N, 4.63. Found: C, 65.40; H, 7.70; N, 4.97.

EXAMPLE 123

Ethyl 2-[4-[[7-[3-(1-acetyl-4-piperidinyl)propanoyl]-2,3,4,5-tetrahydro-1H-3-benzazepin-3-yl]methyl]phenoxy]ethanoate Hydrochloride

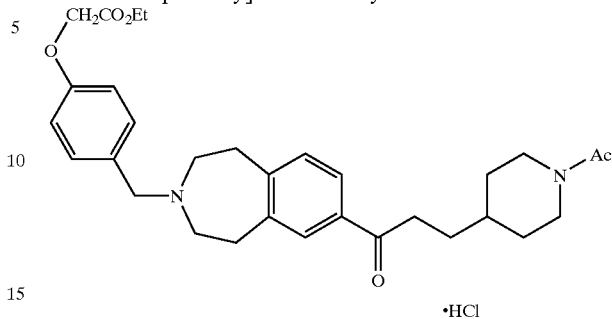

Using 3-(1-acetyl-4-piperidinyl)-1-(2,3,4,5-tetrahydro-1H-3-benzazepin-7-yl)-1-propanone as obtained in Example 23–2) and ethyl 2-[4-(bromomethyl)phenoxy]ethanoate, the procedure of Example 23–3) was similarly repeated to provide the title compound as colorless amorphous powders.

$^1$H NMR (CDCl$_3$, free base) δ: 1.00–1.37 (5H, m), 1.46–1.86 (5H, m), 2.08 (3H, s), 2.43–2.67 (5H, m), 2.90–3.11 (7H, m), 3.57 (2H, s), 3.73–3.88 (1H, m), 4.28 (2H, q, J=7.1 Hz), 4.53–4.67 (3H, m), 6.87 (2H, d, J=8.8 Hz), 7.16 (1H, d, J=7.3 Hz), 7.27 (2H, d, J=8.8 Hz), 7.64–7.73 (2H, m). Elemental analysis, for C$_{31}$H$_{40}$N$_2$O$_5$. HCl. 2H$_2$O. Calcd.: C, 66.83; H, 7.42; N, 5.03. Found: C, 66.60; H, 7.09; N, 4.53.

EXAMPLE 124

3-(1-Acetyl-4-piperidinyl)-1-[3-(cyclohexylmethyl)-2,3,4,5-tetrahydro-1H-3- benzazepin-7-yl]-1-propanone Hydrochloride

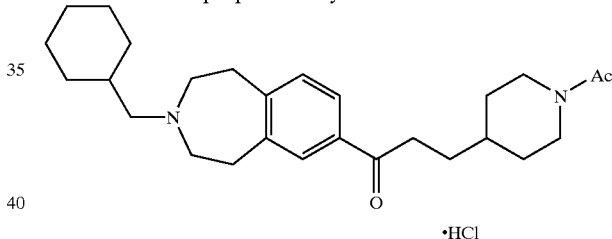

Using 3-(1-acetyl-4-piperidinyl)-1-(2,3,4,5-tetrahydro-1H-3-benzazepin-7-yl)-1-propanone as obtained in Example 23–2) and cyclohexylmethyl bromide, the procedure of Example 23–3) was similarly repeated to provide the title compound as colorless amorphous $^1$H, NMR (CDCl$_3$, free base) δ: 0.77–1.37 (7H, m), 1.43–1.88 (11H, m), 2.08 (3H, s), 2.25 (2H, d, J=7.0 Hz), 2.44–2.68 (5H, m), 2.89–3.12 (7H, m), 3.73–3.88 (1H, m), 4.53–4.68 (1H, m), 7.17 (1H, d, J=8.4 Hz), 7.65–7.75 (2H, m). Elemental analysis, for C$_{27}$H$_{40}$N$_2$O$_2$. HCl. 2.5H$_2$O. Calcd.: C, 64.07; H, 9.16; N, 5.53. Found: C, 64.49; H, 8.93; N, 5.34.

EXAMPLE 125

4-(1-Acetyl-4-piperidinyl)-1-[3-[(2-methylphenyl) methyl]-2,3,4,5-tetrahydro-1H-3-benzazepin-7-yl]-1-butanone

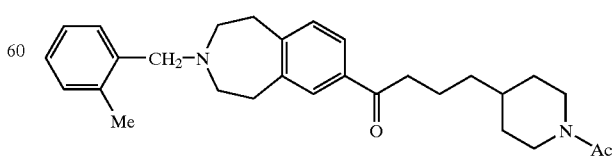

Using 4-(1-acetyl-4-piperidinyl)-1-(2,3,4,5-tetrahydro-1H-3-benzazepin-7-yl)-1-butanone as obtained in Example 25-2) and 2-methylbenzyl bromide, the procedure of Example 25-3) was similarly repeated to provide the title compound as light-yellow oil.

$^1$H NMR (CDCl$_3$) δ: 0.97–1.86 (9H, m), 2.08 (3H, s), 2.40 (3H, s), 2.44–2.70 (5H, m), 2.87–3.10 (7H, m)$_1$ 3.55 (2H, s), 3.72–3.87 (1H, m), 4.52–4.66 (1H, m), 7.13–7.23 (4H, m), 7.25–7.37 (1H, m), 7.67–7.75 (2H, m).

EXAMPLE 126

1-[3-[(2-Methylphenyl)methyl]-2,3,4,5-tetrahydro-1H-3-benzazepin-7-yl]-4-(4-piperidinyl)-1-butanone

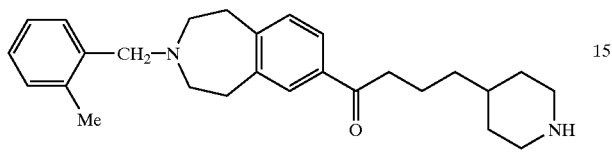

Using 4-(1-acetyl-4-piperidinyl)-1-[3-[(2-methyl-phenyl)methyl]-2,3,4,5-tetrahydro-1H-3-benzazepin-7-yl)-1-butanone as obtained in Example 125, the procedure of Example 24 was similarly repeated to provide the title compound as light-yellow oil.

$^1$H NMR (CDCl$_3$) δ: 1.02–1.53 (5H, m), 1.64–2.08 (5H, m), 2.40 (3H, s), 2.47–2.70 (6H, m), 2.86–3.00 (6H, m), 3.03–3.18 (2H, m), 3.54 (2H, s), 7.12–7.23 (4H, m), 7.26–7.36 (1H, m), 7.65–7.75, (2H, m).

EXAMPLE 127

4-[1-[(2-Methylphenyl)methyl]-4-piperidinyl]-1-[3-[(2-methylphenyl)methyl]-2,3,4,5-tetrahydro-1H-3-benzazepin-7-yl]-1-butanone Dihydrochloride

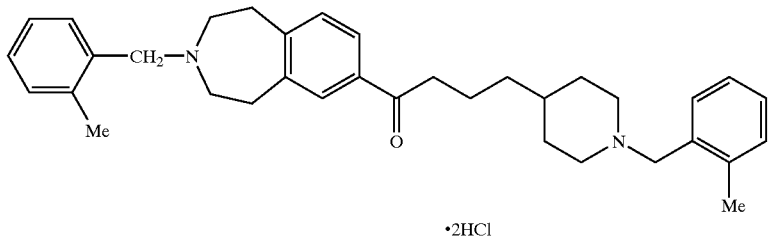

Using 1-[3-[(2-methylphenyl)methyl]-2,3,4,5-tetrahydro-1H-3-benzazepin-7-yl]-4-(4-piperidinyl)-1-butanone as obtained in Example 126 and 2-methylbenzyl bromide, the procedure of Example 28 was similarly repeated to provide the title compound as colorless powders melting at 183–186° C.

$^1$H NMR (CDCl$_3$, free base) δ: 1.14–1.37 (5H, m), 1.58–1.83 (4H, m), 1.90–2.07 (2H, m), 2.35 (3H, s), 2.39 (3H, s), 2.57–2.68 (4H, m), 2.80–3.02 (8H, m), 3.45 (2H, s), 3.54 (2H, s), 7.10–7.22 (7H, m), 7.24–7.35 (2H, m), 7.65–7.75 (2H, m). Elemental analysis, for C$_{35}$H$_{44}$N$_2$O. 2HCl. 0.5H$_2$O. Calcd.: C, 71.17; H, 8.02; N, 4.74. Found: C, 71.20; H, 7.66; N, 4.80.

EXAMPLE 128

4-[1-[(3-Methylphenyl)methyl]-4-piperidinyl]-1-[3-[(2-methylphenyl)methyl]-2,3,4,5-tetrahydro-1H-3-benzazepin-7-yl]-1-butanone Dihydrochloride

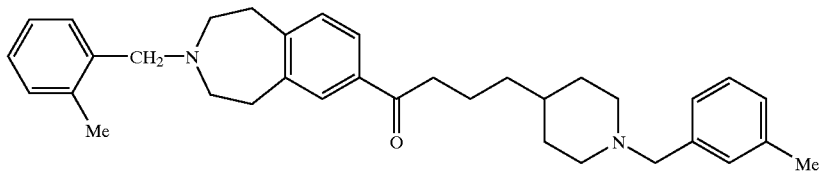

•2HCl

Using 1-[3-[(2-methylphenyl)methyl]-2,3,4,5-tetrahydro-1H-3-benzazepin-7-yl ]-4-(4-piperidinyl)-1-butanone as obtained in Example 126 and 3-methylbenzyl bromide, the procedure of Example 28 was similarly repeated to provide the title compound as colorless powders melting at 179–182° C.

$^1$H NMR (CDCl$_3$, free base) δ: 1.20–1.42 (5H, m), 1.60–1.83 (4H, m), 1.88–2.07 (2H, m), 2.34 (3H, s), 2.40 (3H, s), 2.57–2.69 (4H, m), 2.85–3.02 (8H, m), 3.48 (2H, s), 3.54 (2H, s), 7.03–7.36 (9H1, m);, 7.65–7.74 (2H, m). Elemental analysis, for C$_{35}$H$_{44N2}$O. 2HCl. 0. 5H$_2$O. Calcd.: C, 71.17; H, 8.02; N, 4.74. Found: C, 71.02; H, 7.83; N, 4.65.

EXAMPLE 129

1-[3-[(2-Methylphenyl)methyl]-2,3,4,5-tetrahydro-1H-3-benzazepin-7-yl]-4-[1-(phenylmethyl)-4-piperidinyl]-1-butanone Dihydrochloride

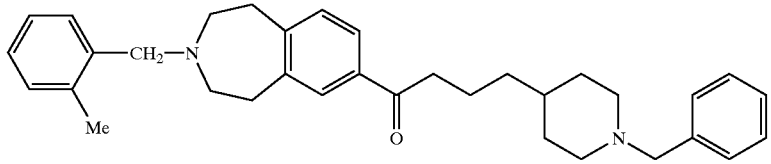

•2HCl

Using 1-[3-[(2-methylphenyl)methyl]-2,3,4,5-tetrahydro-1H-3-benzazepin-7-yl]-4-(4-piperidinyl)-1-butanone as obtained in Example 126 and benzyl bromide, the procedure of Example 28 was similarly repeated to provide the title compound as colorless powders melting at 191–194° C.

$^1$H NMR (CDCl$_3$, free base) δ: 1.14–1.40 (5H, m), 1.57–2.05 (6H, m), 2.39 (3H, s), 2.55–2.67 (41H, m), 2.82–3.00 (8H, m), 3.51 (2H, s), 3.54 (2H, s), 7.10–7.37 (10H, m), 7.65–7.73 (2H, m). Elemental analysis, for C$_{34}$H$_{42}$N$_2$O. 2HCl. 0.5H$_2$O. Calcd.: C, 70.82; H, 7.87; N, 4.86. Found: C, 70.61; H, 7.89; N, 4.75.

EXAMPLE 130

4-[1-[(3-Chlorophenyl)methyl]-4-piperidinyl]-1-3-[(2-methylphenyl)methyl]-2,3,4,5-tetrahydro-1H-3-benzazepin-7-yl]-1-butanone Dihydrochloride.

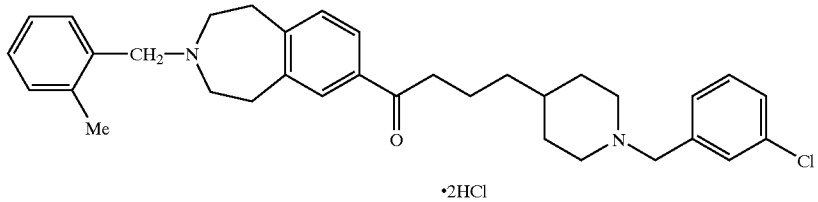

·2HCl

Using 1-[3-[(2-methylphenyl)methyl]-2,3,4,5-tetrahydro-1H-3-benzazepin-7-yl]-4-(4-piperidinyl)-1-butanone as obtained in Example 126 and 3-chlorobenzyl bromide, the procedure of Example 28 was similarly repeated to provide the title compound as colorless powders melting at 180–183° C.

$^1$H NMR (CDCl$_3$, free base) δ: 1.14–1.40 (5H, m), 1.57–1.83 (:4H, m), 1.87–2.04 (2H, m), 2.39 (3H, s), 2.57–2.68 (4H, m), 2.80–3.02 (8H, m), 3.46 (2H, s), 3.54 (2H, s), 7.12–7.37 (9H, m), 7.66–7.75 (2H, m). Elemental analysis, for C$_{34}$H$_{41}$ClN$_2$O. 2HCl. Calcd.: C, 67.83; H, 7.20; N, 4.65. Found: C, 67.39; H, 7.30; N, 4.38.

TEST EXAMPLE 3

Assay of intraadipocyte cAMP increasing activity using murine preadipocyte line (3T3-L1)

Using the compounds obtained in Examples 1 through 130, as well as their salts, their intraadipocyte cAMP increasing activities were assayed by the same procedure as in Test Example 1.

TABLE 14

| Com-<br>pound | cAMP (pmol/ml)<br>Concentration of test compound | | | | | |
|---|---|---|---|---|---|---|
| No. | $10^{-5}$M | $10^{-6}$M | $10^{-7}$M | $10^{-8}$M | $10^{-9}$M | Control |
| 23 | 1369.1* | 127.7* | 11.1* | 4.8* | 2.8 | 2.5 |
| 127 | 554.0* | 100.0* | 10.1* | 4.7 | 3.6 | 2.9 |
| 130 | 430.6* | 23.5* | 5.7* | 4.5 | 3.4 | 2.9 |

It is apparent from Table 14 that compound (I) inclusive of its salt has potent intraadipocyte cAMP increasing activity.

REFERENCE EXAMPLE 6

[1-[(4-Nitrobenzyl)oxycarbonyl]-4-piperidinyl] butyric Acid

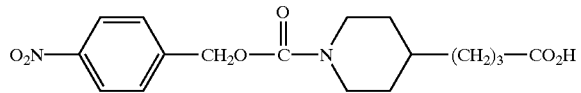

A mixture of (1-acetyl-4-piperidinyl)butyric acid (11.6 g, 54.4 mmol) and concentrated hydrochloric acid (30 ml) was refluxed for 16 hours, at the end of which time the hydrochloric acid was distilled off under reduced pressure. The residue was washed with ether and dissolved in 5N-NaOH/H$_2$O (30 ml), followed by addition of ether (30 ml). To this mixture with ice-bath cooling was added p-nitrobenzyl chlorocarbonate (11.7 g, 54.3 mmol) in small portions, and the mixture was stirred at room temperature for 1 hour. This reaction mixture was acidified with 10% hydrochloric acid and extracted with ethyl acetate. The extract was washed with saturated NaCl/H$_2$O and dried over MgSO$_4$, and the solvent was distilled off under reduced pressure. The residual oil was treated with ether to provide the title compound (13.5 g) as colorless powders.

$^1$H NMR (CDCl$_3$+D$_2$O) δ: 1.00–1.79 (9H, m), 2.36 (2H, t, J=7.3 Hz), 2.65–2.95 (2H, m), 4.06–4.24 (2H, m), 5.22 (2H, s), 7.51 (2H, d, J=88 Hz), 8.22 (2H, d, J=88 Hz).

EXAMPLE 131

3-(1-Acetyl-4-piperidinyl)-1-[3-[(cyclopropyl)methyl]-2,3,4,5-tetrahydro-1H-3-benzazepin-7-yl]-1-propanone Hydrochloride

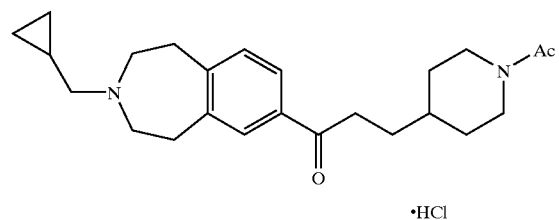

·HCl

Using 3-(1-acetyl-4-piperidinyl)-1-(2,3,4,5-tetrahydro-1H-3-benzazepin-7-yl)-1-propanone (free base) as obtained in Example 23-2) and (cyclopropyl)methyl bromide, the procedure of Example 23-3) was similarly repeated to provide the title compound as colorless amorphous powders.

$^1$H NMR (CDCl$_3$, free base) δ: 0.05–0.17 (2H, m), 0.47–0.60 (2H, m), 0.78–1.30 (3H, m), 1.46–1.95 (5H, m), 2.08 (3H, s), 2.38–2.62 (3H, m), 2.67–2.83 (4H, m), 2.86–3.13 (7H, m), 3.73–3.88 (1H, m), 4.53–4.68 (1H, m), 7.19 (1H, d, J=8.4 Hz), 7.66–7.76 (2H, m). Elemental analysis, for C$_{24}$H$_{34}$N$_2$O$_2$. HCl . 2.5H$_2$O. Calcd.: C, 62.12; H, 8.69; N, 6.04. Found: C, 61.98; H, 8.22; N, 5.55.

EXAMPLE 132

3-(1-Acetyl-4-piperidinyl)-1-(3-(n-butyl)-2,3,4,5-tetrahydro-1H-3-benzazepin-7-yl]-1-propanone Hydrochloride

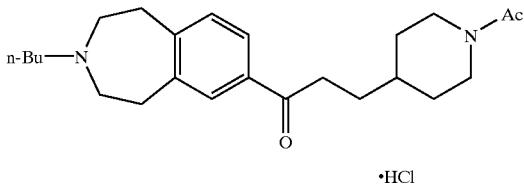

Using 3-(1-acetyl-4-piperidinyl)-1-(2,3,4,5-tetrahydro-1H-3-benzazepin-7-yl)-1-propanone (free base) as obtained in Example 23–2) and n-butyl bromide, the procedure of Example 23–3) was similarly repeated to provide the title compound as colorless amorphous powders.

$^1$H NMR (CDCl$_3$, free base) δ: 0.93 (3H, t, J=7.1 Hz), 1.02–1.87 (1H, m), 2.08 (3H, s), 2.42–2.55 (3H, m), 2.57–2.71 (4H, m), 2.83–3.11 (7H, m), 3.72–3.87 (1H, m), 4.53–4.68 (1H, m), 7.18 (H, d, J=8.4 Hz), 7.66–7.75 (2H, m). Elemental analysis, for C$_{24}$H$_{36}$N$_2$O$_2$. HCl. 2.5H$_2$O. Calcd.: C, 61.85; H, 9.08; N, 6.01. Found: C, 62.05; H, 8.80; N, 5.81.

EXAMPLE 133

3-(1-Acetyl-4-piperidinyl)-1-[3-[(2-methylphenyl)methyl]-2,3,4,5-tetrahydro-1H-3-benzazepin-7-yl]-1-propanone Hydrochloride

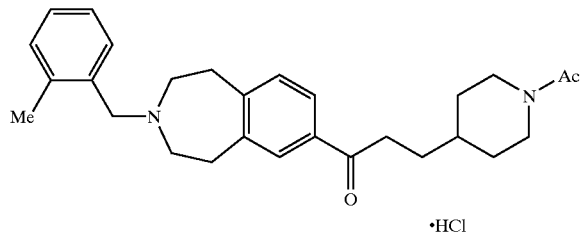

Using 3-(1-acetyl-4-piperidinyl)-1-(2,3,4,5-tetrahydro-1H-3-benzazepin-7-yl)-1-propanone (free base) as obtained in Example 23–2) and 2-methylbenzyl bromide, the procedure of Example 23–3) was similarly repeated to provide the title compound as colorless amorphous powders.

$^1$H NMR (CDCl$_3$, free base) δ: 1.02–1.31 (2H, m), 1.46–1.87 (5H, m), 2.08 (3H, s), 2.40 (3H, s), 2.45–2.69 (5H, m), 2.90–3.12 (7H, m), 3.55 (2H, s), 3.74–3.88 (1H, m), 4.54–4.68 (1H, m), 7.11–7.22 (4H, m), 7.25–7.36 (1H, m), 7.67–7.75 (2H, m). Elemental analysis, for C$_{28}$H$_{36}$N$_2$O$_2$. HCl. 2.5H$_2$O. Calcd.: C, 65.42; H, 8.23; N, 5.45. Found: C, 65.50; H, 7.75; N, 4.97.

EXAMPLE 134

3-(1-Acetyl-4-piperidinyl)-1-[3-[(3-methylphenyl)methyl]-2,3,4,5-tetrahydro-1H-3-benzazepin-7-yl]-1-propanone Hydrochloride

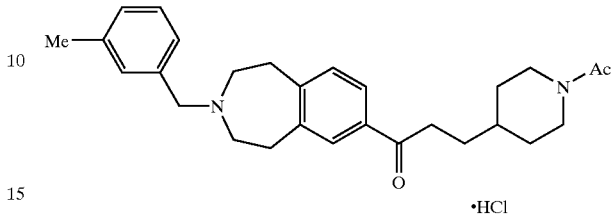

Using 3-(1-acetyl-4-piperidinyl)-1-(2,3,4,5-tetrahydro-1H-3-benzazepin-7yl) -1-propanone (free base) as obtained in Example 23–2) and 3-methylbenzyl bromide, the procedure of Example 23–3) was similarly repeated to provide the title compound as colorless amorphous powders. $^1$H NMR (CDCl$_3$, free base) δ: 1.02–1.30 (2H, m), 1.46–1.85 (5H, m), 2.08 (3H, s), 2.36 (3H, s), 2.44–2.73 (5H, m),2.92–3.12 (7H, m), 3.64 (2H, s), 3.72–3.88 (1H, m), 4.53–4.68 (1H, m), 7.04–7.28 (5H, m), 7.65–7.74 (2H, m). Elemental analysis, for C$_{28}$H$_{36}$N$_2$O$_2$. HCl. 2.5H$_2$O. Calcd.: C, 65.42; H, 8.23; N, 5.45. Found: C, 65.02; H, 7.90; N, 5.13.

EXAMPLE 135

3-(1-Acetyl-4-piperidinyl)-1-[3-[(4-methylphenyl)methyl]-2,3,4,5-tetrahydro-1H-3-benzaepin-7-yl]-1-propanone Hydrochloride

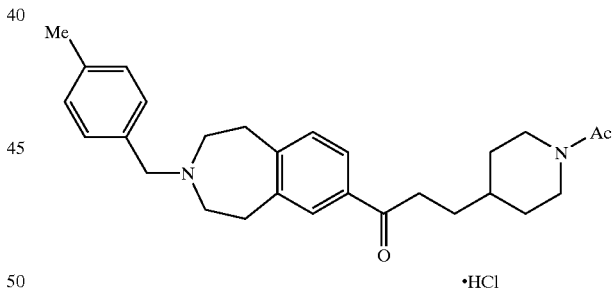

Using 3-(1-acetyl-4-piperidinyl)-1-(2,3,4,5-tetrahydro-1H-3-benzazepin-7-yl) -1-propanone (free base) as obtained in Example 23–2) and 4-methylbenzyl bromide, the procedure of Example 23–3) was similarly repeated to provide the title compound as colorless amorphous powders.

$^1$H NMR (CDCl$_3$, free base) δ: 1.00–1.28 (2H, m), 1.43–1.87 (5H, m), 2.08 (3H, s), 2.35 (3H, s), 2.44–2.70 (5H, m), 2.90–3.10 (7H, m), 3.62 (2H, s), 3.72–3.88 (1H, m), 4.52–4.68 (1H, m), 7.10–7.28 (5H, m), 7.64–7.74 (2H, m). Elemental analysis, for C$_{28}$H$_{36}$N$_2$O$_2$. HCl. 2.5H$_2$O. Calcd.: C, 65.42; H, 8.23; N, 5.45. Found: C, 65.46; H, 7.93; N, 5.23.

EXAMPLE 136

3-(1-Acetyl-4-piperidinyl)-1-[3-[(2-methoxyphenyl)methyl]-2,3,4,5-tetrahydro-1H-3-benzazepin-7-yl]-1-propanone Hydrochloride

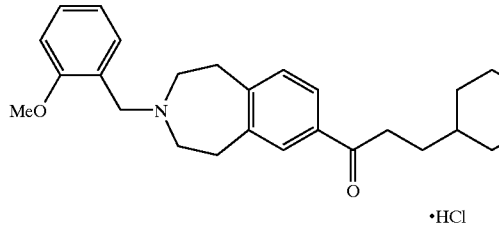
•HCl

Using 3-(1-acetyl-4-piperidinyl)-1-(2,3,4,5-tetrahydro-1H-3-benzazepin-7-yl)-1-propanone (free base) as obtained in Example 23–2), 2-methoxybenzyl alcohol mesylate, and potassium iodide, the procedure of Example 23–3) was similarly repeated to provide the title compound as colorless amorphous powders.

$^1$H NMR (CDCl$_3$, free base) δ: 1.00–1.28 (2H, m), 1.46–1.85 (5H, m), 2.08 (3H, s), 2.43–2.61 (1H, m), 2.65–2.77 (4H, m), 2.90–3.10 (7H, m), 3.68–3.87 (6H, m), 4.53–4.67 (1H, m), 6.83–7.00 (2H, m), 7.11–7.30 (2H, m), 7.43 (1H, dd, J=1.6, 7.5 Hz), 7.64–7.74 (2H, m). Elemental analysis, for C$_{28}$H$_{36}$N$_2$O$_3$. HCl. 3H$_2$O. Calcd.: C, 62.38; H, 8.04; N, 5.20. Found: C, 61.82; H, 7.67; N, 4.90.

EXAMPLE 137

3-(1-Acetyl-4-piperidinyl)-1-[3-[(3-methoxyphenyl)methyl]-2,3,4,5-tetrahydro-1H-3-benzazepin-7-yl]-1-propanone Hydrochloride

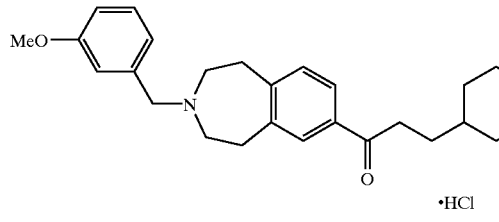
•HCl

Using 3-(1-acetyl-4-piperidinyl)-1-(2,3,4,5-tetrahydro-1H-3-benzazepin-7-yl)-1-propanone (free base) as obtained in Example 23–2), 3-methoxybenzyl chloride, and potassium iodide, the procedure of Example 23–3) was similarly repeated to provide the title compound as colorless amorphous powders.

$^1$H NMR (CDCl$_3$, free base) δ: 1.02–1.29 (2H, m), 1.47–1.86 (5H, m), 2.08 (3H, s), 2.44–2.72 (5H, m), 2.92–3.12 (7H, m), 3.63 (2H, s), 3.71–3.87 (4H, m), 4.54–4.68 (1H, m), 6.77–6.86 (1H, m), 6.90–6.98 (2H, m), 7.13–7.31 (2H, m), 7.66–7.75 (2H, m). Elemental analysis, for C$_{28}$H$_{36}$N$_2$O$_3$. HCl. 3H$_2$O. Calcd.: C, 62.38; H, 8.04; N, 5.20. Found: C, 62.64; H, 7.84; N, 5.06.

EXAMPLE 138

3-(1-Acetyl-4-piperidinyl)-1-[3-[(2-chlorophenyl)methyl]-2,3,4,5-tetrahydro-1H-3-benzazepin-7-yl]-1-propanone Hydrochloride

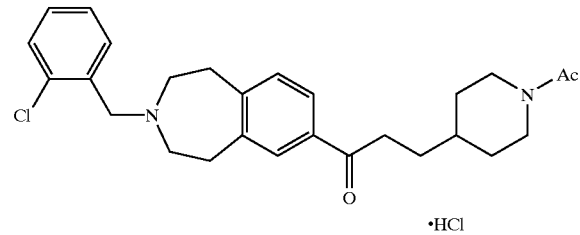
•HCl

Using 3-(1-acetyl-4-piperidinyl)-1-(2,3,4,5-tetrahydro-1H-3-benzazepin-7-yl)-1-propanone (free base) as obtained in Example 23–2), 2-chlorobenzyl chloride, and potassium iodide, the procedure of Example 23–3) was similarly repeated to provide the title compound as colorless amorphous powders.

$^1$H NMR (CDCl$_3$, free base) δ: 1.02–1.29 (2H, m), 1.46–1.87 (5H, m), 2.08 (3H, s), 2.44–2.62 (1H, m), 2.66–2.81 (4H, m), 2.92–3.13 (7H, m), 3.70–3.87 (3H, m), 4.553–4.68 (1H, m), 7.15–7.41 (4H, m), 7.55–7.65 (1H, m), 7.68–7.77 (2H, m). Elemental analysis, for C$_{27}$H$_{33}$ClN$_2$O$_2$. HCl. 3H$_2$O. Calcd.: C, 59.66; H, 7.42; N, 5.15. Found: C, 59.95; H, 6.95; N, 5.02.

EXAMPLE 139

3-(1-Acetyl-4-piperidinyl)-1-[3-[(3-chlorophenyl)methyl]-2,3,4,5-tetrahydro-1H-3-benzazepin-7-yl]-1-propanone Hydrochloride

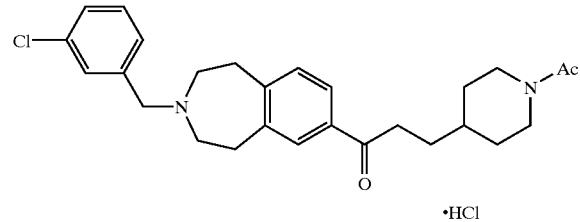
•HCl

Using 3-(1-acetyl-4-piperidinyl)-1-(2,3,4,5-tetrahydro-1H-3-benzazepin-7-yl)-1-propanone (free base) as obtained in Example 23–2) and 3-chlorobenzyl bromide, the procedure of Example 23–3) was similarly repeated to provide the title compound as colorless amorphous powders.

$^1$H NMR (CDCl$_3$, free base) δ: 1.00–1.30 (2H, m), 1.45–1.86 (5H, m), 2.08 (3H, s), 2.43–2.71 (5H, m), 2.85–3.10 (7H, m), 3.62 (2H, s), 3.72–3.87 (1H, m), 4.52–4.68 (1H, m), 7.17 (1H, d, J=7.3 Hz), 7.20–7.29 (3H, m), 7.38 (1H, brs), 7.65–7.75 (2H, m). Elemental analysis, for C$_{27}$H$_{33}$ClN$_2$O$_2$. HCl. 2.5H$_2$O. Calcd.: C, 60.67; H, 7.35; N, 5.24. Found: C, 60.41; H, 6.94; N, 5.03.

EXAMPLE 140

Ethyl2-[3-[[7-[3-(1-acetyl-4-piperidinyl)propanoyl]-2,3,4,5-tetrahydro-1H-3-enzazepin-3-yl]methyl]phenoxy]ethanoate Hydrochloride

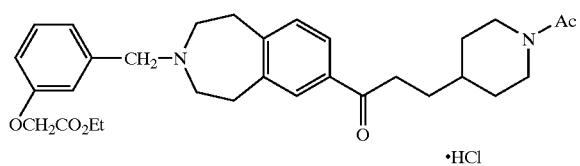

·HCl

Using 3-(1-acetyl-4-piperidinyl)-1-(2,3,4,5-tetrahydro-1H-3-benzazepin-7-yl)-1-propanone (free base) as obtained in Example 23–2) and ethyl 2-[3-(bromomethyl)phenoxy]ethanoate, the procedure of Example 23–3) was similarly repeated to provide the title compound as colorless amorphous powders.

$^1$H NMR (CDCl$_3$, free base). δ: 1.00–1.36 (5H, m), 1.44–1.87 (5H, m), 2.08 (3H, s), 2.43–2.70 (5H, m), 2.90–3.15 (7H, m), 3.62 (2H, s), 3.72–3.88 (1H, m), 4.28 (2H, q, J=7.2 Hz), 4.52–4.68 (3H, m), 6.75–6.84 (1H, m), 6.93–7.02 (2H, m), 7.12–7.30 (2H, m), 7.64–7.78 (2H, m). Elemental analysis, for C$_{31}$H$_{40}$N$_2$O$_5$. HCl. 3H$_2$O. Calcd.: C, 60.92; H, 7.75; N, 4.58. Found: C, 60.92; H, 7.58; N, 4.87.

EXAMPLE 141

Ehyl 2-[2-[[7-[3-(1-acetyl-4-piperidinyl)propanoyl]-2,3,4,5-tetrahydro-1H-3-benzazepin-3-yl]methyl]phenoxy]ethanoate Hydrochloride

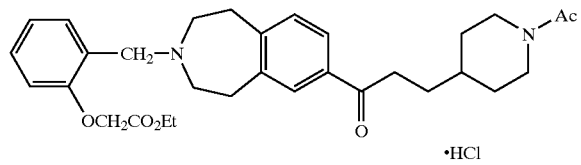

·HCl

Using 3-(1-acetyl-4-piperidinyl)-1-(2,3,4,5-tetrahydro-1H-3-benzazepin-7-yl)-1-propanone (free base) as obtained in Example 23–2) and ethyl 2-(2-(bromomethyl)phenoxy]ethanoate, the procedure of Example 23–3) was similarly repeated to provide the title compound as colorless amorphous powders.

$^1$H NMR (CDCl$_3$, free base) δ: 1.00–1.34 (5:H, m), 1.47–1.94 (5H, m), 2.08 (3H, s), 2.44–2.60 (1H, m), 2.67–2.80 (4H, m), 2.92–3.12 (7H, m), 3.73–3.87 (3H, m) 4.26 (2H, q, J=7.2 Hz), 4.53–4.68 (3H, m), 6.77 (1H, d, J=8.4 Hz), 6.96–7.07 (1H, m), 7.13–7.25 (2H, m), 7.45 (1H, dd, J=1.6, 7.3 Hz), 7.65–7.74 (2H, m). Elemental analysis, for C$_{31}$H$_{40}$N$_2$O$_5$. HCl. 2.5H$_2$O. Calcd.: C, 61.83; H, 7.70; N, 4.65. Found: C, 61.60; H, 7.31; N, 4.33.

EXAMPLE 142

4-(1-Acetyl-4-piperidinyl)-1-[2-(phenylmethyl)-2,3,4,5-tetrahydro-1H-2-benzazepin-8-yl]-1-butanone Hydrochloride

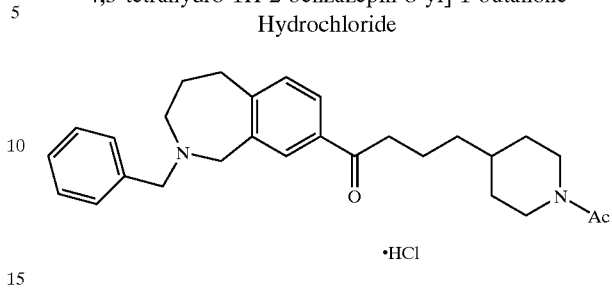

·HCl

1) Using (1-acetyl-4-piperidinyl)butyric acid and 2-formyl-2,3,4,5-tetrahydro-1H-2-benzazepine as obtained in Reference Example 4, the procedure of Example 23–1) was similarly repeated to provide 4-(1-acetyl-4-piperidinyl)-1-(2-formyl-2,3,4,5-tetrahydro-1H-2-benzazepin-8-yl)-1-butanone as light-yellow oil.

$^1$H NMR (CDCl$_3$) δ: 0.98–1.94 (11H, m), 2.08 (3H, s), 2.42–2.65 (1H, m), 2.87–3.12 (5H, m) 3.63–3.88 (3H, m), 4.47–4.67 (3H, m), 7.21–7.30 (1H, m), 7.74–8.17 (3H, m).
2) Using 4-(1-acetyl-4-piperidinyl)-1-(2-formyl-2,3,4,5-tetrahydro-1H-2-benzazepin-8-yl),-1-butanone as obtained in 1), the procedure of Example 23–2) was similarly repeated to provide $^2$-(1-acetyl-4-piperidinyl)-1-(2,3,4,5-tetrahydro-1H-2-benzazepin-8-yl)-1-butanone as light-yellow oil.

$^1$H NMR (CDCl$_3$) δ: 0.97–1.61 (5H, m), 1.66–1.9,4 (6H, m), 2.08 (3H, s), 2.45–2.62 (1H, m), 2.8,5–3.10 (6H, m), 3.23 (2H, t like, J=5.3 Hz), 3.72–3.87 (1H, m), 3.99 (2H, s), 4.52–4.65 (1H, m), 7.24 (1H, d, J=7.7 Hz), 7.68–7.77 (2H, m). 3) Using 2-(1-acetyl-4-piperidinyl)-1-(2,3,4,5-tetrahydro-1H-2-benzazepin-8-yl)-1-butanone as obtained 2), the procedure of Example 23–3) was similarly repeated to provide the title compound as colorless amorphous powders.

$^1$H NMR (CDCl$_3$, free base) δ: 0.97–1.60 (5H, m), 1.65–1.87 (6H, m), 2.08 (3H, s), 2.45–2.62 (1H, m), 2.87–3.18 (7H, m), 3.54 (2H, s), 3.72–3.85 (1H, M), 3.93 (2H, s), 4.52–4.67 (1H, m), 7.17–7.38 (6H, m), 7.51 (1H, d, J=1.8 Hz), 7.76 (1H, dd, J=1.8, 7.8 Hz). Elemental analysis, for C$_{28}$H$_{36}$N$_2$O$_2$. HCl. 3H$_2$O. Calcd.: C, 64.29; H, 8.29; N, 5.36. Found: C, 64.20; H, 7.83; N, 4.97.

EXAMPLE 143

1-[2-(Phenylmethyl)-2,3,4,5-tetrahydro-1H-2-benzazepin-8-yl]-4-(4-piperidinyl)-1-butanone

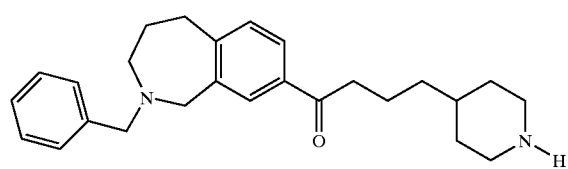

Using 4-(1-acetyl-4-piperidinyl)-1-(2-(phenyl-methyl)-2,3,4,5-tetrahydro-1H-2-benzazepin-8-yl]-1-butanone hydrochloride as obtained in Example 142, the procedure of Example 24 was similarly repeated to provide the title compound as viscous oil.

$^1$H NMR (CDCl3). δ: 0.99–1.48 (5H, m), 1.62–1.85 (6H, m), ca. 2.1 (1H, br), 2.49–2.88 (2H m), 2.83–3.16 (8H, m), 3.49 (2H, s), 3.91 (2H, s), 7.08–7.38 (6H, m), 7.51 (1H, d, J=1.8 Hz), 7.76 (1H, dd, J=1.8, 7.7 Hz).

EXAMPLE 144

1-[2-(Phenylmethyl)-2,3,4,5-tetrahydro-1H-2-enzazepin-8-yl]-4-[1-(phenylmethyl)-4-piperidinyl]-1-butanone Dihydrochloride

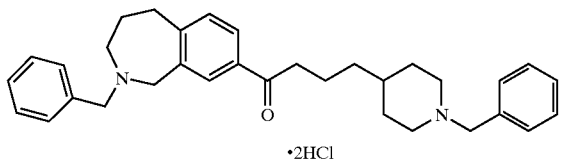

Using 1-[2-(phenylmethyl)-2,3,4,5-tetrahydro-1H-2-benzazepin-8-yl]-4-(4-piperidinyl)-1-butanone (free base) as obtained in Example 143 and benzyl bromide, the procedure of Example 28 was similarly repeated to provide the title compound as colorless amorphous powders.

$^1$H NMR (CDCl$_3$, free base) δ: 1.17–1.39 (5H, m), 1.58–2.04 (8H, m), 2.80–3.03 (6H, m), 3.13 (2H, t-like, J=5.3 Hz), 3.51 (2H, s), 3.54 (2H, s), 3.92 (2H, s), 7.17–7.38 (11H, m), 7.51 (1H, d, J=1.8 Hz), 7.76 (1H, dd, J=8, 7.9 Hz).

Elemental analysis, for $C_{33}H_{40}N_2O_2$. HCl. 2H$_2$O. Calcd.: C, 67.22; H, 7.86; N, 4.75. Found: C, 67.46; H, 8.04; N, 4.72.

EXAMPLE 145

4-(1-[(2-Chlorophenyl)methyl]-4-piperidinyl]-1-(3-[(2-methylphenyl)methyl]-2,3,4,5-tetrahydro-1H-3-benzazepin-7-yl]-1-butanone Dihydrochloride

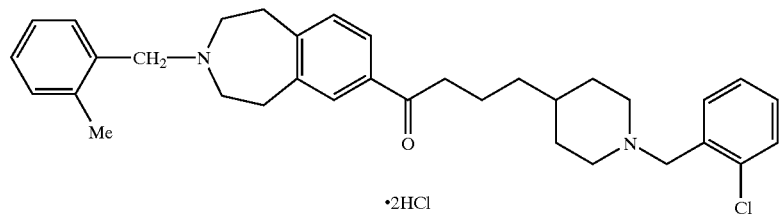

Using 1-[3-[(2-methylphenyl)methyl]-2,3,4,5-tetrahydro-1H-3-benzazepin-7-yl]-4-(4-piperidinyl)-1-butanone as obtained in Example 126, 2-chlorobenzyl chloride, and potassium iodide, the procedure of Example 28 was similarly repeated to provide the title compound as colorless powders melting at 165–168° C.

$^1$H NMR (CDCl$_3$, free base) δ: 1.15–1.38 (5H, m), 1.53–83 (4H, m), 1.97–2.16 (2, H, m), 2.39 (3H, s), 2.55–68 (4H, m), 2.83–3.00 (8H, m), 3.54 (2H, m), 3.61 (2H, s), 7.10–7.37 (8H, m), 7.44–7.53 (1H, m), 7.65–7.73 (2H, m). Elemental analysis, for $C_{34}H_{41}ClN_2O_2$. HCl. 0.5H$_2$O. Calcd.: C, 66.83; H, 7.26; N, 4.58. Found: C, 66.58; H, 7.18; N, 4.45.

EXAMPLE 146

4-[1-[[2-(Trifluoromethyl)phenyl]methyl]-4-piperidinyl]-1-[3-[(2-methylphenyl)methyl]-2,3,4,5-tetrahydro-1H-3-benzazepin-7-yl]-1-butanone Dihydrochloride

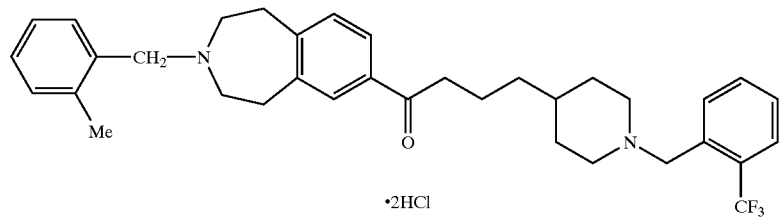

Using 1-[3-[(2-methylphenyl)methyl]-2,3,4,5-tetrahydro-1H-3-benzazepin-7-yl]-4-(4-piperidinyl)-1-butanone as obtained in Example 126 and 2-(trifluoromethyl)benzyl bromide, the procedure of Example 28 was similarly repeated to provide the title compound as colorless powders melting at 150–153° C.

$^1$H NMR (CDCl$_3$, free base) δ: 1.17–1.40 (5H, m), 1.53–1.84 (4H, m), 1.96–2.12 (2H, m), 2.40 (3H, s), 2.57–2.70 (4H, m), 2.77–3.02 (8H, m), 3.55 (2H, s), 3.64 (2H, s), 7.13–7.24 (4H, m), 7.26–7.37 (2H, m), 7.45–7.65 (2H, m), 7.67–7.75 (2H, m), 7.78–7.89 (1H, m). Elemental analysis, for C$_{34}$H$_{41}$F$_3$N$_2$O. 2HCl. 0.5H$_2$O. Calcd.: C, 65.21; H, 6.88; N, 4.35. Found: C, 65.22; H, 6.74; N, 4.42.

EXAMPLE 147

4-[1-[[3-(trifluoromethyl)phenyl]methyl]-4-piperidinyl]-1-[3-[(2-methylphenyl)methyl]-2,3,4,5-tetrahydro-1H-3-benzazepin-7-yl]-1-butanone Dihydrochloride

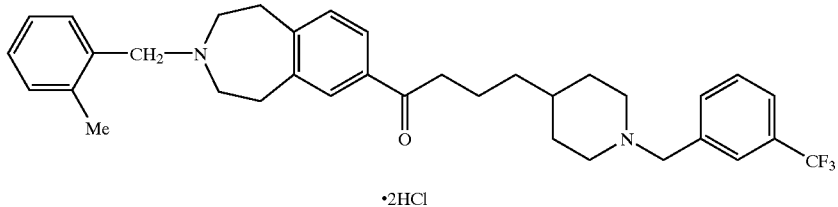

•2HCl

Using 1-(3-[(2-methylphenyl)methyl])-2,3,4,5-tetrahydro-1H-3-benzazepin-7-yl]-4-(4-piperidinyl)-1-butanone as obtained in Example 126 and 3-(trifluoromethyl)benzyl bromide, the procedure of Example 28 was similarly repeated to provide the title compound as colorless powders melting at 205–209° C. (dec.).

$^1$H NMR (CDCl$_3$, free base) δ: 1.14–1.39 (5H, m), 1.53–83 (4H, m), 1.87–2.06 (2H, m), 2.39 (3H, s), 2.57–2:.68 (4H, m), 2.78–3.02 (8H, m), 3.48–3.58 (4H, br), 7.10–7.75 (11H, m). Elemental analysis, for C$_{34}$H$_{41}$F$_3$N$_2$O. 2HCl. 0.5H$_2$O. Calcd.: C, 65.21; H, 6.88; N, 4.35. Found: C, 65.52; H, 6.81; N, 4.04.

EXAMPLE 148

1-[2-(Phenylmethyl)-2,3,4,5-tetrahydro-1H-2-benzazepin-8-yl]-4-[1-[(2-methylphenyl)methyl]-4-piperidinyl]-1-butanone Dihydrochloride

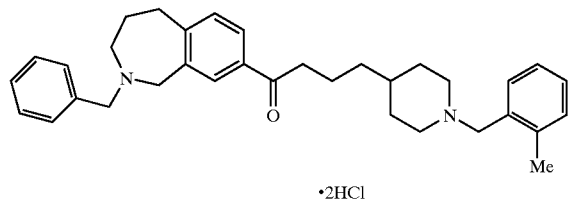

•2HCl

Using 1-[2-(phenylmethyl)-2,3,4,5-tetrahydro-1H-2-benzazepin-8-yl]-4-(4-piperidinyl)-1-butanone (free base) as obtained in Example 143 and 2-methylbenzyl bromide, the procedure of Example28 was similarly repeated to provide the title compound as colorless amorphous powders.

$^1$H NMR (CDCl$_3$, free base) δ: 1.10–1.37 (5H, m), 1.56–1.84 (6H, m), 1.87–2.04 (2H, m), 2.35 (3H, s), 2.80–3.03 (6H, m), 3.12 (2H. t-like, J=5.3 Hz), 3.42 (2H, s), 3.53 (2H, s), 3.92 (2H, s), 7.08–7.40 (10H, m), 7.51 (1H, d, J=1.8 Hz), 7.76 (1H, dd, J=1.8, 7.9 Hz). Elemental analysis, for C$_{34}$H$_{42}$N$_2$O. 2HCl. 1.5H$_2$O. Calcd.: C, 68.67; H, 7.97; N, 4.71. Found: C, 69.02; H, 7.94; N, 4.40.

EXAMPLE 149

1-[2-(Phenylmethyl)-2,3,4,5-tetrahydro-1H-2-benzazepin-8-yl]-4-[1-[(3-methylphenyl)methyl]-4-piperidinyl]-1-butanone Dihydrochloride

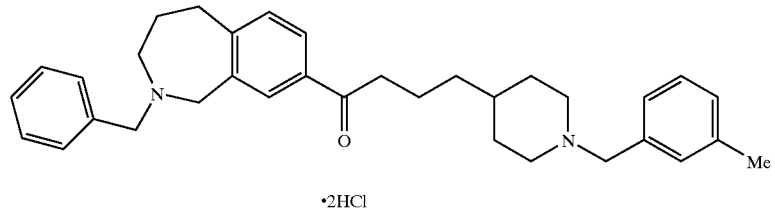

•2HCl

Using 1-[2-(phenylmethyl)-2,3,4,5-tetrahydro-1H-2-benzazepin-8-yl]-4-(4-piperidinyl)-1-butanone (free base)

as obtained in Example 143 and 3-methylbenzyl bromide, the procedure of Example 28 was similarly repeated to provide the title compound as colorless amorphous powders.

$^1$H NMR (CDCl$_3$, free base) δ: 1.14–1.38 (5H, m), 1.58–30 2.00 (8H, m), 2.34 (3H, s), 2.78–3.02 (6H, m ), 3.12 (2H, t-like, J=5.3 Hz), 3.46 (2H, s), 3.53 (2H, s), 3.92 (2H, s), 7.00–7.40 (10H, m), 7.50 (1H, d, J=1.8 Hz), 7.75 (1H, dd, J=1.8, 7.7 Hz). Elemental analysis, for C$_{34}$H$_{42}$N$_2$O. 2HCl. H$_2$O. Calcd.: C, 69.73; H, 7.92; N, 4.78. Found: C, 69.34; H, 8.04; N, 4.43.

EXAMPLE 150

1-[2-(Phenylmethyl)-2,3,4,5-tetrahydro-1H-2-benzazepin-8-yl]-4-[1-[(4-methylphenyl)methyl]-4-piperidinyl)-1-butanone Dihydrochloride

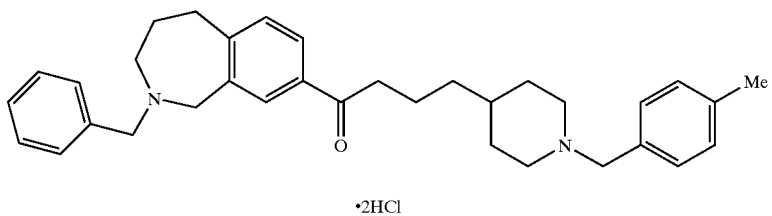

•2HCl

Using 1-[2-(phenylmethyl)-2,3,4,5-tetrahydro-1H-2-benzazepin-8-yl]-4-(4-piperidinyl)-1-butanone (free base) as obtained in Example 143 and 4-methylbenzyl bromide, the procedure of Example 28 was similarly repeated to provide the title compound as colorless amorphous powders.

$^1$H NMR (CDCl$_3$, free base) δ: 1.15–1.40 (5H, m), 1.58–2.02 (81H, m), 2.33 (3H, s), 2.80–3.04 (6H, m), 3.12 (2H, t-like, J=5.3 Hz), 3.46 (2H, s), 3.53 (2H, s), 3.92 (2H, s), 7.07–7.40 (10H, m), 7.50 (1H, d, J=1.8 Hz), 7.75 (1H, dd, J=1.8, 7.7 Hz). Elemental analysis, for C$_{34}$H$_{42}$N$_2$O. 2HCl. 1.5H$_2$O. Calcd.: C, 68.67; H, 7.97; N, 4.71. Found: C, 69.03; H, 7.95; N, 4.40.

EXAMPLE 151

4-[1-[(3-Chlorophenyl)methyl]-4-piperidinyl]-1-[3-(phenylmethyl)-2,3,4,5-tetrahydro-1H-3-benzazepin-7-yl]-1-butanone Dihydrochloride

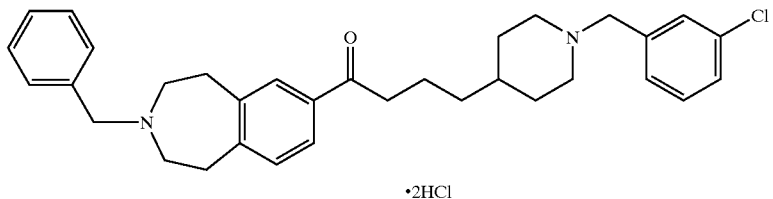

•2HCl

Using 1-(3-(phenylmethyl)-2,3,4,5-tetrahydro-1H-3-benzazepin-7-yl]-4-(4-piperidinyl)-1-butanone (free base) as obtained in Example 26 and 3-chlorobenzyl bromide,-the procedure of Example 28 was similarly repeated to provide the title compound as colorless powders melting at 230–234° C. (dec.).

$^1$H NMR (CDCl$_3$, free base) δ: 1.16–1.39 (4H, m), 1.58–2.01 (7H, m), 2.58–2.70 (4H, m), 2.78–3.02 (8H, m), 3.44 (2H, s), 3.64 (2H, s), 7.11–7.40 (10H, m), 7.64–7.74 (2H, m). Elemental analysis, for C$_{33}$H$_{39}$ClN$_2$O. 2HCl. 0.75H$_2$O. Calcd.: C, 65.88; H, 7.12; N, 4.66. Found: C, 65.88; H, 7.06; N, 4.66.

EXAMPLE 152

Methyl 3-[[4-[4-[3-(phenylmethyl)-2,3,4,5-tetrahydro,-1H-3-benzazepin-7-yl]-4-oxobutyl]-1-piperidinyl]methyl]benzoate Dihydrochloride

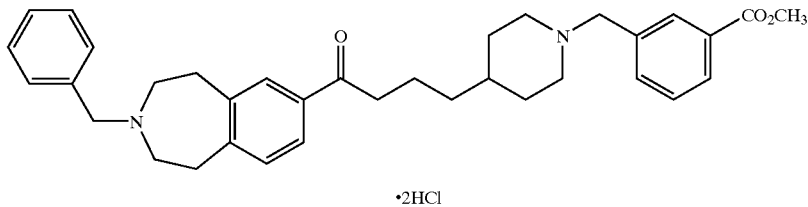

•2HCl

Using 1-[3-(phenylmethyl)-2,3,4,5-tetrahydro-1H-3-benzazepin-7-yl]-4-(4-piperidinyl)-1-butanone (free base) as obtained in Example 26 and methyl 3 (bromomethyl) benzoate, the procedure of Example 28 was similarly repeated to provide the title compound as colorless powders melting at 194–200° C.

$^1$H NMR (CDCl$_3$, free base) δ: 1.20–1.37 (4H, m), 1.60–1.82 (5H, m), 1.85–2.02 (2H, m), 2.58–2.69 (4H, m), 2.78–3.03 (8H, m), 3.52 (2H, s), 3.6;4 (2H, s), 3.92 (3H, s), 7.11–7.19 (1H, m), 7.21–7.44 (6H, m), 7.49–7.58 (1H, m), 7.63–7.73 (2H, m), 7.88–7.99 (2H, m). Elemental analysis, for C$_{35}$H$_{42}$N$_2$O$_3$. 2HCl. 1.5H$_2$O. Calcd.: C, 65.82; H, 7.42; N, 4.39. Found: C, 65.74; H, 7.19; N, 4.35.

EXAMPLE 153

Ethyl 2-methyl-2-[3-[[4-[4-[3-(phenylmethyl)-2,3,4,5-tetrahydro-1H-3-benzazepin-7-yl]-4-oxobutyl]-1-piperidinyl]methyl]phenyl]propionate Dihydrochloride

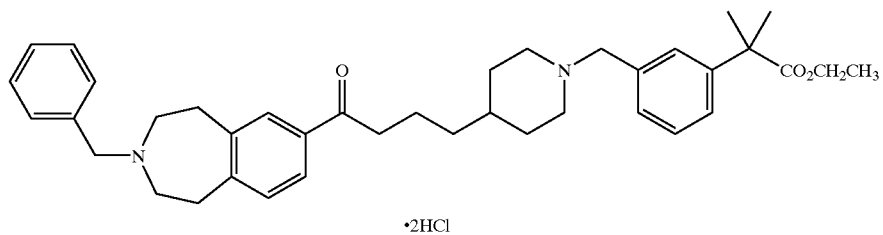

•2HCl

Using 1-[3-(phenylmethyl)-2,3,4,5-tetrahydro-1H-3-benzazepin-7-yl]-4-(4-piperidinyl)-1-butanone (free base) as obtained in Example 26 and ethyl 2-methyl-2-Example 28 was similarly repeated to provide the title compound as colorless powders melting at 146–148° C.

$^1$H NMR (CDCl$_3$, free base) δ: 1.12–1.37 (7H, m), 1.57 (6H, s), 1.60–2.00 (7H, m), 2.58–2.68 (4H, m), 2.79–3.02 (8H, m), 3.48 (2H, s), 3.64 (2H, s), 4.12 (2H, q, J=7 Hz), 7.12–7.39 (10H, m), 7.66–7.74 (2H, m). Elemental analysis, for C$_{39}$H$_{50}$N$_2$O$_3$. 2HCl. H$_2$O. Calcd.: C, 68.31; H, 7.94; N, 4.09. Found: C, 68.46; H, 7.80; N, 3.94.

EXAMPLE 154

4-[1-[(3-Nitrophenyl)methyl]-4-piperidinyl-1-(3-(phenylmethyl)-2,3,4,5-tetrahydro-1H-3-benzazepin-7-yl]-1-butanone Dihydrochloride

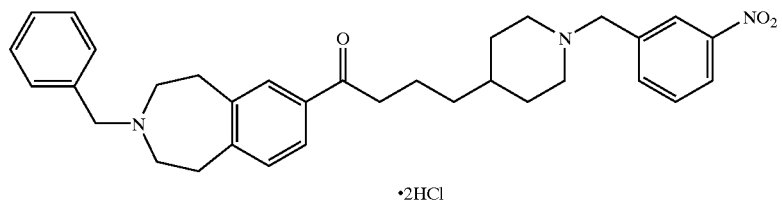

•2HCl

Using 1-[3-(phenylmethyl)-2,3,4,5-tetrahydro-1H-3-benzazepin-7-yl]-4-(4-piperidinyl)-1-butanone (free base) as obtained in.Example 26 and 3-nitrobenzyl bromide, the procedure of Example 28 was similarly repeated to provide the title compound as colorless powders melting at 239–244° C. (dec.).

$^1$H NMR (CDCl$_3$, free base) δ: 1.12–1.39 (4H, m), 1.58–1.82 (5H, m), 1.89–2.08(2H, m), 2.54–2.70 (4H, m), 2.73–3.03 (8H, m), 3.55 (2H, s), 3.64 (2H, s), 7.10–7.52 (7H, m), 7.61–7.74 (3H, m), 8.05–8.15 (2H, m). Elemental analysis, for C$_{33}$H$_{39}$N$_3$O$_3$. 2HCl. 0.5H$_2$O. Calcd.: C, 65.23; H, 6.97; N, 6.92. Found: C, 65.44; H, 6.83; N, 6.80.

EXAMPLE 155

4-[1-[(3-Fluorophenyl)methyl]-4-piperidinyl]-1-(3-(phenylmethyl)-2,3,4,5-tetrahydro-1H-3-benzazepin-7-yl]-1-butanone Dihydrochloride

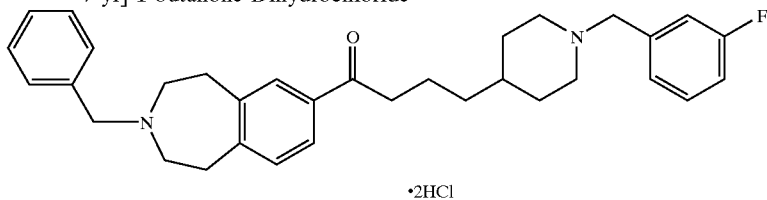

•2HCl

Using 1-(3-(phenylmethyl)-2,3,4,5-tetrahydro-1H-3-benzazepin-7-yl]-4-(4-piperidinyl)-1-butanone (free base) as obtained in Example 26 and 3-fluorobenzyl bromide, the procedure of Example 28 was similarly repeated to provide the title compound as colorless powders melting at 245–248° C. (dec.).

$^1$H NMR (CDCl$_3$, free base) δ: 1.11–1.38 (4H, m), 1.56–2.01 (7H, m), 2.55–2.70 (4H, m), 2.78–3.02 (8H, m), 3.46 (2H, s), 3.64 (2H, s), 6.86–7.40 (10H, m), 7.63–7.73 (2H, m). Elemental analysis, for C$_{33}$H$_{39}$FN$_2$O. 2HCl. Calcd.: C, 69.34; H, 7.23; N, 4.90. Found: C, 68.94; H, 7.29; N, 4.83.

EXAMPLE 156

4-[1-[(3-Methoxyphenyl)methyl]-4-piperidinyl]-1-[3-(phenylmethyl)-2,3,4,5-tetrahydro-1H-3-benzazepin-7-yl]-1-butanone Dihydrochloride

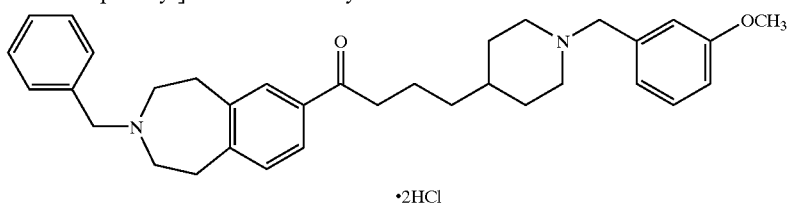

•2HCl

Using 1-[3-(phenylmethyl)-2,3,4,5-tetrahydro-1H-3-benzazepin-7-yl]-4-(4-piperidinyl)-1-butanone (free base) as obtained in Example 26 and mesylate of 3-methoxybenzyl alcohol, the procedure of Example 28 was similarly repeated to provide the title compound as colorless powders melting at 215–218° C. (dec.).

$^1$H NMR (CDCl$_3$, free base) δ: 1.11–1.37 (4H, m), 1.56–2.01 (7H, m), 2.53–2.69 (4H, m), 2.79–3.02 (8H, m), 3.46 (2H, s), 3.63 (2H, s), 3.81 (3H, s), 6.73–6.92 (3H, m), 7.10–7.40 (7H, m), 7.63–7.73 (2H, m).

Elemental analysis, for C$_{34}$H$_{42}$N$_2$O$_2$. 2. HCl. H$_2$O. Calcd.: C, 67.87; H, 7.71; N, 4.66. Found: C, 68.16; H, 7.53; N, 4.59.

EXAMPLE 157

4-[1-[(3-Hydroxyphenyl)methyl]-4-piperidinyl]-1-[3-(phenylmethyl)-2,3,4,5-tetrahydro-1H-3-benzazepin-7-yl]-1-butanone

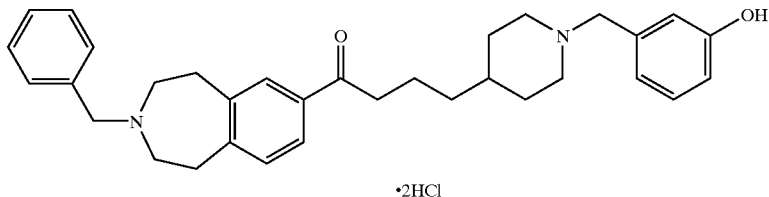

·2HCl

Using 4-[1-[3-methoxyphenyl)methyl]-4-piperidinyl]-1-[3-(phenylmethyl)-2,3,4,5-tetrahydro-1H-3-benzazepin-7-yl]-1-butanone (free base) as obtained in Example 156, the procedure of Example 50 was similarly repeated to provide the title compound as colorless powders melting at 88–94° C.

$^1$H NMR (CDCl$_3$) δ: 1.17–1.4.2 (4H, m), 1.58–1.80 (5H, m), 1.90–2.08 (2H, m), 2.54–2.72 (4H, m), 2.80–3.06 (8H, m), 3.46 (2H, s), 3.64 (2H, s), 6.68–6.88 (3H, m), 7.10–7.41 (8H, m), 7.63–7.73 (2H, m). Elemental analysis, for C$_{33}$H$_{40}$N$_2$O$_2$. 0.5H$_2$O. Calcd.: C, 78.38; H, 8.17; N, 5.54. Found: C, 78.67; H, 8.17; N, 5.24.

EXAMPLE 158

3-[[4-[4-[3-(Phenylmethyl)-2,3,4,5-tetrahydro-1H-benzazepin-7-yl]-4-oxobutyl]-1-piperidinyl]methyl] benzoic acid triethylamine Salt

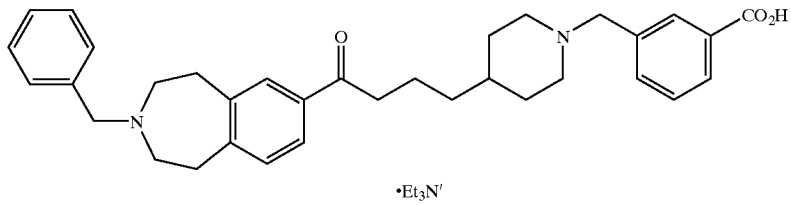

·Et$_3$N'

Using methyl 3-[[4-[4-(3-(phenylmethyl)-2,3,4,5-tetrahydro-1H-3-benzazepin-7-yl]-4-oxobutyl)]-1-piperidinyl]methyl]benzoate (free base) as obtained in Example 152, the procedure of Example 104 was similarly repeated to provide the title compound as colorless powders melting at 150–158° C.

$^1$H NMR (CDCl$_3$+D$_2$O) δ: 1.29–1.48 (13H, m), 1.61–1.93 (7H, m), 2.38–2.78 (5H, m), 2.81–3.19 (12H, m), 3.30–3.47 (1H, m), 3.70 (2H, s), 3.94 (2H, s), 7.10–7.49 (8H, m), 7.62–7.72 (2H, m), 8.03–8.13 (1H, m), 8.30–8.41 (1H, m). Elemental analysis, for C$_{34}$H$_{40}$N$_2$O$_3$. Et$_3$N. 3H$_2$O. Calcd.: C, 70.66; H, 9.04; N, 6.18. Found: C, 70.54; H, 8.76; N, 6.51.

EXAMPLE 159

4-[1-[(4-Nitrophenyl)methyl]-4-piperidinyl]-1-[3-(phenylmethyl)-2,3,4,5-tetrahydro 1H-3-benzazepin-7-yl]-1-butanone Dihydrochloride

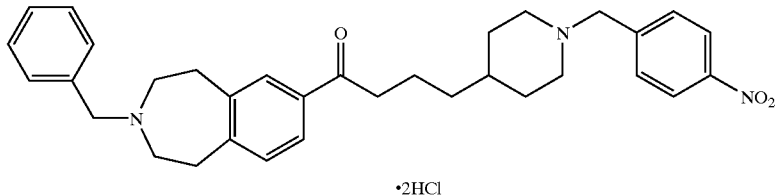

·2HCl

Using 1-[3- (phenylmethyl)-2,3,4,5-tetrahydro-1H-3-benzazepin-7-yl]4-piperidinlyl)-1-butanone (free base) as obtained in Example 26 and 4-nitrobenzyl bromide, the procedure of Example 28 Was similarly repeated to provide the title compound as colorless powders melting at 242–247° C. (dec.).

$^1$H NMR (CDCl$_3$, free base) δ: 1.12–1.39 (4H, m) 1.58–1.83 (5H, m), 1.89–2.08 (2H, m), 2.55–2.70 (4H, m), 2.73–3.02 (8H, m), 3.55 (2H, s) 3.64 (2H, s), 7.10–7.55 (8H, m) 7.63–7.73 (2H, m), 8.11–8.21 (2H, m). Elemental analysis, for C$_{33}$H$_{39}$N$_3$O$_3$. 2HCl. Calcd.: C, 66.21; H, 6.90; N, 7.02. Found: C, 66.06; H, 6.70; N, 6.93.

EXAMPLE 160

1-[2- [(2-Methylphenyl)methyl]-2,3,4,5- tetrahydro-1H-2-benzazepin-8-yl]-4-(4-piperidinyl)-1-butanone

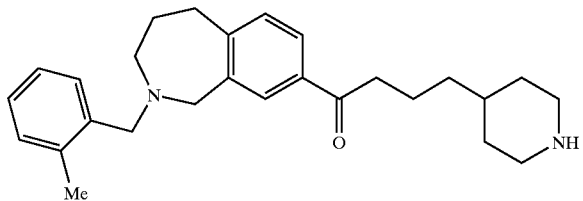

1) Using 2-(1-acetyl-4-piperidinyl)-1-(2,3,4,5-tetrahydro-1H-2-benzazepin-8-yl)-1-butanone as obtained in Example 142–2) and 2-methylbenzyl bromide, the procedure of Example 23–3) was similarly repeated to provide 4-(1-acetyl-4-piperidinyl)-1-[2-[(2-methylphenyl)methyl]-2,3,4,5-tetrahydro-1H-2-benzazepin-8-yl]-1-butanone as light-yellow oil.

$^1$H NMR (CDCl$_3$) δ: 0.98–1.62 (5H, m), 1.67–187 (6H, m), 2.08 (3H, s), 2.27 (3H, s) 2.44–2.61 (1H8 m), 2.85–3.16 (7H, m), 3.49 (2H, s), 3.72–3.86 (1H, m), 3.92 (2H, s), 4.53–4.67 (1H, m), 7.10–7.29 (5H, m), 7.55 (1H, d, J=1.8 Hz), 7.76 (1H, dd, J=1.8, 7.8 Hz). 2) Using 4-(1-acetyl-4-piperidinyl)-1-(2-[(2-methyl-phenyl)methyl]-2,3,4,5-tetrahydro-1H-2-benzazepin-8-yl]-1-butanone as obtained in 1), the procedure of Example 24 was similarly repeated to provide the title compound as viscous oil.

$^1$H NMR (CDCl$_3$) δ: 0.99–1.48 (5H, m), 1.62–1.85 (6H, m), ca. 2.1 (1H, br), 2.27 (3H, s), 2.49–2.88 (2H, m), 2.83–3.16 (8H, m), 3.49 (2H, s), 3.91 (2H, s), 7.08–7.28 (5H, m), 7.55 (1H, d, J=1.98 Hz), 7.76 (1H, dd, J=1.8, 7.7 Hz).

EXAMPLE 161

1-[2-[(2-Methylphenyl)methyl]-2,3,4,5-tetrahydro-1H-2-benzazepin-8-yl]-4-[1-(phenylmethyl)-4-piperidinyl]-1-butanone Dihydrochloride

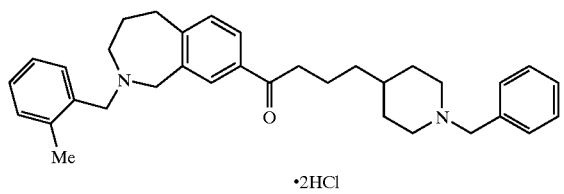

·2HCl

Using 1-[2-[(2-methylphenyl)methyl]-2,3,4,5-tetrahydro-1H-2-benzazepin-8-yl]-4-(4-piperidinyl)-1-butanone as obtained in Example 160 and benzyl bromide, the procedure of Example 28 was similarly repeated to provide the title compound as colorless amorphous powders.

$^1$H NMR (CDCl$_3$, free base) δ: 1.16–1.40 (5H, m), 1.58–2.04 (8H, m), 2.26 (3H, s), 2.82–3.15 (8H, m), 3.48 (2H, s), 3.50 (2H, s), 3.91 (2H, s), 7.10–7.37 (10H, m), 7.54 (1H, d, J=1.8 Hz), 7.75 (1H, dd, J=1.8, 7.8 Hz). Elemental analysis, for C$_{34}$H$_{42}$N$_2$O. 2HCl. H$_2$O. Calcd.: C, 69.73; H, 7.92; N, 4.78. Found: C, 70.27; H, 8.13; N, 4.64.

EXAMPLE 162

4-[1-[(2-Methylphenyl)methyl]-4-piperidinyl]-1-[2-[(2-methylphenyl)methyl]-2,3,4,5-tetrahydro-1H-2-benzazepin-8-yl]-1-butanone Dihydrochloride

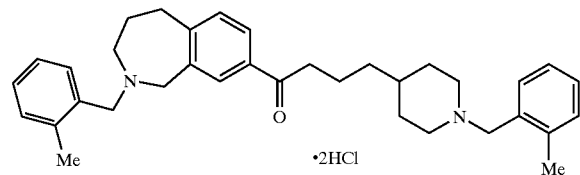

·2HCl

Using 1-[2-[(2-methylphenyl)methyl]-2,3,4,5-tetrahydro-1H-2-benzazepin-8-yl]-4-(4-piperidinyl)-1-butanone as obtained in Example 160 and 2-methylbenzyl bromide, the procedure of Example 28 was similarly repeated to provide the title compound as colorless amorphous powders.

$^1$H NMR (CDCl$_3$, free base) δ: 1.10–1.39 (5H, m), 1.54–2.07 (8H, m), 2.27 (3H, s), 2.35 (3H, s), 2.80–3.15 (8H, m), 3.44 (2H, s), 3.48 (2H, s), 3.91 (2H, s), 7.03–7.32 (9H, m), 7.54 (1H, d, J=1.8 Hz), 7.75 (1H, dd, J=1.8, 7.7

Hz). Elemental analysis, for $C_{35}H_{44}N_2O \cdot 2HCl \cdot H_2O$. Calcd.: C, 70.10; H, 8.07; N, 4.67. Found: C, 70.55; H, 8.04; N, 4.35.

EXAMPLE 163

4-[1-[(3-Methylphenyl)methyl]-4-piperidinyl]-1-[2-[(2-methylphenyl)methyl]-2,3,4,5-tetrahydro-1H-2-benzazepin-8-yl]-1-butanone Dihydrochloride

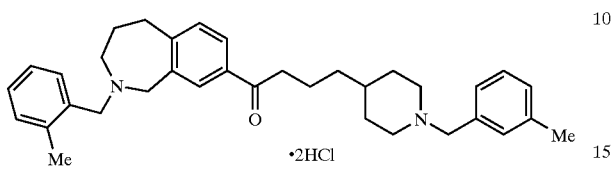

Using 1-[2-[(2-methylphenyl)methyl]-2,3,4,5-tetrahydro-1H-2-benzazepin-8-yl]-4-(4-piperidinyl)-1-butanone as obtained in Example 160 and 3-methylbenzyl bromide, the procedure of Example 28 was similarly repeated to provide the title compound as colorless amorphous powders.

$^1$H NMR (CDCl$_3$, free base) δ: 1.14–1.38 (5H, m), 1.57–2.00 (8H,), 2.26 (3H, s), 2.34 (3H, s), 2.80–3.14 (8H, m), 3.45 (2H, s), 3.48 (2H, s), 3.91 (2H, s), 7.00–7.28 (9H, m), 7.54 (1H, d, J=1.8 Hz), 7.76 (1H, dd, J=1.8, 7.7 Hz). Elemental analysis, for $C_{35}H_{44}N_2O \cdot 2HCl \cdot 0.5H_2O$. Calcd.: C, 71.17; H, 8.02; N, 4.74. Found: C, 70.73; H, 8.12; N, 4.60.

EXAMPLE 164

4-[1-[(4-Methylphenyl)methyl]-4-piperidinyl]-1-[2-[(2-methylphenyl)methyl]-2,3,4,5-tetrahydro-1H-2-benzazepin-8-yl]-1-butanone Dihydrochloride

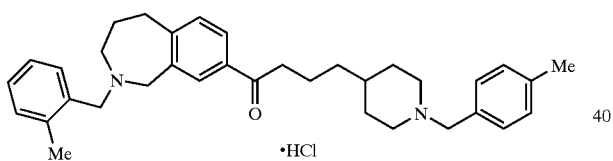

Using 1-[2-[(2-methylphenyl)methyl]-2,3,4,5-tetrahydro-1H-2-benzazepin-8-yl]-4-(4-piperidinyl)-1-butanone as obtained in Example 160 and 4-methylbenzyl bromide, the procedure of Example 28 was similarly repeated to provide the title compound as colorless amorphous powders.

$^1$H NMR (CDCl$_3$, free base) δ: 1.12–1.37 (5H, m), 1.56–2.00 (8H, m), 2.27 (3H, s,), 2.33 (3H, s), 2.80–3.14 (8H, m), 3.46 (2H, s), 3.48 (2H, s), 3.91 (2H, s), 7.07–7.28 (9H, m), 7.54 (1H, d, J=1.8 Hz), 7.75 (1H, dd, J=1.8, 7.7 Hz). Elemental analysis, for $C_{35}H_{44}N_2O \cdot 2HCl \cdot H_2O$. Calcd.: C, 70.10; H, 8.07; N, 4.67. Found: C, 70.61; H, 7.95; N, 4.61.

EXAMPLE 165

4-[1-[(3-Chlorophenyl)methyl]-4-piperidinyl]-1-[2-[(2methylphenyl)methyl]-2,3,4,5-tetrahydro-1H-2-benzazepin-8-yl]-1-butanone Dihydrochloride

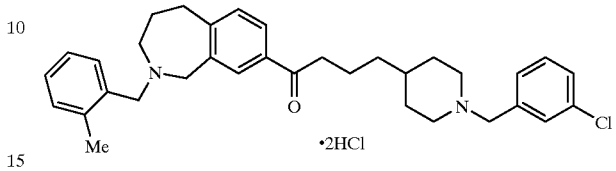

Using 1-[2-[(2-methylphenyl)methyl]-2,3,4,5-tetrahydro-1H-2-benzazepin-8-yl]-4-(4-piperidinyl)-1-butanone as obtained in Example 160 and 3-chlorobenzyl bromide, the procedure of Example 28 was similarly repeated to provide the title compound as colorless amorphous powders.

$^1$H NMR (CDCl$_3$, free base) δ: 1.15–1.38 (5H, m), 1.58–2.04 (8H, m), 2.27 (3H, s), 2.78–3.16 (8H, m), 3.45 (2H, s), 3.49 (2H, s), 3.91 (2H, s), 7.10–7.29 (8H, m), 7.33 (1H, s), 7.55 (1H, d, J=1.7 Hz), 7.76 (1H, dd, J=1.7, 7.7 Hz). Elemental analysis, for $C_{34}H_{41}ClN_2O \cdot 2HCl \cdot 0.5H_2O$. Calcd.: C, 66.83; H, 7.26; N, 4.58. Found: C, 66.90; H, 7.41; N, 4.54.

EXAMPLE 166

Ethyl 2-Methyl-2-[3-[[4-[4-[2-(phenylmethyl)-2,3,4,5-tetrahydro-1H-2-benzazepin-8-yl]-4-oxobutyl]1-piperidinyl]methyl]phenyl]propionate Dihydrochloride

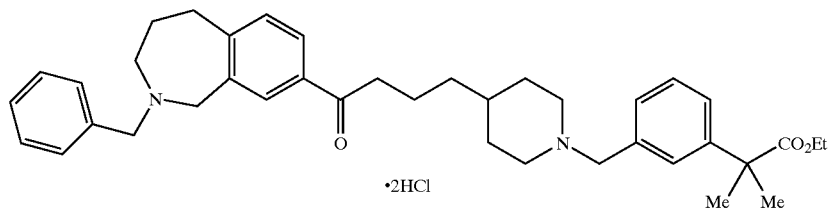

Using 1-[2-(phenylmethyl)-2,3,4,5-tetrahydro-1H-2-benzazepin-8-yl]-4-(4-piperidinyl)-1-butanone as obtained in Example 143 and ethyl 2-methyl-2-[3-(bromomethyl) phenyl]propionate, the procedure of Example 28 was similarly repeated to provide the title compound as colorless amorphous powders.

$^1$H NMR (CDCl$_3$, free base) δ: 1.10–1.37 (8H, m), 1.46–2.02 (14H, m), 2.79–3.02 (6H, m), 3.07–3.18 (2H, m), 3.49 (2H, s), 3.53 (2H, s), 3.92 (2H, s), 4.11 (2H, q, J=7.1 Hz), 7.15–7.34 (10H, m), 7.50 (1H, d, J=1.8 Hz), 7.75 (1H, dd, J=1.8, 7.7 Hz). Elemental analysis, for $C_{39}H_{50}N_2O_3 \cdot 2HCl \cdot 0.5H_2O$. Calcd.: C, 69.21; H, 7.89; N, 4.14. Found: C, 69.47; H, 8.18; N, 4.07.

EXAMPLE 167

Ethyl 2-Methyl-2-[3-[[4-[4-[2-[(2-methylphenyl)methyl]-2,3,4,5-tetrahydro-1H-2-benzazepin-8-yl]-4-oxobutyl]-1-piperidinyl]methyl]phenyl]propionate Dihydrochloride

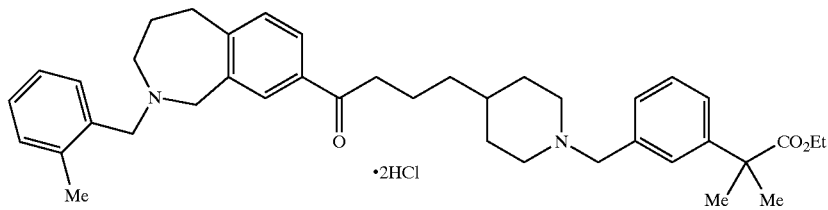

Using 1-[2-[(2-methylphenyl)methyl]-2,3,4,5-tetrahydro-1H-2-benzazepin-8-yl]-4-(4-piperidinyl)-1-butanone as obtained in Example 160 and ethyl 2-methyl-2-[3-(bromomethyl)phenyl]propionate, the procedure of Example 28 was similarly repeated to provide the title compound as colorless amorphous powders.

$^1$H NMR (CDCl$_3$, free base) δ: 1.11–1.38 (8H, m), 1.52–2.06 (14H, m), 2.26 (3H, s), 2.82–3.14 (8H, m), 3.48 (2H, s), 3.52 (2H, s), 3.91 (2H, s), 4.12 (2H, q, J=7.1 Hz), 7.09–7.30 (9H, m), 7.54 (1H, d, J=1.8 Hz), 7.75 (1H, dd, J=1.8, 7.7 Hz). Elemental analysis, for $C_{40}H_{52}N_2O_3 \cdot 2HCl \cdot 0.5H_2O$. Calcd.: C, 69.55; H, 8.03; N, 4.06. Found: C, 69.43; H, 8.25; N, 3.89.

EXAMPLE 168

2-Methyl-2-[3-[[4-[4-[2-[(2-methylphenyl)methyl]-2,3,4,5-tetrahydro-1H-2-benzazepin-8-yl]-4-oxbutyl]-1-piperidinyl]methyl]phenyl]propionic Acid

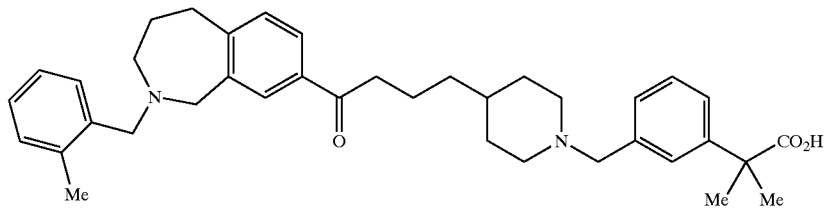

Using ethyl 2-methyl-2-[3-[[4-[4-[2-[(2-methyl-phenyl)methyl]-2,3,4,5-tetrahydro-1H-2-benzazepin-8-yl]-4-oxobutyl]-1-piperidinyl]methyl]phenyl]propionate (free base) as obtained in Example 167, the procedure of Example 104 was similarly repeated to provide the title compound as colorless amorphous powders.

$^1$H NMR (CDCl$_3$+D$_2$O) δ: 1.12–1.84 (17H, m), 2.05–2.30 (5H, m), 2.74–3.21 (8H, m), 3.47 (2H, s), 3.69 (2H, s), 3.90 (2H, s), 6.93–7.40 (8H, m), 7.48–7.78 (3H, m). Elemental analysis, for $C_{38}H_{48}N_2O_3 \cdot 2.5H_2O$. Calcd.: C, 72.93; H, 8.54; N, 4.48. Found: C, 72.92; H, 7.97; N, 4.50.

EXAMPLE 169

Ethyl 2-Methyl-2-[3-[[4-[4-[3-[(2-methylphenyl)methyl]-2,3,4,5-tetrahydro-1H-3-benzazepin-7-yl]-4-oxopropyl]-1-piperidinyl]methyl]phenyl]propionate Dihydrochloride

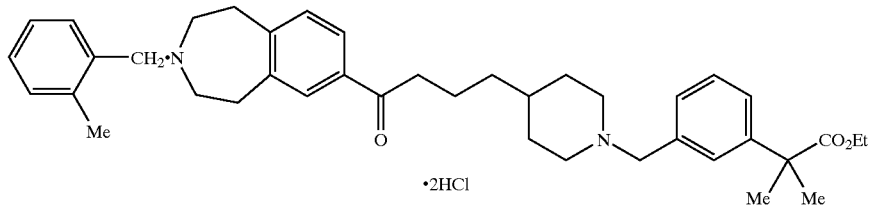

Using 1-[3-[(2-methylphenyl)methyl]-2,3,4,5-tetrahydro-1H-3-benzazepin-7-yl]-4-(4-piperidinyl)-1-butanone as obtained in Example 126 and ethyl 2-methyl-2-[3-(bromomethyl)phenyl]propionate, the procedure of Example 28 was similarly repeated to provide the title compound as colorless amorphous powders.

$^1$H NMR (CDCl$_3$, free base) δ: 1.12–1.38 (8H, m), 1.57 (6H, s), 1.60–2.05 (6H, m), 2.39 (3H, s), 2.56–2.68 (4H, m), 2.80–3.00 (8H, m), 3.52 (2H, s), 3.54 (2H, s), 4.12 (2H, q, J=7.1 Hz), 7.11–7.34 (9H, m), 7.64–7.73 (2H, m). Elemental analysis, for C$_{40}$H$_{52}$N$_2$O$_3$.2HCl.0.5HO. Calcd.: C, 69.55; H, 8.03; N, 4.06. Found: C, 69.29; H, 8.40; N, 3.86.

EXAMPLE 170

1-(3-Acetyl-2,3,4,5-tetrahydro-1H-3-benzazepin-7-yl)-4-[1-[(4-fluorophenyl)methyl]-4-piperidinyl]-1-butanone

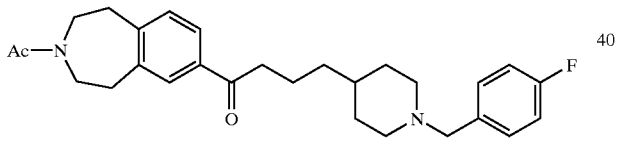

1) Using [1-[(4-nitrobenzyl)oxycarbonyl]-4-piperidinyl]butyric acid (8.0 g, 22.8 mmol) as obtained in Reference Example 6 and 3-acetyl-2,3,4,5-tetrahydro-1H-3-benzazepine (3.3 g, 17.4 mmol), the procedure of Example 23-1) was similarly repeated to provide 4-[1-[(4-nitrobenzyl)oxycarbonyl]-4-piperidinyl]-1-(3-acetyl-2,3,4,5-tetrahydro-1H-3-benzazepin-7-yl)-1-butanone (4.7 g) as light-yellow oil.

$^1$H NMR (CDCl$_3$, free base) δ: 1.00–1.85 (9H, m), 2.19 (3H, s), 2.68–3.05 (8H, m), 3.54–3.78 (4H, m), 4.08–4.24 (2H, m), 5.22 (2H, s), 7.18–7.27 (1H, m), 7.51 (2H, d, J=8.8 Hz), 7.70–7.77 (2H, m), 8.22 (2H, d, J=8.8 Hz).

2) A solution of 4-[1-[(4-nitrobenzyl)oxycarbonyl]-4-piperidinyl]-1-(3-acetyl-2,3,4,5-tetrahydro-1H-3-benzazepin-7-yl)-1-butanone as obtained in 1) (4.5 g, 8.6 mmol) in ethanol (50 ml) was subjected to catalytic hydrogenation using 5% Pd/C (0.6 g) as the catalyst at atmospheric pressure. After completion of the reaction, the catalyst was filtered off, and potassium carbonate (1.5 g, 10.8 mmol) and 4-fluorobenzyl bromide (1.45 g, 7.67 mmol) were successively added to the filtrate. The mixture was stirred at room temperature for 4 hours and the solvent was then distilled off. The residue was dissolved in water-ethyl acetate and extracted with ethyl acetate. The extract was washed with saturated NaCl/H$_2$O and dried over MgSO$_4$, and the solvent was distilled off under reduced pressure. The residue was purified by silica gel column chromatography (eluent: ethyl acetate-methanol=15:1) to provide the title compound (3.3 g) as yellow needles melting at 92–94° C.

$^1$H NMR (CDCl$_3$) δ: 1.11–1.40 (5H, m), 1.58–2.00 (6H, m), 2.19 (3H, s), 2.77–3.06 (8H, m), 3.44 (2H, s), 3.53–3.65 (2H, m), 3.69–3.79 (2H, m), 6.98 (2H, t like, J=8.8 Hz), 7.17–7.33 (3H, m), 7.68–7.77 (2H, m). Elemental analysis, for C$_{28}$H$_{35}$FN$_2$O$_2$.0.5H$_2$O. Calcd.: C, 73.17; H, 7.90; N, 6.10. Found: C, 73.24; H, 7.81; N, 6.18.

EXAMPLE 171

4-[1-[(4-Fluorophenyl)methyl]-4-piperidinyl]-1-(2,3,4,5-tetrahydro-1H-3-benzazepin-7-yl)-1-butanone Dihydrochloride

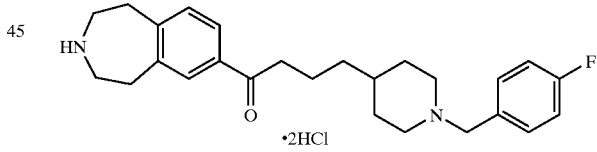

Using 1-(3-acetyl-2,3,4,5-tetrahydro-1H-3-benzazepin-7-yl)-4-[1-[(4-fluorophenyl)methyl]-4-piperidinyl]-1-butanone as obtained in Example 170, the procedure of Example 24 was similarly repeated to provide the title compound as colorless amorphous powders.

$^1$H NMR (CDCl$_3$, free base) δ: 1.08–1.37 (5H, m), 1.60–2.05 (7H, m), 2.76–3.04 (12H, m), 3.44 (2H, s), 6.98 (2H, t like, J=8.8 Hz), 7.13–7.32 (3H, m), 7.65–7.75 (2H, m). Elemental analysis, for C$_{26}$H$_{33}$FN$_2$O.2HCl. Calcd.: C, 64.85; H, 7.32; N, 5.81. Found: C, 64.64; H, 7.50; N, 5.82.

EXAMPLE 172

Ethyl 2-Methyl-2-[4-[[4-[4-[2-[(2-methylphenyl)methyl]-2,3,4,5-tetrahydro-1H-2-benzazepin-8-yl]-4-oxobutyl]-1-piperidinyl]methyl]phenyl]propionate Dihydrochloride

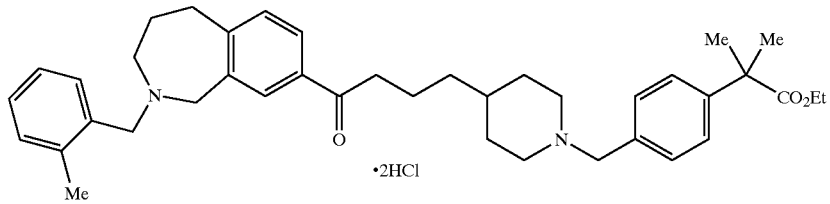

Using 1-[2-[(2-methylphenyl)methyl]-2,3,4,5-tetrahydro-1H-2-benzazepin-8-yl]-4-(4-piperidinyl)-1-butanone as obtained in Example 160 and ethyl 2-methyl-2-[4-(bromomethyl)phenyl]propionate, the procedure of Example 28 was similarly repeated to provide the title compound as colorless amorphous powders.

$^1$H NMR (CDCl$_3$, free base) δ: 1.12–1.40 (8H, m), 1.46–2.03 (14H, m), 2.27 (3H, s), 2.80–3.04 (6H, m), 3.09 (2H, t like, J=5.1 Hz), 3.48 (4H, br), 3.91 (2H, s), 4.12 (2H, q, J=7.2 Hz), 7.11–7.33 (9H, m), 7.54 (1H, d, J=1.8 Hz), 7.75 (1H, dd, J=1.8, 7.7 Hz), Elemental analysis, for C$_{40}$H$_{52}$N$_2$O$_3$.2HCl.0.5H$_2$O. Calcd.: C, 69.55; H, 8.02; N, 4.06. Found: C, 69.47; H, 7.78; N, 3.98.

EXAMPLE 173

2-Methyl-2-[4-[[4-[4-[2-[(2-methylphenyl)methyl]-2,3,4,5-tetrahydro-1H-2-benzazepin-8-yl]-4-oxobutyl]-1-piperidinyl]methyl]phenyl]propionic Acid

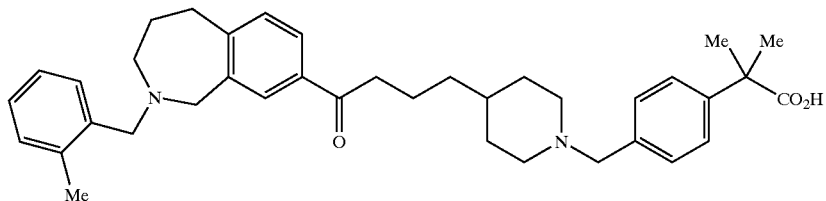

Using ethyl 2-methyl-2-[4-[[4-[4-[2-[(2-methyl-phenyl)methyl]-2,3,4,5-tetrahydro-1H-2-benzazepin-8-yl)-4-oxobutyl]-1-piperidinyl]methyl]phenyl]propionate (free base) as obtained in Example 172, the procedure of Example 104 was similarly repeated to provide the title compound as colorless amorphous powders.

$^1$H NMR (CDCl$_3$+D$_2$O) δ: 1.13–1.87 (17H, m), 2.20–2.43 (5H, m), 2.70–3.17 (6H, m), 3.32–3.54 (4H, m), 3.7–9 (2H, brs), 3.90 (2H, brs), 7.04–7.40 (9H, m), 7.531(1H, brs), 7.69–7.79 (1H, m). Elemental analysis, for C$_{38}$H$_{48}$N$_3$.2H$_2$O. Calcd.: C, 73.99; H, 8.50; N, 4.54. Found: C, 73.70; H, 8.31; N, 4.38.

EXAMPLE 174

4-[1-[(2-Nitrophenyl)methyl]-4-piperidinyl]-1-[3-(phenylmethyl)-2,3,4,5-tetrahydro-1H-3-benzazepin-7-yl]-1-butanone Dihydrochloride

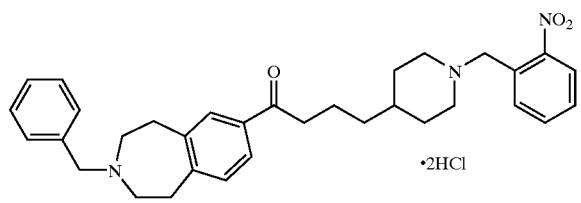

Using 1-[3-(phenylmethyl)-2,3,4,5-tetrahydro-1H-3-benzazepin-7-yl]-4-(4-piperidinyl)-1-butanone(free base), obtained in Example 26, and 2-nitrobenzylbromide, the procedure of Example 28 was similarly repeated to provide the title compound as colorless amorphous powders.

$^1$H NMR (CDCl$_3$, free base) δ: 1.09–1.38 (4H, m), 1.54–1.81 (5H, m), 1.90–2.10 (2H, m), 2.58–3.03 (12H, m), 3.64 (2H, s), 3.74 (2H, s), 7.11–7.41 (7H, m) 7.48–7.73 (4H, m), 7.76–7.83 (1H, m). Elemental analysis, for C$_{33}$H$_{39}$N$_3$O$_3$.2HCl.H$_2$. Calcd.: C, 64.28; H, 7.03; N, 6.81. Found: C, 64.24; H, 6.94; N, 6.88.

EXAMPLE 175

Methyl 2-[[(4-[4-[3-(Phenylmethyl)-2,3,4,5-tetrahydro-1H-3-benzazepin-7-yl]-4-oxobutyl]-1-piperidinyl]methyl]benzoate Dihydrochloride

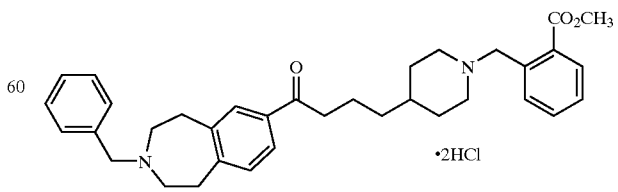

Using 1-(3-(phenylmethyl)-2,3,4,5-tetrahydro-1H-3-benzazepin-7-yl]-4-(4-piperidinyl)-1-butanone(free base), obtained in Example 26, and 2-(bromomethyl) methylbenzoate, the procedure of Example 28 was similarly repeated to provide the title compound as colorless amorphous powders.

¹H NMR (CDCl₃, free base) δ: 1.04–1.37 (4H, m), 1.52–2.07 (7H, m), 2.56–3.02 (12H, m), 3.64 (2H, s), 3.72 (2H, s), 3.87 (3H, s), 7.10–7.19 (1H, m), 7.20–7.48 (8H, m), 7.62–7.72 (3H, m). Elemental analysis, for C₃₅H₄₂N₂O₃.2HCl.1.5H₂O. Calcd.: C, 65.82; H, 7.42; N, 4.39. Found: C, 65.54; H, 7.27; N, 4.42.

EXAMPLE 176

Ethyl 2-[2-[[4-[4-[3-(Phenylmethyl)-2,3,4,5-tetrahydro-1H-3-benzazepin-7-yl]-4-oxobutyl]-1-piperidinyl]methyl]phenoxy]ethanoate Dihydrochloride

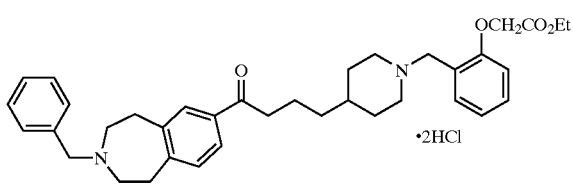

Using 1-[3-(phenylmethyl)-2,3,4,5-tetrahydro-1H-3-benzazepin-7-yl]-4-(4-piperidinyl)-1-butanone(free base), obtained in Example 26, and ethyl 2-[2-(bromomethyl) phenoxy]ethanoate, the procedure of Example 28 was otherwise repeated to provide the title compound as colorless amorphous powders.

¹H NMR (CDCl₃, free base) δ: 1.18–1.40 (7H, m), 1.60–1.80 (5H, m), 1.87–2.15 (2H, m), 2.55–2.70 (4H, m), 2.81–3.02 (8H, m), 3.64 (4H, s), 4.26 (2H, q, J=7.2 Hz), 4.64 (2H, s), 6.70–6.80 (1H, m), 6.91–7.02 (1H, m), 7.10–7.42 (8H, m), 7.63–7.73 (2H, m). Elemental analysis₁ for C₃₇H₄₆N₂O₄.2HCl.2H₂O. Calcd.: C, 64.24; H, 7.58; N, 4.05. Found: C, 64.19; H, 7.44; N, 4.06.

EXAMPLE 177

4-[1-[(2-Fluorophenyl)methyl]-4-piperidinyl]-1-[3-(phenylmethyl)-2,3,4,5-tetrahydro-1H-3-benzazepin-7-yl]-1-butanone Dihydrochloride

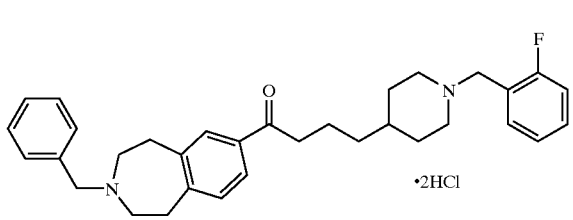

Using 1-[3-(phenylmethyl)-2,3,4,5-tetrahydro-1H-3-benzazepin-7-yl]-4-(4-piperidinyl)-1-butanone(free base), obtained in Example 26, and 2-fluorobenzylbromide, the procedure of Example 28 was otherwise repeated to provide the title compound as colorless amorphous powders.

¹H NMR (CDCl₃, free base) δ: 1.12–1.38 (4H, m) 1.58–2.08 (7H, m), 2.54–2.69 (4H, m), 2.80–3.02 (8H, m), 3.56 (2H, s), 3.64 (2H, s), 6.95–7.42 (10H, m), 7.63–7.73 (2H, m). Elemental analysis₁ for C₃₃H₃₉FN₂O.2HCl.0.5H₂O. Calcd.: C, 68.27; H, 7.29; N, 4.82. Found: C, 68.03; H, 7.31; N, 4.69.

EXAMPLE 178

4-[1-[(2-Chlorophenyl)methyl]-4-piperidinyl]-1-[3-(phenylmethyl)-2,3,4,5-tetrahydro-1H-3-benzazepin-7-yl]-1-butanone Dihydrochloride

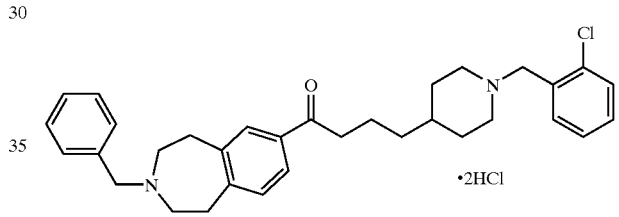

Using 1-[3-(phenylmethyl)-2,3,4,5-tetrahydro-1H-3-benzazepin-7-yl]-4-(4-piperidinyl)-1-butanone(free base), obtained in Example 26, and, 2-chlorobenzylbromide, the procedure of Example 28 was otherwise repeated to provide the title compound as colorless powders melting at 226–229° C.(dec.)

¹H NMR (CDCl₃, free base) δ: 1.13–1.41 (4H, m), 1.58–1.90 (5H, m), 1.94–2.14 (2H, m), 2.55–2.70 (4H, m), 2.80–3.04 (8H, m), 3.59 (2H, s), 3.64 (2H, s), 7.10–7.52 (10H, m), 7.63–7.73 (2H, m). Elemental analysis, for C₃₃H₃₉ClN₂O.2HCl.H₂O. Calcd.: C, 65.40; H, 7.15; N, 4.62. Found: C, 65.66; H, 7.09; N, 4.52.

EXAMPLE 179

N-[3-[[4-[4-[3-(Phenylmethyl)-2,3,4,5-tetrahydro-1H-3-benzazepin-7-yl]-4-oxobutyl]-1-piperidinyl] methyl]phenyl]acetamide Dihydrochloride

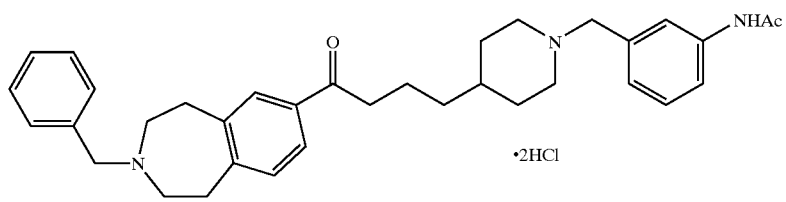

5Using 1-[3-(phenylmethyl)-2,3,4,5-tetrahydro-1H-3-benzazepin-7-yl]-4-(4-piperidinyl)-1-butanone(free base), obtained in Example 26, and mesylate of 3-acetylaminobenzylalchol, the procedure of Example 28 was otherwise repeated to provide the title compound as colorless powders melting at 179–187° C.

$^1$H NMR (CDCl$_3$, free base) δ: 1.09–1.38 (4H, m), 1.52–2.00 (7H, m), 2.14 (3H, s), 2.52–2.70 (4H, m), 2.73–3.02 (8H, m), 3.42 (2H, s), 3.62 (2H, s), 6.98–7.54 (10H, m), 7.62–7.73 (2H, m), 7.92 (1H, br.s). Elemental analysis, for C$_{35}$H$_{43}$N$_3$O$_2$.2HCl.1.5H$_2$O. Calcd.: C, 65.92; H, 7.59; N, 6.59. Found: C, 65.63; H, 7.46; N, 6.24.

EXAMPLE 180

4-[1-[(3-Aminophenyl)methyl]-4-piperidinyl]-1-[3-(phenylmethyl)-2,3,4,5-tetrahydro-1H-3-benzazepin-7-yl]-1-butanone Dihydrochloride

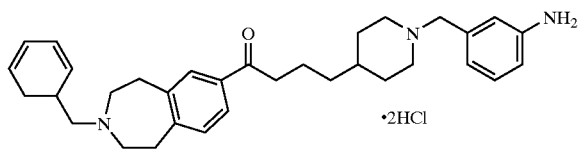

Using N-[3-[[4-[4-[3-(phenylmethyl)-2,3,4,5-tetrahydro-1H-3-benzazepin-7-yl]-4-oxobutyl]-1-piperidinyl]methyl]phenyl]acetamide, obtained in Example 179, the procedure of Example 24 was otherwise repeated to provide the title compound as colorless amorphous powders.

$^1$H NMR (CDCl$_3$, free base) δ: 1.13–1.38 (4H, m), 1.58–1.99 (7H, m), 2.58–2.70 (4H, m), 2.80–3.02 (8H, m), 3.39 (2H, s), 3.57–3.70 (4H, br.s), 6.53–6.72 (3H, m), 7.02–7.40 (7H, m), 7.63–7.73 (2H, m). Elemental analysis, for C$_{33}$H$_{41}$N$_3$O.3HCl.2H$_2$O. Calcd.: C, 61.82; H, 7.55; N, 6.55. Found: C, 61.61; H, 7.57; N, 6.20.

EXAMPLE 181

N-[3-[[4-[4-[3-(Phenylmethyl)-2,3,4,5-tetrahydro-1H-3-benzazepin-7-yl]-4-oxo]-1-piperidinyl]methyl]phenyl]-N'-methylurea Dihydrochloride

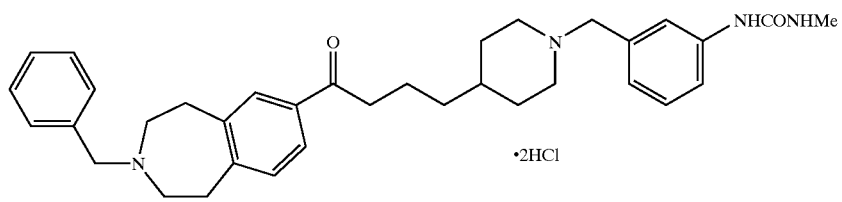

Using 4-[1-[(3-aminophenyl)methyl]-4-piperidinyl]-1-[3-(phenylmethyl)-2,3,4,5-tetrahydro-1H-3-benzazepin-7-yl)-1-butanone(free base), obtained in Example 180 and methylisocianate, the procedure of Example 28 was otherewise repeated to provide the title compound as colorless amorphous powders.

$^1$H NMR (CDCl$_3$, free base) δ: 1.08–1.38 (4H, m), 1.51–2.00 (7H, m), 2.53–2.68 (4H, m), 2.71–3.03 (11H, m), 3.43 (2H, s), 3.63 (2H, s), 4.96–5.09 (1H, m), 6.70 (1H, s), 6.96–7.40 (10H, m), 7.63–7.73 (2H, m). Elemental analysis, for C$_{35}$H$_{44}$N$_4$O$_2$.2HCl.2H$_2$O. Calcd.: C, 63.53; H, 7.62; N, 8.47. Found: C, 63.77; H, 7.45; N, 8.27.

EXAMPLE 182

Methyl 4-[[4-[4-[3-(Phenylmethyl)-2,3,4,5-tetrahydro-1H-3-benzazepin-7-yl]-4-oxobutyl]-1-piperidinyl]methyl]benzoate Dihydrochloride

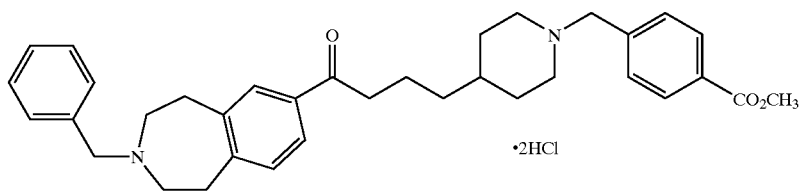

Using 1-[3-(phenylmethyl)-2,3,4,5-tetrahydro-1H-3-benzazepin-7-yl]-4-(4-piperidinyl)-1-butanone(free base), obtained in Example 26, and 4-(bromomethyl)methylbenzoate, the procedure of Example 28 was otherewise repeated to provide the title compound as colorless powders melting at 239–244° C. (dec.).

$^1$H NMR (CDCl$_3$, free base) δ: 1.10–1.38 (4H, m), 1.57–2.06 (7H, m), 2.54–2.69 (4H, m), 2.73–3.02 (8H, m), 3.52 (2H, s), 3.64 (2H, s), 3.91 (3H, s), 7.10–7.44 (8H, m), 7.63–7.73 (2H, m), 7. 98 (2H, d, J=8.0 Hz). Elemental analysis, for C$_{35}$H$_{42}$N$_2$O$_3$.2HCl. Calcd.: C, 68.73; H, 7.25; N, 4.58. Found: C, 68.57; H, 7.04; N, 4.64.

EXAMPLE 183

4-[[4-[4-[3-(Phenylmethyl)-2,3,4,5-tetrahydro-1H-3-benzazepin-7-yl]-4-oxobutyl]-1-piperidinyl]methyl]benzoic Acid

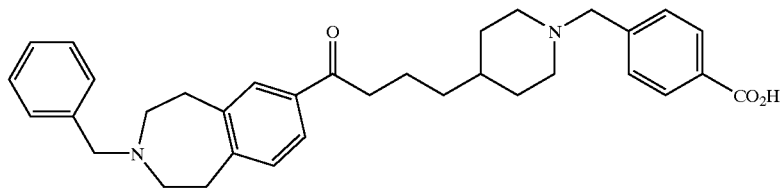

Using methyl 4-[[4-[4-[3-(phenylmethyl)-2,3,4,5-tetrahydro-1H-3-benzazepin-7-yl]-4-oxobutyl]-1-piperidinyl]methyl]benzoate, obtained in Example 182, the procedure of Example 104 was otherwise repeated to provide the title compound as colorless powders melting at 165–176° C.

$^1$H NMR (CDCl$_3$+D$_2$O) δ: 1.16–1.83 (9H, m), 2.01–2.38 (2H, m), 2.58–2.75 (4H, m), 2.80–3.29 (8H, m), 3.69 (2H, s), 3.79 (2H, br.s), 7.08–7.45 (8H, m), 7.60–7.72 (2H, m), 7.93–8.09 (2H, m). Elemental analysis, for C$_{34}$H$_{40}$N$_2$O$_3$.H$_2$O. Calcd.: C, 75.25; H, 7.80; N, 5.16. Found: C, 75.31; H, 7.45; N, 5.08.

EXAMPLE 184

2-Methyl-2-[3-[[4-[4-[3-(phenylmethyl)-2,3,4,5-tetrahydro-1H-3-benzazepin-7-yl]-4-oxopropyl]-1-piperidinyl]methyl]phenyl]proionic Acid

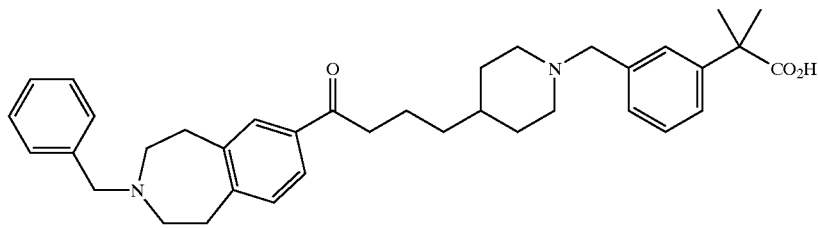

Using ethyl 2-methyl-2-[3-[[4-[4-[3-(phenylmethyl)-2,3,4,5-tetrahydro-1H-3-benzazepin-7-yl]4-oxopropyl]-1-piperidinyl]methyl]phenyl]propionate, obtained in Example 153, the procedure of Example 104 was otherwise repeated to provide the title compound as colorless amorphous powders.

$^1$H NMR (CDCl$_3$) δ: 1.10–1.719 (15H, m), 1.96–2.22 (2H, m), 2.52–2.77 (4H, m), 2.80–3.17 (8H, m), 3.66 (4H, s), 6.99–7.50 (10H, m), 7.62–7.77 (2H, m), 10.3 (1H, br.s). Elemental analysis, for C$_{37}$H$_{46}$N$_2$O$_3$.0.75H$_2$O. Calcd.: C. 76.58; H, 8.25; N, 4.83. Found: C, 76.42; H, 8.18; N, 4.69. (aphenylmethyl)-2,3,4,5-tetrahydro-1H-3-benzazepin-7-yl]-1-butanone(free base), obtained in Example 180, and methanesulfonylchloride, the procedure of Example 28 was otherwise repeated to provide the title compound as colorless powders melting at 158–164° C.

EXAMPLE 185

N-[3-[[4-[4-[3-(Phenylmethyl)-2,3,4,5-tetrahydro-1H-3-benzazepin-7-yl]-4-oxobutyl]-1-piperidinyl]methyl]phenyl]methanesulfonamide Dihydrochloride

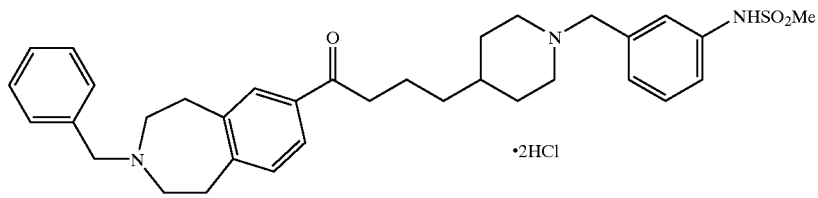

Using 4-[1-[(3-aminophenyl)methyl]-4-piperidinyl]-1-[3-

$^1$H NMR (CDCl$_3$, free base) δ: 1.15–1.38 (4H, m), 1.59–2.08 (7H, m), 2.57–2.70 (4H, m), 2.79–3.03 (11H, m), 3.47 (2H, s), 3.64 (2H, s), 7.10–7.40 (10H, m), 7.66–7.75 (2H, m). Elemental analysis, for C$_{34}$H$_{43}$N$_3$O$_3$S.2HCl.2H$_2$O. Calcd.: C, 59.81; H, 7.23; N, 6.15. Found: C, 59.76; H, 6.95; N, 6.03.

EXAMPLE 186

Ethyl 2-Methyl-2-[4-[[7-[4-[1-[(4-fluorophenyl)methyl]-4-piperidinyl]butanoyl]-2,3,4,5-tetrahydro-1H-3-benzazepin-3-yl]methyl]phenyl]propionate Dihydrochloride

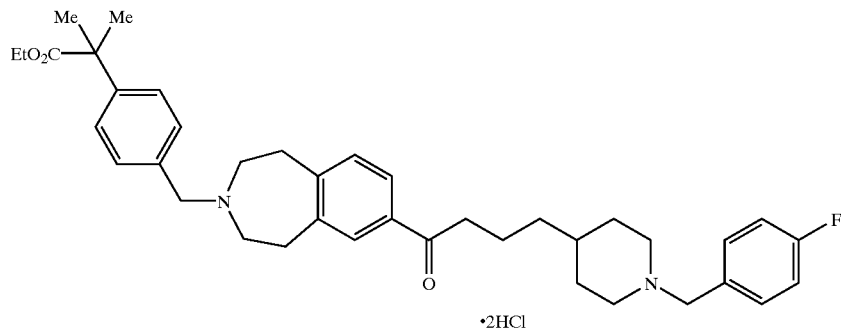

Using 4-[1-[(4fluorophenyl)methyl]-4-piperidinyl]-1-(2,3,4,5-tetrahydro-1H-3-benzazepin-7-yl)-1-butanone(free base), obtained in Example 171, and ethyl 2-methyl-2-[4-(bromomethyl)phenyl]propionate, the procedure of Example 28 was otherewise repeated to provide the title compound as colorless amorphous powders.

$^1$H NMR (CDCl$_3$, free base) δ: 1.09–1.36 (8H, m), 1.45–1.99 (12H, m), 2.53–2.68 (4H, m), 2.76–3.002 (8H, m), 3.44 (2H, s), 03.61 (2H, s), 4.13 (2H, q, J=7.2 Hz), 6.98 (2H, t-like, J=8.8 Hz), 7.15 (1H, d, J=7.7 Hz), 7.20–7.34 (6H, m), 7.63–7.73 (2H, m). Elemental analysis, for C$_{39}$H$_{49}$FN$_2$O$_3$.2HCl.0.5H$_2$O. Calcd.: C, 67.42; H, 7.54; N, 4.03. Found: C, 67.41; H, 7.38; N, 3.87.

EXAMPLE 187

Ethyl 2-Methyl-2-[3-[[7-[4-[1-[(4-fluorophenyl)methyl]-4-piperidinyl]butanoyl]-2,3,4,5-tetrahydro-1H-3-benzazepin-3-yl]methyl]phenyl]propionate Dihydrochloride

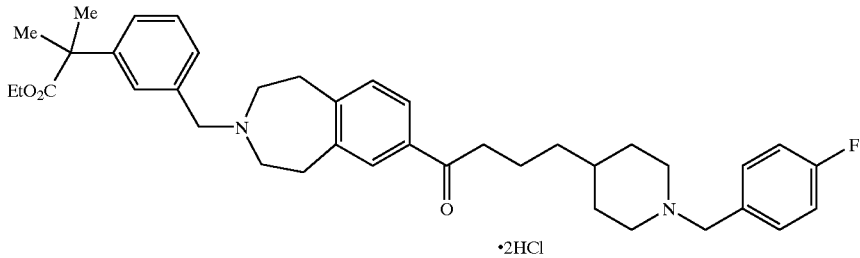

Using 4-[1-[(4-fluorophenyl)methyl]-4-piperidinyl]-1-(2,3,4,5-tetrahydro-1H-3-benzazepin-7-yl)-1-butanone(free base), obtained in Example 171, and ethyl 2-methyl-2-[3-(bromomethyl)phenyl]propionate, the procedure of Example 28 was otherwise repeated to provide the title compound as colorless amorphous powders.

$^1$H NMR (CDCl$_3$, free base) δ: 1.12–1.37 (8H, m), 1.51–2.00 (12H, m), 2.54–2.68 (4H, m), 2.79–3.02 (8H, m), 3.46 (2H, s), 3.63 (2H, s), 4.13 (2H, q, J=7.1 Hz), 6.99 (2H, t-like, J=8.8 Hz), 7.10–7.35 (7H, m), 7.65–7.74 (2H, m). Elemental analysis, for C$_{39}$H$_{49}$FN$_2$O$_3$.2HCl.0.5H$_2$O. Calcd.: C, 67.42; H, 7.54; N, 4.03. Found: C, 67.11; H, 7.52; N, 4.10.

EXAMPLE 188

2-Methyl-2-[4-[[7-[4-[1-[(4-fluorophenyl)methyl]-4-piperidinyl]butanoyl]-2,3,4,5-tetrahydro-1H-3-benzazepin-3-yl]methyl]phenyl]propionic Acid

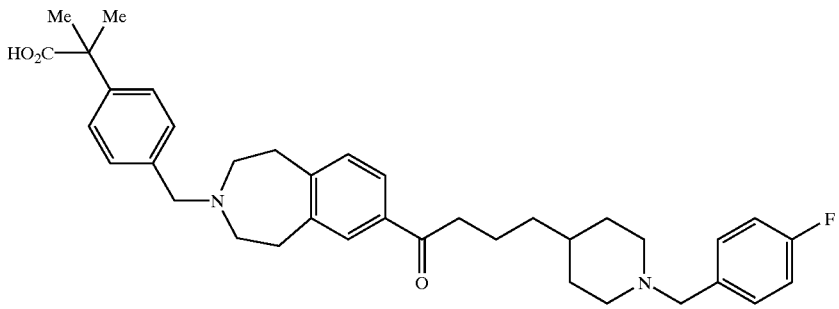

Using ethyl 2-methyl-2-[4-[[7-[4-[1-[(4-fluorophenyl)methyl]4-piperidinyl]butanoyl]-2,3,4,5-tetrahydro-1H-3-benzazepin-3-yl]methyl]phenyl]propionate, obtained in Example 186, the procedure of Example 104 was otherwise repeated to provide the title compound as colorless amorphous powders.

$^1$H NMR (CDCl$_3$+D$_2$O) δ: 1.16–1.40 (5H, m), 1.48–1.79 (10H, m), 1.97–2.17 (2H, m), 2.66–3.12 (12H, m), 3.64 (2H, brs), 3.71 (2H, brs), 7.00 (2H, t-like, J=8.6 Hz), 7.13 (1H, d, J=8.1 Hz), 7.20–7.44 (6H, m), 7.60–7.74 (2H, m). Elemental analysis, for C$_{37}$H$_{45}$FN$_2$O$_3$. Calcd.: C, 75.99; H, 7.69; N, 4.79. Found: C, 75.70; H, 7.75; N, 4.83.

EXAMPLE 189

2-Methyl-2-[3-[[7-[4-(1-[(4-fluorophenyl)methyl]-4-piperidinyl)butanoyl]-2,3,4,5-tetrahydro-1H-3-bepnzazepin-3-yl]methyl]phenyl]propionic Acid

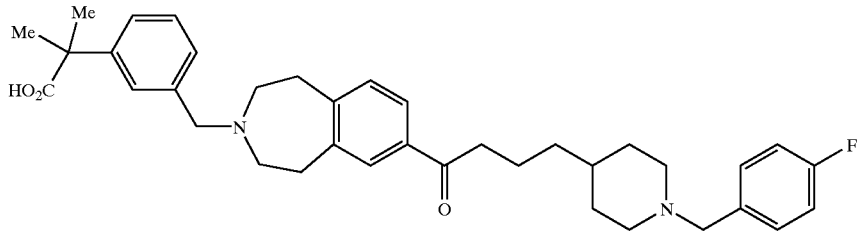

Using ethyl 2-methyl-2-[3-[[7-[4-[1-[(4-fluorophenyl)methyl]-4-piperidinyl]yl)-2,3,4,5-tetrahydro-1H-3-benzazepin-3-yl]methyl]phenyl]propionate, obtained in Example 187, the procedure of Example 104 was otherewise repeated to provide the title compound as colorless amorphous powders.

$^1$H NMR (CDCl$_3$+D$_2$O) δ: 1.10–1.46 (11H, m), 1.56–2.00 (6H, m), 2.42–2.96 (12H, m), 3.42 (4H, brs), 6.90–7.37 (9H, m), 7.55–7.72 (2H, m). Elemental analysis, for C$_{37}$H$_{45}$FN$_2$O$_3$. Calcd.: C, 75.99; H, 7.69; N, 4.79. Found: C, 75.73; H, 7.68; N, 4.99.

EXAMPLE 190

4-[1-[(4-Fluorophenyl)methyl]-4-piperidinyl]-1-[3-[(2-methylphenyl)methyl]-2,3,4,5-tetrahydro-1H-3-benzazepin-7-yl]-1-butanone Dihydrochloride

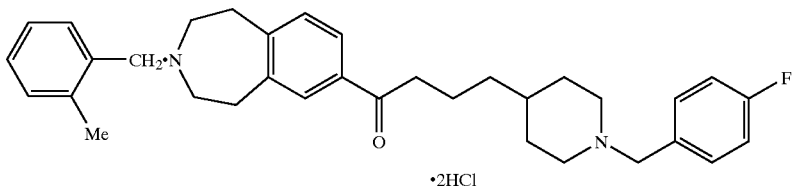

•2HCl

Using 4-[1-[(4-fluorophenyl)methyl]-4-piperidinyl]-1-(2,3,4,5-tetrahydro-1H-3-benzazepin-7-yl)-1-butanone(free base), obtained in Example 171, and 2-methylbenzylbromide, the procedure of Example 28 was otherwise repeated to provide the title compound as colorless powders melting at 197–200° C.

$^1$H NMR (CDCl$_3$, free base) δ: 1.14–1.38 (5H, m), 1.52–2.01 (6H, m), 2.39 (3H, s), 2.56–2.68 (4H, m), 2.80–3.00 (8H, m), 3.45 (2H, s), 3.54 (2H, s), 6.99 (2H, t-like, J=8.6 Hz), 7.11–7.34 (7H, m), 7.65–7.072 (2H, m). Elemental analysis, for C$_{34}$H$_{41}$FN$_2$O.2HCl.0.5H$_2$O. Calcd.: C, 68.68; H, 7.46; N, 4.71. Found: C, 68.72; H, 7.36; N, 4.67.

EXAMPLE 191

4-[1-[(4-Fluorophenyl)methyl]-4-piperidinyl]-1-[3-[(3-methylphenyl)methyl]-2,3,4,5-tetrahydro-1H-3-benzazepin-7-yl]-1-butanone Dihydrochloride

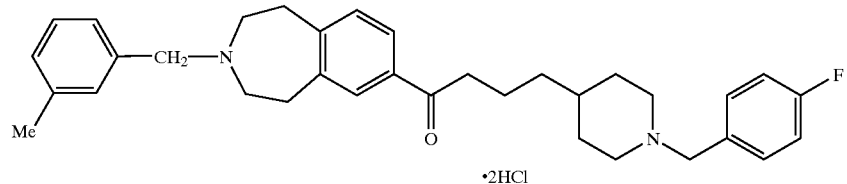

•2HCl

Using 4-[1-[(4-fluorophenyl)methyl]-4-piperidinyl]-1-(2,3,4,5-tetrahydro-1H-3-benzazepin-7-yl)-1-butanone(free base), obtained in Example 171, and 3-methylbenzylbromide, the procedure of Example 28 was otherwise repeated to provide the title compound as colorless powders melting at 209–212° C.

$^1$H NMR (CDCl$_3$, free base) δ: 1.11–1.38 (5H, m), 1.56–2.00 (6H, m), 2.36 (3H, s), 2.57–2.69 (4H, m), 2.79–3.04 (8H, m), 3.44 (2H, s), 3.60 (2H, s), 6.92–7.33 (9H, m), 7.65–7.74 (2H, m). Elemental analysis, for C$_{34}$H$_{41}$FN$_2$O.2HCl.0.5H$_2$O. Calcd.: C, 68.68; H, 7.46; N, 4.71. Found: C, 68.90; H, 7.57; N, 4.78.

EXAMPLE 192

4-[1-[(4-Fluorophenyl)methyl]-4-piperidinyl]-1-[3-[(4-methylphenyl)methyl]-2,3,4,5-tetrahydro-1H-3-benzazepin-7-yl]-1-butanone Dihydrochloride

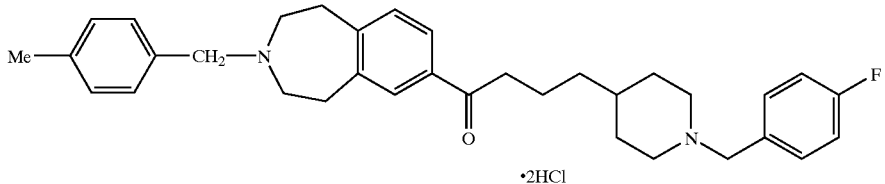

·2HCl

Using 4-[1-[(4-fluorophenyl)methyl]-4-piperidinyl]-1-(2,3,4,5-tetrahydro-1H-3-benzazepin-7-_yl)-1-butanone(free base), obtained in Example 171, and 4-methylbenzylbromide, the procedure of Example 28 was otherwise repeated to provide the title compound as colorless amorphous powders melting at 225–228° C.

$^1$H NMR (CDCl$_3$, free base) δ: 1.12–1.37 (5H, m), 1.50–2.00 (6H, m), 2.34 (3H,s), 2.56–2.69 (4H, m), 2.79–3.02 (8H, m), 3.45 (2H, s), 3.60 (2H, s), 6.99 (2H, t-like, J=8.8 Hz), 7.09–7.33 (7H, m), 7.64–7.72 (2H, m). Elemental analysis, for C$_{34}$H$_{41}$FN$_2$O.2HCl. Calcd.: C, 69.73; H, 7.40; N, 4.78. Found: C, 69.36; H, 7.36; N, 4.63.

EXAMPLE 193

4-[1-[(4-Methylphenyl)methyl]-4-piperidinyl]-1-(2,3,4,5-tetrahydro-1H-3-benzazepin-7-y )-1-butanone

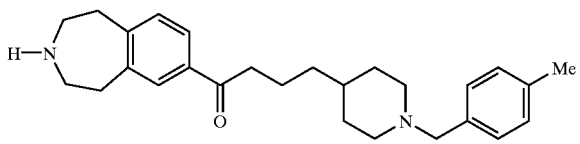

Using 4-[1-[(4-nitrobenzyl)oxycarbonyl]-4-piperidinyl]-1-(3-acetyl-2,3,4,5-tetrahydro-1H-3-benzazepin-7-yl)-1-butanone, obtained in Example 170-1, and 4-methylbenzyl bromide, the procedure of Example 170-2, followed Example 171 was otherwise repeated to provide the title compound as colorless amorphous powders.

$^1$H NMR (CDCl$_3$) δ: 1.11–1.38 (5H, m), 1.60–1.99 (7H, m), 2.33 (3H, s), 2.80–3.04 (12H, m), 3.45 (2H, s), 7.08–7.25 (5H, m), 7.65–7.76 (2H, m).

EXAMPLE 194

1-[3-(Phenylmethyl)-2,3,4,5-tetrahydro-1H-3-benzazepin-7-yl]-3-(1-propionyl-4-piperidinyl)-1-propanone Hydrochloride

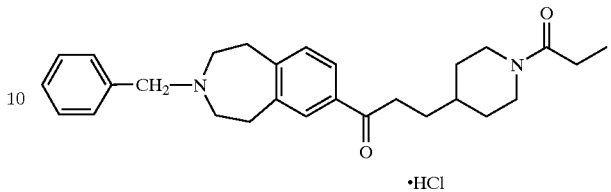

·HCl

Using 1-[3-(phenylmethyl)-2,3,4,5-tetrahydro-1H-3-benzazepin-7-yl]-3-(4-piperidinyl)-1-propanone(free base), obtained in Example 24, and propionyl chloride, the procedure of Example 28 was otherwise repeated to provide the title compound as amorphous powders.

$^1$H NMR (CDCl$_3$, free base) δ: 1.02–1.29 (5H, m), 1.45–1.90 (5H, m), 2.34 (2H, q, J=7.7 Hz), 2.43–2.74 (5H, m), 2.89–3.08 (7H, m), 3.67 (2H, s), 3.77–3.92 (1H, m), 4.56–4.70 (1H, m), 7.16 (1H, d, J=7.7 Hz), 7.22–7.40 (5H, m), 7.64–7.74 (2H, m). Elemental analysis, for C$_{28}$H$_{36}$N$_2$O$_2$.HCl.2.5H$_2$O. Calcd.: C, 65.42; H, 8.23; N, 5.45. Found: C, 65.20; H, 7.72; N, 5.49.

EXAMPLE 195

3-[1-(2-Methyl)propionyl-4-piperidinyl]-1-[3-(phenylmethyl)-2,3,4,5-tetrahydro-1H-3-benzazepin-7-yl]-1-propanone Hydrochloride

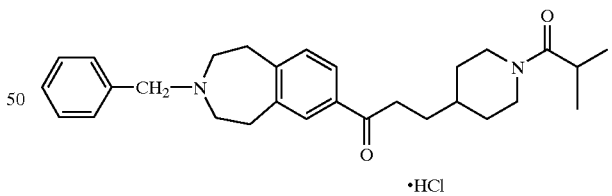

·HCl

Using 1-[3-(phenylmethyl)-2,3,4,5-tetrahydro-1H-3-benzazepin-7-yl]-3-(4-piperidinyl)-1-propanone(free base), obtained in Example 24, and isobutylyl chloride, the procedure of Example 28 was otherwise repeated to provide the title compound as amorphous powders.

$^1$H NMR (CDCl$_3$, free base) δ: 1.00–1.27 (8H, m), 1.47–1.88 (5H, m), 2.38–3.08 (13H, m), 3.67 (2H, s), 3.83–4.00 (1H, m), 4.56–4.72 (1H, m), 7.16 (1H, d, J=7.3 Hz), 07.20–7.40 (5H, m), 7.65–7.74 (2H, m). Elemental analysis, for C$_{29}$H$_{38}$N$_2$O$_2$.HCl.H$_2$O. Calcd.: C, 69.51; H, 8.25; N, 5.59. Found: C, 69.51; H, 8.17; N, 5.58.

EXAMPLE 196

Ethyl 4-[4-[3-[3-(Phenylmethyl)-2,3,4,5-tetrahydro-1H-3-benzazepin-7-yl]-3-oxopropyl]-1-piperidinyl]-4-oxobutanoate Hydrochloride

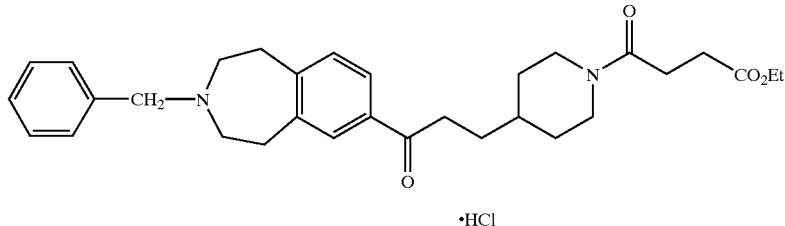

•HCl

Using 1-[3-(phenylmethyl)-2,3,4,5-tetrahydro-1H-3-benzazepin-7-yl]-3-(4-piperidinyl)-1-propanone(free basel), obtained in Example 24, and ethylsuccinylchloride the procedure of Example 28 was otherewise repeated to provide the title compound as amorphous powders.

$^1$H NMR (CDCl$_3$, free base) δ: 1.00–1.31 (5H, m), 1.47–25 1.86 (5H, m), 2.45–2.72 (9H, m), 2.88–3.09 (7H, m), 3.65 (2H, s), 3.81–3.97 (1H, m), 4.15 (2H, q, J=7.2 Hz), 4.52–4.66 (1H, m), 7.16 (1H, d, J=7.3 Hz), 7.23–7.40 (5H, m), 7.64–7.73 (2H, m). Elemental analysis, for C$_{31}$H$_{40}$N$_2$O$_4$.HCl.H$_2$O. Calcd.: C, 66.59; H, 7.75; N, 5.01. Found: C, 66.14; H, 7.67; N, 4.88.

EXAMPLE 197

Ethyl 5-[4-[3-[3-(Phenylmethyl)-2,3,4,5-tetrahydro-1H-3-benzazepin-7-yl]-3-oxopropyl]-1-piperidinyl]-5-oxopentanoate Hydrochloride

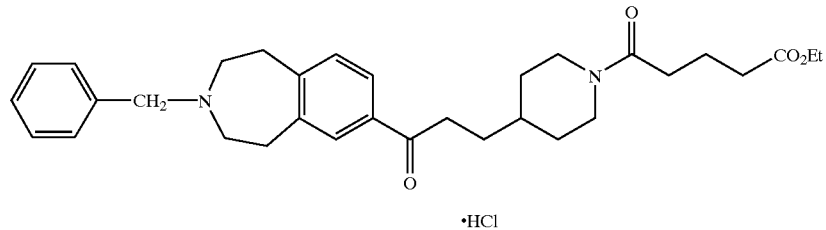

•HCl

Using 1-[3-(phenylmethyl)-2,3,4,5-tetrahydro-1H-3-benzazepin-7-yl]3-(4-piperidinyl)1propanone(free base), obtained in Example 24, and ethylmalonylchloride, the procedure of Example 28 was otherewise repeated to provide the title compound as amorphous powders.

$^1$H NMR (CDCl$_3$, free base) δ: 1.00–1.31 (5H, m), 1.46–2.05 (7H, m), 2.32–3.07 (16H, m), 3.68 (2H, s), 3.79–3.93 (1H, m), 4.13 (2H, q, J=7.2 Hz), 4.54–4.68 (1H, m), 7.17 (1H, d, J=8.0 Hz), 7.22–7.38 (5H, m), 7.65–7.73 (2H, m). Elemental analysis, for C$_{32}$H$_{42}$N$_2$O$_4$.HCl.2.5H$_2$O. Calcd.: C, 64.04; H, 8.06; N, 4.67. Found: C, 64.48; H, 7.75; N, 4.51.

EXAMPLE 198

4-[1-[(4-Methylphenyl)methyl]-4-piperidinyl]-1-[3-[(2-nitrophenyl)methyl]-2,3,4,5-tetrahydro-1H-3-benzazepin-7-yl]-1-butanone Dihydrochloride

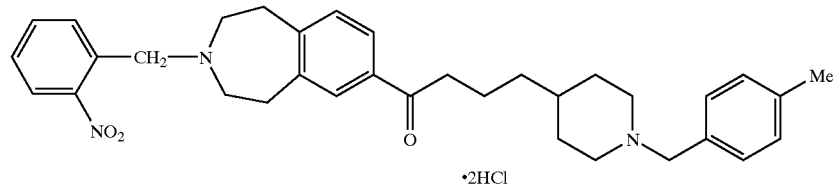

•2HCl

Using 4-[1-[(4-methylphenyl)methyl]-4-piperidinyl]-1-(2,3,4,5-tetrahydro-1H-3-benzazepin-7-yl)-1-butanone(free base), obtained in Example 193, and 2-nitrobenzylbromide, the procedure of Example 28 was otherwise repeated to provide the title compound as colorless powders melting at 164–167° C.

$^1$H NMR (CDCl$_3$, free base) δ: 1.08–1.36 (5H, m), 1.52–35 2.00 (6H, m), 2.33 (3H, s), 2.54–2.64 (4H, m), 2.80–2.97 (8H, m), 3.47 (2H, s), 3.88 (2H, s), 7.07–7.26 (5H, m), 7.35–7.73 (5H, m), 7.82 (1H, d, J=7.7 Hz). Elemental analysis, for C$_{34}$H$_{41}$N$_3$O$_3$.2HCl.H$_2$O. Calcd.: C, 64.75; H, 7.19; N, 6.66. Found: C, 65.10; H, 6.86; N, 6.64.

EXAMPLE 199

4-[1-[(4-Methylphenyl)methyl]-4-piperidinyl]-1-[3-[(3-nitrophenyl)methyl]-2,3,4,5-tetrahydro-1H-3-benzazepin-7-yl]-1-butanone Dihydrochloride

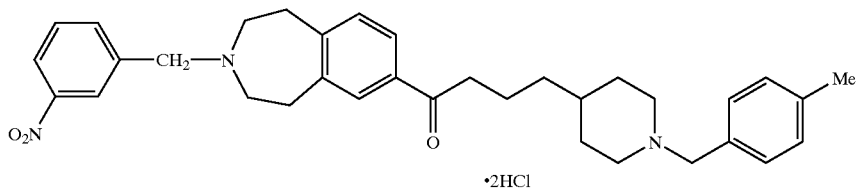

Using 4-[1-[(4-methylphenyl)methyl]-4-piperidinyl]-1-(2,3,4,5-tetrahydro-1H-3-benzazepin-7-yl)-1-butanone(free base), obtained in Example 193, and 3-nitrobenzyl bromide, the procedure of Example 28 was otherwise repeated to provide the title compound as colorless powder melting at 172–174° C.

$^1$H NMR (CDCl$_3$, free base) δ: 1.14–1.38 (5H, m), 1.53–2.02 (6H, m), 2.33 (3H, s), 2.58–2.70 (4H, m), 2.82–3.06 (8H, m), 3.47 (2H, s), 3.71 s(2H, s), 7.08–7.26 (5H, m), 7.51 (1H, t, J=7.9 Hz), 7.66–7.77 (3H, m), 8.10–8.19 (1H, m), 8.26 (1H, brs). Elemental analysis, for C$_{34}$H$_{41}$N$_3$O$_3$.2HCl.H$_2$O. Calcd.: C, 64.75; H, 7.19; N, 6.66. Found: C, 64.81; H, 6.76; N, 6.64.

EXAMPLE 200

4-[1-[(4-Methylphenyl)methyl)-4-piperidinyl]-1-[3-[(4-nitrophenyl)methyl]-2,3,4,5-tetrahydro-1H-3-benzazepin-7-yl]-1-butanone Dihydrochloride

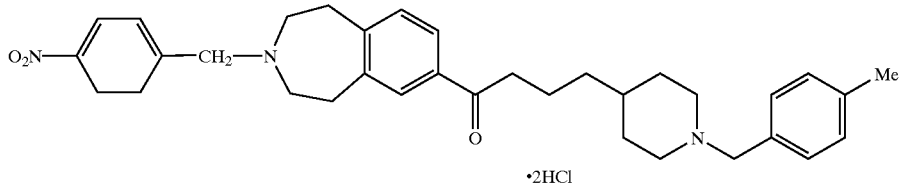

Using 4-[1-[(4-methylphenyl)methyl]-4-piperidinyl]-1-(2,3,4,5-tetrahydro-1H-3-benzazepin-7-yl)-1-butanone(free base), obtained in Example 193, and 4-nitrobenzylbromide, the procedure of Example 28 was otherwise repeated to provide the title compound as colorless powder melting at 208–211° C.

$^1$H NMR (CDCl$_3$, free base) δ: 1.09–1.37 (5H, m), 1.48–1.80 (4H, m), 1.82–2.00 (2H, m), 2.33 (3H, s), 2.57–2.68 (4H, m), 2.80–3.04 (8H, m), 3.47 (2H, s), 3.71 (2H, s), 7.07–7.25 (5H, m), 7.56 (2H, d, J=8.8 Hz), 7.65–7.74 (2H, m), 8.20 (2H, d, J,=8.8 Hz). Elemental analysis, for C$_{34}$H$_{41}$N$_3$O$_3$.2HCl.0.5H$_2$O. Calcd.: C, 65.69; H, 7.13; N, 6.76. Found: C, 65.88; H, 6.91; N, 6.85.

EXAMPLE 201

1-[3-[(2-Chlorophenyl)methyl]-2,3,4,5-tetrahydro-1H-3-benzazepin-7-yl]-4-[1-[(4-methylphenyl)methyl]-4-piperidinyl]-1-butanone Dihydrochloride

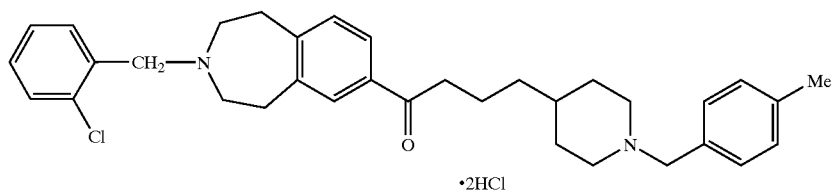

Using 4-[1-[(4-methylphenyl)methyl]-4-piperidinyl]-1-(2,3,4,5-tetrahydro-1H-3-benzazepin-7-yl)-1-butanone(free base), obtained in Example 193, 2-chlorobenzyl chloride, and potassium iodide, the procedure of Example 28 was otherwise repeated to provide the title compound as colorless powders melting at 174–178° C.

$^1$H NMR (CDCl$_3$, free base) δ: 1.08–1.37 (5H, m), 1.48–1.80 (4H, m), 1.84–2.00 (2H, m), 2.33 (3H, s), 2.65–2.75 (4H, m), 2.80–3.04 (8H, m), 3.46 (2H, s), 3.73

(2H, s), 7.07–7.40 (8H, m), 7.57 (1H, dd, J=2.0, 7.4 Hz), 7.66–7.75 (2H, m). Elemental analysis, for $C_{34}H_{41}ClN_2O_2HCl.0.5H_2O$. Calcd.: C, 66.83; H, 7.26; N, 4.58. Found: C, 66.85; H, 6.96; N, 4.59.

EXAMPLE 202

1-[3-[(3-Chlorophenyl)methyl]-2,3,4,5-tetprahydro-1H-3-benzazepin-7-yl]-4-[1-[(4-methylphenyl)methyl]-4-piperidinyl]-1-butanone Dihydrochloride

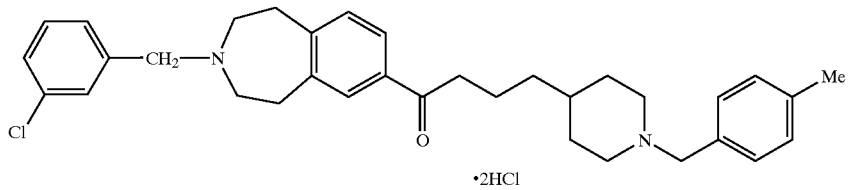

Using 4-[1-[(4-methylphenyl)methyl]-4-piperidinyl]-1-(2,3,4,5-tetrahydro-1H-3-benzazepin-7-yl)-1-butanone(free base), obtained in Example 193, and 3-chlorobenzylbromide, the procedure of Example 28 was otherwise repeated to provide the title compound as colorless powders melting at 195–198° C.

$^1$H NMR (CDCl$_3$, free base) δ: 1.13–1.37 (5H, m), 1.50–1.80 (4H, m), 1.84–2.03 (2H, m), 2.33 (3H, s), 2.56–2.68 (4H, m), 2.82–3.03 (8H, m), 3.48 (2H, s), 3.60 (2H, s), 7.07–7.29 (8H, m), 7.38 (1H, s), 7.65–7.74 (2H, m). Elemental analysis, for $C_{34}H_{41}ClN_2O.2HCl.0.5H_2O$. Calcd.: C, 66.83; H, 7.26; N, 4.58. Found: C, 66.88; H, 7.12; N, 4.69.

EXAMPLE 203

1-[3-[(4-Chlorophenyl)methyl]-2,3,4,5-tetrahydro-1H-3-benzazepin-7-yl]-4-[1-[(4-methylphenyl)methyl]-4-piperidinyl]-1-butanone Dihydrochloride

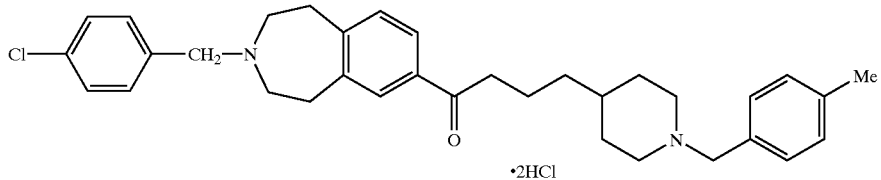

Using 4-[1-[(4-methylphenyl)methyl]-4-piperidinyl]-1-(2,3,4,5-tetrahydro-1H-3-benzazepin-7-yl)-1-butanone(free base), obtained in Example 193, and 4-chlorobenzylbromide, the procedure of Example 28 was otherwise repeated to provide the title compound as colorless powders melting at 230–234° C.

$^1$H NMR (CDCl$_3$, free base) δ: 1.07–1.38 (5H, m), 1.52–2.00 (6H, m), 2.33 (3H, s), 2.54–2.67 (4H, m), 2.80–3.02 (8H, m), 3.46 (2H, s), 3.58 (2H, s), 7.07–7.33 (9H, m), 7.65–7.74 (2H, m). Elemental analysis, for $C_{34}H_{41}ClN_2O.2HCl.0.5H_2O$. Calcd.: C, 66.83; H, 7.26; N, 4.58. Found: C, 66.81; H, 7.03; N, 4.65.

EXAMPLE 204

1-[3-[(2-Cyanophenyl)methyl]-2,3,4,5-tetrahydro-1H-3-benzazepin-7-yl]-4-[1-[(4-methylphenyl)methyl]-4-piperidinyl]-1-butanone Dihydrochloride

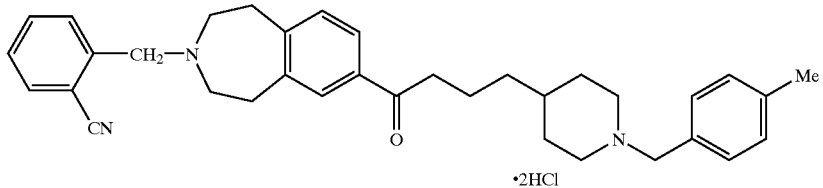

Using 4-[1-[(4-methylphenyl)methyl]-4-piperidinyl]-1-(2,3,4,5-tetrahydro-1H-3-benzazepin-7-yl)-1-butanone(free base), obtained in Example 193, and 2-cyanobenzylbromide, the procedure of Example 28 was otherewise repeated to provide the title compound as colorless powders softing 145–150° C.

$^1$H NMR (CDCl$_3$, free base) δ: 1.14–1.40 (5H, m), 1.55–2.00 (6H, m), 2.33 (3H, s), 2.64–2.76 (4H, m), 2.80–3.05 (8H, m), 3.46 (2H, s), 3.81 (2H, s), 7.08–7.24 (4H, m), 7.32–7.44 (1H, m), 7.56–7.75 (6H, m). Elemental analysis, for C$_{35}$H$_{41}$N$_3$O.2HCl.H$_2$O. Calcd.: C, 68.84; H, 7.43; N, 6.88. Found: C, 68.76; H, 7.67; N, 6.55.

EXAMPLE 205

1-[3-[(3-Cyanophenyl)methyl]-2,3,4,5-tetrahydro-1H-3-benzazepin-7-yl]-4-[1-[(4-methylphenyl)methyl]-4-piperidinyl]-1-butanone Dihydrochloride

Using 4-[1-[(4-methylphenyl)methyl]-4-piperidinyl]-1-(2,3,4,5-tetrahydro-1H-3-benzazepin-7-yl)-1-butanone(free base), obtained in Example 193, and 3-cyanobenzyl bromide, the procedure of Example 28 was otherewise repeated to provide the colorless powders as colorless powders softing 205–212° C.

$^1$H NMR (CDCl$_3$, free base) δ: 1.16–1.38 (5H, m), 1.52–2.02 (6H, m), 2.33 (3H, s), 2.56–2.69 (4H, m), 2.80–3.04 (8H, m), 3.48 (2H, s), 3.64 (2H, s), 7.08–7.25 (5H, m), 7.39–7.50 (1H, m), 7.53–7.64 (2H, m), 7.67–7.77 (3H, m). Elemental analysis, for C$_{35}$H$_{41}$N$_3$O.2HCl.H$_2$O. Calcd.: C, 68.84; H, 7.43; N, 6.88. Found: C, 69.06; H, 7.22; N, 6.66.

EXAMPLE 206

1-[3-[(4-Cyanophenyl)methyl]-2,3,4,5-tetrahydro-1H-3-benzazepin-7-yl]-4-[1-[(4-methylphenyl)methyl]-4-piperidinyl]-1-butanone Dihydrochloride

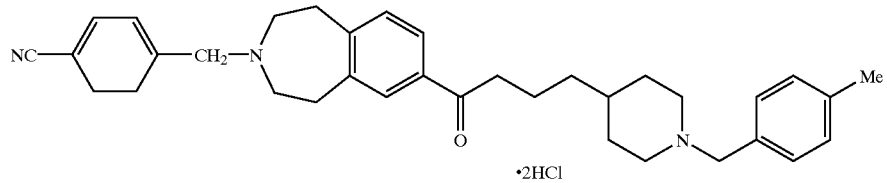

Using 4-[1-[(4-methylphenyl)methyl]-4-piperidinyl]-1-(2,3,4,5-tetrahydro-1H-3-benzazepin-7-yl)-1-butanone(free base), obtained in Example 193, and 4-cyanobenzyl bromide, the procedure of Example 28 was otherwise repeated to provide the title compound as colorless powders melting at 206–209° C. (dec.).

¹H NMR (CDCl₃, free base) δ: 1.14–1.39 (5H, m), 1.58–2.03 (6H, m), 2.34 (3H, s), 2.55–2.69 (4H, m), 2.82–3.04 (8H, m), 3.47 (2H, s), 3.67 (2H, s), 7.09–7.30 (5H, m), 7.47–7.56 (2H, m), 7.61–7.77 (4H, m). Elemental analysis, for $C_{35}H_{41}N_3O \cdot 2HCl \cdot 0.5H_2O$. Calcd.: C, 69.87; H, 7.37; N, 6.98. Found: C, 69.97; H, 7.10; N, 6.98.

EXAMPLE 207

5-(1-Acetyl-4-piperidinyl)-1-(3-acetyl-2,3,4,5-tetrahydro-1H-3-benzazepin-7-yl)-1-pentanone

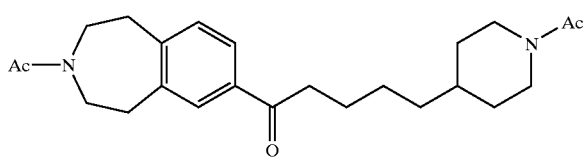

Using 5-(1-acetyl-4-piperidinyl)valeric acid and 3-acetyl-2,3,4,5-tetrahydro-1H-3-benzazepine, the procedure of Example 23-1 was otherwise repeated to provide the title compound as colorless oil.

¹H NMR (CDCl₃) δ: 0.96–1.60 (7H, m), 1.64–1.84 (4H, m), 2.08 (3H, s), 2.20 (3H, s), 2.44–2.61 (1H, m), 2.87–3.10 (7H, m), 3.55–3.86 (5H, m), 4.53–4.67 (1H, m), 7.20–7.30 (1H, m), 7.71–7.80 (2H, m).

EXAMPLE 208

5-(4-Piperidinyl)-1-(2,3,4,5-tetrahydro-1H-3-benzazepin-7-yl)-1-pentanone

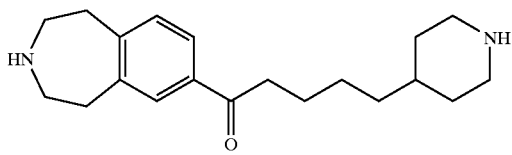

Using 5-(1-acetyl-4-piperidinyl)-1-(3-acetyl-2,3,4,5-tetrahydro-1H-3-benzazepin-7-yl)-1-pentanone, obtained in Example 207, the procedure of Example 24 was otherwise repeated to provide the title compound as colorless oil.

¹H NMR (CDCl₃) δ: 0.97–1.48 (7H, m), 1.60–1.84 (4H, m), 1.91 (2H, brs), 2.56 (2H, dt-like, J=2.6, 12.1 Hz), 2.83–3.12 (12H, m), 7.18 (1H, d, J=8.4 Hz), 7.67–7.74 (2H, m).

EXAMPLE 209

5-[1-(Phenylmethyl)-4-piperidinyl]-1-[3-(phenylmethyl)-2,3,4,5-tetrahydro-1H-3-benzazepin-7-yl]-1-pentanone Dihydrochloride

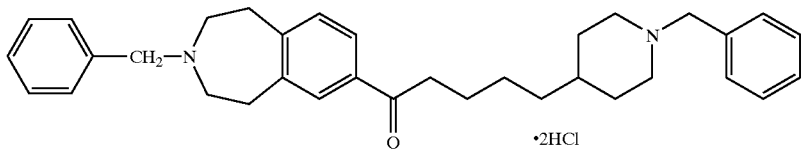

Using 5-(4-piperidinyl)-1-(2,3,4,5-tetrahydro-1H-3-benzazepin-7-yl)-1-pentanone, obtained in Example 208, and 2 molar equivalent benzyl bromide, the, procedure of Example 28 was otherwise repeated to provide the title compound (free base) as colorless powders melting at 81–83° C., and the title compound (dihydrochloride salt) as colorless powders melting at 208–210° C.

¹H NMR (CDCl₃, free base) δ: 1.10–1.47 (7H, m), 1.55–1.81 (4H, m), 1.84–2.00 (2H, m), 2.55–2.69 (4H, m), 2.80–3.03 (8H, m), 3.49 (2H, s), 3.64 (2H, s), 7.16 (1H, d, J=7.7 Hz), 7.20–7.41 (10H, m), 7.65–7.74 (2H, m). Elemental analysis, for $C_{34}H_{42}N_2O \cdot 2HCl \cdot 0.5H_2O$. Calcd.: C, 70.82; H, 7.87; N, 4.86. Found: C, 71.04; H, 7.56; N, 4.84.

EXAMPLE 210

3-(1-Acetyl-4-piperidinyl)-1-[2-[(4-fluorophenyl)methyl]-2,3,4,5-tetrahydro-1H-2-benzazepin-8-yl]-1-propanone Dihydrochloride

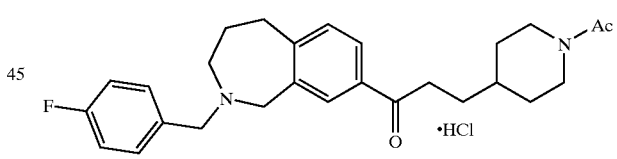

Using 3-(1-acetyl-4-piperidinyl)-1-(2,3,4,5-tetrahydro-1H-2-benzazepin-8-yl)-1-propanone (free base), obtained in Example 51-2, and 4-fluorobenzyl bromide, the procedure of Example 51-3 was otherwise repeated to provide the title compound as colorless amorphous powders.

¹H NMR (CDCl₃, free base) δ: 1.00–1.40 (2H, m), 1.40–1.85 (8H, m), 2.09 (3H, s), 2.53 (1H, dt, J=12.8, 2.6 Hz), 2.85–3.05 (4H, m), 3.11 (2H, t-like, J=5.6 Hz), 3.50 (2H, s), 3.70–3.90 (1H, m), 3.90 (2H, s), 4.50–4.70 (1H, m), 7.00 (2H, t-like, J=8.8 Hz), 7.15–7.30 (3H, m), 7.48 (1H, d, J=2.0 Hz), 7.76 (1H, dd, J=7.8, 2.0 Hz). Elemental analysis, for $C_{27}H_{33}FN_2O_2 \cdot HCl \cdot 1.5H_2O$. Calcd.: C, 64.85; H, 7.46; N, 5.60. Found: C, 64.83; H, 7.34; N, 5.57.

EXAMPLE 211

1-[2-[(4-Fluorophenyl)methyl]-2,3,4,5-tetrahydro-1H-2-benzazepin-8-yl]-3-(4-piperidinyl)-1-propanone dihydrochloride

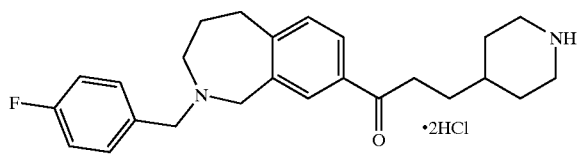

Using 3-(1-acetyl-4-piperidinyl)-1-[2-[(4-fluorophenyl)methyl]-2,3,4,5-tetrahydro-1H-2-benzazepin-8-yl]-1-propanone, obtained in Example 210, the procedure of Example 53 was otherwise repeated to provide the title compound as colorless powders melting at 245–247° C.

$^1$H NMR (CDCl$_3$, free base) δ: 1.00–1.35 (3H, m), 1.35–1.55 (1H, m), 1.60–1.85 (7H, m), 2.58 (2H, dt, J=12.0, 2.0 Hz), 2.85–3.20 (7H, m), 3.49 (2H, s), 3.90 (2H, s), 7.00 (2H, t-like, J=8.8 Hz), 7.15–7.30 (3H, m), 7.49 (1H, d, J=1.8 Hz), 7.76 (1H, dd, J=8.2, 1.8 Hz). Elemental analysis, for C$_{25}$H$_{31}$FN$_2$O.2HCl.H$_2$O. Calcd.: C, 61.85; H, 7.27; N, 5.77. Found: C, 62.08; H, 7.12; N, 5.58.

EXAMPLE 212

1-[2-[(4-Fluorophenyl)methyl]-2,3,4,5-tetrahydro-1H-2-benzazepin-8-yl]-3-[1-(phenylmethyl)-4-piperidinyl]-1-propanone Dihydrochloride

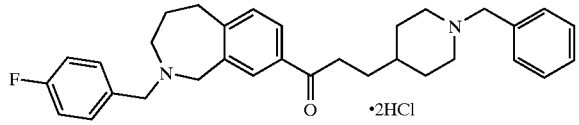

Using 1-[2-[(4-fluorophenyl)methyl]-2,3,4,5-tetrahydro-1H-2-benzazepin-8-yl]-3-(4-piperidinyl)-1-propanone(free base), obtained in Example 211, and benzyl bromide, the procedure of Example 61-3 was otherwise repeated to provide the title compound as colorless amorphous powders.

$^1$H NMR (CDCl$_3$, free base) δ: 1.20–1.45 (3H, m), 1.60–1.80 (6H, m), 1.80–2.05 (2H, m), 2.80–3.00 (6H, m), 3.10 (2H, t-like, J=5.2 Hz), 3.48 (.4H, s), 3.89 (2H, s), 6.98 (2H, t-like, J=8.8 Hz), 7.15–7.35 (88H, m), 7.48 (1H, d, J=1.8 Hz), 7.75 (1H, dd, J=7.6, 1.8 Hz). Elemental analysis, for C$_{32}$H$_{37}$FN$_2$O.2HCl.1.5H$_2$O. Calcd.: C, 65.75; H, 7.24; N, 4.79. Found: C, 65.74; H, 7.60; N, 4.47.

EXAMPLE 213

1-[2-[(4-Fluorophenyl)methyl]-2,3,4,5-tetrahydro-1H-2-benzazepin-8-yl]-3-[1-[(2-methylphenyl)methyl]-4-piperidinyl]-1-propanone Dihydrochloride

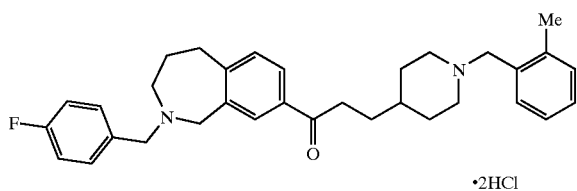

Using 1-[2-[(4-fluorophenyl)methyl]-2,3,4,5-tetrahydro-1H-2-bonzazepin-8-yl]-3-(4-piperidinyl)-1-propanone (free base), obtained in Example 211, and 2-methylbenzyl bromide, the procedure of Example 51-3 was otherwise repeated to provide the title compound as colorless amorphous powders.

$^1$H NMR (CDCl$_3$, free base) δ: 1.15–1.40 (3H, m), 1.60–1.80 (6H, m), 1.85–2.05 (2H, m), 2.35 (3H, s), 2.80–3.00 (6H, m), 3.11 (2H, t-like, J=5.2 Hz), 3.42 (2H, s), 3.48 (2H, s), 3.89 (2H, s), 6.99 (2H, t-like, J=8.8 Hz), 7.15–7.35 (7H, m), 7.48 (1H, d, J=1.8 Hz), 7.76 (1H, dd, J=7.7, 1.8 Hz). Elemental analysis, for C$_{33}$H$_{39}$FN$_2$O.2HCl.H$_2$O. Calcd.: C, 67.22; H, 7.35; N, 4.75. Found: C, 66.89; H, 7.80; N, 4.51.

EXAMPLE 214

1-[2-[(4-Fluorophenyl)methyl]-2,3,4,5-tetrahydro-1H-2-benzazepin-8-yl]-3-[1-[(3-methylphenyl)methyl]-4-piperidinyl]-1-propanone Dihydrochloride

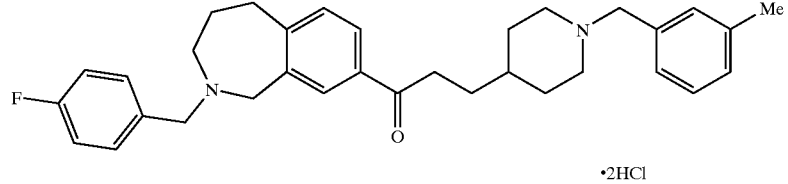

Using 1-[2-[(4-fluorophenyl)methyl]-2,3,4,5-tetrahydro-1H-2-benzazepin-8-yl]-3-(4-piperidinyl)-1-propanone (free base), obtained in Example 211, and 3-methylbenzyl bromide, the procedure of Example 51-3 was otherwise repeated to provide the title compound as colorless amorphous powders.

$^1$H NMR (CDCl$_3$, free base) δ: 1.20–1.45 (3H, m), 1.60–1.80 (6H, m), 1.80–2.05 (2H, m), 2.33 (3H, s), 2.80–3.00 (6H, m), 3.10 (2H, t-like, J=5.2 Hz), 3.45 (2H, s), 3.48 (2H, s), 3.89 (2H, s), 6.98 (2H, t-like, J=8.8 Hz), 7.15–7.30 (7H, m), 7.48 (1H, d, J=1.8 Hz), 7.75 (1H, dd, J=7.6, 1.8 Hz). Elemental analysis, for C$_{33}$H$_{39}$FN$_2$O.2HCl.1.5H$_2$O. Calcd.: C, 66.21; H, 7.41; N, 4.68. Found: C, 66.46; H, 7.50; N, 4.46.

EXAMPLE 215

1-[2-[(4-Fluorophenyl)methyl]-2,3,4,5-tetrahydro-1H-2-benzazepin-8-yl]-3-[1-[(4-methylphenyl)methyl]-4-piperidinyl]-1-propanone Dihydrochloride

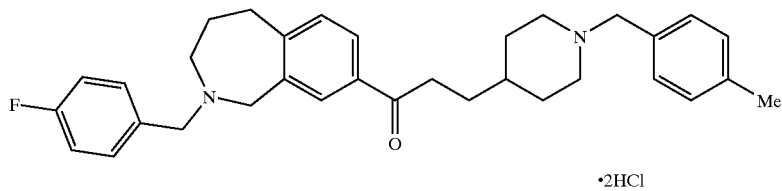

·2HCl

Using 1-[2-[(4-fluorophenyl)methyl]-2,3,4,5-tetrahydro-1H-2-benzazepin-8-yl]-3-(4-piperidinyl)-1-propanone (free base), obtained in Example 211, and 4-methylbenzyl bromide, the procedure of Example 51-3 was otherewise repeated to provide the title compound as colorless amorphous powders.

$^1$H NMR (CDCl$_3$, free base) δ: 1.20–1.45 (3H, m), 1.60–1.80 (6H, m), 1.80–2.00 (2H, m), 2.32 (3H, s), 2.80–3.00 (6H, m), 3.10 (2H, t-like, J=5.2 Hz), 3.45 (2H, s), 3.48 (2H, s), 3.89 (2H, s), 6.98 (2H, t-like, J=8.8 Hz), 7.05–7.30 (7H, m), 7.48 (1H, d, J=1.8 Hz), 7.75 (1H, dd, J=7.6, 1.8 Hz). Elemental analysis., for C$_{33}$H$_{39}$FN$_2$O.2HCl.0.5H$_2$O. Calcd.: C, 68.27; H, 7.29; N, 4.82. Found: C, 68.02; H, 7.00; N, 4.91.

EXAMPLE 216

3-[1-[(2-Chlorophenyl)methyl]-4-piperidinyl]-1-[2-[(4-fluorophenyl)methyl]-2,3,4,5-tetrahydro-1H-2-benzazepin-8-yl]-1-propanone Dihydrochloride

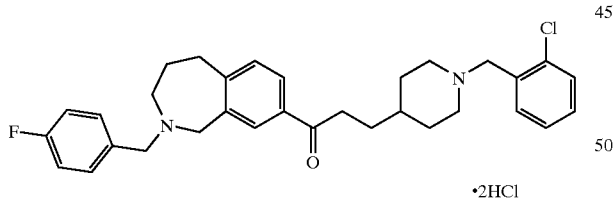

·2HCl

Using 1-[2-[(4-fluorophenyl)methyl]-2,3,4,5-tetrahydro-1H-2-benzazepin-8-yl]-3-(4-piperidinyl)-1-propanone(free base) obtained in Example 211, 2-chlorobenzylchloride, and potassium iodide, the procedure of Example 51-3 was otherewise repeated to provide the title compound as colorless amorphous powders.

$^1$H NMR (CDCl$_3$, free base) δ: 1.20–1.45 (3H, m), 1.50–1.85 (6H, m), 1.85–2.20 (2H, m), 2.80–3.05 (6H, m), 3.11 (2H, t-like, J=5.2 Hz), 3.49 (2H, s), 3.60 (2H, s), 3.90 (2H, s), 6.99 (2H, t-like, J=8.8 Hz), 7.10–7.30 (5H, m), 7.33 (1H, dd, J=7.5, 1.8 Hz), 7.45–7.55 (2H, m), 7.76 (1H, dd, J=7.7, 1.8 Hz). Elemental analysis, for C$_{32}$H$_{36}$ClFN$_2$O.2HCl.1.5H$_2$O. Calcd.: C, 62.09; H, 6.68; N, 4.53. Found: C, 62.26; H, 7.06; N, 4.26.

EXAMPLE 217

3-[1-[(3-Chlorophenyl)methyl]-4-piperidinyl]-1-[2-[(4-fluorophenyl)methyl]-2,3,4,5-tetrahydro-1H-2-benzazepin-8-yl]-1-propanone Dihydrochloride

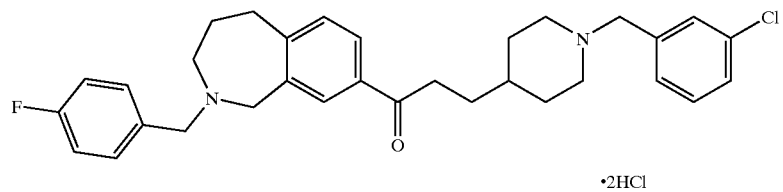

·2HCl

Using 1-[2-[(4-fluorophenyl)methyl]-2,3,4,5-tetrahydro-1H-2-benzazepin-8-yl]-3-(4-piperidinyl)-1-propanone(free base) obtained in Example 211, and 3-chlorobenzyl bromide, the procedure of Example 51-3 was otherwise repeated to provide the title compound as colorless amorphous powders.

¹H NMR (CDCl₃, free base) δ: 1.20–1.45 (3H, m), 1.50–1.80 (6H, m), 1.85–2.05 (2H, m), 2.80–3.00 (6H, m), 3.10 (2H, t-like, J=5.6 Hz), 3.44 (2H, s), 3.48 (2H, s), 3.89 (2H, s), 6.99 (2H, t-like, J=8.8 Hz), 7.10–7.30 (6H, m), 7.32 (1H, s), 7.48 (1H, d, J=1.8 Hz), 7.76 (1H, dd, J=7.7, 1.8 Hz). Elemental analysis, for $C_{32}H_{36}ClFN_2O \cdot 2HCl \cdot H_2O$. Calcd.: C, 63.00; H, 6.61; N, 4.59. Found: C, 62.61; H, 7.10; N, 4.33.

EXAMPLE 218

3-[1-[(4-Chlorophenyl)methyl]-4-piperidinyl]-1-[2-[(4-fluorophenyl)methyl]-2,3,4,5-tetrahydro-1H-2-benzazepin-8-yl]-1-propanone Dihydrochloride

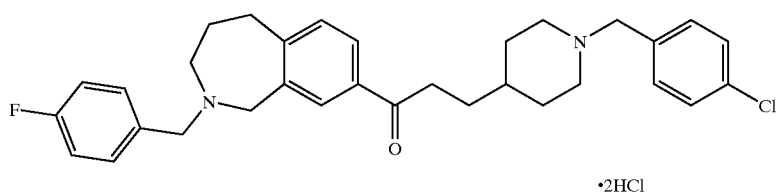

•2HCl

Using 1-[2-[(4-fluorophenyl)methyl]-2,3,4,5-tetrahydro-1H-2-benzazepin-8-yl]-3-(4-piperidinyl)-1-propanone(free base) obtained in Example 211, and 4-chlorobenzyl bromide, the procedure of Example 51-3 was otherwise repeated to provide the title compound as colorless amorphous powders.

¹H NMR (CDCl₃, free base) δ: 1.20–1.40 (3H, m), 1.60–1.80 (6H, m), 1.85–2.00 (2H, m), 2.80–3.00 (6H, m), 3.10 (2H, t-like, J=5.4 Hz), 3.43 (2H, s), 3.48 (2H, s), 3.89 (2H, s), 6.99 (2H, t-like, J=8.8 Hz), 7.15–7.30 (7H, m), 7.48 (1H, d, J=1.8 Hz), 7.75 (1H, dd, J=7.8, 1.8 Hz). Elemental analysis, for $C_{32}H_{36}ClFN_2O \cdot 2HCl \cdot 0.5H_2O$. Calcd.: C, 63.95; H, 6.54; N, 4.66. Found C, 63.71; H, 6.49; N, 4.73.

EXAMPLE 219

1-[2-[(4-Fluorophenyl)methyl]-2,3,4,5-tetrahydro-1H-2-benzazepin-8-yl]-3-[1-[[2-(trifluoromethyl)phenyl]methyl]-4-piperidinyl]-1-propanone Dihydrochloride

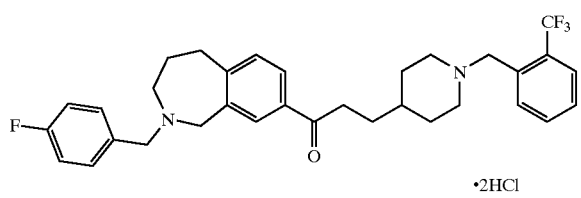

•2HCl

Using 1-[2-[(4-fluorophenyl)methyl]-2,3,4,5-tetrahydro-1H-2-benzazepin-8-yl]-3-(4-piperidinyl)-1-propanone(free base) obtained in Example 211, and 2-(trifluoromethyl)benzyl bromide, the procedure of Example 51-3 was otherwise repeated to provide the title compound as colorless amorphous powders.

¹H NMR (CDCl₃, free base) δ: 1.20–1.45 (3H, m), 1.50–1.90 (6H, m), 1.95–2.10 (2H, m), 2.80–3.00 (6H, m), 3.11 (2H, t-like, J=5.4 Hz), 3.49 (2H, s), 3.63 (2H, s), 3.90 (2H, s), 6.99 (2H, t-like, J=8.8 Hz), 7.20–7.40 (4H, m), 7.45–7.65 (3H, m), 7.75–7.90 (2H, m). Elemental analysis, for $C_{33}H_{36}FN_2O \cdot 2HCl \cdot 0.5H_2O$. Calcd.: C, 62.46; H 6.19; N, 4.41. Found: C, 62.43; H, 6.03; N, 4.39.

EXAMPLE 220

1-[2-[(4-Fluorophenyl)methyl]-2,3,4,5-tetrahydro-1H-2-benzazepin-8-yl]-3-[1-[[3-(trifluoromethyl)phenyl]methyl]-4-piperidinyl]-1-propanone Dihydrochloride

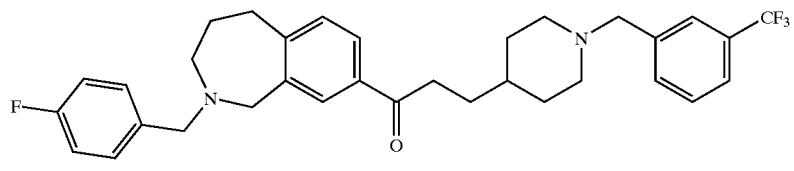

•2HCl

Using 1-[2-[(4-fluorophenyl)methyl]-2,3,4,5-tetrahydro-1H-2-benzazepin-8-yl]-3-(4-piperidinyl)-1-propanone(free base), obtained in Example 211, and 3-(trifluoromethyl) benzyl bromide, the procedure of Example 51-3 was otherwise repeated to provide the title compound as colorless powders melting at 197–199° C.

$^1$H NMR (CDCl$_3$, free base) δ: 1.20–1.45 (3H, m), 1.50–1.85 (6H, m), 1.90–2.10 (2H, m), 2.80–3.00 (6H, m), 3.11 (2H, t-like, J=5.2 Hz), 3.49 (2H, s), 3.52 (2H, s), 3.89 (2H, s), 6.99 (2H, t-like, J=8.8 Hz), 7.15–7.30 (3H, m), 7.35–7.60 (5H, m), 7.76 (1H, dd, J=7.7, 1.8 Hz). Elemental analysis, for C$_{33}$H$_{36}$F$_4$N$_2$O.2HCl. Calcd.: C, 63.36; H, 6.12; N, 4.48. Found: C, 62.88; H, 6.02; N, 4.83.

EXAMPLE 221

1-[2-[(4-Fluorophenyl)methyl]-2,3,4,5-tetrahydro-1H-2-benzazepin-8-yl]-3-[1-[[4-(trifluoromethyl)phenyl]methyl]-4-piperidinyl]-1-propanone Dihydrochloride

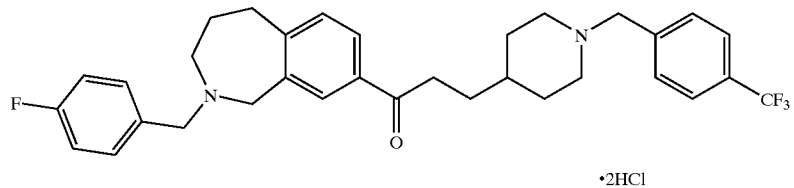

Using 1-[2-[(4-fluorophenyl)methyl]-2,3,4,5-tetrahydro-1H-2-benzazepin-8-yl]-3-(4-piperidinyl)-1-propanone(free base), obtained in Example 211, and 4-(trifluoromethyl) benzyl bromide, the procedure of Example 51-3 was otherwise repeated to provide the title compound as colorless amorphous powders.

$^1$H NMR (CDCl$_3$, free base) δ: 1.20–1.45 (3H, m), 1.50–1.80 (6H, m), 1.85–2.20 (2H, m), 2.80–3.00 (6H, m), 3.11 (2H, t-like, J=5.2 Hz), 3.49 (2H, s), 3.52 (2H, s), 3.89 (2H, s), 6.99 (2H, t-like, J=8.8 Hz), 7.15–7.30 (3H, m), 7.40–7.60 (5H, m), 7.76 (1H, dd, J=7.6, 1.8 Hz). Elemental analysis, for C$_{33}$H$_{36}$F$_4$N$_2$O.2HCl.0.5H$_2$O. Calcd.: C, 62.46; H, 6.19; N, 4.41. Found: C, 62.41; H, 6.24; N, 4.54.

EXAMPLE 222

1-[2-[(4-Fluorophenyl)methyl]-2,3,4,5-tetrahydro-1H-2-benzazepin-8-yl]-3-[1-[(3-nitrophenyl)methyl]-4-piperidinyl]-1-propanone Dihydrochloride

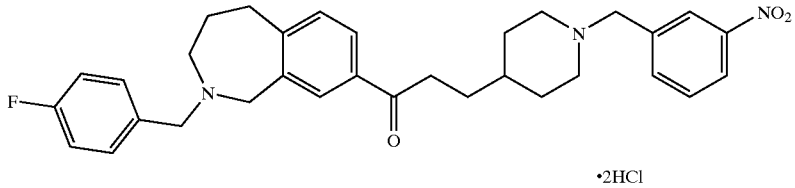

Using 1-[2-[(4-fluorophenyl)methyl]-2,3,4,5-tetrahydro-1H-2-benzazepin-8-yl]-3-(4-piperidinyl)-1-propanone(free base), obtained in Example 211, and 3-nitrobenzyl bromide, the procedure of Example 51-3 was otherwise repeated to provide the title compound as colorless amorphous powders.

$^1$H NMR (CDCl$_3$, free base) δ: 1.20–1.45 (3H, m), 1.50–1.85 (6H, m), 1.90–2.10 (2H, m), 2.80–3.05 (6H, m), 3.11 (2H, t-like, J=5.2 Hz), 3.49 (2H, s), 3.56 (2H, s), 3.89 (2H, s), 6.99 (2H, t-like, J=8.8 Hz), 7.15–7.30 (3H, m), 7.40–7.50 (2H, m), 7.70 (1H, d, J=7.6 Hz), 7.76 (1H, dd, J=7.8, 1.8 Hz), 8.10 (1H, d, J=8.0 Hz), 8.19 (1H, s). Elemental analysis, for C$_{32}$H$_{36}$FN$_3$O$_3$.2HCl.H$_2$O. Calcd.: C, 61.93; H, 6.50; N, 6.77. Found: C, 62.03; H, 6.25; N, 6.74.

EXAMPLE 223

3-[1-[(3-Aminophenyl)methyl]-4-piperidinyl]-1-[2-[(4-fluorophenyl)methyl]-2,3,4,5-tetrahydro-1H-2-benzazepin-8-yl]-1-propanone Dihydrochloride

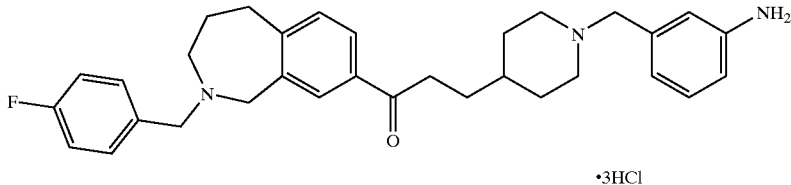

•3HCl

Zinc (3.0 g) was added to an acetic acid solution (25 ml) of 1-[2-[(4-fluorophenyl)methyl]-2,3,4,5-tetrahydro-1H-2-benzazepin-8-yl]-3-[1-[(3-nitrophenyl)methyl]-4-piperidinyl]-1-propanone (free base, 1.15 g, 2.17 mmol), obtained in Example 222, and heated at 100° C. for 3 minutes. The precipitate was removed by filtration and acetic acid was distilled off under reduced pressure. The residue was dissolved in water- ethyl acetate and extracted with ethyl acetate. The extract was washed successively with saturated NaHCO3/H2O and saturated NaCl/H2O and dried over K2CO3, and the solvent was distilled off under reduced pressure. The residue was purified by silica gel column chromatography (eluent: ethyl acetate-triethylamine=25:1) to provide the free base of title compound (337 mg) as a viscous oil.

$^1$H NMR (CDCl$_3$, free base) δ: 1.20–1.45 (3H, m), 1.50–1.80 (6H, m), 1.85–2.00 (2H, m), 2.80–3.00 (6H, m), 3.11 (2H, t-like, J=5.2 Hz), 3.41 (2H, s), 3.49 (2H, s), 3.50–3.80 (2H, br), 3.90 (2H, s), 6.55–6.65 (1H, m), 6.65–6.70 (2H, m), 6.95–7.15 (3H, m), 7.20–7.30 (3H, m), 7.49 (1H, d, J=1.4 Hz), 7.75 (1H, dd, J=8.1, 1.8 Hz).

The above free base (180 mg) was dissolved in ethyl acetate-methanol, treated with 3 molar equivalents of HCl (dissolved in ethyl acetate), and precipitated from ethyl acetate-ether to provide the title compound (186 mg) as colorless amorphous powders.

Elemental analysis, for C$_{32}$H$_{38}$FN$_3$O.3HCl.H$_2$O. Calcd.: C, 61.29; H, 6.91; N, 6.70. Found: C, 61.55; H, 7.04; N, 6.60.

EXAMPLE 224

N-[3-[[4-[3-[2-[(4-Fluorophenyl)methyl]-2,3,4,5-tetrahydro-1H-2-benzazepin-8-yl]-3-oxopropyl]-1-piperidinyl]methyl]phenyl]urea Dihydrochloride Potassium cyanate (134 mg, 1.65 mmol) was added to 3-[1-[(3-aminophenyl)methyl]-4-piperidinyl]-1-[2-[(4-fluorophenyl)methyl]-2,3,4,5-tetrahydro-1H-2-benzazepin-8-yl]-1-propanone (free base, 165 mg, 0.33 mmol), obtained in Example 223, in acetic acid (10 ml)-H2O (10 ml) at room temperature, and stirred for 30 minutes. Acetic acid was distilled off under reduced pressure and extracted with ethyl acetate. The extract was washed with saturated NaCl/H2O and dried over K2CO3, and the solvent was distilled off under reduced pressure. The residue was purified by silica gel column chromatography (eluent: ethyl acetate-methanol-triethylamine=9:1:0.05) to provide the free base of title compound (143 mg) as a viscous oil.

$^1$H NMR (CDCl$_3$, free base) δ: 1.20–1.40 (3H, m), 1.50–1.80 (6H, m), 1.80–2.10 (1H, m), 2.10–2.30 (2H, m), 2.80–3.00 (6H, m), 3.10 (2H, t-like, J=5.2 Hz), 3.46 (2H, s), 3.48 (2H, s), 3.89 (2H, s), 5.00 (2H, s), 6.90–7.05 (3H, m), 7.15–7.30 (6H, m), 7.48 (1H, d, J=2.0 Hz), 7.75 (1H, dd, J=7.6, 1.8 Hz).

The above free base (140 mg) was dissolved in ethyl acetate-methanol, treated with 2 molar equivalents of HCl (dissolved inethyl acetate), and precipitated from ethyl acetate-ether to provide the title compound (140 mg) as colorless amorphous powders.

Elemental analysis, for C$_{33}$H$_{39}$FN$_4$O$_2$.2HCl.2H$_2$O. Calcd.: C, 60.82; H, 6.96; N, 8.64. Found: C, 60.95; H, 6.79; N, 8.47.

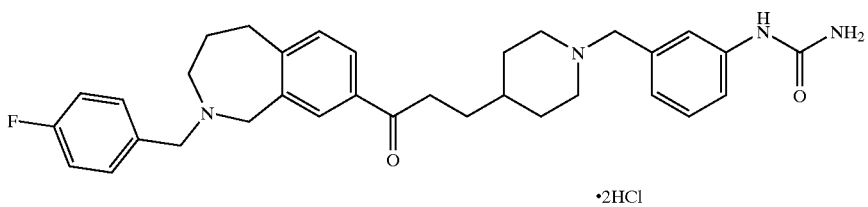

•2HCl

EXAMPLE 225

3-[1-[(2-Cyanophenyl)methyl]-4-piperidinyl]-1-[2-[(4-fluorophenyl)methyl]-2,3,4,5-tetrahydro-1H-2-benzazepin-8-yl]-1-propanone Dihydrochloride

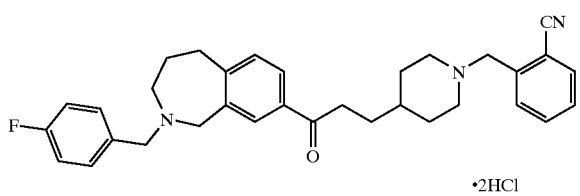

Using 1-[2-[(4-fluorophenyl)methyl]-2,3,4,5-tetrahydro-1H-2-benzazepin-8-yl]-3-(4-piperidinyl)-1-propanone(free base), obtained in Example 211, and 2-cyanobenzyl bromide, the procedure of Example 51-3 was otherewise repeated to provide the title compound as colorless amorphous powders.

$^1$H NMR (CDCl$_3$, free base) δ: 1.20–1.45 (3H, m), 1.50–1.80 (6H, m), 1.95–2.20 (2H, m), 2.75–3.00 (6H, m), 3.11 (2H, t-like, J=5.4 Hz), 3.49 (2H, s), 3.68 (2H, s), 3.89 (2H, s), 6.99 (2H, t-like, J=8.8 Hz), 7.15–7.40 (4H, m), 7.45–7.65 (4H, m), 7.76 (1H, dd, J=7.9, 1.8 Hz). Elemental analysis, for C$_{33}$H$_{36}$FN$_3$O.2HCl.H$_2$O. Calcd.: C, 65.99; H, 6.71; N, 7.00. Found: C, 65.86; H, 6.92; N, 6.86.

EXAMPLE 226

3-[1-[(3-Cyanophenyl)methyl]-4-piperidinyl]-1-(2-[(4-fluorophenyl)methyl]-2,3,4,5-tetrahydro-1H-2-benzazepin-8-yl]-1-propanone Dihydrochloride

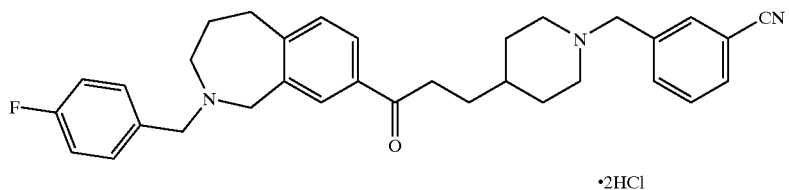

Using 1-[2-[(4-fluorophenyl)methyl]-2,3,4,5-tetrahydro-1H-2-benzazepin-8-yl]-3-(4-piperidinyl)-1-propanone(free base), obtained in Example 211, and 3-cyanobenzyl bromide, the procedure of Example 51-3 was otherewise repeated to provide the title compound as colorless amorphous powders.

$^1$H NMR (CDCl$_3$, free base) δ: 1.10–1.45 (3H, m), 1.50–1.80 (6H, m), 1.80–2.05 (2H, m), 2.75–3.00 (6H, m), 3.11 (2H, t-like, J=5.4 Hz), 3.49 (4H, s), 3.89 (2H, s), 6.99 (2H, t-like, J=8.8 Hz), 7.10–7.30 (3H, m), 7.35–7.65 (5H, m), 7.76 (1H, dd, J=7.8, 1.8 Hz). Elemental analysis, for C$_{33}$H$_{36}$FN$_3$O.2HCl.2.5H$_2$O. Calcd.: C, 65.12; H, 7.12; N, 6.90. Found: C, 65.19; H, 6.83; N, 6.90.

EXAMPLE 227

3-[1-[(4-Cyanophenyl)methyl]-4-piperidinyl]-1-[2-[(4-fluorophenyl)methyl]-2,3,4,5-tetrahydro-1H-2-benzazepin-8-yl]-1-propanone Dihydrochloride

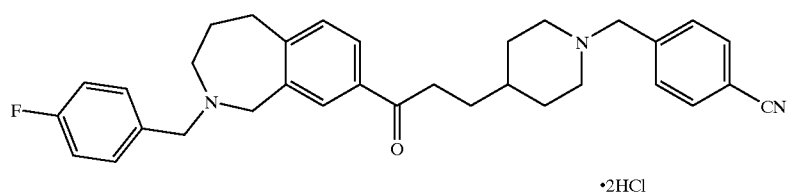

Using 1-[2-[(4-fluorophenyl)methyl]-2,3,4,5-tetrahydro-1H-2-benzazepin-8-yl]-3-(4-piperidinyl)-1-propanone(free base), obtained in Example 211, and 4-cyanobenzyl bromide, the procedure of Example 51-3 was otherewise repeated to provide the title compound as colorless amorphous powders.

$^1$H NMR (CDCl$_3$, free base) δ: 1.20–1.45 (3H, m), 1.50–1.85 (6H, m), 1.90–2.05 (2H, m), 2.75–3.00 (6H, m), 3.11 (2H, t-like, J=5.4 Hz), 3.49 (2H, s), 3.52 (2H, s), 3.89 (2H, s), 6.99 (2H, t-like, J=8.8 Hz), 7.15–7.30 (3H, m), 7.40–7.50 (3H, m), 7.55–7.65 (2H, m), 7.76 (1H, dd, J=7.8, 1.8 Hz). Elemental analysis, for C$_{33}$H$_{36}$FN$_3$O.2HCl.1.5H$_2$O. Calcd.: C, 65.02; H, 6.78; N, 6.89. Found: C, 65.42; H, 6.68; N, 6.88.

EXAMPLE 228

3-[[4-[3-[2-[(4-Fluorophenyl)methyl]-2,3,4,5-tetrahydro-1H-2-benzazepin-8-yl]-3-oxopropyl]-1-piperidinyl]methyl]benzamide Dihydrochloride

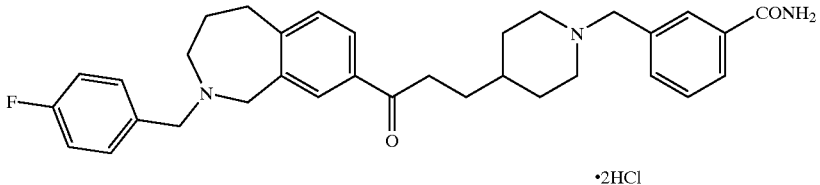

•2HCl

Aqueous solution of 2N NaOH (15 ml) was added to 3-[1-[(3-cyanophenyl)methyl]-4-piperidinyl]-1-[2-[(4-fluorophenyl)methyl]-2,3,4,15-tetrahydro-1H-2-benzazepin-8-yl]-1-propanone (free base, 310; mg, 0.61 mmol), obtained in Example 226, in ethanol (10 ml)-tetrahydrofuran (5 ml), and refluxed for 5 hours. After cooling, the solvent was distilled off under reduced pressure and extracted with ethyl acetate. The extract was washed with saturated NaCl/H$_2$O and dried over K$_2$CO$_3$, and the solvent was distilled off under reduced pressure. The residue was purified by silica gel column chromatography (eluent: ethyl acetate-methanol-triethylamine=9:1:0.05) to provide the free base of title compound (218 mg) as a viscous oil.

$^1$H NMR (CDCl$_3$, free base) δ: 1.20–1.50 (3H, m), 1.60–1.85 (6H, m), 1.90–2.10 (2H, m), 2.80–3.05 (6H, m), 3.11 (2H, t-like, J=5.4 Hz), 3.49 (2H, s), 3.54 (2H, s), 3.90 (2H, s), 5.70–6.40 (2H, br), 7.00 (2H, t-like, J=8.8 Hz), 7.20–7.30 (3H, m), 7.39 (1H, t, J=7.8 Hz), 7.45–7.55 (2H, m), 7.70–7.85 (3H, m).

The above free base (210 mg) was dissolved in ethyl acetate-methanol, treated with 2 molar equivalents of HCl (dissolved in ethyl acetate), and precipitated from ethyl acetate-ether to provide the title compound (241 mg) as colorless amorphous powders.

Elemental analysis, for C$_{33}$H$_{38}$FN$_3$O$_2$.2HCl.3H$_2$O. Calcd.: C, 60.55; H, 7.08; N, 6.42. Found: C, 60.23; H, 7.04; N, 6.40. Found: C, 60.23; H, 7.04; N, 6.40.

EXAMPLE 229

1-[2-[(4-Fluorophenyl)methyl]-2,3,4,5-tetrahydro-1H-2-benzazepin-8-yl]-3-[1-[(2-pyridyl)methyl]-4-piperidinyl]-1-propanone Trihydrochloride

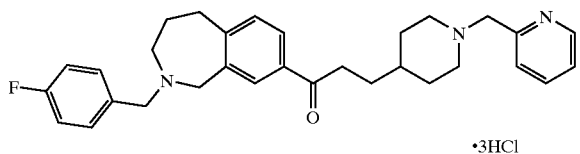

•3HCl

Using 1-[2-[(4-fluorophenyl)methyl]-2,3,4,5-tetrahydro-1H-2-benzazepin-8-yl]-3-(4-piperidinyl)-1-propanone(free base), obtained in Example 211, and 2-(chloromethyl)pyridine (hydrochloride), the procedure of Example 51-3 was otherwise repeated to provide the title compound as colorless amorphous powders.

$^1$H NMR (CDCl$_3$, free base) δ: 1.20–1.50 (3H, m), 1.60–1.80 (6H, m), 1.95–2.15 (2H, m), 2.80–3.00 (6H, m), 3.11 (2H, t-like, J=5.2 Hz), 3.49 (2H, s), 3.64 (2H, s), 3.89 (2H, s), 6.99 (2H, t-like, J=8.8 Hz), 7.05–7.30 (4H, m), 7.42 (1H, d, J=7.6 Hz), 7.49 (1H, d, J=1.8 Hz), 7.64 (1H, dt, J=7.7, 1.8 Hz), 7.76 (1H, dd, J=7.6, 1.8 Hz), 8.55 (1H, dd, J=4.1, 0.8 Hz). Elemental analysis, for C$_{31}$H$_{36}$FN$_3$O.3HCl.0.5H$_2$O. Calcd.: C, 61.64; H, 6.67; N, 6.96. Found: C, 61.36; H, 6.62; N, 6.67.

EXAMPLE 230

1-[2-[(4-Fluorophenyl)methyl)-)2,3,4,5-tetrahydro-1H-2-benzazepin-8-yl]-3-[1-[(3-pyridyl)methyl]-4-piperidinyl]-1-propanone Trihydrochloride

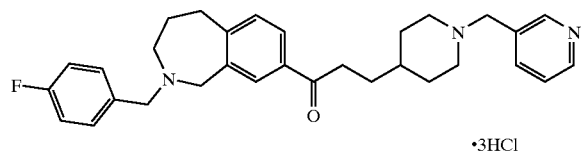

•3HCl

Using 1-[2-[(4-fluorophenyl)methyl]-2,3,4,5-tetrahydro-1H-2-benzazepin-8-yl]-3-(4-piperidinyl)-1-propanone(free base), obtained in Example 211, and 3-(chloromethyl)pyridine (hydrochloride), the procedure of Example 51-3 was otherwise repeated to provide the title compound as colorless amorphous powders.

$^1$H NMR (CDCl$_3$, free base) δ: 1.20–1.40 (3H, m), 1.60–1.85 (6H, m), 1.90–2.05 (2H, m), 2.80–3.00 (6H, m), 3.11 (2H, t-like, J=5.2 Hz), 3.49 (4H, s), 3.89 (2H, s), 6.99 (2H, t-like, J=8.8 Hz), 7.15–7.30 (4H, m), 7.48 (1H, d, J=1.8 Hz), 7.67 (1H, dt, J=7.8, 1.8 Hz), 7.76 (1H, dd, J=7.6, 1.8 Hz), 8.50 (1H, dd, J=4.8, 1.8 Hz), 8.53 (1H, d, J=1.4 Hz). Elemental analysis, for C$_{31}$H$_{36}$FN$_3$O.3HCl.H$_2$O. Calcd.: C, 60.74; H, 6.74; N, 6.85. Found: C, 60.82; H, 6.91; N, 6.76.

EXAMPLE 231

1-[2-[(4-Fluorophenyl)methyl]-2,3,4,5-tetrahydro-1H-2-benzazepin-8-yl]-3-[1-[(4-pyridyl)methyl]-4-piperidinyl]-1-propanone Trihydrochloride

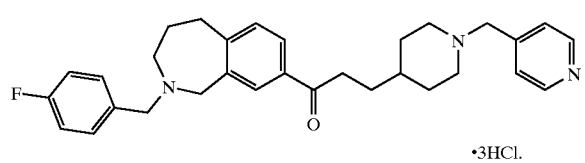

•3HCl.

Using 1-[2-[(4-fluorophenyl)methyl]-2,3,4,5-tetrahydro-1H-2-benzazepin-8-yl]-3-(4-piperidinyl)-1-propanone(free base), obtained in Example 211, and 4-(chloromethyl)pyridine(hydrochloride), the procedure of Example 51-3 was otherwise repeated to provide the title compound as colorless % amorphous powders.

¹H NMR (CDCl₃, free base) δ: 1.20–1.45 (3H, m), 1.50–1.85 (6H, m), 1.90–2.10 (2H, m), 2.80–3.00 (6H, m), 3.11 (2H, t-like, J=5.2 Hz), 3.48 (4H, s), 3.89 (2H, s), 7.00 (2H, t-like, J=8.8 Hz), 7.10–7.40 (, 5H, m), 7.48 (1H, d, J=1.8 Hz), 7.76 (1H, dd, J=7.8, 1.8 Hz), 8.53 (2H, m). Elemental analysis, for $C_{31}H_{36}FN_3O \cdot 3HCl \cdot H_2O$. Calcd.: C, 60.74; H, 6.74; N, 6.85. Found: C, 60.58; H, 7.06; N, 6.73.

EXAMPLE 232

N-[3-[[4-[3-[2-[(4-fluorophenyl)methyl]-2,3,4,5-tetrahydro-1H-2-benzazepin-8-yl]-3-oxopropyl]1-piperidinyl]methyl]phenyl]formamide Dihydrochloride

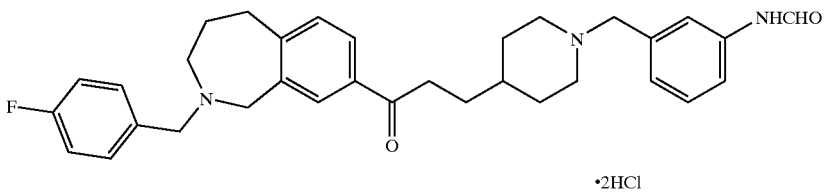

Using 1-[2-[(4-fluorophenyl)methyl]-2,3,4,5-tetrahydro-1H-2-benzazepin-8-yl]-3-(4-piperidinyl)-1-propanone(free base), obtained in Example 211, and mesylate of 3-(formylamino)benzylalchol, the procedure of Example 51-3 was otherewise repeated to provide the title compound as colorless amorphous powders.

¹H NMR (CDCl₃, free base) δ: 1.20–1.40 (3H, m), 1.60–1.85 (6H, m), 1.90–2.05 (2H, m), 2.80–3.00 (6H, m), 3.11 (2H, t-like, J=5.2 Hz), 3.47 (2H, s), 3.49 (2H, s), 3.90 (2H, s), 6.99 (2H, t-like, J=8.8 Hz), 7.00–7.35 (6H, m), 7.40–7.50 (2H, m), 7.50–7.70 and 8.05–8.20 (1H, NHCHO, each br), 7.76 (1H, d, J=7.6 Hz), 8.36 (1/2H, NHCHO, d, J=1.8 Hz) and 8.71 (1/2H, NHCHO, d, J=11.4 Hz). Elemental analysis, for $C_{33}H_{38}FN_3O_2 \cdot 2HCl \cdot 2.5\ H_2O$. Calcd.: C, 61.39; H, 7.03; N, 6.51. Found: C, 61.51; H, 6.80; N, 6.33.

EXAMPLE 233

N-[3-[[4-[3-[2-[(4-Fluorophenyl)methyl]-2,3,4,5-tetrahydro-1H-2-benzazepin-8-yl]-3-oxopropyl]-1-piperidinyl]methyl]phenyl]-N'-methylurea Dihydrochloride

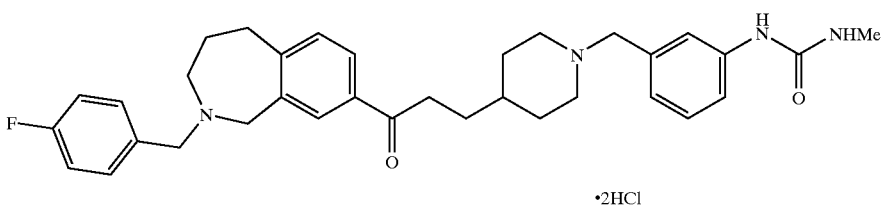

Using 3-[1-[(3-aminophenyl)methyl]-4-piperidinyl]-1-[2-[(4-fluorophenyl)methyl]-2,3,4,5-tetrahydro-1H-2-benzazepin-8-yl])-2-propanone(free base), obtained in Example 223, and methylisocyanate, the procedure of Example 51-3 was otherewise repeated to provide the title compound as colorless amorphous powders.

¹H NMR (CDCl₃, free base) δ: 1.15–1.45 (3H, m), 1.50–1.85 (6H, m), 1.90–2.00 (2H, m), 2.75 (3H, d, J=4.6 Hz), 2.80–3.00 (7H, m), 3.09 (2H, t-like, J=4.4 Hz), 3.44 (2H, s), 3.48 (2H, s), 3.89 (2H, s), 5.52 (1H br), 6.50–6.75 (1H, m), 6.98 (2H, t-like, J=8.8 Hz), 7.05–7.45 (6H, m), 7.48 (1H, s), 7.75 (1H, dd, J=7.8, 1.8 Hz). Elemental analysis, for $C_{34}H_{41}FN_4O_2 \cdot 2HCl \cdot 0.5H_2O$. Calcd.: C, 63.94; H, 6.94; N, 8.77. Found: C, 63.97; H, 6.97; N, 8.07.

TEST EXAMPLE 4

Assay of Thermopenic Activity in Mice

The telethermometer (VltaView™, Mini-Mitter Co., Inc., USA) was inplanted subcutaneously border on the scapulae of male C57BL db/db mice (CLEA Japan Inc., N=6) anesthetized with ether. After 7 days acclimatization, 1 mg/kg of the compound which was obtained in Example 23, was orally administered for 6 days. The 24 hours-average regional temperature after the final administration was measured. The control was administered 0.5% methylcellulose solution. The results are shown in Table 15.

TABLE 15

|  | Regional temperature (° C.) | S. E. (° C.) |
| --- | --- | --- |
| Control | 34.83 | 0.54 |
| Example 23 | 35.54 | 0.12 |

It is apparent from Table 15 that the above mentioned compound (I), inclusive of its salt, has excellent thermogenic activity.

Assay of Reducing Activity Against Weight Gain of Mice.

Male C57BL db/db mice (CLEA Japan Inc., 10 weeks old) was pretreated for 7 days, with solid feed (CLEA Japan Inc., CE-2). After acclimatization, 0.3 mg/kg or 1.0 mg/kg of the compound which, was obtained in Example 23, was oraly administered for 6 weeks. Body weight was measured after the final administration. After the measurement, total blood was successively drawn from the orbital vain, and the visceral fat was collected and its weight was measured. Statistics analysis was carried out with Dunnett anlalysis.

The results are shown in Table 16 and 17.

TABLE 16

| Compound (dose) | Body weight (g) (average ± S.E.) | |
|---|---|---|
| | Starting date of administration | Ending date of administration |
| Control | 40.36 ± 0.51 | 45.08 ± 1.10 |
| Example 23 (0.3 mg/kg) | 40.21 ± 0.48 | 40.87 ± 1.57 |
| Example 23 (0.3 mg/kg) | 40.40 ± 0.69 | 39.75 ± 1.55* |

It is apparent from Table 16 that the above mentioned compound (I), inclusive of its salt, has excellent reducing activity against weight gain.

TABLE 17

| Compound (dose) | Amount of visceral fat (g) (average ± S.E.) |
|---|---|
| Control | 7.14 ± 0.41 |
| Example 23 (0.3 mg/kg) | 5.47 ± 0.36 |
| Example 23 (1.0 mg/kg) | 5.13 ± 0.39* |

It is apparent from Table 17 that the above mentioned compound (I), inclusive of its salt, has excellent reducing activity against body fat reducing activity.

EXAMPLE 234

1-(3-Acetyl-2,3,4,5-tetrahydro-1H-3-benzazepin-7-yl)-4-(4-piperidinyl)-1-butanone Hydrochloride

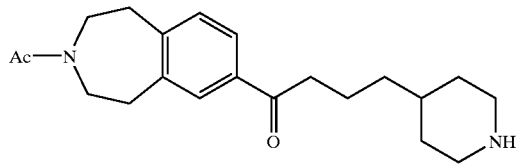

·HCl

[1-[(4-nitrobenzyl)oxycarbonyl]-4-piperidinyl]butanoic acid (28.0 g, 79.9 mmol), obtained in Reference Example 6, was added portionwise to thionyl chloride (70 ml) under ice-cooling. After 5 minutes of stirring, the excess thionyl chloride was distilled off and the residue was washed with hexane to provide [1-[(4-nitrobenzyl)oxycarbonyl]-4-piperidinyl]butanoyl chloride as a pale yellow viscous oil. Aluminum chloride (34.0 g, 0.255 mol) powders were then added portionwise to a mixed solution of the above acid chloride and 3-acetyl-2,3,4,5-tetrahydro-1H-3-benzazepine (13.75 g, 72.65 mmol) in 1,2-dichloroethane (70 ml) under ice-cooling. This mixture was then stirred at room temperature for 14 hours, then at 50° C. for 4 hours, at the end of which time it was poured in ice-water and washed with ethyl acetate. The aqueous layer was made basic with 8N NaOH/H2O and, extracted with ethyl acetate. The extract was washed with saturated NaCl/H$_2$O and dried over MgSO$_4$, and the solvent was distilled off under reduced pressure to provide the free base of title compound (18.5 g) as light-yellow solid.

$^1$H NMR (CDCl$_3$, free base) δ: 1.00–1.52 (5H, m), 1.63–1.85 (4H, m), 1.93 (1H, br), 2.19 (3H, s), 2.49–2.68 (2H, m), 2.87–3.14 (8H, m), 3.55–3.80 (4H, m), 7.18–7.30 (1H, m), 7.70–7.80 (2H, m).

The above free base (0.1 g) was dissolved in ethyl acetate-methanol, treated with one molar equivalent of HCl (dissolved in ethyl acetate) to provide the title compound (80 mg) as light-yellow amorphous powders.

Elemental analysis, for C$_{21}$H$_{30}$N$_2$O$_2$.HCl.1.5H$_2$O. Calcd.: C, 62.13; H, 8.44; N, 6.90. Found: C, 62.42; H, 8.05; N, 6.73.

EXAMPLE 235

1-(3-Acetyl-2,3,4,5-tetrahydro-1H-3-benzazepin-7-yl)-4-]1-[(2-methylphenyl)methyl]-4-piperidlnyl]-1-butanone Hydrochloride

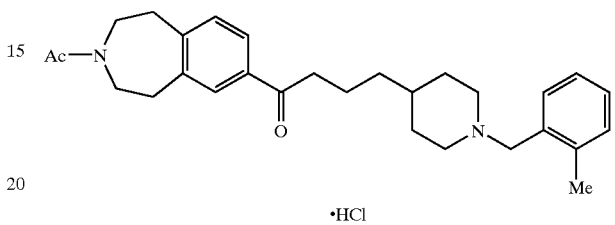

·HCl

Using 1-(3-acetyl-2,3,4,5-tetrahydro-1H-3-bednzazepin-7-yl)-4-(4-piperidinyl)-1-butanone (free base), obtained in Example 234, and 2-methylbenzyl bromide, the procedure of Example 28 was similarly repeated to provide the the free base of title compound as colorless powders melting at 93–94° C. and the title compound as colorless amorphous powders.

$^1$H NMR (CDCl$_3$, free base) δ: 1.10–1.38 (5H, m), 1.56–2.07 (6H, m), 2.19 (3H, s), 2.35 (3H, s), 2.81–3.06 (8H, m), 3.44 (2H, s), 3.55–3.65 (2H, m), 3.68–3.80 (2H, m), 7.10–7.33 (5H, m), 7.69–7.78 (2H, m). Elemental analysis, for C$_{29}$H$_{38}$N$_2$O$_2$.HCl.1.25H$_2$O. Calcd.: C, 68.89; H, 8.27; N, 5.54. Found: C, 68.94; H, 8.17; N, 5.47.

EXAMPLE 236

4-[1-[(2-Methylphenyl)methyl]-4-piperidinyl]-1-(2,3,4,5-tetrahydro-1H-3-benzazepin-7-yl)-1-butanone Dihydrochloride

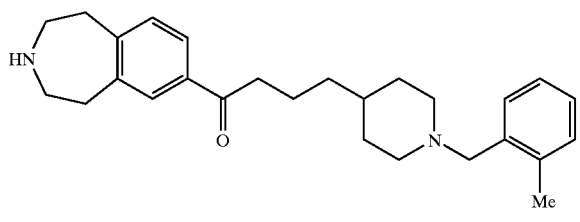

·2HCl

Using 1-(3-acetyl-2,3,4,5-tetrahydro-1H-3-benzazepin-7-yl)-4-[1-[(2-methylphenyl)methyl]-4-piperidinyl]-1-butanone, obtained in Example 235, the procedure of Example 24 was similarly repeated to provide the title compound as colorless powders melting at 213–216° C. (dec.).

$^1$H NMR (CDCl$_3$, free base) δ: 1.08–1.37 (5H, m), 1.57–2.04 (7H, m), 2.35 (3H, s), 2.79–3.05 (12H, m), 3.43 (2H, s), 7.09–7.32 (5H, m), 7.65–7.73 (2H, m). Elemental analysis, for C$_{27}$H$_{36}$N$_2$O.2HCl. Calcd.: C, 67.91; H, 8.02; N, 5.87. Found: C, 67.58; H, 7.93; N, 5.95.

EXAMPLE 237

4-(1-Acetyl-4-piperidinyl)-1-[3-[(2,4-difluorophenyl)methyl]-2,3,4,5-tetrahydro-1H-3-benzazepin-7-yl]-1-butanone

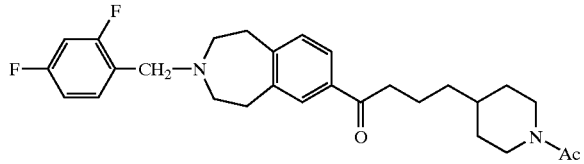

Using 1-(3-acetyl-2,3,4,5-tetrahydro-1H-3-benzazepin-7-yl)-4-(4-piperidinyl)-1-butanone (free base), obtained in Example 25–2, and 2,4-difluorobenzyl bromide, the procedure of Example 25-3 was similarly repeated to provide the title compound as a light yellow oil.

$^1$H NMR (CDCl$_3$) δ: 0.96–1.62 (5H, m), 1.64–1.97 (4H, m), 2.08 (3H, s), 2.44–2.72 (5H, m), 2.86–3.10 (7H, m), 3.69 (2H, s), 3.70–3.86 (1H, m), 4.51–4.66 (1H, m), 6.72–6.92 (2H, m), 7.16 (1H, d, J=7.7 Hz), 7.34–7.47 (1H, m), 7.66–7.74 (2H, m).

EXAMPLE 238

1-[3-[(2,4-Difluorophenyl)methyl]-2,3,4,5-tetrahydro-1H-3-benzazepin-7-yl]-4-(4-piperidinyl)-1-butanone

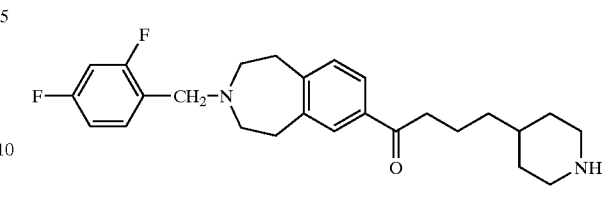

Using 4-(1-acetyl-4-piperidinyl)-1-[3-[(2,4-difluorophenyl)methyl]-2,3,4,5-tetrahydro-1H-3-benzazepin-7-yl]-1-butanone, obtained in Example 237, the procedure of Example 24 was similarly repeated to provide the title compound as a light yellow oil.

$^1$H NMR (CDCl$_3$) δ: 1.02–1.50 (5H, m), 1.63–1.84 (4H, m), 2.33–2.73 (7H, m), 2.83–3.19 (8H, m), 3.67 (2H, s), 6.70–6.93 (2H, m), 7.16 (1H, d, J=8.1 Hz), 7.32–7.47 (1H, m), 7.63–7.75 (2H, m).

EXAMPLE 239

Methyl 2-[[7-[4-[1-[(2-Methylphenyl)methyl]-4-piperidinyl]butanoyl]-2,3,4,5-tetrahydro-1H-3-benzazepin-3-yl]methyl]benzoate Dihydrochloride

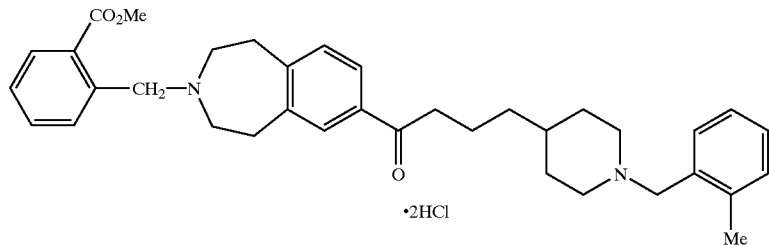

Using 4-[1-[(2-methylphenyl)methyl]-4-piperidinyl]-1-(2,3,4,5-tetrahydro-1H-3-benzazepin-7-yl)-1-butanone (free base), obtained in Example 236, and methyl 2-(bromomethyl)benzoate, the procedure of Example 28 was similarly repeated to provide the free base of title compound as colorless powders melting at 111–113° C. and the dihydrochloride of title compound as colorless amorphous powders.

$^1$H NMR (CDCl$_3$, free base) δ: 1.14–1.39 (5H, m), 1.55–1.82 (4H, m), 1.87–2.07 (2H, m), 2.35 (3H, s), 2.52–2.66 (4H, m), 2.80–3.00 (8H, m), 3.44 (2H, s), 3.84 (2H, s), 3.91 (3H, s), 7.09–7.22 (4H, m), 7.24–7.49 (4H, m), 7.64–7.76 (3H, m). Elemental analysis, for C$_{36}$H$_{44}$N$_2$O$_3$.2HCl.H$_2$O. Calcd.: C, 67.17; H, 7.52; N, 4.35. Found: C, 67.04; H, 7.55; N, 4.31.

EXAMPLE 240

2-[[7-[4-[1-[(2-Methylphenyl)methyl]-4-piperidinyl]butanoyl]-2,3,4,5-tetrahydro-1H-3-benzazepin-3-yl]methyl]benzoic Acid

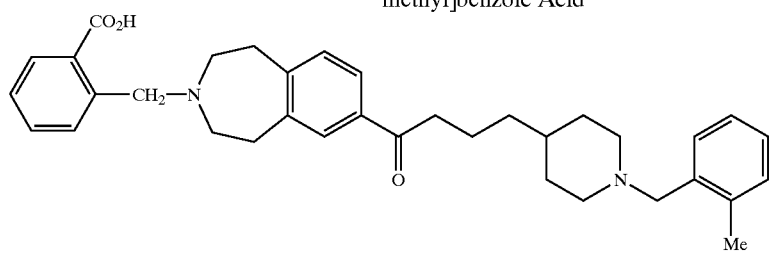

Using methyl 2-[[7-[4-[1-[(2-methylphehyl)methyl]-4-piperidinyl]butanoyl]-2,3,4,5-tetrahydro-1H-3-benzazepin-3-yl]methyl]benzoate, obtained in Example 239, the procedure of Example 104 was similarly repeated to provide the free base of title compound as colorless amorphous powders.

$^1$H NMR (CDCl$_3$) δ: 1.10–1.40 (5H, m), 1.55–1.83 (4H, m), 1.87–2.04 (2H, m), 2.35 (3H, s), ca. 2.55–3.25 (13H, m), 3.41 (2H, s), 3.90 (2H, s), 7.09–7.32 (6H, m), 7.39–7.59 (2H, m), 7.67–7.82 (2H, m), 8.15–8.29 (1H, m). Elemental analysis, for C$_{35}$H$_{42}$N$_2$O$_3$·1.5H$_2$O. Calcd.: C, 74.30; H, 8.02; N, 4.95. Found: C, 74.70; H, 7.96; N, 5.06.

EXAMPLE 241

Ethyl 2-[2-[[7-[4-[1-[(2-Methylphenyl)methyl]-4-piperidinyl]butanoyl]-2,3,4,5-tetrahydro-1H-3-benzazepin-3-yl]methyl]phenoxy]ethanoate Dihydrochloride Using ethyl 2-[2-[[7-[4-[1-[(2-methylphenyl)methyl]-4-piperidinyl]butanoyl]-2,3,4,5-tetrahydro-1H-3-benzazepin-3-yl]methyl]phenoxy]ethanoate, obtained in Example 241, the procedure of Example 104 was similarly repeated to provide the free base of title compound as colorless amorphous powders.

$^1$H NMR (CDCl$_3$, free base) δ: 1.10–1.38 (5H, m), 1.55–1.81 (4H, m), 1.86–2.05 (2H, m), 2.35 (3H, s), ca. 2.70–3.50 (15H, m), 3.97 (2H, brs), 4.75 (2H, brs), 6.92–7.50 (9H, m), 7.64–7.80 (2H, m). Elemental analysis, for C$_{36}$H$_{44}$N$_2$O$_4$·H$_2$O. Calcd.: C, 73.69; H, 7.90; N, 4.77. Found: C, 73.96; H, 7.71; N, 4.58.

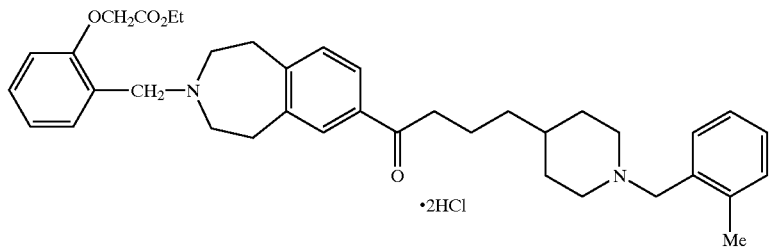

Using 4-[1-[(2-methylphenyl)methyl]-4-piperidinyl]-1-(2,3,4,5-tetrahydro-1H-3-benzazepin-7-yl)-1-butanone (free base), obtained in Example 236, and ethyl 2-[2-(bromomethyl)phenoxy]ethanoate, the procedure of Example 28 was similarly repeated to provide the title compound as colorless amorphous powders.

$^1$H NMR (CDCl$_3$, free base) δ: 1.13–1.40 (8H, m), 1.59–2.06 (6H, m), 2.35 (3H, s), 2.68–3.07 (12H, m), 3.44 (2H, s), 3.81 (2H, s), 4.26 (2H, q, J=7.1 Hz), 4.64 (21H, s), 6.76 (1H, d, J=8.4 Hz), 7.01 (1H, t, J=7.5 Hz), 7.10–7.32 (6H, m), 7.45 (1H, d, J=7.3 Hz), 7.64–7.73 (2H, m). Elemental analysis, for C$_{38}$H$_{48}$N$_2$O$_4$·2HCl·1.5H$_2$O. Calcd.: C, 65.51; H, 7.67; N, 4.02. Found: C, 65.77; H, 7.43; N, 4.11.

EXAMPLE 242

[2-[[7-[4-[1-[(2-Methylphenyl)methyl]-4-piperidinyl]butanoyl]-2,3,4,5-tetrahydro-1H-3-benzazepin-3-yl]methyl]phenoxy]acetic Acid

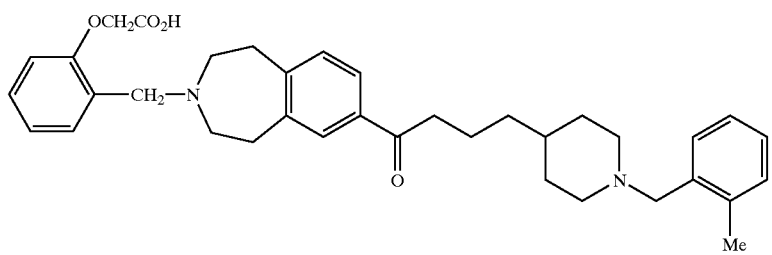

EXAMPLE 243

4-[1-[(2-Methylphenyl)methyl]-4-piperidinyl]-1-[3-[[2-[(4-methyl-1-piperazinyl)carbonyl]phenyl]methyl]-2,3,4,5-tetrahydro-1H-3-benzazepin-7-yl]-1-butanone Trihydrochloride

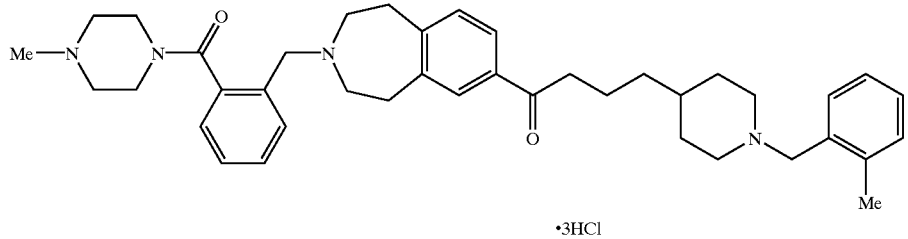

·3HCl

Diethyl cyanophosphonate (61 mg, 0.37 mmol) was added to a mixture of (2-[[7-[4-[1-[(2-methylphenyl)methyl]-4-piperidinyl]butanoyl]-2,3,4,5-tetrahydro-1H-3-benzazepin-3-yl]methyl]phenoxy]acetic acid (0.2 g, 0.37 mmol), obtained in Example 242, 1-methylpiperazine (37 mg, 0.37 mmol) and triethylamine (0.057 ml) in N,N-dimethylformamide (2 ml) at 0–5° C. This mixture was stirred at 0–5° C. for 10 minutes, after which it was diluted with water and extracted with ethyl acetate. The extract was washed saturated NaCl/H2O and dried over MgSO4. The solvent was then distilled off under reduced pressure and the residue was purified by column chromatography using activated basic Alumina (eluent: n-hexane-ethyl acetate=1:1) to provide the title compound (0.2 g) as a colorless viscous oil.

$^1$H NMR (CDCl$_3$, free base) δ: 1.14–1.40 (5H, m), 1.59–1.83 (4H, m), 1.87–2.06 (2H, m), 2.17–2.51 (10H, m), 2.55–2.69 (4H, m), 2.80–3.01 (8H, m), 3.16–3.64 (6H, m), 3.87 (1H, d, J=13.6 Hz), 4.10–4.16 (1H, brd, J=ca. 13.6 Hz), 7.09–7.46 (9H, m), 7.64–7.73 (2H, m).

The above free base (0.18 g) was dissolved in ethyl acetate-methanol, treated with 3 molar equivalent of HCl (dissolved in ethyl acetate), and triturated in diethyl ether to provide the title compound (0.15 g) as colorless amorphous powders. Elemental analysis, for C$_{40}$H$_{52}$N$_4$O$_2$·3HCl·1.5H$_2$O. Calcd.: C, 63.44; H, 7.72; N, 7.40. Found: C, 63.59; H, 8.21; N, 7.05.

Example 244

1-[3-(2-Diethyaminoethyl)-2,3,4,5-tetrahydro-1H-3-benzazepin-7-yl]-4-[1-[(2-methylphenyl)methyl]-4-piperidinyl]-1-butanone Trihydrochloride

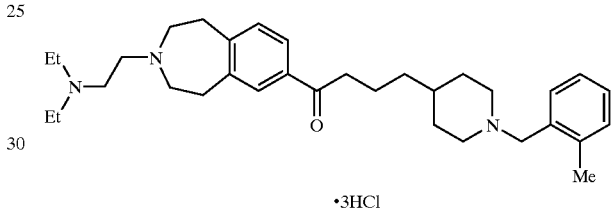

·3HCl

Using 4-[1-[(2-methylphenyl)methyl]-4-piperidinyl]-1-(2,3,4,5-tetrahydro-1H-3-benzazepin-7-yl)-1-butanone (free base), obtained in Example 236, 2-diethyaminoethylchloride hydrochloride, and potassium iodide, the procedure of Example 28 was similarly repeated to provide the title compound as colorless powders melting at 211–213° C.

$^1$H NMR (CDCl$_3$, free base) δ: 1.05 (6H, t, J=7.1 Hz), 1.13–1.38 (5H, m), 1.57–2.03 (6H, m), 2.35 (3H, s), 2.48–2.75 (12H, m), 2.78–3.03 (8H, m), 3.41 (2H, s), 7.07–7.20 (4H, m), 7.22–7.30 (1H, m), 7.65–7.76 (2H, Elemental analysis, for C$_{33}$H$_{49}$N$_3$O·3HCl·0.5H$_2$O. Calcd.: C, 63.71; H, 8.59; N, 6.75. Found: C, 64.08; H, 8.59; N, 6.85.

EXAMPLE 245

4-[1-[(2-Chlorophenyl)methyl]-4-piperidinyl]-1-[3-[(2,4-difluorophenyl)methyl]-2,3,4,5-tetrahydro-1H-3-benzazepin-7-yl]-1-butanone Dihydrochloride

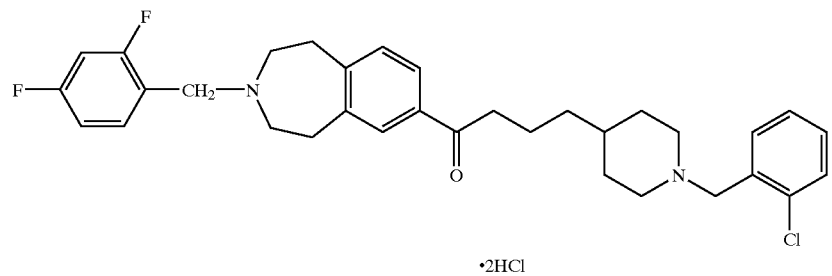

·2HCl

Using 4-[1-[(2-methylphenyl)methyl]-4-piperidinyl]-1-(2,3,4,5-tetrahydro-1H-3-benzazepin-7-yl)-1-butanone (free base), obtained in Example 236, and ethyl 2-chlorobenzyl bromide, the procedure of Example 28 was similarly repeated to provide the title compound as colorless amorphous, powders melting at 193–196° C.

¹H NMR (CDCl₃, free base) δ: 1.16–1.40 (5H, m), 1.53–1.83 (4H, m), 1.98–2.16 (2H, m), 2.60–2.71 (4H, m), 2.83–3.04 (8H, m), 3.61 (2H, s), 3.68 (2H, s), 6.72–6.93 (2H, m), 7.11–7.56 (6H, m), 7.66–7.75 (2H, m). Elemental analysis, for C₃₃H₃₇ClF₂N₂O.2HCl.0.5H₂O. Calcd.: C, 62.61; H, 6.37; N, 4.43. Found: C, 62.57; H, 6.24; N, 4.38.

EXAMPLE 246

1-[3-[(2,4-Difluorophenyl)methyl]-2,3,4,5-tetrahydro-1H-3-benzazepin-7-yl]-4-[1-[(2-methylphenyl)methyl]-4-piperidinyl]-1-butanone Dihydrochloride Using 4-[1-[(2-methylphenyl)methyl]-4-piperidinyl]-1-(2,3,4,5-tetrahydro-1H-3-benzazepin-7-yl)-1-butanone (free base), obtained in Example 236, and ethyl 2-methylbenzyl bromide, the procedure of Example 28 was similarly repeated to provide the title compound as colorless amorphous powders melting at 208–210° C.

¹H NMR (CDCl₃, free base) δ: 1.12–1.38 (5H, m), 1.55–1.82 (4H, m), 1.88–2.07 (2H, m), 2.35 (3H, s), 2.60–2.72 (4H, m), 2.81–3.04 (8H, m), 3.43 (2H, s), 3.68 (2H, s), 6.72–6.93 (2H, m), 7.09–7.20 (4H, m), 7.24–7.47 (2H, m), 7.66–7.74 (2H, m). Elemental analysis, for C₃₄H₄₀F₂N₂O.2HCl.0.5H₂O. Calcd.: C, 66.66; H, 7.07; N, 4.57. Found: C, 66.94; H, 6.88; N, 4.47.

EXAMPLE 247

4-[1-[(2-Methylphenyl)methyl]-4-piperidinyl)]-1-[3-[(3-pyridyl)methyl]-2,3,4,5-tetrahydro-1H-3-benzazepin-7-yl]-1-butanone Trihydrochloride

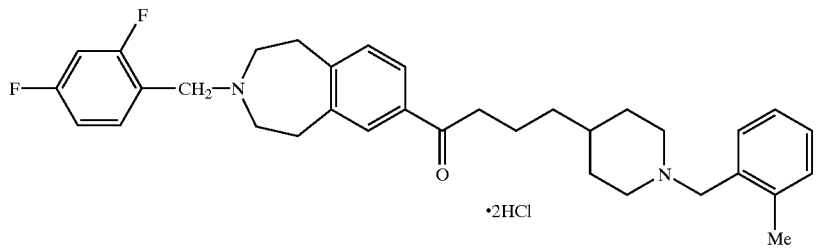

Using 1-(2,3,4,5-tetrahydro-1H-3-benzazepin-7-yl)-4-[1-[(2-methylphenyl)methyl]-4-piperidinyl]-1-butanone (free base), obtained in Example 236, (3-chloromethyl)pyridine hydrochloride and potassium iodide, the procedure of Example 28 was similarly repeated to provide the title compound as colorless amorphous powders.

¹H NMR (CDCl₃, free base) δ: 1.11–1.38 (5H, m), 1.52–1.81 (4H, m), 1.87–2.06 (2H, m), 2.35 (3H, s), 2.56–2.70 (4H, m), 2.80–3.03 (8H, m), 3.44 (2H, s), 3.64 (2H, s), 7.09–7.20 (4H, m), 7.23–7.34 (2H, m), 7.65–7.76 (3H, m), 8.52 (1H, dd, J=1.5, 4.7 Hz), 8.57 (1H, d, J=1.8 Hz). Elemental analysis, for C₃₃H₄₁N₃O.3HCl.1.5H₂O. Calcd.: C, 62.70; H, 7.49; N, 6.65. Found: C, 62.66; H, 7.39; N, 6.47.

EXAMPLE 248

N-[2-[[4-[4-[3-[(2-methylphenyl)methyl]-2,3,4,5-tetrahydro-1H-3-benzazepin-7-yl]-4-oxobutyl]-1-piperidinyl]methyl]phenyl]acetamide Dihydrochloride

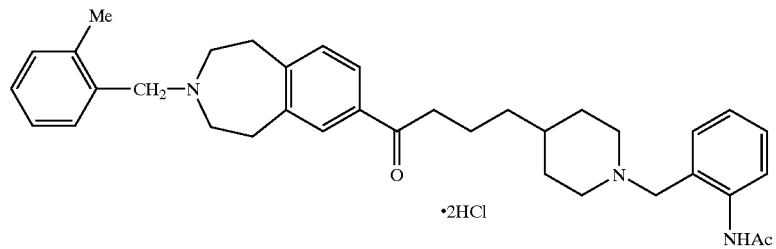

251

Using 1-[3-[(2-methylphenyl)methyl]-2,3,4,5-tetrahydro-1H-3-benzazepin-7-yl]-4-(4-piperidinyl)-1-butanone (free base), obtained in Example 126, and mesylate of 2-acetylaminobenzyl alcohol, the procedure of Example 28 was similarly repeated to provide the title compound as colorless powders melting at 172–178° C.

$^1$H NMR (CDCl$_3$, free base) δ: 1.07–1.44 (4H, m), 1.61–1.86 (5H, m), 1.93–2.18 (5H, m), 2.39 (3H, s), 2.55–2.70 (4H, m), 2.79–3.01 (8H, m), 3.54 (2H, s), 3.56 (2H, s), 6.90–7.17 (8H, m), 7.63–7.74 (2H, m), 8.26 (1H, d, J=8 Hz), 11.12 (1H, brs). Elemental analysis, for C$_{36}$H$_{45}$N$_3$O$_2$.2HCl.2H$_2$O. Calcd.: C, 65.44; H, 7.78; N, 6.36. Found: C, 65.70; H, 7.76; N, 6.29.

EXAMPLE 249

4-[1-[(2-Aminophenyl)methyl]-4-piperidinyl]-1-[3-[(2-methylphenyl)methyl]-2,3,4,5-tetrahydro-1H-3-benzazepin-7-yl]-1-butanone Trihydrochloride

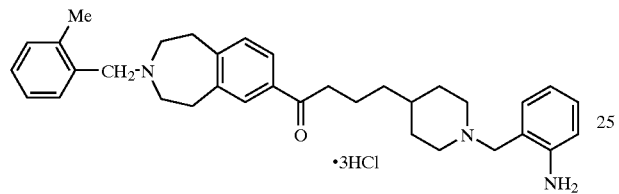

252

Using N-[2-[[4-[4-[3-[(2-methylphenyl)methyl]-2,3,4,5-tetrahydro-1H-3-benzazepin-7-yl]-4-oxobutyl]-1-piperidinyl]methyl]phenyl]acetamide, obtained in Example 248, the procedure of Example 24 was similarly repeated to provide the title compound as colorless powders melting at 230–235° C.

$^1$H NMR (CDCl$_3$, free base) δ: 1.05–1.41 (5H, m), 1.60–1.97 (6H, m), 2.40 (3H, s), 2.55–2.68 (4H, m), 2.75–3.00 (10H, m), 3.47 (2H, s), 3.54 (2H, s), 6.00–6.70 (2H, m), 6.93–7.36 (7H, m), 7.66–7.75 (2H, m). Elemental analysis, for C$_{34}$H$_{43}$N$_3$O.3HCl.2H$_2$O. Calcd.: C, 62.33; H, 7.69; N, 6.41. Found: C, 62.11; H, 7.53; N, 6.49.

EXAMPLE 250

N-[2-[[4-[4-[3-[(2-Methylphenyl)methyl]-2,3,4,5-tetrahydro-1H-3-benzazepin-7-yl]-4-oxobutyl]-1-piperidinyl]methyl]phenyl]methanesulfonamide Dihydrochloride

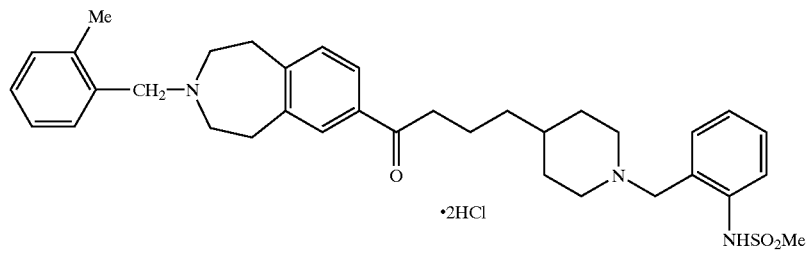

Using 4-[1-[(2-aminophenyl)methyl]-4-piperidinyl]-1-[3-[(2-methyl]-2,3,4,5-tetrahydro-1H-3-benzazepin-7-yl]-1-butanone (free base), obtained in Example 249, and methanesulfonyl chloride, the procedure of Example 28 was similarly repeated to provide the title compound as colorless powders melting at 185–195° C. (dec.).

$^1$H NMR (CDCl$_3$, free base) δ: 1.01–1.38 (5H, m), 1.56–2.00 (6H, m), 2.39 (3H, s), 2.54–2.70 (4H, m), 2.73–3.00 (8H, m), 3.55 (2H, s), 3.58 (5H, s), 7.11–7.21 (4H, m), 7.23–7.51 (6H, m), 7.63–7.73 (2H, m). Elemental analysis, for C$_{35}$H$_{45}$N$_3$O$_3$S.2HCl.5H$_2$O. Calcd.: C, 55.99; H, 7.65; N, 5.60. Found: C, 56.20; H, 7.73; N, 5.37.

EXAMPLE 251

N-[2-[[4-[4-[3-[(2-Methylphenyl)methyl]-2,3,4,5-tetrahydro-1H-3-benzazepin-7-yl]-4-oxobutyl]-1-piperidinyl]methyl]phenyl]-N'-methylurea Dihydrochloride

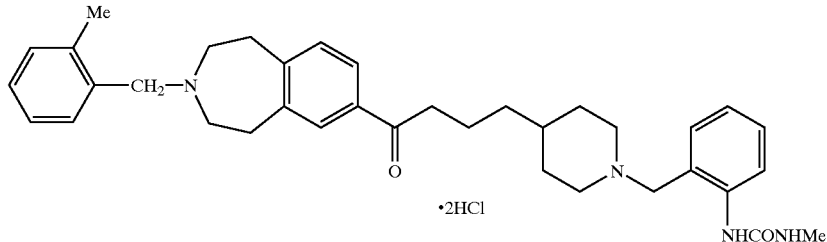

Using 4-[1-[(2-aminophenyl)methyl]-4-piperidinyl]-1-[3-[(2-methylphenyl)methyl]-2,3,4,5-tetrahydro-1H-3-benzazepin-7-yl]-1-butanone (free base), obtained in Example 249, and methyl isocyanate, the procedure of Example 28 was similarly repeated to provide the title compound as colorless powders melting at 176–189° C. (dec.).

$^1$H NMR (CDCl$_3$, free base) δ: 1.03–1.41 (5H, m), 1.58–2.04 (6H, m), 2.39 (3H, s), 2.55–2.68 (4H, m), 2.79–3.00 (8H, m), 3.46–3.58 (5H, m), 3.69–3.81 (2H, m), 4.37–4.50 (1H, m), 6.86–7.35 (8H, m), 7.63–7.73 (2H, m), 7.98 (1H, d, J=8.2 Hz), 9.60–9.75 (1H, brs). Elemental analysis, for C$_{36}$H$_{46}$N$_4$O$_2$.2HCl.2H$_2$O. Calcd.: C, 63.99; H, 7.76; N, 8.29.

Found: C, 64.01; H, 7.46; N, 8.21.

EXAMPLE 252

Methyl 2-[[4-[4-[3-[(2-methylphenyl)methyl]2,3,4,5-tetrahydro-1H-3-benzazepin-7-yl]-4-oxobutyl]-1-piperidinyl]methyl]benzoate Dihydrochloride

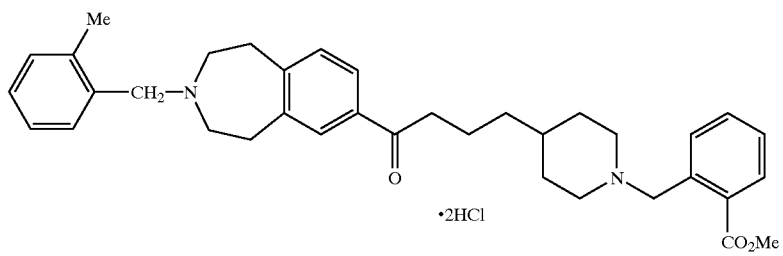

Using 1-[3-[(2-methylphenyl)methyl]-2,3,4,5-tetrahydro-1H-3-benzazepin-7-yl]-4-(4-piperidinyl)-1-butanone (free base), obtained in Example 126, and methyl 2-(bromomethyl)benzoate, the procedure of Example 28 was similarly repeated to provide the title compound as colorless powders melting at 189–192° C.

$^1$H NMR (CDCl$_3$, free base) δ: 1.03–1.36 (4H, m), 1.61–1.81 (5H, m), 1.83–2.05 (2H, m), 2.39 (3H, s), 2.55–3.00 (12H, m), 3.54 (2H, s), 3.70 (2H, s), 3.87 (3H, s), 7.10–7.43 (8H, m), 7.62–7.7:3 (3H, m). Elemental analysis, for C$_{36}$H$_{44}$N$_2$O$_3$.2HCl.3H$_2$O Calcd.: C, 63.61; H, 7.71; N, 4.12.

Found: C, 63.71; H, 7.55; N., 3.80.

EXAMPLE 253

2-[[4-[4-[3-[(2-Methylphenyl)methyl]-2,3,4,5-tetrahydro-1H-3-benzazepin-,7-yl]-4-oxobutyl]-1-piperidinyl]methyl)benzoic Acid

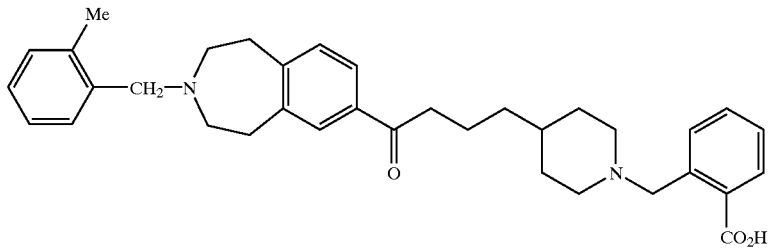

Using methyl 2-[[4-[4-[3-[(2-methylphenyl)methyl)-2,3,4,5-tetrahydro-1H-3-benzazepin-7-yl]-4-oxobutyl]-1-piperidinyl]methyl]benzoate, obtained in Example 252, the procedure of Example 104 was similarly repeated to provide the title compound as colorless powders melting at 129–132° C.

$^1$H NMR (CDCl$_3$+D$_2$O) δ: 1.24–1.56 (5H, m), 1.62–1.92 (4H, m), 2.26–2.51 (5H, m),2.54–2.70 (4H, m), 2.86–3.11 (8H, m), 3.54 (2H, s), 3.84 (2H, s), 7.07–7.50 (8H, m), 7.61–7.74 (2H, m), 8.10–8.21 (1H, m). Elemental analysis, for C$_{35}$H$_{42}$N$_2$O$_3$.0.25H$_2$O. Calcd.: C, 77.39; H, 7.89; N, 5.16. Found: C, 77.52; H, 7.95; N, 5.17.

EXAMPLE 254

2-[[4-[4-[3-[(2-Methylphenyl)methyl]-2,3,4,5-tetrahydro-1H-3-benzazepin-7-yl]-4-oxobutyl]-1-piperidinyl]methyl]benzamide Dihydrochloride

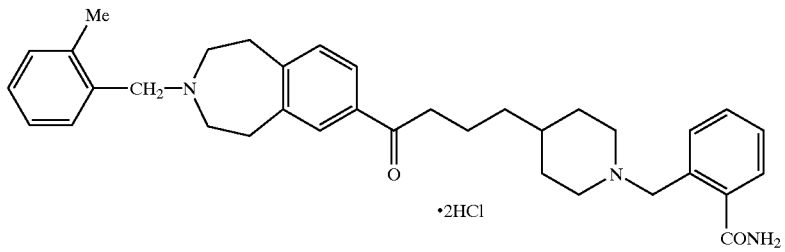

A mixture of 2-[[4-[4-[3-[(2-methylphenyl)methyl)]-2,3,4,5tetrahydro-1H-3-benzazepin-7-yl]-4-oxobutyl]-1-piperidinyl]methyl]benzoic acid (270 mg, 0.50 mmol), obtained in Example 253, and N,N'-carbonyldiimidazole (163 mg, 1.0 mmol) in tetrahydrofuran (7 ml) was stirred at room temperature for 3 hours, then ammonium chloride (268 ml, 5.0 mmol) and triethylamine (506 mg, 5.0 mmol) was added to the mixture. This mixture was then stirred at room temperature for 18 hours, at the end of which time it was poured in water and extracted with ethyl acetate. The extract was washed with saturated NaCl/H$_2$O and dried over MgSO$_4$, and the solvent was distilled off under reduced pressure and the residue was purified by silica gel column chromatography (eluent: ethyl acetate-methanol=10:1) to provide the free base of title compound (168 mg) as a colorless viscous oil.

$^1$H NMR (CDCl$_3$, free base) δ: 0.98–1.37 (5H, m), 1.60–1.80 (4H, m), 1.98–2.17 (2H, m), 2.39 (3H, s), 2.53–2.68 (4H, m), 2.88–3.00 (8H, m), 3.54 (4H, s), 5.70–50.80 (1H, brs), 7.08–7.21 (8H, m), 7.62–7.73 (2H, m), 7.91–8.02 (1H, m), 10.50–10.61 (1H, brs).

The above free base (165 mg) was dissolved in ethyl acetate-methanol, treated with 2 molar equivalents of HCl (dissolved in ethyl acetate) to provide the title compound (187 mg) as colorless powders melting at 201–220° C. (dec.).

Elemental analysis, for C$_{35}$H$_{43}$N$_3$O$_2$.2HCl.2.5H$_2$O. Calcd.: C, 64.11; H, 7.69; N, 6.41. Found,: C, 63.81; H, 7.40; N, 6.15.

EXAMPLE 255

1-[3-(2-Methylphenyl)methyl]-2,3,4,5-tetrahydro-1H-3-benzazepin-7-yl]-4-(4-piperidinyl)-1-butanone Dihydrochloride

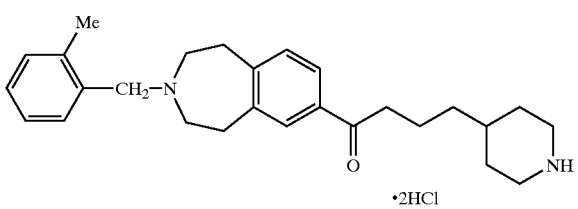

1-[3-[(2-methylphenyl)methyl)-2,3,4,5-tetrahydro-1H-3-benzazepin-7-yl]-4-(4-piperidinyl)-1-butanone (free base), obtained in Example 126, was dissolved in ethyl acetate-

EXAMPLE 256

4-(1-Acetyl-4-piperidinyl)-1-[3-[(2-methylphenyl)methyl)]-2,3,4,5-tetrahydro-1H-3-benzazepin-7-yl]-1-butanone

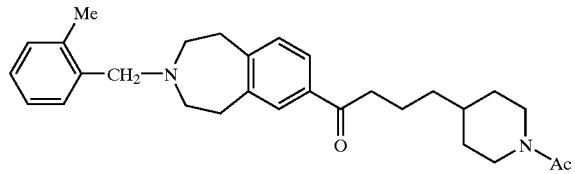

methanol, treated with 2 molar equivalent of HCl (dissolved in ethyl,acetate) and triturated in ethyl acetate to provide the title compound as colorless powders melting at 192–203° C. (dec.). Elemental analysis, for $C_{27}H_{36}N_2O \cdot 2HCl \cdot 0.5H_2O$. Calcd.: C, 66.66; H, 8.08; N, 5.76. Found: C, 66.79; H, 8.22; N? 5.48.

4-(1-acetyl-4-piperidinyl)-1-[3-[(2-methylphenyl)methyl]-2,3,4,5-tetrahydro-1H-3-benzazepin-7-yl]-1-butanone (free base), obtained in Example 125, was solidified on standing at room temperature, and washed with n-hexane to provide the title compound as colorless powders melting at 94–95° C.

Elemental analysis, for $C_{29}H_{38}N_2O_2$ Calcd.: C, 77.99; H, 8.58; N, 6.27. Found: C, 77.91; H, 8.56; N, 6.32.

EXAMPLE 257

4-[[4-[4-(3-(Phenylmethyl)-2,3,4,5-tetrahydro-1H-3-benzazepin-7-yl]-4-oxobutyl]-1-piperidinyl]methyl] benzamide Dihydrochloride

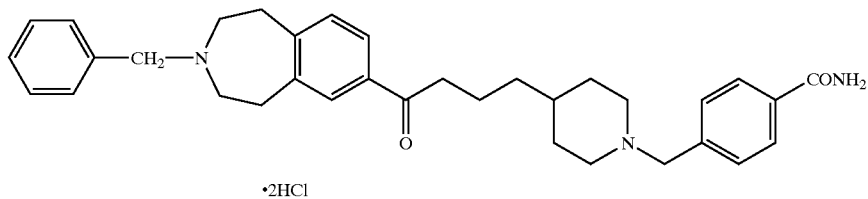

Using 4-[[4-[4-[3-(phenylmethyl)-2,3,4 5-tetrahydro-1H-3-benzazepin-7-yl]-4-oxobutyl]-1-piperidinyl]methyl] benzoic acid, obtained in Example. 183, the procedure of Example 254 was similarly repeated to provide the title compound as colorless amorphous powders.

$^1$H NMR (CDCl$_3$ free base) δ: 1.11–1.39 (5H, m), 1.58–1.81 (4H, m), 1.85–2.03 (2H, m), 2.53–2.70 (4H, m), 2.78–3.04 (8H, m), 3.53 (2H, s), 3.64 (2H, s), 5.53–6.27 (2H, br.), 7.09–7.48 (8H, m) 7.64–7.82 (4H, m).

EXAMPLE 258

4-[1-[(3-Cyanophenyl)methyl-4-piperidinyl]-1-[3-benzazepin-7-yl]-1-butanone Dihydrochloride

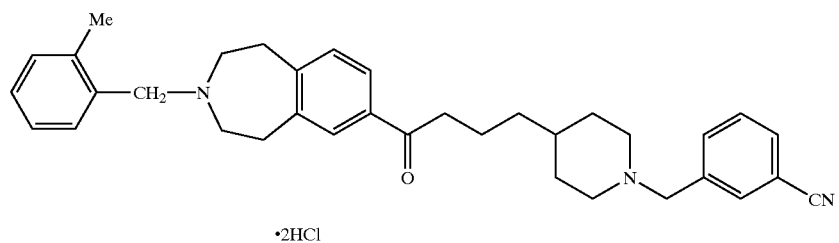

Using 1-(3-[(2-methylphenyl)methyl]-2,3,4,5-tetrahydro-1H-3-benzazepin-7-yl]-4-(4-piperidinyl))-1-butanone (free base), obtained in Example 126, and 3-cyan6benzyl bromide, the procedure of Example 28 was similarly repeated to provide the title compound as colorless amorphous powders.

$^1$H NMR (CDCl$_3$, free base) δ: 1.10–1.40 (5H, m), 1.60–1.85 (4H, m), 1.85–2.10 (2H, m), 2.40 (3H, s), 2.55–2.70 (4H, m), 2.75–3.00 (8H, m), 3.48 (2H, s), 3.54 (2H, s), 7.10–7.25 (4H, m), 7.25–7.85 (7H, m). Elemental analysis, for $C_{35}H_{41}N_3O \cdot 2HCl \cdot 1.5H_2O$. Calcd.: C, 67.84; H, 7.48; N, 6.78.

Found: C, 67.66; H, 7.62; N, 6.73.

EXAMPLE 259

3-[[4-[4-[3-((2-Methylphenyl)methyl)-2,3,4,5-tetrahydro-1H-3-benzazepin-7-yl]-4-oxobutyl]-1-piperidinyl]methyl]benzamide Dihydrochloride

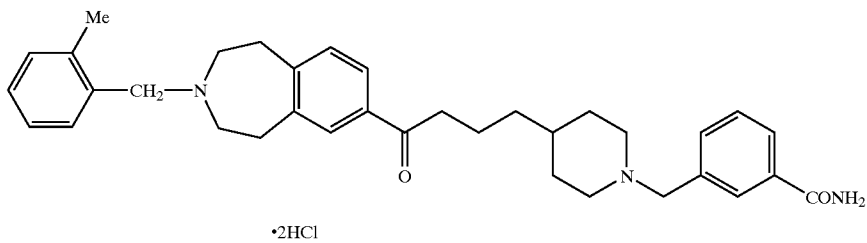

·2HCl

Using 4-[1-[(3-cyanophenyl)methyl]-4-piperidinyl]-1-[(3-[(2-methylphenyl)methyl]-2,3,4,5-tetrahydro-1H-3-benzazepin-7-yl]-1-butanone, obtained in Example 258, the procedure of Example 228 was similarly repeated to provide the title compound as colorless amorphous powders.

$^1$H NMR (CDCl$_3$, free base) δ: 1.10–1.40 (5H, m), 1.60–1.80 (4H, m), 1.85–2.05 (2H, m), 2.39 (3H, s), 2.55–2.70 (4H, m), 20.80–3.05 (8H, m), 3.51 (2H, s), 3.54 (2H, s), 5.80–6.45 (2H, br), 7.10–7.25 (4H, m), 7.25–7.55 (3H, m), 7.65–7.80 (4H, m). Elemental analysis, for C$_{35}$H$_{43}$N$_3$O$_2$.2HCl.H$_2$O. Calcd.: C, 66.87; H, 7.54; N, 6.68. Found: C, 66.85; H, 8.00; N, 6.31.

EXAMPLE 260

3-[[4-[4-3-[(2-Methylphenyl)methyl]-2,3,4,5-tetrahydro-1H-3-benzazepin-7yl]-4-oxobutyl)-1-piperidinyl]methyl]-1-benzenecarboximidamide A mixture of 4-[1-((3-cyanophenyl)methyl]-4-piperidinyl]-1-(3-[(2-methylphenyl)methyl]-2,3,4,5-tetrahydro-1H-3-benzazepin-7-yl]-1-butanone (500 mg, 0.96 mmol), obtained in Example 258, and 9.8 N hydrochloric acid in ethanol (30 ml) was stirred at room temperature for 16 hours and the solvent was distilled off under reduced pressure to give a residue. A mixture of the residue dissolved in ethanol (10 ml) and 5% ammonia in ethanol (w/w, 15 ml) in a sealed stainless tube was heated at 120° C. for 30 minutes. The solvent was distilled off under reduced pressure and the-residue was dissolved in ethyl acetate-1N NaOH/H$_2$O then extracted with ethyl acetate. The extract was washed with saturated NaCl/H$_2$O and dried over K$_2$CO$_3$. The solvent was then distilled off under reduced pressure and the residue was purified by column chromatography using activated basic Alumina (eluent: ethyl acetate-methanol-NH$_4$OH=1:1:0.03), followed by recrystallization from ethanol-ethyl acetate to provide the title compound (307 mg) as colorless crystals melting at 150–152° C.

$^1$H NMR (CDCl$_3$) δ: 1.10–1.40 (5H, m), 1.60–1.82 (4H, m), 1.84–2.05 (5H, m), 2.39 (3H, s), 2.55–2.70 (4H, m), 2.74–3.02 (8H, m), 3.45–3.60 (4H, m), 7.10–7.37 (5H, m) 7.40–7.80 (6H, m). Elemental analysis, for C$_{35}$H$_{44}$N$_4$O.3H$_2$O. Calcd.: C, 71.15; H, 8.53; N, 9.48. Found: C, 71.52; H, 8.19; N, 8.98.

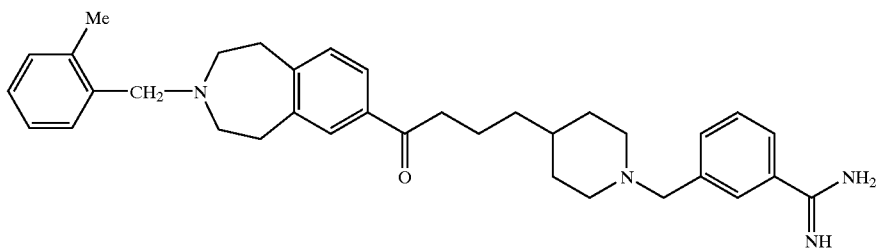

EXAMPLE 261

4-[1-[[3-(4,5-Dihydro-2-thiazolyl)phenyl]0methyl]-
4-piperidinyl]-1-[3-[(2-methylphenyl)methyl]-2,3,4,
5-tetrahydro-1H-3-benzazepin-7-yl]-1-butanone
Dihydrochloride

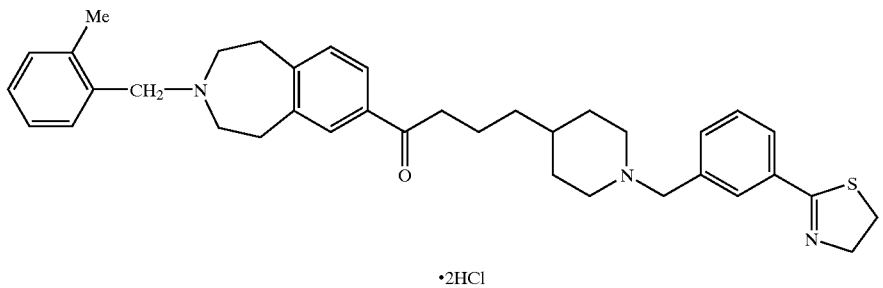

·2HCl

Using 4-[1-[(3-cyanophenyl)methyl]-4-piperidinyl]-1-[3-[(2-methylphenyl)methyl]-2,3,4,5-tetrahydro-1H-3-benzazepin-7-yl]-1-butanone (free base), obtained in Example 258, and 2-aminoethanethiol hydrochloride, the procedure of Example 260 was similarly repeated to provide the title compound as colorless amorphous powders.

$^1$H NMR (CDCl$_3$, free base) δ: 1.15–1.40 (5H, m), 1.55–1.80 (4H, m), 1.85–2.05 (2H, m), 2.60 (3H, m), 2.55–2.70 (4H, m), 2.80–3.05 (8H, m), 3.41 (2H, t, J=8.2 Hz), 3.53 (2H, s), 3.54 (2H, s), 4.46 (2H, t, J=8.2 Hz), 7.10–7.50 (7H, m), 7.65–7.75 (3H, m), 7.77 (1H, s). Elemental analysis, for C$_{37}$H$_{45}$N$_3$OS.2HCl.5.5H$_2$O. Calcd.: C, :59:.11; H, 7.78; N, 5.59. Found C, 59.28; H, 7.57; N, 5.33.

EXAMPLE 262

4-[1-[[3-(4,5-Dihydro-1H-2-imidazolyl)phenyl]
methyl]-4-piperidinyl]-1-[3-[(2-methylphenyl)
methyl]-2,3,4,5-tetrahydro-1H-3-benzazepin-7-yl]-1-
butanone Trihydrochloride

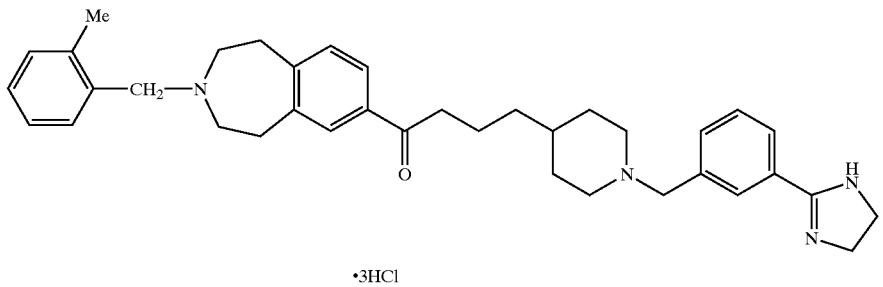

·3HCl

Using 4-[1-[(3-cyanophenyl)methyl]-4-piperidinyl]-1-[3-[(2-methylphenyl)methyl]-2,3,4,5-tetrahydro-1H-3-benzazepin-7-yl]-1-butanone (free base), obtained in Example 258, and ethylenediamine, the procedure of Example 260 was similarly repeated to provide the title compound as colorless powders melting at 183–185° C.

$^1$H NMR (CDCl$_3$, free base) δ: 1.10–1.40 (5H, m), 1.60–1.80 (4H, m), 1.80–2.00 (2H, m), 2.3–9 (3H, s), 2.55–2.70 (4H, m), 2.75–3.00 (9H, m), 3.49 (2H, s), 3.54 (2H, s), 3.78 (4H, s), 7.10–7.20 (4H, m), 7.25–7.45 (3H, m), 7.60–7.75 (4H, m).

EXAMPLE 263

1-(3-Acetyl-2,3,4,5-tetrahydro-1H-3-benzazepin-7-yl)-4-[1-[(2-chlorophenyl)methyl]-4-piperidinyl]-1-butanone

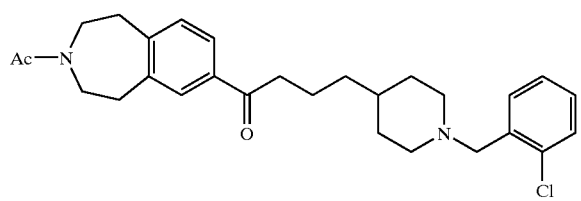

Using 1-(3-acetyl-2,3,4,5-tetrahydro-1H-3-benzazepin-7-yl)-4-(4-piperidinyl)-1-butanone (free base), obtained in Example 234, and 2-chlorobenzyl bromide, the procedure of Example 28 was similarly repeated to provide the title compound as colorless powders melting at 99–100° C.

$^1$H NMR (CDCl$_3$) δ: 1.20–1.40 (5H, m), 1.60–1.80 (5H, m), 200–2.15 (2H, m), 2.20 (3H, s), 2.85–3.10 (8H, m), 3.55–3.65 (3H, m), 3.70–3.80 (2H, m), 7.15–7.40 (4H, m), 7.45–7.55 (1H, m), 7.70–7.80 (2H, m). Elemental analysis, for C$_{28}$H$_{35}$ClN$_2$O$_2$. Calcd.: C, 72.01; H, 7.55; N, 6.00. Found: C, 71.93; H, 7.55; N, 5.95.

EXAMPLE 264

4-[1-[(2-Chlorophenyl)methyl]-4-piperidinyl]-1-(2,3,4,5-tetrahydro-1H-3-benzazepin-7-yl)-1-butanone

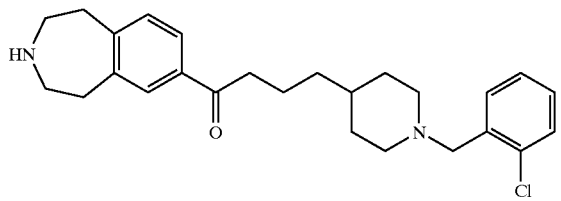

Using 1-(3-acetyl-2,3,4,5-tetrahydro-1H-3-benzazepin-7-yl)-4-[1-[(2-chlorophenyl)methyl]-4-piperidinyl]-1-butanone, obtained in Example 263, the procedure of Example 24 was similarly repeated to provide the title compound as a colorless viscous oil.

$^1$H NMR (CDCl$_3$) δ: 1.15–1.40 (5H, m), 1.60–1.85 (4H, m), 1.90–2.15 (4H, m), 2.80–3.10 (11H, m), 3.59 (2H, s), 7.15–7.30 (3H, m), 7.33 (1H, dd, J=7.4, 1.8 Hz), 7.48 (1H, dd, J=7.4, 2.0 Hz),. 7.65–7.75 (2H, m).

EXAMPLE 265

4-[1-[(2-Chlorophenyl)methyl]-4-piperidinyl]-1-[3-[(2-cyanophenyl)methyl]-2,3 4,5-tetrahydro-1H-3-benzazepin-7-yl]-1-butanone

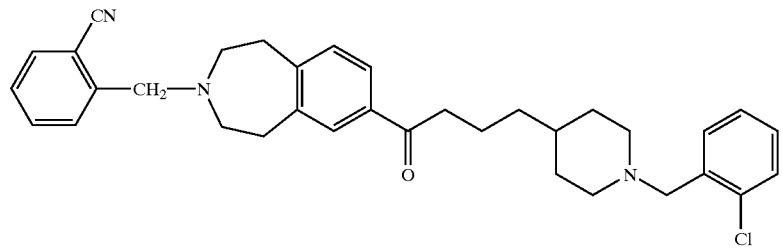

Using 4-[1-[(2-chlorophenyl)methyl]-4-piperidinyl]-1-(2,3,4,5-tetrahydro-1H -3-benzazepin-7-yl)-1-butanone, obtained in Example 264, and 2-cyanobenzyl bromide, the procedure of Example 28 was similarly repeated to provide the title compound as colorless powders melting at 103–104° C.

$^1$H NMR (CDCl$_3$) δ: 1.15–1.40 (5H, m), 1.55–1.85 (5H, m), 1.95–2.20 (2H, m), 2.60–2.80 (4H, m), 2.80–3.05 (7H, m), 3.59 (2H, s), 3.81 (2H, s), 7.10–7.80 (11H, m). Elemental analysis, for C$_{34}$H$_{38}$ClN$_3$O. Calcd.: C, 75.60; H. 7.09; N, 7.78. Found: C, 75.6.4; H, 7.13; N. 7.64.

EXAMPLE 266

2-[[7-[4-[1-[(2-Chlorophenyl)methyl]-4-piperidinyl]butanoyl]-2,3,4,5-tetrahydro-1H-3-benzazepin-3-yl]methyl]benzamide Dihydrochloride

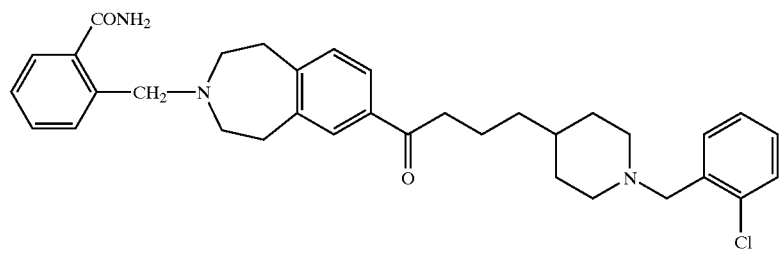

•2HCl

Using 4-[1-[(2-chlorophenyl)methyl]-4 piperidinyl]-1-[3-[(2-cyanophenyl)methyl]-2,3,4,5tetrahydro-1H-3-benzazepin-7-yl]-1-butanone, obtained in Example 265, the procedure of Example 228 was similarly repeated to provide the title compound as colorless amorphous powders.

$^1$H NMR (CDCl$_3$, free base) δ: 1.15–1.40 (5H, m), 1.60–1.85 (4H, m), 1.95–2.20 (2H, m), 2.60–2.80 (4H, m), 2.80–3.00 (8H, m), 3.59 (2H, s), 3.68 (2H, s), 5.95–6.10 (1H, br), 7.05–7.50 (8H, m), 7.65–7.80 (2H, m), 8.00–8.10 (1H, m), 10.33 (1H, br). Elemental analysis, for C$_{34}$H$_{40}$ClN$_3$O$_2$.2HCl.3.5H$_2$O. Calcd.: C, 58.83; H, 7.12; N, 6.05. Found: C, 58.80; H, 6.88; N. 5.99.

EXAMPLE 267

4-[1-[(2-Chlorophenyl)methyl]-4-piperidinyl]-1-[3-[(3-cyanophenyl)methyl]-2,3,4,5-tetrahydro-1H-3-benzazepin-7-yl]-1-butanone Using 4-[1-[(2-chlorophenyl)methyl]-4-piperidinyl]-1-[3-[(3-cyanophenyl)methyl]-2,3,4,5-tetrahydro-1H-3-benzazepin-7-yl]-1-butanone, obtained in Example 267, the procedure of Example 228 was similarly repeated to provide the title compound as colorless amorphous powders.

$^1$H NMR (CDCl$_3$, free base) δ: 1.10–1.40 (5H, m), 1.55–1.80 (4H, m), 1.95–2.15 (2H, m), 2.55–2.70 (4H, m), 2.80–3.05 (8H, m), 3.58 (2H, s), 3.65 (2H, s), 6.15–15 6.5:0 (2H, br), 7.10–7.60 (7H, m), 7.65–7.80 (3H, m), 7.84 (1H, s). Elemental analysis, for C$_{34}$H$_{40}$ClN$_3$O$_2$.2HCl.1.5H$_2$O. Calcd.: C, 62.05; H, 6.89; N, 6.39. Found: C, 62.02; H, 7.16; N, 6.19.

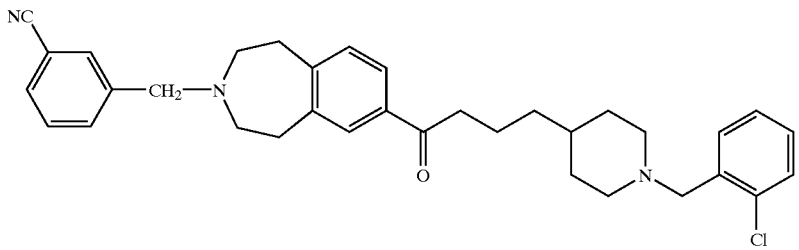

Using 4-[1-[(2-chlorophenyl)methyl]-4-piperidinyl]-1-(2,3,4,5-tetrahydro-1H-3-benzazepin-7-yl)-1-butanone, obtained in Example 264, and 3-cyanobenzyl bromide, the procedure of Example 28 was similarly repeated to provide the title compound as colorless powders melting at 121–122° C.

$^1$H NMR (CDCl$_3$) δ: 1.15–1.40 (5H, m), 1.60–1.80 (5H, m), 1.95–2.15 (2H, m), 2.55–2.70 (4H, m), 2.80–3.05 (7H, m), 3.59 (2H, s), 3.64 (2H, s), 7.10–7.75 (11H, m). Elemental analysis, for C$_{34}$H$_{38}$ClN$_3$O. Calcd.: C, 75.60; H, 7.09; N, 7.78. Found: C, 75.29; H, 7.30; N, 7.71.

EXAMPLE 268

3-[[7-[4-[1-[(2-Chlorophenyl)methyl]-4-piperidinyl] butanoyl]-2,3,4,5-tetrahydro-1H-3-benzazepin-3-yl] methyl]benzamide Dihydrochloride

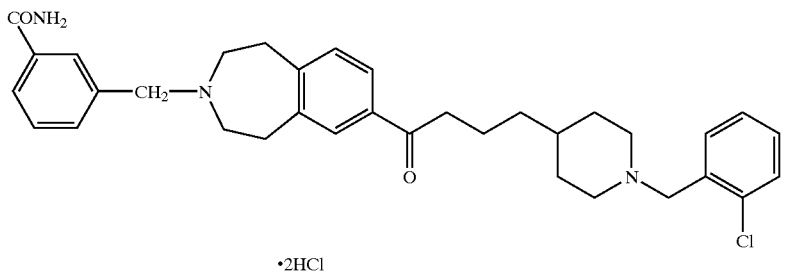

•2HCl

EXAMPLE 269

3-[[7-[4-[1-[(2-Chlorophenyl)methyl]-4-piperidinyl]butanoyl]-2,3,4,5-tetrahydro-1H-3-benzazepin-3-yl]methyl]-1-benzenecarboximidamide Trihydrochloride $^1$H NMR (CDCl$_1$, free base) δ: 1.05–1.40 (5H, m), 1.55–1.80 (4H, m), 1.95–2.15 (2H, m), 2.55–2.70 (4H, m), 2.80–3.05 (8H, m), ca. 3.5–3.9 (9H, m), 7.10–7.50 (7H, m), 7.60–7.75 (3H, m), 7.79 (1H, s). Elemental analysis, for C$_{36}$H$_{43}$ClN$_4$O.3HCl.3H$_2$O. Calcd.: C, 57.91; H, 7.02; N, 7.50. Found: C,58.07; H, 7.18; N, 7.79.

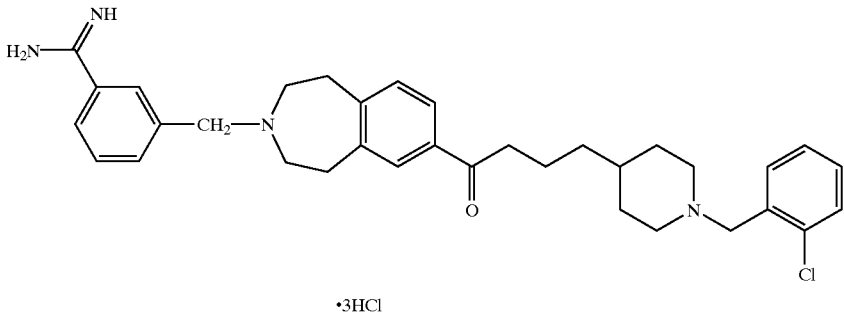

•3HCl

Using 4-[1-[(2-chlorophenyl)methyl]-4-piperidinyl]-1-[3-[(3-cyanophenyl)methyl]-2,3,4,5-tetrahydro-1H-3-benzazepin-7-yl]-1-butanone, obtained in Example 267, the procedure of Example 260 was similarly repeated to provide the title compound as colorless amorphous powders.

$^1$H NMR (CDCl$_3$, free base) δ: 1.10–1.40 (5H, m), 1.55–1.80 (4H, m), 1.95–2.15 (2H, m), 2.55–2.75 (5H, m), 2.80–3.05 (7H, m,) 3.58 (2H, s), 3.65 (2H, s), 4.20–5.20 (3H, br), 7.10–7.75 (11H, m). Elemental analysis, for C$_{34}$H$_{41}$ClN$_4$O.3HCl.2.5H$_2$O. Calcd.: C, 57.39; H, 6.94; N, 7.87. Found: C, 57.58; H, 7.30; N, 8.03.

EXAMPLE 270

4-[1-[(2-Chlorophenyl)methyl]-4-piperidinyl]-1-[3-[[3-(4,5-dihydro-1H-2-imidazolyl)phenyl]methyl]-2,3,4,5-1-tetrahydro-1H-3-benzazepin-7-yl]-1-butanone Trihydrochloride

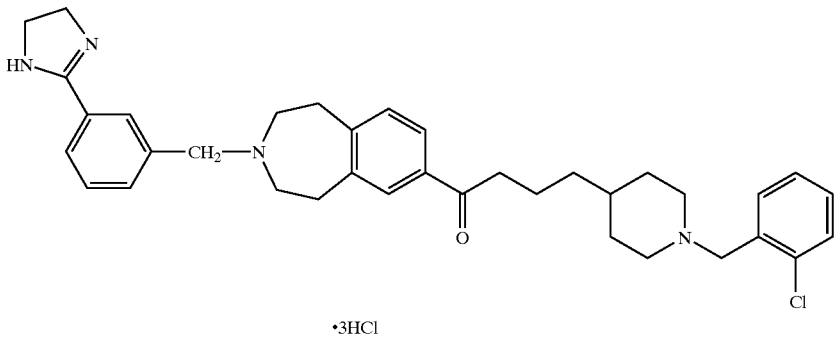

•3HCl

Using 4-[1-[(3-cyanophenyl)methyl]-4-piperidinyl]-1-[3-[(2-methylphenyl)methyl]-2,3,4,5-tetrahydro-1H-3-benzazepin-7-yl]-1-butanone (free base), obtained in Example 267, and ethylenediamine, the procedure of Example 260 was similarly repeated to provide the title compound as colorless amorphous powders.

EXAMPLE 271

4-[1-[(2-Chlorophenyl)methyl]-4-piperidinyl]-1-[3-[(4-cyanophenyl)methyl]-2,3,4,5-tetrahydro-1H-3-benzazepin-7-yl]-1-butanone

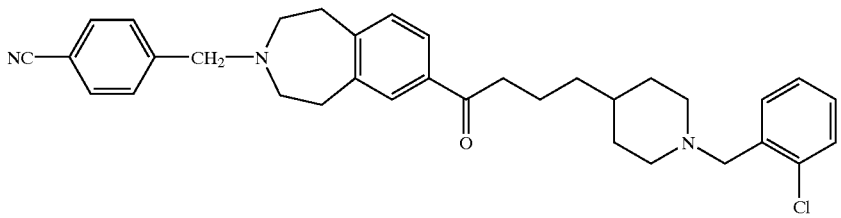

Using 4-[1-[(2-chlorophenyl)methyl]-4-piperidinyl]-1-(2,3,4,5-tetrahydro-1H-3-benzatepin-7-yl)-1-butanone (free base), obtained in Example 264, and 4-cyanobenzyl bromide, the procedure of Example 28 was similarly repeated to provide the title compound as colorless powders melting at 118–119° C.

$^1$H NMR (CDCl$_3$) δ: 1.15–1.40 (5H, m), 1.55–1.65 (4H, m), 1.95–2.15 (2H, m) 2.55–2.70 (4H, m), 2.80–305 (8H, m), 3.59 (2H, s), 3.66 (2H, s), 7.10–7.40 (4H, m), 7.45–7.55 (3H, m), 7.60–7.75 (4H, m). Elemental analysis, for C$_{34}$H$_{38}$ClN$_3$O. Calcd.: C, 75.60; H, 7.09; N, 1.78. Found: C, 75.30; H 7.33; N, 7.65.

EXAMPLE 272

4-[[7-[4-[1-[(2-Chlorophenyl)methyl]-4-piperdinyl]butanoyl)-2,3,4,5-tetrahydro-1H-3-benzazepin-3-yl]methyl]benzamide

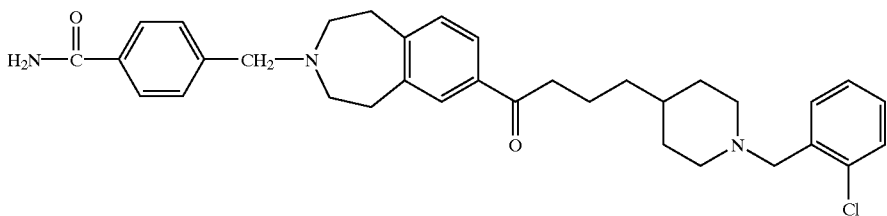

Using 4-[1-[(2-chlorophenyl)methyl]-4-piperidinyl]-1-[3-[(4-cyanophenyl)methyl]-2,3,4,5-tetrahydro-1H-3-benzazepin-7-yl]-1-butanone, obtained in Example 271, the procedure of Example 228 was similarly repeated to provide the title compound as colorless powders melting at 150–151° C.

$^1$H NMR (CDCl$_3$) δ: 1.15–1.40 (5H, m), 1.55–1.80 (4H, m), 1.90–2.15 (2H, m), 2.55–2.70 (4H, m), 2.80–3.00 (8H, m), 3.60 (2H, s), 3.67 (2H, s), 5.50–6.30 (2H, br), 7.10–7.50 (7H, m), 7.65–7.85 (4H, m). Elemental analysis, for C$_{34}$H$_{40}$ClN$_3$O$_2$·H$_2$O. Calcd.: C, 72.00; H, 7.29; N, 7.41. Found: C, 71.84; H, 7.11; N, 7.30.

EXAMPLE 273

Ethyl 2-Methyl-2-[3-[[7-[4-[1-[(2-chlorophenyl)methyl]-4-piperidinyl]butanoyl]2,3,4,5-tetrahydro-1H-3-benzazepin-3-yl]methyl]phenyl]propionate Dihydrochloride

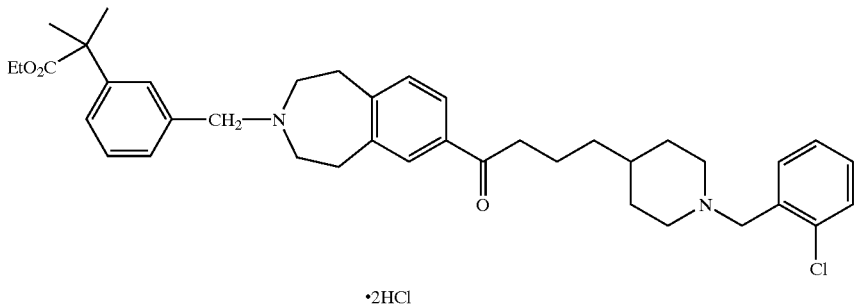

·2HCl

Using 4-[1-[(2-chlorophenyl)methyl]-4-piperidinyl]-1-(2,3,4,5-tetrahydro-1H-3-benzazepin-7-yl)-1-butanone (free base), obtained in Example 264, and ethyl 2-methyl-2-(3-(bromomethyl)phenyl]propionate, the procedure of Example 28 was similarly repeated to provide the title compound as colorless amorphous powders.

$^1$H NMR (CDCl$_3$, free base) δ: 1.05–1.40 (8H, m), 1.55–1.80 (10H, m), 1.95–2.15 (2H, m), 2.55–2.70 (4H, m), 2.80–3.05 (8H, m), 3.58 (2H, s), 3.63 (2H, s), 4.12 (2H, q, J=7.2 Hz), 7.10–7.35 (8H, m), 7.45–7.50 (1H, m), 7.65–7.70 (2H, m). Elemental analysis, for C$_{39}$H$_{49}$ClN$_2$O$_3$.2HCl.1.5H$_2$O. Calcd.: C, 64.24; H., 7.46; N, 3.84. Found: C, 64.19; H, 7.59; N, 3.75.

EXAMPLE 274

2-Methyl-2-[3-[[7-[4-[1-[(2-chlorophenyl)methyl]-4-piperidinyl]butanoyl]-2,3,4,5-tetrahydro-1H-3-benzazepin-3-yl]methyl]phenyl]propionic Acid Dihydrochloride

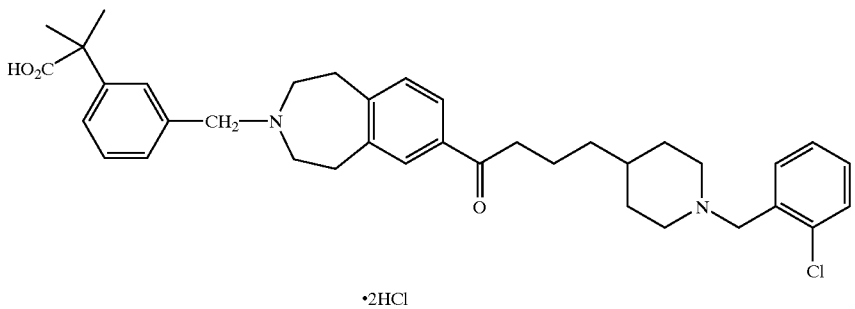

·2HCl

Using ethyl 2-methyl-2-[3-[[7-[4-[1-[(2-chlorophenyl)methyl]-4-piperidinyl]butanoyl]-2,3,4,5-tetrahydro-1H-3-benzazepin-3-yl]methyl]phenyl]propionate, obtained in Example 273, the procedure of Example 104 was similarly repeated to provide the title compound as colorless amorphous powders.

Elemental analysis, for C$_{37}$H$_{45}$ClN$_2$O$_3$.2HCl.3.5H$_2$O. Calcd.: C, 60.28; H, 7.38; N. 3.80. Found: C, 60.45; H, 7.42; N, 3.52.

EXAMPLE 275

Ethyl 2-[2-[[4-[3-[2-[(4-Fluorophenyl)methyl]-2,3,4,5-tetrahydro-1H-2-benzazepin-8-yl]-3-oxopropyl]-1-piperidinyl]methyl]phenoxy]ethanoate Dihydrochloride

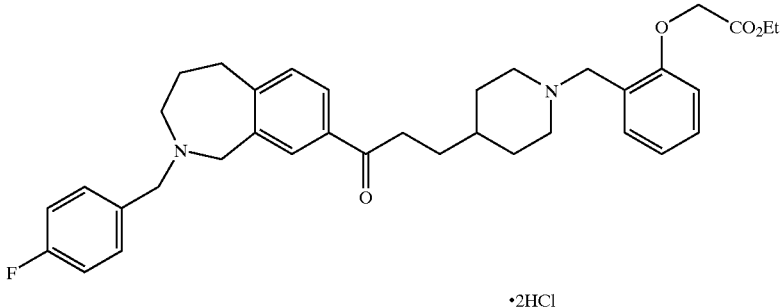

•2HCl

Using 1-[2-[(4-fluorophenyl)methyl]-2,3,4,5-tetrahydro-1H-2-benzazepin-8-yl]-3-(4-piperidinyl)-1-propanone (free base), obtained in Example 211, and ethyl 2-[2-(bromomethyl)phenoxy]ethanoate, the procedure of Example 28 was similarly repeated to provide the title compound as colorless amorphous powders.

$^1$H NMR (CDCl$_3$, free base) δ: 1.20–1.45 (6H, m), 1.60–1.85 (6H, m), 1.95–2.15 (2H, m), 2.80–3.05 (6H, m), 3.11 (2H, t-like, J=5.2 Hz), 3.48 (2H, s), 3.64 (2H, s), 3.90 (2H, s), 4.26 (2H, q, J=7.2 Hz), 4.64 (2H, s), 6.75 (1H, dd, J=8.2, 0.8 Hz), 6.90–7.05 (3H, m), 7.15–7.30 (4H, m), 7.38 (1H, dd, J=7.6, 1.8 Hz), 7.49 (1H, d, J=1.8 Hz), 7.75 (1H, dd, J=7.6, 1.8 Hz). Elemental analysis, for C$_{36}$H$_{43}$FN$_2$O$_4$.2HCl.H$_2$O. Calcd.: C, 63.81; H, 6.99; N, 4.13. Found: C, 63.88; H, 7.03; N, 4.20.

EXAMPLE 276

[2-[[4-[3-[2-[(4-Fluorophenyl)methyl]-2,3,4,5-tetrahydro-1H-2-benzazepin-8-yl]-3-oxopropyl]-1-piperidinyl]methyl]phenoxy]acetic Acid

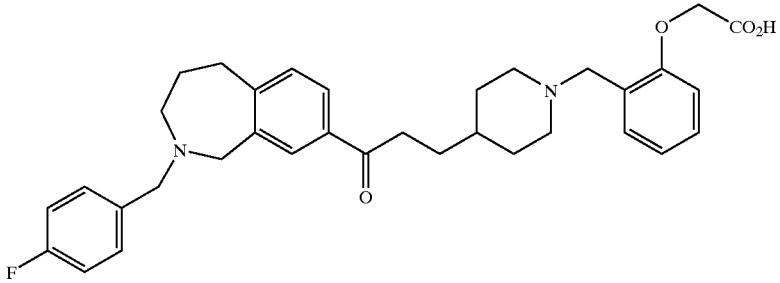

Using ethyl 2-[2-[[4-[3-[2-[(4-fluorohenyl)methyl]2,3,4,5-tetrahydro-1H-2-benzazepin-8-yl]-3-oxopropyl]-1-piperidinyl]methyl]phenoxy]ethanoate, obtained in Example 275, the procedure of Example 104 was similarly repeated to provide the title compound as colorless amorphous powders.

$^1$H NMR (CDCl$_3$) δ: 1.40–2.20 (11H, m), 2.45–2.70 (1H, m), 2.80–3.20 (6H, m), 3.25–3.50 (2H, m), 3.50 (2H, s), 3.90 (2H, s), 3.94 (2H, s), 4.73 (2H, s), .6.90–7.55 (9H, m), 7.60–7.80 (2H, m). Elemental analysis, for C$_{34}$H$_{39}$FN$_2$O$_4$.H$_2$O. Calcd.: C, 70.81; H, 7.17; N, 4.86. Found: C, 70.87; H, 7.09; N, 4.56.

EXAMPLE 277

1-(2-Acetyl-2,3,4,5-tetrahydro-1H-2-benzazepin-8-yl)-3-(4-piperidinyl)-1-propanone Hydrochloride

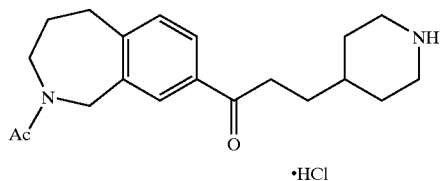

•HCl

Using [1-[(4-nitrobenzyl)oxycarbonyl]-4-piperidinyl] propanoic acid and 2-acetyl-2,3,4,5-tetrahydro-1H-2-benzazepine, the procedure of Example 234 was similarly repeated to provide the title compound as colorless amorphous powders.

$^1$H NMR (CDCl$_3$, free base) δ: 1.00–1.95 (8H, m), 2.04 (3H, s), 2.20–2.40 (1H, m), 2.45–2.65 (2H, m), 2.90–3.15 (6H, m), 3.65–3.95 (2H, m), 4.45–4.65 (2H, m) 4.75–4.85 (1H, m), 6.90–7.35 (1.5H, m), 7.75–7.85 (1H, m), 7.90–8.00 (0.5H, m). Elemental analysis, for C$_{20}$H$_{28}$N$_2$O$_2$HCl.H$_2$O. Calcd.: C, 62.73; H. 8.16; N, 7.32. Found: C, 62.80; H, 8.22; N, 6.95.

EXAMPLE 278

1-(2-Acetyl-2,3,4,5-tetrahydro-1H-2-benzazepin-8-yl)-3-[1-[(2-methylphenyl)methyl]-4-piperidinyi]-1-propanone Hydrochloride

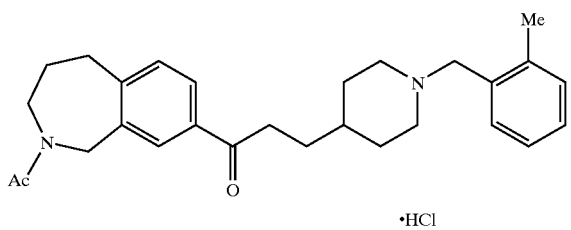

•HCl

Using 1-(2-acetyl-2,3,4,5-tetrahydro-1H-2-benzazepin-8-yl)-3-(4-piperidinyl)-1-propanone, (free base), obtained in Example 277, and 2-methylbenzyl bromide, the procedure of Example 28 was similarly repeated to provide the title compound as colorless amorphous powders.

$^1$H NMR (CDCl$_3$, free base) δ: 1.15–1.40 (3H, m,) 1.55–35 2.15 (8H, m), 2.04 (3H, s), 2.35 (3H, s), 2.80–3.10 (6H, m), 3.42 (2H, s), 3.73 (1H, t-like, J=5.4 Hz), 3.87 (1H, t-like, J=5.4 Hz) 4.55 (1H, s), 4.60 (1H, s), 7.10–7.35 (5.5H, m), 7.65–7.85 (1H, m), 7.90–8.00 (0.5H, m). Elemental analysis, for C$_{28}$H$_{36}$N$_2$O$_2$.HCl.1.5H$_2$O. Calcd.: C, 67.79; H, 8.13; N, 5.65. Found: C, 67.56; H, 8.34; N, 5.49.

EXAMPLE 279

3-[1-[(2-Methylphenyl)methyl]-4-piperidinyl]-1-(2,3,4,5-tetrahydro-1H-2-benzazepin-8-yl)-1-propanone Dihydrochloride

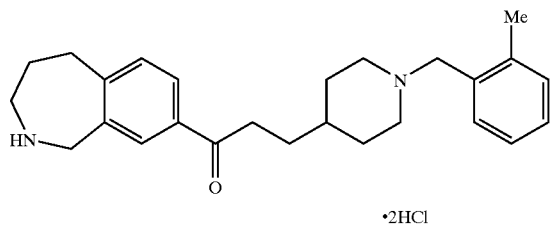

•2HCl

Using 1-(2-acetyl-2,3,4,5-tetrahydro-1H-2-benzazepin-8-yl)-3-[1-[(2-methylphenyl)methyl]-4-piperidinyl]-1-propanone, obtained in Example 278, the procedure of Example 24 was similarly repeated to provide the title compound as colorless amorphous powders.

$^1$H NMR (CDCl$_3$, free base) δ: 1.15–1.40 (3H, m) 1.55–1.80 (7H, m), 1.85–2.05 (2H, m), 2.34 (3H, s), 2.80–3.05 (6H, m), 3.21 (2H, t-like, J=5.4 Hz), 3.41, (2H, s s), 3.97 (2H, s), 7.10–7.30 (5H, m), 7.65–7.70 (2H, m). Elemental analysis, for C$_{26}$H$_{34}$N$_2$O.2HCl.H$_2$O. Calcd.: C, 64.86; H, 7.95; N, 5.82. Found: C, 65.04; H, 8.35; N, 5.75.

EXAMPLE 280

1-[2-[(2-Methylphenyl)methyl]-2,3,4,5-tetrahydro-1H-2-benzazepin-8-yl]-3-[1-[(2-methylphenyl) methyl]-4-piperidinyl]-1-propanone Dihydrochloride

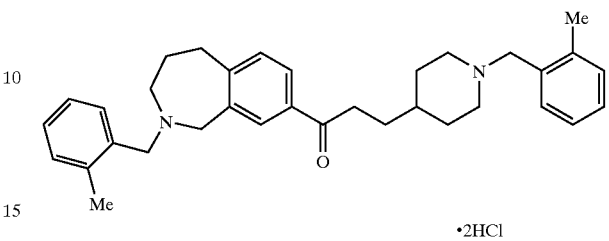

•2HCl

Using 3-[1-[(2-methylphenyl)methyl]-4-piperidinyl]-1(2,3,4,5-tetrahydro-1H-2-benzazepin-8-yl)-1-propanone (free base), obtained in Example 279, and 2-methylbenzyl bromide, the procedure of Example 28 was similarly repeated to provide the title compound as colorless amorphous powders.

$^1$H NMR (CDCl$_3$, free base) δ: 1.15–1.40 (3H, m), 1.55–1.80 (6H, m), 1.85–2.05 (2H, m), 2.26 (3H, s), 2.35 (3H, s), 2.80–3.05 (6H, m), 3.09 (2H, t-like, J=5.2 Hz), 3.42 (2H, s), 3.48 (2H, s), 3.90 (2H, s), 7.05–7.30 (9H, m), 7.53 (3H, d, J=1.4 Hz), 7.75 (1H, dd, J=7.6, 1.8 Hz). Elemental analysis, for C$_{35}$H$_{42}$N$_2$O.2HCl$_2$O. Calcd.: C, 69.73; H, 7.92; N, 4.78. Found: C, 69.93; H, 8.15; N, 4.51.

EXAMPLE 281

1-[2-[(3-Methylphenyl)methyl]-2,3,4,5-tetrahydro-1H-2-benzazepin-8-yl]-3-[1-[(2-methylphenyl) methyl]-4-piperidinyl]-1-propanone Dihydrochloride

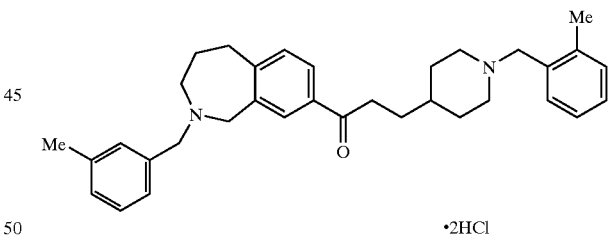

•2HCl

Using 3-[1-[(2-methylphenyl)methyl]-4-piperidinyl]-1(2,3,4,5-tetrahydro-1H-2-benzazepin-8-yl)-1-propanone (free base), obtained in Example 279, and 3-methylbenzyl bromide, the procedure of Example 28 was similarly repeated to provide the title compound as colorless amorphous powders.

$^1$H NMR (CDCl$_3$, free base) δ: 1.15–1.40 (3H m) 1.60–1.85 (6H, m), 1.85–2.05 (2H, m), 2.33 (3H, s), 2.35 (3H, s), 2.80–3.05 (6H, m), 3.12 (2H, t-like, J=5.2 Hz), 3.42 (2H, s), 3.49 (2H, s), 3.91 (2H, s), 7.00–07.30 (9H, m), 7.52(1H, d, J=1.4 Hz), 7.76 (1H, dd, J=8.0, 1.8 Hz). Elemental analysis, for C$_{35}$H$_{42}$N$_2$O.2HCl$_2$O. Calcd.: C, 69.73; H. 7.92; N, 4.78. Found: C, 70.02; H, 8.11; N, 4.51.

EXAMPLE 282

1-[2-[(4-Methylphenyl)methyl]-2,3,4,5-tetrahydro-
1H-2-benzazepin-8-yl]-3-[1-[(2-methylphenyl)
methyl]-4 piperidinyl]-1-propanone Dihydrochloride

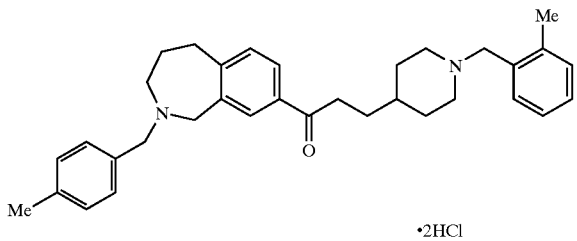

·2HCl

Using 3-[1-[(2-methylphenyl)methyl]-4-piperidinyl]-1-(2,3,4,5-tetrahydro-1H-2-benzazepin-8-yl)-1-propanone (free base), obtained in Example 279, and 4-methylbenzyl bromide, the procedure of Example 28 was similarly repeated to provide the title compound as colorless-amorphous powders.

$^1$H NMR (CDCl$_3$, free base) δ: 1.15–1.40 (3H, m), 1.60–1.85 (6H, m), 1.85–2.05 (2H, m), 2.33 (3H, s), 2.35 (3H, s), 2.80–3.05 (6H, m), 3.12 (2H, t-like, J=5.2 Hz), 3.42 (2H, s), 3.49 (2H, s), 3.90 (2H, s), 7.05–7.35 (9H, m), 7.50 (1H, d, J=1.6 Hz), 7.75 (1H, dd, J=7.6, 1.8 Hz). Elemental analysis, for C$_{35}$H$_{42}$N$_2$O.2HCl.H$_2$O. Calcd.: C, 69.73; H, 7.92; N, 4.78. Found: C, 69.47; H, 8.04; N, 4.45.

EXAMPLE 283

1-[2-[(2-Chlorophenyl)methyl]-2,3,4,5-tetrahydro-
1H-2-benzazepin-8-yl]-3-[1-[(2-methylphenyl)
methyl]-4-piperidinyl]-1-propanone Dihydrochloride

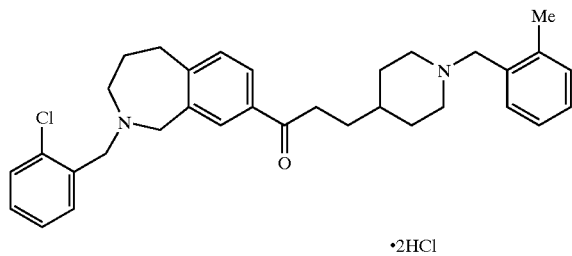

·2HCl

Using 3-[1-[(2-methylphenyl)methyl]-4-piperidinyl]-1-(2,3,4,5-tetrahydro-1H-2-benzazepin-8-yl)-1-propanone (free base), obtained in Example 279, and 2-chlorobenzyl bromide, the procedure of Example 28 was similarly repeated to provide the title compound as colorless amorphous powders.

$^1$H NMR (CDCl$_3$, free base) δ: 1.10–1.45 (3H, m), 1.55–1.85 (6H, m), 1.85–2.05 (2H, m), 2.35 (3H, s), 2.80–3.05 (6H, m), 3.14 (2H, t-like, J=5.2 Hz), 3.41 (2H, s), 3.62 (2H, s), 3.94 (2H, s), 7.05–7.50 (9H, m), 7.57 (1H, d, J=1.4 Hz), 7.76 (1H, dd, J=7.8, 1.8 Hz). Elemental analysis, for C$_{33}$H$_{39}$ClN$_2$O.2HCl.H$_2$O. Calcd.: C, 65.40; H, 7.15; N, 4.62. Found: C, 65.34; H, 7.27; N, 4.33.

EXAMPLE 284

2-[2-[(3-Chlorophenyl)methyl]-2,3,4,5-tetrahydro-
1H-2-benzazepin-8-yl]-3-[1-[(2-methylphenyl)
methyl]-4-piperidinyl]-1-propanone Dihydrochloride

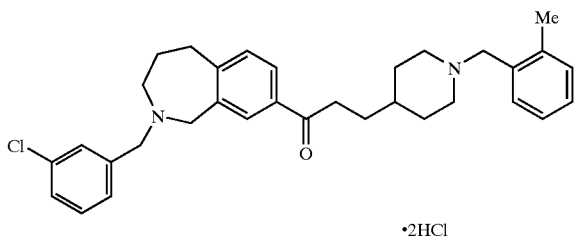

·2HCl

Using 3-[1-[(2-methylphenyl)methyl]-4-piperidinyl]-1-(2,3,4 5-tetrahydro-1H-2-benzazepin-8-yl)-1-propanone (free base), obtained in Example 279, and 3-chlorobenzyl bromide, the procedure of Example 28 was similarly repeated to provide the title compound as colorless amorphous powders.

$^1$H NMR (CDCl$_3$, free base) δ: 1.15–1.40 (3H, m), 1.60–1.80 (6H, m), 1.85–2.05 (2H, m), 2.35 (3H, s), 2.80–3.05 (6H, m), 3.11 (2H, t-like, J=5.2 Hz), 3.42 (2H, s), 3.48 (2H, s), 3.89 (2H, s), 7.10–7.30 (9H, m), 7.47 (1H, d, J=1.4 Hz), 7.76 (1H, dd, J=7.8, 1.8 Hz). Elemental analysis, for C$_{33}$H$_{39}$ClN$_2$O.2HCl$_2$O. Calcd.: C, 64.44; H, 7.21; N, 4.55. Found: C, 64.64; H, 7.00; N, 3.99.

EXAMPLE 285

1-[2-[(4-Chlorophenyl)methyl]-2,3,4,5-tetrahydro-
1H-2-benzazepin-8-yl]-3-[1-[(2-methylphenyl)
methyl]-4-piperidinyl]-1-propanone Dihydrochloride

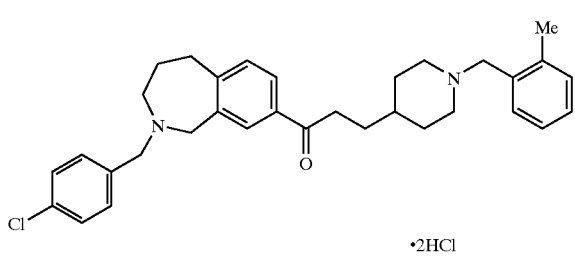

·2HCl

Using 3-[1-[(2-methylphenyl)methyl]-4-piperidinyl]-1-(2,3,4,5-tetrahydro-1H-2-benzazepin-8-yl)-1-propanone (free base), obtained in Example 279, and 4-chlorobenzyl bromide, the procedure of Example 28 was similarly repeated to provide the title compound as colorless amorphous powders.

$^1$H NMR (CDCl$_3$, free base) δ: 1.15–1.40 (3H, m), 1.60–1.85 (6H, m), 1.85–2.05 (2H, m), 2.35 (3H, s), 2.80–3.05 (6H, m), 3.12 (2H, t-like, J=5.2 Hz), 3.42 (2H, s), 3.49 (2H, s), 3.90 (2H, s), 7.05–7.40 (9H, m), 7.49 (1H, d, J=1.6 Hz), 7.77 (1H, dd, J=7.6, 1.8 Hz). Elemental analysis, for C$_{33}$H$_{39}$ClN$_2$O.2HCl.H$_2$O. Calcd.: C, 65.40; H, 7.15; N, 4.62: Found: C, 65.36; H, 7.09; N, 4.61.

EXAMPLE 286

Ethyl 2-Methyl-2-[3-[[4-[3-[2-[(4-fludrophenyl)methyl]-2,3,4,5-tetrahydro-1H-2-benzazepin-8-yl]-3-oxopropyl ]-1-piperidinyl methyl]phenyl]propionate Dihydrochloride

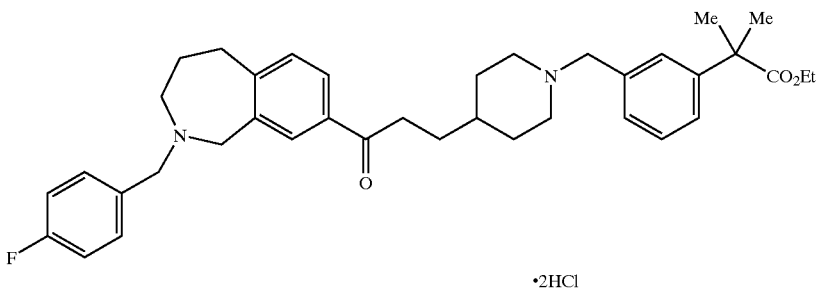

•2HCl

Using 1-[2-[(4-fluorophenyl)methyl]-2,3,4,5-tetrahydro-1H-2-benzazepin-8-yl]-3-(4-piperidinyl)-1-propanone (free base), obtained in Example 211, and ethyl 2-methyl-2-[3-(bromomethyl)phenyl]propionate, the procedure of Example 28 was similarly repeated to provide the title compound as colorless amorphous powders.

$^1$H NMR (CDCl$_3$, free base) δ: 1.17 (3H, t, J=7.2 Hz), 1.15–1.40 (3H, m), 1.57 (6H, s), 1.60–1.85 (6H, m) 1.85–2.05 (2H, m), 2.80–3.05 (6H, m), 3.11 (2H, t-like, J=5.2 Hz), 3.48 (4H, s), 3.89 (2H, s), 4.12 (2H, q, J=7.2 Hz), 6.99 (2H, t-like, J=8.6 Hz), 7.15–7.30 (7H, m), 7.48 (1H, d, J=1.8 Hz), 7.75 (1H, dd, J=7.7, 1.8 Hz). Elemental analysis, for C$_{38}$H$_{47}$FN$_2$O$_3$.2HCl.0.5H$_2$O. Calcd.: C, 67.05; H, 7.40; N, 4.12. Found: C, 66.85; H, 7.49; N, 4.10.

EXAMPLE 287

2-Methyl-2-[3-[[4-[3-[2-[(4-fluorophenyl)methyl]-2,3,4,5-tetrahydro-1H-2-benzazepin-8-yl]-3-oxopropyl]-1-piperidinyl]methyl]phenyl]propanoic Acid

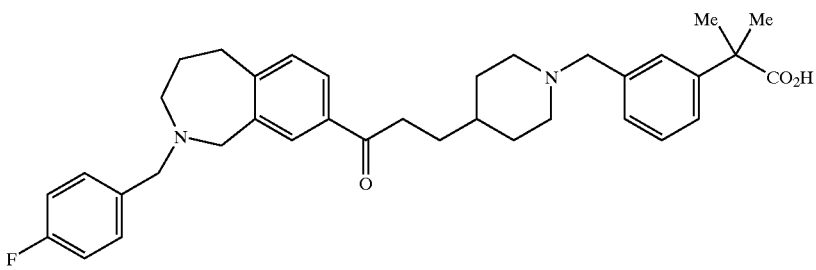

Using ethyl 2-methyl-2-[3-[[4-[3-[2-[(4-fluorophenyl)methyl]-2,3,4,5-tetrahydro-1H-2-benzazepin-8-yl]-3-oxopropyl]-1-piperidinyl]methyl]phenyl]propionate, obtained in Example 286, the procedure of Example 104 was similarly repeated to provide the title compound as colorless amorphous powders.

$^1$H NMR (CDCl$_3$, free base) δ: 1.15–2.05 (17H, m), 2.75–3.00 (6H, m), 3.09 (2H, t-like, J=4.8 Hz), 3.41 (2H, s), 3.47 (2H, s), 3.89 (2H, s), 6.10–6.80 (1H, br), 6.90–7.40 (9H, m), 7.49 (1H, d, J=1.4 Hz), 7.73 (1H, dd, J=7.6, 1.8 Hz). Elemental analysis, for C$_{36}$H$_{43}$FN$_2$O$_3$.2HCl.3H$_2$O. Calcd.: C, 61.97; H, 7.37; N, 4.02. Found: C, 62.22; H, 6.76; N, 3.74.

EXAMPLE 288

Ethyl [4-[3-[2-[(4-Fluorophenyl)methyl]-2,3,4,5-tetrahydro-1H-2-benzazepin-8-yl]-3-oxopropyl]-1-piperidinyl]acetate Dihydrochloride

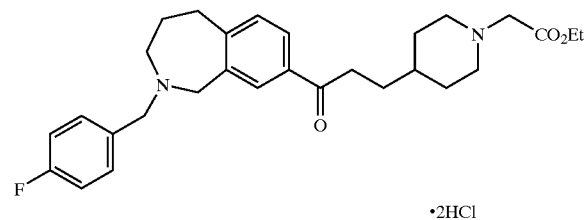

•2HCl

Using 1-[2-[(4-fluorophenyl)methyl]-2,3,4,5-tetrahydro-1H-2-benzazepin-8-yl]-3-(4-piperidinyl)-1-propanone (free base), obtained in Example 211, and ethyl bromoacetate, the procedure of Example 28 was similarly repeated to provide the title compound as colorless amorphous powders.

$^1$H NMR (CDCl$_3$, free base) δ: 1.20–1.50 (3H, m), 1.27 (3H, t, J=7.2 Hz), 1.60–1.85 (6H, m), 2.05–2.25 (2H, m), 2.85–3.05 (6H, m), 3.11 (2H, t-like, J=5.2 Hz), 3.20 (2H, s), 3.49 (2H, s), 3.90 (2H, s), 4.19 (2H, q, J=7.2 Hz), 7.00 (2H, t-like, J=8.6 Hz), 7.15–7.30 (3H, m), 7.49 (1H, d, J=1.6 Hz), 7.77 (1H, dd, J=7.8, 1.8 Hz). Elemental analysis, for C$_{29}$H$_{37}$FN$_2$O$_3$.2HCl. 0.5H$_2$O. Calcd.: C, 61.92; H, 7.17; N, 4.98. Found: C, 62.07; H, 7.17; N, 4.83.

EXAMPLE 289

Ethyl 4-[4-[3-[2-[(4-Fluorophenyl)methyl]-2,3,4,5-tetrahydro-1H-2-benzazepin-8-yl]-3-oxopropyl]1-piperidinyl]butanoate Dihydrochloride

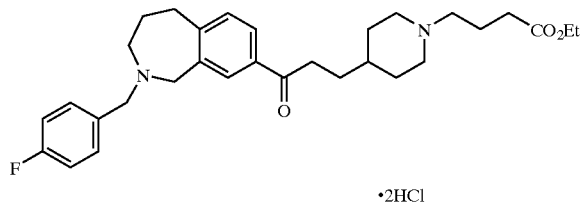

·2HCl

Using 1-[2-[(4-fluorophenyl)methyl]-2,3,4,5-tetrahydro-1H-2-benzazepin-8-yl]-3-(4-piperidinyl)-1-propanone (free base), obtained in Example 211, and ethyl 4-bromobutyrate, the procedure of Example 28 was similarly repeated to provide the title compound as colorless amorphous powders.

$^1$H NMR (CDCl$_3$, free base) δ: 1.25–1.45: (3H, m), 1.26 (3H, t, J=7.2 Hz), 1.60–2.10 (10H, m), 2.25–2.45 (4H, m), 2.85–3.05 (6H, m), 3.12 (2H, t-like, J=55.2 Hz), 3.49 (2H, s), 3.90 (2H, s), 4.13 (2H, q, J=7.2 Hz), 7.00 (2H, t-like, J=8.6 Hz), 7.15–7.30 (3H, m), 7.49 (1H, d, J=1.4 Hz), 7.77 (1H, dd, J=7.7, 1.8 Hz). Elemental analysis, for $C_{31}H_{41}FN_2O_3$·2HCl·0.5H$_2$O. Calcd.: C, 63.04; H, 7.51; N, 4.74. Found: C, 63.08; H, 7.14; N, 4.72.

EXAMPLE 290

1-[2-[(4-Fluorophenyl)methyl]-2,3,4,5-tetrahydro-1H-2-benzazepin-8-yl]-3-[1-(2-hydroxyethyl)-4-piperidinyl]-1-propanone Dihydrochloride

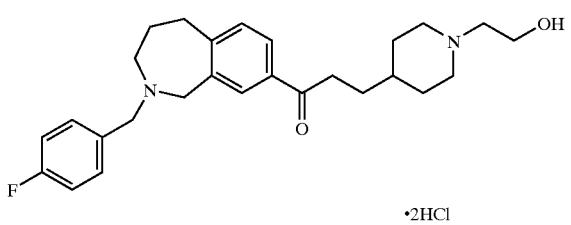

·2HCl

Using 1-[2-[(4-fluorophenyl)methyl]-2,3,4,5-tetrahydro-1H-2-benzazepin-8-yl]-3-(4-piperidinyl)-1-propanone (free base), obtained in Example 211, and 2-bromoethanol, the procedure of Example 28 was similarly repeated to provide the title compound as colorless amorphous powders.

$^1$H NMR (CDCl$_3$, free base) δ: 1.15–1.45 (3H, m), 1.60–1.80 (6H, m), 1.95–2.15 (2H, m), 2.51 (2H, t, J=5.4 Hz), 2.80–3.05 (7H, m), 3.12 (2H, t-like, J=5.2 Hz), 3.50 (2H, s), 3.61 (2H, t, J=5.4 Hz), 3.90 (2H, s), 7.00 (2H, t-like, J=8.6 Hz), 7.15–7.35 (3H, m), 7.49 (1H, d, J=1.6 Hz), 7.77 (1H, dd, J=7.8, 1.8 Hz). Elemental analysis, for $C_{27}H_{35}FN_2O_2$·2HCl·0.5H$_2$O. Calcd.: C, 63.30; H, 7.36; N. 5.38. Found: C, 62.78; H, 7.35; N, 5.33.

EXAMPLE 291

3-[1-[2-(Diethylamino)ethyl]-4-piperidinyl-]1-[2-[(4-fluorophenyl)methyl]-2,3,4,5-tetrahydro-1H-2-benzazepin-8-yl]-1-propanone Trihydrochloride

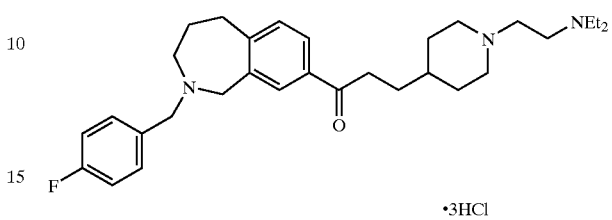

·3HCl

Using 1-[2-[(4-fluorophenyl)methyl]-2,3,4,5-tetrahydro-1H-2-benzazepin-8-yl]-3-(4-peridinyl)-1-propanone (free base), obtained in Example 211, and 2-dimethylaminoethyl chloride hydrochloride, the procedure of Example 28 was similarly repeated to provide the title compound as colorless amorphous powders.

$^1$H NMR (CDCl$_3$, free base) δ: 1.04 (6H, t, J=7.2 Hz), 1.20–1.40 (3H, m), 1.60–1.85 (6H, m), 1.85–2.05(2H, m), 2.40–2.65 (8H, m), 2.85–3.00 (6H, m), 3.11 (2H, t-like, J=5.2 Hz), 3.49 (2H, s), 3.90 (2H, s), 7.00 (2H, t-like, J=8.6 Hz), 7.15–7.30 (3H, m), 7.48 (1H, d J=1.8 Hz), 7.76 (1H, dd, J=7.6, 1.8 Hz). Elemental analysis, for $C_{31}H_{44}FN_3O$·3HCl·0.5H$_2$O. Calcd.: C, 60.83; H, 7.90; N, 6.87. Found: C, 60.42; H, 7.39; N, 6.74.

EXAMPLE 292

3-[1-(Chloroacetyl)-4-piperidinyl]-1-[2-[(4-fluorophenyl)methyl]-2,3,4,5-tetrahydro-1H-2-benzazepin-8-yl]-1-propanone

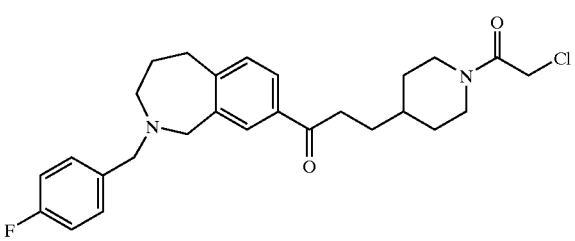

Using 1-[2-[(4-fluorophenyl)methyl]-2,3,4,5-tetrahydro-1H-2-benzazepin-8-yl]-3-(4-piperidinyl)-1-propanone (free base), obtained in Example 211, and chloroacetyl chloride, the procedure of Example 28 was similarly repeated to provide the title compound as colorless amorphous powders.

¹H NMR (CDCl₃) δ: 1.05–1.40 (2H, m), 1.45–1.90 (8H, m), 2.62 (1H, dt, J=12.8, 2.6 Hz), 2.85–3.20 (6H, m), 3.50 (2H, s), 3.85–3.95 (1H, m), 3.90 (2H, s), 4.07 (1H, s), 4.08 (1H, s), 4.45–4.65 (1H, m), 7.00 (2H, t-like, J=8.8 Hz), 7.15–7.30 (3H, m), 7.48 (1H, d, J=1.8 Hz), 7.76 (1H, dd, J=7.8, 1.8 Hz).

EXAMPLE 293

3-[1-(Dimethylaminoacetyl)-4-piperidinyl]-1-[2-[(4-fluorophenyl)methyl]-2,3,4,5-tetrahydro-1H-2-benzazepin-8-yl]-1-propanone Hydrochloride

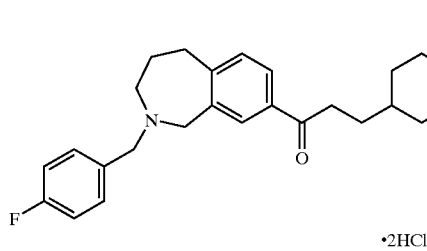

·2HCl

Using 3-[1-(chloroacetyl)-4-piperidinyl]-1-[2-[(4-methylphenyl)methyl]-2,3,4,5-tetrahydro-1H-2-benzazepin-8-yl]-1-propanone (free base), obtained in Example 292, and dimethylamine hydrochloride, the procedure of Example 28 was similarly repeated to provide the title compound as colorless amorphous powders.

¹H NMR (CDCl₃, free base) δ: 1.00–1.25 (2H, m), 1.40–1.85 (7H, m), 2.32 (6H, s), 2.45–2.70 (1H, m), 2.85–3.20 (9H, m), 3.50 (2H, s), 3.91 (2H, s), 4.00–4.15 (1H, m), 4.50–4.65 (1H, m), 7.00 (2H, t-like, J=8.6 Hz), 7.15–7.30 (3H, m), 7.49 (1H, d, J=1.6 Hz), 7.77 (1H, dd, J=7.8, 1.8 Hz). Elemental analysis, for $C_{29}H_{38}FN_3O.2HCl.0.5H_2O$. Calcd.: C, 62.03; H, 7.36; N, 7.48. Found: C, 61.80; H, 7.36; N, 7.29.

EXAMPLE 294

1-[2-[(4-Fluorophenyl)methyl]-2,3,4,5-tetrahydro-1H-2-benzazepin-8-yl]-3-[1-(2-oxiranylmethyl) 4-piperidinyl]-1-propanone

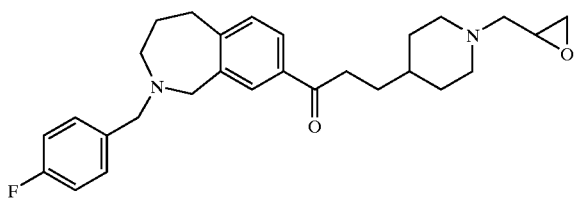

Using 1-[2-[(4-fluorophenyl)methyl]-2,3,4,5-tetrahydro-1H-2-benzazepin-8-yl]-3-(4-piperidinyl)-1-propanone (free base), obtained in Example 211, and epibromohydrin, the procedure of Example 28 was similarly repeated to provide the title compound as colorless amorphous powders.

¹H NMR (CDCl₃) δ: 1.10–1.30 (3H, m), 1.60–1.85 (6H, m), 1.90–2.15 (2H, m), 2.29 (1H, dd, J=13.2, 6.6 Hz), 2.48 (1H, dd, J=4.9, 2.6 Hz), 2.65–2.80 (2H, m), 2.85–3.20 (9H, m), 3.49 (2H, s), 3.90 (2H, s ), 6.99 (2H, t-like, J=8.6 Hz), 7.15–7.30 (3H, m), 7.49 (1H, d, J-1.6 Hz), 7.76 (1H, dd, J=7.9, 1.6 Hz).

EXAMPLE 295

3-[1-(3-Dimethylamino-2-hydroxypropyl)-4-piperidinyl]-1-[2-[(4-fluorophenyl)methyl]-2,3,4,5-(tetrahydro-1H-2-benzazepin-8-yl]-1-propanone Trihydrochloride

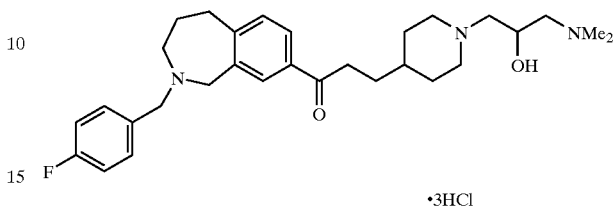

·3HCl

Using 1-[2-[(4-fluorophenyl)methyl]-2,3,4,5-tetrahydro-1H-2-benzazepin-8-yl]-3-[1-(2-oxiranylmethyl)-4-piperidinyl]-1-propanone, obtained in Example 294, and dimethylamine, (2.0 molar solution in tetrahydrofuran), the procedure of Example 28 was similarly repeated to provide the title compound as colorless amorphous powders.

¹H NMR (CDCl₃, free base) δ: 1.20–1.45 (3H, m), 1.60–1.85 (6H, m), 1.85–2.05 (2H, m), 2.10–2.40 (9H, m), 2.85–3.05 (6H, m), 3.11 (2H, t-like, J=5.2 Hz), 3.20–3.50 (4H, m), 3.75–3.92 (3H, m), 6.99 (2H, t-like, J=8.6 Hz), 7.15–7.30 (3H, m), 7.48 (1H, d, J=1.6 Hz), 7.76 (1H, dd, J=7.7, 1.8 Hz). Elemental analysis, for $C_{36}H_{42}FN_3O_2.3HCl.0.5H_2O$. Calcd.: C, 58.68; H, 7.55; N, 6.84. Found: C, 58.77; H, 7.49; N, 6.71.

EXAMPLE 296

3-[1-(Cyanomethyl)-4-piperidinyl]-1-[2-[(4-fluorophenyl)methyl]-1,2,3,4,5-tetrahydro-1H-2-benzazepin-8-yl]-1-propanone

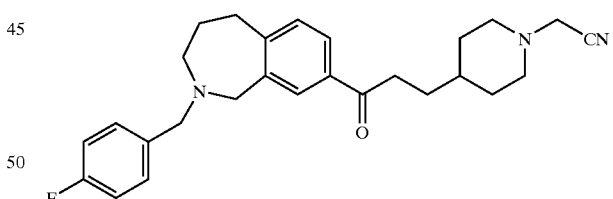

Using, 1-[2-[(4-fluorophenyl)methyl]-2,3,4,5-tetrahydro-1H-2-benzazepin-8-yl]-3-(4-piperidinyl)-1-propanone (free base), obtained in Example 211, and bromoacetonitrile, the procedure of Example 28 was similarly repeated to provide the title compound as colorless powders melting at 132–133° C.

¹H NMR (CDCl₃, free base) δ: 1.15–1.45 (3H, m), 1.55–1.90 (6H, m), 2.25–2.40 (2H, m), 2.75–3.05 (6H, m), 3.11 (2H, t-like, J=5.2 Hz), 3.50 (2H, s), 3.53 (2H, s), 3.90 (2H, s), 7.00 (2H, t-like, J=8.6 Hz), 7.15–7.30 (3H, m), 7.49 (1H, d, J=1.8 Hz), 7.7:6 (1H, dd, J=8.0, 1.8 Hz).

EXAMPLE 297

N-[3-[[7-[4-[1-[(2-chlorophenyl)methyl]-4-piperidinyl]butanoyl]-2,3,4,5-tetrahydro-1H-3-benzazepin-3-yl]methyl]phenyl]acetamide
Dihydrochloride

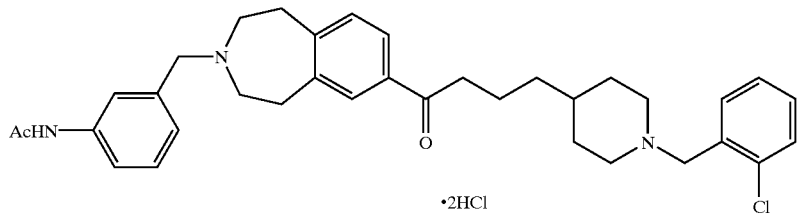

Using 4-[1-[(2-chlorophenyl)methyl]-4-piperidinyl]-1-(2,3,4,5-tetrahydro-1H-3-benzazepin-7-yl)-1-butanone (free base), obtained in Example 264, and 3-(acetylamino)benzyl bromide, the procedure of Example 28 was similarly repeated to provide the title compound as colorless amorphous powders.

$^1$H NMR (CDCl$_3$, free base) δ: 1.20–1.55 (4H, m), 1.60–1.90 (5H, m), 2.18 (3H, s), 2.40–2.60 (2H, m), 2.70–2.95 (7H, m), 3.00–3.30 (6H, m), 3.77 (2H, s), 4.05 (2H, s), 7.00–7.40 (6H, m), 7.50–7.75 (4H, m), 7.90–8.00 (1H, m).

EXAMPLE 298

1-[3-[(3-Aminophenyl)methyl]-2,3,4,5-tetrahydro-1H-3-benzazepin-7-yl]-4-[1-[(2-chlorophenyl)methyl]-4-piperidinyl]-1-butanone Trihydrochloride

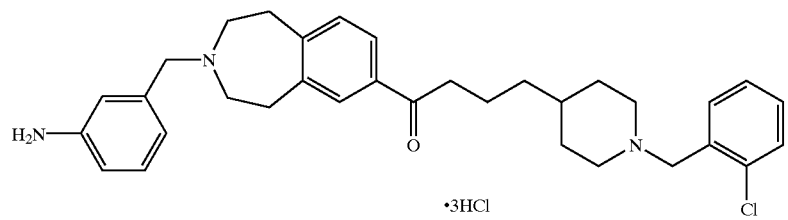

Using N-[3-[[7-[4-[1-[(2-chlorophenyl)methyl]-4-piperidinyl]butanoyl]-2,3,4,5-tetrahydro-1H-3-benzazepin-3-yl]methyl]phenyl]acetamide, obtained in Example 297, the procedure of Example 24 was similarly repeated to provide the title compound as colorless amorphous powders.

$^1$H NMR (CDCl$_3$, free base) δ: 1.15–1.45 (5H, m), 1.55–1.80 (4H, m), 1.95–2.15 (2H, m), 2.50–2.70 (4H, m), 2.80–3.05 (8H, m), 3.40–3.80 (6H, m), 6.50–6.65 (1H, m), 6.65–6.80 (2H, m), 7.05–7.30 (4H, m), 7.32 (1H, dd, J=7.1, 2.0 Hz), 7.48 (1H, dd, J=7.3, 2.0 Hz), 7.65–7.75 (2H, m).

EXAMPLE 299

N-[3-[[7-[4-[1-[(2-chlorophenyl)methyl]-4-piperidinyl]butanoyl]-2,3,4,5-tetrahydro-1H-3-benzazepin-3-yl]methyl]phenyl]urea
Dihydrochloride

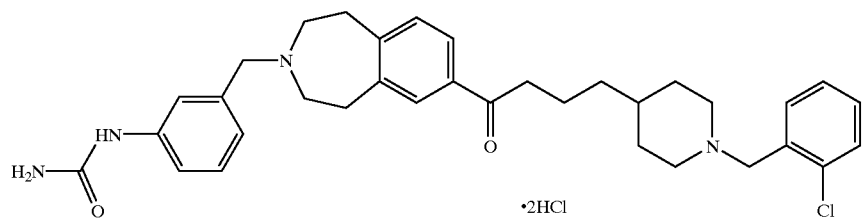

Using 1-[3-[(3-aminophenyl)methyl]-2,3,4,5-tetrahydro-1H-3-benzazepin-7-yl]-4-[1-[(2-chlorophenyl)methyl]-4-piperidinyl]-1-butanone (free base), obtained in Example 298, the procedure of Example 224 was similarly repeated to provide the free base of title compound as colorless powders melting at 123–124° C., and the title compound as colorless amorphous powders.

¹H NMR (CDCl₃, free base) δ: 1.10–1.40 (5H, m), 1.55–1.95 (4H, m), 1.95–2.15 (2H, m), 2.50–2.70 (4H, m), 2.80–3.05 (8H, m), 3.59 (4H, s), 4.75–4.95 (2H, br), 6.75–7.00 (1H, br), 7.00–7.35 (8H, m), 7.40–7.50 (1H, m), 7.60–7.75 (2H, m).

EXAMPLE 300

4-[1-[(2-Chlorophenyl)methyl]-4-piperidinyl]-1-[3-[(3-methylphenyl)methyl]-2,3,4,5-tetrahydro-1H-3-benzazepin-7-yl]-1-butanone Dihydrochloride

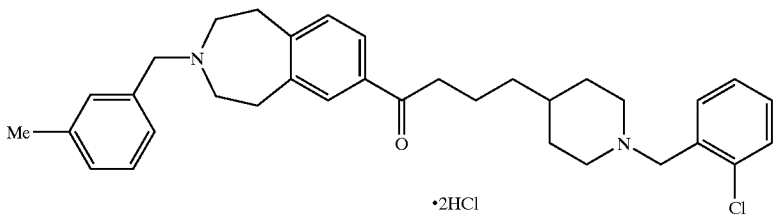

Using 4-[1-[(2-chlorophenyl)methyl]-4-piperidinyl]-1-(2,3,4,5-tetrahydro-1H-3-benzazepin-7-yl)-1-butanone (free base), obtained in Example 264, and 3-methylbenzyl bromide, the procedure of Example 28 was similarly repeated to provide the title compound as colorless amorphous powders.

¹H NMR (CDCl₃, free base) δ: 1.15–1.40 (5H, m), 1.60–1.80 (4H, m), 1.95–2.15 (2H, m), 2.36 (3H, s), 2.50–2.70 (4H, m), 2.80–3.05 (8H, m), 3.59 (2H, s), 3.60 (2H, s), 7.00–7.25 (7H, m), 7.33 (1H, dd, J=7.4, 1.8 Hz), 7.48 (1H, dd, J=7.4, 1.8 Hz), 7.65–7.75 (2H, m).

EXAMPLE 301

4-[1-[(2-Chlorophenyl)methyl]-4-piperidinyl]-1-[3-[(4-methylphenyl)methyl]-2,3,4,5-tetrahydro-1H-3-benzazepin-7-yl]-1-butanone Dihydrochloride

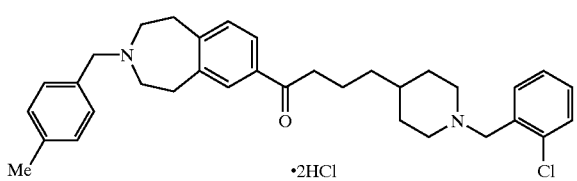

Using 4-[1-[(2-chlorophenyl)methyl]-4-piperidinyl]-1-(2,3,4,5-tetrahydro-1H-3-benzazepin-7-yl)-1-butanone (free base), obtained in Example 264, and 4-methylbenzyl bromide, the procedure of Example 28 was similarly repeated to provide the title compound as colorless powders melting at 196–198° C.

¹H NMR (CDCl₃, free base) δ: 1.15–1.40 (5H, m), 1.55–1.85 (4H, m), 1.95–2.20 (2H, m), 2.34 (3H, s), 2.50–2.70 (4H, m), 2.80–3.05 (8H, m), 3.59 (4H, S), 7.05–17.35 (8H, m), 7.40–7.50 (1H, m), 7.60–7.75 (2H, m).

EXAMPLE 302

1-[3-[(2-Chlorophenyl)methyl]-2,3,4,5-tetrahydro-1H-3-benzazepin-7-yl]-4-[1-[(2-methylphenyl)methyl]-4-piperidinyl]-1-butanone Dihydrochloride

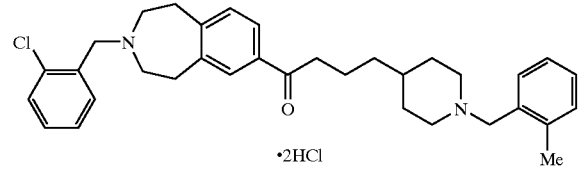

Using 4-[1-[(2-methylphenyl)methyl]-4-piperidinyl]-1-(2,3,4,5-tetrahydro-1H-3-benzazepin-7-yl)-1-butanone (free base), obtained in Example 236, and 2-chlorobenzyl bromide, the procedure of Example 28 was similarly repeated to provide the title compound as colorless powders melting at 195–197° C.

¹H NMR (CDCl₃, free base) δ: 1.10–1.45 (5H, m), 1.55–1.85 (4H, m), 1.85–2.05 (2H, m), 2.34 (3H, s), 2.60–2.75 (4H, m), 2.80–3.10 (8H, m), 3.41 (2H, s), 3.73 (2H, s), 7.00–7.30 (7H, m), 7.36 (1H, dd, J=7.4, 1.8 Hz), 7.56 (1H, dd, J=7.0, 1.8 Hz), 7.65–7.80 (2H, m).

EXAMPLE 303

1-[3-[(2,6-Dichlorophenyl)methyl]-2,3,4,5-tetrahydro-1H-3-benzazepin-7-yl]-4-[1-[(2-methylphenyl)methyl]-4-piperidinyl]-1-butanone Dihydrochloride

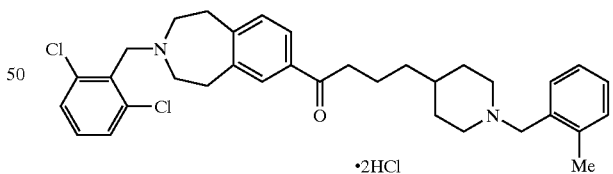

Using 4-[1-[(2-methylphenyl)methyl]-4-piperidinyl]-1-(2,3,4,5-tetrahydro-1H-3-benzazepin-7-yl)-1-butanone (free base), obtained in Example 236, and 2,6-dichlorobenzyl bromide, the procedure of Example 28 was similarly repeated to provide the title compound as colorless amorphous powders.

¹H NMR (CDCl₃, free base) δ: 1.10–1.40 (5H, m), 1.60–1.80 (4H, m), 1.85–2.05 (2H, m), 2.35 (3H, s), 2.70–2.85 (4H, m), 2.85–3.00 (8H, m), 3.41 (2H, s), 3.86 (2H, s), 7.10–7.35 (8H, m), 7.65–7.75 (2H, m).

EXAMPLE 304

1-[3-[(2,3-Dichlorophenyl)methyl]-2,3,4,5-tetrahydro-1H-3-benzazepin-7-yl]-4-[1-[(2-methylphenyl)methyl]-4-piperidinyl]-1-butanone Dihydrochloride

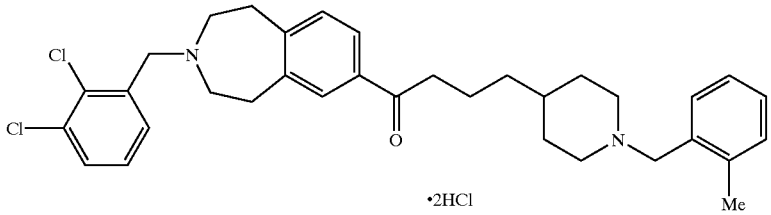

Using 4-[1-[(2-methylphenyl)methyl]-4-piperidinyl]-1-(2,3,4,5-tetrahydro-1H-3-benzazepin-7-yl)-1-butanone (free base), obtained in Example 236, and 2,3-dichlorobenzyl chloride, the procedure of Example 28 was similarly repeated to provide the title compound as colorless amorphous powders.

$^1$H NMR (CDCl$_3$, free base) δ: 1.10–1.40 (S5H, m), 1.55–1.85 (4H, m), 1.85–2.05 (2H, m), 2.34 (3H, s), 2.60–2.80 (4H, m), 2.80–3.10 (8H, m), 3.41 (2H, s), 3.73 (2H, s), 7.10–7.30 (6H, m), 7.30–7.40 (1H, m), 7.45–7.55 (1H, m), 7.65–7.80 (2H, m).

EXAMPLE 305

1-[3-[[2-(Trifluoromethyl)phenyl]methyl]-2,3,4,5-tetrahydro-1H-3-benzazepin-7-yl]-4-[1-[(2-methylphenyl)methyl]-4-piperidinyl]-1-butanone Dihydrochloride

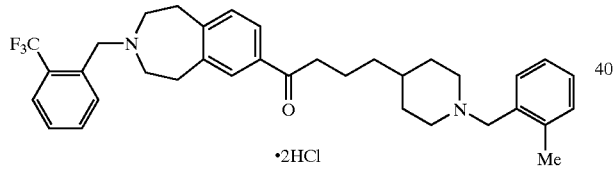

Using 4-[1-[(2-methylphenyl)methyl]-4-piperidinyl]-1-(2,3,4,5-tetrahydro-1H-3-benzazepin-7-yl)-1-butanone (free base), obtained in Example 236, and 2-(trifluoromethyl)benzyl bromide, the procedure of Example 28 was similarly repeated to provide the title compound as colorless amorphous powders.

$^1$H NMR (CDCl$_3$, free base) δ: 1.20–1.40 (5H, m), 1.60–1.85 (4H, m), 1.90–2.10 (2H, m), 2.36 (3H, s), 2.60–2.75 (4H, m), 2.85–3.10 (8H, m), 3.46 (2H, s), 3.76 (2H, s), 7.10–7.4.0 (6H, m), 7.50–7.75 (4H, m), 7.93 (1H, d, J=7.8 Hz).

EXAMPLE 306

1-[3-[[3-(Trifluoromethyl)phenyl]methyl]-2,3,4,5-tetrahydro-1H-3-benzazepin-7-yl]-4-[1-[(2-methylphenyl)methyl]-4-piperidinyl]-1-butanone Dihydrochloride

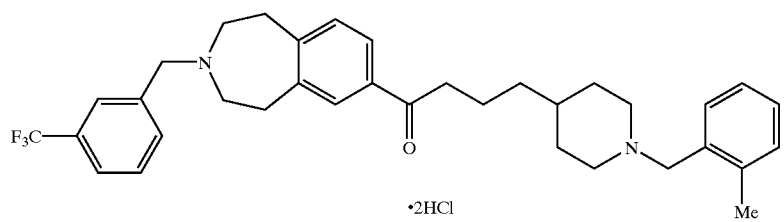

Using 4-[1-[(2-methylphenyl)methyl]-4-piperidinyl]-1-(2,3,4,5-tetrahydro-1H-3-benzazepin-7-yl)-1-butanone (free base), obtained in Example 236, and 3-(trifluoromethyl)benzyl bromide, the procedure of Example 28 was similarly repeated to provide the title compound as colorless powders melting at 198–200° C.

$^1$H NMR (CDCl$_3$, free base) δ: 1.10–1.40 (5H, m), 1.50–1.80 (4H, m), 1.8.5–2.10 (2H, m), 2.34 (3H, s), 2.50–2.70 (4H, m), 2.80–3.05 (8H, m), 3.41 (2H, s), 3.66 (2H, s), 7.00–7.30 (5H, m), 7.35–7.75 (6H, m).

EXAMPLE 307

1-[3-[[3-(Trifluoromethoxy)phenyl]methyl]-2,3,4,5-tetrahydro-1H-3-benzazepin-7-yl]-4-[1-[(2-methylphenyl)methyl]-4-piperidinyl]-1-butanone Dihydrochloride

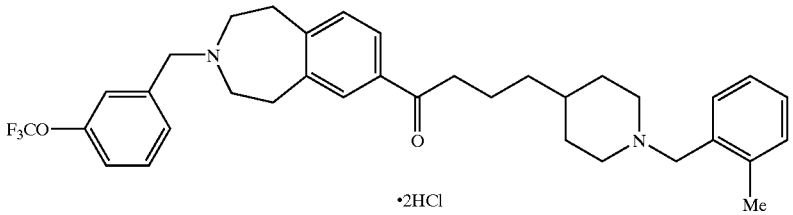

Using 4-[1-[(2-methylphenyl)methyl]-4-piperidinyl]-1-(2,3,4,5-tetrahydro-1H-3-benzazepin-7-yl)-1-butanone (free base), obtained in Example 236, and 3-(trifluoromethoxy)benzyl bromide, the procedure of Example 28 was similarly repeated to provide the title compound as colorless amorphous powders.

$^1$H NMR (CDCl$_3$, free base) δ: 1.10–1.40 (5H, m), 1.55–1.85 (4H, m), 1.85–2.05 (2H, m), 2.34 (3H, s), 2.55–2.70 (4H, m), 2.80–3.05 (8H, m), 3.41 (2H, s), 3.63 (2H, s), 7.05–7.20 (5H, m), 7.20–7.40 (4H, m), 7.65–7.75 (2H, m).

EXAMPLE 308

4-[1-[(2-Methylphenyl)methyl]-4-piperidinyl]-1-[3-[3-nitrophenyl)methyl]-2,3,4,5-tetrahydro-1H-3-benzazepin-7-yl]-1-butanone Dihydrochloride

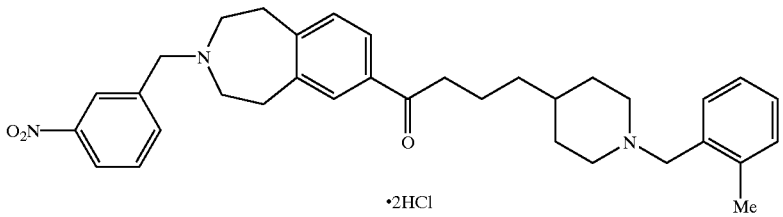

Using 4-[1-[(2-methylphenyl)methyl]-4-piperidinyl]-1-(2,3,4,5-tetrahydro-1H-3-benzazepin-7-yl)-1-butanone (free base), obtained in Example 236, and 3-nitrobenzyl chloride, the procedure of Example 28 was similarly repeated to provide the-free base of title compound as colorless, powders melting at 107–108° C., and the title compound as colorless amorphous powders.

$^1$H NMR (CDCl$_3$, free base) δ: 1.10–1.40 (5H, m), 1.55–1.80 (4H, m), 1.85–2.05 (2H, m), 2.35 (3H, s), 2.60–2.75 (4H, m), 2.80–3.05 (8H, m), 3.42 (2H, s), 3.72 (2H, s), 7.10–7.40 (6H, m), 7.51 (1H, t, J=7.8 Hz), 7.65–7.75 (2H, m), 8.14 (1H, d, J=8.2 Hz), 8.27 (1H, s).

EXAMPLE 309

1-[3-[(2-Bromophenyl)methyl]-2,3,4,5-tetrahydro-1H-3-benzazepin-7-yl]-4-[1-[(2-methylphenyl)methyl]-4-piperidinyl]-1-butanone Dihydrochloride

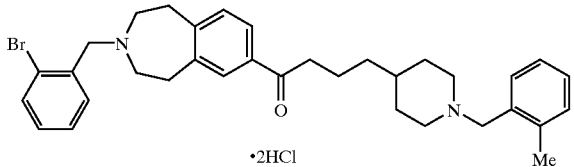

Using 4-[1-[(2-methylphenyl)methyl]-4-piperidinyl]-1-(2,3,4,5-tetrahydro-1H-3-benzazepin-7-yl)-1-butanone (free base), obtained in Example 236, and 2-bromobenzyl bromide, the procedure of Example 28 was similarly repeated to provide the title compound as colorless amorphous powders.

$^1$H NMR (CDCl$_3$, free base) δ: 1.10–1.40 (5H, m), 1.55–1.80 (4H, m), 1.85–2.05 (2H, m), 2.35 (3H, s), 2.65–2.75 (4H, m), 2.80–3.05 (8H, m), 3.41 (2H, s), 3.71 (2H, s), 7.05–7.20 (5H, m), 7.20–7.40 (2H, m), 7.50–7.60 (2H, m), 7.65–7.75 (2H, m).

EXAMPLE 310

1-[3-[(2,6-Difluorophenyl)methyl]-2,3,4,5-tetrahydro-1H-3-benzazepin-7-yl]-4-[1-[(2-methylphenyl)methyl]-4-piperidinyl]-1-butanone Dihydrochloride

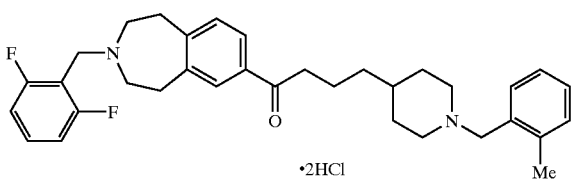

Using 4-[1-[(2-methylphenyl)methyl]-4-piperidinyl]-1-(2,3,4,5-tetrahydro-1H-3-benzazepin-7-yl)-1-butanone (free base), obtained in Example 236, and 2,6-difluorobenzyl chloride, the procedure of Example 28 was similarly repeated to provide the title compound as colorless amorphous powders.

¹H NMR (CDCl₃, free base) δ: 1.10–1.40 (5H, m), 1.55–1.80 (4H, m), 1.85–2.05 (2H, m), 2.34 (3H, s), 2.65–2.75 (4H, m), 2.75–3.05 (8H, m), 3.40 (2H, s), 3.85 (2H, s), 6.80–6.95 (2H, m), 7.05–7.35 (6H, m) 7.65–7.75 (2H, m).

EXAMPLE 311

1-[3-[[3,5-Bis(trifluoromethyl)phenyl]methyl]-2,3,4,5-tetrahydro-1H-3-benzazepin-7-yl]-4-[1-[(2-methylphenyl)methyl]-4-piperidinyl]-1-butanone Dihydrochloride Using 4-[1-[(2-methylphenyl)methyl]-4-piperidinyl]-1-(2,3,4,5-tetrahydro-1H-3-benzazepin-7-yl)-1-butanone (free base), obtained in Example 236, and mesylate of helio alcohol, the procedure of Example 28 was similarly repeated to provide the title compound as colorless powders melting at 253° C. (dec.).

¹H NMR (CDCl₃, free base) δ: 1.10–1.40 (5H, m), 1.55–1.80 (4H, m), 1.85–2.05 (2H, m), 2.34 (3H, s), 2.55–2.75 (4H, m), 2.75–3.00 (8H, m), 3.41 (2H, s), 3.53 (2H, s), 5.94 (2H, s), 6.75 (1H, s), 6.76 (1H, s), 6.91 (1H, s), 7.10–7.30 (5H, m), 7.65–7.75 (2H, m).

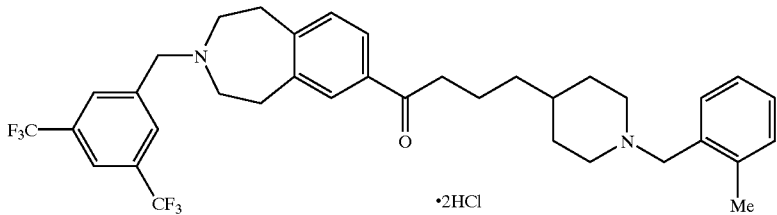

Using 4-[1-[(2-methylphenyl)methyl]-4-piperidinyl]-1-(2,3,4,5-tetrahydro-1H-3-benzazepin-7-yl),-1-butanone (free base), obtained in Example 236, and mesylate of 3,5-bis(trifluoromethyl)benzyl alcohol, the procedure of Example 28 was similarly repeated to provide the title compound as colorless amorphous powders.

¹H NMR (CDCl₃₁ free base) δ: 1.10–1.40 (5H, m), 1.55–1.80 (4H, m), 1.85–2.05 (2H, m), 2.34 (3H, s), 2.55–2.70 (4H, m), 2.80–3.05 (8H, m), 3.41 (2H, s), 3.71 (2H, s), 7.05–7.30 (5H, m), 7.65–7.90 (5H, m).

EXAMPLE 312

5-[[7-[4-[1-[(2-Methylphenyl)methyl]-4-piperidinyl]butanoyl]-2,3,4,5-tetrahydro-1H-3-benzazepin-3-yl]methyl]-1,3-benzodioxole Dihydrochloride

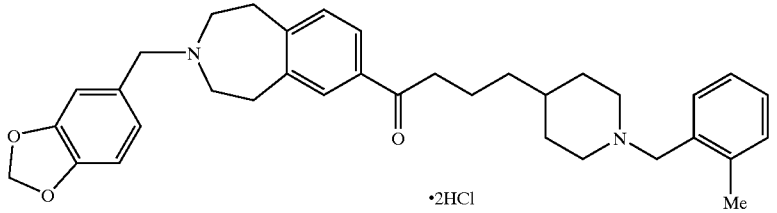

EXAMPLE 313

4-[1-[[2-[(4-methyl-1-pipiperazinyl)carbonyl]
phenyl]methyl]-4-piperidinyl]-1-[3[(2-
methylphenyl)methyl]-2,3,4,5-tetrahydro-1H-3-
benzazepin-7-yl]-1-butanone Trihydrochloride

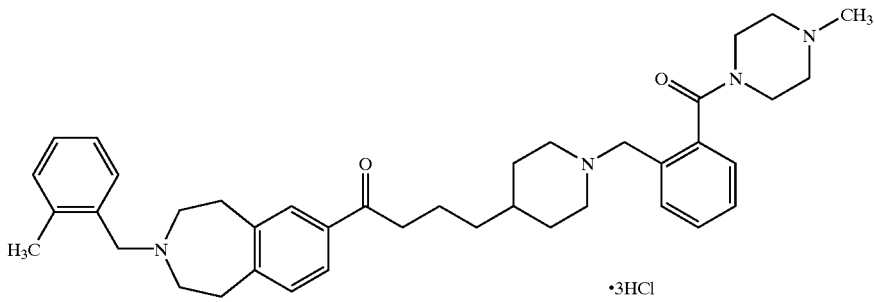

Using 2-[[4-[4-[3-[(2-methylphenyl)methyl]-2,3,4,5-tetrahydro-1H-3-benzazepin-7-yl]-4-oxobutyl]-1-piperidinyl]methyl]benzoic acid, obtained in Example 253, the procedure of Example 243 was similarly repeated to provide the title compound as colorless powders melting at 186–193° C. (dec.).

$^1$H NMR (CDCl$_3$, free base) δ: 1.00–1.38 (5H, m), 1.55–2.09 (8H, m), 2.12–2.53 (8H, m), 2.53–2.80 (5H, m), 2.80–3.02 (7H, m), 3.11–3.38 (3H, m), 3.47–3.67 (3H, m), 3.70–3.85 (1H, m), 3.95–4.20 (1H, m), 7.10–7.43 (9H, m), 7.65–7.75 (2H, m). Elemental analysis, for C$_{40}$H$_{52}$N$_4$O$_2$.3HCl.3.5H$_2$O. Calcd.: C, 60.56; H, 7.88; N, 7.06. Found: C, 60.71; H, 7.61; N, 6.88.

EXAMPLE 314

1-[3-[(2-Methylphenyl)methyl]-2,3,4,5-tetrahydro-
1H-3-benzazepin-7-yl]-4-[1-[[2-
(morpholinocarbonyl)phenyl]methyl]-4-piperidinyl]-
1-butanone Dihydrochloride

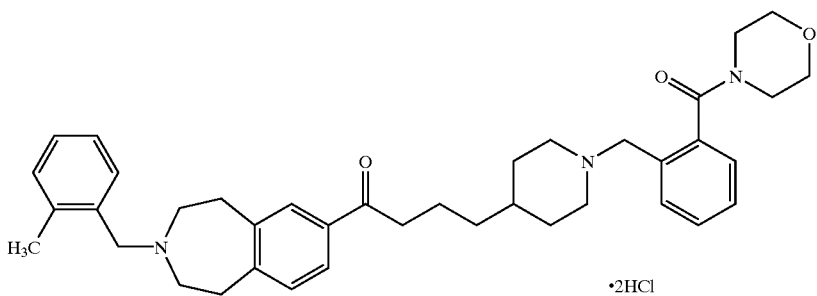

Using 2-[[4-[4-[3-[(2-methylphenyl)methyl]-2,3,4,5-tetrahydro-1H-3-benzazepin-7-yl]-4-oxobutyl]-1-piperidinyl]methyl]benzoic acid, obtained in Example 253, and morpholine, the procedure of Example 243 was similarly repeated to provide the title compound as colorless powders melting at 168–172° C.

$^1$H NMR (CDCl$_3$, free base) δ: 1.19–1.40 (4H, m), 1.57–2.10 (7H, m), 2.39 (3H, s), 2.57–2.80 (5H, m), 2.82–3.03 (7H, m), 3.10–3.30 (4H, m), 3.50–4.04 (8H, m), 7.10–7.41 (9H, m), 7.64–7.75 (2H, m). Elemental analysis, for C$_{39}$H$_{49}$N$_3$O$_3$.2HCl.2.5H$_2$O. Calcd.: C, 64.54; H, 7.78; N, 5.79. Found: C, 64.56; H, 7.83; N, 5.74.

EXAMPLE 315

N-[2-[[7-[4-[1-[(2-chlorophenyl)methyl]-4-piperidinyl]butanoyl]-2,3,4,5-tetrahydro-1H-3-benzazepin-3-yl]methyl]phenyl]acetamide Dihydrochloride

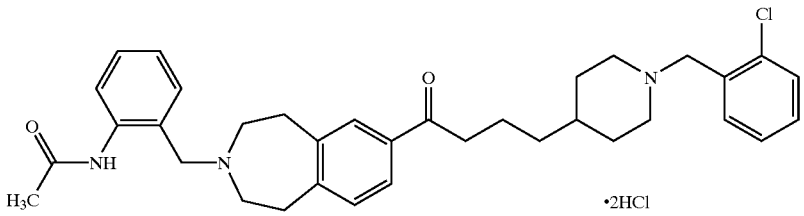

Using 4-[1-[(2-chlorothenyl)methyl]-4-piperidinyl]1-(2,3,4,5-tetrahydro-1H-3-benzazepin-7-yl)-1-butanone (free base), obtained in Example 264, and 2-(acetylamino)benzyl bromide, the procedure of Example 28 was similarly repeated to provide the title compound as colorless powders melting at 138–144° C.

$^1$H NMR (CDCl$_3$, free base) δ: 1.15–1.40 (5H, m), 1.59–1.90 (4H, m), 1.94–2.14 (2H, m), 2.16 (3H, s) 2.58–2.78 (4H, m), 2.81–3.04 (8H, m), 3.59 (2H, s) 3.68 (2H, s), 6.95–7.39 (7H, m), 7.43–7.53 (1H, m), 7.70–7.79 (2H, m), 8.30 (1H, d, J=8.4 Hz), 10.90 (1H, brs). Elemental analysis, for C$_{35}$H$_{42}$ClN$_3$O$_2$.2HCl. 2.5H$_2$O. Calcd.: C, 60.91; H, 7.16; N, 6.09. Found: C, 60.82; H, 7.01; N, 6.04.

EXAMPLE 316

1-[3-[(2-Aminophenyl)methyl]-2,3,4,5-tetrahydro-1H-3-benzazepin-7-yl]-4-[1-[(2-chlorophenyl)methyl]-4-piperidinyl]-1-butanone Trihydrochloride

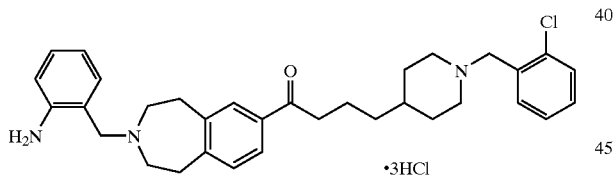

Using N-[2-[[7-[4-[1-[(2-chlorophenyl)methyl]-4-piperidinyl]butanoyl]-2,3,4,5-tetrahydro-1H-3-benzazepin-3-yl]methyl]phenyl]acetamide, obtained in Example 315, the procedure of Example 24 was similarly repeated to provide the title compound as colorless powders melting at 155–164° C. (dec.).

$^1$H NMR (CDCl$_3$; free base) δ: 1.13–1.39 (5H, m), 1.52–1.82 (6H, m), 1.95–2.13 (2H, m), 2.49–2.68 (4H, m), 2.81–3.00(8H, m) 3.59 (4H, s), 6.62–6.78 (2H, m), 6.92–7.00 (1H, m), 7.07–7.39 (5H, m), 7.44–7.53 (1H, m) 7.67–7.80 (2H, m). Elemental analysis, for C$_{33}$H$_{40}$ClN$_3$O.3HCl.1.5H$_2$O. Calcd.: C, 59.46; H, 6.96; N, 6.30. Found: C, 59.34; H, 6.70; N, 6.37.

EXAMPLE 317

N-[3-[[7-[4-[1-[(2-chlorophenyl)methyl]-4-piperidinyl]butanoyl]-2,3,4,5-tetrahydro-1H-3-benzazepin-3-yl]methyl]phenyl]-N'-methylurea Dihydrochloride

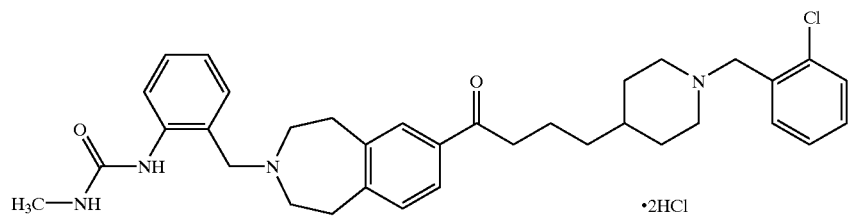

Using 1-[3-[(2-aminophenyl)methyl]-2,3,4,5-tetrahydro-1H-3-benzazepin-7-yl]-4-[1-[(2-chlorophenyl)methyl]-4-piperidinyl]-1-butanone (free base), obtained in Example 316, and methyl isocyanate, the procedure of Example 28 was similarly repeated to provide the title compound as colorless powders melting at 145–150° C.

$^1$H NMR (CDCl$_3$, free base) δ: 1.17–1.38 (5H m), 1.50–1.80 (4H, m), 1.94–2.14 (2H, m), 2.53–2.72 (4H, m), 2.78–3.03 (11H, m), 3.59 (2H, s), 3.62 (2H, s), 4.18–4.33 (1H, m), 6.90–7.38 (7H, m), 7.44–7.52 (1H, m), 7.68–7.78 (2H, m), 7.92–8.01 (1H, m), 9.41 (1H, brs).

EXAMPLE 318

N-[2-[[7-[4-[1-[(2-chlorophenyl)methyl]-4 piperidinyl]butanoyl]-2,3,4,5-tetrahydro-1H-3-benzazepin-3-yl]methyl]phenyl]-4-methylbenzenesulfonamide Dihydrochloride Using 1-[3-[2-aminophenyl)methyl]-2,3,4,5-tetrahydro-1H-3-benzazepin-7-yl]-4-[1-[(2-chlorophenyl)methyl]-4-piperidinyl]-1-butanone (free base), obtained in Example 316, and methanesulfonyl chloride, the procedure of Example 28 was similarly repeated to provide the title compound as colorless powders melting at 157–163° C.

$^1$H NMR (CDCl$_3$, free base) δ: 1.10–1.38 (5H, m), 1.50–1.83 (4H, m), 1.93–2.12 (2H, m) 2.50–2.71 (4H, m), 2.80–3.00 (8H, m), 3.48–3.61 (5H, m), 3.74 (2H, s), 7.01–7.57 (9H, m), 7.60–7.78 (3H, m).

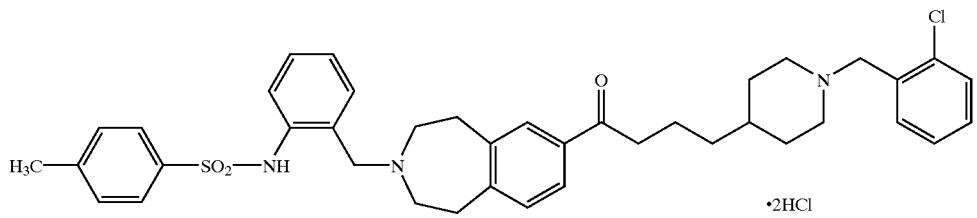

Using 1-[3-[(2-aminophenyl)methyl]-2,3,4,5-tetrahydro-1H-3-benzazepin-7-yl]-4-[1-[(2-chlorophenyl)methyl]-4-piperidinyl]-1-butanone (free base), obtained in Example 316, and p-toluenesulfonyl chloride, the procedure of Example 28 was similarly repeated to provide the title compound as colorless powders melting at 171–175° C.

$^1$H NMR (CDCl$_3$, free base) δ: 1.19–1.40 (5H, m), 1.60–1.82 (4H, m), 1.97–2.15 (2H, m), 2.30–2.65 (7H, m), 2.82–3.09 (8H, m), 3.32 (2H, s), 3.60 (2H, s), 6.90–7.07 (2H, m), 7.10–7.39 (8H, m), 7.45–7.56 (2H, m), 7.63–7.87 (4H, m).

EXAMPLE 319

N-[2-[[7-[4-[1-[(2-chlorophenyl)methyl]-4-piperidinyl]butanoyl]-2,3,4,5-tetrahydro-1H-3-benzazepin-3-yl]methyl]phenyl]methanesulfonamide Dihydrochloride

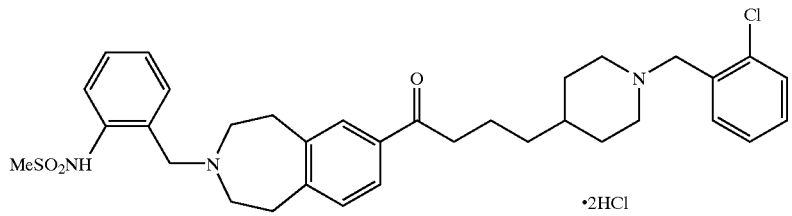

EXAMPLE 320

N-[2-[[4-[4-[3-[(2-methylphenyl)methyl]-2,3,4,5-tetrahydro-1H-3-benzazepin-7-yl]-4-oxobutyl]-1-piperidinyl]methyl]phenyl]-4-methylbenzenesulfonamide Dihydrochloride

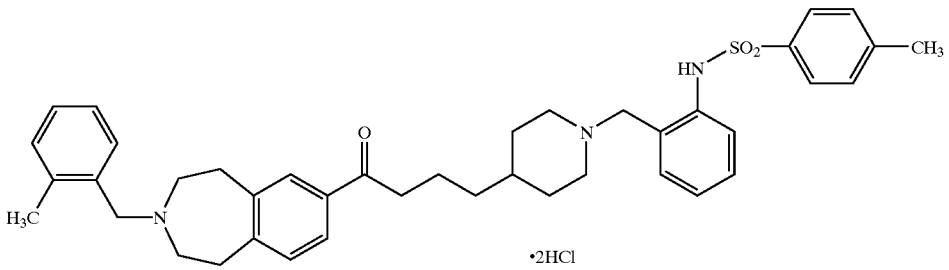

Using 4-[1-[(2-aminophenyl)methyl]-4-piperidinyl]-1-[3-[(2-methylphenyl)methyl]-2,3,4,5-tetrahydro-1H-3-benzazepin-7-yl]-1-butanone (free base), obtained in Example 249, and p-toluenesulfonyl chloride, the procedure of Example 28was similarly repeated to provide the title compound as colorless powders melting at 161–170° C. (dec.).

$^1$H NMR (CDCl$_3$, free base) δ: 1.20–1.42 (5H), m), 1.60–2.03 (6H, m), 2.37 (3H, s), 2.39 (3H, S), 2.58–2.83 (6H, m), 2.87–3.05 (6H, m), 3.18 (2H, s), 3.57 (2H, s), 6.91–7.03 (2H, m), 7.12–7.53 (11H, m), 7.62–7.78 (3H, m).

EXAMPLE 321

3-1-Acetyl-4-piperidinyl)-1-[3-[(2-naphthyl)methyl]-2,3,4,5-tetrahydro-1H-3-benzazepin-7-yl]-1-propanone Hydrochloride

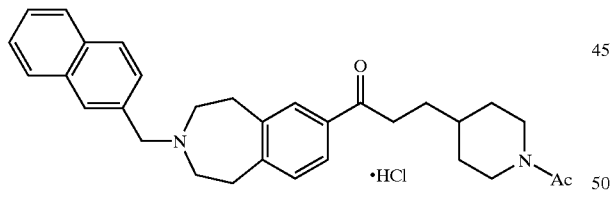

Using 3-(1-acetyl-4-piperidinyl)-1-(2,3,4,5-tetrahydro-1H-3-benzazepin-7-yl)-1-propanone (free base), obtained in.Example 23-2, and 2-(bromomethyl)naphthalene, the procedure of Example 28 was similarly repeated to provide the title compound as colorless amorphous powders.

$^1$H NMR (CDCl$_{31}$ free base) δ: 1.01–1.30 (2H, m), 1.46–1.85 (4H, m), 2.08 (3H, s), 2.42–2.60 (1H, m) 2.62–2.77 (4H, m), 2.90–3.10 (8H, m), 3.71–3.87 (3H, m), 4.52–4.68 (1H, m), 7.16 (1H, d, J=7.6 Hz), 7.40–7.60 (3H, m), 7.63–7.88 (6H, m). Elemental analysis, for C$_{31}$H$_{36}$N$_2$O$_2$.HCl.2H$_2$O. Calcd.: C, 68.81; H, 7.64; H, 5.18. Found: C, 68.70; H, 7.53; N, 4.86.

EXAMPLE 322

3-(1-Acetyl-4-piperidinyl)-1-(3-benzoyl-2,3,4,5-tetrahydro-1H-3-benzazepin-7-yl)-1-propanone Hydrochloride

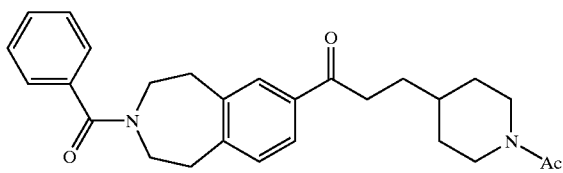

Using 3-(1-acetyl-4-piperidinyl)-1-(2,3,4,5-tetrahydro-1H-3-beanzazebin-7-yl)-1-propanone (free base), obtained in Example 23-2, and benzoyl chloride, the procedure of Example 28 was similarly repeated to provide the title compound as colorless amorphous powders.

$^1$H NMR (CDCl$_3$) δ: 1.02–1.30 (2H, m), 1.49–1.86(5H, m), 2.09 (3H, s), 2.43–2.61 (1H, m), 2.85–3.20 (7H, m), 3.47–3.63 (2H, m), 3.72–3.98 (3H, m), 4.53–4.69 (1H, m), 7.13–7.49 (6H, m), 7.70–7.81 (2H, m). Elemental analysis, for C$_{27}$H$_{32}$N$_2$O$_3$. Calcd.: C, 74.97; H, 7.46; N, 6.48. Found: C, 75.10; H, 7.50; N, 6.54.

EXAMPLE 323

3-(1-Acetyl-4-piperidinyl)-1-[3-(2-thiophenecarbonyl) -2,3,4,5-tetrahydro-1H-3-benzazepin-7-yl]-1-propanone

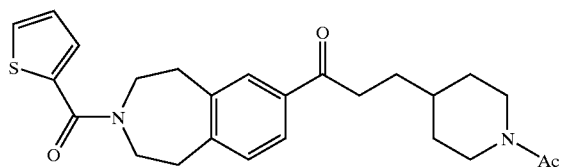

Using 3-(1-acetyl-4-piperidinyl)-1-(2,3,4,5-tetrahydro-1H-3-benzazepin-7-yl)-1-propanone (free base), obtained in Example 23-2, and 2-thiophenecarbonyl chloride, the procedure of Example 28 was similarly repeated to provide the title compound as colorless amorphous powders.

$^1$H NMR (CDCl$_3$) δ: 1.04–1.30 (2H, m), 1.50–1.88 (5H, m), 2.09 (3H, s), 2.43–2.61 (1H, m), 2.92–3.13 (7H, m), 3.72–3.92 (5H, m), 4.53–4.70 (1H, m), 7.05–7.12 (1H, m), 7.21–7.37 (2H, m), 7.43–7.50 (1H, m), 7.71–7.80 (2H, m). Elemental analysis, for $C_{25}H_{30}N_2O_3S$. Calcd.: C, 68.46; H, 6.86; N, 6.39. Found: C, 68.39; H, 6.86; N, 6.41.

EXAMPLE 324

3-(1-Acetyl-4-piperidinyl)-1-[3-(2-furoyl)-2,3,4,5-tetrahydro-1H-3-benzazepin-7-yl]-1-propanone

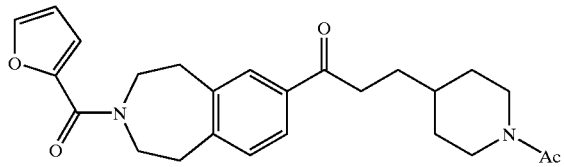

Using 3-(1-acetyl-4-piperidinyl)-1-(2,3,4,5-tetrahydro-1H-3-benzazepin-7-yl)-1-propanone (free base), obtained in Example 23–2, and 2-furoyl chloride, the procedure of Example 28 was similarly repeated to provide the title compound as colorless amorphous powders.

$^1$H NMR (CDCl$_3$) δ: 1.06–1.30 (2H, m), 1.48–1.88 (5H, m), 2.09 (3H, s), 2.43–2.61 (1H, m), 2.91–3.18 (7H, m), 3.72–3.98 (5H, m), 4.53–4.70 (1H, m), 6.49–6.56 (1H, m), 7.00–7.08 (1H, m), 7.20–7.30 (1H, m), 7.50–7.56 (1H, m), 7.70–7.80 (2H, m). Elemental analysis, for $C_{25}H_{30}N_2O_4$. Calcd.: C, 71.07; H, 7.16; N, 6.63. Found: C, 71.22; H, 7.22; N, 6.57.

EXAMPLE 325

3-(1-Acetyl-4-piperidinyl)-1-[3-(3-pyridylcarbonyl)-2,3,4 5-tetrahydro-1H-3-benzazepin-7-yl)-1-propanone Hydrochloride

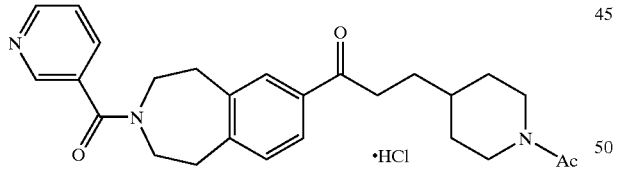

Using 3-(1-acetyl-4-piperidinyl)-1-(2,3,4,5-tetrahydro-1H-3-benzazepin-7-yl)-1-propanone (free base), obtained in Example 23-2, and 3-pyridylcarbonyl chloride, the procedure of Example 28 was similarly repeated to provide the title compound as colorless amorphous powders.

$^1$H NMR (CDCl$_3$, free base) δ: 1.02–1.31 (2H, m), 1.50–35 1.88 (5H, m), 2.09 (3H, s) 2.44–2.62 (1H, m), 2.89–3.21 (7H, m), 3.47–3.67 (2H, m), 3.72–4.00 (3H, m), 4.53–4.70 (1H, m), 7.13–7.44 (2H, m), 7.68–7.82 (3H, m), 8.63–8.73 (2H, m). Elemental analysis, for $C_{26}H_{31}N_3O_2 \cdot HCl \cdot 2.5H_2O$. Calcd.: C, 60.63; H, 7.24; N, 8.16. Found: C, 60.67; H, 6.58; N, 7.87.

EXAMPLE 326

3-[1-[(1-Naphthyl)methyl]-4-piperidinyl]-1-[3-(phenylmethyl)-2,3,4,5-tetrahydro-1H-3-benzazepin-7-yl]-1-propanone Dihydrochloride

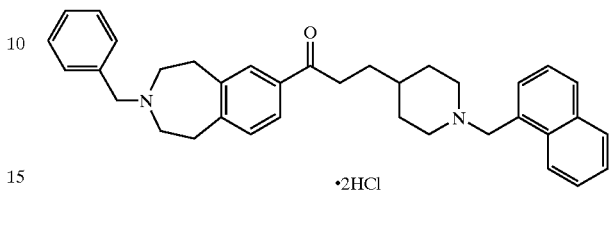

Using 1-[3-(phenylmethyl)-2,3,4,5-tetrahydro-1H-3-benzazepin-7-yl]-3-(4-piperidinyl)-1-propanone (free base), obtained in Example 24, and 1-(chloromethyl)naphthalene, the procedure of Example 28 was similarly repeated to provide the title compound as colorless amorphous powders.

$^1$H NMR (CDCl$_3$, free base) δ: 1.16–1.40 (3H, m), 1.57–1.80 (4H, m), 1.92–2.10 (2H, m), 2.54–2.68 (4H, m), 2.82–3.02 (8H, m), 3.63 (2H, s), 3.87 (2H, s), 7.10–7.55 (10H, m), 7.–63–7.88 (4H, m), 8.24–8.34 (1H, m). Elemental analysis for $C_{36}H_{40}N_2O \cdot 2HCl \cdot 2H_2O$. Calcd.: C, 69.11; H, 7.41; N, 4.48. Found: C, 69.11; H, 7.23; N, 4.48.

EXAMPLE 327

3-[1-[(2-Naphthyl)methyl]-4-piperidinyl]-1-[3-(phenylmethyl)-2,3,4,5-tetrahydro-1H-3-benzazepin-7-yl]-1-propanone Dihydrochloride

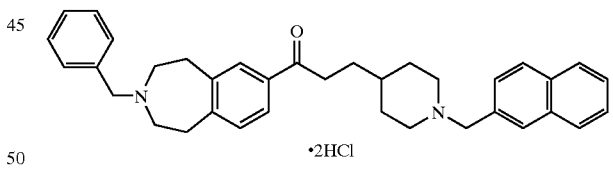

Using 1-[3-(phenylmethyl)-2,3,4,5-tetrahydro-1H-3-benzazepin-7-yl]-3-(4-piperidinyl)-1-propanone (free base), obtained in Example 24, and 2-(bromomethyl)naphthalene, the procedure of Example 28 was similarly repeated to provide the title compound as colorless amorphous powders.

$^1$H NMR (CDCl$_3$, free base) δ: 1.20–1.45 (3H, m), 1.58–1.80 (4H, m), 1.89–2.09 (2H, m), 2.55–2.70 (4H, m), 2.85–3.04 (8H, m), 3.63 (2H, s), 3.64 (2H, s), 7.15 (1H, d, J=7.4 Hz), 7.24–7.54 (8H, m), 7.63–7.89 (6H, m). Elemental analysis, for $C_{36}H_{40}N_2O \cdot 2HCl \cdot H_2O$. Calcd.: C, 71.16; H, 7.30; N, 4.61. Found: C, 71.44; H, 7.34; N, 4.49.

EXAMPLE 328

3-(1-Acetyl-4-piperidinyl)-1-[3-(2-pyridylmethyl)-2,3,4,5-tetrahydro-1H-3-benzazepin-7-yl]-1-propanone Dihydrochloride

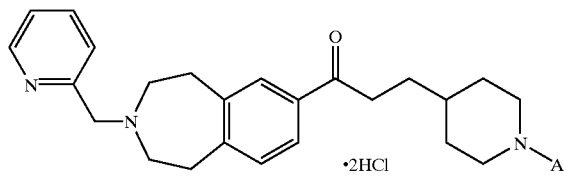

Using 3-(1-acetyl-4-piperidinyl)-1-(2,3,4,5-tetrahydro-1H-3-benzazepin-7-yl)-1-propanone (free base), obtained in Example 23-2, and mesylate of 2-pyridylmethanol, the procedure of Example 28 was similarly repeated to provide the title compound as colorless amorphous powders.

$^1$H NMR (CDCl$_3$, free base) δ: 1.04–1.30 (2H, m), 1.48–35 1.85 (5H, m), 2.08 (3H, s), 2.42–2.61 (1H, m), 2.62–2.79 (4H, m), 2.90–3.10 (7H, m), 3.72–3.87 (3H, m), 4.52–4.68 (1H, m), 7.12–7.22 (2H, m), 7.48:(1H, d, J=7.6 Hz), 7.61–7.77 (3H, m), 8.53–8.60 (1H, m). Elemental analysis, for C$_{26}$H$_{33}$N$_3$O$_2$.2HCl.2.5H$_2$O. Calcd.: C, 58.10; H, 7.50; N, 7.82. Found: C, 58.35; H, 7.31; N, 7.66.

EXAMPLE 329

3-(1-Acetyl-4-piperidinyl)-1-[3-(3-pyridylmethyl)-2,3,4,5-tetrahydro-1H-3-benzazepin-7-yl]-1-propanone Dihydrochloride

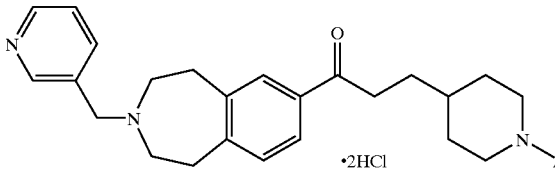

Using 3-(1-acetyl-4-piperidinyl)-1-(2,3,4,5-tetrahydro-1H-3-benzazepin-7-yl)-1-propanone (free base), obtained in Example 23-2, and mesylate of 3-pyridylmethanol, the procedure of Example 28 was, similarly repeated to provide the title compound as colorless amorphous powders.

$^1$H NMR (CDCl$_3$, free base) δ: 1.05–1.30 (2H, m), 1.47–1.87 (5H, m), 2.08 (3H, s), 2.43–2.71 (5H, m), 2.90–3.10 (7H, m), 3.65 (2H, s), 3.72–3.88 (1H, m), 4.53–4.68 (1H, m), 7.17 (1H, d, J=7.6 Hz), 7.22–7.32 (1H, m), 7.64–7.76 (3H, m), 8.48–8.60 (2H, m). Elemental analysis, for C$_{26}$H$_{33}$N$_3$O$_2$HCl3H$_2$O. Calcd.: C, 57.14; H, 7.56; N, 7.69. Found: C, 57.17; H, 7.43; N, 7.44.

EXAMPLE 330

3-(1-Acetyl-4-piperidinyl)-1-[3-(4-pyridylmethyl)-2,3,4,5-tetrahydro-1H-3-benzazepin-7-yl]-1-propanone Dihydrochloride

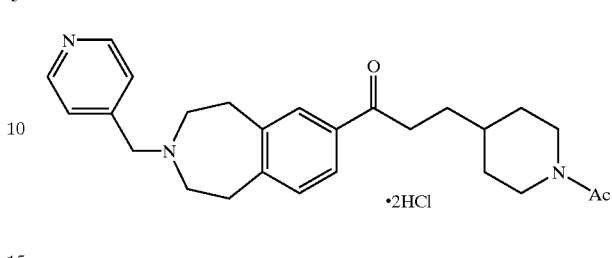

Using 3-(1-acetyl-4-piperidinyl)-1-(2,3,4,5-tetrahydro-1H-3-benzazepin-7-yl)-1-propanone (free base), obtained in Example 23-2, and mesylate of, 4-pyridylmethanol, the procedure of Example 28 was similarly repeated to provide the title compound as colorless amorphous powders.

$^1$H NMR (CDCl$_3$, free base) δ: 1.01–1.30 (2H, m), 1.48–1.8–7 (5H, m), 2.08 (3H, s), 2.43–2.70 (5H, m), 2.90–03.10 (7H, m), 3.63 (2H, s), 3.73–3.88 (1H, m), 4.53–4.68 (1H, m), 7.18 (1H, d, J=7.4 Hz), 7.29–7.37 (2H, m), 7.67–7.77 (2H, m), 8.53–8.60 (2H, m).

Example 331

3-(1-Acetyl-4-piperidinyl)-1-[3-(2-thienylmethyl)-2,3,4,5-tetrahydro-1H-3-benzazepin-7-yl]-1-propanone hydrochloride

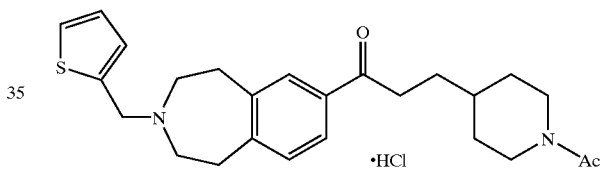

Using 3-(1-acetyl-4-piperidinyl)-1-(2,3,4,5-tetrahydro-1H-3-benzazepin-7-yl)-1-propanone (free base), obtained in Example 23–2, and mesylate of 2-thienylmethanol, the procedure of Example 28 was similarly repeated to provide the title compound as colorless amorphous powders.

$^1$H NMR (CDCl$_3$, free base) δ: 1.01–1.30 (2H, m), 1.46–1.88 (5H, m), 2.08 (3H, s), 2.42–2.74 (5H, m), 2.90–3.15 (7H, m), 3.72–3.90 (3H, m), 4.53–4.68 (1H, m), 6.87–6.98 (2H, m), 7.12–7.27 (2H, m), 7.64–7.76 (2H, m). Elemental analysis, for C$_{25}$H$_{32}$N$_2$O$_2$S.HCl3H$_2$O. Calcd.: C, 58.29; H, 7.63; N, 5.44. Found: C, 58.19; H, 7.16; N, 5.08.

EXAMPLE 332

3-(1-Acetyl-4-piperidinyl)-1-[3-(2-furylmethyl)-2,3,4,5-tetrahydro-1H-3-benzazepin-7-yl]-1-propanone Hydrochloride

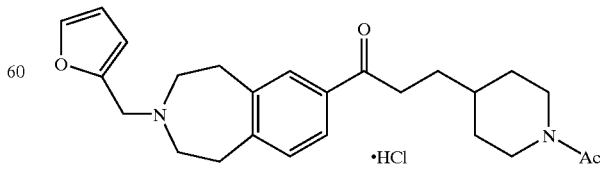

Using 3-(1-acetyl-4-piperidinyl)-1-(2,3,4,5-tetrahydro-1H-3-benzazepin-7-yl)-1-propanone (free base), obtained in Example 23–2, and mesylate of 2-furylmethyl, the procedure of Example 28 was similarly repeated to provide the title compound as colorless amorphous powders.

¹NMR (CDCl₃, free base) δ: 1.00–1.30 (2H, m), 1.47–1.87 (5H, m), 2.08 (3H, s), 2.42–2.72 (5H, m), 2.90–3.10:(7H, m), 3.70 (2H, s), 3.72–3.87 (1H, m), 4.53–4.68 (1H, m), 6.17–6.22 (1H, m), 6.29–6.34 (1H, m), 7.17 (1H, d, J=7.8 Hz), 7.35–7.40 (1H, m), 7.64–7.74 (2H, m). Elemental analysis, for $C_{25}H_{32}N_2O_3 \cdot HCl \cdot 2.5H_2O$. Calcd.: C, 61.28; H. 7.82; N, 5.72. Found: C, 61.31; H, 7.61; N, 5.57.

EXAMPLE 333

Methyl 2-[[7-[3-(1-acetyl-4-piperidinyl)propanoyl]-2,3,4,5-tetrahydro-1H-3-benzazepin-3-yl]methyl] benzoate Hydrochloride

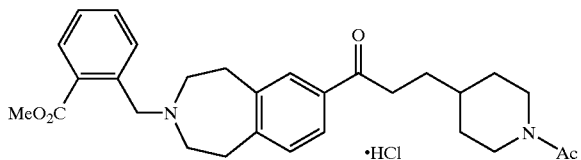

Using 3-(1-acetyl-4-piperidinyl)-1-(2,3,4,5-tetrahydro-1H-3-benzazepin-7-yl)-1-propanone (free base), obtained in Example 23-2, and methyl 2-(bromomethyl)benzoate, the procedure of Example 28 was similarly repeated to provide the title compound as colorless amorphous powders.

¹H NMR (CDCl₃, free base) δ: 1.01–1.30 (2H, m), 1.48–1.77 (5H, m), 2.08 (3H, s), 2.43–2.67 (5H, m), 2.87–3.11 (7H, m), 3.72–3.88 (3H, m), 3.91 (3H, s), 4.52–4.69 (1H, m), 7.16 (1H, d, J=7.6 Hz), 7.27–7.48 (3H, m), 7.65–7.76 (3H, m). Elemental analysis, for $C_{29}H_{36}N_2O_4 \cdot HCl \cdot 2.5H_2O$. Calcd.: C, 62.41; H, 7.59; N, 5.02. Found: C, 62.44; H, 7.36; N, 4.96.

EXAMPLE 334

Methyl 3-[[7-(3-(1-acetyl-4-piperidinyl)propanoyl]-2,3,4,5-tetrahydro-1H-3-benzazepin-3-yl]methyl] benzoate Hydrochloride

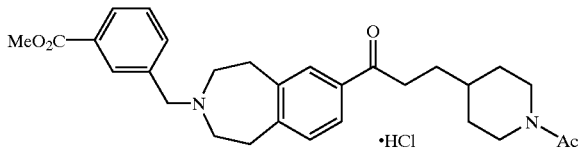

Using 3-(1-acetyl-4-piperidinyl)-1-(2,3,4,5-tetrahydro-1H-3-benzazepin-7-yl)-1-propanone (free base), obtained in Example 23-2, and methyl 3-(bromomethyl)benzoate, the procedure of Example 28 was similarly repeated to provide the title compound as colorless amorphous powders.

¹H NMR (CDCl₃, free base) δ: 1.01–1.30 (2H, m), 1.47–1.88 (5H, m), 2.08 (3H, s), 2.43–2.70 (5H, m), 2.91–3.11 (7H, m), 3.68 (2H, s), 3.72–3.88 (1H, m), 3.93 (3H, s), 4.53–4.69 (1H, m), 7.17 (1H, d, J=7.6 Hz), 7.37–7.75 (4H, m), 7.91–8.05 (2H, m). Elemental analysis, for $C_{29}H_{36}N_2O_4 \cdot HCl \cdot 3.25H_2O$. Calcd.: C, 60.93; H, 7.67; N, 4.90. Found: C, 61.01; H, 7.31; N, 4.94.

EXAMPLE 335

Methyl 4-[[7-[3-(1-acetyl-4-piperidinyl)propanoyl]-2,3,4,5-tetrahydro-1H-3-benzazepin-3-yl]methyl] benzoate Hydrochloride

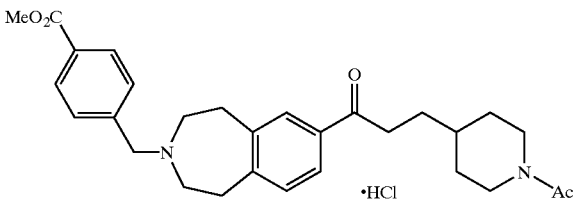

Using 3-(1-acetyl-4-piperidinyl)-1-(2,3,4,5-tetrahydro-1H-3-benzazepin-7-yl)-1-propanone (free base), obtained in Example 23-2, and methyl 4-(bromomethyl)benzoate, the procedure of Example 28 was similarly repeated to provide the title compound as colorless amorphous powders.

¹H NMR (CDCl₃, free base) δ: 1.01–1.30 (2H, m), 1.48–1.88 (5H, m), 2.08 (3H, s), 2.43–2.70 (5H, m), 2.92–3.11 (7H, m), 3.68 (2H, s), 3.72–3.88(1H, m), 3.92 (3H, s), 4.53–4.69 (1H, m), 7.17 (1H, d, J=7.6 Hz), 7.45 (2H, d, J=8.3 Hz), 7.67–7.77 (2H, m), 8.01 (2H, d, J=8.3 Hz). Elemental analysis, for $C_{29}H_{36}N_2O_4 \cdot HCl \cdot 2.5H_2O$. Calcd.: C, 62.41; H, 7.59; N, 5.02. Found: C, 62.70; H, 7.20; N, 4.89.

EXAMPLE 336

Tert-butyl 3-[3-[[7-[4-[1-[(2-chlorophenyl)methyl]-4-piperidinyl]butanoyl]-2,3,4,5-tetrahydro-1H-3-benzazepin-3-yl]methyl]phenyl]-2,2-dioxo-216-diazathiane-1-carboxylate

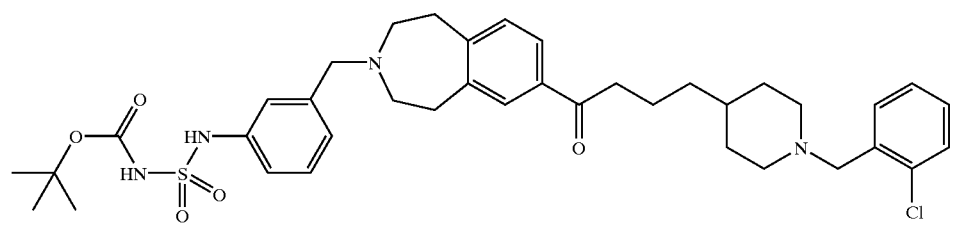

Using 1-[3-[(3-aminophenyl)methyl]-2,3,4,5-tetrahydro-1H-3-benzazepin-7-yl]-4-[1-[(2-chlorophenyl)methyl]-4-piperidinyl]-1-butanone (free base), obtained in Example 298, and tert-butyl(chlorosulfonfyl)carbamate, the procedure of Example 28 was similarly repeated to provide the title compound as colorless powders melting at 159° C. (dec.).

$^1$H NMR (CDCl$_3$) δ: 1.05–1.40 (5H, m), 1.36 (9H, s), 1.55–1.75 (4H, m), 2.20–2.40 (2H, m), 2.50–2.65 (4H, m), 2.70–3.30 (2H, br), 2.80–3.00 (6H, m), 3.05–3.20 (2H, m), 3.51 (2H, s), 3.88 (2H, s), 7.00–7.30 (7H, m), 7.35–7.40 (1H, m), 7.50–7.55 (1H, m), 7.60–7.75 (2H, m).

INDUSTRIAL APPLICABILITY

Compound (1) of the present invention, inclusive of its salt, promotes lipolysis, thermogenesis, reduces body weight (strictly, adipose mass), and suppresses body weight gain suppressive activity and is of value as a prophylactic and/or therapeutic drug for obesity and obesity-associated diseases.

What is claimed is:

1. A method for accelerating thermogenesis to treat obesity or obesity-associated disease in a mammal in need thereof, comprising administering to said mammal an effective amount of a compound of the formula:

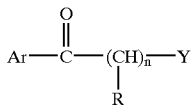

wherein Ar represents a benzazepinyl group which may be substituted;

n represents an integer of 1 to 10;

R represents a hydrogen atom or a hydrocarbon group which may be substituted, which may not be the same in n occurrences;

Y represents an amino group which may be substituted or a nitrogen-containing saturated heterocyclic group which may be substituted, or a salt thereof, such that obesity or obesity-associated disease is treated in said mammal.

2. A method according to claim 1, wherein Ar represents a group of the formula:

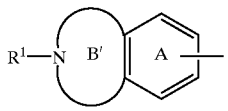

wherein R$^1$ represents a hydrogen atom, a hydrocarbon group which may be substituted, an acyl group, or a heterocyclic group which may be substituted;

ring A represents a benzene ring which may be substituted;

ring B' represents an azepine ring which may be substituted by oxo.

3. A method according to claim 1, wherein Ar represents a group of the formula:

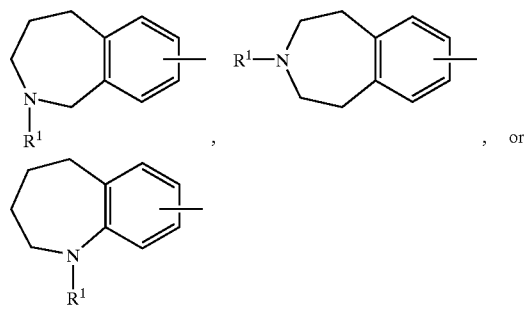

wherein R$^1$ represents a hydrogen atom, a hydrocarbon group which may be substituted, an acyl group, or a heterocyclic group which may be substituted.

4. A method according to claim 1, wherein R represents a hydrogen atom.

5. A method according to claim 1, wherein Y represents a group of the formula:

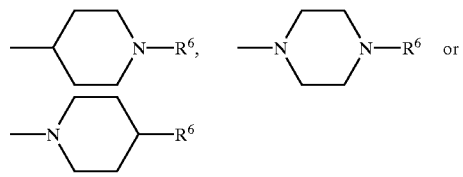

wherein R$^6$ represents (i) a phenyl-C$_{1-6}$ alkyl group which may be substituted by C$_{1-6}$ alkyl which may be substituted, C$_{1-6}$ alkoxy which may be substituted, halogen, nitro, mono- or di-C$_{1-6}$ alkyl-carbamoyloxy, hydroxy, cyano, carboxyl, C$_{1-6}$ alkoxy-carbonyl, carbamoyl, mono-lower alkyl-carbamoyl, di-lower alkyl-carbamoyl, cyclic aminocarbonyl which may be substituted, amino, mono-lower alkylamino, di-lower alkylamino, C$_{1-6}$ alkyl-carbonylamino, phenylsulfonylamino which may be substituted, C$_{1-6}$ alkylsulfonylamino, amidino which may be substituted, ureido which may be substituted, sulfo, or heterocyclic group which may be substituted, (ii) a hydrogen atom, (iii) a C$_{1-6}$ alkyl group which may be substituted by halogen, hydroxy, C$_{1-6}$ alkoxy, amino, mono- or di-C$_{1-6}$ alkylamino, carboxyl, cyano, heterocyclic group which may be substituted, or C$_{1-6}$ alkoxy-carbonyl, (iv) a C$_{1-6}$ alkyl-carbonyl group which may be substituted by mono- or di-C$_{1-6}$ alkylamino, or C$_{1-6}$ alkoxy-carbonyl, (v) a benzoyl group which may be substituted, (vi) a C$_{1-6}$ alkylsulfonyl group, (vii) an aminocarbonyl group which may be substituted, (viii) a C$_{1-6}$ alkoxy-carbonyl group, (ix) a fluorenyl group which may be substituted, or (x) a naphthyl-C$_{1-6}$ alkyl group which may be substituted.

6. A method according to claim 1, wherein Y represents a 1-benzyl-4-piperidinyl group, a 4-benzyl-1-piperazinyl group or a 4-benzyl-1-piperidinyl group, each benzyl of which may be substituted respectively.

7. A method according to claim 1, wherein n represents an integer of 1 to 6.

8. A method according to claim 1, wherein R represents a hydrogen atom, n represents 2, and Y represents a 1-benzyl-4-piperidinyl group.

9. A method according to claim 1, wherein the compound is of the formula:

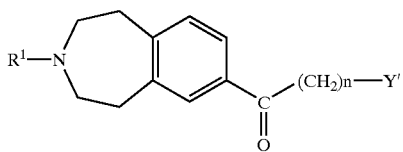

wherein $R^1$ represents a hydrogen atom, a hydrocarbon group which may be substituted, an acyl group, or a heterocyclic group which may be substituted;

Y' represents a 4-piperidinyl group in which nitrogen may be substituted;

n represents an integer of 3 to 6, or a salt thereof.

10. A method according to claim 1, wherein the compound is of the formula:

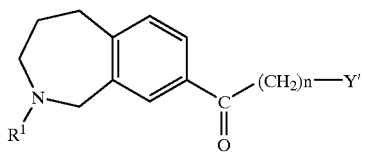

wherein $R^1$ represents a hydrogen atom, a hydrocarbon group which may be substituted, an acyl group, or a heterocyclic group which may be substituted;

Y' represents a 4-piperidinyl group in which nitrogen may be substituted;

n represents an integer of 3 to 6, or a salt thereof.

11. A method for treating obesity in a mammal in need thereof, comprising administering to said mammal an effective amount of a compound of the formula:

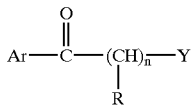

wherein Ar represents a benzazepinyl group which may be substituted;

n represents an integer of 1 to 10;

R represents a hydrogen atom or a hydrocarbon group which may be substituted, which may not be the same in n occurrences;

Y represents an amino group which may be substituted or a nitrogen-containing saturated heterocyclic group which may be substituted, or a salt thereof.

12. A method for accelerating lipolysis to treat obesity or obesity-associated disease in a mammal in need thereof, comprising administering to said mammal an effective amount of a compound of the formula:

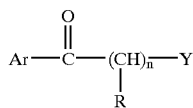

wherein Ar represents a benzazepinyl group which may be substituted;

n represents an integer of 1 to 10;

R represents a hydrogen atom or a hydrocarbon group which may be substituted, which may not be the same in n occurrences;

Y represents an amino group which may be substituted or a nitrogen-containing saturated heterocyclic group which may be substituted, or a salt thereof.

13. A method for treating obesity-associated disease or diabetes in a mammal in need thereof, comprising administering to said mammal an effective amount of a compound of the formula:

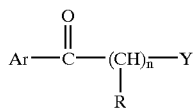

wherein Ar represents a benzazepinyl group which may be substituted;

n represents an integer of 1 to 10;

R represents a hydrogen atom or a hydrocarbon group which may be substituted, which may not be the same in n occurrences;

Y represents an amino group which may be substituted or a nitrogen-containing saturated heterocyclic group which may be substituted, or a salt thereof.

* * * * *